(12) United States Patent
Du et al.

(10) Patent No.: US 10,316,049 B2
(45) Date of Patent: Jun. 11, 2019

(54) TANK-BINDING KINASE INHIBITOR COMPOUNDS

(71) Applicant: Gilead Sciences, Inc., Foster City, CA (US)

(72) Inventors: Zhimin Du, Belmont, CA (US); David Dornan, Burlingame, CA (US); Juan A. Guerrero, Concord, CA (US); Joshua A. Kaplan, Foster City, CA (US); John E. Knox, San Carlos, CA (US); Devan Naduthambi, San Bruno, CA (US); Barton W. Phillips, San Mateo, CA (US); Susanna Y. Stinson, Belmont, CA (US); Chandrasekar Venkataramani, Redwood City, CA (US); Peiyuan Wang, San Mateo, CA (US); William J. Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 185 days.

(21) Appl. No.: 15/380,836

(22) Filed: Dec. 15, 2016

(65) Prior Publication Data
US 2017/0174713 A1 Jun. 22, 2017

Related U.S. Application Data

(60) Provisional application No. 62/425,396, filed on Nov. 22, 2016, provisional application No. 62/268,846, filed on Dec. 17, 2015.

(51) Int. Cl.
| | |
|---|---|
| *A61K 31/505* | (2006.01) |
| *A61K 45/06* | (2006.01) |
| *C07D 239/42* | (2006.01) |
| *C07D 401/10* | (2006.01) |
| *C07D 413/12* | (2006.01) |
| *C07F 9/6558* | (2006.01) |
| *C07D 405/12* | (2006.01) |
| *A61K 31/4433* | (2006.01) |
| *A61K 31/519* | (2006.01) |
| *A61K 9/00* | (2006.01) |
| *C07D 403/10* | (2006.01) |
| *A61K 31/4439* | (2006.01) |
| *C07D 401/12* | (2006.01) |
| *A61K 31/4545* | (2006.01) |

(Continued)

(52) U.S. Cl.
CPC ........ *C07F 9/65583* (2013.01); *A61K 9/0053* (2013.01); *A61K 31/4433* (2013.01); *A61K 31/4439* (2013.01); *A61K 31/4545* (2013.01); *A61K 31/505* (2013.01); *A61K 31/506* (2013.01); *A61K 31/519* (2013.01); *A61K 31/675* (2013.01); *A61K 45/06* (2013.01); *C07D 239/42* (2013.01); *C07D 401/10* (2013.01); *C07D 401/12* (2013.01); *C07D 401/14* (2013.01); *C07D 403/10* (2013.01); *C07D 405/12* (2013.01); *C07D 405/14* (2013.01); *C07D 409/14* (2013.01); *C07D 413/12* (2013.01); *C07D 413/14* (2013.01); *C07D 417/14* (2013.01)

(58) Field of Classification Search
CPC .............. C07F 9/65583; A61K 9/0053; A61K 31/4433; A61K 31/505; A61K 45/06; C07D 239/42; C07D 401/10; C07D 403/10; C07D 405/12; C07D 409/14; C07D 413/12; C07D 417/14
See application file for complete search history.

(56) References Cited

U.S. PATENT DOCUMENTS

| | | |
|---|---|---|
| 8,969,335 B2 | 3/2015 | Hoelzemann et al. |
| 10,040,781 B2 | 8/2018 | Du et al. |

(Continued)

FOREIGN PATENT DOCUMENTS

| | | |
|---|---|---|
| CN | 103251600 A | 8/2013 |
| WO | WO-2005/075465 A1 | 8/2005 |

(Continued)

OTHER PUBLICATIONS

Bamborough et al., (2006) "5-(1 H-Benzimidazol-1-yl)-3-alkoxy-2-thiophenecarbonitriles as Potent, Selective, Inhibitors of IKK-ε Kinase," *Bioorganic & Medicinal Chemistry Letters* 16: 6236-6240.

(Continued)

*Primary Examiner* — Yong S. Chong
(74) *Attorney, Agent, or Firm* — Morrison & Foerster LLP

(57) ABSTRACT

Compounds having the following formula (I) and methods of their use and preparation are disclosed:

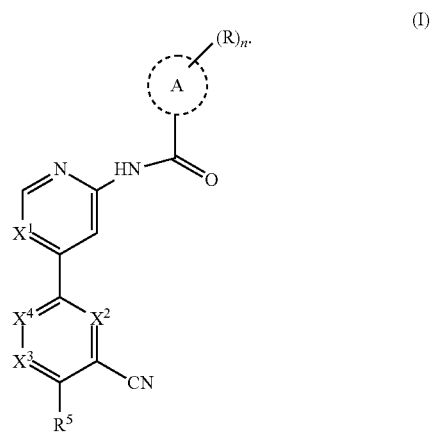

59 Claims, No Drawings

(51) Int. Cl.
| | |
|---|---|
| *C07D 401/14* | (2006.01) |
| *A61K 31/506* | (2006.01) |
| *C07D 413/14* | (2006.01) |
| *C07D 405/14* | (2006.01) |
| *C07D 409/14* | (2006.01) |
| *C07D 417/14* | (2006.01) |
| *A61K 31/675* | (2006.01) |

(56) References Cited

U.S. PATENT DOCUMENTS

| | | |
|---|---|---|
| 10,072,001 B2 | 9/2018 | Du et al. |
| 2012/0238540 A1 | 9/2012 | Holcombe et al. |
| 2013/0217951 A1 | 8/2013 | Dorsch et al. |
| 2013/0289017 A1 | 10/2013 | Dorsch et al. |
| 2014/0275027 A1 | 9/2014 | Gong et al. |
| 2014/0323481 A1 | 10/2014 | Dorsch et al. |
| 2015/0005284 A1 | 1/2015 | Eggenweiler et al. |
| 2015/0344473 A1 | 12/2015 | Zhimin et al. |
| 2015/0352108 A1 | 12/2015 | Holcomb et al. |
| 2016/0096827 A1 | 4/2016 | Du et al. |
| 2016/0289684 A1 | 10/2016 | Feng et al. |
| 2016/0376283 A1 | 12/2016 | Sherer et al. |
| 2018/0265543 A1 | 9/2018 | Du et al. |

FOREIGN PATENT DOCUMENTS

| | | |
|---|---|---|
| WO | WO-2007/002433 A1 | 1/2007 |
| WO | WO-2008/090181 A1 | 7/2008 |
| WO | WO-2009/030890 A1 | 3/2009 |
| WO | WO-2009/087225 A2 | 7/2009 |
| WO | WO-2009/091388 A2 | 7/2009 |
| WO | WO-2009/118567 A2 | 10/2009 |
| WO | WO-2009/122180 A1 | 10/2009 |
| WO | WO-2010/100431 A1 | 9/2010 |
| WO | WO-2010/127754 A1 | 11/2010 |
| WO | WO-2011/046970 A1 | 4/2011 |
| WO | WO-2011/048082 A1 | 4/2011 |
| WO | WO-2012/010826 A1 | 1/2012 |
| WO | WO-2012/104007 A2 | 8/2012 |
| WO | WO-2012/142329 A1 | 10/2012 |
| WO | WO-2012/161877 A1 | 11/2012 |
| WO | WO-2012/161879 A1 | 11/2012 |
| WO | WO-2012/171337 A1 | 12/2012 |
| WO | WO-2013/024282 A2 | 2/2013 |
| WO | WO-2013/026516 A1 | 2/2013 |
| WO | WO-2013/026890 A1 | 2/2013 |
| WO | WO-2013/034238 A1 | 3/2013 |
| WO | WO-2013/075785 A1 | 5/2013 |
| WO | WO-2013/085802 A1 | 6/2013 |
| WO | WO-2013/117285 A1 | 8/2013 |
| WO | WO-2014/004863 A2 | 1/2014 |
| WO | WO-2014/128486 A1 | 8/2014 |
| WO | WO-2014/139328 A1 | 9/2014 |
| WO | WO-2015/089327 A1 | 6/2015 |
| WO | WO-2015/134171 A1 | 9/2015 |
| WO | WO-2016/049211 A1 | 3/2016 |
| WO | WO-2016/057338 A1 | 4/2016 |
| WO | WO-2017/003995 A1 | 1/2017 |

OTHER PUBLICATIONS

Hideshima, T. et al. (Dec. 1, 2003). "Antitumor Activity of Lysophosphatidic Acid Acyltransferase-Inhibitors, a Novel Class of Agents, in Multiple Myeloma," *Cancer Research* 63(23):8428-8436.

International Preliminary Report on Patentability dated Dec. 15, 2016 for PCT/US2015/033769, 9 pages.

International Preliminary Report on Patentability dated Mar. 28, 2017 for PCT/US2015/051757, 6 pages.

International Search Report—Written Opinion dated Feb. 3, 2017 for PCT/US2016/067022, 9 pages.

International Search Report—Written Opinion dated Aug. 20, 2015 for PCT/US2015/033769, 14 pages.

International Search Report—Written Opinion dated Nov. 13, 2015 for PCT/US2015/051757, 8 pages.

Liu, S. et al. (2013, e-pub. Jun. 21, 2013), "Crystal Structure of a Human IκB Kinase β Asymmetric Dimer," *J. Biol. Chem.* 288(31):22758-22767, 11 pages.

McLver, E.G. et al., (2012) "Synthesis and Structure-activity Relationships of a Novel Series of Pyrimidines as Potent Inhibitors of TBK1/IKKε Kinases," *Bioorganic & Medicinal Chemistry Letters* 22:7169-7173.

Office Action dated Feb. 7, 2018, for Taiwanese Patent Application No. 105141945, filed Dec. 16, 2016, 6 pages (including English Translation).

Wang et al. (2012, e-pub. Jan. 14, 2012). "Discovery of Azabenzimidazole Derivatives as Potent, Selective Inhibitors of TBK1/IKKε Kinases," *Bioorganic & Medicinal Chemistry Letters* 22:2063-2069.

Yu, J. et al. (Jan. 21, 2015, e-pub. Jan. 21, 2015) "Regulation of T-Cell Activation and Migration by the Kinase TBK1 During Neuroinflammation," *Nature Communications* 6:6074; 1-13.

Zhang et al. (2016). "IκB Kinase ε Is an NFATc1 Kinase That Inhibits T Cell Immune Response" *Cell Reports* 16:1-27.

Cuban Office Action dated Jun. 26, 2018 for Patent Application No. 2018-0059, filed Dec. 15, 2016, 5 pages (including English translation).

European Office Action dated Oct. 5, 2018 for Patent Application No. 16820135.8, filed Dec. 15, 2016, 3 pages.

International Preliminary Report on Patentability dated Jun. 28, 2018 for PCT/US2016/067022, 8 pages.

Panama Office Action dated Jun. 18, 2018 for Patent Application No. 92260, filed Dec. 15, 2016, 2 pages (including English translation).

Vietnamese Office Action dated Sep. 12, 2018, for Patent Application No. 1-2018-03039, filed Dec. 15, 2016, 2 pages (including English translation).

TANK-BINDING KINASE INHIBITOR COMPOUNDS

CROSS REFERENCE TO RELATED APPLICATIONS

This patent application claims the benefit of priority of U.S. Provisional Patent Application Ser. No. 62/268,846, filed Dec. 17, 2015, and U.S. Provisional Patent Application Ser. No. 62/425,396, filed Nov. 22, 2016. The contents of these applications are each incorporated herein by reference.

FIELD OF THE INVENTION

This application relates to chemical compounds which may inhibit or otherwise modulate the activity of TANK-binding kinase (TBK1) and/or I-Kappa-B kinase (IKKε, IKBKE), and to compositions and formulations containing such compounds, and methods of using and making such compounds.

BACKGROUND

TBK1 is a serine/threonine kinase with diverse roles in cancer, inflammation, and the host-pathogen response. Shen, R. R. and W. C. Hahn (2011) Oncogene 30(6): 631-641. TBK1 activates its substrates IRF3 and IRF7 transcription factors by direct phosphorylation of specific sites that induces their localization to the nucleus to drive transcription of type I IFN genes (Sankar, S., H. Chan, et al., (2006) Cell Signal 18(7): 982-993). In addition, NFkB activation can be bolstered by the kinase activity of TBK1 by phosphorylating the inhibitors of NFkB, which enables activation of the canonical or non-canonical NFkB transcription factors.

TBK1 has been implicated as being a key gene required for KRAS-dependent cancers, required for HER2+ breast cancers, and contributing to the acquisition of resistance to erlotinib. Depletion of TBK1 by shRNA results in synthetic lethality with KRAS-dependent cancer cell lines and xenograft models (Barbie, D. A., P. Tamayo, et al. (2009) Nature 462(7269): 108-112) and TBK1 is required for RAS-mediated transformation of murine embryonic fibroblasts (Ou, Y. H., M. Tones, et al. (2011) Mol Cell 41(4): 458-470). TBK1 is downstream of RAS and elicits its oncogenic properties via the RALB-NFkB and AKT pathways (Chien, Y., S. Kim, et al. (2006) Cell 127(1): 157-170). In addition, TBK1 directly phosphorylates AKT at 5473 and results in the downstream activation of the mTORC1/2 pathway (Ou, Y. H., M. Tones, et al. (2011) Mol Cell 41(4): 458-470). TBK1 was also identified as being important for the survival of HER2+ breast cancer cell lines via an shRNA kinome screen and showed combination effects with the EGFR/HER2 kinase inhibitor, lapatinib (Deng, T., J. C. Liu, et al. (2014) Cancer Res 74(7): 2119-2130). Additionally, integrin alphaVbeta3 was identified as a marker of cells that are resistant to EGFR therapies and have stem-like properties. The signaling cascade required for the survival of these cells was attributed to KRAS-TALB-TBK1-NFkB axis and inhibiting TBK1 was sufficient to block the survival of these cells. Seguin, L., S. Kato, et al. (2014), Nat Cell Biol 16(5): 457-468.

IKKε is a serine/threonine kinase and its gene amplifications have been identified in up to 30% of breast cancers. Depleting IKKε in cell lines with shRNA that have these amplifications results in their decreased viability (Boehm, J. S., J. J. Zhao, et al. (2007) Cell 129(6): 1065-1079). Over-expression of IKKε in ovarian cancer has been demonstrated to mediate resistance to cisplatin and is a poor prognostic factor (Guo, J. P., S. K. Shu, et al. (2009) Am J Pathol 175(1): 324-333).

TBK1 and IKKε are also both implicated in inflammatory responses and associated disorders. IKKε has been shown to be involved in manifestations of rheumatoid arthritis (RA) that include extracellular matrix destruction, synovial inflammation, and activation of the innate immune response (Sweeney, S. E., D. Hammaker, et al. (2005) J Immunol 174(10): 6424-6430). IKKε and IRF3 protein levels are increased in the synovium of RA patients and mice deficient in IKKε show reduced clinical signs of arthritis in a collagen-induced arthritis model as well as associated reduction of inflammation and erosion. Con, M., D. L. Boyle, et al. (2009), *Ann Rheum Dis* 68(2): 257-263. Other inflammatory disorders that manifest as a result of Type I IFN response and upstream activation of TLR$^3$/TLR$^4$ or cytosolic nucleic acid sensors are likely to also rely on a TBK1/IKKε signaling axis to initiate and maintain their pathogenic state such as Sjogrens syndrome, inflammatory bowel disease (IBD), chronic obstructive pulmonary disease (COPD), systemic lupus erythematosus (SLE), dermatomyositis, polymyositis, systemic sclerosis. Baccala, R., K. Hoebe, et al. (2007), Nat Med 13(5): 543-551. Furthermore, both TBK1 and IKKε have been shown to play a role in maintaining macrophages in an activated state in response to IFN. Solis, M., R. Romieu-Mourez, et al. (2007) Eur J Immunol 37(2): 528-539.

In addition to inflammation and cancer, IKKε is implicated in obesity, type 2 diabetes, and insulin resistance. Mice deficient for IKKε are protected from obesity induced by a high-fat diet, hepatic steatosis, insulin resistance, and chronic inflammation of the liver and fat. Chiang, S. H., M. Bazuine, et al. (2009) Cell 138(5): 961-975. Consistent with this, high levels of NFkB activation have been seen in the liver, adipocytes, and adipose tissue resident macrophages as well as increase levels of IKKε over healthy mice. Treatment with a kinase inhibitor to TBK1/IKKε improved obesity-related metabolic dysfunction in mice fed a high fat diet (Reilly, S. M., S. H. Chiang, et al. (2013) Nat Med 19(3): 313-321).

Accordingly, there is a need for inhibitors of the kinase activity of TBK1 and/or IKKε for treating cancers, inflammatory, and metabolic disorders that may have an active TBK1 and/or IKKε pathway.

SUMMARY

The present disclosure provides a compound of formula (I):

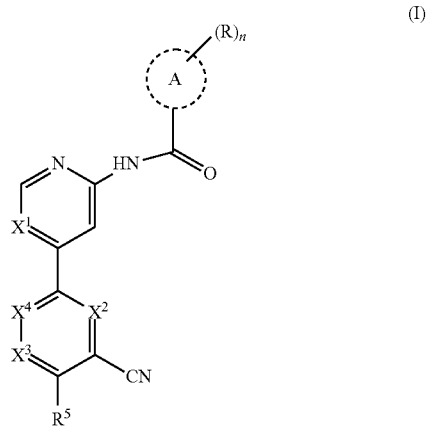

wherein,
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;
Ring A is C$_3$-C$_8$ cycloalkyl or C$_5$-C$_8$ cycloalkenyl;
X$^1$ is CR$^1$ or N;
X$^2$ is CR$^2$ or N;
X$^3$ is CR$^3$ or N;
X$^4$ is CR$^4$ or N; provided that no more than two of X$^2$, X$^3$ and X$^4$ are N; and provided that when X$^2$ is N, X$^4$ is CR$^4$;
R$^1$ is H, halo, CN, C$_1$-C$_3$ haloalkyl, or C$_1$-C$_3$ alkyl;
R$^2$ is H or halo;
R$^3$ is selected from the group consisting of H, halo, OR$^a$, C$_{1-6}$ alkyl, C$_0$-C$_3$alkylC$_{6-10}$ aryl, and C$_0$-C$_3$alkylC$_{3-6}$ cycloalkyl;
R$^4$ is H or halo;
R$^5$ is selected from the group consisting of H, hydroxyl, C$_{1-6}$ alkyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$R$^c$, —S(O)$_2$NR$^a$R$^b$, —NR$^a$S(O)$_2$R$^b$, C$_{6-10}$ aryl, C$_{3-10}$ cycloalkyl, 5-10 membered heteroaryl, 3-12 membered heterocyclyl and —O—R$^6$, wherein each C$_{1-6}$ alkyl, C$_{6-10}$ aryl, C$_{3-10}$ cycloalkyl, 5-10 membered heteroaryl and 3-12 membered heterocyclyl is optionally substituted with from one to five R$^7$ groups; provided that when X$^1$ is CR$^1$, R$^5$ is not H, hydroxyl, C$_{1-6}$ alkyl, halogen, or C$_{3-10}$ cycloalkyl;
R$^6$ is C$_{1-6}$ alkyl, C$_{1-6}$ haloalkyl, C$_{6-10}$ aryl, 5-10 membered heteroaryl, C$_{3-10}$ cycloalkyl, or 3-12 membered heterocyclyl, each of which is optionally substituted with from one to five R$^7$ groups; provided that when X$^1$ is CR$^1$, R$^6$ is not C$_{1-6}$ alkyl or C$_{1-6}$ haloalkyl;
each R$^7$ is independently C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-10}$ cycloalkyl, C$_{1-6}$ heteroalkyl, 3-12 membered heterocyclyl, C$_{6-10}$ aryl, and 5-10 membered heteroaryl is optionally substituted with from one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O) NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;

each R$^a$ and each R$^b$ are independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O) NH$_2$, —C(O)NH(C$_{1-6}$ alkyl), —C(O)N(C$_{1-6}$ alkyl)$_2$ or absent, each of which is optionally substituted with from one to three groups independently selected from C$_{1-6}$ alkyl, C$_{2-6}$ alkenyl, CN, OH, OC$_1$—C$_3$ alkyl, and —NH$_2$; or R$^a$ and R$^b$ together with the atoms to which they are attached form a 3-12 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$;
or a pharmaceutically acceptable salt thereof.

In some embodiments, n is 0 or 1 in a compound having formula (I). In some embodiments, n is 0. In some embodiments, n is 1.

In some embodiments, Ring A is C$_3$-C$_8$ cycloalkyl in a compound having formula (I). In some embodiments, Ring A is a cyclopropyl group.

Another embodiment provides a compound having the following formula (Ia):

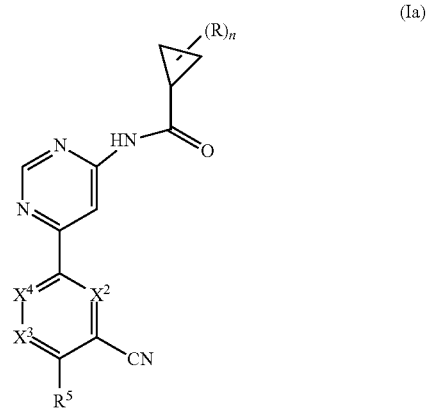

(Ia)

wherein
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O) NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;
X$^1$ is CR$^1$ or N;
X$^2$ is CR$^2$ or N;
X$^3$ is CR$^3$ or N;
X$^4$ is CR$^4$ or N; provided that no more than two of X$^2$, X$^3$ and X$^4$ are N; and provided that when X$^2$ is N, X$^4$ is CR$^4$;
R$^1$ is H, halo, CN, C$_1$-C$_3$ haloalkyl, or C$_1$-C$_3$ alkyl;
R$^2$ is H or halo;

$R^3$ is selected from the group consisting of H, halo, $OR^a$, $C_{1-6}$ alkyl, $C_0$-$C_3$alkyl$C_{6-10}$ aryl, and $C_0$-$C_3$alkyl$C_{3-6}$ cycloalkyl;

$R^4$ is H or halo;

$R^5$ is selected from the group consisting of H, hydroxyl, $C_{1-6}$ alkyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}$ $R^c$, $-S(O)_2NR^aR^b$, $-NR^aS(O)_2R^b$, $C_{6-10}$ aryl, $C_{3-10}$ cycloalkyl, 5-10 membered heteroaryl, 3-12 membered heterocyclyl and $-O-R^6$, wherein each $C_{1-6}$ alkyl, $C_{6-10}$ aryl, $C_{3-10}$ cycloalkyl, 5-10 membered heteroaryl and 3-12 membered heterocyclyl is optionally substituted with from one to five $R^7$ groups; provided that when $X^1$ is $CR^1$, $R^5$ is not H, hydroxyl, $C_{1-6}$ alkyl, halogen, or $C_{3-10}$ cycloalkyl;

$R^6$ is $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with from one to five $R^7$ groups; provided that when $X^1$ is $CR^1$, $R^6$ is not $C_{1-6}$ alkyl or $C_{1-6}$ haloalkyl;

each $R^7$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)(R^a)$ $=NR^b$, $-S(O)_2NR^aR^b$, $-NR^aS(O)_2R^b$, $-N_3$, $-CN$, or $-NO_2$; or two $R^7$ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $S(O)(R^a)=NR^b$, $-NR^aS(O)_2R^b$, $-N_3$, $-CN$, or $-NO_2$;

each $R^a$ and each $R^b$ are independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, $-C(O)NH_2$, $-C(O)NH(C_{1-6}$ alkyl), $-C(O)N(C_{1-6}$ alkyl)$_2$ or absent, each of which is optionally substituted with from one to three groups independently selected from $C_{1-6}$ alkyl, $C_{2-6}$ alkenyl, CN, OH, $OC_1$-$C_3$ alkyl, and $-NH_2$; or $R^a$ and $R^b$ together with the atoms to which they are attached form a 3-12 membered heterocyclyl optionally substituted with one to three groups independently selected from $C_{1-6}$ alkyl, $C_{1-6}$ alkyl-OH, $C_{2-6}$ alkenyl, CN, OH, $OC_1$-$C_3$ alkyl, and $NH_2$;

or a pharmaceutically acceptable salt thereof.

In some embodiments, n is 0 or 1 in a compound having formula (Ia). In some embodiments, n is 0. In some embodiments, n is 1.

Another embodiment provides a compound having the following formula (Ib):

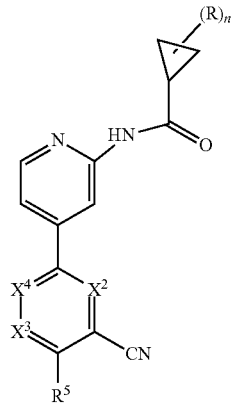

(Ib)

wherein
n is 0, 1, 2 or 3;
each R is independently halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)(R^a)$ $=NR^b$, $-S(O)_2NR^aR^b$, $-NR^aS(O)_2R^b$, $-N_3$, $-CN$, $-NO_2$, $C_{1-6}$ alkyl, $C_1$-$C_6$ haloalkyl, $C_{1-6}$ alkyl-OH, $C_{3-10}$ cycloalkyl, $C_{1-6}$ heteroalkyl, 3-12 membered heterocyclyl, $C_{6-10}$ aryl, or 5-10 membered heteroaryl; or two R groups together with the atom(s) to which they are attached form a fused, spiro or bridged $C_{3-10}$ cycloalkyl or 3-12 membered heterocyclyl; and wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, fused, spiro or bridged cycloalkyl or heterocyclic is optionally substituted with from one to five groups independently selected from halogen, $C_{1-6}$ alkyl, $C_{1-6}$ heteroalkyl, $C_{1-6}$ haloalkyl, oxo, imino, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $-NR^aS(O)_2R^b$, $S(O)(R^a)$ $=NR^b$, $-N_3$, $-CN$, and $-NO_2$;

$X^2$ is $CR^2$ or N;
$X^3$ is $CR^3$ or N;
$X^4$ is $CR^4$ or N; provided that no more than two of $X^2$, $X^3$ and $X^4$ are N; and provided that when $X^2$ is N, $X^4$ is $CR^4$;
$R^2$ is H or halo;
$R^3$ is selected from the group consisting of H, halo, $OR^a$, $C_{1-6}$ alkyl, $C_0$-$C_3$alkyl$C_{6-10}$ aryl, and $C_0$-$C_3$alkyl$C_{3-6}$ cycloalkyl;
$R^4$ is H or halo;
$R^5$ is selected from the group consisting of $-NR^aR^b$, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}$ $R^c$, $-S(O)_2NR^aR^b$, $-NR^aS(O)_2R^b$, $C_{6-10}$ aryl, 5-10 membered heteroaryl, 3-12 membered heterocyclyl and $-O-R^6$, wherein each $C_{1-6}$ alkyl, $C_{6-10}$ aryl, $C_{3-10}$ cycloalkyl, 5-10 membered heteroaryl and 3-12 membered heterocyclyl is optionally substituted with from one to five $R^7$ groups; provided that when $X^1$ is $CR^1$,
$R^6$ is $C_{6-10}$ aryl, 5-10 membered heteroaryl, $C_{3-10}$ cycloalkyl, or 3-12 membered heterocyclyl, each of which is optionally substituted with from one to five $R^7$ groups;
each $R^7$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)(R^a)$ $=NR^b$, $-S(O)_2NR^aR^b$, $-NR^aS(O)_2R^b$, $-N_3$, $-CN$, or —NO₂; or two R⁷ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;

each R$^a$ and each R$^b$ are independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)NH$_2$, —C(O)NH($C_{1-6}$ alkyl), —C(O)N($C_{1-6}$ alkyl)$_2$ or absent, each of which is optionally substituted with from one to three groups independently selected from $C_{1-6}$ alkyl, $C_{2-6}$ alkenyl, CN, OH, OC$_1$—C$_3$ alkyl, and —NH$_2$; or R$^a$ and R$^b$ together with the atoms to which they are attached form a 3-12 membered heterocyclyl optionally substituted with one to three groups independently selected from $C_{1-6}$ alkyl, $C_{1-6}$ alkyl-OH, $C_{2-6}$ alkenyl, CN, OH, OC$_1$—C$_3$ alkyl, and NH$_2$; or a pharmaceutically acceptable salt thereof.

In some embodiments, n is 0 or 1 in a compound having formula (Ib). In some embodiments, n is 0. In some embodiments, n is 1.

Another embodiment provides a compound having the following formula (Ic):

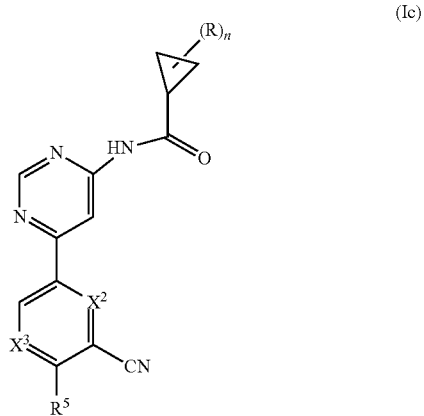

(Ic)

wherein
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, $C_{1-6}$ alkyl, $C_1$-$C_6$ haloalkyl, $C_{1-6}$ alkyl-OH, $C_{3-10}$ cycloalkyl, $C_{1-6}$ heteroalkyl, 3-12 membered heterocyclyl, $C_{6-10}$ aryl, or 5-10 membered heteroaryl; or two R groups together with the atom(s) to which they are attached form a fused, spiro or bridged $C_{3-10}$ cycloalkyl or 3-12 membered heterocyclyl; and wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, fused, spiro or bridged cycloalkyl or heterocyclic is optionally substituted with from one to five groups independently selected from halogen, $C_{1-6}$ alkyl, $C_{1-6}$ heteroalkyl, $C_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;

$X^2$ is CR$^2$ or N;
$X^3$ is CR$^3$ or N;
R$^2$ is H or halo;
R$^3$ is selected from the group consisting of H, halo, OR$^a$, $C_{1-6}$ alkyl, $C_0$-$C_3$alkyl$C_{6-10}$ aryl, and $C_0$-$C_3$alkyl$C_{3-6}$ cycloalkyl;

R$^5$ is selected from the group consisting of H, hydroxyl, $C_{1-6}$ alkyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$ R$^c$, —S(O)$_2$NR$^a$R$^b$, —NR$^a$S(O)$_2$R$^b$, $C_{6-10}$ aryl, $C_{3-10}$ cycloalkyl, 5-10 membered heteroaryl, 3-12 membered heterocyclyl and —O—R$^6$, wherein each $C_{1-6}$ alkyl, $C_{6-10}$ aryl, $C_{3-10}$ cycloalkyl, 5-10 membered heteroaryl and 3-12 membered heterocyclyl is optionally substituted with from one to five R$^7$ groups;

R$^6$ is H, $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with from one to five R$^7$ groups;

each R$^7$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;

each R$^a$ and each R$^b$ are independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)NH$_2$, —C(O)NH($C_{1-6}$ alkyl), —C(O)N($C_{1-6}$ alkyl)$_2$ or absent, each of which is optionally substituted with from one to three groups independently selected from $C_{1-6}$ alkyl, $C_{2-6}$ alkenyl, CN, OH, OC$_1$—C$_3$ alkyl, and —NH$_2$; or R$^a$ and R$^b$ together with the atoms to which they are attached form a 3-12 membered heterocyclyl optionally substituted with one to three groups independently selected from $C_{1-6}$ alkyl, $C_{1-6}$ alkyl-OH, $C_{2-6}$ alkenyl, CN, OH, OC$_1$—C$_3$ alkyl, and NH$_2$; or a pharmaceutically acceptable salt thereof.

In some embodiments, n is 0 or 1 in a compound having formula (Ic). In some embodiments, n is 0. In some embodiments, n is 1.

Another embodiment provides a compound having the formula (Id)

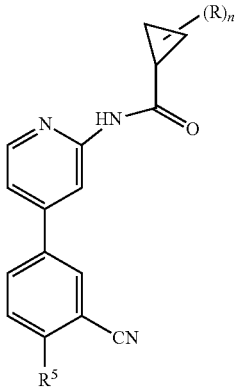

(Id)

wherein
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;
R$^5$ is selected from the group consisting of —NR$^a$R$^b$, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$ R$^c$, —S(O)$_2$NR$^a$R$^b$, —NR$^a$S(O)$_2$R$^b$, C$_{6-10}$ aryl, 5-10 membered heteroaryl, 3-12 membered heterocyclyl and —O—R$^6$, wherein each C$_{1-6}$ alkyl, C$_{6-10}$ aryl, C$_{3-10}$ cycloalkyl, 5-10 membered heteroaryl and 3-12 membered heterocyclyl is optionally substituted with from one to five R$^7$ groups;
R$^6$ is C$_{6-10}$ aryl, 5-10 membered heteroaryl, C$_{3-10}$ cycloalkyl, or 3-12 membered heterocyclyl, each of which is optionally substituted with from one to five R$^7$ groups;
each R$^7$ is independently C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-10}$ cycloalkyl, C$_{1-6}$ heteroalkyl, 3-12 membered heterocyclyl, C$_{6-10}$ aryl, and 5-10 membered heteroaryl is optionally substituted with from one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;
each R$^a$ and each R$^b$ are independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with from one to three groups independently selected from C$_{1-6}$ alkyl, C$_{2-6}$ alkenyl, CN, OH, OC$_1$—C$_3$ alkyl, and —NH$_2$; or R$^a$ and R$^b$ together with the atoms to which they are attached form a 3-12 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$;
or a pharmaceutically acceptable salt thereof.

In some embodiments, n is 0 or 1 in a compound having formula (Id). In some embodiments, n is 0. In some embodiments, n is 1.

Another embodiment provides a compound having the following formula (Ie):

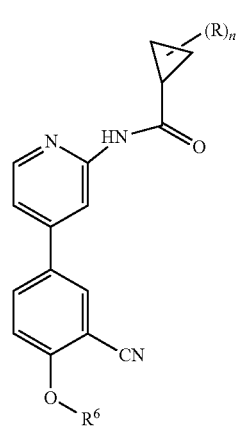

(Ie)

wherein
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-8}$ cycloalkyl, C$_{1-6}$ heteroalkyl, 3-8 membered heterocyclyl, C$_{6-10}$ aryl, or 5-10 membered heteroaryl; or two R groups together with the atom(s) to which they are attached form a fused, spiro or bridged C$_{3-6}$ cycloalkyl or 3-8 membered heterocyclyl; and wherein each C$_{1-6}$ alkyl, C$_{3-8}$ cycloalkyl, C$_{1-6}$ heteroalkyl, 3-8 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, or —NO$_2$;
R$^6$ is C$_{6-10}$ aryl, 5-10 membered heteroaryl, C$_{3-10}$ cycloalkyl, or 3-8 membered heterocyclyl, each of which is optionally substituted with from one to five R$^7$ groups;
each R$^7$ is independently C$_{1-6}$ alkyl, C$_{3-10}$ cycloalkyl, C$_{1-6}$ heteroalkyl, 3-8 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-8}$ cycloalkyl, C$_{1-6}$ heteroalkyl, 3-8 membered heterocyclyl, C$_{6-10}$ aryl, and 5-10 membered heteroaryl is optionally substituted with from one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;

each R$^a$ and each R$^b$ are independently H, C$_{1-6}$ alkyl, C$_{2-6}$ alkenyl, C$_{3-8}$ cycloalkyl, C$_{1-6}$ heteroalkyl, 3-8 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with from one to three groups independently selected from C$_{1-6}$ alkyl, C$_{2-6}$ alkenyl, CN, OH, OC$_1$—C$_3$ alkyl, and —NH$_2$; or R$^a$ and R$^b$ together with the atoms to which they are attached form a 3-8 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$; or a pharmaceutically acceptable salt thereof.

In some embodiments, n is 0 or 1 in a compound having formula (Ie). In some embodiments, n is 0. In some embodiments, n is 1.

In another embodiment, the present disclosure provides a compound of formula (If)

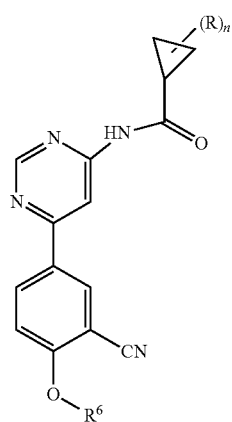

(If)

wherein
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-8}$ cycloalkyl, C$_{1-6}$ heteroalkyl, 3-8 membered heterocyclyl, C$_{6-10}$ aryl, or 5-10 membered heteroaryl; or two R groups together with the atom(s) to which they are attached form a fused, spiro or bridged C$_{3-6}$ cycloalkyl or 3-8 membered heterocyclyl; and wherein each C$_{1-6}$ alkyl, C$_{3-8}$ cycloalkyl, C$_{1-6}$ heteroalkyl, 3-8 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, or —NO$_2$;

R$^6$ is C$_{6-10}$ aryl, 5-10 membered heteroaryl, C$_{3-10}$ cycloalkyl, or 3-8 membered heterocyclyl, each of which is optionally substituted with from one to five R$^7$ groups;

each R$^7$ is independently C$_{1-6}$ alkyl, C$_{3-10}$ cycloalkyl, C$_{1-6}$ heteroalkyl, 3-8 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-8}$ cycloalkyl, C$_{1-6}$ heteroalkyl, 3-8 membered heterocyclyl, C$_{6-10}$ aryl, and 5-10 membered heteroaryl is optionally substituted with from one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;

each R$^a$ and each R$^b$ are independently H, C$_{1-6}$ alkyl, C$_{2-6}$ alkenyl, C$_{3-8}$ cycloalkyl, C$_{1-6}$ heteroalkyl, 3-8 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with from one to three groups independently selected from C$_{1-6}$ alkyl, C$_{2-6}$ alkenyl, CN, OH, OC$_1$—C$_3$ alkyl, and —NH$_2$; or R$^a$ and R$^b$ together with the atoms to which they are attached form a 3-8 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$; or a pharmaceutically acceptable salt thereof.

In some embodiments, n is 0 or 1 in a compound having formula (If). In some embodiments, n is 0. In some embodiments, n is 1.

In another embodiment, the present disclosure provides a compound of formula (Ig):

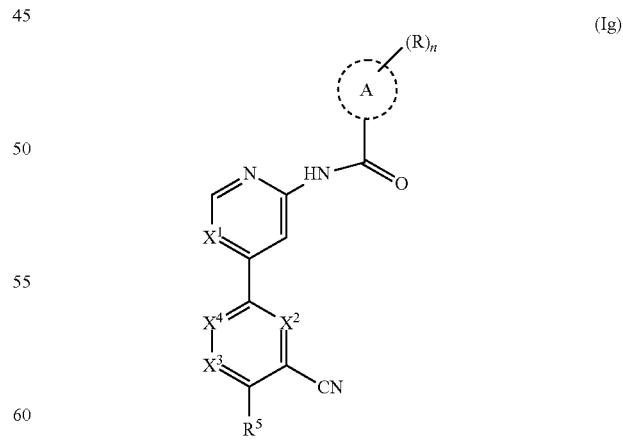

(Ig)

wherein,
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)

=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ alkoxyhaloalkyl, C$_3$-C$_8$ cycloalkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;

Ring A is C$_3$-C$_8$ cycloalkyl or C$_5$-C$_8$ cycloalkenyl;
X$^1$ is CR$^1$ or N;
X$^2$ is CR$^2$ or N;
X$^3$ is CR$^3$ or N;
X$^4$ is CR$^4$ or N; provided that no more than two of X$^2$, X$^3$ and X$^4$ are N; and provided that when X$^2$ is N, X$^4$ is CR$^4$;
R$^1$ is H, halo, CN, C$_1$-C$_3$ haloalkyl, or C$_1$-C$_3$ alkyl;
R$^2$ is H or halo;
R$^3$ is selected from the group consisting of H, halo, OR$^a$, C$_{1-6}$ alkyl, C$_0$-C$_3$alkylC$_{6-10}$ aryl, and C$_0$-C$_3$alkylC$_{3-6}$ cycloalkyl;
R$^4$ is H or halo;
R$^5$ is selected from the group consisting of H, hydroxyl, C$_{1-6}$ alkyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$ R$^c$, —S(O)$_2$NR$^a$R$^b$, —NR$^a$S(O)$_2$R$^b$, C$_{6-10}$ aryl, C$_{3-10}$ cycloalkyl, 5-10 membered heteroaryl, 3-12 membered heterocyclyl and —O—R$^6$, wherein each C$_{1-6}$ alkyl, C$_{6-10}$ aryl, C$_{3-10}$ cycloalkyl, 5-10 membered heteroaryl and 3-12 membered heterocyclyl is optionally substituted with from one to five R$^7$ groups; provided that when X$^1$ is CR$^1$, R$^5$ is not H, hydroxyl, C$_{1-6}$ alkyl, halogen, or C$_{3-10}$ cycloalkyl;
R$^6$ is C$_{1-6}$ alkyl, C$_{1-6}$ haloalkyl, C$_{6-10}$ aryl, 5-10 membered heteroaryl, C$_{3-10}$ cycloalkyl, or 3-12 membered heterocyclyl, each of which is optionally substituted with from one to five R$^7$ groups; provided that when X$^1$ is CR$^1$, R$^6$ is not C$_{1-6}$ alkyl or C$_{1-6}$ haloalkyl;
each R$^7$ is independently C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-10}$ cycloalkyl, C$_{1-6}$ heteroalkyl, 3-12 membered heterocyclyl, C$_{6-10}$ aryl, and 5-10 membered heteroaryl is optionally substituted with from one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, S(O)(R$^a$)=NR$^b$, —NR$^a$S(O)$_2$R$^b$, —N$_3$, —CN, or —NO$_2$;
each R$^a$ and each R$^b$ are independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O) NH$_2$, —C(O)NH(C$_{1-6}$ alkyl), —C(O)N(C$_{1-6}$ alkyl)$_2$, —C(O) N(OC$_{1-6}$ alkyl) (C$_{1-6}$ alkyl), or absent, each of which is optionally substituted with from one to three groups independently selected from C$_{1-6}$ alkyl, C$_{2-6}$ alkenyl, halogen, oxo, CN, OH, OC$_1$—C$_3$ alkyl, —NH$_2$, —OC(O)CH(Me) NH$_2$, —OP(O)(OH)$_2$; or R$^a$ and R$^b$ together with the atoms to which they are attached form a 3-12 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$;
or a pharmaceutically acceptable salt thereof.

In some embodiments, n is 0 or 1 in a compound having formula (Ig). In some embodiments, n is 0. In some embodiments, n is 1.

In some embodiments, Ring A is C$_3$-C$_8$ cycloalkyl in a compound having formula (Ig). In some embodiments, Ring A is a cyclopropyl group.

In some embodiments, the present disclosure provides a compound of formula (Ih):

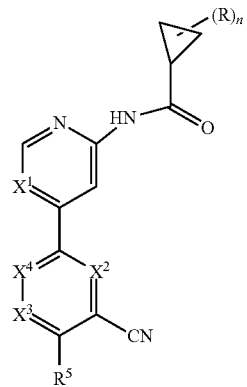

(Ih)

wherein,
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ alkoxyhaloalkyl, C$_3$-C$_8$ cycloalkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;

X$^1$ is CR$^1$ or N;
X$^2$ is CR$^2$;
X$^3$ is CR$^3$;
X$^4$ is CR$^4$;
R$^1$ is H, halo, CN, C$_1$-C$_3$ haloalkyl, or C$_1$-C$_3$ alkyl;
R$^2$ is H or halo;
R$^3$ is selected from the group consisting of H, halo, OR$^a$, C$_{1-6}$ alkyl, C$_0$-C$_3$alkylC$_{6-10}$ aryl, and C$_0$-C$_3$alkylC$_{3-6}$ cycloalkyl;
R$^4$ is H or halo;

$R^5$ is selected from the group consisting of H, hydroxyl, $C_{1-6}$ alkyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^c$, —$S(O)_2NR^aR^b$, —$NR^aS(O)_2R^b$, $C_{6-10}$ aryl, $C_{3-10}$ cycloalkyl, 5-10 membered heteroaryl, 3-12 membered heterocyclyl and —O—$R^6$, wherein each $C_{1-6}$ alkyl, $C_{6-10}$ aryl, $C_{3-10}$ cycloalkyl, 5-10 membered heteroaryl and 3-12 membered heterocyclyl is optionally substituted with from one to five $R^7$ groups; provided that when $X^1$ is $CR^1$, $R^5$ is not H, hydroxyl, $C_{1-6}$ alkyl, halogen, or $C_{3-10}$ cycloalkyl;

$R^6$ is $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with from one to five $R^7$ groups; provided that when $X^1$ is $CR^1$, $R^6$ is not $C_{1-6}$ alkyl or $C_{1-6}$ haloalkyl;

each $R^7$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)(R^a)$=$NR^b$, —$S(O)_2NR^aR^b$, —$NR^aS(O)_2R^b$, —$N_3$, —CN, or —$NO_2$; or two $R^7$ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, $S(O)(R^a)$=$NR^b$, —$NR^aS(O)_2R^b$, —$N_3$, —CN, or —$NO_2$;

each $R^a$ and each $R^b$ are independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —$C(O)NH_2$, —$C(O)NH(C_{1-6}$ alkyl), —$C(O)N(C_{1-6}$ alkyl)$_2$, —$C(O)N(OC_{1-6}$ alkyl) ($C_{1-6}$ alkyl), or absent, each of which is optionally substituted with from one to three groups independently selected from $C_{1-6}$ alkyl, $C_{2-6}$ alkenyl, halogen, oxo, CN, OH, $OC_1$—$C_3$ alkyl, —$NH_2$, —$OC(O)CH(Me)NH_2$, —$OP(O)(OH)_2$; or $R^a$ and $R^b$ together with the atoms to which they are attached form a 3-12 membered heterocyclyl optionally substituted with one to three groups independently selected from $C_{1-6}$ alkyl, $C_{1-6}$ alkyl-OH, $C_{2-6}$ alkenyl, CN, OH, $OC_1$—$C_3$ alkyl, and $NH_2$;

or a pharmaceutically acceptable salt thereof.

In some embodiments, n is 0 or 1 in a compound having formula (Ih). In some embodiments, n is 0. In some embodiments, n is 1.

In some embodiments, the present disclosure provides a compound of formula (Ii):

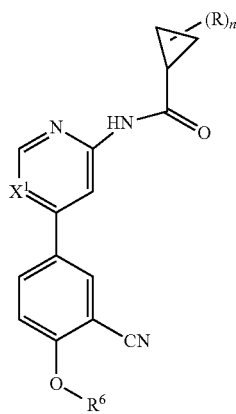

(Ii)

wherein, n is 0, 1, 2 or 3;

each R is independently halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)(R^a)$=$NR^b$, —$S(O)_2NR^aR^b$, —$NR^aS(O)_2R^b$, —$N_3$, —CN, —$NO_2$, $C_{1-6}$ alkyl, $C_1$-$C_6$ haloalkyl, $C_{1-6}$ alkyl-OH, $C_{3-10}$ cycloalkyl, $C_{1-6}$ heteroalkyl, 3-12 membered heterocyclyl, $C_{6-10}$ aryl, or 5-10 membered heteroaryl; or two R groups together with the atom(s) to which they are attached form a fused, spiro or bridged $C_{3-10}$ cycloalkyl or 3-12 membered heterocyclyl; and wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, fused, spiro or bridged cycloalkyl or heterocyclic is optionally substituted with from one to five groups independently selected from halogen, $C_{1-6}$ alkyl, $C_{1-6}$ alkoxyhaloalkyl, $C_3$-$C_8$ cycloalkyl, $C_{1-6}$ heteroalkyl, $C_{1-6}$ haloalkyl, oxo, imino, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, $S(O)(R^a)$=$NR^b$, —$N_3$, —CN, and —$NO_2$;

$X^1$ is $CR^1$ or N;

$R^1$ is H, halo, CN, $C_1$-$C_3$ haloalkyl, or $C_1$-$C_3$ alkyl;

$R^6$ is $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with from one to five $R^7$ groups; provided that when $X^1$ is $CR^1$, $R^6$ is not $C_{1-6}$ alkyl or $C_{1-6}$ haloalkyl;

each $R^7$ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)(R^a)$=$NR^b$, —$S(O)_2NR^aR^b$, —$NR^aS(O)_2R^b$, —$N_3$, —CN, or —$NO_2$; or two $R^7$ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, $S(O)(R^a)$=$NR^b$, —$NR^aS(O)_2R^b$, —$N_3$, —CN, or —$NO_2$;

each $R^a$ and each $R^b$ are independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —$C(O)NH_2$, —$C(O)NH(C_{1-6}$ alkyl), —$C(O)N(C_{1-6}$ alkyl)$_2$, —$C(O)N(OC_{1-6}$ alkyl) ($C_{1-6}$ alkyl), or absent, each of which is optionally substituted with from one to three groups independently selected from $C_{1-6}$ alkyl, $C_{2-6}$ alkenyl, halogen, oxo, CN, OH, $OC_1$—$C_3$ alkyl, —$NH_2$, —$OC(O)CH(Me)NH_2$, —$OP(O)(OH)_2$; or $R^a$ and $R^b$ together with the atoms to which they are attached form a 3-12 membered heterocyclyl optionally substituted with one to three groups independently selected from $C_{1-6}$ alkyl, $C_{1-6}$ alkyl-OH, $C_{2-6}$ alkenyl, CN, OH, $OC_1$—$C_3$ alkyl, and $NH_2$;

or a pharmaceutically acceptable salt thereof.

In some embodiments, n is 0 or 1 in a compound having formula (Ii). In some embodiments, n is 0. In some embodiments, n is 1.

In some embodiments, the pharmaceutically acceptable salt of a compound as described herein is the hydrochloride salt.

Definitions

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A wavy line drawn through a line in a structure indicates a point of attachment of a group, e.g.:

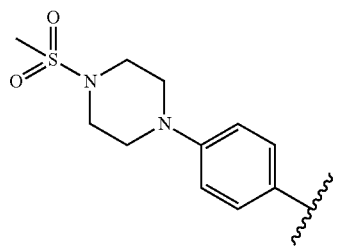 [SMILES: *c1ccc(N2CCN(S(C)(=O)=O)CC2)cc1]

A dashed line indicates an optional bond. A dash at the front or end of a chemical group is a matter of convenience; chemical groups may be depicted with or without one or more dashes without losing their ordinary meaning. When used, a dash indicates the point of attachment, e.g. —S(O)(R$^c$)=NR$^b$ indicates the following structure with point of attachment at the S:

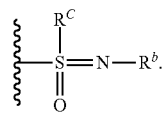

Whenever the graphical representation of a group terminates in a singly bonded oxygen atom, that group represents an —OH group unless otherwise indicated. Similarly, unless otherwise expressed, hydrogen atom(s) are implied and deemed present where necessary in view of the knowledge of one of skill in the art to complete valency or provide stability.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

For example, (S)—N-(4-(3-cyano-4-((3,3-difluoro-1-(2-hydroxyacetyl)piperidin-4-yl)oxy)phenyl)pyridin-2-yl)cyclopropanecarboxamide can be represented by either Formula (i) or Formula (ii), which are shown below.

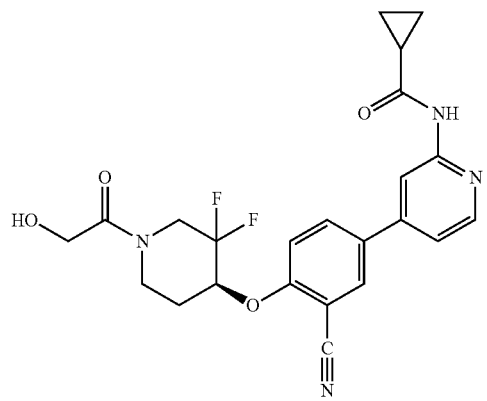

Formula (i)

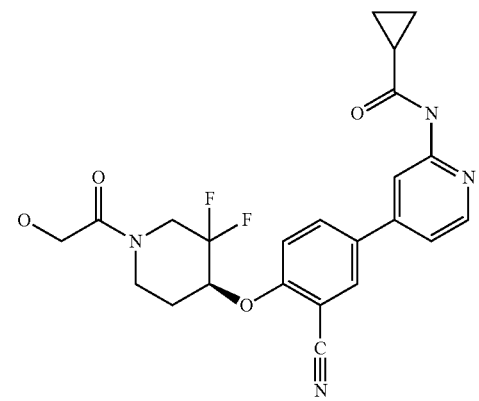

Formula (ii)

Where multiple substituent groups are identified the point of attachment is at the terminal substituent (e.g., for "alkylaminocarbonyl" the point of attachment is at the carbonyl substituent).

The prefix "$C_{x-y}$" indicates that the following group has from x (e.g., 1) to y (e.g., 6) carbon atoms, one or more of which, in certain groups (e.g., heteroalkyl, heteroaryl, heteroarylalkyl, etc.), may be replaced with one or more heteroatoms or heteroatomic groups. For example, "$C_{1-6}$ alkyl" indicates that the alkyl group has from 1 to 6 carbon atoms. Likewise, the term "x-y membered" rings, wherein x and y are numerical ranges, such as "3-12 membered heterocyclyl," refers to a ring containing x-y atoms (e.g., 3-12), of which up to half may be heteroatoms, such as N, O, S, P, and the remaining atoms are carbon.

The prefix $R_x$ or $R_y$, e.g. $R^2$ or $R^3$ are used only to identify and/or distinguish differently positioned or populated groups.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"Alkyl" refers to any group derived from a linear or branched saturated hydrocarbon. Alkyl groups include, but are not limited to, methyl, ethyl, propyl such as propan-1-yl, propan-2-yl (iso-propyl), butyls such as butan-1-yl, butan-2-yl (sec-butyl), 2-methyl-propan-1-yl (iso-butyl), 2-methyl-propan-2-yl (t-butyl), pentyls, hexyls, octyls, dectyls, and the like. Unless otherwise specified, an alkyl group has from 1 to 10 carbon atoms, for example from 1 to 6 carbon atoms, for example from 1 to 4 carbon atoms.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—CH$_2$C≡CH), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 carbon atoms.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

"Cycloalkyl" refers to a cyclic alkyl and alkenyl groups. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like. Another example includes $C_{5-7}$ cycloakenyl.

"Halo" and "halogen" refer to fluoro, chloro, bromo and iodo.

"Haloalkyl" refers to an alkyl wherein one or more hydrogen atoms are each replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Hydroxyalkyl" or "alkyl-OH" refers to an alkyl wherein one or more hydrogen atoms are each replaced by a hydroxyl group. Examples include, but are not limited to, —CH$_2$OH, —CH$_2$CH$_2$OH, —C(CH$_3$)$_2$OH, and the like.

"Halo 3-6 membered heterocyclyl" refers to a heterocyclyl group substituted at a carbon atom with at least one halogen atom, and may include multiple halogen atoms, such as 3,3-difluoroazetidinyl.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl, each of which may be optionally substituted. A heteroalkyl group comprises from 1 to 10 carbon and up to three hetero atoms, e.g., from 1 to 6 carbon and from 1 to 2 hetero atoms.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, thiomorpholine, tetrahydro-2H-thiopyran, 1-iminotetrahydro-2H-thiopyran 1-oxide, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members.

"Hydroxyl" and "hydroxy" are used interchangeably and refer to —OH. "Oxo" refers to =O, or oxide where N-oxide or S-oxide exist. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl"

would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)$—) $C_{1-6}$ alkoxycarbonyl (e.g. $CH_3O$—C(O)—), 5-7 membered heterocyclyl-$C_{1-6}$ alkyl (e.g. piperazinyl-$CH_2$—), $C_{1-6}$ alkylsulfonyl-5-7 membered heterocyclyl (e.g. $CH_3S(O)_2$-morpholinyl-), 5-7 membered heterocyclyl $C_{1-6}$ alkoxy (e.g. pyrrolidinyl-O—), 5-7 membered heterocyclyloxy, (4-7 membered heterocyclyl)-4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_2$ alkynyl (e.g. N-piperazinyl-$CH_2C\equiv CCH_2$-), and $C_{6-10}$ arylaminocarbonyl (e.g. phenyl-NH—C(O)—).

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

The term "pharmaceutically acceptable" with respect to a substance refers to that substance which is generally regarded as safe and suitable for use without undue toxicity, irritation, allergic response, and the like, commensurate with a reasonable benefit/risk ratio.

The compounds described herein include isomers, stereoisomers and the like. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present disclosure and includes geometric isomers. It is understood that a substituent may be attached at a chiral center of a carbon atom. Therefore, the disclosure includes enantiomers, diastereomers, scalemic mixtures, or racemates of the compound. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s).

The term "fused" refers to a ring which is bound to an adjacent ring.

The phrase ortho refers to the position on the ring where the substituent is adjoined with respect to the point of attachment of the ring, and is shown below with an arrow, wherein z represents a carbon atom or nitrogen:

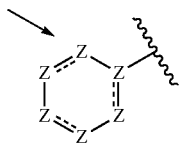

Similarly, "para" refers to attachment of a substituent at the 4-position with respect to the point of attachment of the ring and "meta" refers to attachment of a substituent at the 3-position with respect to the point of attachment of the ring.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, scalemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

"Subject" and "subjects" refers to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like.

"Treating" and "treatment" of a disease include the following:
(1) preventing or reducing the risk of developing the disease, i.e., causing the clinical symptoms of the disease not to develop or reducing the risk thereof in a subject that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"Effective amount" refers to an amount that may be effective to elicit the desired biological, clinical, or medical response, including the amount of a compound that, when administered to a subject for treating a disease, is sufficient to effect such treatment. The effective amount will vary depending on the compound, the disease and its severity and the age, weight, etc., of the subject to be treated. The effective amount can include a range of amounts.

Reference to a compound that is "selective" against an enzyme, such as JAK2, indicates relative activity versus a target enzyme, such as TBK1 or IKKε. For example a compound that has 2-10 fold greater inhibitory activity—as measured by $IC_{50}$ values—for a desired enzyme(s), such as TBK1 and/or IKKε, as compared to the enzyme for which the compound is selective against, such as JAK2, is selective against the referenced enzyme.

The compounds of the present disclosure include solvates, hydrates, tautomers, stereoisomers and salt forms thereof.

Provided are also compounds in which from 1 to n hydrogen atoms attached to a carbon atom may be replaced by a deuterium atom, or tritiated with a tritium atom, in which n is the number of hydrogen atoms in the molecule. As known in the art, the deuterium atom is a non-radioactive isotope of the hydrogen atom and tritium is a radioactive isotope. Such compounds, particularly deuterated compounds, may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

The term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer.

DETAILED DESCRIPTION $R^5$ is selected from the group consisting of H, hydroxyl, $C_{1-6}$ alkyl, $-NR^aR^b$, halogen, $-C(O)R^a$, $-C(O)OR^a$, $-C(O)NR^aR^b$, $-OC(O)NR^aR^b$, $-NR^aC(O)R^b$, $-NR^aC(O)OR^b$, $-S(O)_{0-2}R^c$, $-S(O)_2NR^aR^b$, $-NR^aS(O)_2R^b$, $C_{6-10}$ aryl, $C_{3-10}$ cycloalkyl, 5-10 membered heteroaryl, 3-12 membered heterocyclyl and $-O-R^6$, wherein each $C_{1-6}$ alkyl, $C_{6-10}$ aryl, $C_{3-10}$ cycloalkyl, 5-10 membered heteroaryl and 3-12 membered heterocyclyl is optionally substituted with from one to five $R^7$ groups; provided that when $X^1$ is $CR^1$, $R^5$ is not H, hydroxyl, $C_{1-6}$ alkyl, halogen, or $C_{3-10}$ cycloalkyl.

In some embodiments, $R^5$ is selected from the group consisting of H, hydroxyl, $C_{1-6}$ alkyl, $-NR^aR^b$, halogen, $-C(O)R^a$, $-C(O)NR^aR^b$, 3-12 membered heterocyclyl, and $-O-R^6$, wherein each $C_{1-6}$ alkyl and 3-12 membered heterocyclyl is optionally substituted with from one to five $R^7$ groups; provided that when $X^1$ is $CR^1$, $R^5$ is not H, hydroxyl, $C_{1-6}$ alkyl, halogen, or $C_{3-10}$ cycloalkyl.

In one embodiment, $R^5$ is $-NR^aR^b$. In another embodiment, $R^a$ and $R^b$ of $-NR^aR^b$ of $R^5$ join together with the atoms to which they are attached form a 3-12 membered heterocyclyl which is optionally substituted with one to three groups selected from halo, hydroxyl, oxo, $C_{1-6}$ alkyl, $C_{1-6}$ alkoxy, $C_{1-6}$ haloalkyl, $C_{1-6}$ haloalkoxy, CN, amino, and $C_{1-6}$ alkylamino.

In some embodiments, $R^5$ is $-O-R^6$, wherein $R^6$ is selected from the group consisting of unsubstituted or substituted tetrahydropyranyl, tetrahydrofuranyl, pyrrolidinyl, oxetanylmethyl, 1-(oxetan-3-yl)pyrrolidinyl, oxo-propanyl-nitrile-pyrrolinyl and piperidinyl. In another embodiment, $R^6$ is unsubstituted or substituted tetrahydropyranyl. In another embodiment, $R^6$ is unsubstituted or substituted piperidinyl.

In another embodiment, $R^5$ is N-pyrrolidinyloxy or N-piperidinyloxy substituted with $C_{1-6}$ alkoxycarbonyl, hydroxyl $C_{1-6}$ alkylcarbonyl, hydroxyl 3-6 membered heterocyclyl, halo 3-6 membered heterocyclyl, $C_{1-6}$ alkoxycarbonyl, cyano $C_{1-6}$ alkylcarbonyl or $C_{3-6}$ cycloalkyl-$C_{1-6}$ alkoxy.

In another embodiment, $R^6$ is substituted with one to three $R^7$ groups selected from halogen, $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)(R^a)=NR^b$, $-S(O)_2NR^aR^b$, $-NR^aS(O)_2R^b$, $-N_3$, $-CN$, or $-NO_2$; or two $R^7$ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $S(O)(R^a)=NR^b$, $-NR^aS(O)_2R^b$, $-N_3$, $-CN$, or $-NO_2$.

In some embodiments, $R^5$ is $-O-R^6$, wherein $R^6$ is selected from the group consisting of unsubstituted or substituted tetrahydropyranyl, tetrahydrofuranyl, pyrrolidinyl, oxetanylmethyl, 1-(oxetan-3-yl)pyrrolidinyl, oxo-propanyl-nitrile-pyrrolinyl and piperidinyl. In another embodiment, $R^6$ is unsubstituted tetrahydropyranyl. In another embodiment, $R^6$ is $R^6$ is substituted piperidinyl.

In another embodiment, $R^5$ is N-pyrrolidinyloxy or N-piperidinyloxy substituted with halogen, $C_{1-6}$ alkoxycarbonyl, hydroxyl $C_{1-6}$ alkylcarbonyl, hydroxyl 3-6 membered heterocyclyl, halo 3-6 membered heterocyclyl, $C_{1-6}$ alkoxycarbonyl, cyano $C_{1-6}$ alkylcarbonyl or $C_{3-6}$ cycloalkyl-$C_{1-6}$ alkoxy.

In another embodiment, $R^6$ is substituted with one to three $R^7$ groups selected from halogen, $C_{1-6}$ alkyl, $C_{1-6}$ heteroalkyl, 3-12 membered heterocyclyl, 5-10 membered heteroaryl, halogen, oxo, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$; wherein each $C_{1-6}$ alkyl, $C_{1-6}$ heteroalkyl, 3-12 membered heterocyclyl, and 5-10 membered heteroaryl is optionally substituted with from one to five groups independently selected from the group consisting of halogen, $C_{1-6}$ alkyl, $C_{1-6}$ heteroalkyl, $C_{1-6}$ haloalkyl, oxo, imino, $-OR^a$, $-C(O)R^a$, $-C(O)OR^a$, $-C(O)NR^aR^b$, $-OC(O)NR^aR^b$, $-NR^aR^b$, $-NR^aC(O)R^b$, $-NR^aC(O)OR^b$, $-S(O)_{0-2}R^a$, $-S(O)_2NR^aR^b$, $S(O)(R^a)=NR^b$, $-NR^aS(O)_2R^b$, $-N_3$, $-CN$, or $-NO_2$.

In another embodiment, $R^5$ is —O—$R^6$. In another embodiment, $R^6$ is selected from the group consisting of tetrahydropyranyl, tetrahydrofuranyl, pyrrolidinyl, oxetanylmethyl, 1-(oxetan-3-yl)pyrrolidinyl, oxo-propanylnitrile-pyrrolinyl and piperidinyl. In another embodiment, $R^6$ is unsubstituted tetrahydropyranyl. In another embodiment, $R^5$ is N-pyrrolidinyloxy or N-piperidinyloxy substituted with $C_{1-6}$ alkoxycarbonyl, hydroxyl $C_{1-6}$ alkylcarbonyl, hydroxyl 3-6 membered heterocyclyl, halo 3-6 membered heterocyclyl, $C_{1-6}$ alkoxycarbonyl, cyano $C_{1-6}$ alkylcarbonyl or $C_{3-6}$ cycloalkyl-$C_{1-6}$ alkoxy. In another embodiment, $R^6$ is substituted with one $R^7$ group selected from $C_{1-6}$ alkoxycarbonyl, hydroxyl $C_{1-6}$ alkylcarbonyl, $C_{1-6}$ alkoxycarbonyl, cyano $C_{1-6}$ alkylcarbonyl or $C_{3-6}$ cycloalkyl-$C_{1-6}$ alkoxy.

In another embodiment, the $R^6$ group is substituted with one or two fluoro groups. More particularly, in one embodiment, the fluoro groups are substituted at the ortho position with respect to the point of attachment of the $R^6$ group.

In another embodiment, the $R^6$ group is substituted with two fluoro groups. More particularly, in one embodiment, the fluoro groups are substituted at the ortho position with respect to the point of attachment of the $R^6$ group. In some embodiments, the $R^6$ group is substituted with two fluoro groups at the ortho position with respect to the point of attachment of the $R^6$ group and a —C(O)$C_{1-6}$ alkyl group substituted with one to three hydroxyl groups.

In another embodiment, $R^6$ is selected from the group consisting of:

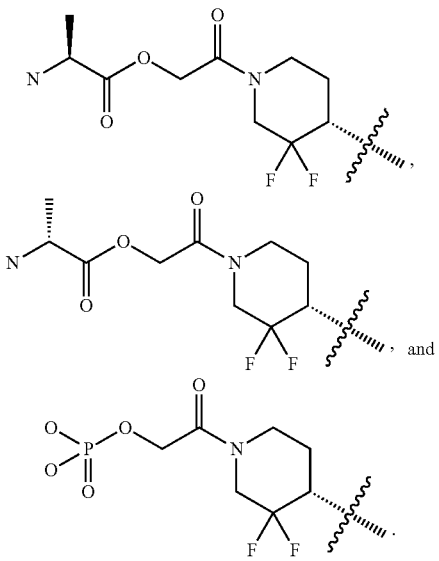

In another embodiment, $R^5$ is:

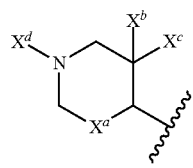

$X^a$ is a bond or C($R^x$)($R^y$), wherein $R^x$ and $R^y$ are independently selected from the group consisting of H, halo or methyl;

$X^b$ and $X^c$ are independently selected from the group consisting of H, halo or methyl;

$X^d$ is selected from the group consisting of H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)$C_{1-6}$ alkyl, each of which is optionally substituted with from one to five groups selected from $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH$_2$, —C(O)NH($C_{1-6}$ alkyl), —C(O)N($C_{1-6}$ alkyl)$_2$, —COOH, —C(O)$C_{1-6}$ alkyl, —C(O)O$C_{1-6}$ alkyl, or halogen.

In another embodiment, $X^d$ is —C(O)$C_{1-6}$ alkyl substituted with hydroxyl. In another embodiment, $X^a$ is CH$_2$. In another embodiment, $X^b$ is fluoro. In another embodiment, $X^c$ is fluoro.

In another embodiment, $R^5$ is:

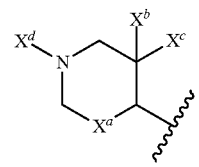

$X^a$ is a bond or C($R^x$)($R^y$), wherein $R^x$ and $R^y$ are independently selected from the group consisting of H, halo or methyl;

$X^b$ and $X^c$ are independently selected from the group consisting of H, halo or methyl;

$X^d$ is selected from the group consisting of H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, each of which is optionally substituted with from one to five groups selected from $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH$_2$, —C(O)NH($C_{1-6}$ alkyl), —C(O)N($C_{1-6}$ alkyl)$_2$, —COOH, —C(O)$C_{1-6}$ alkyl, —C(O)O$C_{1-6}$ alkyl, or halogen.

In another embodiment, $X^d$ is $C_{1-6}$ alkyl substituted with hydroxyl. In another embodiment, $X^a$ is CH$_2$. In another embodiment, $X^b$ is fluoro. In another embodiment, $X^c$ is H.

In another embodiment, $R^5$ is:

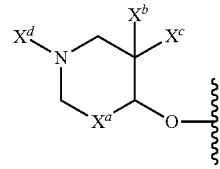

$X^a$ is a bond or C($R^x$)($R^y$), wherein $R^x$ and $R^y$ are independently selected from the group consisting of H, halo or methyl;

$X^b$ and $X^c$ are independently selected from the group consisting of H, halo or methyl;

$X^d$ is selected from the group consisting of H; or $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)C$_{1-6}$ alkyl, each of which is optionally substituted with from one to five groups selected from C$_{1-6}$ alkyl, C$_{3-10}$ cycloalkyl, C$_{1-6}$ heteroalkyl, 3-12 membered heterocyclyl, C$_6$-C$_{10}$ aryl, 5-10 membered heteroaryl, hydroxyl, C$_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, or halogen.

In another embodiment, X$^d$ is —C(O)C$_{1-6}$ alkyl substituted with hydroxyl. In another embodiment, X$^a$ is CH$_2$. In another embodiment, X$^b$ is fluoro. In another embodiment, X$^c$ is fluoro.

In another embodiment, R$^5$ is:

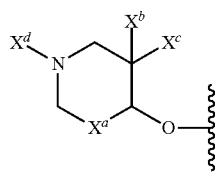

X$^a$ is a bond or C(R$^x$)(R$^y$), wherein R$^x$ and R$^y$ are independently selected from the group consisting of H, halo or methyl;

X$^b$ and X$^c$ are independently selected from the group consisting of H, halo or methyl;

X$^d$ is selected from the group consisting of H; or C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, each of which is optionally substituted with from one to five groups selected from C$_{1-6}$ alkyl, C$_{3-10}$ cycloalkyl, C$_{1-6}$ heteroalkyl, 3-12 membered heterocyclyl, C$_6$-C$_{10}$ aryl, 5-10 membered heteroaryl, hydroxyl, C$_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, or halogen.

In some embodiments, n=0 such that R is nonexistent. In some embodiments, each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_1$-C$_6$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ alkoxyhaloalkyl, C$_3$-C$_8$ cycloalkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;

each R$^a$ and each R$^b$ are independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$, —C(O)N(OC$_{1-6}$ alkyl) (C$_{1-6}$ alkyl), or absent, each of which is optionally substituted with from one to three groups independently selected from C$_{1-6}$ alkyl, C$_{2-6}$ alkenyl, halogen, oxo, CN, OH, OC$_1$—C$_3$ alkyl, —NH$_2$, —OC(O)CH(Me)NH$_2$, —OP(O)(OH)$_2$; or R$^a$ and R$^b$ together with the atoms to which they are attached form a 3-12 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$.

In some embodiments, each R is independently each R is independently halogen, —OR$^a$, —C(O)R$^a$, —C(O)OR$^a$, —C(O)NR$^a$R$^b$, —NR$^a$R$^b$, —NR$^a$C(O)R$^b$—CN, —NO$_2$, C$_{1-6}$ alkyl, C$_1$-C$_6$ haloalkyl, C$_{1-6}$ alkyl-OH, C$_{3-10}$ cycloalkyl, heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclic is optionally substituted with from one to five groups independently selected from halogen, C$_{1-6}$ alkyl, C$_{1-6}$ alkoxyhaloalkyl, C$_3$-C$_8$ cycloalkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, S(O)(R$^a$)=NR$^b$, —N$_3$, —CN, and —NO$_2$;

each R$^a$ and each R$^b$ are independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$, —C(O)N(OC$_{1-6}$ alkyl) (C$_{1-6}$ alkyl), or absent, each of which is optionally substituted with from one to three groups independently selected from C$_{1-6}$ alkyl, C$_{2-6}$ alkenyl, halogen, oxo, CN, OH, OC$_1$—C$_3$ alkyl, —NH$_2$, —OC(O)CH(Me)NH$_2$, —OP(O)(OH)$_2$; or R$^a$ and R$^b$ together with the atoms to which they are attached form a 3-12 membered heterocyclyl optionally substituted with one to three groups independently selected from C$_{1-6}$ alkyl, C$_{1-6}$ alkyl-OH, C$_{2-6}$ alkenyl, CN, OH, OC$_1$—C$_3$ alkyl, and NH$_2$.

In yet another embodiment, the group R is halo, —CN, C$_1$-C$_3$ alkyl, C$_1$-C$_3$ alkyl halide, C$_1$-C$_3$ alkyl-OH, —C(O)H, —C(O)—NH$_2$, —COOH, —C(O)OC$_1$-C$_3$alkyl, —C(O)NHC$_1$-C$_3$alkyl, CH$_2$N(CH$_3$)$_2$, —C(O)-azetidinyl-OH, phenyl, or 5-6 membered heterocyclic optionally substituted with C$_1$-C$_3$ alkyl, NH$_2$, or OH.

In some embodiments, n=0 such that R is nonexistent. In various embodiments, the Ring A-(R)$_n$ group in the compounds of Formula (I)-(If)

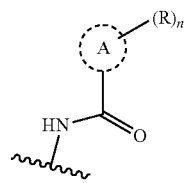

is selected from the group consisting of:

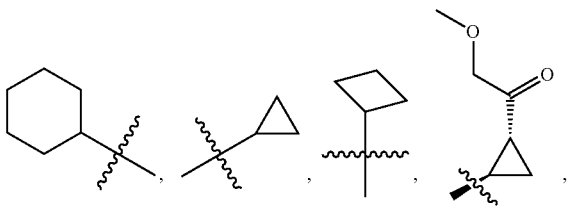

29
-continued
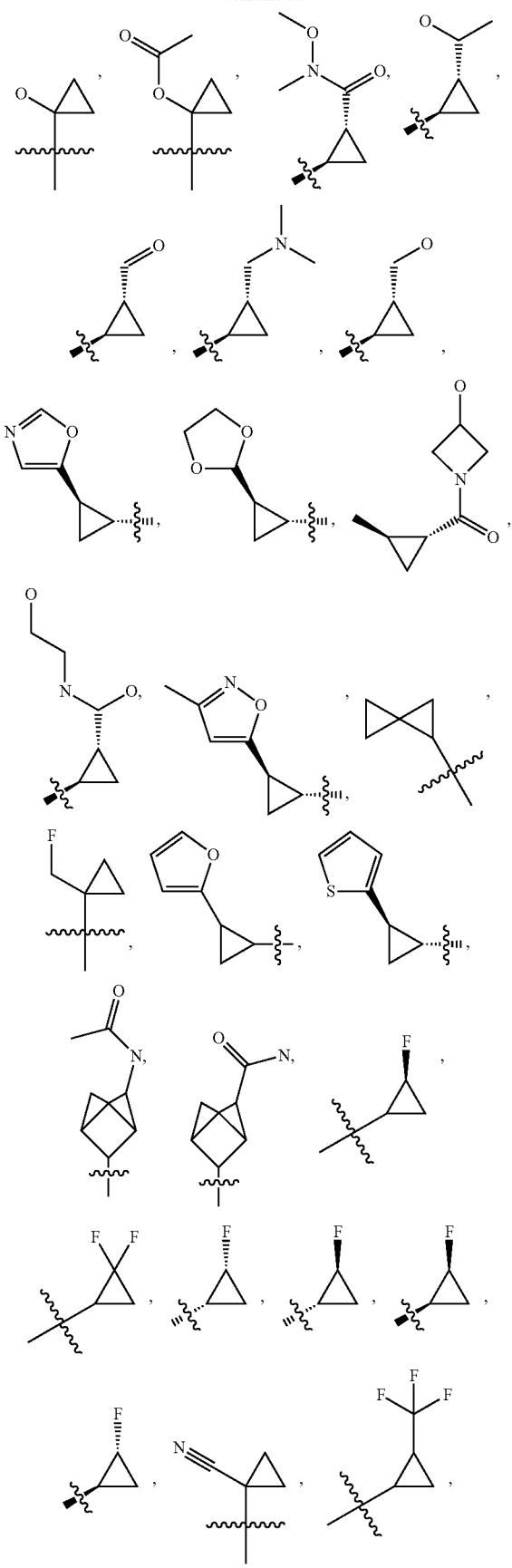
30
-continued
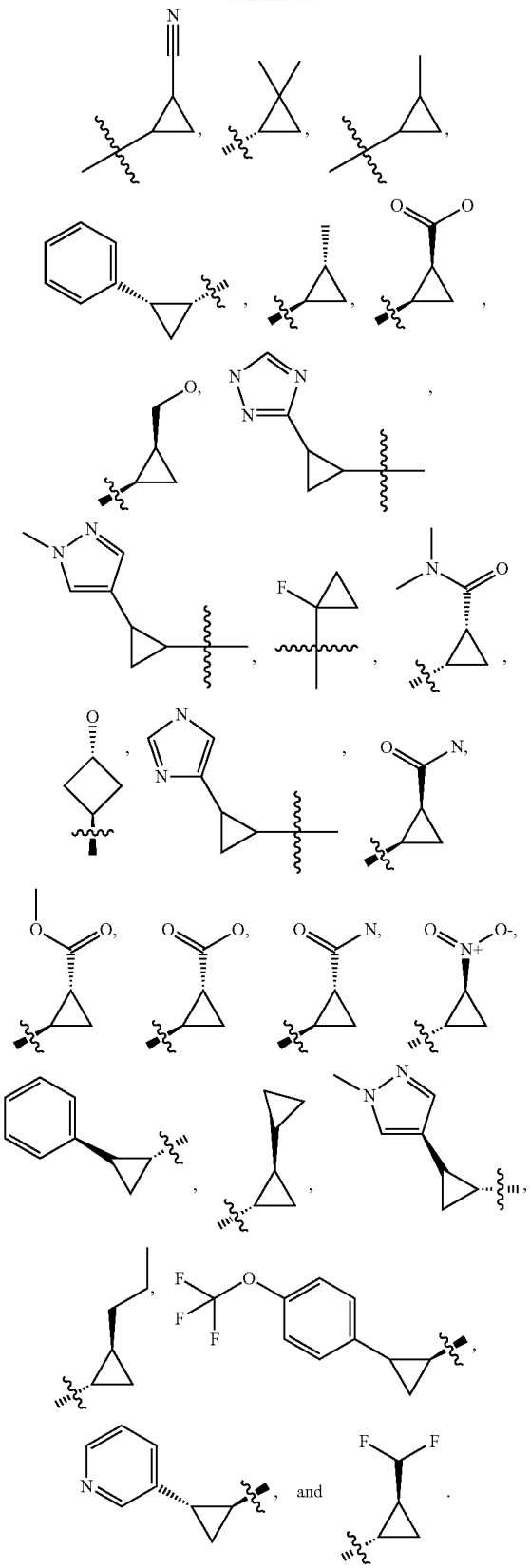
In some embodiments, the Ring A-(R)$_n$ group in the compounds of Formula (I)-(Ii)

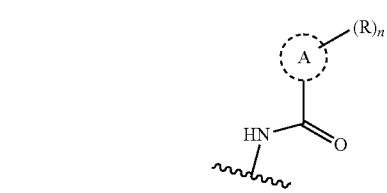
is selected from the group consisting of:
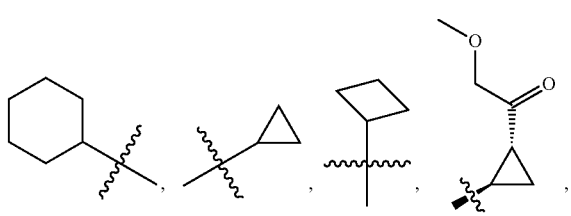
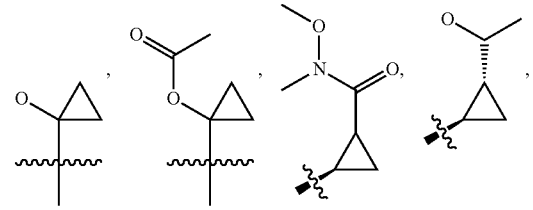
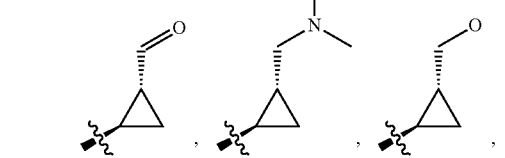
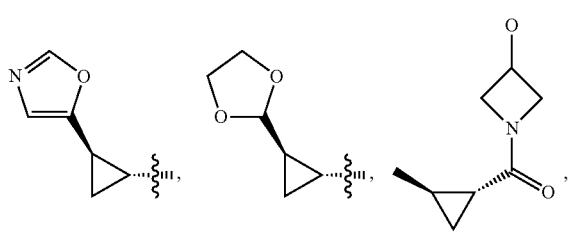
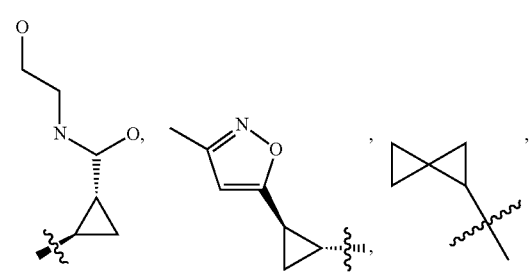
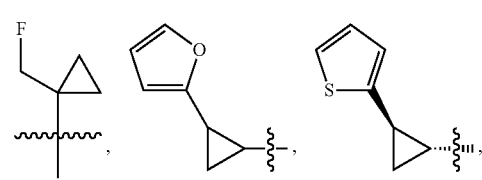
-continued
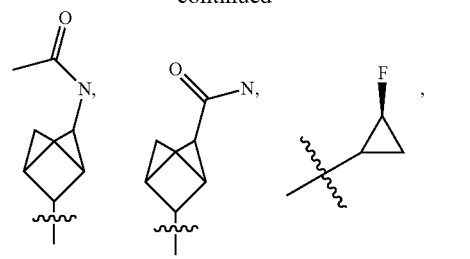
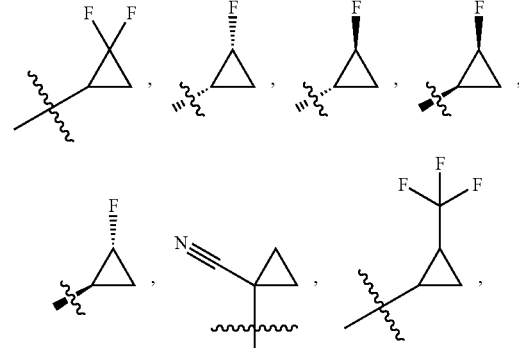
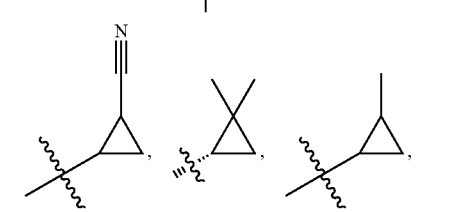
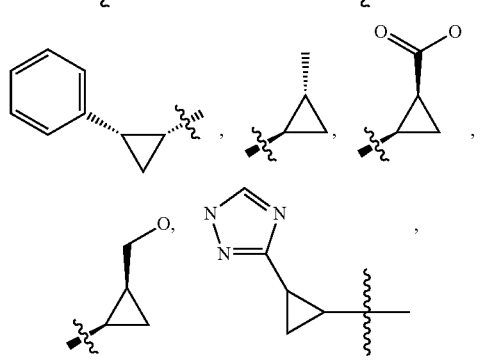
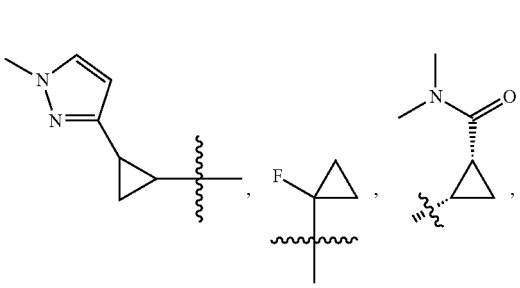
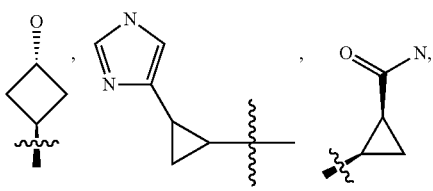

-continued
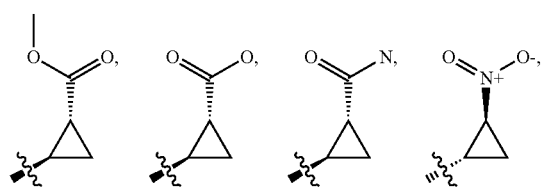
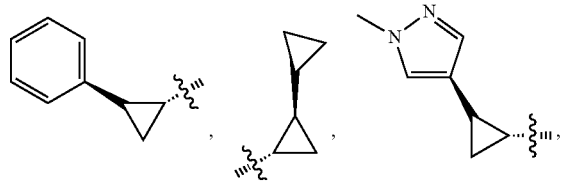
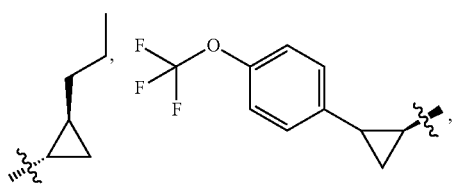
In another embodiment, the Ring A-(R)$_n$ group in the compounds of Formula (I)-(Ii)
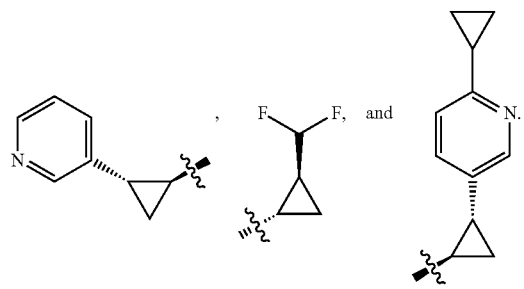
In another embodiment, R$^5$ is selected from the group consisting of:
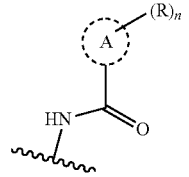, 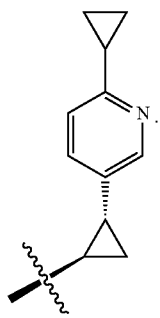,
-continued
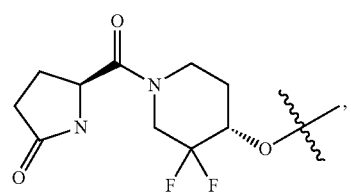
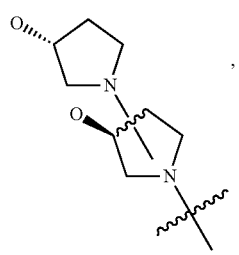
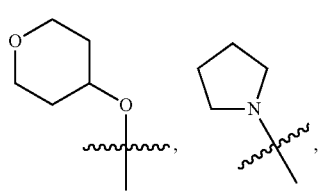
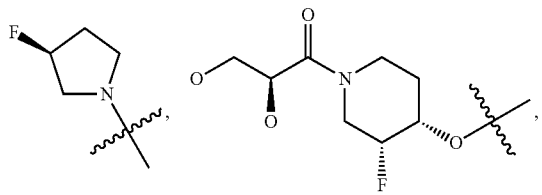

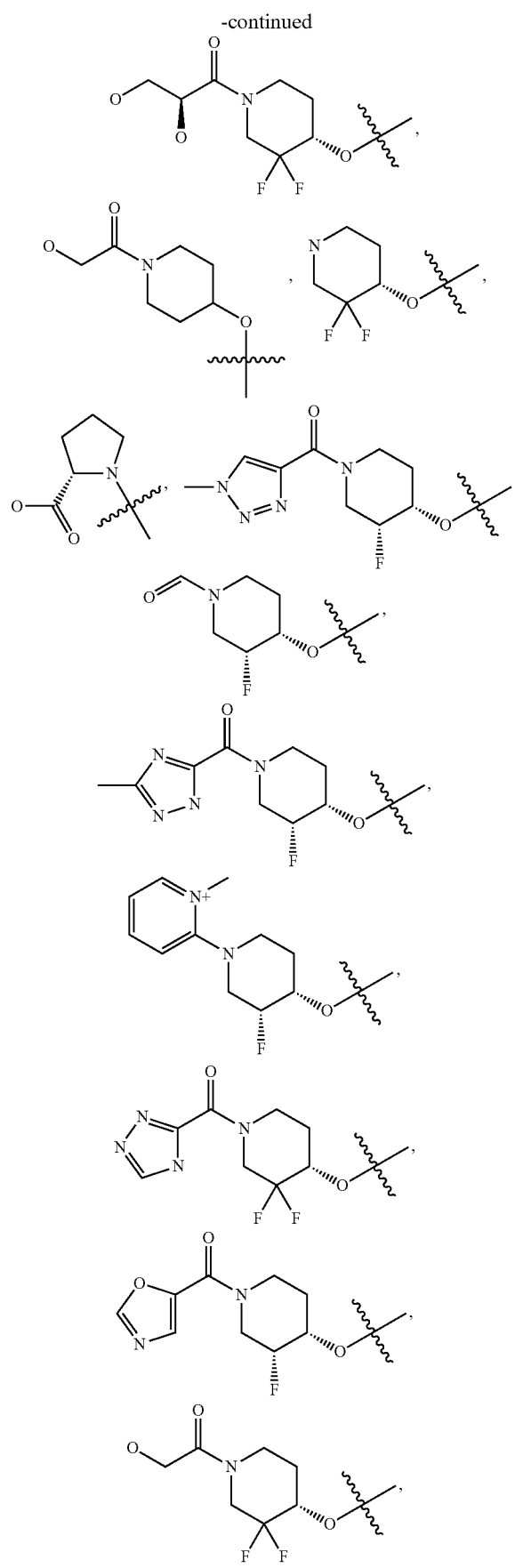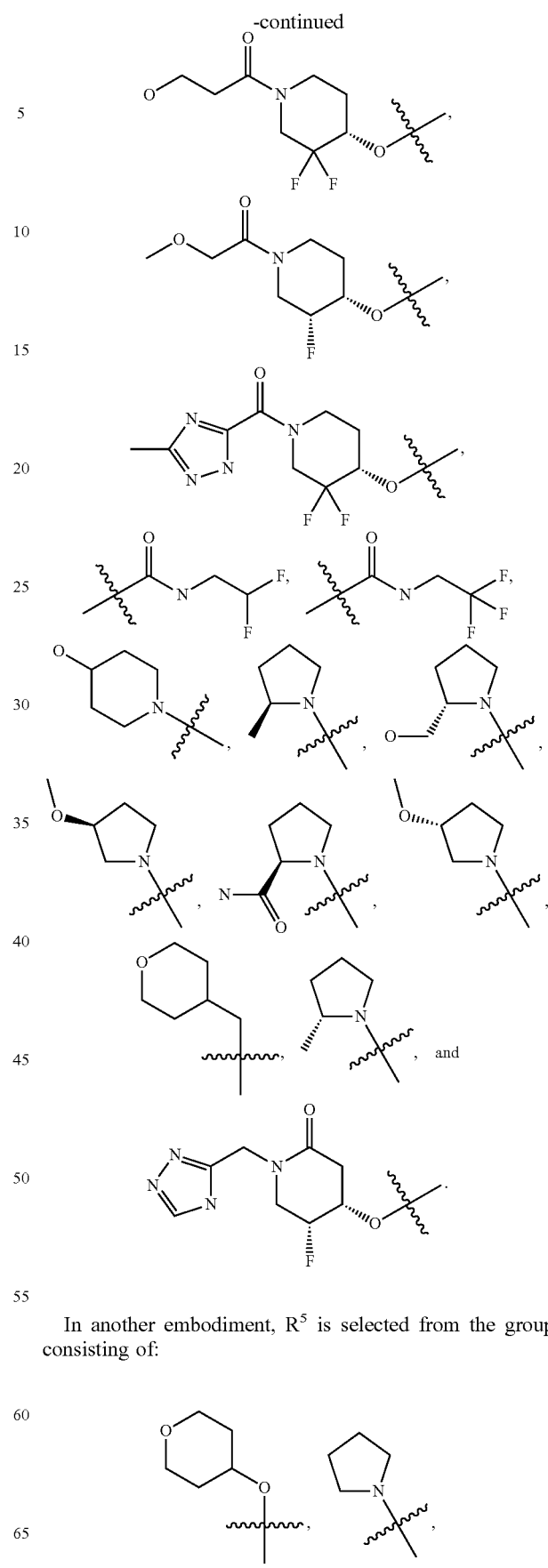
In another embodiment, $R^5$ is selected from the group consisting of:
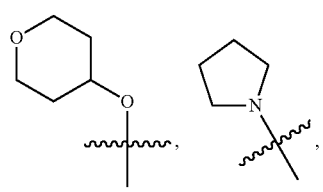

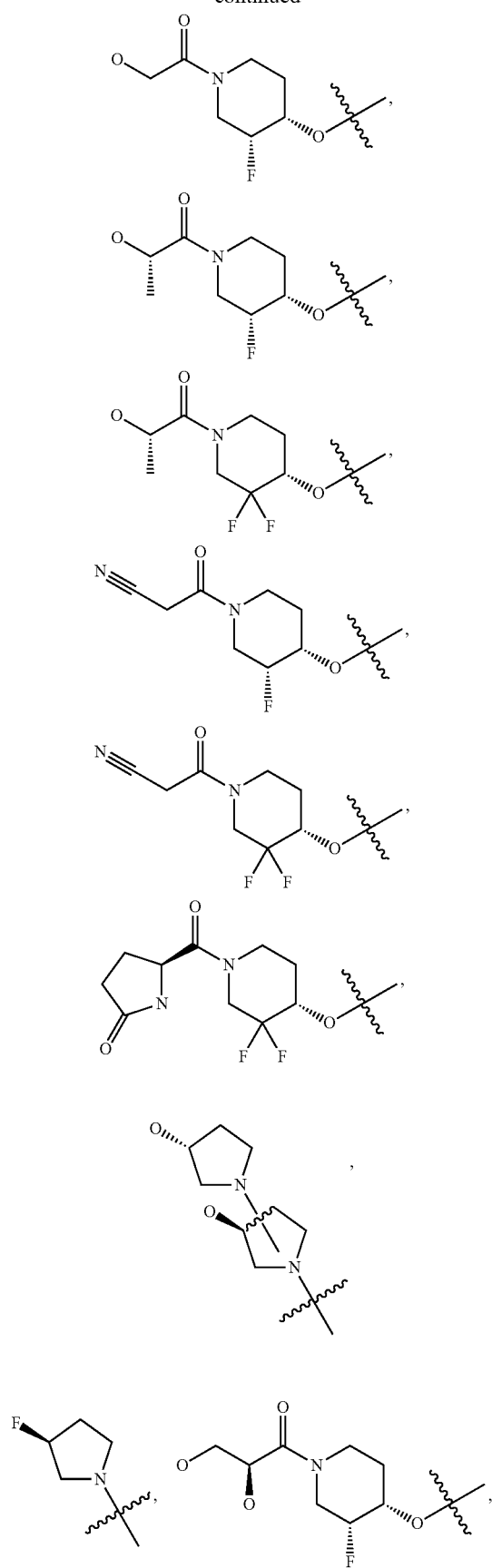
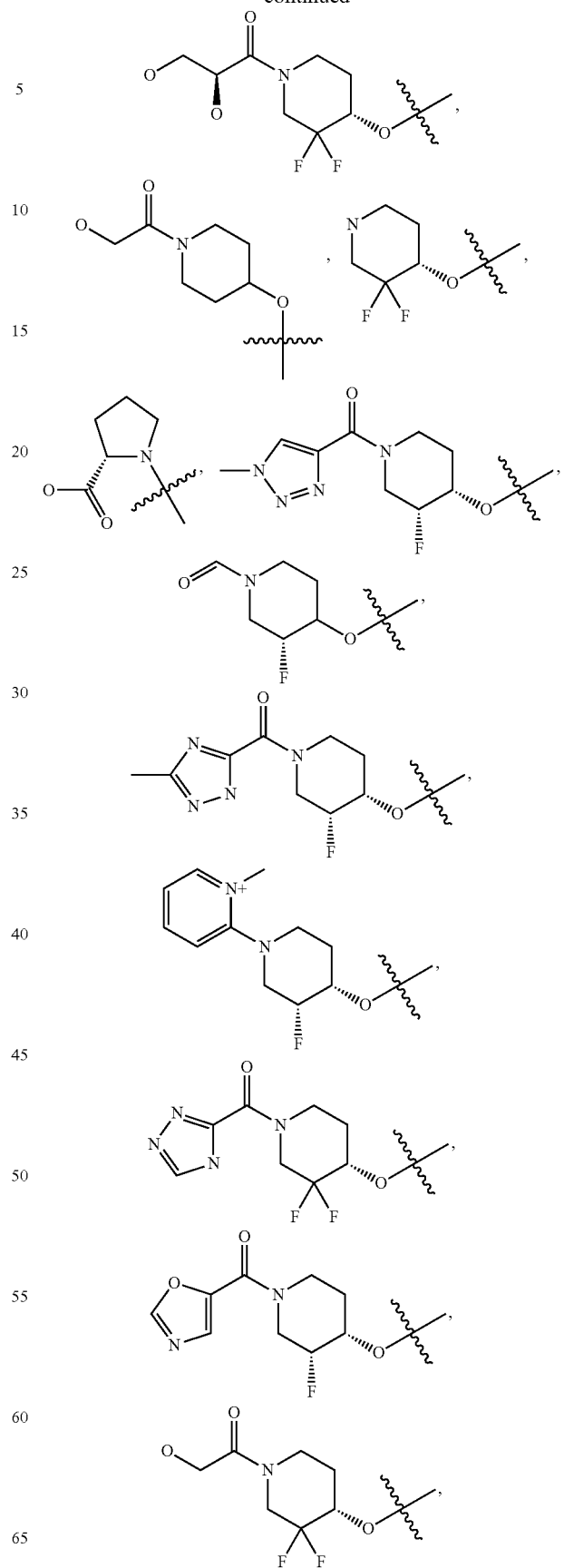

-continued
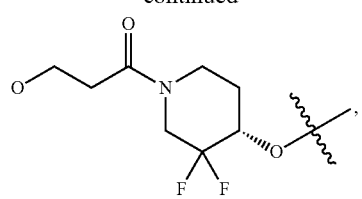
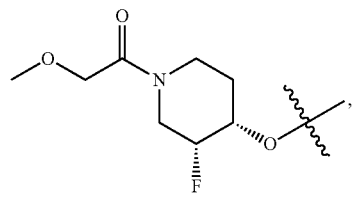
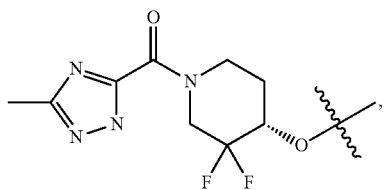
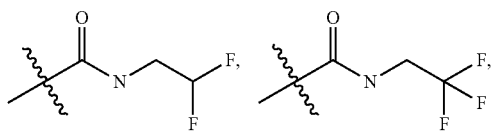
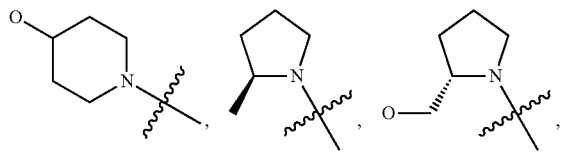
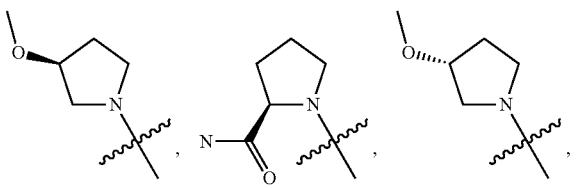
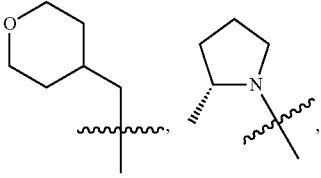
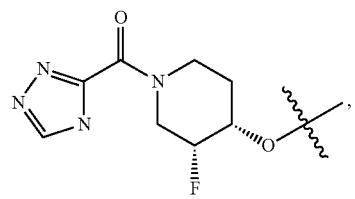
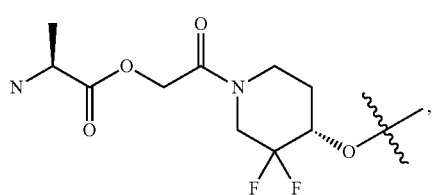
-continued
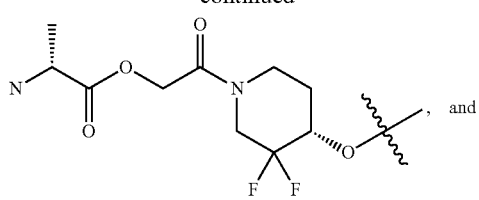, and
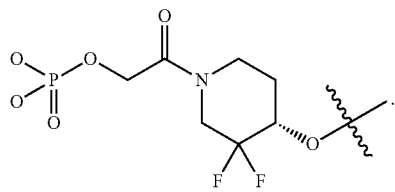.
In another embodiment, $R^5$ is selected from the group consisting of:
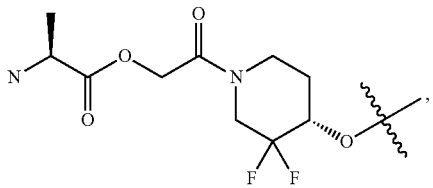,
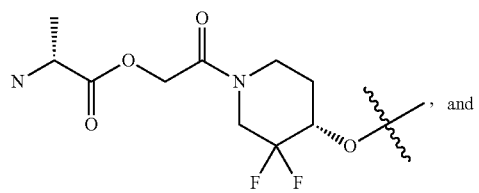, and
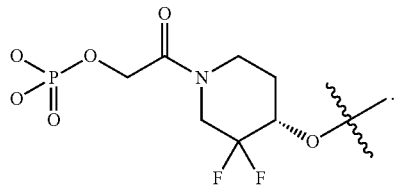.
In one embodiment, the compound of the present disclosure is selected from the group consisting of:
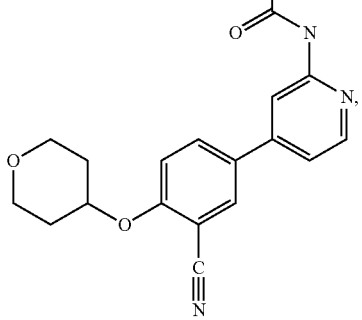

-continued
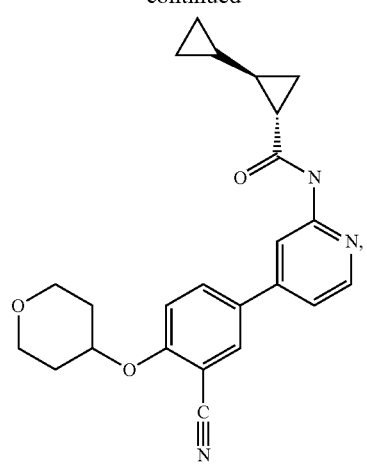
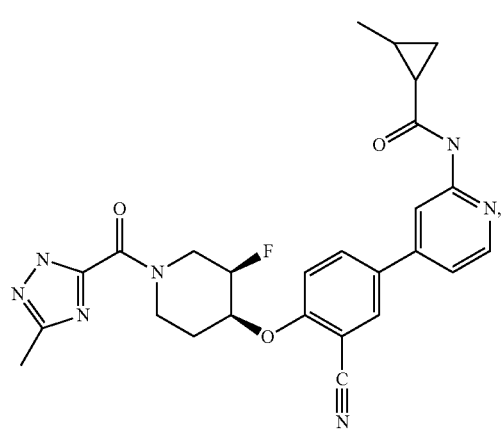
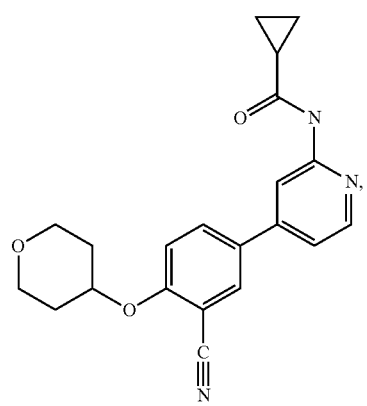
-continued
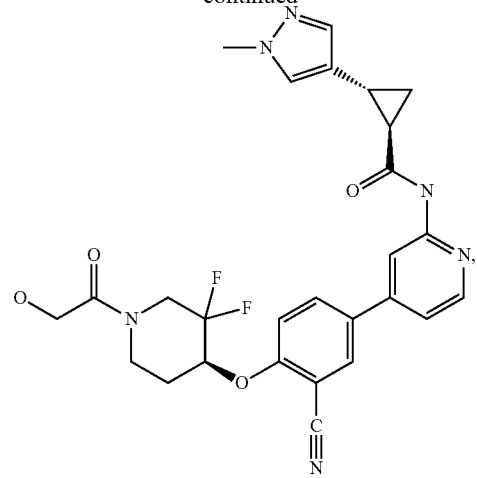
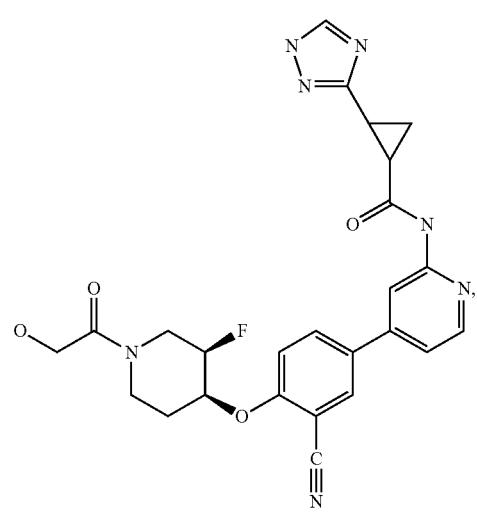
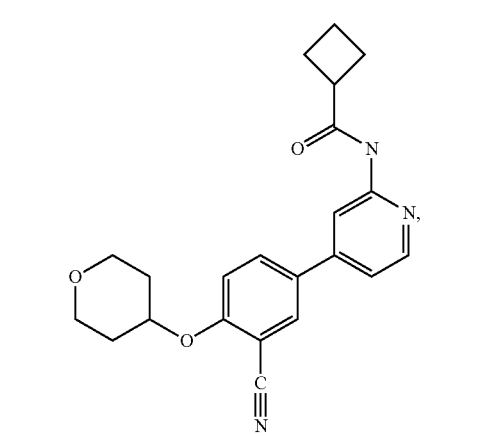

43
-continued
44
-continued
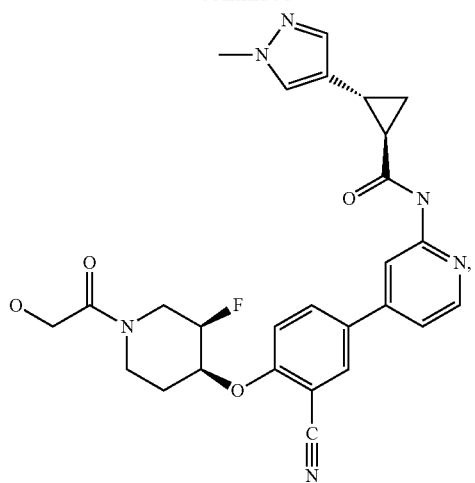
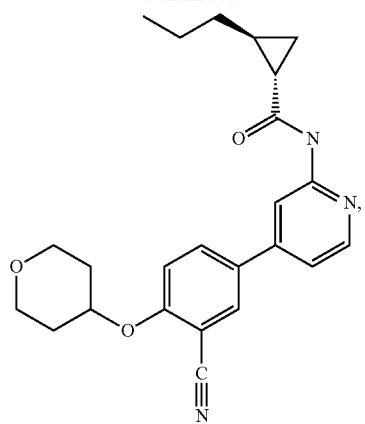
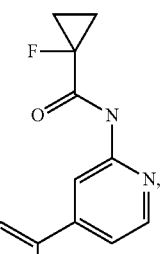
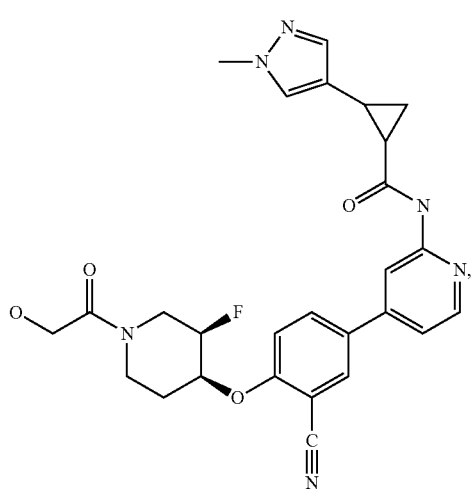
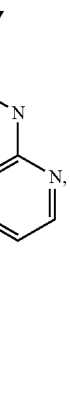
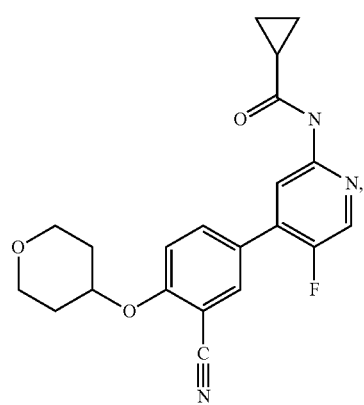
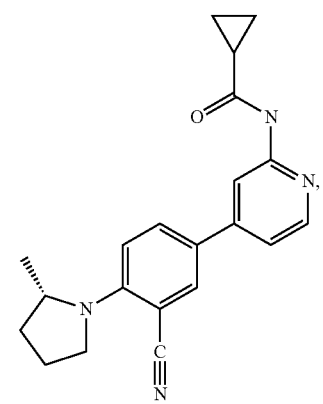

-continued
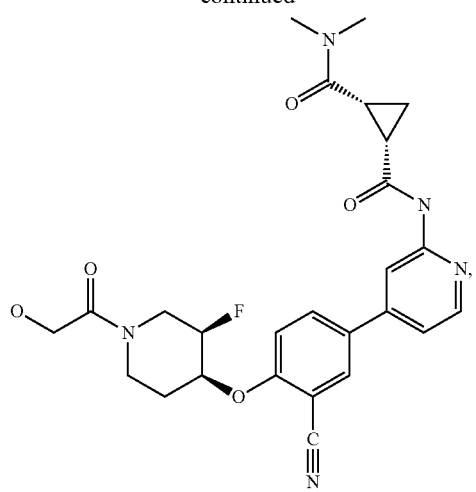
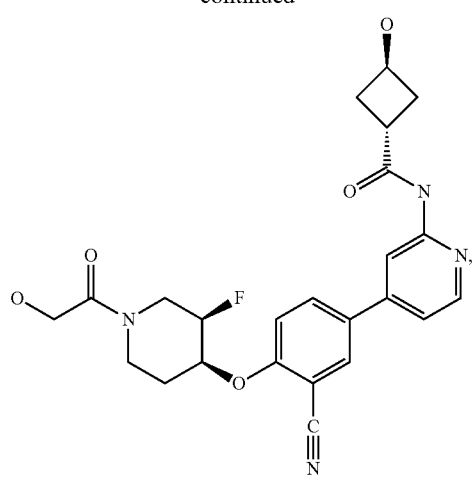
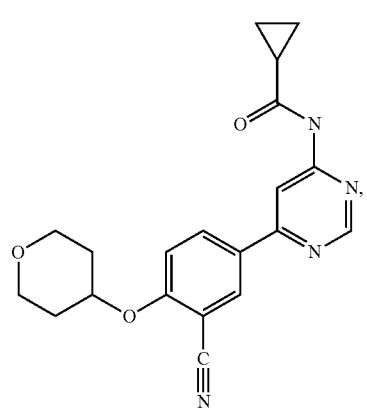
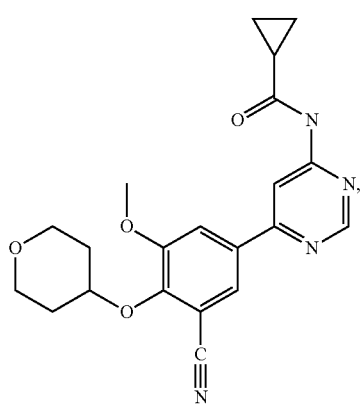
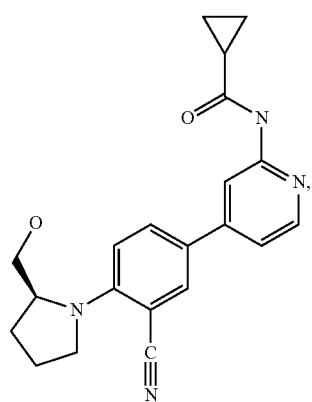
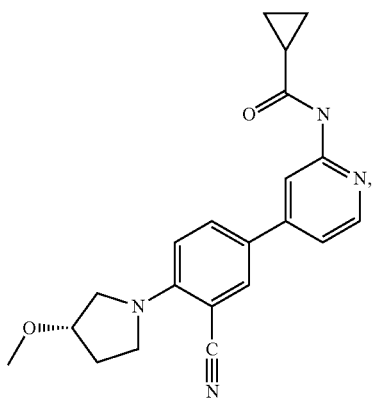

47
-continued
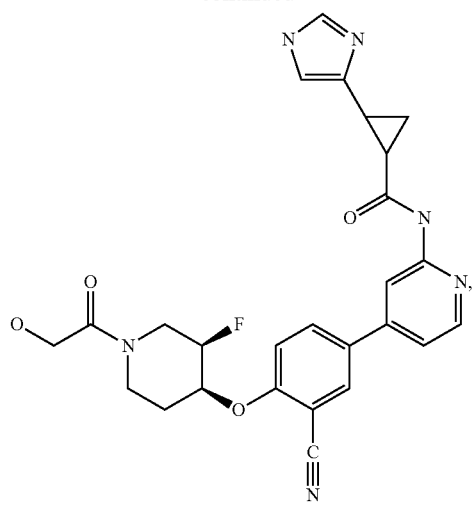
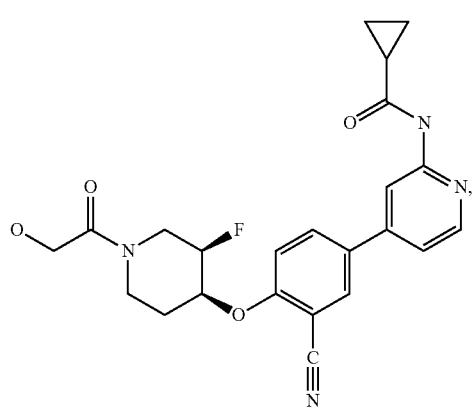
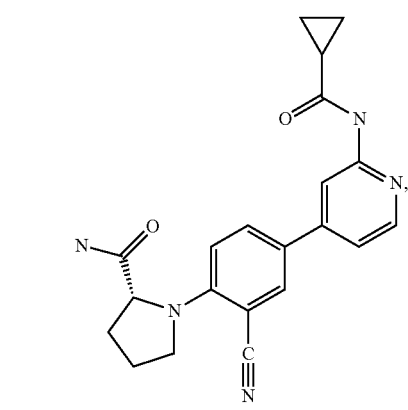
48
-continued
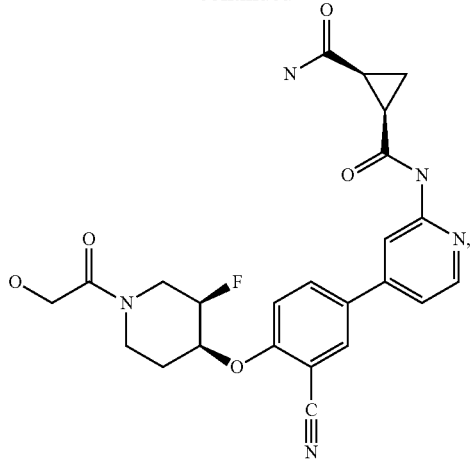
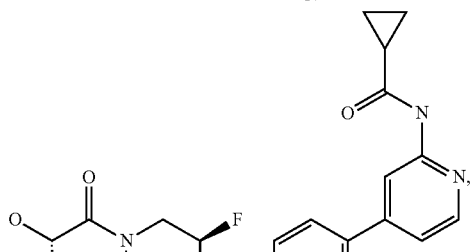
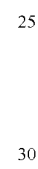
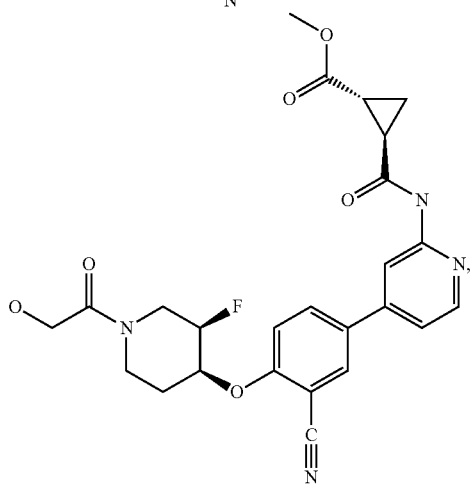

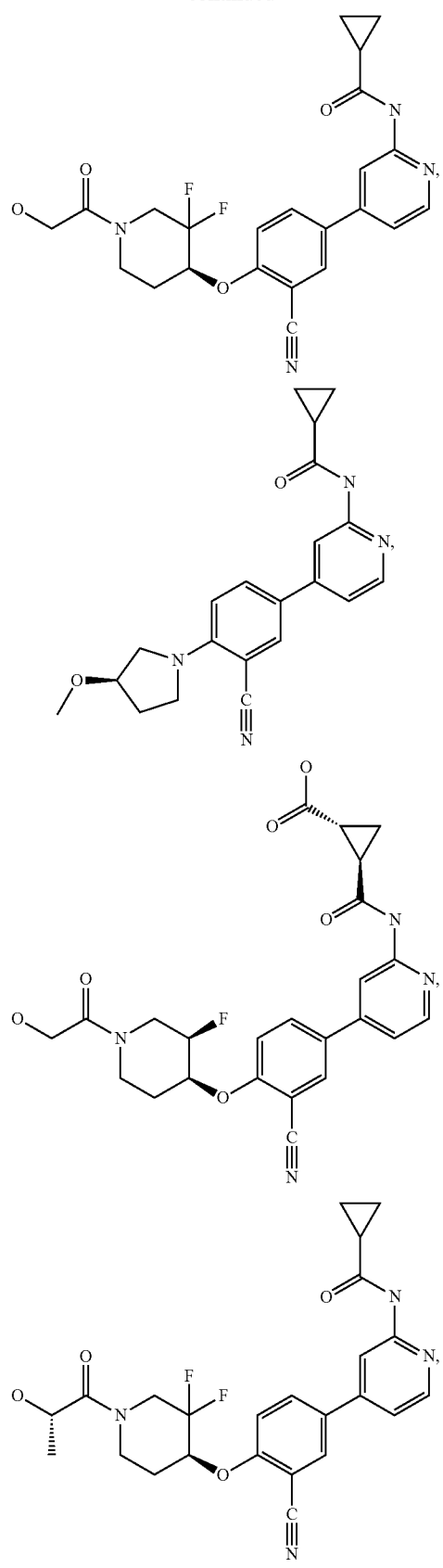
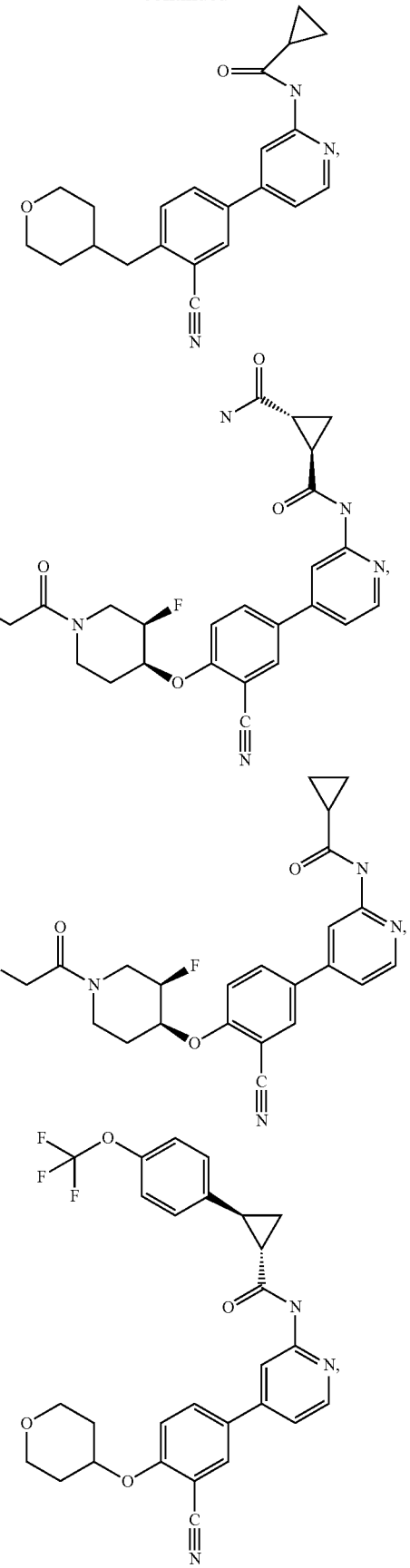

51
-continued
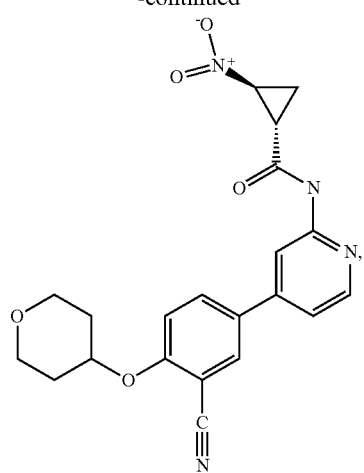
52
-continued
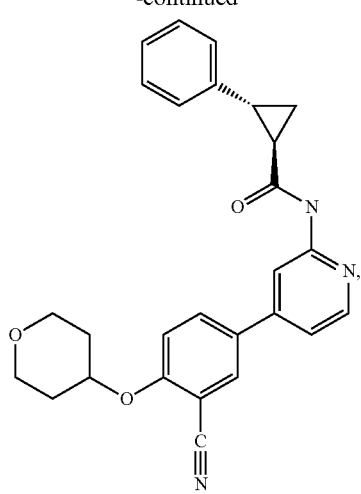
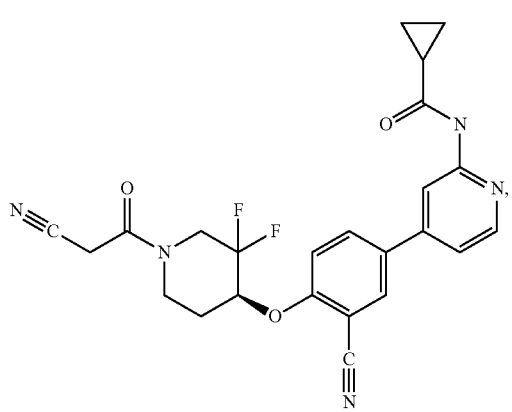
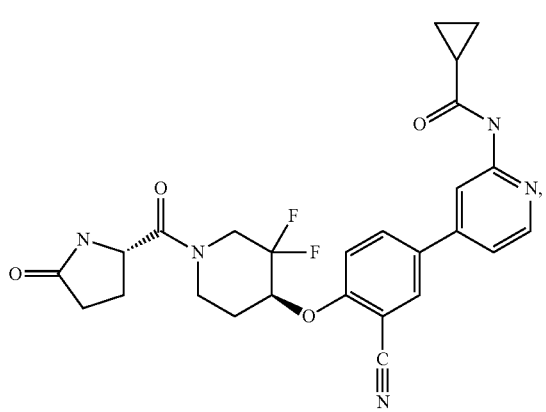
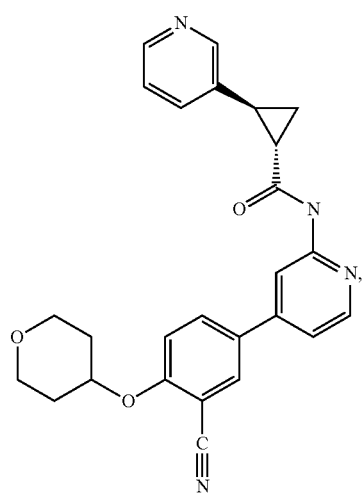
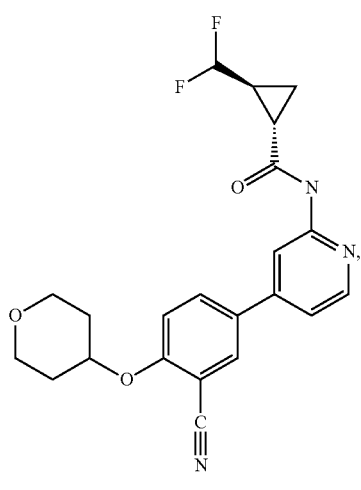

53
-continued
54
-continued
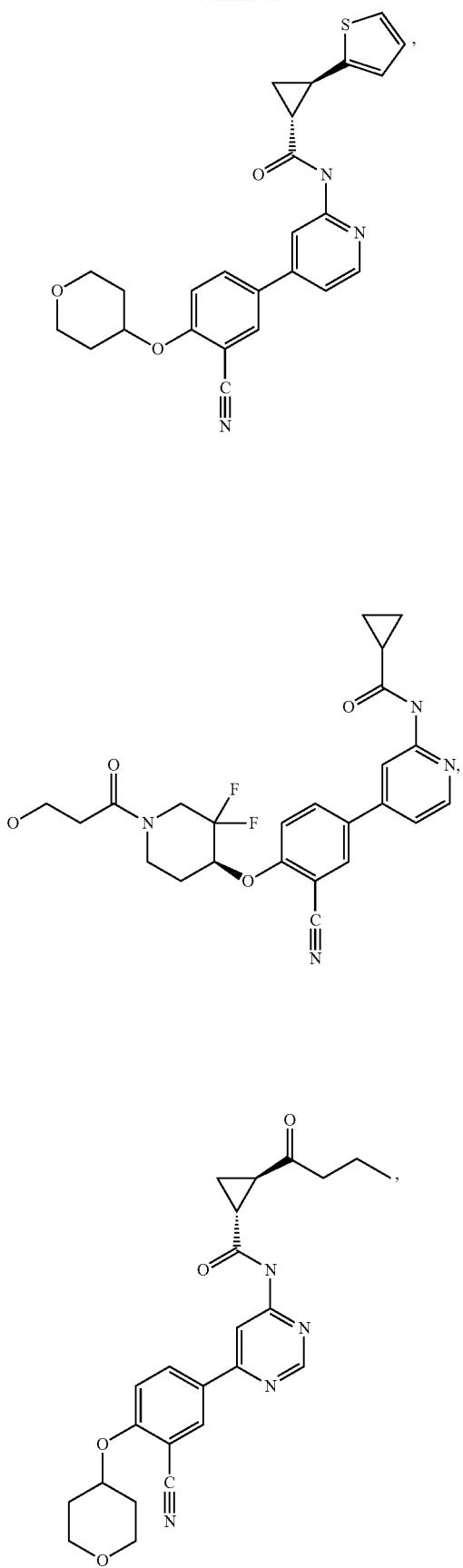
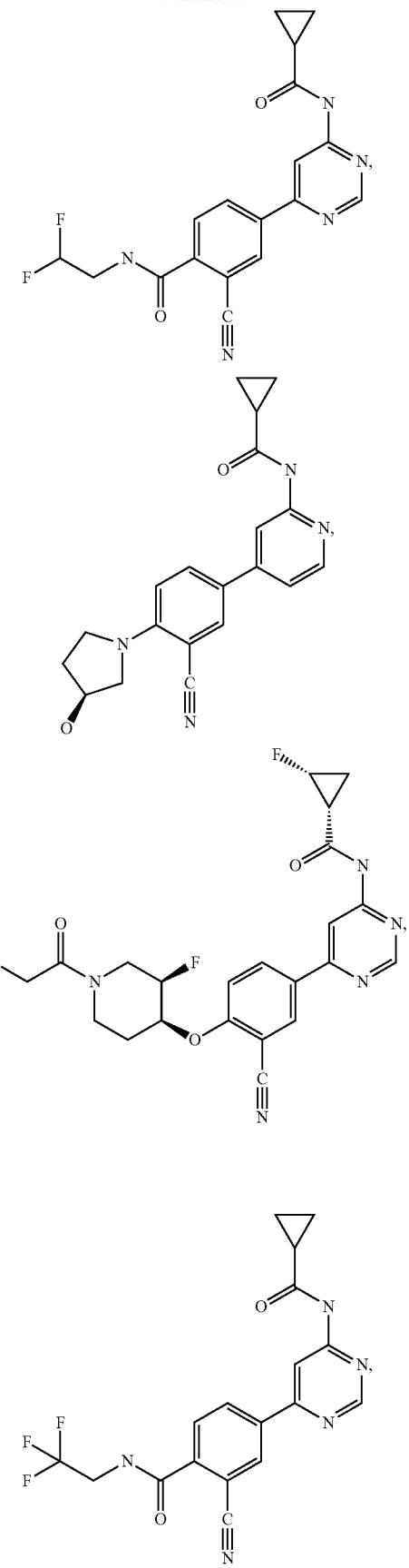

-continued
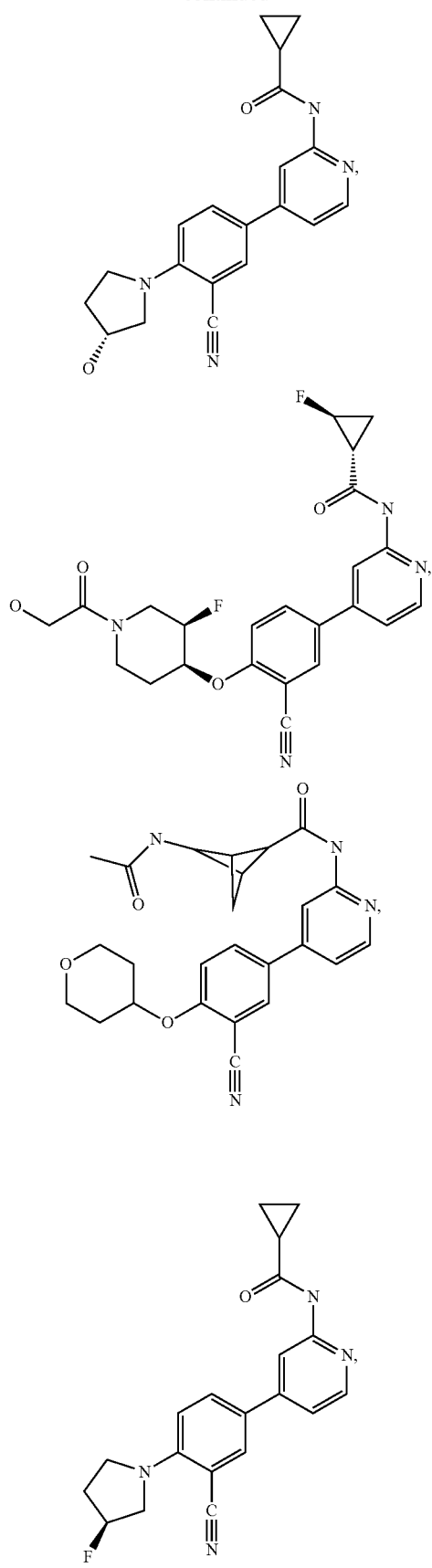
-continued
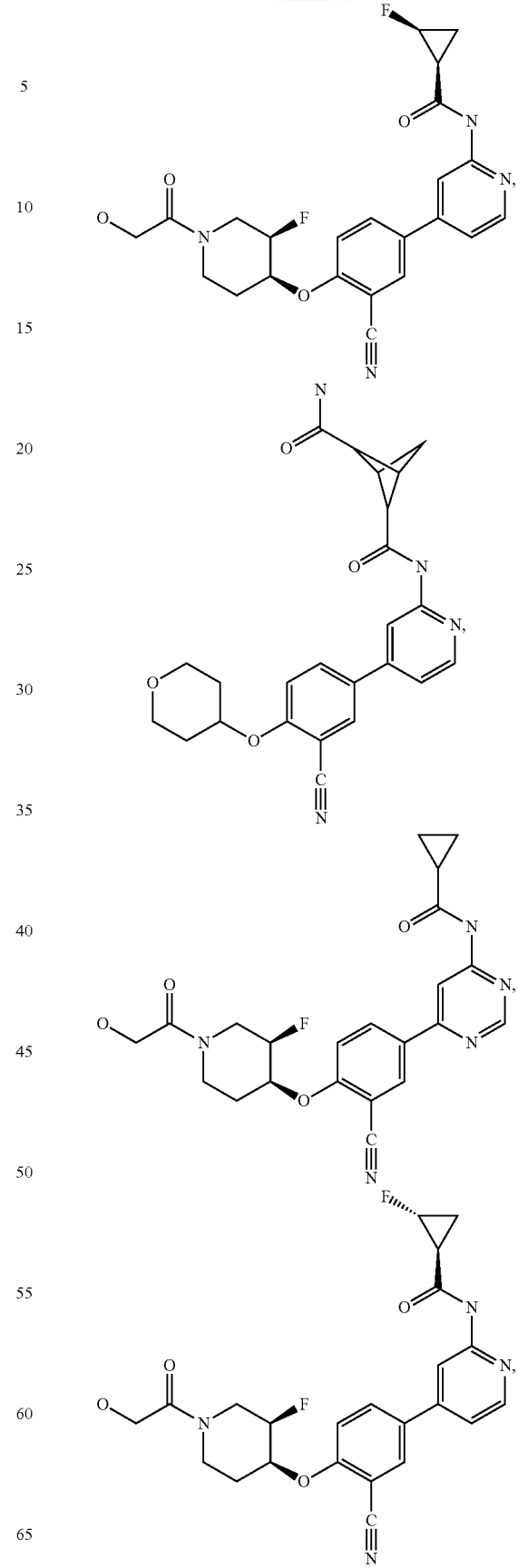

57
-continued
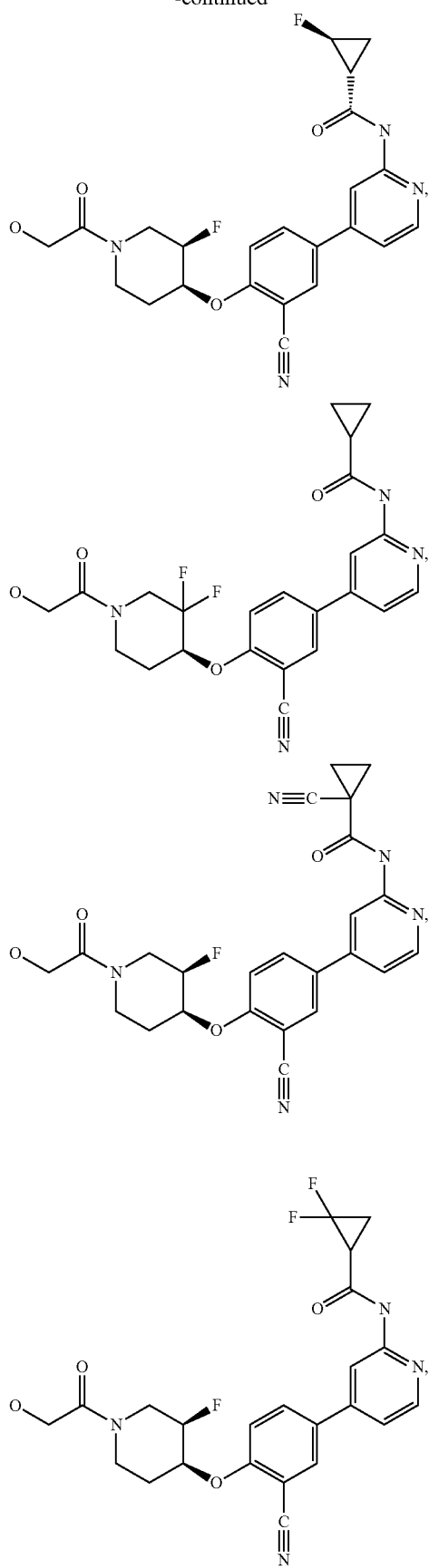
58
-continued
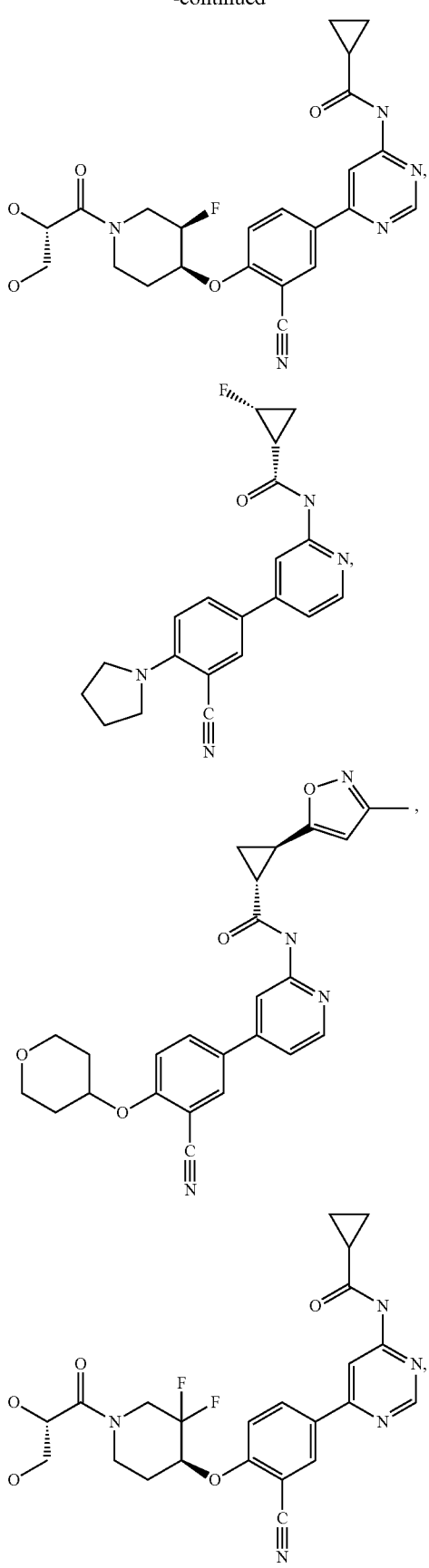

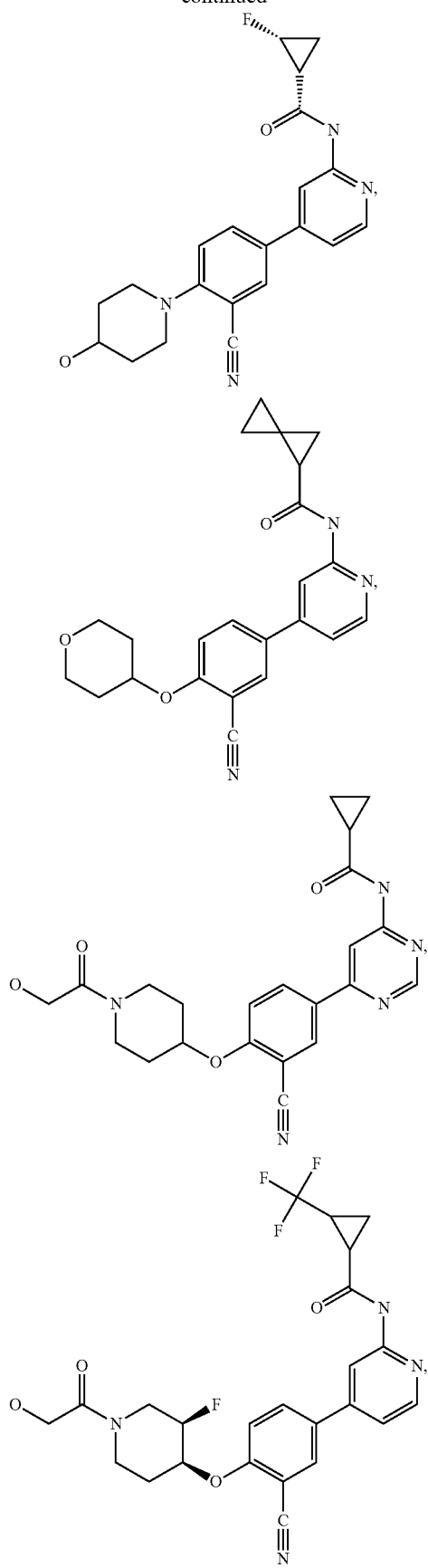
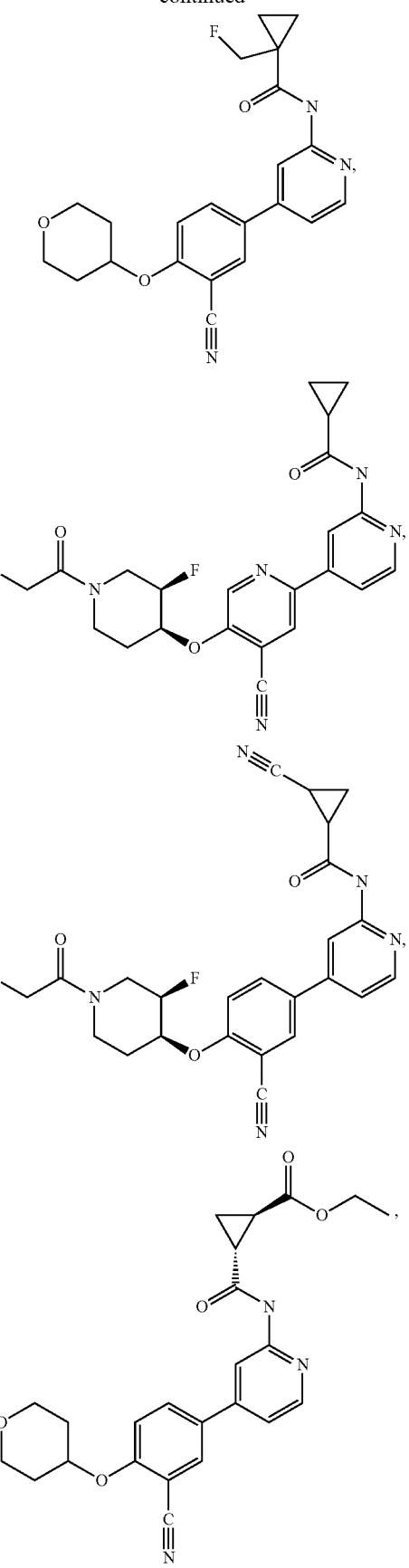

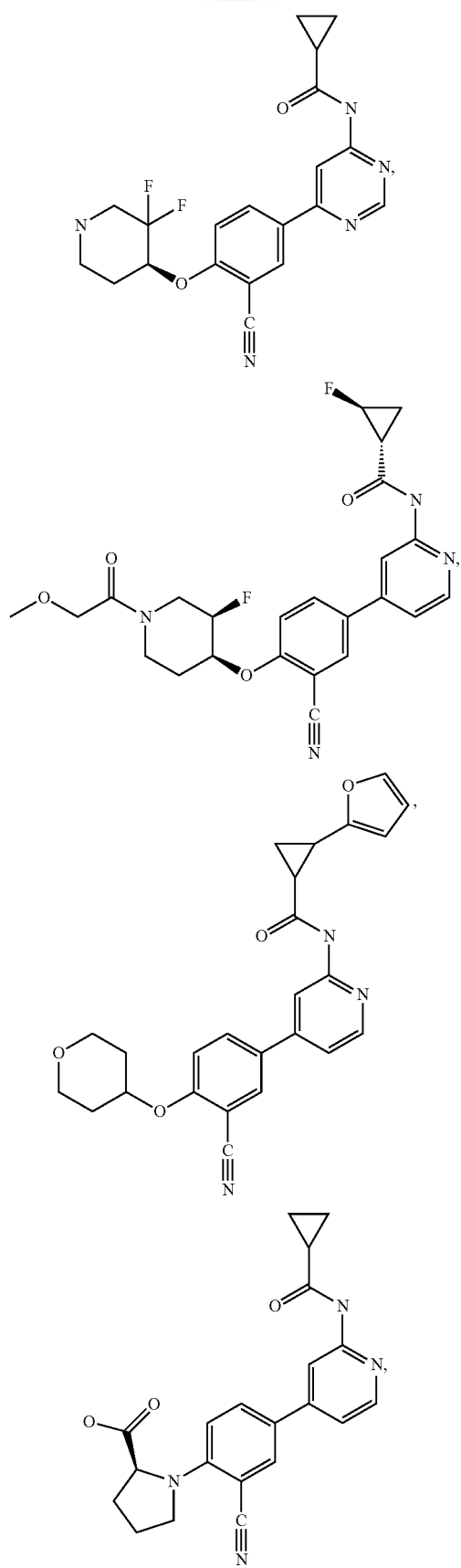
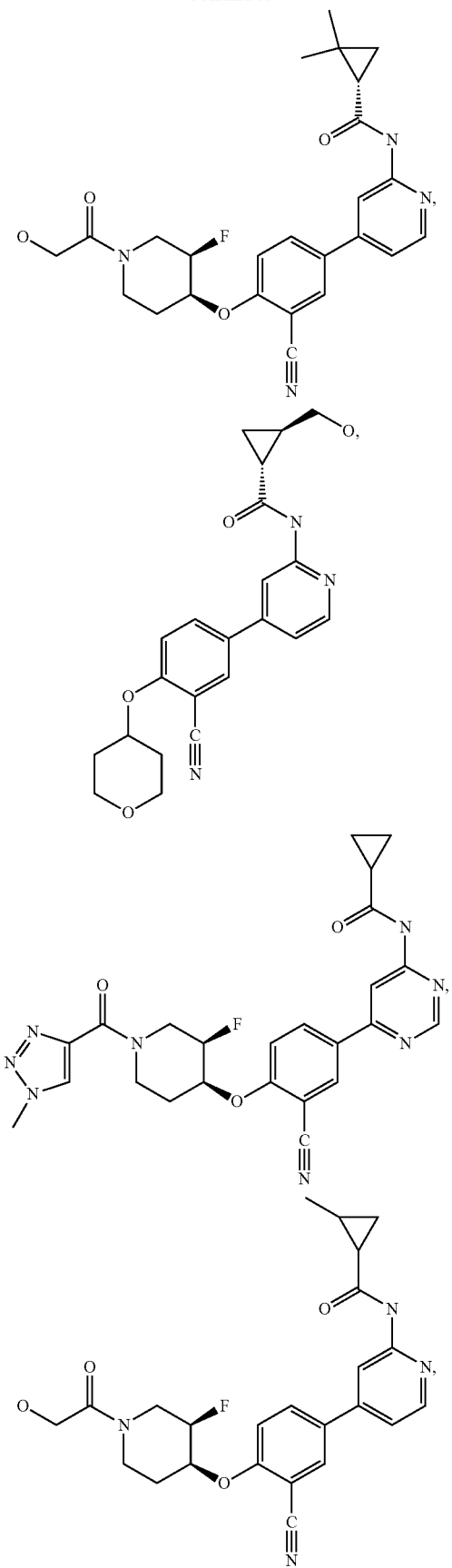

63
-continued
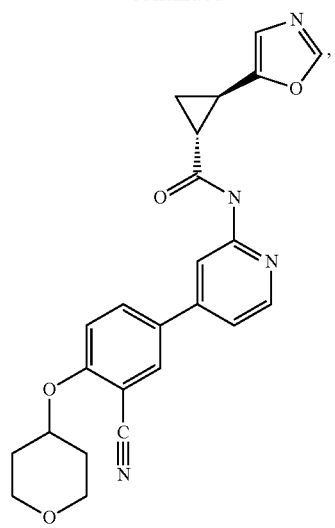
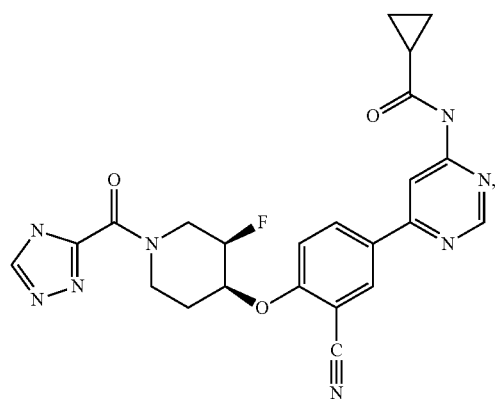
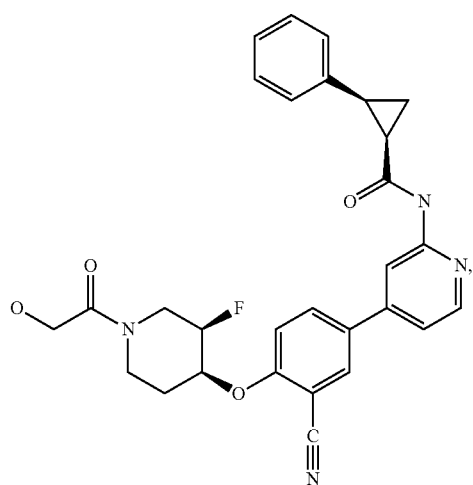
64
-continued
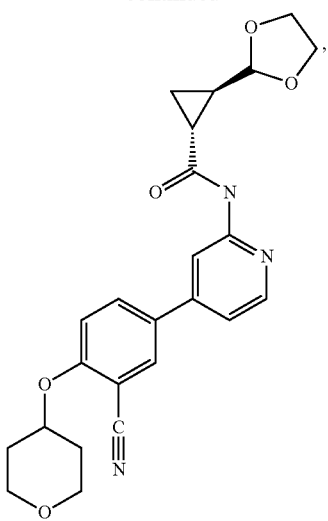
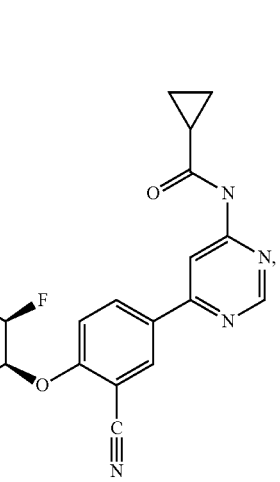
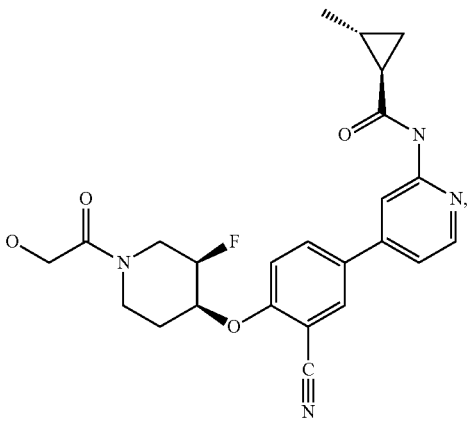

65
-continued
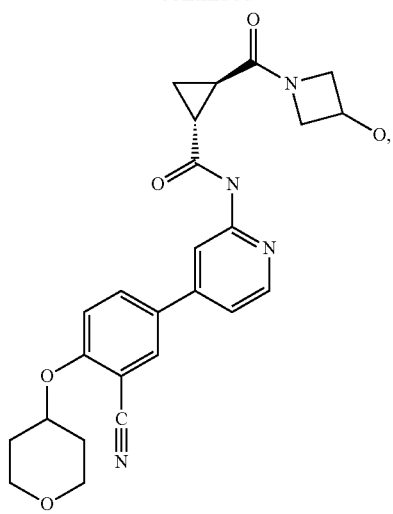
66
-continued
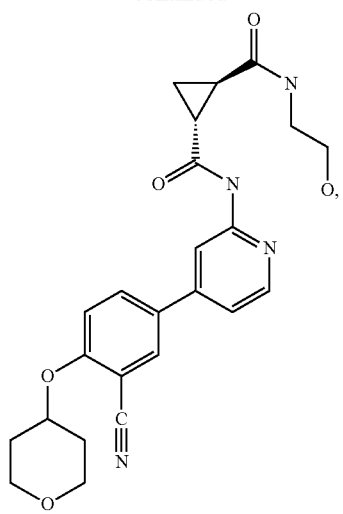
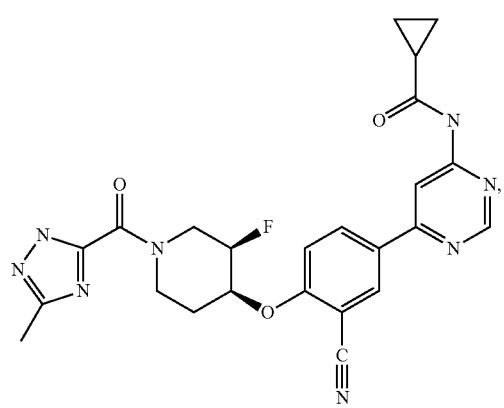
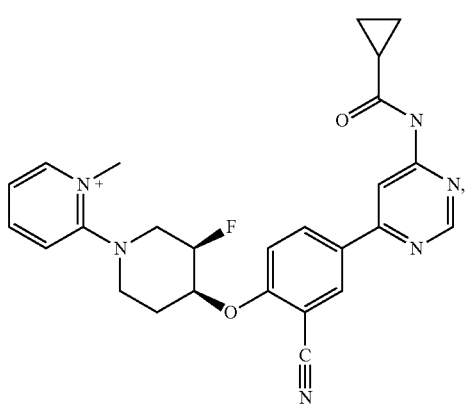
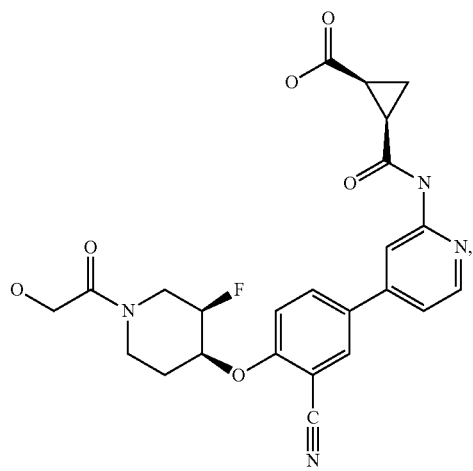
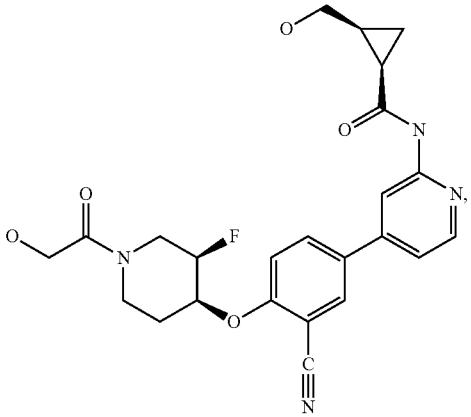

67
-continued
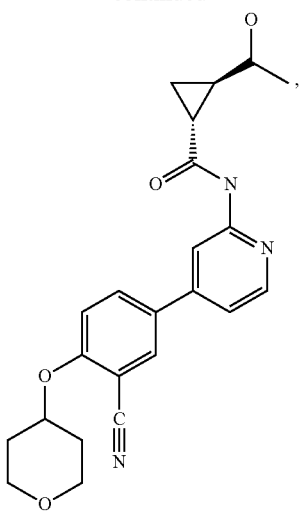
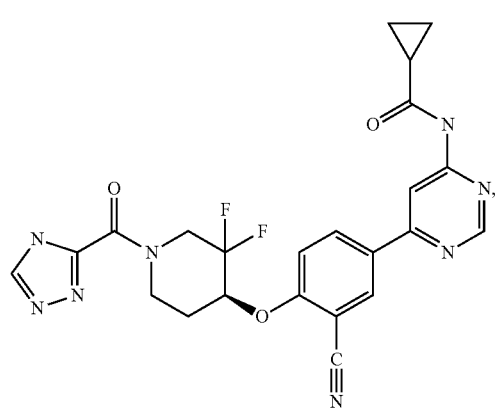
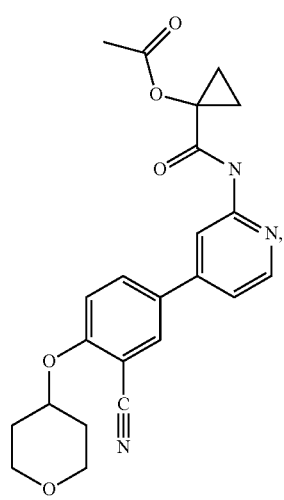
68
-continued
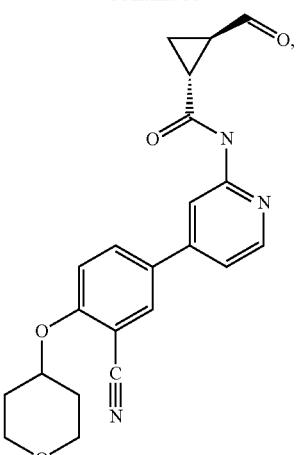
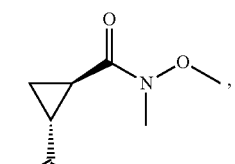

69
-continued
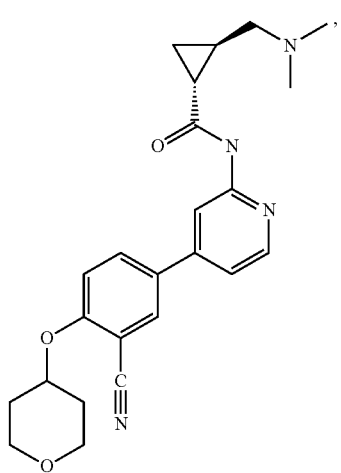
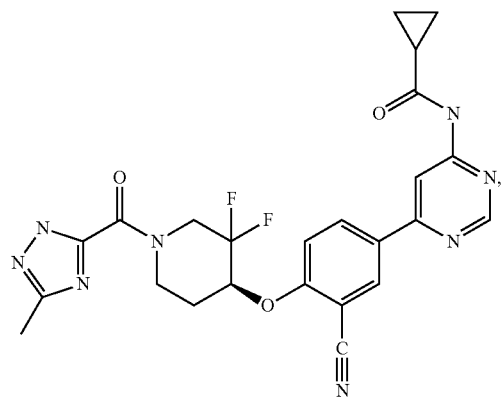
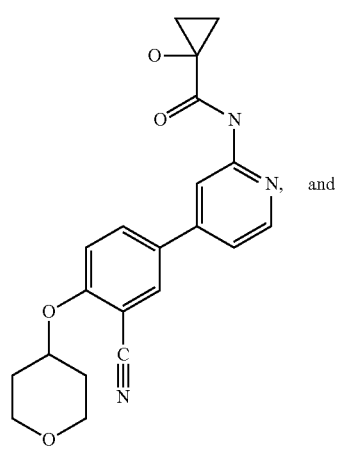
and
70
-continued
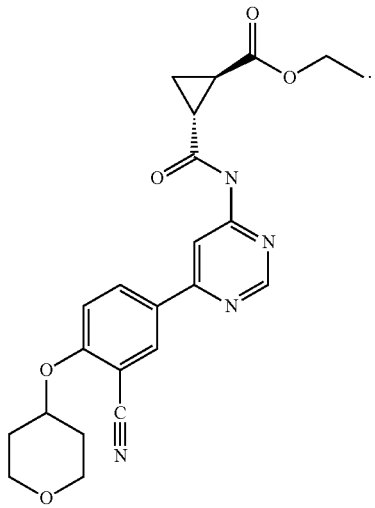
In one embodiment, the compound of the present disclosure is selected from the group consisting of:
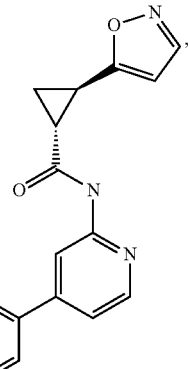
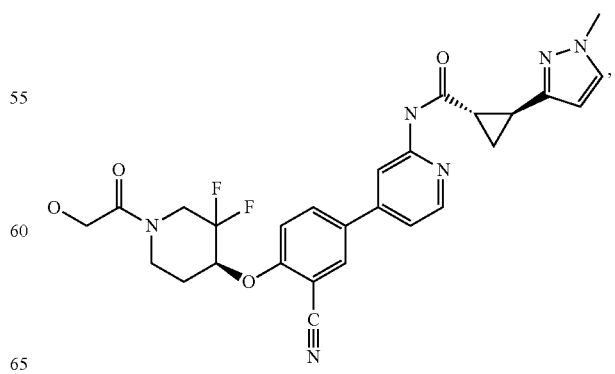

71
-continued
72
-continued
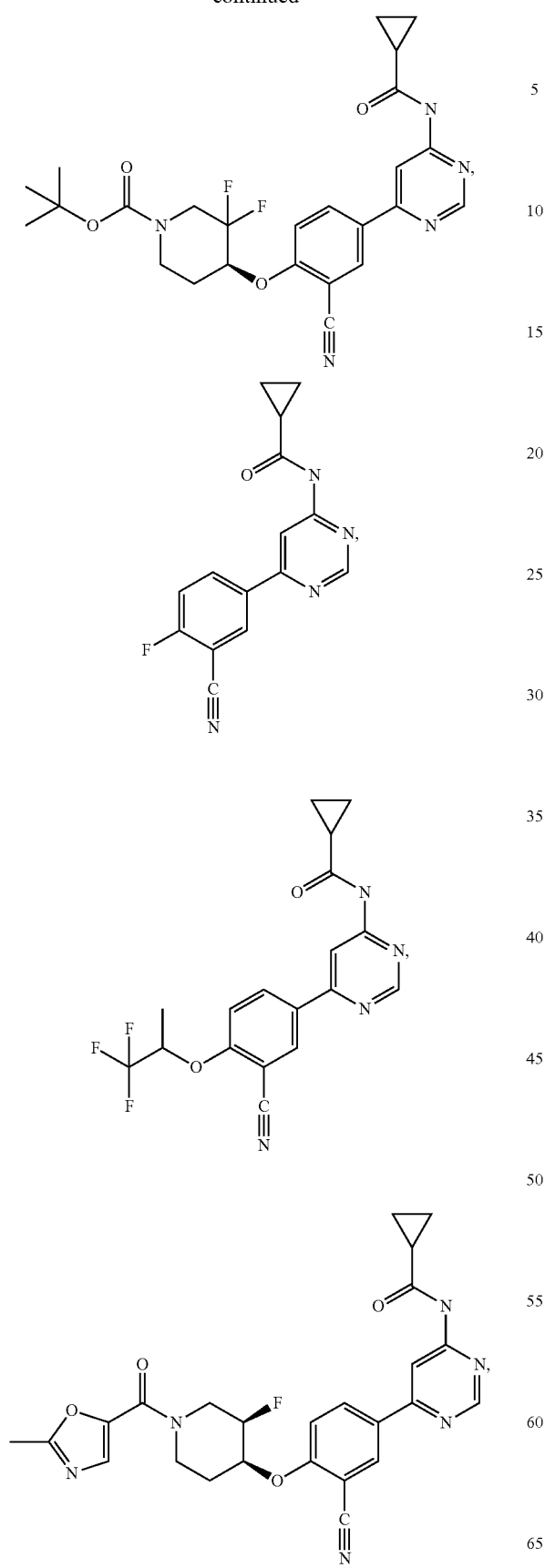
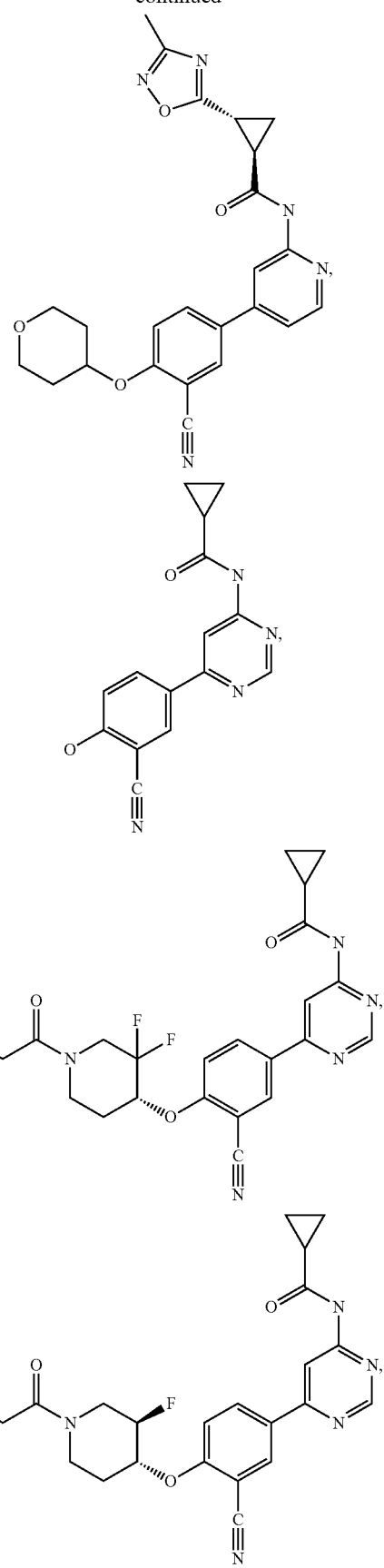

73
-continued
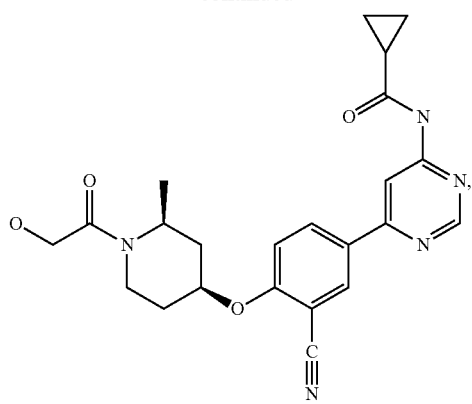
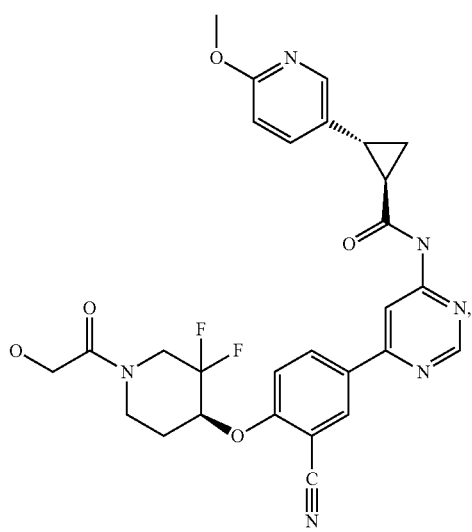
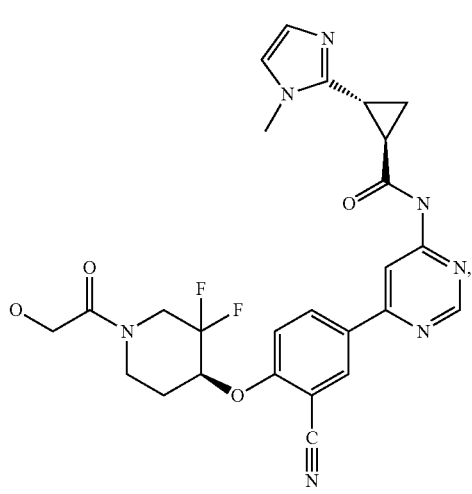
74
-continued
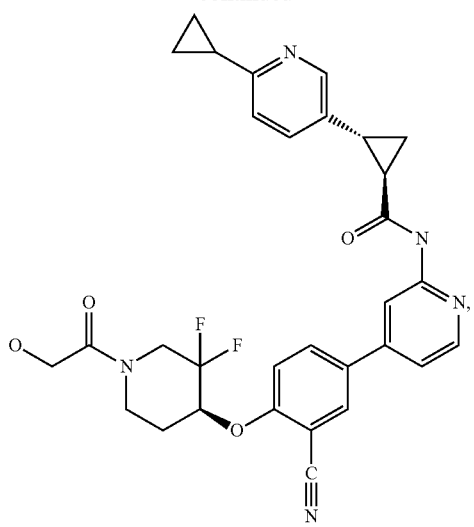
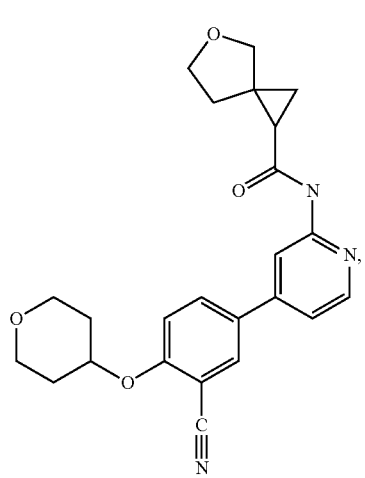

75
-continued
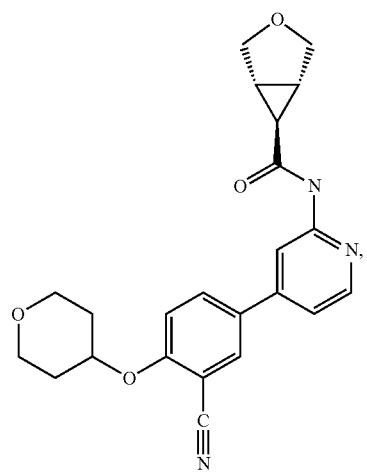
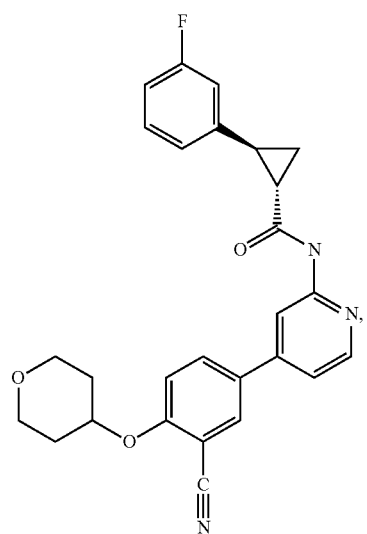
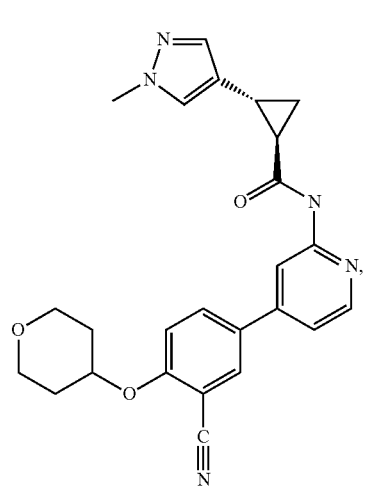
76
-continued
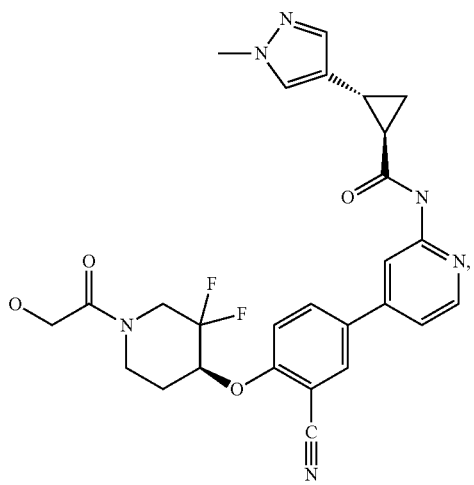
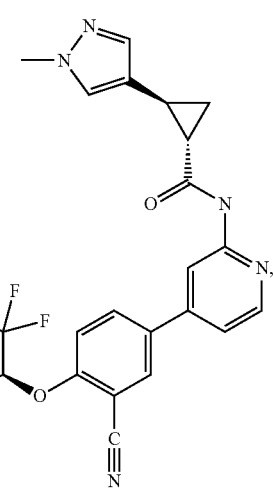
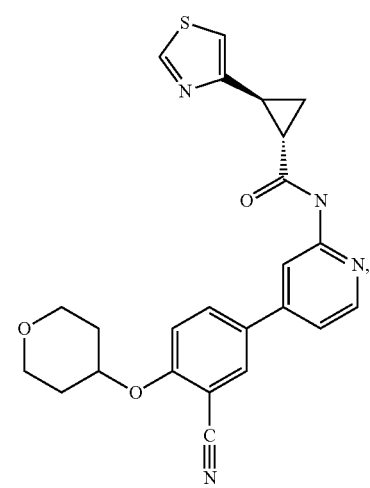

77
-continued
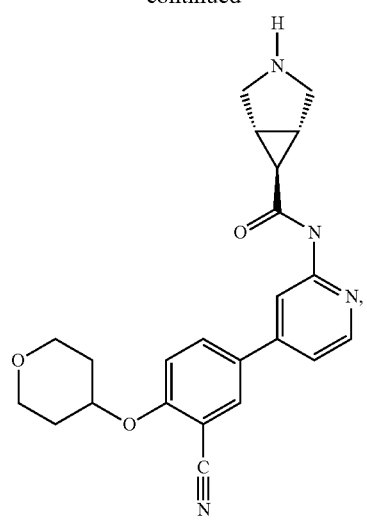
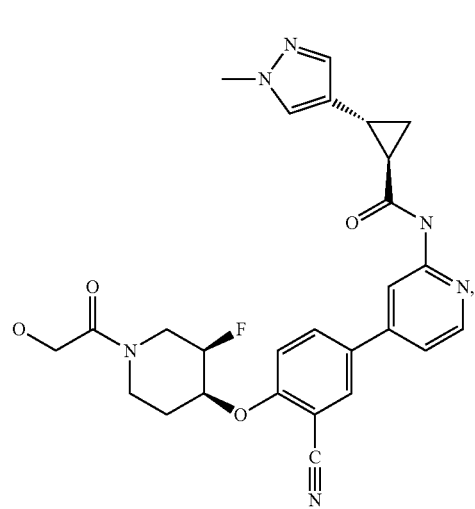
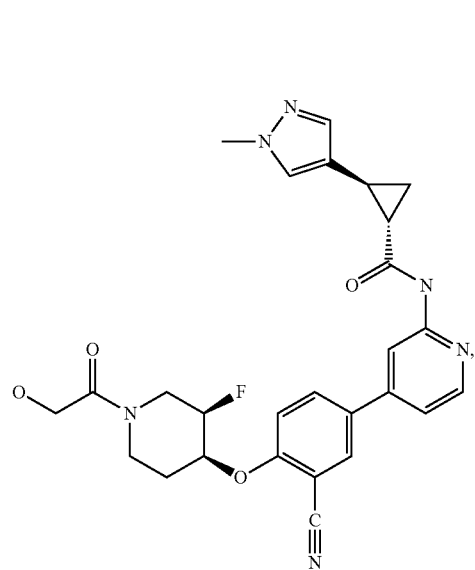
78
-continued
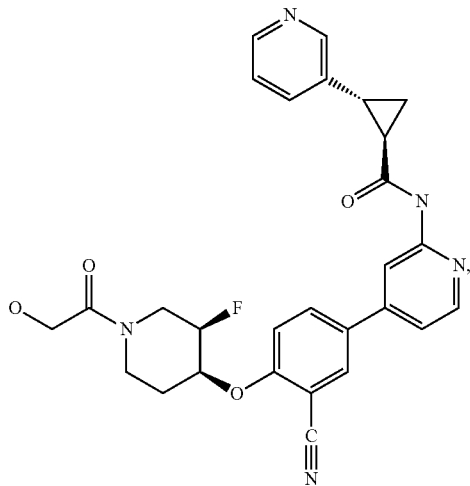
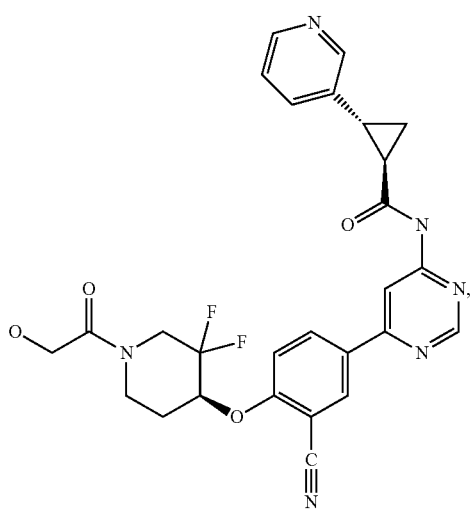

79
-continued
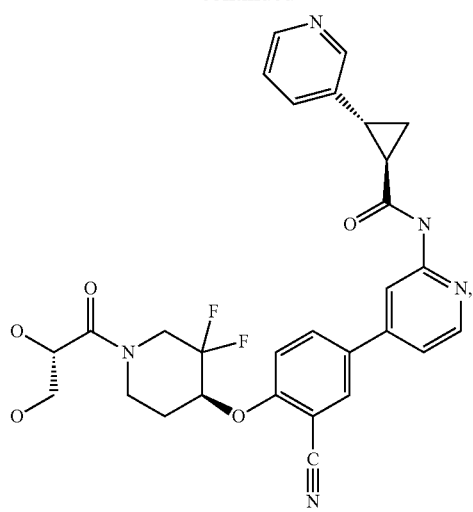
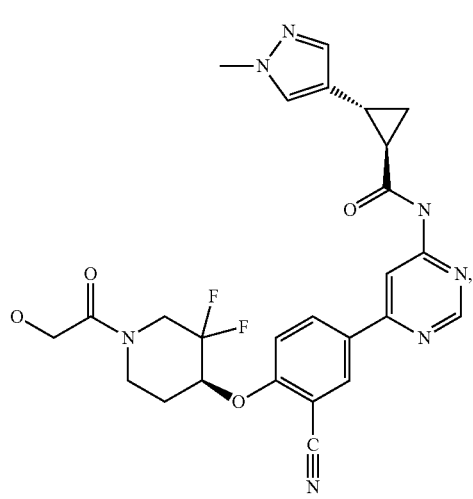
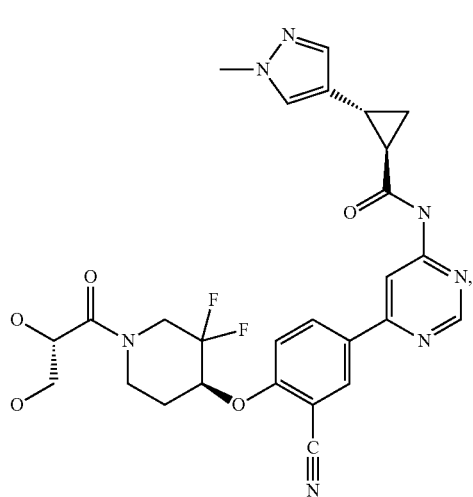
80
-continued
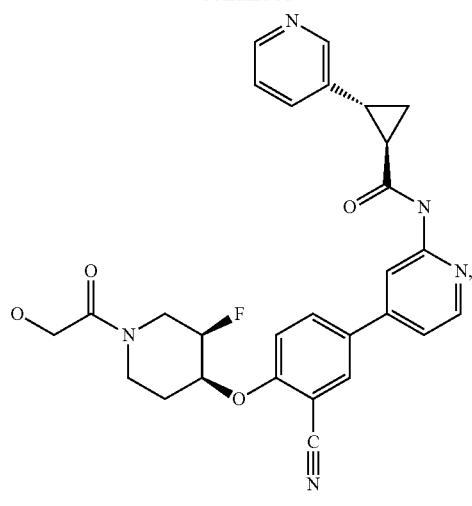
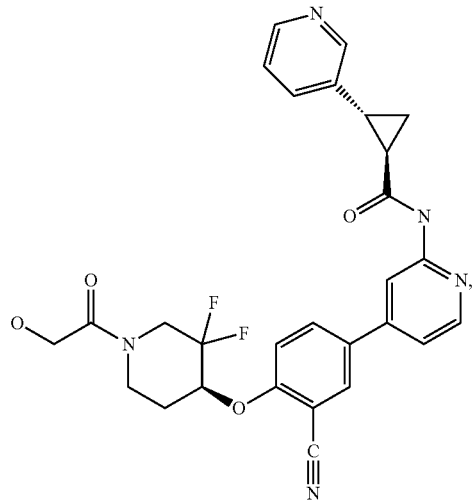
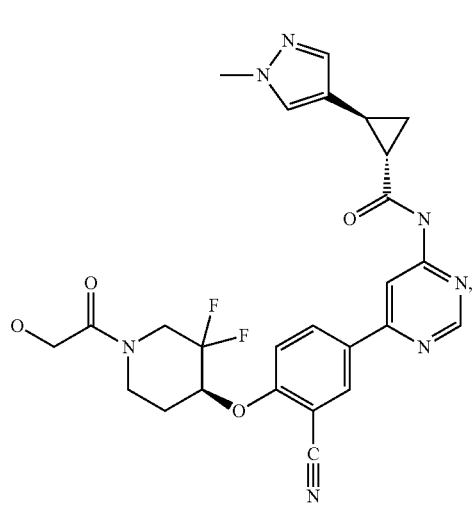

81
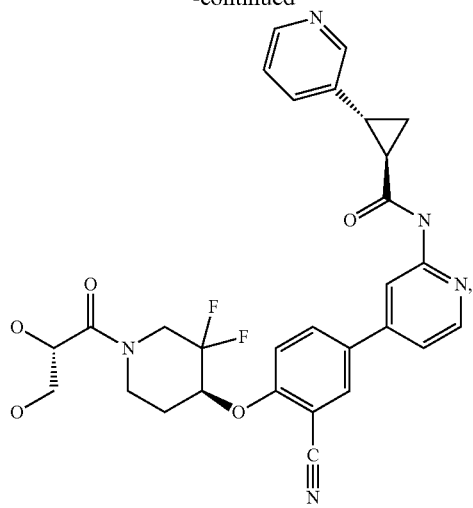
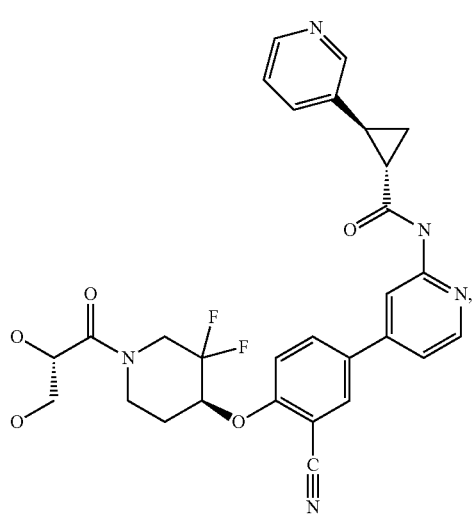
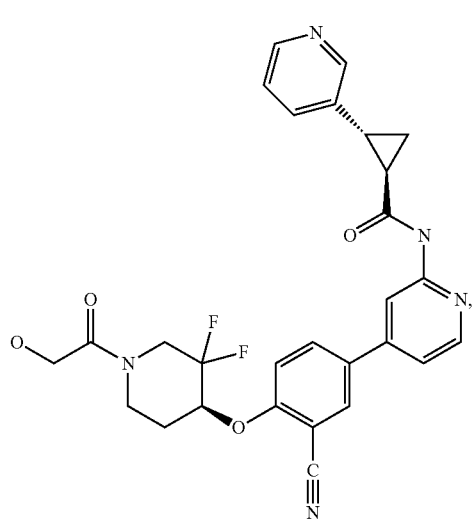
82
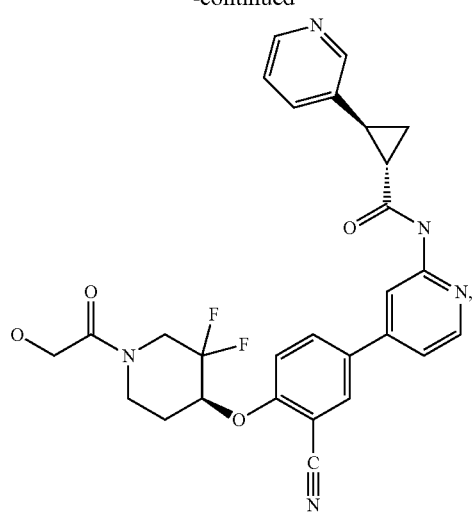
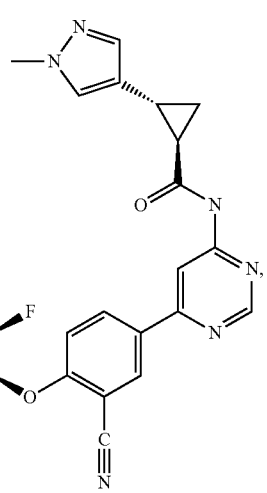
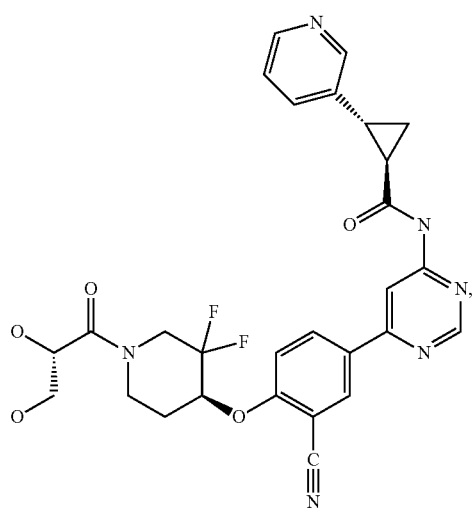

83
-continued
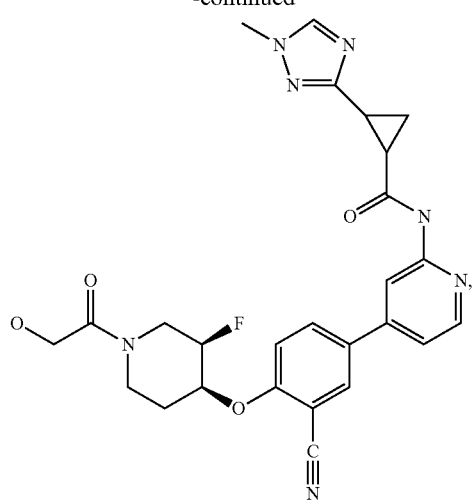
84
-continued
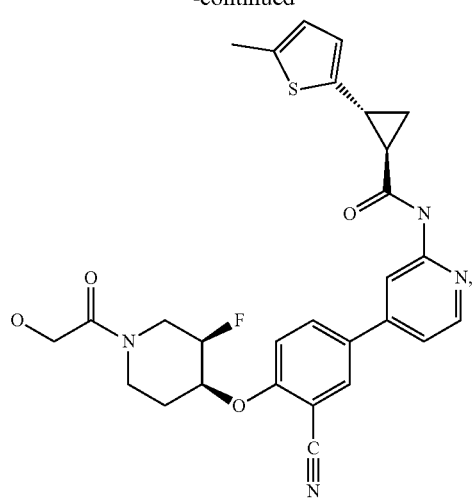
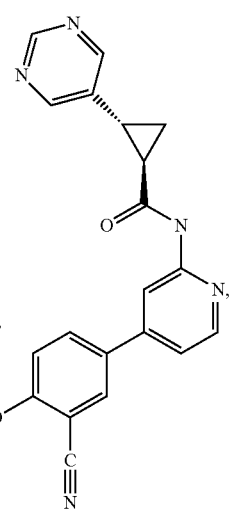
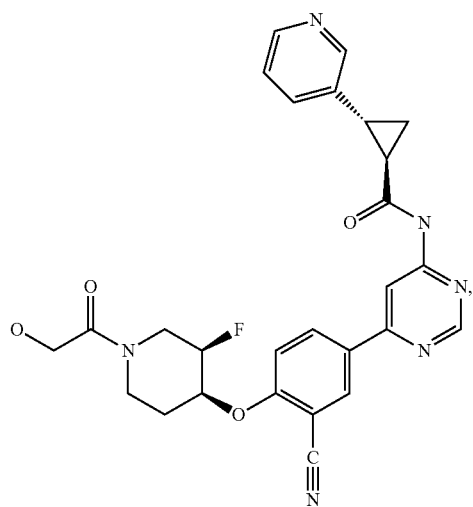
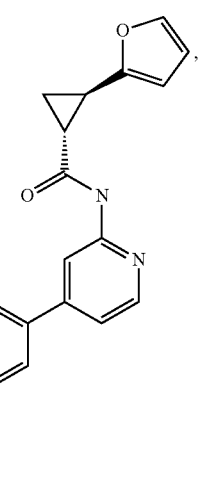

85
-continued
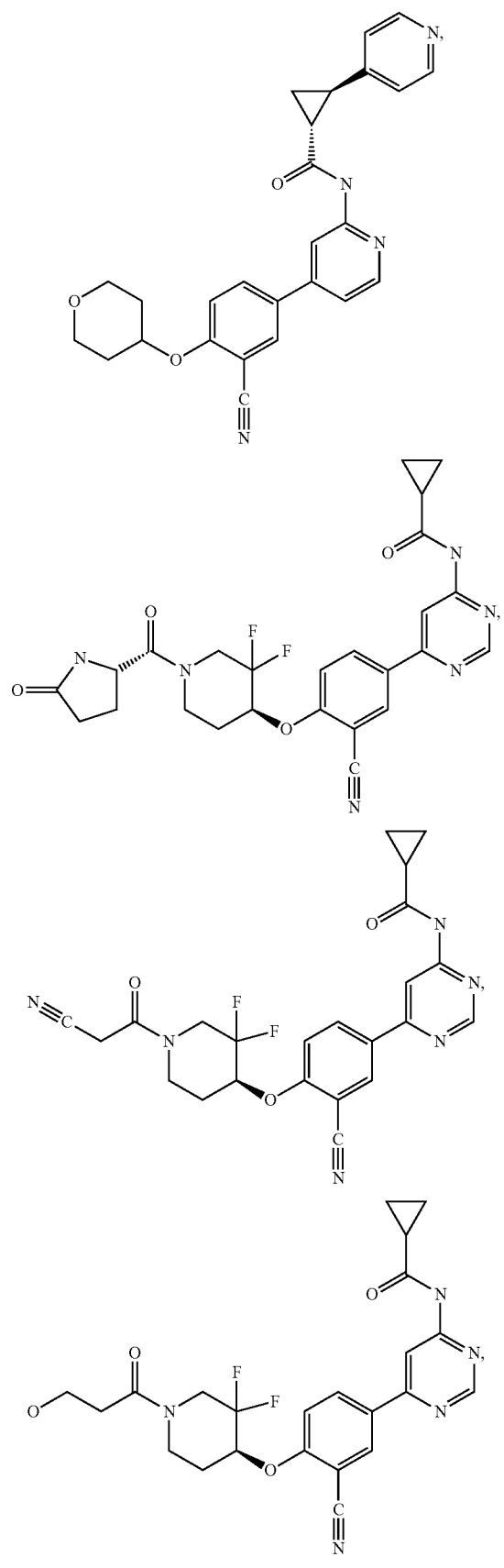
86
-continued
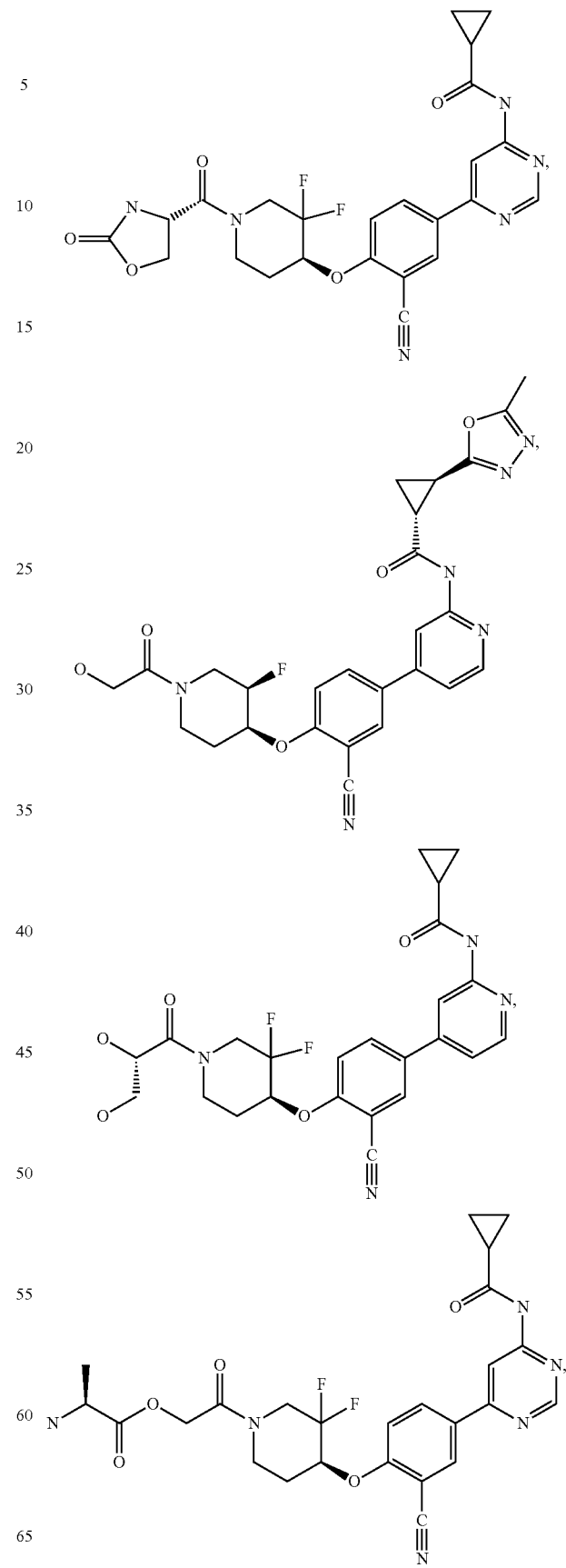

-continued
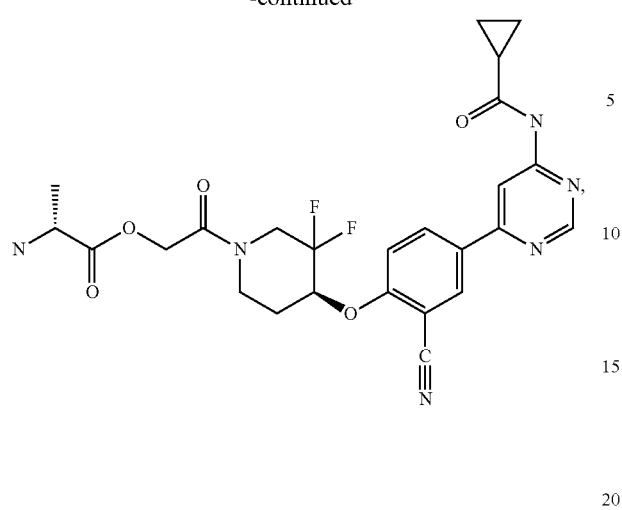
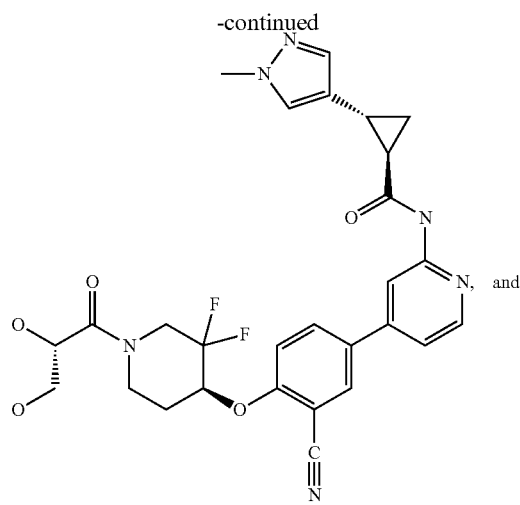
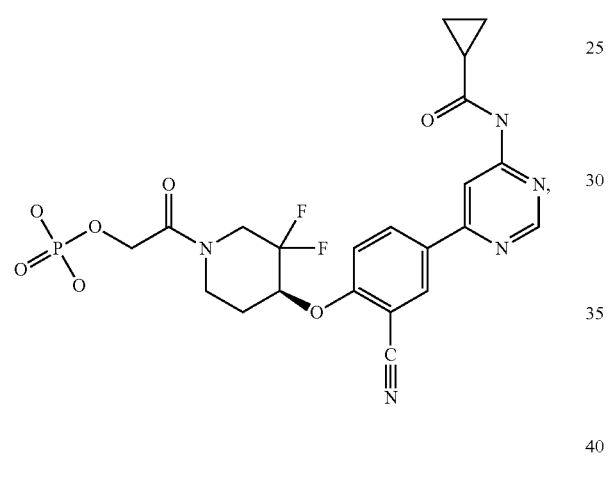
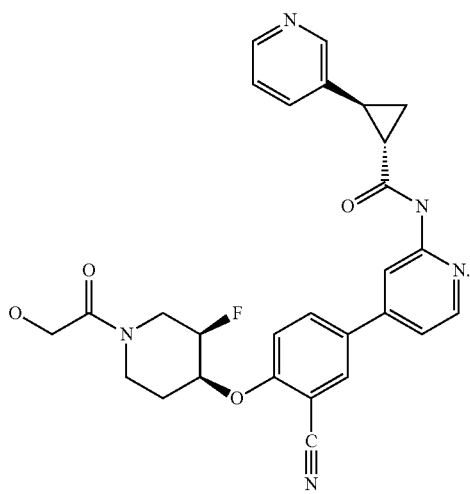
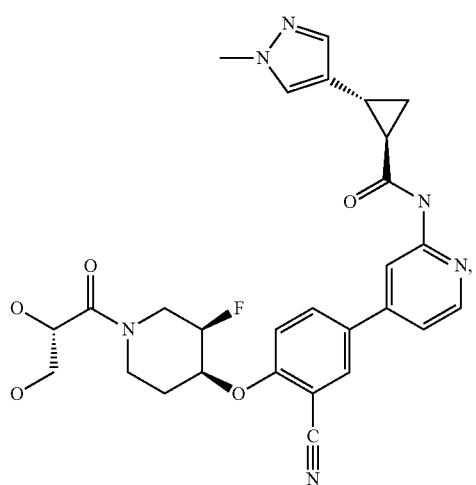
In some embodiments, the compound of the present disclosure is selected from the group consisting of:
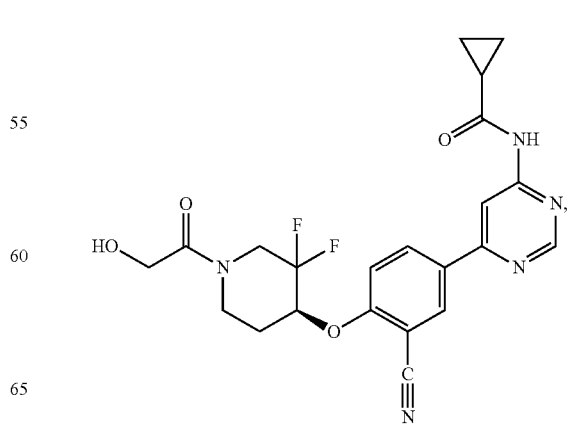

-continued

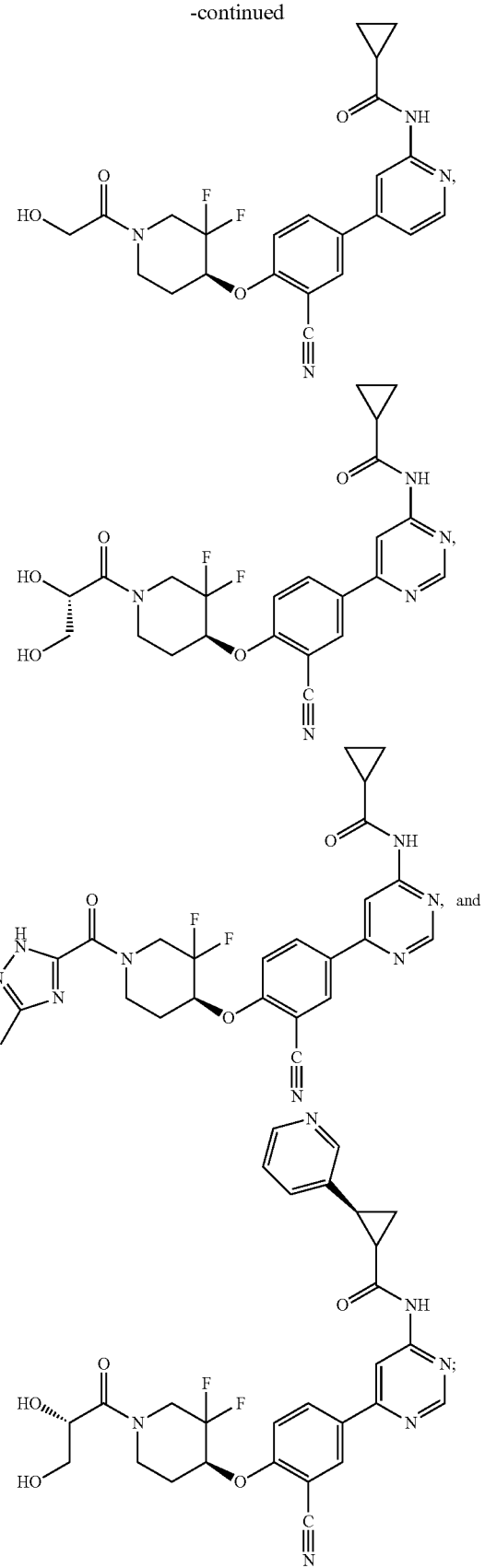

or a pharmaceutically acceptable salt thereof.

In some embodiments, provided herein is (S)—N-(6-(3-cyano-4-((3,3-difluoro-1-(2-hydroxyacetyl)piperidin-4-yl)oxy)phenyl)pyrimidin-4-yl)cyclopropanecarboxamide, having the following structure:

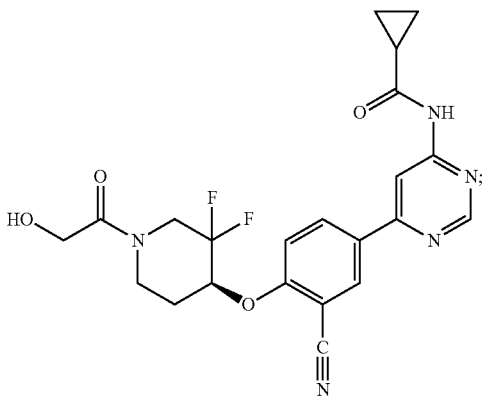 [SMILES: N#Cc1cc(-c2cc(NC(=O)C3CC3)ncn2)ccc1O[C@H]1CCN(C(=O)CO)CC1(F)F]

or a pharmaceutically acceptable salt thereof.

In some embodiments, provided herein is (S)—N-(4-(3-cyano-4-((3,3-difluoro-1-(2-hydroxyacetyl)piperidin-4-yl)oxy)phenyl)pyridin-2-yl)cyclopropanecarboxamide, having the following structure:

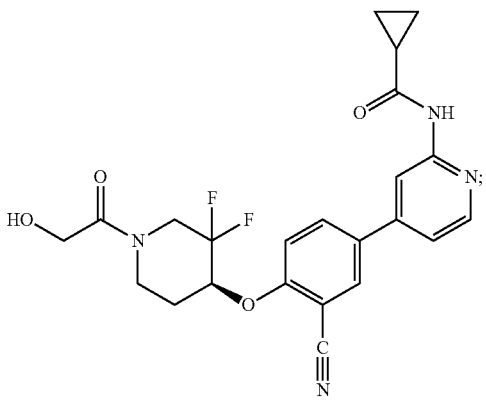 [SMILES: N#Cc1cc(-c2ccnc(NC(=O)C3CC3)c2)ccc1O[C@H]1CCN(C(=O)CO)CC1(F)F]

or a pharmaceutically acceptable salt thereof.

In some embodiments, provided herein is N-(6-(3-cyano-4-(((S)-1-((S)-2,3-dihydroxypropanoyl)-3,3-difluoropiperidin-4-yl)oxy)phenyl)pyrimidin-4-yl)cyclopropanecarboxamide, having the following structure:

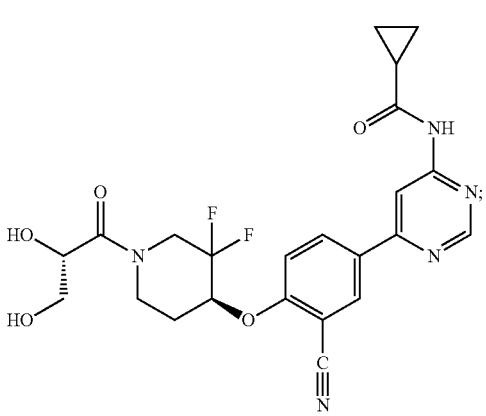 [SMILES: N#Cc1cc(-c2cc(NC(=O)C3CC3)ncn2)ccc1O[C@H]1CCN(C(=O)[C@@H](O)CO)CC1(F)F]

or a pharmaceutically acceptable salt thereof.

In some embodiments, provided herein is (S)—N-(6-(3-cyano-4-((3,3-difluoro-1-(3-methyl-1H-1,2,4-triazole-5-carbonyl)piperidin-4-yl)oxy)phenyl)pyrimidin-4-yl)cyclopropanecarboxamide, having the following structure:

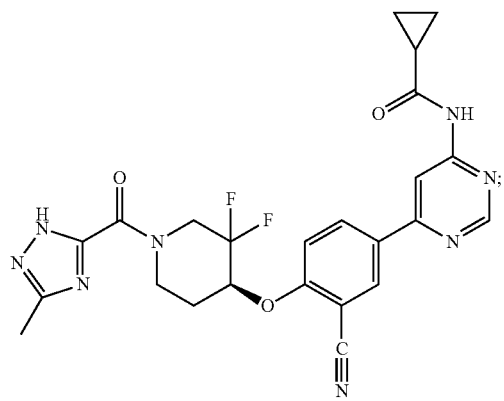 [SMILES: Cc1n[nH]c(C(=O)N2CC[C@H](Oc3ccc(-c4cc(NC(=O)C5CC5)ncn4)cc3C#N)C(F)(F)C2)n1]

or a pharmaceutically acceptable salt thereof.

In some embodiments, provided herein is (1S, 2S)—N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide, having the following structure:

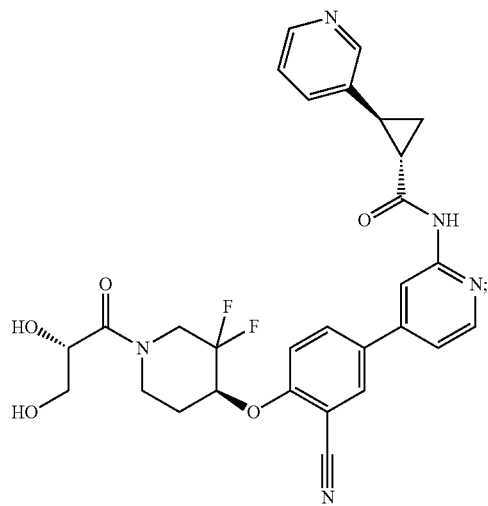 [SMILES: N#Cc1cc(-c2ccnc(NC(=O)[C@H]3C[C@@H]3c3cccnc3)c2)ccc1O[C@H]1CCN(C(=O)[C@@H](O)CO)CC1(F)F]

or a pharmaceutically acceptable salt thereof.

In some embodiments, the compound of the present disclosure is selected from the group consisting of:

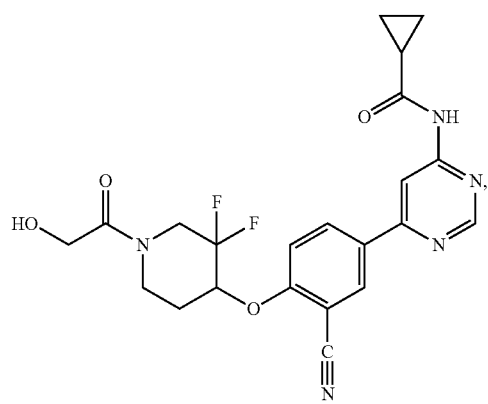

-continued

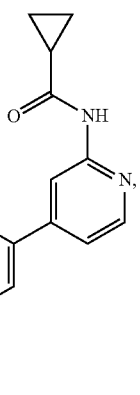

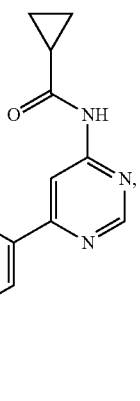

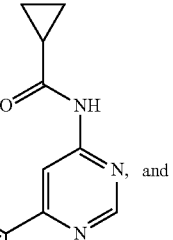, and

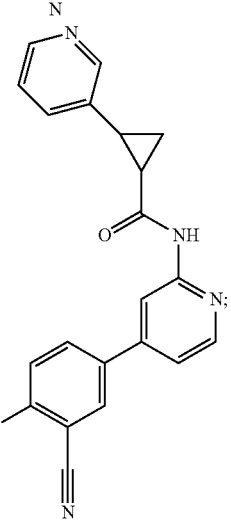

or a pharmaceutically acceptable salt thereof.

In some embodiments, provided herein is N-(6-(3-cyano-4-((3,3-difluoro-1-(2-hydroxyacetyl)piperidin-4-yl)oxy)phenyl)pyrimidin-4-yl)cyclopropanecarboxamide, having the following structure:

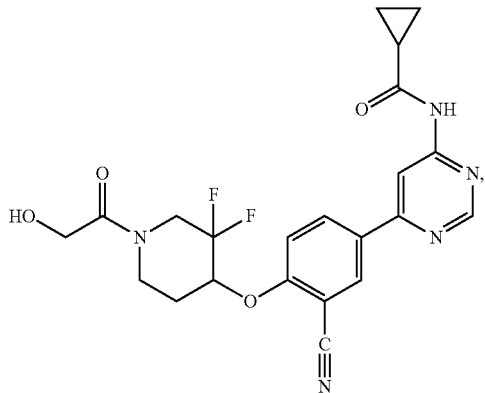

or a pharmaceutically acceptable salt thereof.

In some embodiments, provided herein is N-(4-(3-cyano-4-((3,3-difluoro-1-(2-hydroxyacetyl)piperidin-4-yl)oxy)phenyl)pyridin-2-yl)cyclopropanecarboxamide, having the following structure:

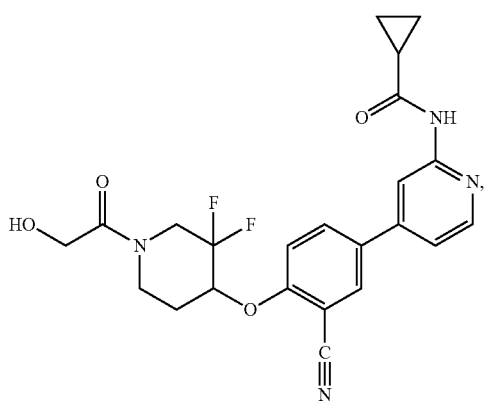 [SMILES: N#Cc1cc(-c2ccnc(NC(=O)C3CC3)c2)ccc1OC1CCN(C(=O)CO)CC1(F)F]

or a pharmaceutically acceptable salt thereof.

In some embodiments, provided herein is N-(6-(3-cyano-4-((1-(2,3-dihydroxypropanoyl)-3,3-difluoropiperidin-4-yl)oxy)phenyl)pyrimidin-4-yl)cyclopropanecarboxamide, having the following structure:

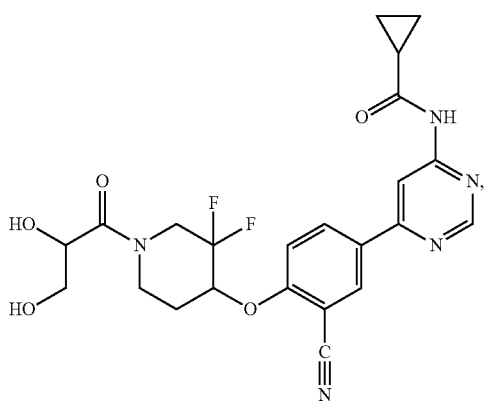 [SMILES: N#Cc1cc(-c2cc(NC(=O)C3CC3)ncn2)ccc1OC1CCN(C(=O)C(O)CO)CC1(F)F]

or a pharmaceutically acceptable salt thereof.

In some embodiments, provided herein is N-(6-(3-cyano-4-((3,3-difluoro-1-(3-methyl-1H-1,2,4-triazole-5-carbonyl)piperidin-4-yl)oxy)phenyl)pyrimidin-4-yl)cyclopropanecarboxamide, having the following structure:

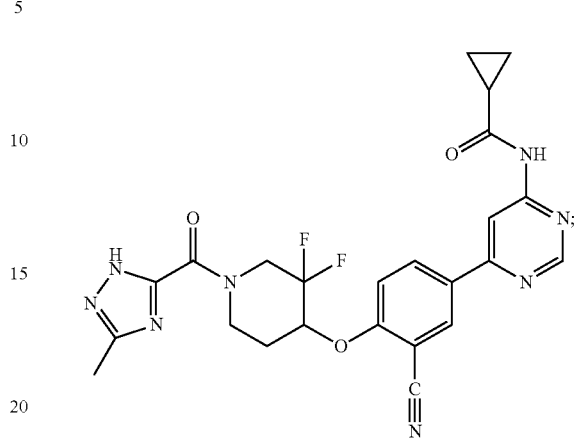

or a pharmaceutically acceptable salt thereof.

In some embodiments, provided herein is N-(4-(3-cyano-4-((-1-2,3-dihydroxypropanoyl)-3,3-difluoropiperidin-4-yl)oxy)phenyl)pyridin-2-yl)-2-(pyridin-3-yl)cyclopropane-1-carboxamide, having the following structure:

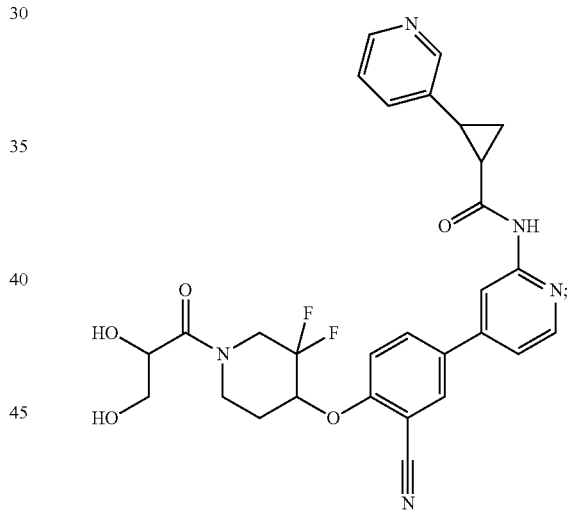

or a pharmaceutically acceptable salt thereof.

In some embodiments, the pharmaceutically acceptable salt of a compound as described herein is the hydrochloride salt.

Another embodiment provides a pharmaceutical composition comprising a compound as described herein, or a pharmaceutically acceptable salt thereof, and a pharmaceutically acceptable carrier.

Another embodiment provides a method of treating a subject having a disease or condition responsive to the inhibition of TBK1, comprising administering to the subject a therapeutically effective amount of a compound as described herein, or a pharmaceutically acceptable salt thereof. In another embodiment, the disease is cancer.

Another embodiment provides a method of treating a subject having a disease or condition responsive to the inhibition of IKKε, comprising administering to the subject a therapeutically effective amount of a compound as described herein, or a pharmaceutically acceptable salt thereof.

Another embodiment provides a method of treating a subject suffering from a RAS-dependent/mutant cancer, comprising administering to the subject a therapeutically effective amount of a compound as described herein. In another embodiment, the RAS-dependent/mutant cancer is selected from the group consisting of non-small cell lung cancer, colorectal cancer, pancreatic cancer, AML, and melanoma.

In some embodiments, disclosed herein is a first line treatment of a subject suffering from a cancer comprising administering to the subject a therapeutically effective amount of a compound as described herein. In some embodiments, disclosed herein is a first line treatment of a subject suffering from a RAS-dependent/mutant cancer (e.g., non-small cell lung cancer, colorectal cancer, pancreatic cancer, AML, and melanoma).

In some embodiments, disclosed herein is a method of treating a subject suffering from a cancer that is advanced, metastatic, refractory, and/or relapsed, comprising administering to the subject a therapeutically effective amount of a compound as described herein. In some embodiments, the cancer is a RAS-dependent/mutant cancer. In some embodiments, the RAS-dependent/mutant cancer is selected from the group consisting of non-small cell lung cancer, colorectal cancer, pancreatic cancer, AML, and melanoma, wherein the cancer is advanced, metastatic, refractory, and/or relapsed. In some embodiments, the cancer is refractory to chemotherapy and/or immunotherapy (e.g., immunotherapy with a PD-1 inhibitor such as nivolumab, and/or a PD-L1 inhibitor such as atezolizumab).

In some embodiments, the RAS-dependent/mutant cancer is RAS-mutant cancer. In various embodiments, the RAS-mutant cancer is KRAS-mutant cancer. In some embodiments, the KRAS-mutant cancer is selected from the group consisting of non-small cell lung cancer, colorectal cancer, and pancreatic cancer.

In some embodiments, the RAS-mutant cancer is NRAS-mutant cancer. In various embodiments, the NRAS-mutant cancer selected from the group consisting of acute myeloid leukemia (AML) and melanoma.

In some embodiments, the RAS-mutant cancer is HRAS-mutant cancer. In various embodiments, the HRAS-mutant cancer is selected from the group consisting of bladder cancer, thyroid and salivary duct carcinoma, epithelial-myoepithelial carcinoma, and kidney cancer.

Another embodiment provides a method of treating a subject suffering from breast or ovarian cancer, comprising administering to the subject a therapeutically effective amount of a compound as described herein. Another embodiment provides a method of treating a subject suffering from cancer resistant to HER2 and/or EGFR targeted therapies comprising administering to the subject a therapeutically effective amount of a compound as described herein.

In some embodiments, the subject may be a human who is (i) refractory to at least one chemotherapy treatment, or (ii) is in relapse after treatment with chemotherapy, or both (i) and (ii). In some embodiments, the subject is refractory to at least one, at least two, at least three, or at least four chemotherapy treatments (including standard or experimental chemotherapies). In some embodiments, the subject was previously treated with an immune checkpoint inhibitor (e.g., a PD1 inhibitor and/or a PD-L1 inhibitor, etc.). In some embodiments, the checkpoint inhibitor is a monoclonal antibody. In some embodiments, the monoclonal antibody administered subcutaneously or intravenously. In some embodiments, the checkpoint inhibitor is a small molecule.

In some embodiments, the checkpoint inhibitor is a PD1 inhibitor, a PD-L1 inhibitor, a PD1 and a PD-L1 inhibitor, a TIM-3 inhibitor, a TIM-3 and PD1 inhibitor, a LAG-3 inhibitor, or a LAG-3 and PD-1 inhibitor.

In some embodiments, the checkpoint inhibitor is selected from the group consisting of nivolumab, pembrolizumab, lambrolizumab, pidilizumab, durvalumab, avelumab, and atezolizumab, PDR001, TSR-042, BMS-986016, or a pharmaceutically acceptable salt or solvate of any of the forgoing.

In some embodiments, the subject was previously treated with a PD1 inhibitor and/or a PD-L1 inhibitor. In some embodiments, the PD1 inhibitor is nivolumab, pembrolizumab, lambrolizumab, or pidilizumab, or a pharmaceutically acceptable salt or solvate of any of the forgoing. In some embodiments, the PD-L1 inhibitor is atezolizumab, durvalumab, or avelumab, or a pharmaceutically acceptable salt or solvate of any of the forgoing. In some embodiments, the subject was previously treated with nivolumab.

Another embodiment provides a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

In some embodiments, disclosed herein is a method of promoting T cell immune response in a subject, comprising administering to the subject a therapeutically effective amount of a compound as described herein. In some embodiments, a compound as disclosed herein may be administered with at least one additional therapeutic agent selected from T cell immunomodulators (e.g., an inhibitory RNA). In some embodiments, the T cell immunomodulator is selected from the group consisting of inhibitory RNA, HPK1 inhibitors, IL2/15/17 fusion proteins, OX40 agonists, CD27 agonists, MKNK1/2 inhibitors, CD40 agonists, CD137 agonists, CD28 agonists, and GITR agonists. In some embodiments, promoting T cell immune response is identified by an increase in T cell count, induction and secretion of IL-2 and/or IFNg, and/or upregulation of CD25 and CD69 on the cell surface.

Another embodiment provides a compound as described herein, or a pharmaceutically acceptable salt thereof, for use in a method of treating a subject having a disease or condition responsive to the inhibition of TBK1. In an embodiment, the disease is cancer. Another embodiment provides a compound as described herein, or a pharmaceutically acceptable salt thereof for use in a method of treating a subject having a disease or condition responsive to the inhibition of IKKε.

Another embodiment provides a compound as described herein, or a pharmaceutically acceptable salt thereof, for use in a method of treating a subject suffering from a RAS-dependent/mutant cancer. In an embodiment, the RAS-dependent/mutant cancer is selected from the group consisting of non-small cell lung cancer, colorectal cancer, pancreatic cancer, AML, and melanoma.

Another embodiment provides a compound as described herein, or a pharmaceutically acceptable salt thereof, for use in a method of treating a subject suffering from breast or ovarian cancer. Another embodiment provides a compound as described herein, or a pharmaceutically acceptable salt thereof, for use in a method of treating a subject suffering from cancer resistant to HER2 and/or EGFR targeted therapies.

In some embodiments, disclosed herein is a compound as described herein for use in method of treatment of cancer, wherein the method is a first line method. In some embodiments, the cancer is a RAS-dependent/mutant cancer. In some embodiments, the RAS-dependent/mutant cancer is selected from the group consisting of non-small cell lung cancer, colorectal cancer, pancreatic cancer, AML, and melanoma.

In some embodiments, disclosed herein is a compound as described herein for use in a method of treating a subject suffering from a cancer that is advanced, metastatic, refractory, and/or relapsed. In some embodiments, the cancer is a RAS-dependent/mutant cancer. In some embodiments, the RAS-dependent/mutant cancer is selected from the group consisting of non-small cell lung cancer, colorectal cancer, pancreatic cancer, AML, and melanoma, wherein the cancer is advanced, metastatic, refractory, and/or relapsed. In some embodiments, the cancer is refractory to chemotherapy and/or immunotherapy (e.g., immunotherapy with a PD-1 inhibitor such as nivolumab, and/or a PD-L1 inhibitor such as atezolizumab).

Another embodiment provides a compound as described herein, or a pharmaceutically acceptable salt thereof, for use in a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides a compound as described herein, or a pharmaceutically acceptable salt thereof, for use in a method of promoting T cell immune response in a subject, comprising administering to the subject a therapeutically effective amount of a compound as described herein.

Another embodiment provides a compound as described herein, or a pharmaceutically acceptable salt thereof, for use in a method of treating a subject suffering from cancer.

Another embodiment provides a compound as described herein, or a pharmaceutically acceptable salt thereof, for use in a method of inhibiting TBK1 in a subject. Another embodiment provides a compound as described herein, or a pharmaceutically acceptable salt thereof, for use in a method of inhibiting IKKε in a subject.

Another embodiment provides the use of a compound as described herein, or a pharmaceutically acceptable salt thereof, in the manufacture of a medicament for treating a subject having a disease or condition responsive to the inhibition of TBK1. In an embodiment, the disease is cancer. Another embodiment the use of a compound as described herein, or a pharmaceutically acceptable salt thereof, in the manufacture of a medicament for treating a subject having a disease or condition responsive to the inhibition of IKKε.

Another embodiment provides the use of a compound as described herein, or a pharmaceutically acceptable salt thereof, in the manufacture of a medicament for treating a subject suffering from a RAS-dependent/mutant cancer. In an embodiment, the RAS-dependent/mutant cancer is selected from the group consisting of non-small cell lung cancer, colorectal cancer, pancreatic cancer, AML, and melanoma.

Another embodiment provides the use of a compound as described herein, or a pharmaceutically acceptable salt thereof, in the manufacture of a medicament for treating a subject suffering from breast or ovarian cancer. Another embodiment provides the use of a compound as described herein, or a pharmaceutically acceptable salt thereof, in the manufacture of a medicament for treating a subject suffering from cancer resistant to HER2 and EGFR targeted therapies.

Another embodiment provides the use of a compound as described herein, or a pharmaceutically acceptable salt thereof, in the manufacture of a medicament for promoting T cell immune response in a subject.

In some embodiments, disclosed herein is the use of a compound as described herein, or a pharmaceutically acceptable salt thereof, in the manufacture of a medicament for treating cancer, wherein the medicament is a first line method. In some embodiments, the cancer is a RAS-dependent/mutant cancer. In some embodiments, the RAS-dependent/mutant cancer is selected from the group consisting of non-small cell lung cancer, colorectal cancer, pancreatic cancer, AML, and melanoma.

In some embodiments, disclosed herein is the use of a compound as described herein, or a pharmaceutically acceptable salt thereof, in the manufacture of a medicament for treating cancer that is advanced, metastatic, refractory, and/or relapsed. In some embodiments, the cancer is a RAS-dependent/mutant cancer. In some embodiments, the RAS-dependent/mutant cancer is selected from the group consisting of non-small cell lung cancer, colorectal cancer, pancreatic cancer, AML, and melanoma, wherein the cancer is advanced, metastatic, refractory, and/or relapsed. In some embodiments, the cancer is refractory to chemotherapy and/or immunotherapy (e.g., immunotherapy with a PD-1 inhibitor such as nivolumab, and/or a PD-L1 inhibitor such as atezolizumab.

Another embodiment provides the use of a compound as described herein, or a pharmaceutically acceptable salt thereof, in the manufacture of a medicament for treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis.

Another embodiment provides the use of a compound as described herein, or a pharmaceutically acceptable salt thereof, in the manufacture of a medicament for inhibiting TBK1 in a subject. Another embodiment provides the use of a compound as described herein, or a pharmaceutically acceptable salt thereof, in the manufacture of a medicament for inhibiting IKKε in a subject.

The pharmaceutical compositions of compounds of Formula (I) (including compounds of Formulae (Ia)-(If)) may be administered in either single or multiple doses by any of the accepted modes of administration of agents having similar utilities, for example as described in those patents and patent applications incorporated by reference herein, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The pharmaceutical compositions of compounds of Formulae (I)-(Ii) may be administered in either single or multiple doses by any of the accepted modes of administration of agents having similar utilities, for example as described in those patents and patent applications incorporated by reference herein, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In one aspect, the compounds described herein may be administered orally. Oral administration may be via, for example, capsule or enteric coated tablets. In making the pharmaceutical compositions that include at least one compound of Formula (I)-(If), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

In some embodiments, pharmaceutical compositions that include at least one compound of Formula (I)-(Ii), or a pharmaceutically acceptable salt, may be administered orally. Oral administration may be via, for example, capsule or enteric coated tablets. In making the pharmaceutical compositions that include at least one compound of Formula (I)-(Ii), or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound of Formula (I)-(If), or a pharmaceutically acceptable salt, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See e.g., U.S. Pat. Nos. 5,023,252, 4,992,445 and 5,001,139. Such patches may be constructed for continuous, pulsatile, or on demand delivery of pharmaceutical agents.

In some embodiments, the compositions that include at least one compound of Formula (I)-(Ii), or a pharmaceutically acceptable salt, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845, 770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See e.g., U.S. Pat. Nos. 5,023,252, 4,992,445 and 5,001,139. Such patches may be constructed for continuous, pulsatile, or on demand delivery of pharmaceutical agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule).

The compounds are generally administered in a pharmaceutically effective amount. In some embodiments, for oral administration, each dosage unit contains from about 1 mg to about 1000 mg of a compound described herein, for example from about 50 mg to about 500 mg, for example about 10 mg, 50 mg, about 75 mg, about 100 mg, about 150 mg, about 200 mg, about 250 mg, or about 300 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 500 mg of an active ingredient.

Frequency of dosing may also vary depending on the compound used and the particular disease or condition treated. In some embodiments, for example, for the treatment of an autoimmune and/or inflammatory disease, a dosage regimen of 4 times daily or less is used. In some embodiments, a dosage regimen of 1 or 2 or 3 times daily is used. It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease in the subject undergoing therapy.

For preparing solid compositions such as tablets, the principal active ingredient may be mixed with a pharmaceutical excipient to form a solid preformulation composition containing a homogeneous mixture of a compound of Formula (I)-(If), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

In some embodiments, for preparing solid compositions such as tablets, the principal active ingredient may be mixed with a pharmaceutical excipient to form a solid preformulation composition containing a homogeneous mixture of a compound of Formula (I)-(Ii), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Kits that include a compound of Formula (I)-(If), or a pharmaceutically acceptable salt, thereof, and suitable packaging are provided. In one embodiment, a kit further includes instructions for use. In one aspect, a kit includes a compound of Formula (I)-(If), or a pharmaceutically acceptable salt thereof, and instructions for use of the compounds in the treatment of the diseases or conditions described herein.

Kits that include a compound of Formula (I)-(Ii), or a pharmaceutically acceptable salt, thereof, and suitable packaging are provided. In some embodiments, a kit further includes instructions for use. In some embodiments, a kit includes a compound of Formula (I)-(Ii), or a pharmaceutically acceptable salt thereof, and instructions for use of the compounds in the treatment of the diseases or conditions described herein.

Articles of manufacture that include a compound of Formula (I)-(If), or a pharmaceutically acceptable salt thereof, in a suitable container are provided. The container may be a vial, jar, ampoule, preloaded syringe, and intravenous bag.

In some embodiments, articles of manufacture that include a compound of Formula (I)-(Ii), or a pharmaceutically acceptable salt thereof, in a suitable container are provided. The container may be a vial, jar, ampoule, preloaded syringe, and intravenous bag.

The compounds described herein may be used or combined with one or more therapeutic agents, such as a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof. These therapeutic agents may be in the form of compounds, antibodies, polypeptides, or polynucleotides. In some embodiments, the application provides a product comprising a compound described herein and an additional therapeutic agent as a combined preparation for simultaneous, separate, or sequential use in therapy, e.g., a method of treating cancer.

Targets

In some embodiments, the compounds described herein may be used or combined with one or more of the additional therapeutic agents. The one or more therapeutic agents include, but are not limited to, an inhibitor, agonist, antagonist, ligand, modulator, stimulator, blocker, activator or suppressor of a gene, ligand, receptor, protein, factor such as:

Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1, CHK2), chemokine (C—C motif) receptor (such as CCR2, CCR4, CCR5), chemokine (C—X—C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement C3, Connective tissue growth factor, COPS signalosome subunit 5, CSF-1 (colony-stimulating factor 1 receptor), CSF2 gene, CTLA-4 (cytotoxic T-lymphocyte protein 4) receptor, Cyclin D1, Cyclin G1, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase, Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releaseing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB1 gene, Human leukocyte antigen (HLA), Human papillomavirus (such as E6, E7) protein, Hyaluronic acid, Hyaluronidase, Hypoxia inducible factor-1 alpha, Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAK1, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KISS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPK1), Hepatocyte growth factor receptor (MET) gene, macrophage colony-stimulating factor (MCSF) ligand, Macrophage migration inhibitory fact, MAGEC1 gene, MAGEC2 gene, Major vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2,3,6), Membrane copper amine oxidase, Mesothelin, MET tyrosine kinase, Metabotropic glutamate receptor 1, Metalloreductase STEAP1 (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor, platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Proto-oncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Ros1 tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E2I (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

Mechanism of Action

The compounds described herein may be used or combined with one or more additional therapeutic agents, which may be, for example, categorized by their mechanism of action into the following groups:

- anti-metabolites/anti-cancer agents, such as pyrimidine analogs floxuridine, capecitabine, cytarabine, CPX-351 (liposomal cytarabine, daunorubicin), and TAS-118;
- purine analogs, folate antagonists (such as pralatrexate), and related inhibitors;
- antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);
- DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;
- DNA-hypomethylating agents, such as guadecitabine (SGI-110);
- antibiotics such as dactinomycin, daunorubicin, doxorubicin, idarubicin, anthracyclines, mitoxantrone, bleomycins, plicamycin (mithramycin);
- enzymes such as L-asparaginase which systemically metabolizes L-asparagine and deprives cells which do not have the capacity to synthesize their own asparagine;
- antiplatelet agents;
- DNAi oligonucleotides targeting Bcl-2, such as PNT2258;
- agents that activate or reactivate latent human immunodeficiency virus (HIV), such as panobinostat and romidepsin;
- asparaginase stimulators, such as crisantaspase (Erwinase®) and GRASPA (ERY-001, ERY-ASP);
- pan-Trk, ROS1 and ALK inhibitors, such as entrectinib;
- anaplastic lymphoma kinase (ALK) inhibitors, such as alectinib;
- antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);
- antiproliferative/antimitotic antimetabolites, such as folic acid analogs (methotrexate);
- platinum coordination complexes (cisplatin, oxiloplatinim, and carboplatin), procarbazine, hydroxyurea, mitotane, and aminoglutethimide;
- hormones, hormone analogs (estrogen, tamoxifen, goserelin, bicalutamide, and nilutamide), and aromatase inhibitors (letrozole and anastrozole);
- anticoagulants such as heparin, synthetic heparin salts, and other inhibitors of thrombin;
- fibrinolytic agents such as tissue plasminogen activator, streptokinase, urokinase, aspirin, dipyridamole, ticlopidine, and clopidogrel;
- antimigratory agents;
- antisecretory agents (breveldin);
- immunosuppressives, such as tacrolimus, sirolimus, azathioprine, and mycophenolate;
- growth factor inhibitors, and vascular endothelial growth factor inhibitors;
- fibroblast growth factor inhibitors, such as FPA14;
- angiotensin receptor blockers, nitric oxide donors;
- antisense oligonucleotides, such as AEG35156;
- DNA interference oligonucleotides, such as PNT2258, AZD-9150;
- anti-ANG-2 antibodies, such as MEDI3617, and LY3127804;
- anti-MET/EGFR antibodies, such as LY3164530;
- anti-EFGR antibodies, such as ABT-414;
- anti-CSF1R antibodies, such as emactuzumab, LY3022855, AMG-820;
- anti-CD40 antibodies, such as RG7876;
- anti-endoglin antibodies, such as TRC105;
- anti-CD45 antibodies, such as 131I-BC8 (lomab-B);
- anti-HER3 antibodies, such as LJM716;
- anti-HER2 antibodies, such as margetuximab, MEDI4276;
- anti-HLA-DR antibodies, such as IMMU-114;
- anti-IL-3 antibodies, such as JNJ-56022473;
- anti-OX40 antibodies, such as MEDI6469, MEDI6383, MEDI0562, MOXR0916, PF-04518600, RG-7888, GSK-3174998;
- anti-EphA3 antibodies, such as KB-004;
- anti-CD20 antibodies, such as obinutuzumab;
- anti-CD20/CD3 antibodies, such as RG7828;
- anti-CD37 antibodies, such as AGS67E;
- anti-ENPP3 antibodies, such as AGS-16C3F;
- anti-FGFR-3 antibodies, such as LY3076226;
- anti-folate receptor alpha antibodies, such as IMGN853;
- MCL-1 inhibitors, such as AMG-176;
- anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, BGB-A317, and anti-programmed death-ligand 1 (anti-PD-L1) antibodies such as BMS-936559, atezolizumab (MPDL3280A), durvalumab (MEDI4736), avelumab (MSB0010718C), MEDI0680, and MDX1105-01;
- PD-L1/VISTA antagonists such as CA-170;
- ATM (ataxia telangiectasia) inhibitors, such as AZD0156;
- Bromodomain-containing protein 4 (BRD4) inhibitors, such as birabresib dehydrate, FT-1101, PLX-51107, CPI-0610;
- CHK1 inhibitors, such as GDC-0575, LY2606368;

CXCR4 antagonists, such as BL-8040, LY2510924, burixafor (TG-0054), X$^4$P-002;
EXH2 inhibitors, such as GSK2816126;
HER2 inhibitors, such as neratinib, tucatinib (ONT-380);
KDM1 inhibitors, such as ORY-1001, IMG-7289, INCB-59872, GSK-2879552;
CXCR2 antagonists, such as AZD-5069;
GM-CSF antibodies, such as lenzilumab;
Selective estrogen receptor downregulators (SERD), such as fulvestrant (Faslodex®), RG6046, RG6047, and AZD9496;
transforming growth factor-beta (TGF-beta) kinase antagonists, such as galunisertib;
bispecific antibodies, such as MM-141 (IGF-1/ErbB3), MM-111 (Erb2/Erb3), JNJ-64052781 (CD19/CD3);
Mutant selective EGFR inhibitors, such as PF-06747775, EGF816, ASP8273, ACEA-0010, BI-1482694;
Anti-GITR (glucocorticoid-induced tumor necrosis factor receptor-related protein) antibodies, such as MEDI1873;
Adenosine A2A receptor antagonists, such as CPI-444;
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2);
interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME;
claudin-18 inhibitors, such as claudiximab;
β-catenin inhibitors, such as CWP-291;
CD73 antagonists, such as MEDI-9447;
c-PIM inhibitors, such as PIM447;
BRAF inhibitors, such as dabrafenib, vemurafenib, encorafenib (LGX818);
sphingosine kinase-2 (SK2) inhibitors, such as Yeliva® (ABC294640);
cell cycle inhibitors, such as selumetinib (MEK1/2), and sapacitabine;
AKT inhibitors such as MK-2206, ipatasertib, afuresertib, and AZD5363;
anti-CTLA-4 (cytotoxic T-lymphocyte protein-4) inhibitors, such as tremelimumab;
c-MET inhibitors, such as AMG-337, savolitinib, tivantinib (ARQ-197), capmatinib, and tepotinib;
Pan-RAF inhibitors, such as LY3009120;
Raf/MEK inhibitors, such as RG7304;
CSF1R/KIT and FLT3 inhibitors, such as pexidartinib (PLX3397);
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291);
topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150;
corticosteroids, such as cortisone, dexamethasone, hydrocortisone, methylprednisolone, prednisone, prednisolone;
growth factor signal transduction kinase inhibitors;
nucleoside analogs, such as DFP-10917;
Axl inhibitors, such as BGB-324;
BET inhibitors, such as INCB-054329, TEN-010, and the compounds in U.S. Pat. No. 9,458,145;
PARP inhibitors, such as olaparib, rucaparib, veliparib;
Proteasome inhibitors, such as ixazomib, carfilzomib (Kyprolis®);
Glutaminase inhibitors, such as CB-839;
Vaccines, such as peptide vaccine TG-01 (RAS), bacterial vector vaccines such as CRS-207/GVAX, autologous Gp96 vaccine, dendritic cells vaccines, Oncoquest-L vaccine, DPX-Survivac, ProstAtak, DCVAC, ADXS31-142, and rocapuldencel-T (AGS-003), oncolytic vaccine talimogene laherparepvec;
anti-cancer stem cells, such as demcizumab (anti-DLL4, Delta-like ligand 4, Notch pathway), napabucasin (BBI-608);
smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;
interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus) (Inmutag, Inter 2A), interferon alfa-2b follow-on biologic (Biosidus—Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-n1 (Humoferon, SM-10500, Sumiferon);
interferon gamma ligand modulators, such as interferon gamma (OH-6000, Ogamma 100);
IL-6 receptor modulators, such as tocilizumab, siltuximab, AS-101 (CB-06-02, IVX-Q-101);
Telomerase modulators, such as tertomotide (GV-1001, HR-2802, Riavax) and imetelstat (GRN-163, JNJ-63935937);
DNA methyltransferases inhibitors, such as temozolomide (CCRG-81045), decitabine, guadecitabine (S-110, SGI-110), KRX-0402, and azacitidine;
DNA gyrase inhibitors, such as pixantrone and sobuzoxane;
Bcl-2 family protein inhibitors, such as ABT-263, venetoclax (ABT-199), ABT-737, and AT-101;
Notch inhibitors, such as LY3039478, tarextumab (anti-Notch2/3), BMS-906024;
anti-myostatin inhibitors, such as landogrozumab;
hyaluronidase stimulators, such as PEGPH-20;
Wnt pathway inhibitors, such as SM-04755, PRI-724;
gamma-secretase inhibitors, such as PF-03084014;
Grb-2 (growth factor receptor bound protein-2) inhibitors, such as BP1001;
TRAIL pathway-inducing compounds, such as ONC201;

Focal adhesion kinase inhibitors, such as VS-4718, defactinib;

hedgehog inhibitors, such as saridegib, sonidegib (LDE225), glasdegib and vismodegib;

Aurora kinase inhibitors, such as alisertib (MLN-8237), and AZD-2811;

HSPB1 modulators (heat shock protein 27, HSP27), such as brivudine, apatorsen;

ATR inhibitors, such as AZD6738, and VX-970;

mTOR inhibitors, such as sapanisertib and vistusertib (AZD2014);

Hsp90 inhibitors, such as AUY922, onalespib (AT13387);

Murine double minute (mdm2) oncogene inhibitors, such as DS-3032b, RG7775, AMG-232, and idasanutlin (RG7388);

CD137 agonists, such as urelumab;

Anti-KIR monoclonal antibodies, such as lirilumab (IPH-2102);

Antigen CD19 inhibitors, such as MOR208, MEDI-551, AFM-11, inebilizumab;

CD44 binders, such as A6;

CYP17 inhibitors, such as seviteronel (VT-464), ASN-001, ODM-204;

RXR agonists, such as IRX4204;

hedgehog/smoothened (hh/Smo) antagonists, such as taladegib;

complement C3 modulators, such as Imprime PGG;

IL-15 agonists, such as ALT-803

EZH2 (enhancer of zeste homolog 2) inhibitors, such as tazemetostat, CPI-1205, GSK-2816126;

Oncolytic viruses, such as pelareorep;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD1775;

MET inhibitors, such as merestinib;

Rho kinase (ROCK) inhibitors, such as AT13148;

ERK inhibitors, such as GDC-0994;

IAP inhibitors, such as ASTX660;

RNA polymerase II inhibitors, such has lurbinectedin (PM-1183);

Tubulin inhibitors, such as PM-184;

Toll-like receptor 4 (TL4) agonists, such as G100 and PEPA-10;

Elongation factor 1 alpha 2 inhibitors, such as plitidepsin.

Classes

The compounds described herein may be used or combined with one or more additional therapeutic agents, which may belong to, for example, a class of compounds and/or molecules in one of the following groups:

Apoptosis Signal Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences).

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951, tirabrutinib (ONO-4059), PRN-1008, spebrutinib (CC-292), TAK-020.

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

Cyclin-dependent Kinase (CDK) Inhibitors: CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02.

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat.

Indoleamine-pyrrole-2,3-dioxygenase (IDO1) inhibitors: Examples of IDOL inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST.

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019.

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555) and those described in WO 2012/027721 (Gilead Biologics).

Mitogen-activated Protein Kinase (NIEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib.

Phosphatidylinositol 3-kinase (PI3K) Inhibitors: PI3K inhibitors include inhibitors of PI3Kγ, PI3Kδ, PI3Kβ, PI3Kα, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, VTX-1463, and VTX-763.

Toll-like receptor 9 (TLR9) inhibitors: Examples of TLR9 inhibitors include, but are not limited to, IMO-2055, IMO-2125, lefitolimod, litenimod, MGN-1601, and PUL-042.

Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

In some embodiments, a compound of Formula (I)-(Ii), or a pharmaceutically acceptable salt thereof, may be combined with a MEK inhibitor (e.g., binimetinib, selumetinib, trametinib). In some embodiments, the MEK inhibitor is trametinib, or a pharmaceutically acceptable salt or solvate thereof.

In some embodiments, a compound of Formula (I)-(Ii), or a pharmaceutically acceptable salt thereof, may be combined with a JAK inhibitor (e.g., momelotinib, filgotinib). In some embodiments, the JAK inhibitor is momelotinib, or a pharmaceutically acceptable salt or solvate thereof. In some embodiments, the JAK inhibitor is filgotinib, or a pharmaceutically acceptable salt or solvate thereof.

In some embodiments, a compound of Formula (I)-(Ii), or a pharmaceutically acceptable salt thereof, may be combined with a MEK inhibitor and a JAK inhibitor. In some embodiments, the MEK inhibitor is trametinib, or a pharmaceutically acceptable salt or solvate thereof, and the JAK inhibitor is momelotinib, or a pharmaceutically acceptable salt or solvate thereof.

Additional Therapeutic Agents

The compounds described herein may be used or combined with one or more additional therapeutic agents, which may be, for example, a chemotherapeutic agent.

Examples of chemotherapeutic agents include: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone;

2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Anti-Hormonal Agents

In some embodiments, the definition of "chemotherapeutic agent" includes anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®). Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

Examples of progesterone receptor antagonist include onapristone.

Anti-Angiogenic Agents

In some embodiments, the compounds described herein may be used or combined with one or more anti-angiogenic agents.

In some embodiments, anti-angiogenic agents include retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In some embodiments, the compounds described herein may be used or combined with one or more anti-fibrotic agents.

In some embodiments, anti-fibrotic agents include compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds that inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors that block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

In some embodiments, the compounds described herein may be used or combined with one or more immunotherapeutic agents.

In some embodiments, the immunotherapeutic agents include therapeutic antibodies suitable for treating patients. In some embodiments, examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX- 101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

In some embodiments, the compounds described herein may be combined with a cytotoxic T-lymphocyte antigen 4 (CTLA-4)-blocking antibody. In some embodiments, the cytotoxic T-lymphocyte antigen 4 (CTLA-4)-blocking antibody is ipilimumab.

In some embodiments, the compounds described herein may be combined with an immunotherapeutic agent that targets PD-1 and/or PD-L1. In some embodiments, the compounds described herein are combined with at least one PD1 inhibitor and/or a PD-L1 inhibitor selected from the group consisting of nivolumab, lambrolizumab, pembrolizumab, pidilizumab, PDR001, TSR-001, atezolizumab, durvalumab, and avelumab, or a pharmaceutically acceptable salt or solvate of any of the forgoing.

In some embodiments, the compounds described herein may be combined with a PD1 inhibitor selected from the group consisting of nivolumab, lambrolizumab, pembrolizumab, pidilizumab, PDR001, and TSR-001, or a pharmaceutically acceptable salt or solvate of any of the forgoing.

In some embodiments, the compounds described herein may be combined with a PD-L1 inhibitor. In some embodiments, the PD-L1 inhibitor is atezolizumab, durvalumab, or avelumab, or a pharmaceutically acceptable salt or solvate thereof.

The exemplified therapeutic antibodies may be further labeled or combined with a radioisotope particle such as indium-111, yttrium-90 (90Y-clivatuzumab), or iodine-131.
Cancer Gene Therapy and Cell Therapy In some embodiments, the compounds described herein may be used or combined with one or more cancer gene therapy and cell therapy.

In some embodiments, cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019), KTE-C19, JCAR015, BXP-501, AU-105; activated allogeneic natural killer cells CNDO-109-AANK, LFU-835 hematopoietic stem cells.

In another embodiment, the present disclosure provides a method of administering to the subject an additional therapeutic agent in combination with a compound of the present disclosure. Thus, a compound of Formula (I)-(If) may be combined with one or more additional therapeutic agents. The present application provides methods, compositions, kits and articles of manufacture thereof that use or include one or more therapeutic agents inhibiting one or more targets that relate directly or indirectly to cell growth, proliferation, or apoptosis for treating hyperproliferative disorders such as cancers or myeloproliferative neoplasms. The one or more additional therapeutic agent is a compound or molecule that is an Abl inhibitor, an ACK inhibitor, an A2B inhibitor, an ASK inhibitor, an Auroa kinase inhibitor, a BTK inhibitor, a BRD inhibitor, a c-Kit inhibitor, a c-Met inhibitor, a CAK inhibitor, a CaMK inhibitor, a CDK inhibitor, a CK inhibitor, a DDR inhibitor, an EGFR inhibitor, a FAK inhibitor, a Flt-3 inhibitor, a FYN inhibitor, a GSK inhibitor, a HCK inhibitor, a HDAC inhibitor, an IKK inhibitor, an IDH inhibitor, an IKK inhibitor, a JAK inhibitor, a KDR inhibitor, a LCK inhibitor, a LOX inhibitor, a LOXL inhibitor, a LYN inhibitor, a MMP inhibitor, a MEK inhibitor, a MAPK inhibitor, a NEK9 inhibitor, a NPM-ALK inhibitor, a p38 kinase inhibitor, a PDGF inhibitor, a PI3 kinase (PI3K), a PK inhibitor, a PLK inhibitor, a PK inhibitor, a PYK inhibitor, a SYK inhibitor, a TPL2 inhibitor, a STK inhibitor, a STAT inhibitor, a SRC inhibitor, a TBK inhibitor, a TIE inhibitor, a TK inhibitor, a VEGF inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiment, the therapeutic agents are compounds or molecules that target a PI3 kinase (PI3K), a spleen tyrosine kinase (SYK), a Janus kinase (JAK), a Bruton's tyrosine kinase (BTK), or any combination thereof, resulting in the inhibition of one or more targets. In certain embodiments, the therapeutic agent is a PI3δ inhibitor that selectively inhibits PI3K p110 delta isoform (PI3Kδ). In some embodiments, the additional therapeutic agents are a PI3Kδ inhibitor and a JAK1/2 inhibitor.

In some embodiments, the present disclosure provides a method of administering to the subject an additional therapeutic agent in combination with a compound of the present disclosure. Thus, a compound of Formula (I)-(Ii) may be combined with one or more additional therapeutic agents. The present application provides methods, compositions, kits and articles of manufacture thereof that use or include one or more therapeutic agents inhibiting one or more targets that relate directly or indirectly to cell growth, proliferation, or apoptosis for treating hyperproliferative disorders such as cancers or myeloproliferative neoplasms. The one or more additional therapeutic agent is a compound or molecule that is an Abl inhibitor, an ACK inhibitor, an A2B inhibitor, an ASK inhibitor, an Aurora kinase inhibitor, a BTK inhibitor, a BRD inhibitor, a c-Kit inhibitor, a c-Met inhibitor, a CAK inhibitor, a CaMK inhibitor, a CDK inhibitor, a CK inhibitor, a DDR inhibitor, an EGFR inhibitor, a FAK inhibitor, a Flt-3 inhibitor, a FYN inhibitor, a GSK inhibitor, a HCK inhibitor, a HDAC inhibitor, an IKK inhibitor, an IDH inhibitor, an IKK inhibitor, a JAK inhibitor, a KDR inhibitor, a LCK inhibitor, a LOX inhibitor, a LOXL inhibitor, a LYN inhibitor, a MMP inhibitor, a MEK inhibitor, a MAPK inhibitor, a NEK9 inhibitor, a NPM-ALK inhibitor, a p38 kinase inhibitor, a PDGF inhibitor, a PI3 kinase (PI3K), a PK inhibitor, a PLK inhibitor, a PK inhibitor, a PYK inhibitor, a SYK inhibitor, a TPL2 inhibitor, a STK inhibitor, a STAT inhibitor, a SRC inhibitor, a TBK inhibitor, a TIE inhibitor, a TK inhibitor, a VEGF inhibitor, a YES inhibitor, a chemotherapeutic agent, an immunotherapeutic agent, a radiotherapeutic agent, an anti-neoplastic agent, an anti-cancer agent, an anti-proliferation agent, an anti-fibrotic agent, an anti-angiogenic agent, a therapeutic antibody, or any combination thereof. In some embodiment, the therapeutic agents are compounds or molecules that target a PI3 kinase (PI3K), a spleen tyrosine kinase (SYK), a Janus kinase (JAK), a Bruton's tyrosine kinase (BTK), or any combination thereof, resulting in the inhibition of one or more targets. In certain embodiments, the therapeutic agent is a PI3δ inhibitor that selectively inhibits PI3K p110 delta isoform (PI3Kδ). In some embodiments, the additional therapeutic agents are a PI3Kδ inhibitor and a JAK1/2 inhibitor.

In some embodiments, the present disclosure provides a method of administering to the subject an additional therapeutic agent in combination with a compound of the present disclosure. Thus, a compound of Formula (I)-(Ii) may be combined with one or more additional therapeutic agents. The present application provides methods, compositions, kits and articles of manufacture thereof that use or include one or more therapeutic agents inhibiting one or more targets that relate directly or indirectly to cell growth, proliferation, or apoptosis for treating hyperproliferative disorders such as cancers or myeloproliferative neoplasms. The one or more additional therapeutic agent is a compound or molecule that is selected from the group consisting of Inducible T-cell costimulator (ICOS) agonists (e.g. JTX-2011), T-Cell Immunoreceptor with Ig and ITIM Domains (TIGIT) antagonists, Poliovirus Receptor Related Immunoglobulin Domain Containing (PVRIG) antagonists (e.g. COM701), cytotoxic T-lymphocyte antigen 4 (CTLA-4)-blocking antibodies, PD1 and/or PD-L1 inhibitors, Apoptosis Signal-Regulating Kinase (ASK) inhibitors, Bruton's Tyrosine Kinase (BTK) Inhibitors, Cluster of Differentiation 47 (CD47) inhibitors, Cyclin-dependent Kinase (CDK) Inhibitors, Discoidin Domain Receptor (DDR) Inhibitors, Histone Deacetylase (HDAC) Inhibitors, Hematopoietic Progenitor Kinase (HPK1) inhibitors, AKT inhibitors, LIF inhibitors, ERK inhibitors, RAF inhibitors, RAS inhibitors, mTOR inhibitors, YAP inhibitors, TAZ inhibitors, MCL1 inhibitors, BCL2 inhibitors, BCL-XL inhibitors, PLK inhibitors, ROCK inhibitors, Acetyl-CoA Carboxylase (ACC) inhibitors, Fatty Acid Synthase (FASN) inhibitors, Toll-like receptor 7 (TLR7) agonists, MKNK1/2 inhibitors, IL-2, IL-7, and IL-15 fusion proteins or derivatives thereof, T cell vaccines, OX40 agonists, GITR agonists, CD40 agonists, CD40L agonists, CD137 agonists, CD27 agonists, Indoleamine-pyrrole-2,3-dioxygenase (IDO1) inhibitors, Lysyl Oxidase-Like Protein (LOXL) Inhibitors, Matrix Metalloprotease (MMP) Inhibitors, Phosphatidylinositol 3-kinase (PI3K) Inhibitors, Spleen Tyrosine Kinase (SYK) Inhibitors, Toll-like receptor 8 (TLR8) agonists, Toll-like receptor 9 (TLR9) agonists, Tyrosine-kinase Inhibitors (TKIs), T cell immunoglobulin and mucin domain-3 (TIM-3) inhibitors, and lymphocyte activation gene 3 (LAG-3) inhibitors.

The JAK inhibitor binds and inhibits one or more members of JAK family, including JAK1, JAK2, and/or JAK3.

In one embodiment, the JAK inhibitor is Compound A having the structure:

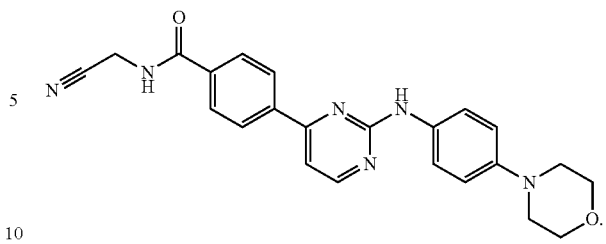

Compound A may be referred to by its compound name: N-(cyanomethyl)-4-[2-(4-morpholinoanilino)pyrimidin-4-yl]benzamide using ChemDraw. Compound A, also referred to as CYT0387 or momelotinib, is a selective inhibitor to JAK2 and JAK1, relative to JAK3. Methods for synthesizing compounds of formula I and Compound A are previously described in U.S. Pat. No. 8,486,941. This reference is hereby incorporated herein by reference in its entirety.

In some embodiments, momelotinib, or a pharmaceutically acceptable salt or solvate thereof, is administered at a dose ranging from about 150 mg to about 300 mg. In some embodiments, the dose is about 150 mg. In some embodiments, the dose is about 300 mg. In some embodiments, momelotinib is administered once daily (QD), twice daily (BID), or three times daily (TID).

In one embodiment, the JAK inhibitor is Filgotinib or salt thereof. Filgotinib is represented by the structure:

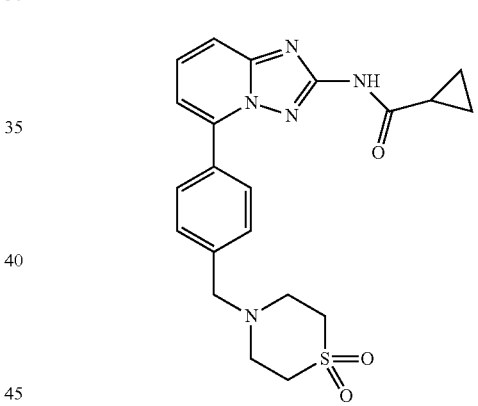

Methods of making and using Filgotinib are known to one of skill in the art. See for example, United States patent publication, US2008135920 incorporated herein by reference.

In some embodiments, filgotinib, or a pharmaceutically acceptable salt or solvate thereof, is administered at a dose ranging from about 50 mg to about 250 mg. In some embodiments, filgotinib is administered at a dose of about 50 mg, about 100 mg, about 125 mg, about 150 mg, about 175 mg, or about 200 mg. In some embodiments, filgotinib is administered once daily (QD), twice daily (BID), or three times daily (TID).

Additional JAK inhibitors include, but are not limited to, ruxolitinib (INCB018424), fedratinib (SAR$^3$02503, TG101348), tofacitinib, baricitinib, lestaurtinib, pacritinib (SB1518), XL019, AZD1480, INCB039110, LY2784544, BMS911543, and NS018.

The PI3K inhibitors inhibit one or more isoforms of Class I PI3K, including PI3Kα, PI3Kβ, PI3Kδ, PI3Kγ, or any combination thereof.

In one embodiment, the additional therapeutic agents are PD-1/PD-L1 check point for inhibitors. In one embodiment, the additional therapeutic agent is a PD-1/PD-L1 inhibitor selected from the group consisting of nivolumab, pidilizumab, pembrolizumab, atezolizumab and MEDI 4736. One if skill in the art is aware of methods of making or using one or more of the additional therapeutic agents in combination with compounds of the present disclosure.

In some embodiments, the compounds described herein are combined with at least one PD1 inhibitor and/or PD-L1 inhibitor. In some embodiments, the PD1 inhibitor is nivolumab, lambrolizumab, pembrolizumab, pidilizumab, PDR001, or TSR-001, or a pharmaceutically acceptable salt or solvate of any of the forgoing. In some embodiments, the PD-L1 inhibitor is atezolizumab, durvalumab, or avelumab, or a pharmaceutically acceptable salt or solvate of any of the forgoing.

In some embodiments, the PI3δ inhibitor is Compound B having the structure:

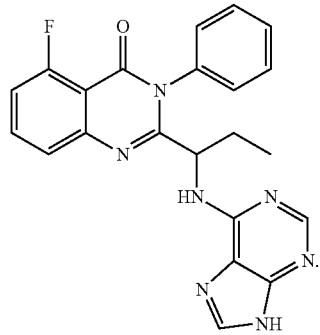

(B)

In other embodiments, Compound B is predominantly the S-enantiomer, having the structure:

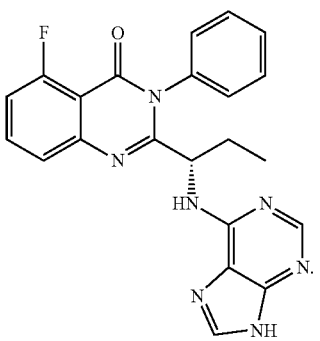

(B)S

The (S)-enantiomer of Compound B may also be referred to by its compound name: (S)-2-(1-((9H-purin-6-yl)amino)propyl)-5-fluoro-3-phenylquinazolin-4(3H)-one using ChemDraw.

In certain embodiments, the PI3δ inhibitor is Compound C having the structure:

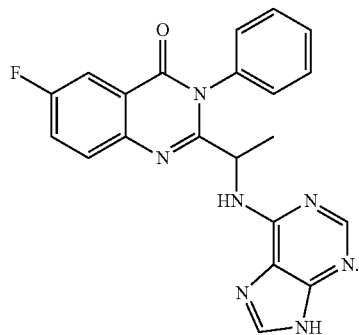

(C)

In additional embodiments, Compound C is predominantly the S-enantiomer, having the structure:

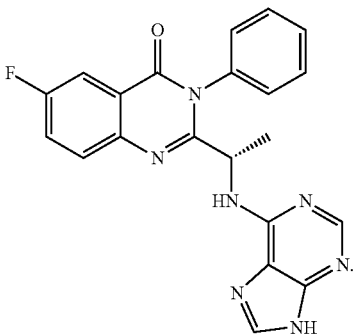

(C)S

The (S)-enantiomer of Compound C may also be referred to by its compound name: (S)-2-(1-((9H-purin-6-yl)amino)ethyl)-6-fluoro-3-phenylquinazolin-4(3H)-one using ChemDraw.

In another embodiment, the PI3K inhibitor is Compound D, having the structure:

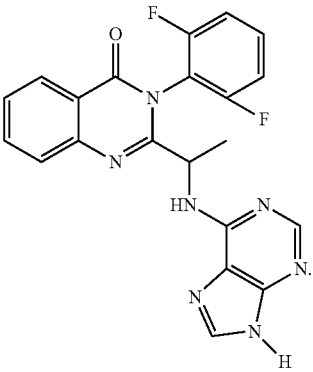

(D)

In one embodiment, Compound D is predominantly the S-enantiomer, having the structure:

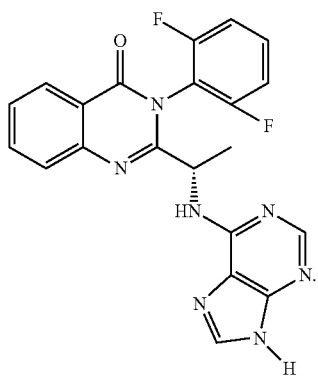

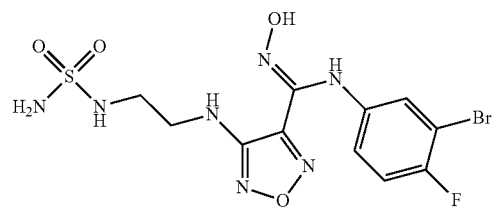 [SMILES: NS(=O)(=O)NCCNc1nonc1/C(=N/O)Nc1ccc(F)c(Br)c1]

In another embodiment, the IDO1 inhibitor is NLG-919 having the following structure:

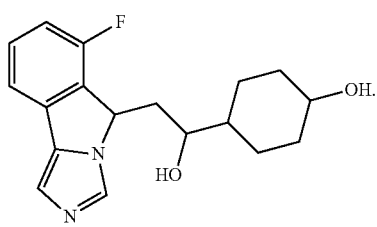 [SMILES: OC1CCC(C(O)CC2c3c(F)cccc3-c3cncn32)CC1]

In another embodiment, the IDO1 inhibitor is indoximod having the following structure:

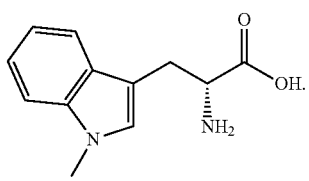 [SMILES: Cn1cc(C[C@@H](N)C(=O)O)c2ccccc21]

The (S)-enantiomer of Compound D may also be referred to by its compound name: (S)-2-(1-((9H-purin-6-yl)amino)ethyl)-3-(2,6-difluorophenyl)quinazolin-4(3H)-one using ChemDraw.

In yet other embodiment, the PI3K inhibitor is Compound E which is named by its compound name: (S)-4-amino-6-((1-(5-chloro-4-oxo-3-phenyl-3,4-dihydroquinazolin-2-yl)ethyl)amino)pyrimidine-5-carbonitrile using ChemDraw. In some other embodiment, the PI3K inhibitor includes the compounds described in U.S. Provisional Application Nos. 61/543,176; 61/581,528; 61/745,429; 61/745,437; and 61/835,333. The references are hereby incorporated herein by reference in their entirety.

Compounds B, C, D, and E are PI3Kδ inhibitors, selectively inhibiting PI3K p110δ compared to other PI3K isoforms. Methods for synthesizing the compounds of formula II, Compounds B, C, D, and E are previously described in U.S. Pat. No. 7,932,260 or U.S. Provisional Application No. 61/581,528. The references are hereby incorporated herein by reference in their entirety.

Additional PI3K inhibitors include but are not limited to XL147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, AS252424, TGX221, TG100115, IC87114, and ZSTK474.

The SYK inhibitor includes but is not limited to 6-(1H-indazol-6-yl)-N-(4-morpholinophenyl)imidazo[1,2-a]pyrazin-8-amine, R406 (tamatinib), R788 (fostamatinib), PRT062607, BAY-61-3606, NVP-QAB 205 AA, R112, or R343, or a pharmaceutically acceptable salt thereof. See Kaur et al., European Journal of Medicinal Chemistry 67 (2013) 434-446. In one embodiment, the Syk inhibitor is 6-(1H-indazol-6-yl)-N-(4-morpholinophenyl)imidazo[1,2-a]pyrazin-8-amine as described in U.S. Pat. No. 8,450,321.

In various embodiments, compounds of Formula (I) may be combined with one or more therapeutic agents, which are IDO1 inhibitors. In one embodiment, the IDO1 inhibitor is INCB24360 having the structure:

In some embodiments, compounds of Formula (I)-(Ii) may be combined with one or more therapeutic agents, which are IDO1 inhibitors. In one embodiment, the IDO1 inhibitor is INCB24360 having the structure:

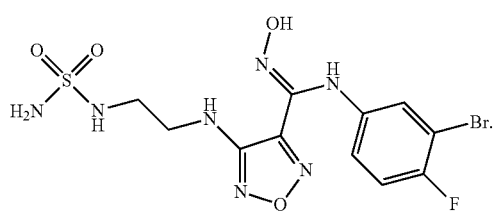 [SMILES: NS(=O)(=O)NCCNc1nonc1/C(=N/O)Nc1ccc(F)c(Br)c1]

In another embodiment, the IDO1 inhibitor is NLG-919 having the following structure:

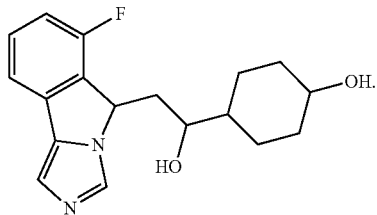 [SMILES: OC1CCC(C(O)CC2c3c(F)cccc3-c3cncn32)CC1]

In another embodiment, the IDO1 inhibitor is indoximod having the following structure:

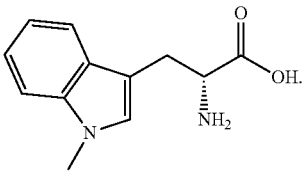 [SMILES: Cn1cc(C[C@@H](N)C(=O)O)c2ccccc21]

In some embodiments, a compound of Formula (I)-(Ii) may be combined with one or more therapeutic agents, which are Mitogen-activated Protein Kinase (MEK) inhibitors. In some embodiments, the MEK inhibitor is trametinib (GSK1120212), or a pharmaceutically acceptable salt or solvate thereof, having the structure:

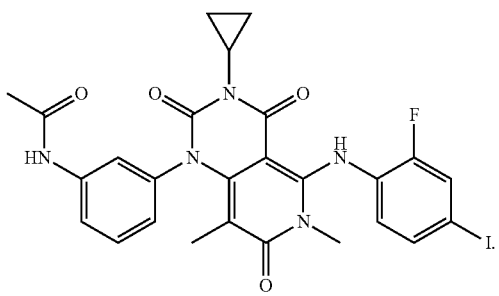 [SMILES: CC(=O)Nc1cccc(-n2c(=O)n(C3CC3)c(=O)c3c(Nc4ccc(I)cc4F)n(C)c(=O)c(C)c32)c1]

Trametinib may be referred to by its compound name: N-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide using ChemDraw. Trametinib inhibits MEK1 and MEK2.

In some embodiments, trametinib is administered as a solvate. In some embodiments, trametinib dimethyl sulfoxide, having the following structure, is administered to the subject.

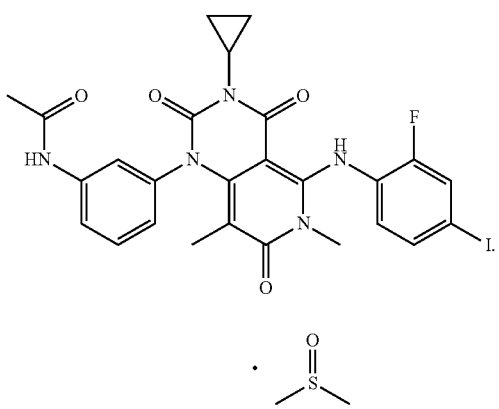

In some embodiments, trametinib, or a pharmaceutically acceptable salt or solvate thereof, is administered at a dose ranging from about 0.5 mg to about 2.0 mg. In some embodiments, trametinib is administered at a dose of about 0.5 mg, about 1.0 mg, about 1.5 mg, or about 2.0 mg. In some embodiments, trametinib is administered once daily (QD), twice daily (BID), or three times daily (TID).

In some embodiments, the MEK inhibitor is selumetinib, or a pharmaceutically acceptable salt or solvate thereof, having the structure:

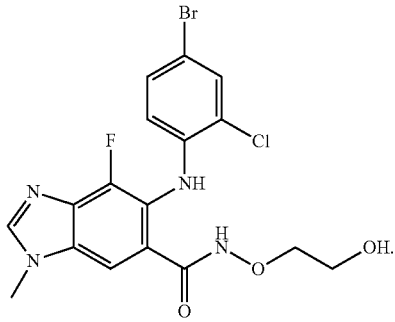 [SMILES: Cn1cnc2c(F)c(Nc3ccc(Br)cc3Cl)c(C(=O)NOCCO)cc21]

Selumetinib may be referred to by its compound name: 6-(4-bromo-2-chloroanilino)-7-fluoro-N-(2-hydroxyethoxy)-3-methylbenzimidazole-5-carboxamide using ChemDraw. Selumetinib inhibits MEK1 and MEK2. In some embodiments, selumetinib, or a pharmaceutically acceptable salt or solvate thereof, is administered at a dose ranging from about 100 mg to about 1500 mg. In some embodiments, selumetinib is administered at a dose of about 100 mg, about 150 mg, and about 1500 mg. In some embodiments, selumetinib is administered once daily (QD), twice daily (BID), or three times daily (TID).

In some embodiments, the MEK inhibitor is binimetinib, or a pharmaceutically acceptable salt or solvate thereof, having the structure:

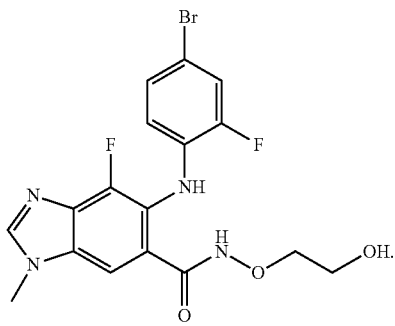 [SMILES: Cn1cnc2c(F)c(Nc3ccc(Br)cc3F)c(C(=O)NOCCO)cc21]

Binimetinib may be referred to by its compound name: 5-((4-bromo-2-fluorophenyl)amino)-4-fluoro-N-(2-hydroxyethoxy)-1-methyl-1H-benzo[d]imidazole-6-carboxamide using ChemDraw. Binimetinib inhibits MEK1 and MEK2.

In some embodiments, binimetinib, or a pharmaceutically acceptable salt or solvate thereof, is administered at a dose ranging from about 30 mg to about 45 mg. In some embodiments, binimetinib is administered at a dose of about 30 mg. In some embodiments, binimetinib is administered at a dose of about 45 mg. In some embodiments, binimetinib is administered once daily (QD), twice daily (BID), or three times daily (TID).

In some embodiments, the compounds described herein are combined with a cytotoxic T-lymphocyte antigen 4 (CTLA-4)-blocking antibody. In some embodiments, the cytotoxic T-lymphocyte antigen 4 (CTLA-4)-blocking antibody is ipilimumab.

In some embodiments, the compounds described herein are combined with a Toll-like receptor 7 (TLR7) agonist. Examples of TLR7 modulators include vesatolimod, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences). In some embodiments, the compounds described herein are combined with vesatolimod.

Another embodiment provides a compound of Formula (I)-(If), or a pharmaceutically acceptable salt thereof, in combination with a one or more additional therapeutic agents, for example one or more additional therapeutic agents from the above list of additional therapeutic agents, for use in: therapy; a method of treating a subject having a disease or condition responsive to the inhibition of TBK1, such as cancer; a method of treating a subject having a disease or condition responsive to the inhibition of IKKε; a method of treating a subject suffering from a RAS-dependent/mutant cancer, such as non-small cell lung cancer, colorectal cancer, pancreatic cancer, AML, and melanoma; a method of treating a subject suffering from breast or ovarian cancer; a method of treating a subject suffering from cancer resistant to HER2 and EGFR targeted therapies; a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or a method of treating a subject suffering from cancer.

In some embodiments, a compound of Formula (I)-(Ii), or a pharmaceutically acceptable salt thereof, in combination with a one or more additional therapeutic agents, for example one or more additional therapeutic agents from the above list of additional therapeutic agents, for use in: therapy; a method of treating a subject having a disease or condition responsive to the inhibition of TBK1, such as cancer; a method of treating a subject having a disease or condition responsive to the inhibition of IKKε; a method of treating a subject suffering from a RAS-dependent/mutant cancer, such as non-small cell lung cancer, colorectal cancer, pancreatic cancer, AML, and melanoma; a method of treating a subject suffering from breast or ovarian cancer; a method of treating a subject suffering from cancer resistant to HER2 and EGFR targeted therapies; a method of treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or a method of treating a subject suffering from cancer.

Another embodiment provides the use of a compound of Formula (I)-(If), or a pharmaceutically acceptable salt thereof, in combination with a one or more additional therapeutic agents, for example one or more additional therapeutic agents from the above list of additional therapeutic agents, in the manufacture of a medicament for: therapy; treating a subject having a disease or condition responsive to the inhibition of TBK1, such as cancer; treating a subject having a disease or condition responsive to the inhibition of IKKε; treating a subject suffering from a RAS-dependent/mutant cancer, such as non-small cell lung cancer, colorectal cancer, pancreatic cancer, AML, and melanoma; treating a subject suffering from breast or ovarian cancer; treating a subject suffering from cancer resistant to HER2 and EGFR targeted therapies; treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or treating a subject suffering from cancer.

Various embodiments provide the use of a compound of Formula (I)-(Ii), or a pharmaceutically acceptable salt thereof, in combination with a one or more additional therapeutic agents, for example one or more additional therapeutic agents from the above list of additional therapeutic agents, in the manufacture of a medicament for: therapy; treating a subject having a disease or condition responsive to the inhibition of TBK1, such as cancer; treating a subject having a disease or condition responsive to the inhibition of IKKε; treating a subject suffering from a RAS-dependent/mutant cancer, such as non-small cell lung cancer, colorectal cancer, pancreatic cancer, AML, and melanoma; treating a subject suffering from breast or ovarian cancer; treating a subject suffering from cancer resistant to HER2 and EGFR targeted therapies; treating a subject suffering from a disease selected from the group consisting of Rheumatoid arthritis (RA), Inflammatory bowel disease (IBD), Chronic obstructive pulmonary disease (COPD), Systemic lupus erythematosus (SLE), Polymositis, Systemic sclerosis, Type 2 diabetes, Obesity and Hepatic steatosis; or treating a subject suffering from cancer.

In an embodiment, the above combinations comprise one additional therapeutic agent, for example one additional therapeutic agent selected from the additional therapeutic agents listed above.

Another embodiment of the present disclosure provides a product comprising a compound of Formula (I)-(If), or a pharmaceutically acceptable salt thereof, and one or more additional therapeutic agents, such as one or more of the additional therapeutic agents listed above, as a combined preparation for simultaneous, separate or sequential use in therapy.

In some embodiments of the present disclosure provides a product comprising a compound of Formula (I)-(Ii), or a pharmaceutically acceptable salt thereof, and one or more additional therapeutic agents, such as one or more of the additional therapeutic agents listed above, as a combined preparation for simultaneous, separate or sequential use in therapy.

Method of Making

Synthesis of certain compounds and intermediates used to prepare compounds, are detailed in the following sections.

Abbreviations

The following is a list of abbreviations and acronyms used throughout the application:

| Abbreviation | Meaning |
| --- | --- |
| °C. | Degree Celsius |
| ATP | Adenosine-5'-triphosphate |
| AcOH | Acetic acid |
| ACN | Acetonitrile |
| CAN | Ceric ammonium nitrate |
| CDI | 1,1'-carbonyldiimidazole |
| conc. | Concentrated |
| d | Doublet |
| DABCO | 1,4-Diazabicyclo[2.2.2]octane |
| DAST | (Diethylamino)sulfur trifluoride |
| dd | Doublet of doublets |
| DCE | 1,2-dichloroethane |

| Abbreviation | Meaning |
| --- | --- |
| DCM | Dichloromethane |
| DEAD | Diethyl azodicarboxylate |
| DIAD | Diisopropyl azodicarboxylate |
| DIPEA/DIEA | N,N-diisopropylethylamine |
| DMAP | 4-dimethylaminopyridine |
| DME | 1,2-dimethoxyethane |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| ETOAC | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| hERG | human Ether-a-go-go Related Gene |
| HMDS | hexamethyldisilazane(azide) |
| HPLC | High-performance liquid chromatography |
| h/hr | Hours |
| Hz | Hertz |
| $IC_{50}$ | The half maximal inhibitory concentration |
| J | Coupling constant |
| Kg | Kilogram |
| LAH | Lithium ammonium hydride |
| LCMS/LC-MS | Liquid chromatography-mass spectrometry |
| LDA | Lithium diisopropylamide |
| M | Molar |
| m | multiplet |
| m/z | mass-to-charge ratio |
| M+ | Mass peak |
| M + H | Mass peak plus hydrogen |
| mCPBA | 3-chloroperoxybenzoic acid |
| Me | Methyl |
| MeOH | Methyl alcohol/methanol |
| mg | Milligram |
| MHz | Megahertz |
| min/m | Minute |
| ml/mL | Milliliter |
| mM | Millimolar |
| mmol | Millimole |
| MS | Mass spectroscopy |
| mw | Microwave |
| N | Normal |
| mol | Mole |
| NMP | N-methylpyrrolidinone |
| NMR | Nuclear magnetic resonance |
| Ph | Phenyl |
| Pd(PPh$_3$)$_4$ | Tetrakis(triphenylphosphine)palladium(0) |
| PEPPSI™-IPr | [1,3-Bis(2,6-Diisopropylphenyl)imidazol-2-ylidene](3-chloropyridyl)palladium(II) dichloride |
| ppm | Parts per million |
| prep | Preparative |
| Rf | Retention factor |
| RP | Reverse phase |
| RT/rt | Room temperature |
| s | Second |
| s | Singlet |
| SEM | 2-(Trimethylsilyl)ethoxymethyl |
| t | Triplet |
| TEA | Triethylamine |
| TFA | Trifluoroacetic acid |
| THF | Tetrahydrofuran |
| 2-MeTHF/Me—THF | 2-Methyl Tetrahydrofuran |
| TLC | Thin layer chromatography |
| TMS | trimethylsilyl |
| WT | Wild type |
| δ | Chemical shift |
| μg | Microgram |
| μL/μl | Microliter |
| μM | Micromolar |
| μm | Micrometer |
| μmol | Micromole |

Example numbers for reactions or compounds are listed for convenience.

All operations involving moisture and/or oxygen sensitive materials were conducted under an atmosphere of dry nitrogen in pre-dried glassware. Unless noted otherwise, materials were obtained from commercially available sources and used without further purification.

Nuclear magnetic resonance ("NMR") spectra were recorded on a Varian 400 MHz resonance spectrometer. 1H NMR chemical shifts are given in parts per million (δ) downfield from tetramethylsilane ("TMS") using TMS or the residual solvent signal (CHCl3=δ 7.24, DMSO=δ 2.50) as internal standard. 1H NMR information is tabulated in the following format: multiplicity (s, singlet; d, doublet; t, triplet; q, quartet; m, multiplet), coupling constant(s) (J) in Hertz, number of protons. The prefix app is occasionally applied in cases where the true signal multiplicity was unresolved and br indicates the signal in question was broadened.

The compounds were named using ChemBioDraw Ultra Version 12.0.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. Compounds containing —SO$_2$F substituents are prepared according to Sulfur(VI) Fluoride Exchange (SuFEx): Another Good Reaction for Click Chemistry, Angew et al., Chem. Int. Ed. 2014, 53, 2-21. The methods or features described in various Examples may be combined or adapted in various ways to provide additional ways of making the compounds described herein.

General Scheme 1

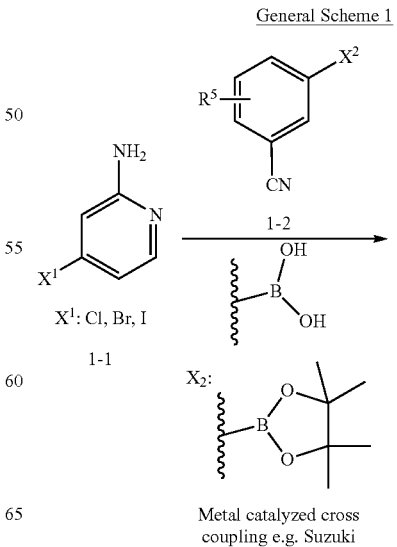

Metal catalyzed cross coupling e.g. Suzuki

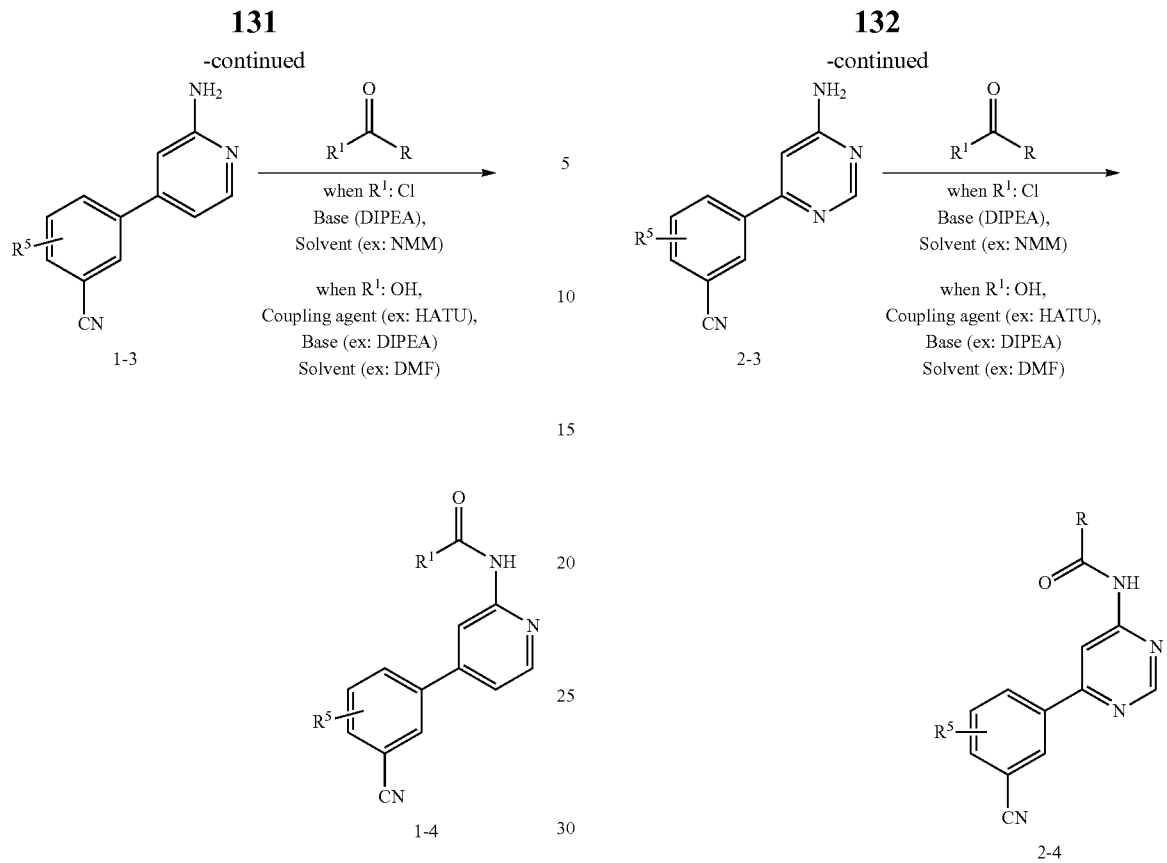

Scheme 1 shows a general synthesis of compounds beginning with metal catalyzed cross coupling reactions (e.g. Suzuki) of the halo aminopyridine analogs (1-1) with the boronate or boronic acid analogs (1-2) to yield aminopyridine analogs (1-3) which undergoes coupling reaction with either acid in the presence of a coupling reagent such as HATU, HOBt and base or with acid chlorides in the presence of a base such as TEA or DIPEA in appropriate solvent to yield final compounds of the type 1-4. One of skill in the art is aware of methods of preparing the desired Compound 1-2.

General Scheme 2

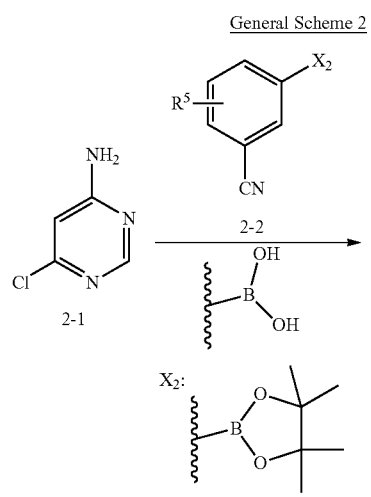

Scheme 2 shows a general synthesis of compounds beginning with metal catalyzed cross coupling reactions (e.g. Suzuki) of the 6-chloropyrimidin-4-amine (2-1) with the boronate or boronic acid partner (2-2) to yield aminopyrimidine analogs (2-3) which undergoes coupling reaction with either acids in the presence of a coupling reagent such as HATU, HOBt and base or with acid chlorides in the presence of a base such as TEA or DIPEA in appropriate solvent to yield final compounds of the type 2-4. One of skill in the art is aware of methods of preparing the desired Compound 2-2.

General Scheme 3

3-1

$R^2$: F, Me, $CF_2H$, $CF_3$, CN etc $X^1$: Cl, Br

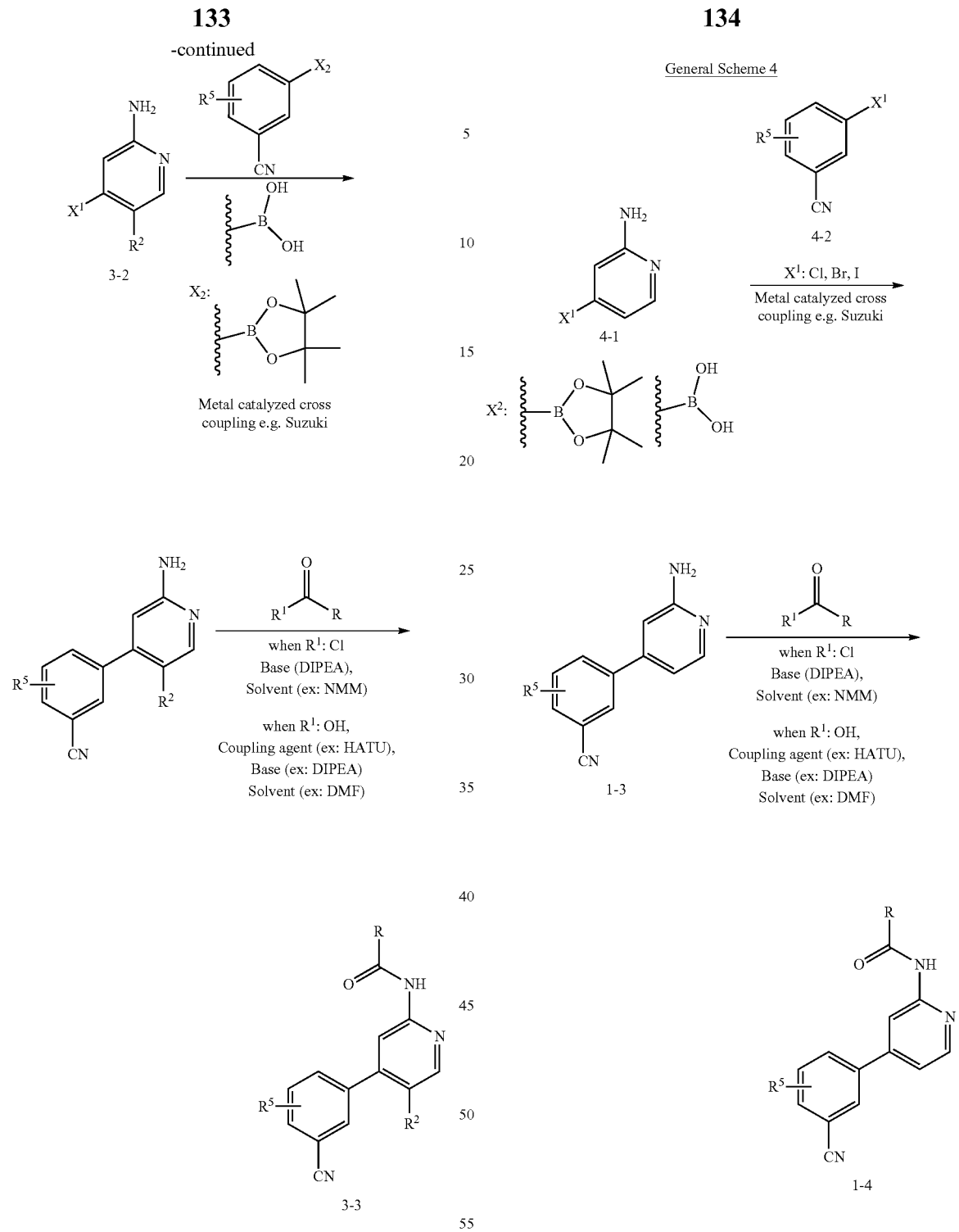

Scheme 3 shows a general synthesis of compounds beginning with displacement of the fluorine from 2-fluoropyridine analogs (3-1) via SNAr with ammonia (ex: ammonium hydroxide) at elevated temperature to give the corresponding aminopyridine analogs (3-2). The Amino pyridimidine analog (3-2) undergoes similar reaction sequence to General Scheme 1 to yield the final compounds of type 3-3.

Final Compounds of type 1-4 can also be prepared by starting from the boronate or boronic acid of the 2-aminopyridine analogs (4-1) which undergoes metal catalyzed cross coupling reactions (e.g. Suzuki) with the benzonitrile analog ($X^1$: Cl, Br, I, OTf) (4-2) to yield aminopyridine analogs (1-3) which undergoes coupling reaction with either acid in the presence of a coupling reagent such as HATU, HOBt and base or with acid chlorides in the presence of a base such as TEA or DIPEA in appropriate solvent.

General Scheme 5

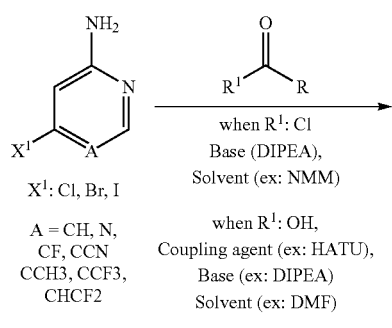

General Scheme 6

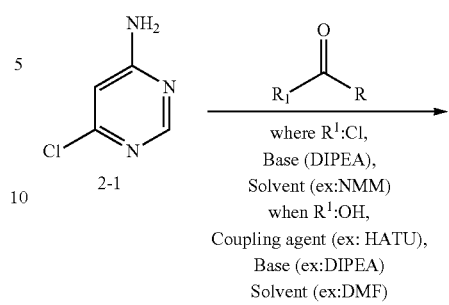

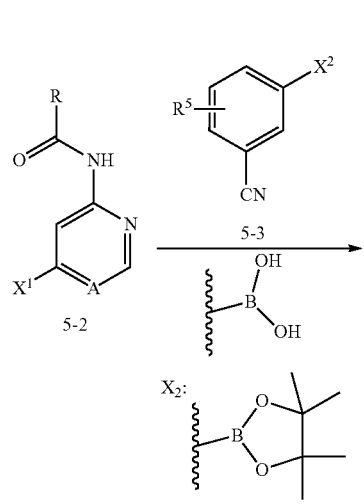

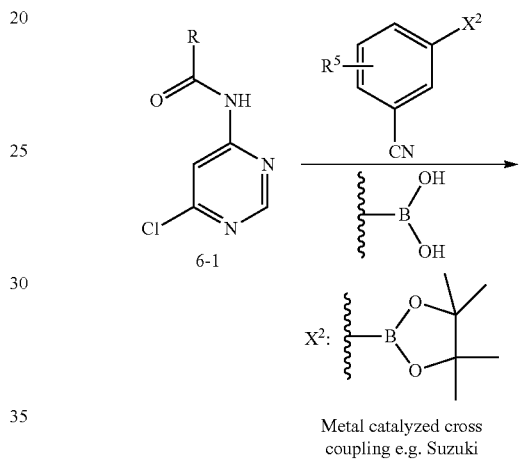

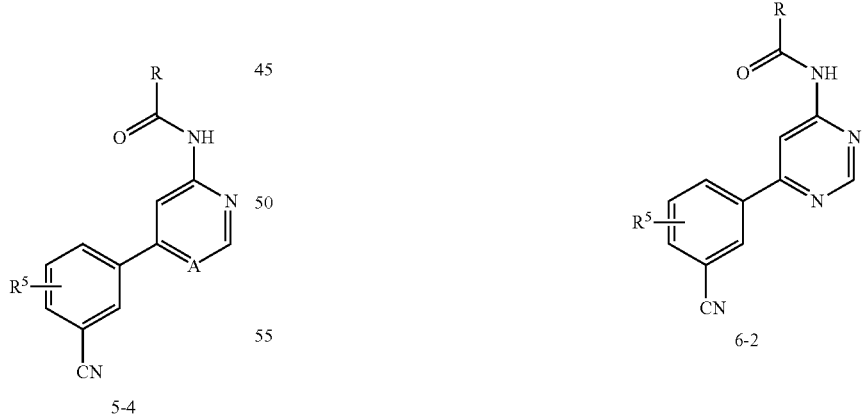

Final Compounds of type 5-4 can also be prepared by first coupling the substituted aminopyridine/pyrimidine analogs (5-1) with either acid in the presence of a coupling reagent such as HATU or HOBt and base or with acid chlorides in the presence of a base such as TEA or DIPEA in appropriate solvent to give intermediate 5-2 which undergoes metal catalyzed cross coupling reactions (e.g. Suzuki) with boronate or boronic acid analogs (5-3)

Final Compounds of type 6-2 can also be prepared by first coupling 6-chloropyrimidin-4-amine (2-1) the with either acid in the presence of a coupling reagent such as HATU, HOBt and base or with acid chlorides in the presence of a base such as TEA or DIPEA in appropriate solvent to give acylamino pyrimidine analogs (6-1) which undergoes metal catalyzed cross coupling reactions (e.g. Suzuki) with boronate or boronic acid analogs.

General Scheme 7

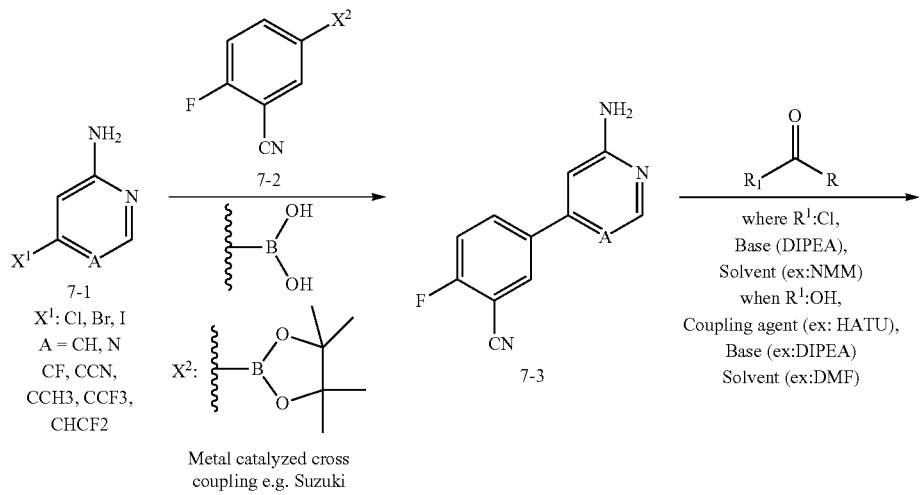

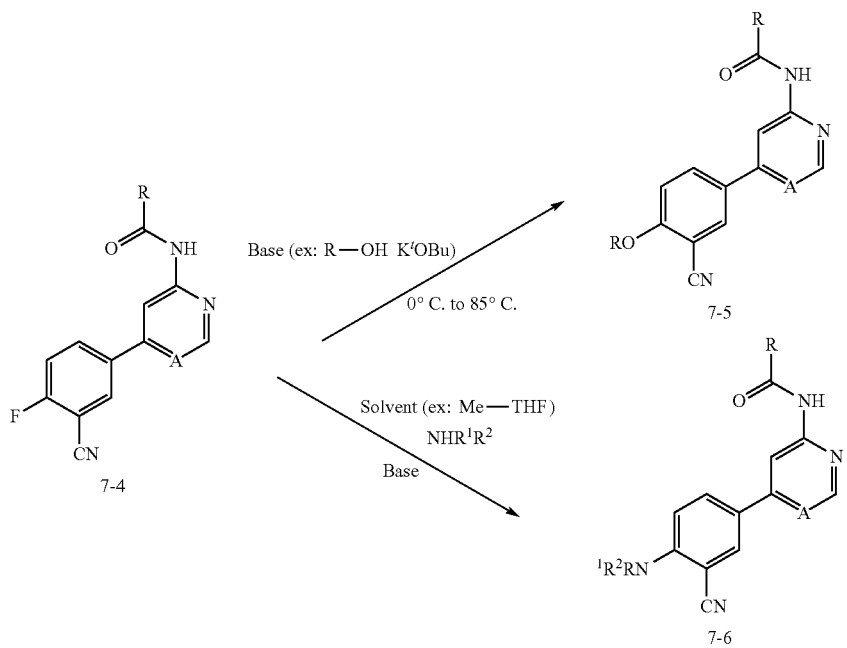

Scheme 7 shows a general synthesis of compounds beginning with metal catalyzed cross coupling reactions (e.g. Suzuki) of the aminopyridine/pyrimidine analogs (7-1) with the substituted Fluorobenzonitrile boronate or boronic acid analogs (7-2) to yield the coupling products (7-3) which undergoes coupling reaction with either acids in the presence of a coupling reagent such as HATU, HOBt and base or with acid chlorides in the presence of a base such as TEA or DIPEA in appropriate solvent to yield the fluoro intermediate 7-4. Displacement of the fluoro group from the intermediate 7-4 with alcohols in the presence of base (ex: KtOBu) in appropriate solvent (ex: 2-Me THF or THF) yields final compounds of type 7-5. Displacement of the fluoro from the intermediate 7-4 with amines (primary or secondary) in the presence of base (ex: DIPEA) in appropriate solvent (ex: NMP) at elevated temperature yields final compounds of type 7-6.

General Scheme 8

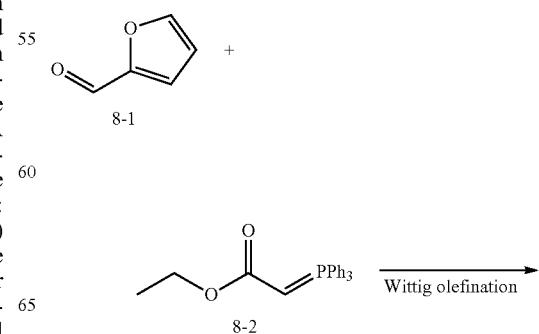

-continued

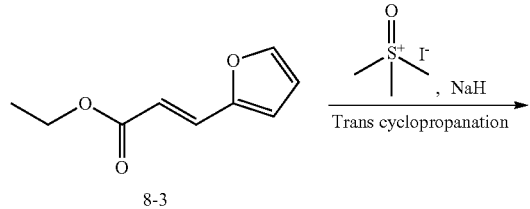
8-3

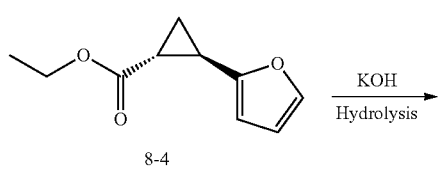
8-4

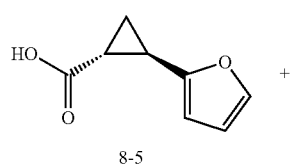
8-5

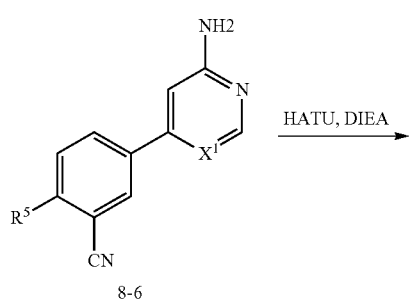
8-6

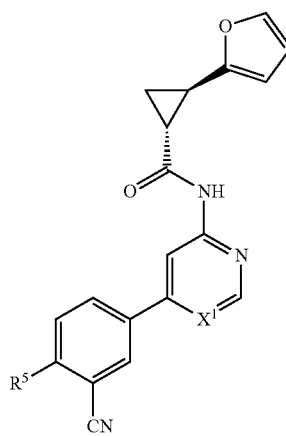
8-7

General Scheme 9

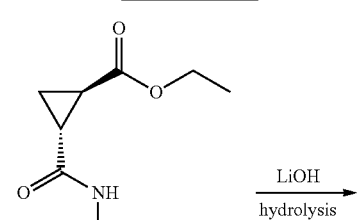
9-1

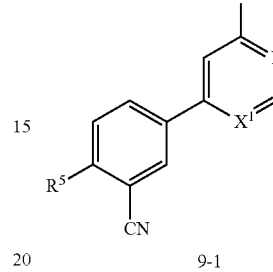

9-2

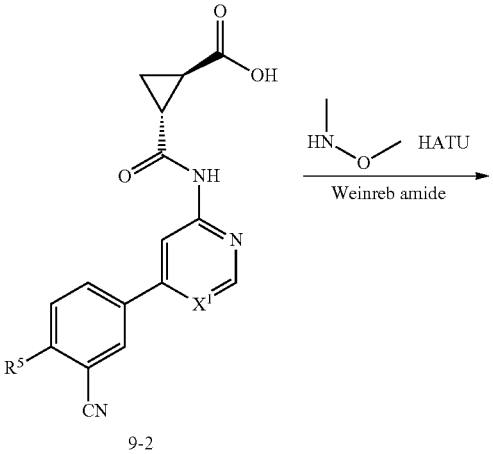
9-3

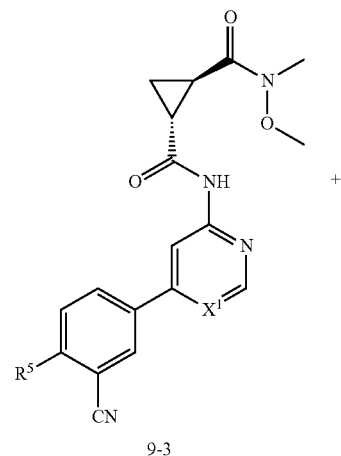

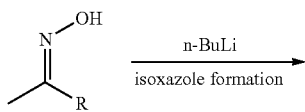

Scheme 8 shows a general synthesis of compounds of the present disclosure beginning with Wittig olefination reactions of heterocyclic-carboxaldehydes such as 8-1, followed by cyclopropanation of the trans alkene 8-3 via the Corey-Chaykovsky Reaction or the like to provide trans cyclopropane intermediates 8-4. Hydrolysis to free acid 8-5 or the like followed by amide bond coupling with 8-6 using a coupling reagent such as HATU or oxalyl chloride provided trans-final compounds of the type 8-7.

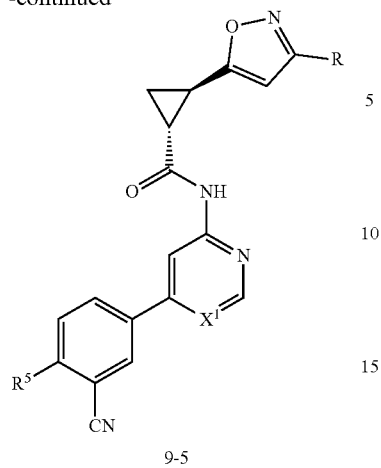

9-5

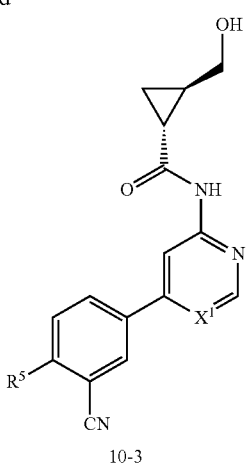

10-3

Scheme 9 describes a general synthesis of compounds of the present disclosure beginning with hydrolysis with a base such as LiOH of the ester intermediates 9-1 yielding the free acid intermediates 9-2. Amide bond formation of the intermediate 9-2 with N,O-dimethylhydroxylamine with a coupling reagent such as HATU yields intermediates 9-3. Condensation with oxime reagents 9-4 in the presence of a base such as nBuLi results in intramolecular cyclization to provide final compounds of the type 9-5.

Scheme 10 describes a general synthesis of compounds of the present disclosure beginning with reduction of Weinreb amide intermediates 10-1 using a reagent such as DIBAL to provide the aldehyde intermediate 10-2. Further reduction with a mild reducing agent such as sodium triacetoxyborohydride yields final compounds of the type 10-3.

General Scheme 11:

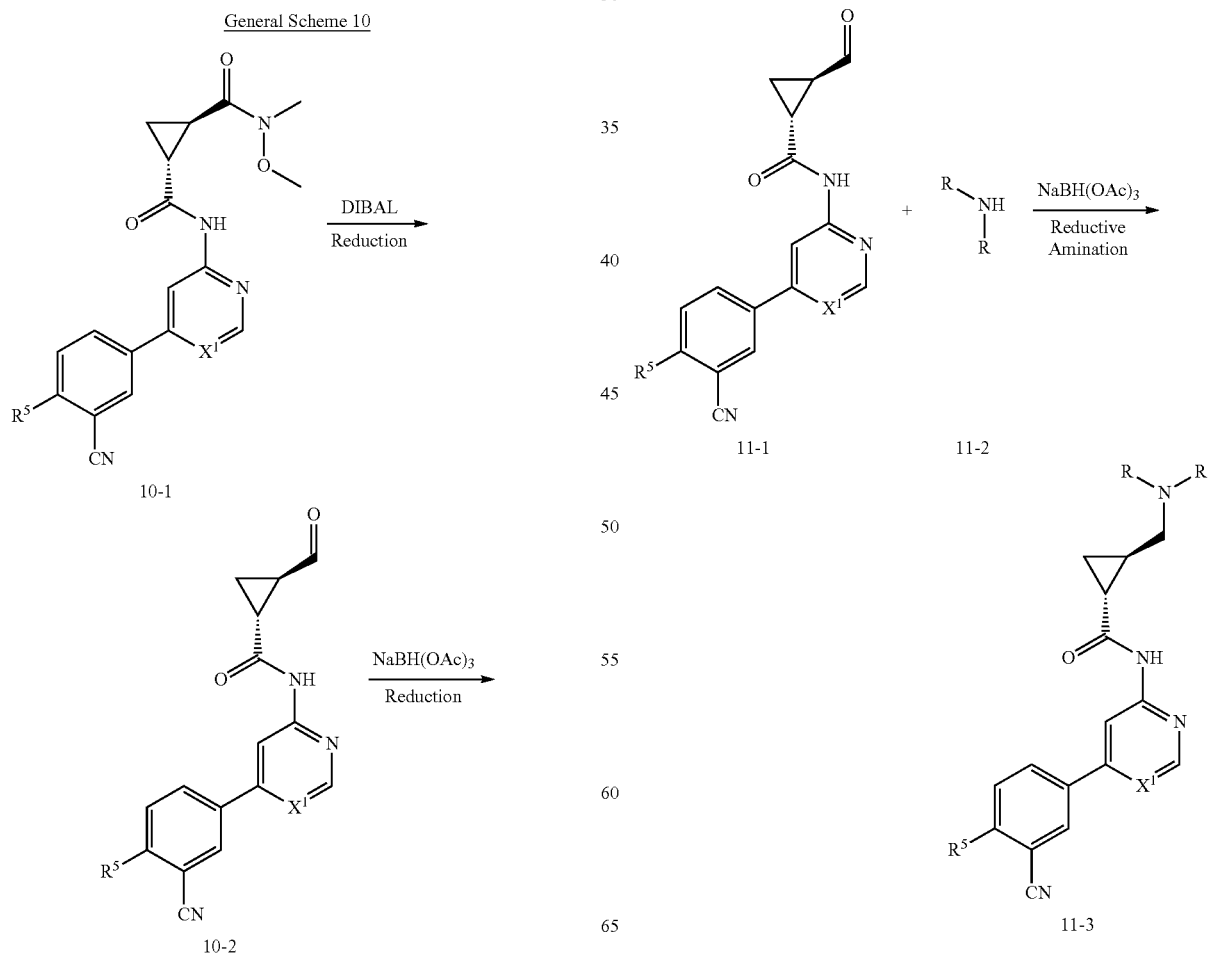

Scheme 11 describes a general synthesis of compounds of the present disclosure involving reductive amination aldehydes of type 11-1 with amines of type 11-2 using a selective reducing agent such as sodium triacetoxyborohydride or the like yielding final compounds of the type 11-3.

General Scheme 12

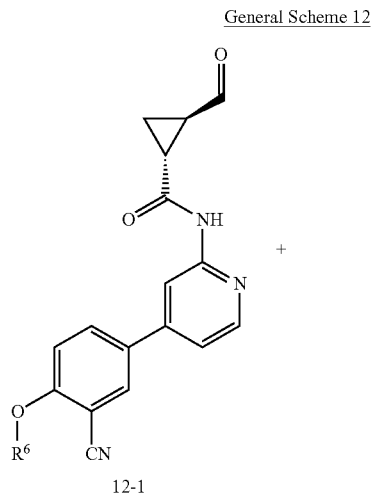

12-1

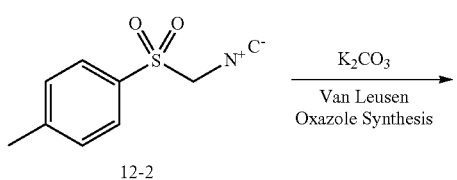

12-2

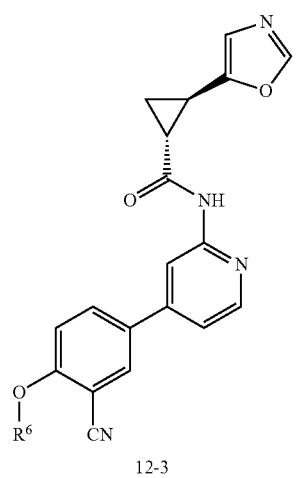

12-3

Scheme 5 shows a general synthesis of compounds of the present disclosure involving condensation of intermediates of type 12-1 with toluenesulfonylmethyl isocyanide 12-2 in the presence of a base such as potassium carbonate, yielding cyclized final compounds of the type 12-3.

General Scheme 13

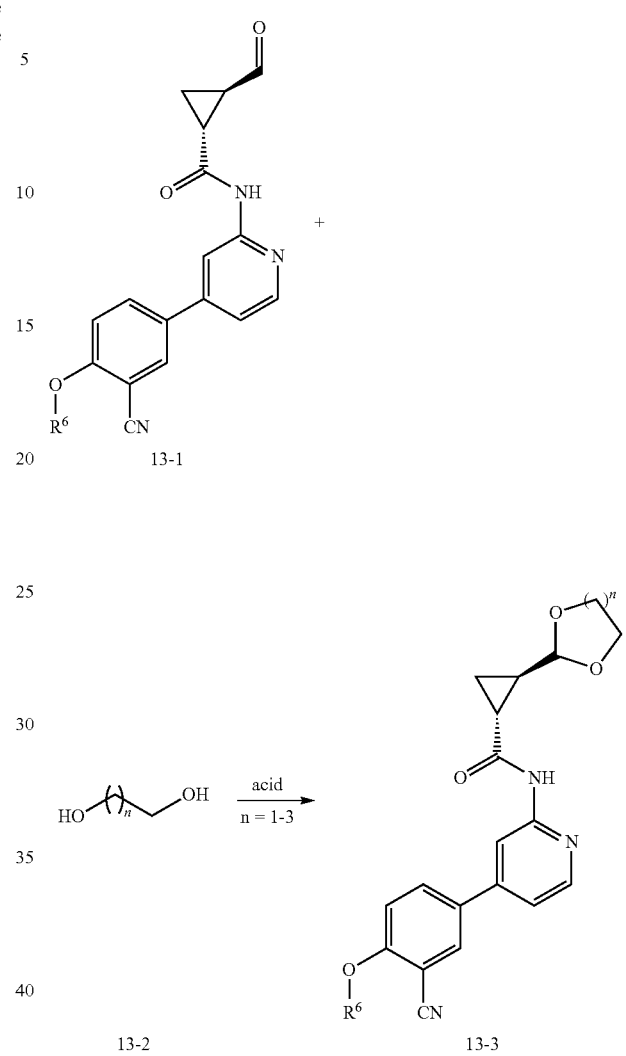

Scheme 13 describes a general synthesis of compounds of the present disclosure involving cyclization of intermediates of type 13-1 with diols such as 13-2 in the presence of an acid such as tolunesulfonic acid final compounds of the type 13-3.

General Scheme 14

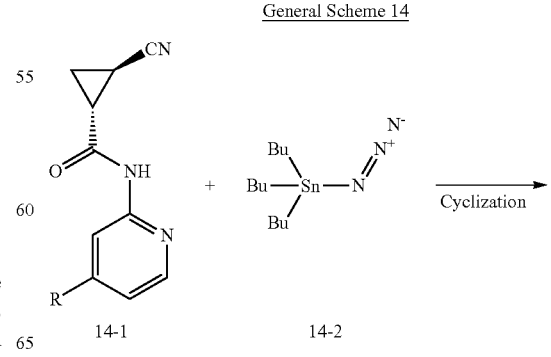

-continued

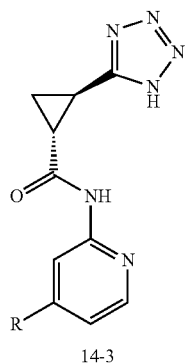

14-3

Scheme 14 describes a general synthesis of compounds of the present disclosure involving condensation of intermediates of type 14-1 with an azide reagent such as tributyl tin azide to form tetrazole containing final compounds of the type 14-3.

EXAMPLES

Methods for obtaining the novel compounds described herein will be apparent to those of ordinary skill in the art, with suitable procedures being described, for example, in the reaction schemes and examples below, and in the references cited herein.

While the foregoing description describes specific embodiments and aspects, those with ordinary skill in the art will appreciate that various modifications and alternatives can be developed. Accordingly, the particular embodiments and aspects described above are meant to be illustrative only, and not to limit the scope of the present disclosure, which is to be given the full breadth of the appended claims, and any and all equivalents thereof. Each of the foregoing references are hereby incorporated by reference.

Example 1: N-(4-(3-cyano-4-((tetrahydro-2H-pyran-4-yl)oxy)phenyl)pyridin-2-yl)cyclohexanecarboxamide

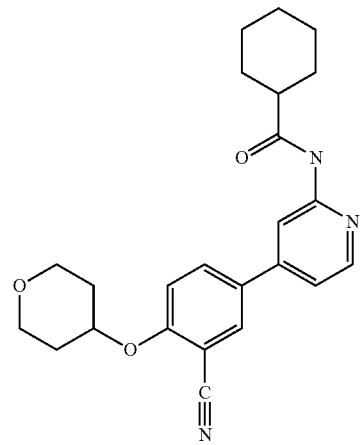 [SMILES: N#Cc1cc(-c2ccnc(NC(=O)C3CCCCC3)c2)ccc1OC1CCOCC1]

Step 1: To a mixture 4-bromopyridin-2-amine (200 mgs, 0.61 mmol) and 2-((tetrahydro-2H-pyran-4-yl)oxy)-5-(4,4,5,5-tetramethyl-1,3,2-dioxaborolan-2-yl)benzonitrile (116 mgs, 0.67 mmol), in DME (2 mL) was added 2.0 M aq Na$_2$CO$_3$ (1.1 mL, 2.1 mmol) and Pd(PPh$_3$)$_4$ catalyst (21 mgs, 0.018 mmol). The reaction mixture was heated at 140° C. for 1 hr. The mixture was then diluted with water (15 mL) and the stirred at rt. The resulting solids were filtered, washed with water and dried to give N-(4-(3-cyano-4-((tetrahydro-2H-pyran-4-yl)oxy)phenyl)pyridin-2-yl)cyclopropanecarboxamide which was used for next step without purification. LCMS-ESI$^+$ (m/z): [M+H]$^+$ calcd for C$_{17}$H$_{17}$N$_3$O$_2$ 296.5. found: 296.1.

Step 2: To above solution of N-(4-(3-cyano-4-((tetrahydro-2H-pyran-4-yl)oxy)phenyl)pyridin-2-yl)cyclopropanecarboxamide (30 mgs, 0.102 mmol) in NMP (0.7 mL) and DIPEA (0.04 mL, 0.203 mmol) was added cyclohexanecarbonyl chloride (0.03 mL, 0.203 mmol). The reaction mixture was heated at 80° C. for 3 hrs. The reaction mixture was then diluted with acetonitrile/water in TFA and purified by reverse phase chromatography to give the title compound. LCMS-ESI$^+$ (m/z): [M+H]$^+$ calcd for C$_{24}$H$_{27}$N$_3$O$_3$ 405.5. found: 406.2.

Example 2: N-(4-(3-cyano-4-((tetrahydro-2H-pyran-4-yl)oxy)phenyl)pyridin-2-yl)cyclopropanecarboxamide

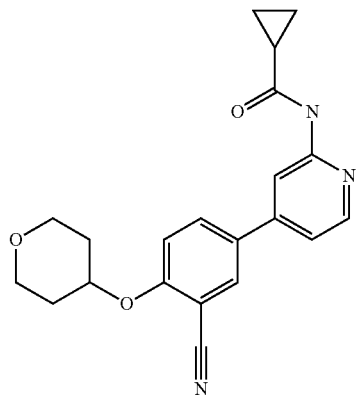 [SMILES: N#Cc1cc(-c2ccnc(NC(=O)C3CC3)c2)ccc1OC1CCOCC1]

To a solution of N-(4-(3-cyano-4-((tetrahydro-2H-pyran-4-yl)oxy)phenyl)pyridin-2-yl)cyclopropanecarboxamide (30 mgs, 0.102 mmol) in NMP (0.7 mL) and DIPEA (0.04 mL, 0.203 mmol) was added cyclopropanecarbonyl chloride (0.02 mL, 0.203 mmol). The reaction mixture was heated at 85° C. for 3 hrs. The reaction mixture was then diluted with acetonitrile/water in TFA and purified by reverse phase chromatography to give the title compound. LCMS-ESI$^+$ (m/z): [M+H]$^+$ calcd for C$_{21}$H$_{21}$N$_3$O$_3$ 363.4. found: 364.1. $^1$H NMR (400 MHz, DMSO-d$_6$) δ 10.94 (s, 1H), 8.35-8.30 (m, 2H), 8.10-8.09 (m, 1H), 7.97-7.94 (m, 1H), 7.49-7.43 (m, 2H), 4.91-4.86 (m, 1H), 3.87-3.82 (m, 2H), 3.56-3.50 (m, 2H), 2.02-1.98 (m, 3H), 1.70-1.61 (m, 2H), 0.83-0.81 (m, 4H).

Example 3: N-(4-(3-cyano-4-((tetrahydro-2H-pyran-4-yl)oxy)phenyl)pyridin-2-yl)cyclobutanecarboxamide

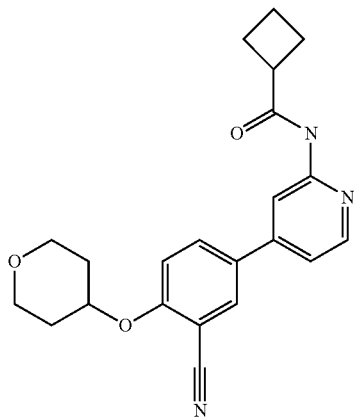 [SMILES: N#Cc1cc(-c2ccnc(NC(=O)C3CCC3)c2)ccc1OC1CCOCC1]

To a solution of N-(4-(3-cyano-4-((tetrahydro-2H-pyran-4-yl)oxy)phenyl)pyridin-2-yl)cyclopropanecarboxamide (30 mgs, 0.102 mmol) in NMP (0.7 mL) and DIPEA (0.06 mL, 0.508 mmol) was added cyclobutanecarbonyl chloride (0.06 mL, 0.508 mmol). The reaction mixture was heated at 70° C. for 45 min. The reaction mixture was then cooled to rt and Ammonia in Methanol (7N, 1 mL) was added and stirred at rt. After 45 min, the reaction mixture was concentrated and diluted with acetonitrile/water in TFA and purified by reverse phase chromatography to give the title compound. LCMS-ESI$^+$ (m/z): [M+H]$^+$ calcd for $C_{22}H_{23}N_3O_3$ 377.4. found: 377.1.

Example 4: N-(4-(3-cyano-4-((tetrahydro-2H-pyran-4-yl)oxy)phenyl)-5-fluoropyridin-2-yl)cyclopropanecarboxamide

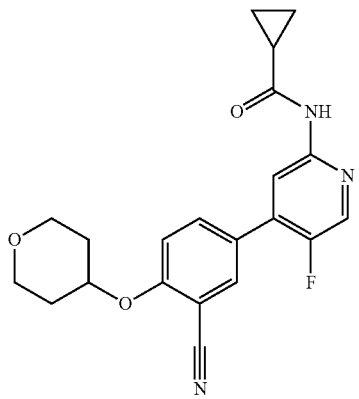 [SMILES: N#Cc1cc(-c2cc(NC(=O)C3CC3)ncc2F)ccc1OC1CCOCC1]

Step 1: To a mixture 2,5-difluoro-4-iodopyridine (732 mgs, 3.03 mmol) and 2-((tetrahydro-2H-pyran-4-yl)oxy)-5-(4,4,5,5-tetramethyl-1,3,2-dioxaborolan-2-yl)benzonitrile (1000 mgs, 3.03 mmol), in DME (10 mL) was added 2.0 M aq Na$_2$CO$_3$ (5.0 mL, 10.0 mmol) and Pd(PPh$_3$)$_4$ catalyst (105 mgs, 0.091 mmol). The reaction mixture was heated at 140° C. for 1 hr. The mixture was then diluted with water (15 mL) and the stirred at rt. The resulting solids were filtered and washed with water and dried to give 5-(2,5-difluoropyridin-4-yl)-2-((tetrahydro-2H-pyran-4-yl)oxy)benzonitrile which was used further without purification. LCMS-ESI$^+$ (m/z): [M+H]$^+$ calcd for $C_{17}H_{14}F_2N_2O_2$ 316.3. found: 337.1.

Step 2: In microwave vial, to a solution of 5-(2,5-difluoropyridin-4-yl)-2-((tetrahydro-2H-pyran-4-yl)oxy)benzonitrile (100 mgs, 0.316 mmol) in DMSO (1 mL) was added 2 mL of aq ammonium hydroxide solution (30%) very slowly at rt. The reaction mixture was heated at 125° C. in heating block for 3 h. Cooled to rt and then additional ammonium hydroxide solution (1 mL) was added and heated at 125° C. in heating block for 72 h. The mixture was then cooled to rt and diluted with water and the resulting solids were filtered and washed with water and dried to give 5-(2-amino-5-fluoropyridin-4-yl)-2-((tetrahydro-2H-pyran-4-yl)oxy)benzonitrile which was used further without purification. LCMS-ESI$^+$ (m/z): [M+H]$^+$ calcd for $C_{17}H_{16}FN_3O_2$ 313.3. found: 314.1.

Step 3: To a solution of 5-(2-amino-5-fluoropyridin-4-yl)-2-((tetrahydro-2H-pyran-4-yl)oxy)benzonitrile (50 mgs, 0.16 mmol) in NMP (1.0 mL) and DIPEA (0.06 mL, 0.318 mmol) was added cyclopropanecarbonyl chloride (0.03 mL, 0.318 mmol). The reaction mixture was heated at 70° C. for 16 h. The reaction mixture was then cooled to rt and ammonia in methanol (7N, 1 mL) was added and stirred at rt. After 4 h, the reaction mixture was concentrated and diluted with acetonitrile/water in TFA and purified by reverse phase chromatography to give the title compound. LCMS-ESI$^+$ (m/z): [M+H]$^+$ calcd for $C_{12}H_{20}FN_3O_3$ 381.4. found: 382.1. $^1$H NMR (400 MHz, DMSO-d$_6$) δ 10.94 (s, 1H), 8.39 (d, J=2.0 Hz, 1H), 8.22 (d, J=6.4 Hz, 1H), 7.97 (s, 1H), 7.86 (d, J=8.8 Hz, 1H), 7.51 (d, J=8.8 Hz, 1H), 4.90-4.88 (m, 1H), 3.87-3.82 (m, 2H), 3.56-3.50 (m, 2H), 2.03-1.97 (m, 3H), 1.70-1.64 (m, 2H), 0.82 (d, J=6.0 Hz, 4H).

Example 5: N-(4-(3-cyano-4-(pyrrolidin-1-yl)phenyl)pyridin-2-yl)cyclopropanecarboxamide

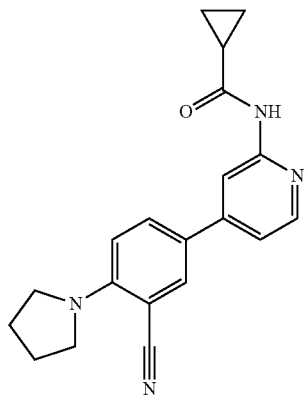 [SMILES: N#Cc1cc(-c2ccnc(NC(=O)C3CC3)c2)ccc1N1CCCC1]

Step 1: To a mixture 4-bromopyridin-2-amine (47 mgs, 0.16 mmol) and 2-(pyrrolidin-1-yl)-5-(4,4,5,5-tetramethyl-1,3,2-dioxaborolan-2-yl)benzonitrile (30 mgs, 0.17 mmol), in DME (2 mL) was added 2.0 M aq Na$_2$CO$_3$ (0.27 mL, 0.55 mmol) and Pd(PPh$_3$)$_4$ catalyst (5 mgs, 0.005 mmol). The reaction mixture was heated at 140° C. for 1 hr. The mixture was then diluted with DCM (15 mL) and dried over MgSO$_4$. Filtration, followed by concentration gave 5-(2-aminopyridin-4-yl)-2-(pyrrolidin-1-yl)benzonitrile which was used for next step without purification. LCMS-ESI+ (m/z): [M+H]+ calcd for $C_{16}H_{16}N_4$ 264.3. found: 265.1.

Step 2: To above solution of 5-(2-aminopyridin-4-yl)-2-(pyrrolidin-1-yl)benzonitrile (42 mgs, 0.16 mmol) in NMP (1.0 mL) and DIPEA (0.06 mL, 0.318 mmol) was added cyclopropanecarbonyl chloride (0.03 mL, 0.318 mmol). The reaction mixture was heated at 70° C. for 16 h. Cooled to rt and then additional cyclopropanecarbonyl chloride (0.03 mL, 0.318 mmol) and DIPEA (0.06 mL, 0.318 mmol) was added and heated at 70° C. in heating block for 72 h. The reaction mixture was then cooled to rt and mixture was purified by reverse phase chromatography to give the title compound. LCMS-ESI+ (m/z): [M+H]+ calcd for $C_{20}H_{20}N_4O$, 333.4. found: 333.1. $^1$H NMR (400 MHz, DMSO-$d_6$) δ 10.94 (s, 1H), 8.28-8.24 (m, 2H), 7.86 (d, J=1.6 Hz, 1H), 7.78-7.75 (m, 1H), 7.44-7.42 (m, 1H), 6.90 (d, J=8.8 Hz, 1H), 3.60-3.57 (m, 4H), 2.01-1.94 (m, 5H), 0.83-0.81 (m, 4H).

Example 6: N-(6-(3-cyano-4-((tetrahydro-2H-pyran-4-yl)oxy)phenyl)pyrimidin-4-yl)cyclopropanecarboxamide

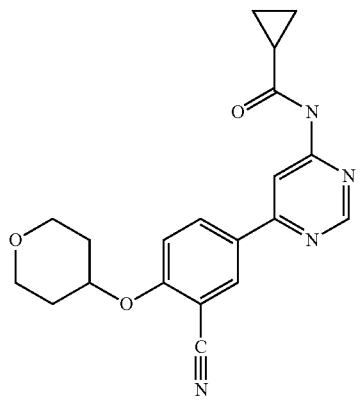 [SMILES: N#Cc1cc(-c2cc(NC(=O)C3CC3)ncn2)ccc1OC1CCOCC1]

Step 1: To a mixture 6-chloropyrimidin-4-amine (65 mgs, 0.50 mmol) and 2-((tetrahydro-2H-pyran-4-yl)oxy)-5-(4,4,5,5-tetramethyl-1,3,2-dioxaborolan-2-yl)benzonitrile (150 mgs, 0.46 mmol), in DME (1.5 mL) was added 2.0 M aq $Na_2CO_3$ (0.75 mL, 1.5 mmol) and $Pd(PPh_3)_4$ catalyst (16 mgs, 0.014 mmol). The reaction mixture was heated at 140° C. for 1 hr. The mixture was then diluted with water and the stirred at rt for 16 h The resulting solids were filtered and purified by flash chromatography (1-20% Methanol/Ethyl acetate) to give 5-(6-aminopyrimidin-4-yl)-2-((tetrahydro-2H-pyran-4-yl)oxy)benzonitrile. LCMS-ESI+ (m/z): [M+H]+ calcd for $C_{16}H_{16}N_4O_2$ 296.3. found: 296.1.

Step 2: To above solution of 5-(6-aminopyrimidin-4-yl)-2-((tetrahydro-2H-pyran-4-yl)oxy)benzonitrile (33 mgs, 0.11 mmol) in NMP (1.0 mL) and DIPEA (0.1 mL, 0.57 mmol) was added cyclopropanecarbonyl chloride (0.05 mL, 0.56 mmol). The reaction mixture was heated at 70° C. for 16 h. Cooled to rt and then additional cyclopropanecarbonyl chloride (0.05 mL, 0.56 mmol) and DIPEA (0.1 mL, 0.57 mmol) was added and heated at 70° C. in heating block for 72 h. The reaction mixture was then cooled to rt and mixture was purified by reverse phase chromatography to give the title compound. LCMS-ESI+ (m/z): [M+H]+ calcd for $C_{20}H_{20}N_4O_3$ 365.4. found: 365.1. $^1$H NMR (400 MHz, DMSO-$d_6$) δ 11.30 (s, 1H), 8.91 (d, J=1.2 Hz, 1H), 8.50 (d, J=0.8 Hz, 1H), 8.35 (d, J=2.4 Hz, 1H), 8.30-8.27 (m, 1H), 7.51 (d, J=9.2 Hz, 1H), 4.93-4.89 (m, 1H), 3.94-3.82 (m, 2H), 3.67-3.50 (m, 2H), 2.08-1.98 (m, 3H), 1.70-1.63 (m, 2H), 0.89-0.87 (m, 4H).

Example 7: N-(4-(3-cyano-5-methoxy-4-((tetrahydro-2H-pyran-4-yl)oxy)phenyl)pyridin-2-yl)cyclopropanecarboxamide

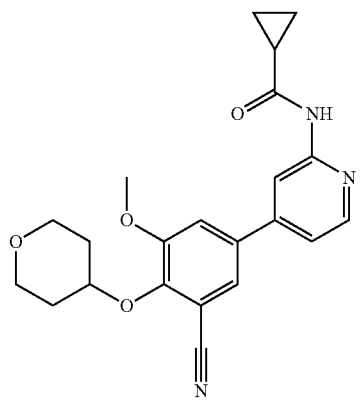 [SMILES: COc1cc(-c2ccnc(NC(=O)C3CC3)c2)cc(C#N)c1OC1CCOCC1]

Step 1: To a mixture 4-bromopyridin-2-amine (159 mgs, 0.92 mmol) and 3-methoxy-2-((tetrahydro-2H-pyran-4-yl)oxy)-5-(4,4,5,5-tetramethyl-1,3,2-dioxaborolan-2-yl)benzonitrile (300 mgs, 0.84 mmol), in DME (3 mL) was added 2.0 M aq $Na_2CO_3$ (1.25 mL, 2.5 mmol) and $Pd(PPh_3)_4$ catalyst (29 mg, 0.025 mmol). The reaction mixture was heated at 140° C. for 1 hr. The mixture was then diluted with DCM (15 mL), dried over $MgSO_4$, filtered and purified by flash chromatography (0-20% Methanol/Ethyl acetate) to give 5-(2-aminopyridin-4-yl)-3-methoxy-2-((tetrahydro-2H-pyran-4-yl)oxy)benzonitrile. LCMS-ESI+ (m/z): [M+H]+ calcd for $C_{18}H_{19}N_3O_3$ 326.3. found: 326.1.

Step 2: To above solution of 5-(2-aminopyridin-4-yl)-3-methoxy-2-((tetrahydro-2H-pyran-4-yl)oxy)benzonitrile (30 mgs, 0.09 mmol) in NMP (1.0 mL) and DIPEA (0.1 mL, 0.57 mmol) was added cyclopropanecarbonyl chloride (0.04 mL, 0.46 mmol). The reaction mixture was heated at 70° C. for 3 h. The reaction mixture was then cooled to rt and Ammonia in Methanol (7N, 1 mL) was added and stirred at rt. After 1 h, the reaction mixture was concentrated and diluted with acetonitrile/water in TFA and purified by reverse phase chromatography to give the title compound. LCMS-ESI+ (m/z): [M+H]+ calcd for $C_{22}H_{23}N_3O_4$ 394.4. found: 394.1.

Example 8: N-(4-(3-cyano-4-(((3R,4S)-3-fluoro-1-(2-hydroxyacetyl)piperidin-4-yl)oxy)phenyl)pyridin-2-yl)cyclopropanecarboxamide

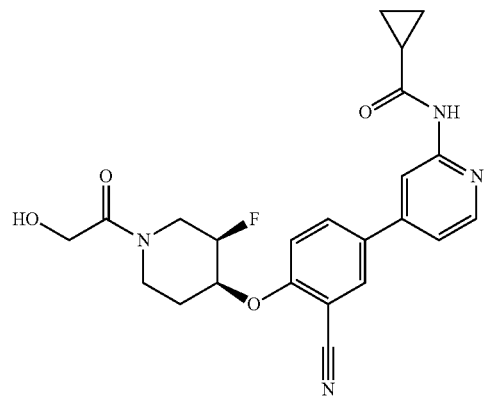 [SMILES: N#Cc1cc(-c2ccnc(NC(=O)C3CC3)c2)ccc1O[C@H]1CCN(C(=O)CO)C[C@H]1F]

Step 1: To a mixture 4-bromopyridin-2-amine (352 mgs, 2.03 mmol) and 2-fluoro-5-(4,4,5,5-tetramethyl-1,3,2-dioxaborolan-2-yl)benzonitrile (450 mgs, 1.82 mmol), in DME (4 mL) was added 2.0 M aq Na$_2$CO$_3$ (2.7 mL, 5.46 mmol) and Pd(PPh$_3$)$_4$ catalyst (63 mg, 0.055 mmol). The reaction mixture was heated at 140° C. for 1 hr. The mixture was then diluted with water (30 mL) and the stirred at rt. The resulting solids were filtered and washed with water and dried to give 5-(2-aminopyridin-4-yl)-2-fluorobenzonitrile which was used further without purification. LCMS-ESI$^+$ (m/z): [M+H]$^+$ calcd for C$_{12}$H$_8$FN$_3$ 389.3. found: 389.1.

Step 2: To a solution of 5-(2-aminopyridin-4-yl)-2-fluorobenzonitrile (380 mgs, 1.78 mmol) in NMP (1.8 mL) and DIPEA (1.0 mL, 6.0 mmol) was added cyclopropanecarbonyl chloride (0.48 mL, 5.0 mmol). The reaction mixture was heated at 85° C. for 1 h. The reaction mixture was then cooled to rt and Ammonia in Methanol (7N, 3 mL) was added and stirred at rt. After 1 h, the reaction mixture was concentrated, diluted with water (30 mL) and the resulting solids were filtered and washed with water and dried to give N-(4-(3-cyano-4-fluorophenyl)pyridin-2-yl)cyclopropanecarboxamide which was used further without purification. LCMS-ESI$^+$ (m/z): [M+H]$^+$ calcd for C$_{16}$H$_{12}$FN$_3$O, 282.3. found: 282.1.

Step 3: To a solution of tert-butyl (3R,4S)-3-fluoro-4-hydroxypiperidine-1-carboxylate (203 mg, 0.92 mmol) in Me-THF (10 mL) at 0° C. was added potassium tert-butoxide solution (1.0 M, 1.06 mL, 1.06 mmol) in one portion and stirred at that temperature. After 45 min, N-(4-(3-cyano-4-fluorophenyl)pyridin-2-yl)cyclopropanecarboxamide (200 mg, 0.71 mmol) was added in one portion and warmed to room temperature. The reaction was heated at 60° C. for 2 h. The reaction was quenched with minimum amount of water, concentrated to dryness to give tert-butyl (3R,4S)-4-(2-cyano-4-(2-(cyclopropanecarboxamido)pyridin-4-yl)phenoxy)-3-fluoropiperidine-1-carboxylate which was used further without purification. LCMS-ESI$^+$ (m/z): [M+H]$^+$ calcd for C$_{26}$H$_{29}$FN$_4$O$_4$, 481.5. found: 481.1.

Step 4: To a solution of tert-butyl (3R,4S)-4-(2-cyano-4-(2-(cyclopropanecarboxamido)pyridin-4-yl)phenoxy)-3-fluoropiperidine-1-carboxylate in DCM (5 mL), was added TFA (3 mL) and stirred at room temperature for 1 h. The reaction mixture was then diluted with DCM and washed with saturated solution of NaHCO$_3$ (3×), brine and dried (MgSO$_4$). Filtration and concentration gave N-(4-(3-cyano-4-(((3R,4S)-3-fluoropiperidin-4-yl)oxy)phenyl)pyridin-2-yl)cyclopropanecarboxamide which was used further without purification. LCMS-ESI$^+$ (m/z): [M+H]$^+$ calcd for C$_{26}$H$_{21}$FN$_4$O$_2$ 381.4. found: 381.1.

Step 5: To solution of N-(4-(3-cyano-4-(((3R,4S)-3-fluoropiperidin-4-yl)oxy)phenyl)pyridin-2-yl)cyclopropanecarboxamide (90 mg, 0.24 mmol), Glycolic acid (36 mg, 0.47 mmol), HATU (135 mg, 0.36 mmol) in DMF (1 mL) was added DIPEA (0.12 mL, 0.71 mmol) and stirred at rt for 2 h. The mixture was concentrated purified via prep HPLC (5-95% acetonitrile in water, 0.1% trifluoroacetic acid buffer) to give the title compound. LCMS-ESI$^+$ (m/z): [M+H]$^+$ calcd for C$_{23}$H$_{23}$FN$_4$O$_4$ 439.4. found: 439.2. $^1$H NMR (400 MHz, DMSO-d$_6$) δ 10.92 (s, 1H), 8.35-8.32 (m, 2H), 8.10 (s, 1H), 7.99-7.97 (m, 1H), 7.53 (d, J=8.8 Hz, 1H), 7.44 (d, J=5.6 Hz, 1H), 5.11-5.05 (m, 1H), 4.31-4.01 (m, 3H), 3.66-3.17 (m, 4H), 2.05-1.78 (m, 3H), 0.83-0.80 (m, 4H).

Example 9: N-(4-(3-cyano-4-(((3R,4S)-3-fluoro-1-((S)-2-hydroxypropanoyl)piperidin-4-yl)oxy)phenyl)pyridin-2-yl)cyclopropanecarboxamide

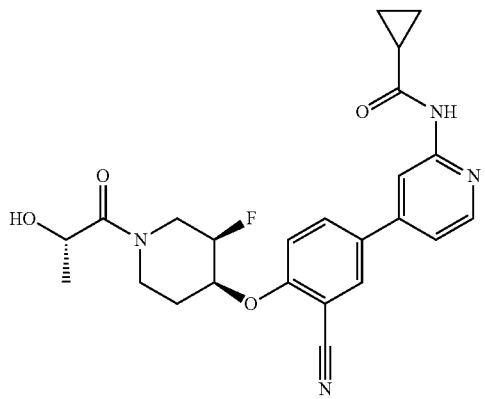 [SMILES: C[C@H](O)C(=O)N1CC[C@H](Oc2ccc(-c3ccnc(NC(=O)C4CC4)c3)cc2C#N)[C@H](F)C1]

To solution of N-(4-(3-cyano-4-(((3R,4S)-3-fluoropiperidin-4-yl)oxy)phenyl)pyridin-2-yl)cyclopropanecarboxamide (42 mg, 0.11 mmol), L-Lactic acid (20 mg, 0.22 mmol), HATU (63 mg, 0.17 mmol) in DMF (1 mL) was added DIPEA (0.06 mL, 0.33 mmol) and stirred at rt for 1 h. The mixture was concentrated purified via prep HPLC (5-95% acetonitrile in water, 0.1% trifluoroacetic acid buffer) to give the title compound. LCMS-ESI$^+$ (m/z): [M+H]$^+$ calcd for C$_{24}$H$_{25}$FN$_4$O$_4$ 453.5. found: 453.2.

Example 10: (S)—N-(4-(3-cyano-4-((3,3-difluoro-1-(2-hydroxyacetyl)piperidin-4-yl)oxy)phenyl)pyridin-2-yl)cyclopropanecarboxamide

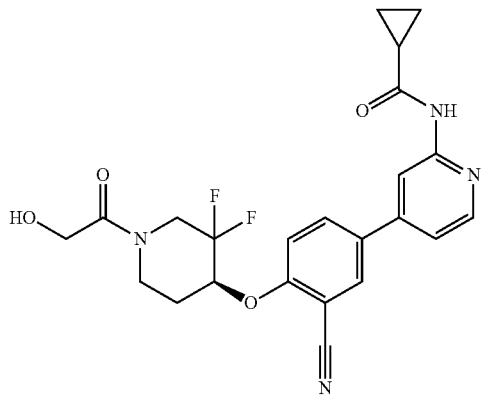 [SMILES: N#Cc1cc(-c2ccnc(NC(=O)C3CC3)c2)ccc1O[C@H]1CCN(C(=O)CO)CC1(F)F]

Step 1: Preparation of tert-butyl (S)-3,3-difluoro-4-hydroxypiperidine-1-carboxylate and tert-butyl (R)-3,3-difluoro-4-hydroxypiperidine-1-carboxylate: From the commercial available starting material tert-butyl 3,3-difluoro-4-hydroxypiperidine-1-carboxylate (CAS Number: 1209780-71-1), the two enantiomers were separated by semi-preparative chiral HPLC fitted with a Chiralpak AD-H column running a 90:10 mixture of Hexane:Ethanol. The first eluent was assigned as tert-butyl (R)-3,3-difluoro-4-hydroxypiperidine-1-carboxylate (Rt: 3.9 min UV-214 nM) and the second eluent was assigned as tert-butyl (S)-3,3-difluoro-4-hydroxypiperidine-1-carboxylate (Rt=6.4 min, UV-214 nM).

Step 2: To a solution of tert-butyl (S)-3,3-difluoro-4-hydroxypiperidine-1-carboxylate (148 mg, 0.62 mmol) in Me-THF (8 mL) at 0° C. was added potassium tert-butoxide solution (1.0 M, 0.72 mL, 0.72 mmol) in one portion and stirred at that temperature. After 45 min, N-(4-(3-cyano-4-fluorophenyl)pyridin-2-yl)cyclopropanecarboxamide (135 mg, 0.48 mmol) was added in one portion and warmed to room temperature. The reaction was heated at 60° C. for 2 h. The reaction was quenched with minimum amount of water, concentrated to dryness to give tert-butyl (S)-4-(2-cyano-4-(2-(cyclopropanecarboxamido)pyridin-4-yl)phenoxy)-3,3-difluoropiperidine-1-carboxylate which was used further without purification. LCMS-ESI$^+$ (m/z): [M+H]$^+$ calcd for $C_{26}H_{28}F_2N_4O_4$ 499.5. found: 499.1.

Step 3: To a solution of tert-butyl (S)-4-(2-cyano-4-(2-(cyclopropanecarboxamido)pyridin-4-yl)phenoxy)-3,3-difluoropiperidine-1-carboxylate in DCM (5 mL), was added TFA (3 mL) and stirred at room temperature for 1 h. The reaction mixture was then diluted with DCM and washed with saturated solution of NaHCO$_3$ (3×), brine and dried (MgSO$_4$). Filtration and concentration gave (S)—N-(4-(3-cyano-4-((3,3-difluoropiperidin-4-yl)oxy)phenyl)pyridin-2-yl)cyclopropanecarboxamide which was used further without purification. LCMS-ESI$^+$ (m/z): [M+H]$^+$ calcd for $C_{21}H_{20}F_2N_4O_2$ 399.5. found: 399.1.

Step 4: To solution of (S)—N-(4-(3-cyano-4-((3,3-difluoropiperidin-4-yl)oxy)phenyl)pyridin-(45 mg, 0.11 mmol), Glycolic acid (17 mg, 0.23 mmol), HATU (65 mg, 0.17 mmol) in DMF (1 mL) was added DIPEA (0.06 mL, 0.34 mmol) and stirred at rt for 1 h. The mixture was concentrated purified via prep HPLC (5-95% acetonitrile in water, 0.1% trifluoroacetic acid buffer) to give the title compound. LCMS-ESI$^+$ (m/z): [M+H]$^+$ calcd for $C_{23}H_{22}F_2N_4O_4$ 457.4. found: 457.2. $^1$H NMR (400 MHz, DMSO-d$_6$) δ 10.95 (s, 1H), 8.41-8.24 (m, 2H), 8.14 (d, J=2.4 Hz, 1H), 8.02 (dd, J=9.0, 2.4 Hz, 1H), 7.60 (d, J=9.0 Hz, 1H), 7.45 (dd, J=5.3, 1.7 Hz, 1H), 5.34-5.29 (m, 1H), 4.23-3.69 (m, 5H), 3.61-3.52 (m, 2H), 2.25-1.76 (m, 3H), 0.91-0.72 (m, 4H).

Example 11: N-(4-(3-cyano-4-(((S)-3,3-difluoro-1-((S)-2 hydroxypropanoyl)piperidin-4-yl)oxy)phenyl)pyridin-2-yl)cyclopropanecarboxamide

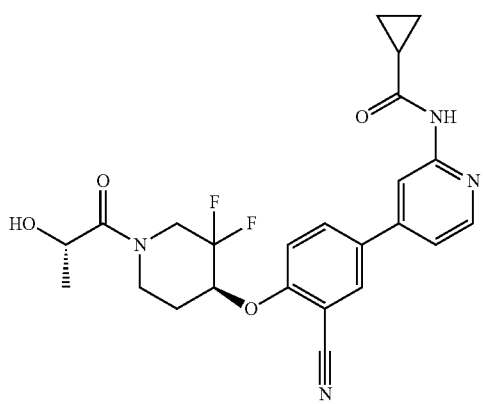 [SMILES: C[C@H](O)C(=O)N1CC[C@H](Oc2ccc(-c3ccnc(NC(=O)C4CC4)c3)cc2C#N)C(F)(F)C1]

To solution of (S)—N-(4-(3-cyano-4-((3,3-difluoropiperidin-4-yl)oxy)phenyl)pyridin-2-yl)cyclopropanecarboxamide (45 mg, 0.11 mmol), L-Lactic acid (20 mg, 0.23 mmol), HATU (65 mg, 0.17 mmol) in DMF (1 mL) was added DIPEA (0.06 mL, 0.33 mmol) and stirred at rt for 1 h. The mixture was concentrated purified via prep HPLC (5-95% acetonitrile in water, 0.1% trifluoroacetic acid buffer) to give the title compound. LCMS-ESI$^+$ (m/z): [M+H]$^+$ calcd for $C_{24}H_{24}F_2N_4O_4$ 471.4. found: 471.2. $^1$H NMR (400 MHz, DMSO-d$_6$) δ 10.92 (s, 1H), 8.45-8.26 (m, 2H), 8.14 (d, J=2.4 Hz, 1H), 8.02 (dd, J=8.9, 2.4 Hz, 1H), 7.60 (d, J=9.1 Hz, 1H), 7.44 (dd, J=5.3, 1.7 Hz, 1H), 5.34-5.31 (m, 1H), 4.51-4.46 (m, 1H), 4.21-3.89 (m, 2H), 3.86-3.76 (m, 2H), 3.65-3.45 (m, 1H), 2.18-1.75 (m, 3H), 1.20 (d, J=6.5 Hz, 3H), 0.91-0.72 (m, 4H).

Example 12: N-(4-(3-cyano-4-(((3R,4S)-1-(2-cyanoacetyl)-3-fluoropiperidin-4-yl)oxy)phenyl)pyridin-2-yl)cyclopropanecarboxamide

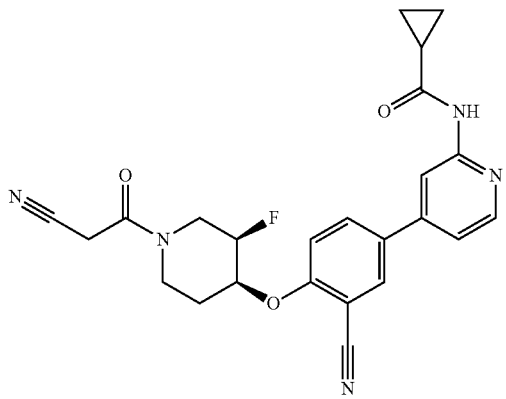

To solution of N-(4-(3-cyano-4-(((3R,4S)-3-fluoropiperidin-4-yl)oxy)phenyl)pyridin-2-yl)cyclopropanecarboxamide (34 mg, 0.09 mmol), cyano acetic acid (15 mg, 0.18 mmol), HATU (51 mg, 0.13 mmol) in DMF (1 mL) was added DIPEA (0.05 mL, 0.27 mmol) and stirred at rt for 2 h. The mixture was concentrated purified via prep HPLC (5-95% acetonitrile in water, 0.1% trifluoroacetic acid buffer) to give the title compound. LCMS-ESI$^+$ (m/z): [M+H]$^+$ calcd for $C_{24}H_{22}FN_5O_3$ 448.4. found: 448. $^1$H NMR (400 MHz, DMSO-d$_6$) δ 10.97 (s, 1H), 8.42-8.26 (m, 2H), 8.13 (d, J=2.4 Hz, 1H), 7.99 (dd, J=8.9, 2.4 Hz, 1H), 7.55 (dd, J=9.1, 1.5 Hz, 1H), 7.46 (dd, J=5.4, 1.7 Hz, 1H), 5.14-4.94 (m, 1H), 4.35-3.84 (m, 4H), 3.67-3.18 (m, 3H), 2.10-1.76 (m, 3H), 0.90-0.77 (m, 4H).

Example 13: (S)—N-(4-(3-cyano-4-((1-(2-cyanoacetyl)-3,3-difluoropiperidin-4-yl)oxy)phenyl)pyridin-2-yl)cyclopropanecarboxamide

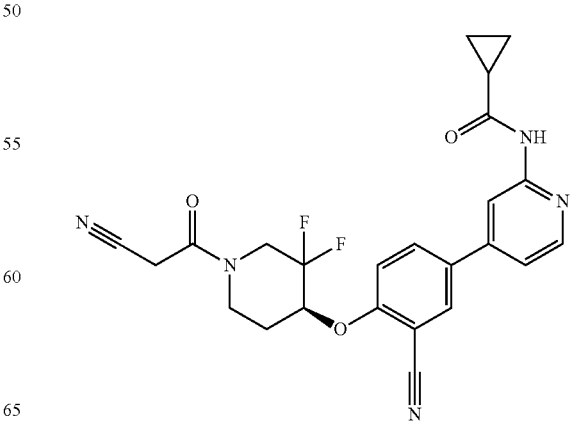

To solution of (S)—N-(4-(3-cyano-4-((3,3-difluoropiperidin-4-yl)oxy)phenyl)pyridin-2-yl)cyclopropanecarboxamide (27 mg, 0.07 mmol), cyano acetic acid (12 mg, 0.14 mmol), HATU (39 mg, 0.10 mmol) in DMF (1 mL) was added DIPEA (0.04 mL, 0.20 mmol) and stirred at rt for 2 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{24}H_{21}F_2N_5O_3$ 466.4. found: 466.22. ¹H NMR (400 MHz, DMSO-$d_6$) δ 10.96 (s, 1H), 8.45-8.22 (m, 2H), 8.15 (d, J=2.4 Hz, 1H), 8.02 (dd, J=8.9, 2.4 Hz, 1H), 7.60 (d, J=9.0 Hz, 1H), 7.46 (dd, J=5.4, 1.8 Hz, 1H), 5.35-5.22 (m, 1H), 4.20 (s, 2H), 4.10-3.35 (m, 4H), 2.20-1.80 (m, 3H), 0.91-0.72 (m, 4H).

Example 14: N-(4-(3-cyano-4-(((S)-3,3-difluoro-1-((S)-5-oxopyrrolidine-2-carbonyl)piperidin-4-yl)oxy)phenyl)pyridin-2-yl)cyclopropanecarboxamide

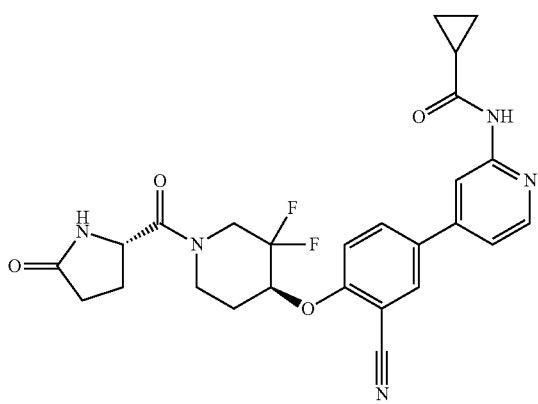 [SMILES: N#Cc1cc(-c2ccnc(NC(=O)C3CC3)c2)ccc1O[C@H]1CCN(C(=O)[C@@H]2CCC(=O)N2)CC1(F)F]

To solution of (S)—N-(4-(3-cyano-4-((3,3-difluoropiperidin-4-yl)oxy)phenyl)pyridin-2-yl)cyclopropanecarboxamide (27 mg, 0.07 mmol), (S)-5-oxopyrrolidine-2-carboxylic acid (18 mg, 0.14 mmol), HATU (39 mg, 0.10 mmol) in DMF (1 mL) was added DIPEA (0.04 mL, 0.20 mmol) and stirred at rt for 2 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{26}H_{25}F_2N_5O_4$ 510.5. found: 510.2. ¹H NMR (400 MHz, DMSO-$d_6$) δ 10.91 (s, 1H), 8.37-8.22 (m, 2H), 8.10 (d, J=2.4 Hz, 1H), 7.98 (dd, J=8.9, 2.5 Hz, 1H), 7.55 (dd, J=9.0, 5.6 Hz, 1H), 7.41 (dd, J=5.3, 1.7 Hz, 1H), 5.31-5.24 (m, 1H), 4.59 (dd, J=9.2, 4.2 Hz, 1H), 4.18-3.99 (m, 1H), 3.72 (dd, J=20.8, 13.5 Hz, 2H), 3.44 (dt, J=22.4, 9.9 Hz, 1H), 2.38-2.20 (m, 1H), 2.13-1.71 (m, 6H), 0.84-0.69 (m, 4H).

Example 15: (S)—N-(4-(3-cyano-4-((3,3-difluoro-1-(3-hydroxypropanoyl)piperidin-4-yl)oxy)phenyl)pyridin-2-yl)cyclopropanecarboxamide

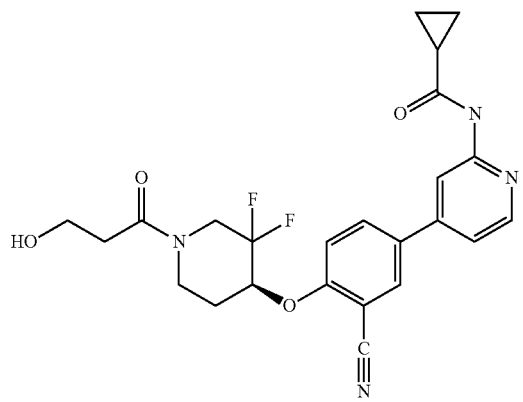 [SMILES: N#Cc1cc(-c2ccnc(NC(=O)C3CC3)c2)ccc1O[C@H]1CCN(C(=O)CCO)CC1(F)F]

To solution of (S)—N-(4-(3-cyano-4-((3,3-difluoropiperidin-4-yl)oxy)phenyl)pyridin-2-yl)cyclopropanecarboxamide (27 mg, 0.07 mmol), 3-hydroxypropanoic acid (12 mg, 0.14 mmol), HATU (39 mg, 0.10 mmol) in DMF (1 mL) was added DIPEA (0.04 mL, 0.20 mmol) and stirred at rt for 2 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{24}H_{24}F_2N_4O_4$ 471.4. found: 471.2. ¹H NMR (400 MHz, DMSO-$d_6$) δ 10.89 (s, 1H), 8.37-8.21 (m, 2H), 8.09 (d, J=2.4 Hz, 1H), 7.97 (dd, J=8.9, 2.4 Hz, 1H), 7.55 (d, J=8.9 Hz, 1H), 7.40 (dd, J=5.3, 1.7 Hz, 1H), 5.31-5.21 (m, 1H), 4.21-3.35 (m, 7H), 2.55-2.44 (m, 2H), 2.14-1.67 (m, 3H), 0.81-0.69 (m, 4H).

Example 16: (S)—N-(4-(3-cyano-4-(3-hydroxypyrrolidin-1-yl)phenyl)pyridin-2-yl)cyclopropanecarboxamide

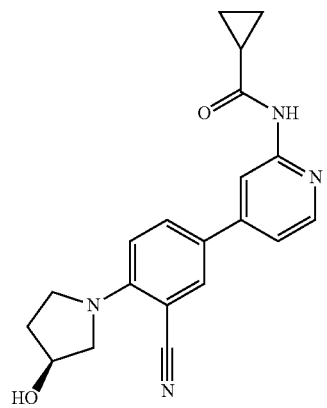 [SMILES: N#Cc1cc(-c2ccnc(NC(=O)C3CC3)c2)ccc1N1CC[C@H](O)C1]

To a suspension of N-(4-(3-cyano-4-fluorophenyl)pyridin-2-yl)cyclopropanecarboxamide (50 mgs, 0.18 mmol) in 2-propanol in microwave vial was added (S) pyrrolidinol-3-ol (46 mgs, 0.53 mmol) and DIPEA (0.1 mL, 0.57 mmol) and heated at 150° C. for 3 h in heating block. The reaction mixture was cooled to rt and purified by flash chromatography (0-20% Methanol/Ethyl acetate) to give the title compound. LCMS-ESI+ (m/z): [M+H]+ calcd for C20H20N4O2 349.4. found: 349.1. 1H NMR (400 MHz, DMSO-d6) δ 10.80 (s, 1H), 8.39-8.20 (m, 2H), 7.84 (d, J=2.4 Hz, 1H), 7.76 (dd, J=9.1, 2.4 Hz, 1H), 7.38 (dd, J=5.3, 1.8 Hz, 1H), 6.88 (d, J=9.1 Hz, 1H), 5.08 (d, J=3.6 Hz, 1H), 4.41 (s, 1H), 3.88-3.37 (m, 4H), 2.09-2.00 (m, 2H), 1.98-1.89 (m, 1H), 0.89-0.76 (m, 4H).

Example 17: (R)—N-(4-(3-cyano-4-(3-hydroxypyrrolidin-1-yl)phenyl)pyridin-2-yl)cyclopropanecarboxamide

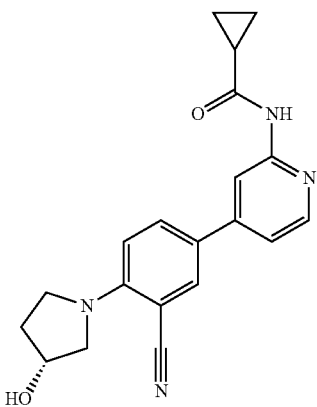 [SMILES: N#Cc1cc(-c2ccnc(NC(=O)C3CC3)c2)ccc1N1CC[C@@H](O)C1]

To a suspension of N-(4-(3-cyano-4-fluorophenyl)pyridin-2-yl)cyclopropanecarboxamide (50 mgs, 0.18 mmol) in 2-propanol in microwave vial was added (R) pyrrolidinol-3-ol (46 mgs, 0.53 mmol) and DIPEA (0.1 mL, 0.57 mmol) and heated at 150° C. for 3 h in heating block. The reaction mixture was cooled to rt and purified by flash chromatography (0-20% Methanol/Ethyl acetate) to give the title compound. LCMS-ESI+ (m/z): [M+H]+ calcd for C20H20N4O2 349.4. found: 349.1. 1H NMR (400 MHz, DMSO-d6) δ 10.80 (s, 1H), 8.35-8.22 (m, 2H), 7.84 (d, J=2.4 Hz, 1H), 7.76 (dd, J=9.1, 2.4 Hz, 1H), 7.38 (dd, J=5.3, 1.8 Hz, 1H), 6.88 (d, J=9.1 Hz, 1H), 5.07 (d, J=3.6 Hz, 1H), 4.40 (d, J=5.1 Hz, 1H), 3.88-3.55 (m, 3H), 3.47-3.43 (m, 1H), 2.10-1.86 (m, 3H), 0.86-0.72 (m, 4H).

Example 18: (S)—N-(4-(3-cyano-4-(3-fluoropyrrolidin-1-yl)phenyl)pyridin-2-yl)cyclopropanecarboxamide

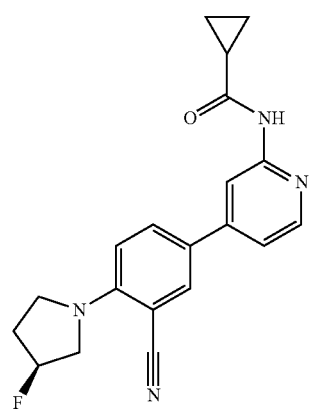 [SMILES: N#Cc1cc(-c2ccnc(NC(=O)C3CC3)c2)ccc1N1CC[C@H](F)C1]

To a suspension of N-(4-(3-cyano-4-fluorophenyl)pyridin-2-yl)cyclopropanecarboxamide (50 mgs, 0.18 mmol) in 2-propanol in microwave vial was added (S)-3-fluoropyrrolidine (48 mgs, 0.53 mmol) and DIPEA (0.1 mL, 0.57 mmol) and heated at 150° C. for 3 h in heating block. Cooled to rt and then additional S)-3-fluoropyrrolidine (50 mgs, 0.54 mmol) and DIPEA (0.3 mL) was added and heated at 155° C. in heating block for 2 h. The reaction mixture was cooled to rt and purified by flash chromatography (SiO2, 0-5% Methanol/Ethyl acetate) to give the title compound. LCMS-ESI+ (m/z): [M+H]+ calcd for C20H19FN4O, 351.4. found: 351.1. 1H NMR (400 MHz, DMSO-d6) δ 10.81 (s, 1H), 8.37-8.22 (m, 2H), 7.89 (d, J=2.2 Hz, 1H), 7.84-7.73 (m, 1H), 7.40 (dt, J=5.4, 1.3 Hz, 1H), 6.94 (d, J=9.1 Hz, 1H), 5.48 (d, J=53.2 Hz, 1H), 4.07-3.65 (m, 4H), 2.36-1.90 (m, 3H), 0.86-0.80 (m, 4H).

Example 19: N-(6-(3-cyano-4-(((3R,4S)-3-fluoro-1-(2-hydroxyacetyl)piperidin-4-yl)oxy)phenyl)pyrimidin-4-yl)cyclopropanecarboxamide

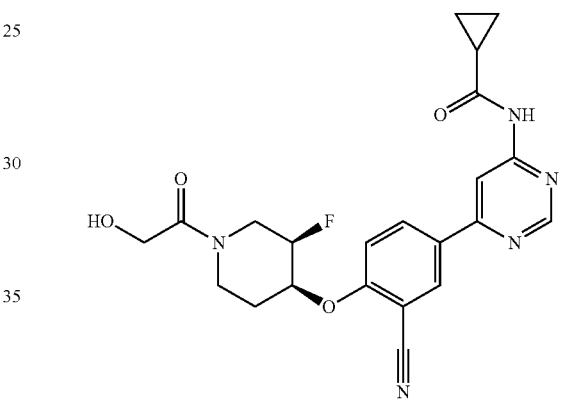

Step 1: To a mixture 6-chloropyrimidin-4-amine (500 mgs, 3.86 mmol) and 2-fluoro-5-(4,4,5,5-tetramethyl-1,3,2-dioxaborolan-2-yl)benzonitrile (954 mgs, 3.86 mmol) in DME (10 mL) was added 2.0 M aq Na2CO3 (4.2 mL, 8.34 mmol) and Pd(PPh3)4 catalyst (122 mgs, 0.11 mmol). The reaction mixture was heated at 130° C. for 2 hr. The mixture was then diluted with water and the stirred at rt. The resulting solids were filtered and washed with water and dried to give 5-(6-aminopyrimidin-4-yl)-2-fluorobenzonitrile which was used further without purification. LCMS-ESI+ (m/z): [M+H]+ calcd for C11H17FN4 215.2. found: 215.1.

Step 2: To above solution of 5-(6-aminopyrimidin-4-yl)-2-fluorobenzonitrile (621 mgs, 2.9 mmol) in NMP (4.0 mL) and DIPEA (1.55 mL, 9.0 mmol) cyclopropanecarbonyl chloride (0.8 mL, 9.0 mmol) was slowly added. After 30 min at rt, the reaction mixture was heated at 85° C. for 2 h. The reaction mixture was then cooled to rt and Ammonia in Methanol (7N, 8.0 mL) was added and stirred at rt. After 1 h, the reaction mixture was concentrated, diluted with water (30 mL) and the resulting solids were filtered and washed with water and diethyl ether and dried to give N-(6-(3-cyano-4-fluorophenyl)pyrimidin-4-yl)cyclopropanecarboxamide which was used further without purification. LCMS-ESI+ (m/z): [M+H]+ calcd for C15H11FN4O, 283.3. found: 283.1.

Step 3: To a solution of tert-butyl (3R,4S)-3-fluoro-4-hydroxypiperidine-1-carboxylate (202 mg, 0.92 mmol) in Me-THF (10 mL) at 0° C. was added potassium tert-butoxide solution (1.0 M, 1.06 mL, 1.06 mmol) in one portion and stirred at that temperature. After 45 min, N-(6-(3-cyano-4-fluorophenyl)pyrimidin-4-yl)cyclopropanecarboxamide (200 mgs, 0.71 mmol) was added in one portion and warmed to room temperature. The reaction was heated at 60° C. for 2 h. The reaction was quenched with minimum amount of water, concentrated to dryness to give tert-butyl (3R,4S)-4-(2-cyano-4-(6-(cyclopropanecarboxamido)pyrimidin-4-yl)phenoxy)-3-fluoropiperidine-1-carboxylate which was used further without purification. LCMS-ESI⁺ (m/z): [M+H]⁺ calcd for $C_{25}H_{28}FN_5O_4$ 482.5. found: 482.1.

Step 4: To a solution of tert-butyl (3R,4S)-4-(2-cyano-4-(6-(cyclopropanecarboxamido)pyrimidin-4-yl)phenoxy)-3-fluoropiperidine-1-carboxylate (342 mgs, 0.71 mmol) in DCM (5 mL), was added TFA (3 mL) and stirred at room temperature for 1 h. The reaction mixture was then diluted with DCM and washed with saturated solution of NaHCO₃ (3×), brine and dried (MgSO₄). Filtration and concentration gave N-(6-(3-cyano-4-(((3R,4S)-3-fluoropiperidin-4-yl)oxy)phenyl)pyrimidin-4-yl)cyclopropanecarboxamide which was used further without purification. LCMS-ESI⁺ (m/z): [M+H]⁺ calcd for $C_{20}H_{20}FN_5O_2$ 382.4. found: 382.1.

Step 5: To solution of N-(6-(3-cyano-4-(((3R,4S)-3-fluoropiperidin-4-yl)oxy)phenyl)pyrimidin-4-yl)cyclopropanecarboxamide (50 mg, 0.13 mmol), Glycolic acid (20 mg, 0.26 mmol), HATU (75 mg, 0.2 mmol) in DMF (1 mL) was added DIPEA (0.07 mL, 0.39 mmol) and stirred at rt for 1 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{22}H_{22}FN_5O_4$ 440.4. found: 440.2. ¹H NMR (400 MHz, Methanol-d₄) δ 11.3 (s, 1H), 8.93 (d, J=1.2 Hz, 1H), 8.52 (d, J=1.3 Hz, 1H), 8.42-8.23 (m, 2H), 7.59 (d, J=9.1 Hz, 1H), 5.15-4.89 (m, 2H), 4.23-3.98 (m, 3H), 3.73-3.09 (m, 3H), 2.09-1.73 (m, 3H), 1.02-0.75 (m, 4H).

Example 20: (S)—N-(6-(3-cyano-4-((3,3-difluoro-1-(2-hydroxyacetyl)piperidin-4-yl)oxy)phenyl)pyrimidin-4-yl)cyclopropanecarboxamide

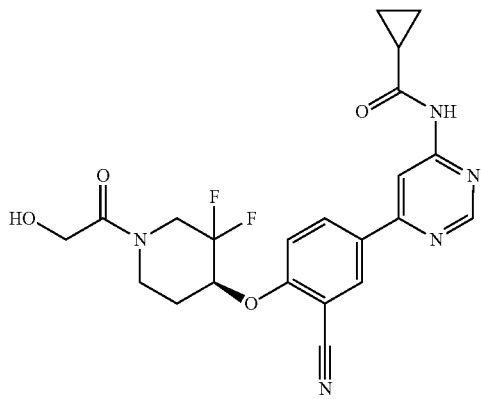 [SMILES: N#Cc1cc(-c2cc(NC(=O)C3CC3)ncn2)ccc1O[C@H]1CCN(C(=O)CO)CC1(F)F]

Step 1: To a solution of tert-butyl (S)-3,3-difluoro-4-hydroxypiperidine-1-carboxylate (219 mg, 0.92 mmol) in Me-THF (10 mL) at 0° C. was added potassium tert-butoxide solution (1.0 M, 1.06 mL, 1.06 mmol) in one portion and stirred at that temperature. After 45 min, N-(6-(3-cyano-4-fluorophenyl)pyrimidin-4-yl)cyclopropanecarboxamide (200 mgs, 0.71 mmol) was added in one portion and warmed to room temperature. The reaction was heated at 60° C. for 3 h. The reaction was quenched with minimum amount of water, concentrated to dryness to give tert-butyl (S)-4-(2-cyano-4-(6-(cyclopropanecarboxamido)pyrimidin-4-yl)phenoxy)-3,3-difluoropiperidine-1-carboxylate which was used further without purification. LCMS-ESI⁺ (m/z): [M+H]⁺ calcd for $C_{25}H_{27}F_2N_5O_4$ 500.5. found: 500.1.

Step 2: To a solution of tert-butyl (S)-4-(2-cyano-4-(6-(cyclopropanecarboxamido)pyrimidin-4-yl)phenoxy)-3,3-difluoropiperidine-1-carboxylate (342 mgs, 0.68 mmol) in DCM (5 mL), was added TFA (3 mL) and stirred at room temperature for 1 h. The reaction mixture was then diluted with DCM and washed with saturated solution of NaHCO₃ (3×), brine and dried (MgSO₄). Filtration and concentration gave (S)—N-(6-(3-cyano-4-((3,3-difluoropiperidin-4-yl)oxy)phenyl)pyrimidin-4-yl)cyclopropanecarboxamide which was used further without purification. LCMS-ESI⁺ (m/z): [M+H]⁺ calcd for $C_{20}H_{19}F_2N_5O_2$ 400.4. found: 400.1.

Step 3: To solution of (S)—N-(6-(3-cyano-4-((3,3-difluoropiperidin-4-yl)oxy)phenyl)pyrimidin-4-yl)cyclopropanecarboxamide (50 mg, 0.13 mmol), Glycolic acid (20 mg, 0.26 mmol), HATU (72 mg, 0.2 mmol) in DMF (1 mL) was added DIPEA (0.07 mL, 0.39 mmol) and stirred at rt for 2 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{22}H_{21}F_2N_5O_4$ 458.4. found: 458.1. ¹H NMR (400 MHz, DMSO-d₆) δ 11.28 (s, 1H), 8.88 (d, J=1.2 Hz, 1H), 8.47 (d, J=1.3 Hz, 1H), 8.38-8.17 (m, 2H), 7.57 (d, J=9.1 Hz, 1H), 5.33-5.26 (m, 1H), 4.24 (brs), 4.12-3.76 (m, 4H), 3.58-3.39 (m, 2H), 2.15-1.71 (m, 3H), 1.03-0.66 (m, 4H).

Example 21: N-(6-(3-cyano-4-(((3R,4S)-1-((S)-2,3-dihydroxypropanoyl)-3-fluoropiperidin-4-yl)oxy)phenyl)pyrimidin-4-yl)cyclopropanecarboxamide

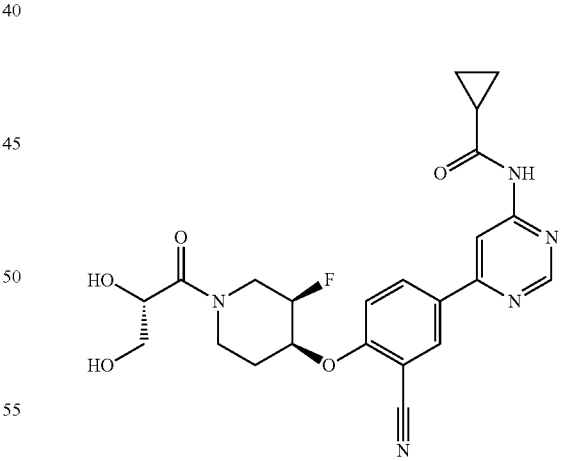

To solution of N-(6-(3-cyano-4-(((3R,4S)-3-fluoropiperidin-4-yl)oxy)phenyl)pyrimidin-4-yl)cyclopropanecarboxamide (50 mg, 0.13 mmol), (S)-2,3-dihydroxypropanoic acid (25 mg, 0.24 mmol), HATU (100 mg, 0.26 mmol) in DMF (1 mL) was added DIPEA (0.07 mL, 0.39 mmol) and stirred at rt for 2 h. The mixture was concentrated purified via prep HPLC (5-95% acetonitrile in water, 0.1% trifluoroacetic acid buffer) to give the title compound. LCMS-ESI⁺ (m/z): [M+H]⁺ calcd for $C_{23}H_{24}FN_5O_5$ 470.5. found: 470.2.

¹H NMR (400 MHz, DMSO-d₆) δ 11.32 (s, 1H), 8.92 (d, J=1.1 Hz, 1H), 8.52 (d, J=1.2 Hz, 1H), 8.40-8.23 (m, 2H), 7.58 (d, J=9.0 Hz, 1H), 5.22-4.89 (m, 1H), 4.71-4.59 (m, 1H), 4.42-4.25 (m, 1H), 4.18-4.07 (m, 1H), 3.99-3.85 (m, 1H), 3.63-3.39 (m, 2H), 2.14-1.67 (m, 3H), 0.96-0.81 (m, 4H).

Example 22: N-(6-(3-cyano-4-(((S)-1-((S)-2,3-dihydroxypropanoyl)-3,3-difluoropiperidin-4-yl)oxy)phenyl)pyrimidin-4-yl)cyclopropanecarboxamide

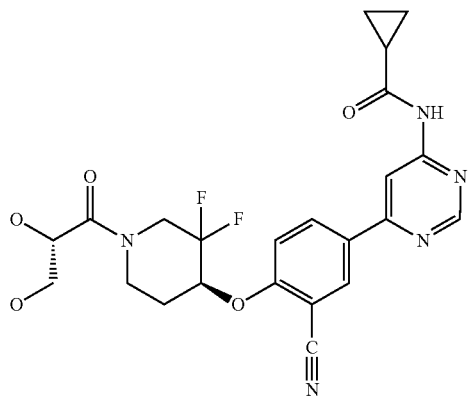 [SMILES: N#Cc1cc(-c2cc(NC(=O)C3CC3)ncn2)ccc1O[C@H]1CCN(C(=O)[C@@H](O)CO)CC1(F)F]

To solution of (S)—N-(6-(3-cyano-4-((3,3-difluoropiperidin-4-yl)oxy)phenyl)pyrimidin-4-yl)cyclopropanecarboxamide (50 mg, 0.13 mmol), (S)-2,3-dihydroxypropanoic acid (25 mg, 0.24 mmol), HATU (95 mg, 0.25 mmol) in DMF (1 mL) was added DIPEA (0.07 mL, 0.39 mmol) and stirred at rt for 2 h. The mixture was concentrated purified via prep HPLC (5-95% acetonitrile in water, 0.1% trifluoroacetic acid buffer). The fractions containing the desired compound were then mixed, concentrated, dissolved in Methanol and passed through the MP-carbonate resin. The filtrate were then concentrated and re-purified by flash chromatography (SiO₂, 0-10% Methanol/Ethyl acetate) to give the title compound. LCMS-ESI⁺ (m/z): [M+H]⁺ calcd for C₂₃H₂₃F₂N₅O₅ 488.4. found: 488.2. ¹H NMR (400 MHz, DMSO-d₆) δ 11.33 (s, 1H), 8.93 (d, J=1.2 Hz, 1H), 8.53 (d, J=1.2 Hz, 1H), 8.43-8.30 (m, 2H), 7.62 (d, J=9.1 Hz, 1H), 5.41-5.20 (m, 2H), 4.80-4.68 (m, 1H), 4.41-4.30 (m, 1H), 4.25-3.95 (m, 2H), 3.90-3.85 (m, 1H), 3.70-3.42 (m, 2H), 2.18-1.78 (m, 3H), 1.01-0.82 (m, 4H).

Example 23: N-(6-(3-cyano-4-((1-(2-hydroxyacetyl)piperidin-4-yl)oxy)phenyl)pyrimidin-4-yl)cyclopropanecarboxamide

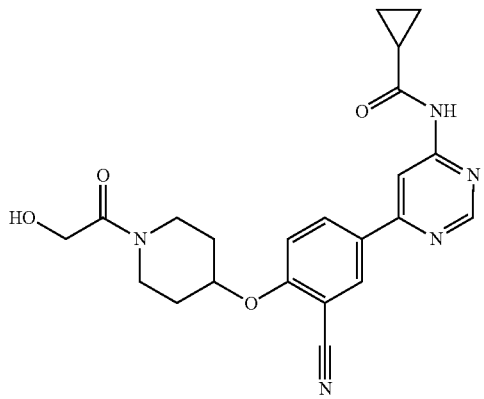 [SMILES: N#Cc1cc(-c2cc(NC(=O)C3CC3)ncn2)ccc1OC1CCN(C(=O)CO)CC1]

Step 1: To a solution of tert-butyl 4-hydroxypiperidine-1-carboxylate (86 mg, 0.43 mmol) in Me-THF (5 mL) at 0° C. was added potassium tert-butoxide solution (1.0 M, 0.5 mL, 0.5 mmol) in one portion and stirred at that temperature. After 45 min, N-(6-(3-cyano-4-fluorophenyl)pyrimidin-4-yl)cyclopropanecarboxamide (100 mgs, 0.35 mmol) was added in one portion and warmed to room temperature. The reaction was heated at 60° C. for 2 h. The reaction was quenched with minimum amount of water and purified by flash chromatography (SiO₂, 0-20% Methanol/DCM) to tert-butyl 4-(2-cyano-4-(6-(cyclopropanecarboxamido)pyrimidin-4-yl)phenoxy)piperidine-1-carboxylate. LCMS-ESI⁺ (m/z): [M+H]⁺ calcd for C₂₅H₂₉N₅O₄ 464.5. found: 464.1.

Step 2: To a solution of tert-butyl 4-(2-cyano-4-(6-(cyclopropanecarboxamido)pyrimidin-4-yl)phenoxy)piperidine-1-carboxylate (165 mgs, 0.35 mmol) in DCM (3 mL), was added TFA (0.5 mL) and stirred at room temperature for 1 h. The reaction mixture was then concentrated to dryness (azeotrope with Toluene and Methanol) to give N-(6-(3-cyano-4-(piperidin-4-yloxy)phenyl)pyrimidin-4-yl)cyclopropanecarboxamide as TFA salt which was used further without purification. LCMS-ESI⁺ (m/z): [M+H]⁺ calcd for C₂₀H₂₁N₅O₂ 364.5. found: 364.1.

Step 3: To solution of N-(6-(3-cyano-4-(piperidin-4-yloxy)phenyl)pyrimidin-4-yl)cyclopropanecarboxamide in DMF (4 mL) was added Glycolic acid (53 mg, 0.7 mmol), HATU (133 mg, 0.35 mmol), DIPEA (0.18 mL, 1.05 mmol) and stirred at rt. After 16 h, more Glycolic acid (53 mg, 0.7 mmol), HATU (133 mg, 0.35 mmol), DIPEA (0.18 mL, 1.05 mmol) was added and stirred at rt for 1 h. The reaction mixture was then diluted with Ethyl acetate (30 mL) and washed with 1N HCl (1×), water and the aqueous layer were then back extracted with ethyl acetate. The combined organic layers were then washed with saturated solution of NaHCO₃ (3×), water and brine. The organic layer was concentrated and purified via prep HPLC (5-95% acetonitrile in water, 0.1% trifluoroacetic acid buffer) to give the title compound. LCMS-ESI⁺ (m/z): [M+H]⁺ calcd for C₂₂H₂₃N₅O₄ 422.4. found: 422.1.

Example 24: N-(4-cyano-5-(((3R,4S)-3-fluoro-1-(2-hydroxyacetyl)piperidin-4-yl)oxy)-[2,4'-bipyridin]-2'-yl)cyclopropanecarboxamide

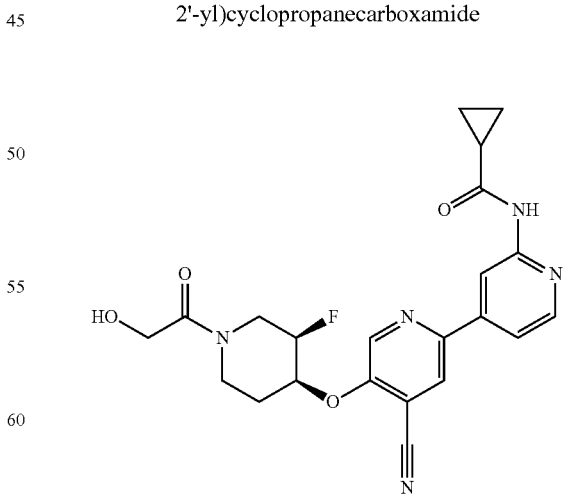

Step 1: To a solution of tert-butyl (3R,4S)-3-fluoro-4-hydroxypiperidine-1-carboxylate (1300 mgs, 5.93 mmol) in Me-THF (30 mL) at 0° C. was added potassium tert-butoxide solution (1.0 M, 10 mL, 10 mmol) in one portion and stirred at that temperature. After 50 min, 2-bromo-5-fluoroisonicotinonitrile (1000 mgs, 4.98 mmol) in Me-THF (10 mL) was added in one portion and warmed to room temperature. The reaction was heated at 60° C. for 2 h. The reaction was quenched with water and extracted with DCM. The combined organic layers were then concentrated and purified by flash chromatography (SiO$_2$, 0-10% Methanol/DCM) to give tert-butyl (3R,4S)-4-((6-bromo-4-cyanopyridin-3-yl)oxy)-3-fluoropiperidine-1-carboxylate. LCMS-ESI$^+$ (m/z): [M+H]$^+$ calcd for C$_{16}$H$_{19}$BrFN$_3$O$_3$ 401.2. found: 401.1.

Step 2: To a solution of tert-butyl (3R,4S)-4-((6-bromo-4-cyanopyridin-3-yl)oxy)-3-fluoropiperidine-1-carboxylate (300 mgs, 0.75 mmol) and 4-(4,4,5,5-tetramethyl-1,3,2-dioxaborolan-2-yl)pyridin-2-amine (181 mgs, 0.82 mmol) in DME (3 mL) was added 2.0 M aq Na$_2$CO$_3$ (1.1 mL, 2.25 mmol) and Pd(PPh$_3$)$_4$ catalyst (26 mgs, 0.02 mmol). The reaction mixture was heated at 140° C. for 1 hr. The reaction mixture was then purified by flash chromatography (SiO$_2$, 0-15% Methanol/DCM) to give tert-butyl (3R,4S)-4-42'-amino-4-cyano-[2,4'-bipyridin]-5-yl)oxy)-3-fluoropiperidine-1-carboxylate. LCMS-ESI$^+$ (m/z): [M+H]$^+$ calcd for C$_{21}$H$_{24}$FN$_5$O$_3$ 310.9. found: 310.1.

Step 3: To above solution of tert-butyl (3R,4S)-4-((2'-amino-4-cyano-[2,4'-bipyridin]-5-yl)oxy)-3-fluoropiperidine-1-carboxylate (36 mgs, 0.09 mmol) in NMP (1.0 mL) and DIPEA (0.1 mL) cyclopropanecarbonyl chloride (0.1 mL) was slowly added. After 10 min at rt, the reaction mixture was heated at 85° C. for 2 h. The reaction mixture was then cooled to rt and ammonia in methanol (7N, 1.0 mL) was added and stirred at rt. After 1 h, the reaction mixture was concentrated, diluted with water and the resulting solids were filtered and washed with water and diethyl ether and dried to give tert-butyl (3R,4S)-4-((4-cyano-2'-(cyclopropanecarboxamido)-[2,4'-bipyridin]-5-yl)oxy)-3-fluoropiperidine-1-carboxylate which was used further without purification. LCMS-ESI$^+$ (m/z): [M+H]$^+$ calcd for C$_{25}$H$_{28}$FN$_5$O$_4$ 482.5. found: 482.1.

Step 4: To a solution of tert-butyl (3R,4S)-4-((4-cyano-2'-(cyclopropanecarboxamido)-[2,4'-bipyridin]-5-yl)oxy)-3-fluoropiperidine-1-carboxylate in DCM (3 mL), was added TFA (0.5 mL) and stirred at room temperature for 1 h. The reaction mixture was then concentrated to dryness (azeotrope with Toluene and Methanol) to give N-(4-cyano-5-(((3R,4S)-3-fluoropiperidin-4-yl)oxy)-[2,4'-bipyridin]-2'-yl)cyclopropanecarboxamide as TFA salt which was used further without purification. LCMS-ESI$^+$ (m/z): [M+H]$^+$ calcd for C$_{20}$H$_{20}$FN$_5$O$_2$ 382.4. found: 382.1.

Step 5: To solution of N-(4-cyano-5-(((3R,4S)-3-fluoropiperidin-4-yl)oxy)-[2,4'-bipyridin]-2'-yl)cyclopropanecarboxamide (33 mgs, 0.087 mmol) in DMF (2 mL) was added Glycolic acid (13 mg, 0.17 mmol), HATU (41 mg, 0.11 mmol), DIPEA (0.05 mL, 0.26 mmol) and stirred at rt. The reaction mixture was then concentrated and purified via prep HPLC (5-95% acetonitrile in water, 0.1% trifluoroacetic acid buffer) to give the title compound. LCMS-ESI$^+$ (m/z): [M+H]$^+$ calcd for C$_{22}$H$_{22}$FN$_5$O$_4$ 440.4. found: 440.1.

Example 25: (S)—N-(6-(3-cyano-4-((3,3-difluoropiperidin-4-yl)oxy)phenyl)pyrimidin-4-yl)cyclopropanecarboxamide

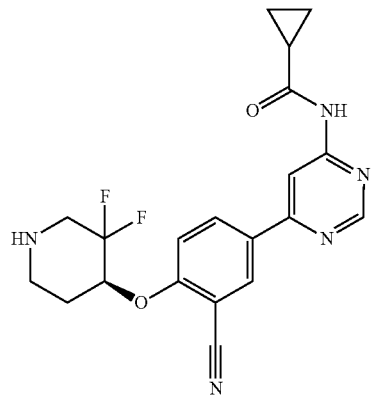 [SMILES: N#Cc1cc(-c2cc(NC(=O)C3CC3)ncn2)ccc1O[C@H]1CCNCC1(F)F]

Step 1: To a solution of tert-butyl (S)-3,3-difluoro-4-hydroxypiperidine-1-carboxylate (100 mg, 0.42 mmol) in Me-THF (3 mL) at 0° C. was added potassium tert-butoxide solution (1.0 M, 0.5 mL, 0.5 mmol) in one portion and stirred at that temperature. After 45 min, N-(6-(3-cyano-4-fluorophenyl)pyrimidin-4-yl)cyclopropanecarboxamide (100 mgs, 0.27 mmol) in Me-THF (5 mL) was added in one portion and warmed to room temperature. The reaction was heated at 60° C. for 1 h. The reaction was quenched with minimum amount of water, concentrated to dryness and purified by flash chromatography (SiO$_2$, 0-10% Methanol/DCM) to give tert-butyl (S)-4-(2-cyano-4-(6-(cyclopropanecarboxamido)pyrimidin-4-yl)phenoxy)-3,3-difluoropiperidine-1-carboxylate. LCMS-ESI$^+$ (m/z): [M+H]$^+$ calcd for C$_{25}$H$_{27}$F$_2$N$_5$O$_4$ 500.5. found: 500.1.

Step 2: To a solution of tert-butyl (S)-4-(2-cyano-4-(6-(cyclopropanecarboxamido)pyrimidin-4-yl)phenoxy)-3,3-difluoropiperidine-1-carboxylate (132 mgs, 0.27 mmol) in DCM (5 mL), was added TFA (3 mL) and stirred at room temperature for 30 min. The reaction mixture was then concentrated and purified via prep HPLC (5-95% acetonitrile in water, 0.1% trifluoroacetic acid buffer) to give the title compound. LCMS-ESI$^+$ (m/z): [M+H]$^+$ calcd for C$_{20}$H$_{19}$F$_2$N$_5$O$_2$ 400.4. found: 400.1.

Example 26: (2-Cyano-4-(2-(cyclopropanecarboxamido)pyridin-4-yl)phenyl)-L-proline

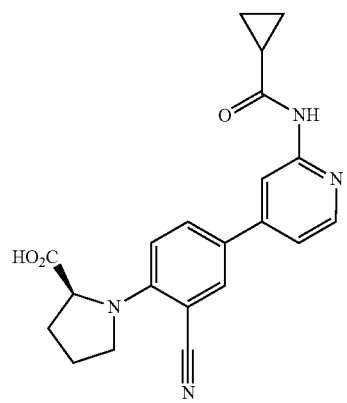 [SMILES: N#Cc1cc(-c2ccnc(NC(=O)C3CC3)c2)ccc1N1CCC[C@H]1C(=O)O]

To a solution of N-(4-(3-cyano-4-fluorophenyl)pyridin-2-yl)cyclopropanecarboxamide (194 mg, 0.69 mmol) in 5 mL iPrOH was added (S)-pyrrolidine methyl ester (267 mg, 2.07 mmol) and DIEA (0.721 mL, 4.14 mmol) and stirred at rt for 1 h. The reaction mixture was then treated with t-BuOH (232 mg, 2.07 mmol) and heated at 150° C. in a microwave for 15 min. Purification by flash column chromatography gave (2-Cyano-4-(2-(cyclopropanecarboxamido)pyridin-4-yl) phenyl)-L-proline as a white solid. 1H NMR (400 MHz, DMSO-d6) δ 10.97 (s, 1H), 8.36-8.21 (m, 2H), 7.87 (d, J=2.4 Hz, 1H), 7.79 (dd, J=9.1, 2.4 Hz, 1H), 7.44 (dd, J=5.5, 1.7 Hz, 1H), 6.82 (d, J=9.1 Hz, 1H), 4.77 (dd, J=8.3, 3.9 Hz, 1H), 3.82-3.63 (m, 2H), 2.39-2.25 (m, 1H), 2.15-1.85 (m, 3H), 1.98 (s, 1H), 0.83 (dt, J=8.5, 2.8 Hz, 4H). ES/MS 377.24 (M+H$^+$).

Example 27: N-(6-(3-cyano-4-(((3R,4S)-3-fluoro-1-(1-methyl-1H-1,2,3-triazole-4-carbonyl)piperidin-4-yl)oxy)phenyl)pyrimidin-4-yl)cyclopropanecarboxamide

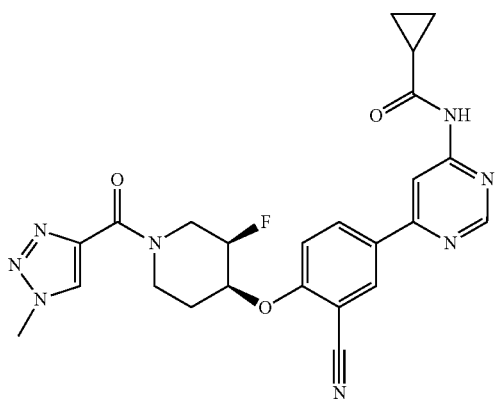 [SMILES: Cn1cc(C(=O)N2CC[C@H](Oc3ccc(-c4cc(NC(=O)C5CC5)ncn4)cc3C#N)[C@H](F)C2)nn1]

To a mixture of 6-chloropyrimidin-4-amine (2 g, 15.4 mmol), 2-fluoro-5-(4,4,5,5-tetramethyl-1,3,2-dioxaborolan-2-yl)benzonitrile (3.8 g, 15.4 mmol), PEPPSI catalyst (1.0 g) and cesium carbonate (10 g, 30.9 mmol) in argon atmosphere was added a mixture of de-gassed solvents (1,4-dioxane and water (2:1)). This mixture was heated under argon atmosphere at 105° C. for 30 min in a heating block. After cooling to room temperature, it was poured into water, and extracted with dichloromethane. The combined organic layers was washed with brine, dried with magnesium sulfate, filtered and concentrated under reduced pressure to yield 5-(6-aminopyrimidin-4-yl)-2-fluorobenzonitrile.

To a solution of 5-(6-aminopyrimidin-4-yl)-2-fluorobenzonitrile (1.2 g, 5.6 mmol), DIPEA (1.7 mL, 16.8 mmol) in NMP in a 100 mL round bottle flask was added slowly cyclopropanecarbonyl chloride (1.9 g, 18.5 mmol). The reaction mixture was stirred at 80° C. for 2 hrs. After cooling to room temperature 7N of NH$_3$ in methanol was added to the mixture and it was stirred for 1 hr. The mixture was evaporated under reduced pressure and solids were suspended and stirred in water. After 3 hrs, solids were filtered off and dried in high vacuum to yield N-(6-(3-cyano-4-fluorophenyl)pyrimidin-4-yl)cyclopropanecarboxamide. A solution of a tert-butyl (3R,4S)-3-fluoro-4-hydroxypiperidine-1-carboxylate (300 mg, 1.4 mmol) in methyl-tetrahydrofuran was stirred in an ice-water bath under an atmosphere of Argon. Potassium tert-butoxide solution (1.0 M, 1.4 mL) was added in a single portion and the mixture was stirred at 0° C. for 40 minutes. N-(6-(3-cyano-4-fluorophenyl)pyrimidin-4-yl)cyclopropanecarboxamide (351 mg, 1.2 mmol) was added and mixture was stirred for 1 hr at 60° C. After the mixture was cooled to room temperature, water was added, and mixture evaporated under reduced pressure to yield the crude tert-butyl (3R,4S)-4-(2-cyano-4-(6-(cyclopropanecarboxamido)pyrimidin-4-yl)phenoxy)-3-fluoropiperidine-1-carboxylate.

Tert-butyl (3R,4S)-4-(2-cyano-4-(6-(cyclopropanecarboxamido)pyrimidin-4-yl)phenoxy)-3-fluoropiperidine-1-carboxylate was dissolved in a mixture of DCM/TFA (2:1) and stirred at room temperature for 1 hr. Reaction mixture was evaporated under reduced pressure and solids were re-dissolved in DCM and then a saturated aqueous solution of NaHCO$_3$ was added. Organics were collected and evaporated under reduced pressure to yield N-(6-(3-cyano-4-(((3R,4S)-3-fluoropiperidin-4-yl)oxy)phenyl)pyrimidin-4-yl)cyclopropanecarboxamide.

To a solution of 1-methyl-1H-1,2,3-triazole-4-carboxylic acid (17 mgs, 0.13 mmol), 2-chloro-1-methylpyridin-1-ium iodide (34 mgs, 0.13 mmol) and DIPEA in DMF in a 20 ml sealed microwave tube was heated at 60° C. for 30 min and then N-(6-(3-cyano-4-(((3R,4S)-3-fluoropiperidin-4-yl)oxy) phenyl)pyrimidin-4-yl)cyclopropanecarboxamide (50 mgs, 0.13 mmol) was added. Reaction mixture was heated at 60° C. for 1 hr. After cooling to room temperature reaction mixture was evaporated under reduced pressure and purified via preparative HPLC (5-65% acetonitrile in water, 0.1% trifluoroacteic acid buffer) to yield N-(6-(3-cyano-4-(((3R,4S)-3-fluoro-1-(1-methyl-1H-1,2,3-triazole-4-carbonyl)piperidin-4-yl)oxy)phenyl)pyrimidin-4-yl)cyclopropanecarboxamide. 1H NMR (400 MHz, DMSO-d6) δ 11.34 (s, 1H), 8.92 (d, J=1.2 Hz, 1H), 8.51 (d, J=1.6 Hz, 2H), 8.37 (d, J=2.2 Hz, 1H), 8.32 (dd, J=9.0, 2.4 Hz, 1H), 7.60 (d, J=9.1 Hz, 1H), 5.27-4.91 (m, 2H), 4.69-4.24 (m, 1H), 4.07 (s, 3H), 3.95-3.75 (m, 3H), 2.12-1.79 (m, 3H), 0.88 (h, J=3.3 Hz, 4H). LCMS-ESI$^+$ (m/z): [M+H]$^+$ calcd for C$_{24}$H$_{23}$FN$_8$O$_3$: 491.2; found: 491.2.

Example 28: N-(6-(3-cyano-4-(((3R,4S)-3-fluoro-1-(4H-1,2,4-triazole-3-carbonyl)piperidin-4-yl)oxy) phenyl)pyrimidin-4-yl)cyclopropanecarboxamide

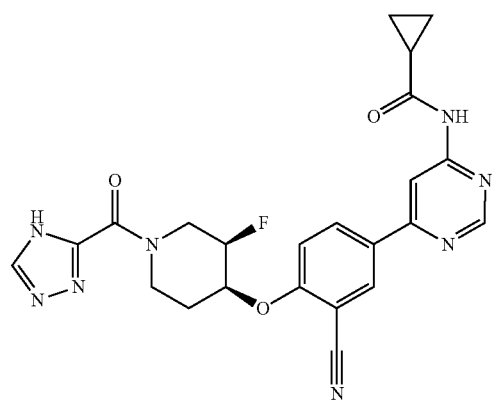 [SMILES: N#Cc1cc(-c2cc(NC(=O)C3CC3)ncn2)ccc1O[C@H]1CCN(C(=O)c2nnc[nH]2)C[C@H]1F]

The title compound was prepared following a similar procedure to Example 27 using 4H-1,2,4-triazole-3-carboxylic acid. 1H NMR (400 MHz, DMSO-d6) δ 11.29 (s, 1H), 8.88 (d, J=1.2 Hz, 1H), 8.47 (d, J=1.1 Hz, 1H), 8.33 (t, J=2.4

Hz, 1H), 8.27 (dd, J=9.0, 2.4 Hz, 1H), 7.55 (dd, J=9.2, 1.7 Hz, 1H), 5.10 (d, J=36.3 Hz, 2H), 4.59-4.21 (m, 1H), 3.90-3.75 (m, 3H), 2.07-1.83 (m, 3H), 0.84 (dt, J=4.8, 2.2 Hz, 4H). LCMS-ESI$^+$ (m/z): [M+H]$^+$ calcd for $C_{23}H_{21}FN_8O_3$: 477.2; found: 477.2.

Example 29: N-(6-(3-cyano-4-(((3R,4S)-3-fluoro-1-formylpiperidin-4-yl)oxy)phenyl)pyrimidin-4-yl) cyclopropanecarboxamide

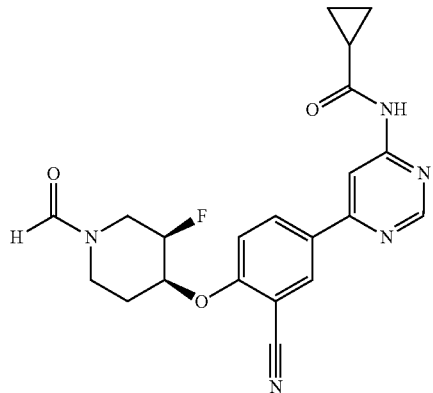 [SMILES: N#Cc1cc(-c2cc(NC(=O)C3CC3)ncn2)ccc1O[C@H]1CCN(C=O)C[C@H]1F]

The title compound was prepared as by product following a similar procedure Example 27 using 1H-imidazole-5-carboxylic acid. $^1$H NMR (400 MHz, DMSO-d$_6$) δ 11.34 (s, 1H), 8.92 (d, J=1.2 Hz, 1H), 8.51 (d, J=1.3 Hz, 1H), 8.37 (d, J=2.3 Hz, 1H), 8.31 (dd, J=9.0, 2.3 Hz, 1H), 8.09 (s, 0.5H), 7.99 (s, 0.5H), 7.58 (d, J=9.1 Hz, 1H), 5.24-4.90 (m, 2H), 4.30-3.82 (m, 2H), 3.7-3.3 (m, 3H), 2.12-1.63 (m, 2H), 0.88 (dt, J=8.0, 2.2 Hz, 4H). LCMS-ESI$^+$ (m/z): [M+H]$^+$ calcd for $C_{21}H_{20}FN_5O_3$: 410.2; found: 410.1.

Example 30: N-(6-(3-cyano-4-(((3R,4S)-3-fluoro-1-(3-methyl-1H-1,2,4-triazole-5-carbonyl)piperidin-4-yl)oxy)phenyl)pyrimidin-4-yl)cyclopropanecarboxamide

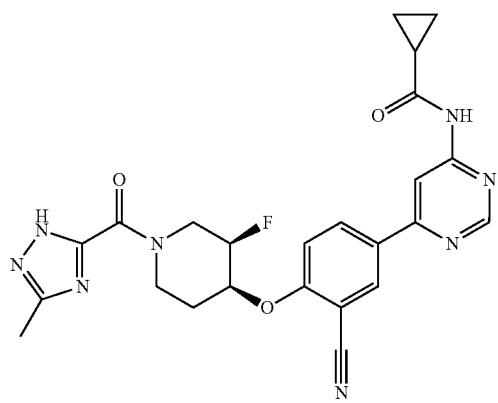 [SMILES: Cc1n[nH]c(C(=O)N2CC[C@H](Oc3ccc(-c4cc(NC(=O)C5CC5)ncn4)cc3C#N)[C@H](F)C2)n1]

The title compound was prepared following a similar procedure Example 27 using 3-methyl-1H-1,2,4-triazole-5-carboxylic acid. 1H NMR (400 MHz, DMSO-d6) δ 11.34 (s, 1H), 8.92 (d, J=1.2 Hz, 1H), 8.51 (s, 1H), 8.37 (t, J=2.4 Hz, 1H), 8.31 (dd, J=9.0, 2.3 Hz, 1H), 7.58 (dd, J=9.2, 1.7 Hz, 1H), 5.27-4.88 (m, 2H), 4.57-4.23 (m, 1H), 3.9-3.7 (m, 3H), 2.36 (s, 3H), 2.13-1.94 (m, 3H), 0.98-0.79 (m, 4H). LCMS-ESI$^+$ (m/z): [M+H]$^+$ calcd for $C_{24}H_{23}FN_8O_3$: 491.2; found: 491.1.

Example 31: 2-((3R,4S)-4-(2-cyano-4-(6-(cyclopropanecarboxamido)pyrimidin-4-yl)phenoxy)-3-fluoropiperidin-1-yl)-1-methylpyridin-1-ium 2,2,2-trifluoroacetate

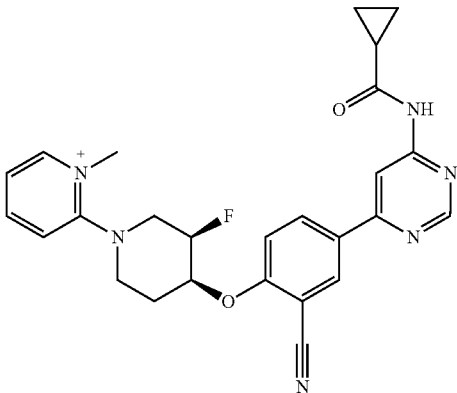

The title compound was obtained as a by-product in the synthesis of Example 28. 1H NMR (400 MHz, DMSO-d6) δ 11.2 (s, 1H), 8.93 (d, J=1.2 Hz, 1H), 8.61 (dd, J=6.5, 1.7 Hz, 1H), 8.53 (d, J=1.2 Hz, 1H), 8.40 (d, J=2.3 Hz, 1H), 8.37-8.27 (m, 2H), 7.74 (dd, J=8.6, 1.2 Hz, 1H), 7.64 (d, J=9.1 Hz, 1H), 7.53 (ddd, J=7.5, 6.3, 1.3 Hz, 1H), 5.15 (d, J=5.1 Hz, 2H), 3.94-3.57 (m, 4H), 2.27-2.01 (m, 3H), 0.98-0.79 (m, 4H). LCMS-ESI$^+$ (m/z): [M+H]$^+$ calcd for $C_{26}H_{26}FN_6O_2$: 473.2; found: 473.2.

Example 32: (S)—N-(6-(3-cyano-4-((3,3-difluoro-1-(4H-1,2,4-triazole-3-carbonyl)piperidin-4-yl)oxy)phenyl)pyrimidin-4-yl)cyclopropanecarboxamide

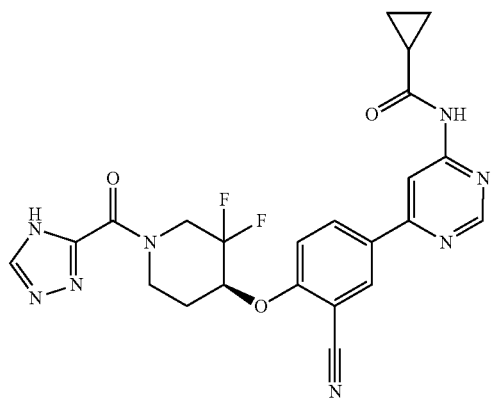 [SMILES: N#Cc1cc(-c2cc(NC(=O)C3CC3)ncn2)ccc1O[C@H]1CCN(C(=O)c2nnc[nH]2)CC1(F)F]

To a solution of 4H-1,2,4-triazole-3-carboxylic acid (10 mg, 0.08 mmol) and 0.1 ml of DMF in DCM at 0° C. was added oxalyl chloride (6 uL, 0.075 mmol). Reaction mixture was stirred at room temperature for 1 hr and then evaporated under reduced pressure. Solids were re-dissolved in DMF and (S)—N-(6-(3-cyano-4-((3,3-difluoropiperidin-4-yl)oxy)

phenyl)pyrimidin-4-yl)cyclopropanecarboxamide (30 mgs, 0.075 mmol) was added together with DMAP (18 mgs, 0.15 mmol). Reaction mixture was stirred at room temperature for 18 hr and then purified via preparative HPLC (5-65% acetonitrile in water, 0.1% trifluoroacteic acid buffer) to yield (S)—N-(6-(3-cyano-4-((3,3-difluoro-1-(4H-1,2,4-triazole-3-carbonyl)piperidin-4-yl)oxy)phenyl)pyrimidin-4-yl)cyclopropanecarboxamide. 1H NMR (400 MHz, DMSO-d6) δ 11.30 (s, 1H), 8.88 (d, J=1.2 Hz, 1H), 8.48 (d, J=1.2 Hz, 2H), 8.36 (d, J=2.3 Hz, 1H), 8.30 (dd, J=9.0, 2.3 Hz, 1H), 7.59 (d, J=9.1 Hz, 1H), 5.37 (s, 1H), 4.06-3.54 (m, 4H), 2.15 (s, 1H), 2.07-1.93 (m, 2H), 0.84 (dt, J=7.8, 2.1 Hz, 4H). LCMS-ESI+ (m/z): [M+H]+ calcd for $C_{23}H_{20}F_2N_8O_3$: 495.2; found: 495.1.

Example 33: N-(6-(3-cyano-4-(((3R,4S)-3-fluoro-1-(oxazole-5-carbonyl)piperidin-4-yl)oxy)phenyl)pyrimidin-4-yl)cyclopropanecarboxamide

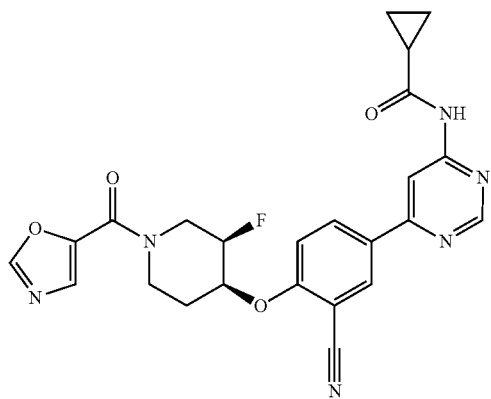 [SMILES: N#Cc1cc(-c2cc(NC(=O)C3CC3)ncn2)ccc1O[C@H]1CCN(C(=O)c2cnco2)C[C@H]1F]

The title compound was prepared following a similar procedure to Example 27 using oxazole-5-carboxylic acid. 1H NMR (400 MHz, DMSO-d6) δ 11.34 (s, 1H), 8.93 (d, J=1.2 Hz, 1H), 8.57 (s, 1H), 8.52 (d, J=1.3 Hz, 1H), 8.38 (d, J=2.3 Hz, 1H), 8.33 (dd, J=9.0, 2.3 Hz, 1H), 7.75 (s, 1H), 7.61 (d, J=9.1 Hz, 1H), 5.17 (s, 2H), 4.39 (s, 2H), 3.3-3.1 (m, 2H), 2.06 (p, J=7.2 Hz, 3H), 0.98-0.81 (m, 4H). LCMS-ESI+ (m/z): [M+H]+ calcd for $C_{24}H_{21}FN_6O_4$: 477.2; found: 477.1.

Example 34: (S)—N-(6-(3-cyano-4-((3,3-difluoro-1-(3-methyl-1H-1,2,4-triazole-5-carbonyl)piperidin-4-yl)oxy)phenyl)pyrimidin-4-yl)cyclopropanecarboxamide

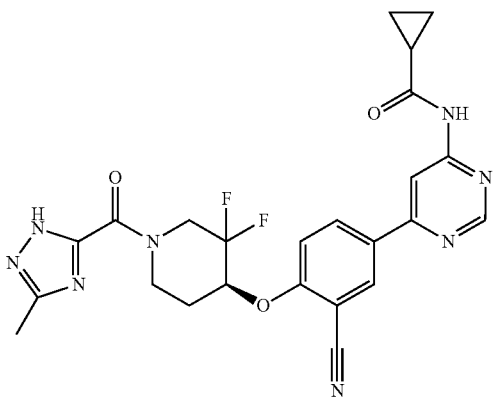 [SMILES: Cc1n[nH]c(C(=O)N2CC[C@H](Oc3ccc(-c4cc(NC(=O)C5CC5)ncn4)cc3C#N)C(F)(F)C2)n1]

The title compound was prepared following a similar procedure to Example 32 using 3-methyl-1H-1,2,4-triazole-5-carboxylic acid. 1H NMR (400 MHz, DMSO-d6) δ 11.35 (s, 1H), 8.93 (d, J=1.2 Hz, 1H), 8.53 (d, J=1.2 Hz, 1H), 8.41 (d, J=2.2 Hz, 1H), 8.35 (dd, J=8.9, 2.4 Hz, 1H), 7.63 (d, J=9.1 Hz, 1H), 5.41 (s, 1H), 2.38 (d, J=4.0 Hz, 4H), 2.23-1.82 (m, 3H), 0.96-0.77 (m, 4H). LCMS-ESI+ (m/z): [M+H]+ calcd for $C_{24}H_{22}F_2N_8O_3$: 509.2; found: 509.1.

Example 35: (trans)-ethyl 2-((6-(3-cyano-4-((tetrahydro-2H-pyran-4-yl)oxy)phenyl)pyrimidin-4-yl)carbamoyl)cyclopropanecarboxylate

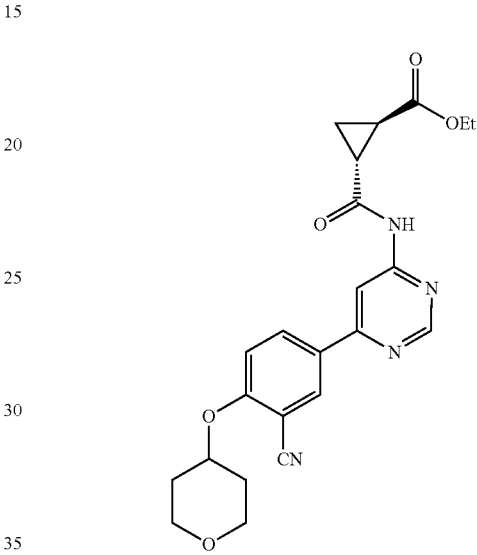

Trans-ethyl 2-(chlorocarbonyl)cyclopropanecarboxylate (2.741 g, 16 mmol) was added to a solution of 5-(6-aminopyrimidin-4-yl)-2-((tetrahydro-2H-pyran-4-yl)oxy)benzonitrile (2.30 g, 8 mmol) and DIEA (6.642 mL, 39 mmol) in 100 mL DCM and stirred at room temperature for 3 days. The reaction mixture was then diluted with EtOAc and saturated NaHCO3 and the organic layer dried and concentrated. Purification by silica gel chromatography provided (trans)-ethyl 2-((6-(3-cyano-4-((tetrahydro-2H-pyran-4-yl)oxy)phenyl)pyrimidin-4-yl)carbamoyl)cyclopropanecarboxylate and a light brown solid. 1H NMR (400 MHz, DMSO) δ 11.42 (s, 1H), 8.93 (d, J=1.2 Hz, 1H), 8.46 (d, J=1.2 Hz, 1H), 8.35 (d, J=2.3 Hz, 1H), 8.29 (dd, J=9.0, 2.4 Hz, 1H), 7.50 (d, J=9.1 Hz, 1H), 4.10 (q, J=7.1 Hz, 2H), 3.92-3.76 (m, 2H), 3.54 (ddd, J=11.5, 8.4, 3.2 Hz, 2H), 2.68-2.56 (m, 1H), 2.12-1.92 (m, 3H), 1.73-1.57 (m, 2H), 1.49-1.33 (m, 2H), 1.19 (q, J=8.9, 8.0 Hz, 4H). ES/MS 437.17 (M+H).

Example 36: N-(4-(3-cyano-4-((tetrahydro-2H-pyran-4-yl)oxy)phenyl)pyridin-2-yl)-1-hydroxycyclopropanecarboxamide

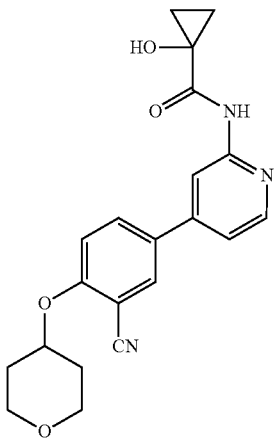 [SMILES: N#Cc1cc(-c2ccnc(NC(=O)C3(O)CC3)c2)ccc1OC1CCOCC1]

A solution of 1-((4-(3-cyano-4-((tetrahydro-2H-pyran-4-yl)oxy)phenyl)pyridin-2-yl)carbamoyl)cyclopropyl acetate (29 mg), 0.069 mmol) in 1 mL MeOH and 0.2 mL water was treated with potassium carbonate (52 µL, 0.10 mmol, 2.0 M) and allowed to stir at rt overnight. After partitioning the reaction mixture between EtOAc and saturated NaHCO$_3$, the organic layer separated and dried with sodium sulfate. Purification by RP HPLC provided as a white solid. N-(4-(3-cyano-4-((tetrahydro-2H-pyran-4-yl)oxy)phenyl)pyridin-2-yl)-1-hydroxycyclopropanecarboxamide as a white solid. $^1$H NMR (400 MHz, DMSO-d$_6$) δ 9.66 (s, 1H), 8.36 (dd, J=16.6, 3.5 Hz, 2H), 8.14 (d, J=2.4 Hz, 1H), 7.99 (dd, J=8.9, 2.4 Hz, 1H), 7.58-7.46 (m, 2H), 4.90 (tt, J=7.9, 3.9 Hz, 1H), 3.85 (ddd, J=10.5, 6.0, 3.9 Hz, 2H), 3.53 (ddd, J=11.5, 8.3, 3.2 Hz, 2H), 2.07-1.96 (m, 1H), 2.00 (s, 1H), 1.67 (dtd, J=12.3, 8.1, 3.8 Hz, 2H), 1.21 (q, J=4.4, 3.9 Hz, 2H), 1.06 (q, J=4.4 Hz, 2H). ES/MS 380.14 (M+H$^+$).

Example 37: 1-((4-(3-cyano-4-((tetrahydro-2H-pyran-4-yl)oxy)phenyl)pyridin-2-yl)carbamoyl)cyclopropyl acetate

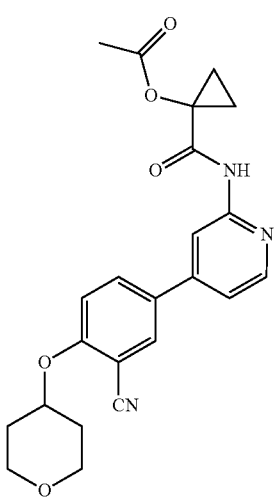 [SMILES: CC(=O)OC1(C(=O)Nc2cc(-c3ccc(OC4CCOCC4)c(C#N)c3)ccn2)CC1]

A solution of 5-(2-aminopyridin-4-yl)-2-((tetrahydro-2H-pyran-4-yl)oxy)benzonitrile (170 mg, 0.58 mmol), 1-(chlorocarbonyl)cyclopropyl acetate (94 mg, 0.58 mmol), pyridine (214 µL, 3 mmol) and 1 crystal of DMAP in 2.5 mL DCM was stirred at room temperature for 16 h. The reaction was then diluted with conc. NH$_4$OH (143 µL, 1.01 mmol) and allowed to stir for 2 h. After partitioning the reaction mixture between EtOAc and saturated NaHCO$_3$, the organic layer separated and dried with sodium sulfate. Purification by silica gel chromatography provided 1-((4-(3-cyano-4-((tetrahydro-2H-pyran-4-yl)oxy)phenyl)pyridin-2-yl)carbamoyl)cyclopropyl acetate as a white solid. $^1$H NMR (400 MHz, DMSO-d$_6$) δ 10.34 (s, 1H), 8.39 (d, J=5.3 Hz, 1H), 8.22 (d, J=1.6 Hz, 1H), 8.13 (d, J=2.4 Hz, 1H), 7.98 (dd, J=8.9, 2.4 Hz, 1H), 7.54-7.45 (m, 2H), 4.90 (tt, J=7.8, 3.8 Hz, 1H), 3.85 (ddd, J=11.4, 5.9, 3.9 Hz, 2H), 3.53 (ddd, J=11.5, 8.3, 3.1 Hz, 2H), 2.10 (s, 3H), 2.01 (dq, J=13.6, 3.8 Hz, 2H), 1.67 (dtd, J=12.4, 8.2, 3.9 Hz, 2H), 1.53-1.45 (m, 2H), 1.23-1.14 (m, 2H). ES/MS 422.16 (M+H$^+$).

Example 38: (1,2-trans)-N1-(6-(3-cyano-4-((tetrahydro-2H-pyran-4-yl)oxy)phenyl)pyridin-4-yl)-N2-methoxy-N2-methylcyclopropane-1,2-dicarboxamide

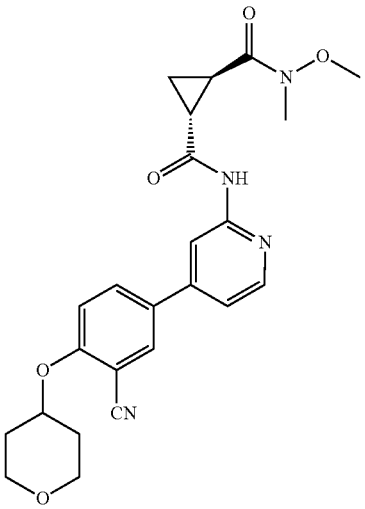 [SMILES: CON(C)C(=O)[C@@H]1C[C@H]1C(=O)Nc1cc(-c2ccc(OC3CCOCC3)c(C#N)c2)ccn1]

A solution of (trans-1,2)-2-((4-(3-cyano-4-((tetrahydro-2H-pyran-4-yl)oxy)phenyl)pyridin-2-yl)carbamoyl)cyclopropanecarboxylic acid (2.02 g, 4.96 mmol) in 25 mL DMF and treated with HATU (1.88 g, 4.96 mmol) and stirred at rt for 2 min. N,O-Dimethylhydroxylamine hydrochloride (0.725 g, 7.44 mmol) and DIEA (3.39 mL. 19.8 mmol) were added and the mixture stirred at rt for 1 h. After partitioning the reaction mixture between EtOAc and saturated NaHCO$_3$, the organic layer separated and dried with sodium sulfate. Purification by flash column chromatography provided (1,2-trans)-N1-(6-(3-cyano-4-((tetrahydro-2H-pyran-4-yl)oxy)phenyl)pyridin-4-yl)-N2-methoxy-N2-methylcyclopropane-1,2-dicarboxamide as a white solid. 1H NMR (400 MHz, DMSO-d6) δ 11.03 (s, 1H), 8.38-8.28 (m, 2H), 8.10 (d, J=2.4 Hz, 1H), 7.96 (dd, J=8.9, 2.4 Hz, 1H), 7.52-7.42 (m, 2H), 4.89 (dt, J=8.0, 4.0 Hz, 1H), 3.84 (ddd, J=11.5, 6.0, 4.0 Hz, 2H), 3.70 (s, 3H), 3.53 (ddd, J=11.5, 8.3, 3.1 Hz, 2H), 3.12 (s, 3H), 2.54 (d, J=5.0 Hz, 1H), 2.47-2.44 (m, 1H), 2.05-1.95 (m, 2H), 1.65 (dtd, J=12.4, 8.2, 3.8 Hz, 2H), 1.29 (dddd, J=17.4, 8.8, 5.7, 3.2 Hz, 2H). ES/MS 451.20 (M+H$^+$).

Example 39: (1,2-trans)-N-(4-(3-cyano-4-((tetrahydro-2H-pyran-4-yl)oxy)phenyl)pyridin-2-yl)-2-(-1-hydroxyethyl)cyclopropane-1-carboxamide

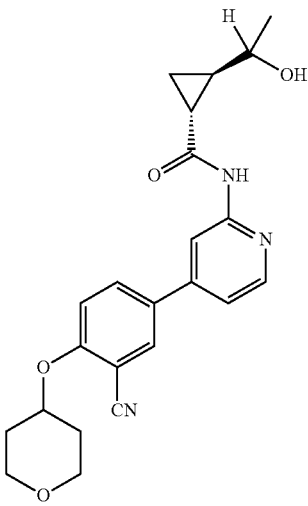 [SMILES: CC(O)[C@@H]1C[C@H]1C(=O)Nc1cc(-c2ccc(OC3CCOCC3)c(C#N)c2)ccn1]

A solution of (trans-1,2)-N-(4-(3-cyano-4-((tetrahydro-2H-pyran-4-yl)oxy)phenyl)pyridin-2-yl)-2-formylcyclopropane-1-carboxamide (200 mg, 0.51 mmol) in 3 mL THF was cooled to −78° C. and treated with methyl magnesium bromide (0.33 mL, 1.12 mmol, 3.4 M in THF) and stirred at −78° C. for 30 min. The reaction was quenched with MeOH and diluted with EtOAc and water. Organic layer was dried with sodium sulfate and concentrated. Purification by RP-HPLC provided (trans-1,2)-N-(4-(3-cyano-4-((tetrahydro-2H-pyran-4-yl)oxy)phenyl)pyridin-2-yl)-2-(-1-hydroxyethyl)cyclopropane-1-carboxamide as a white solid. ES/MS 408.19 (M+H$^+$).

Example 40: (1,2-trans)-N-(4-(3-cyano-4-((tetrahydro-2H-pyran-4-yl)oxy)phenyl)pyridin-2-yl)-2-formylcyclopropane-1-carboxamide

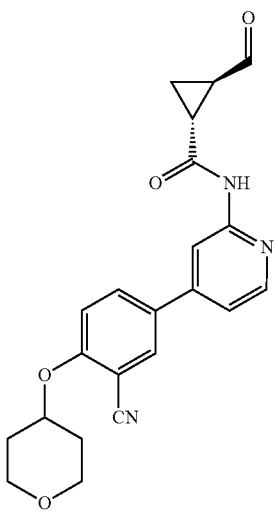 [SMILES: N#Cc1cc(-c2ccnc(NC(=O)[C@@H]3C[C@H]3C=O)c2)ccc1OC1CCOCC1]

A solution of (trans-1,2)-N1-(6-(3-cyano-4-((tetrahydro-2H-pyran-4-yl)oxy)phenyl)pyrimidin-4-yl)-N2-methoxy-N2-methylcyclopropane-1,2-dicarboxamide (200 mg, 0.44 mmol) in 4 mL of THF was cooled to −78° C. and treated dropwise with DIBAL (0.89 mL, 0.89 mmol, 1M in THF. After stirring at −78° C. for 1 h the reaction was quenched with MeOH and diluted with EtOAc and water. The organic layer was dried with sodium sulfate and concentrated. Purification by RP-HPLC provided (trans-1,2)-N-(4-(3-cyano-4-((tetrahydro-2H-pyran-4-yl)oxy)phenyl)pyridin-2-yl)-2-formylcyclopropane-1-carboxamide as a white solid. 1H NMR (400 MHz, DMSO-d6) δ 11.09 (s, 1H), 9.15 (d, J=5.0 Hz, 1H), 8.36 (dd, J=5.3, 0.7 Hz, 1H), 8.29 (d, J=1.6 Hz, 1H), 8.10 (d, J=2.4 Hz, 1H), 7.95 (dd, J=8.9, 2.4 Hz, 1H), 7.51-7.43 (m, 2H), 4.89 (tt, J=8.0, 3.9 Hz, 1H), 3.84 (ddd, J=11.5, 5.9, 3.9 Hz, 2H), 3.52 (ddd, J=11.5, 8.3, 3.1 Hz, 2H), 2.70 (ddd, J=9.0, 5.8, 3.7 Hz, 1H), 2.24 (dtd, J=8.9, 5.4, 3.7 Hz, 1H), 2.07-1.94 (m, 2H), 1.72-1.44 (m, 4H). ES/MS 392.15 (M+H$^+$).

Example 41: (1,2-trans)-N-(4-(3-cyano-4-((tetrahydro-2H-pyran-4-yl)oxy)phenyl)pyridin-2-yl)-2-((dimethylamino)methyl)cyclopropane-1-carboxamide

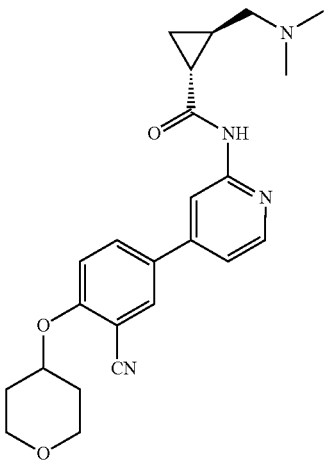 [SMILES: CN(C)C[C@@H]1C[C@H]1C(=O)Nc1cc(-c2ccc(OC3CCOCC3)c(C#N)c2)ccn1]

A solution of (trans-1,2)-N-(4-(3-cyano-4-((tetrahydro-2H-pyran-4-yl)oxy)phenyl)pyridin-2-yl)-2-formylcyclopropane-1-carboxamide (111 mg, 0.28 mmol) in 2 mL of DCE was treated with dimethylamine (0.57 mL, 1.13 mmol, 2M in MeOH), sodium triacetoxyborohydride (301 mg, 1.141 mmol) and AcOH (0.016 mL, 0.28 mmol) and stirred at rt for 2 h. The reaction was diluted with EtOAc and 2M Na$_2$CO$_3$. Organic layer was dried with sodium sulfate and concentrated. Purification by RP-HPLC provided (trans-1,2)-N-(4-(3-cyano-4-((tetrahydro-2H-pyran-4-yl)oxy)phenyl)pyridin-2-yl)-2-((dimethylamino)methyl)cyclopropane-1-carboxamide as a white solid 1H NMR (400 MHz, DMSO-d6) δ 10.99 (s, 1H), 9.70 (s, 1H), 8.39-8.28 (m, 2H), 8.08 (d, J=2.4 Hz, 1H), 7.94 (dd, J=8.9, 2.4 Hz, 1H), 7.52-7.42 (m, 2H), 4.88 (tt, J=7.9, 3.9 Hz, 1H), 3.84 (ddd, J=11.5, 5.9, 3.9 Hz, 2H), 3.52 (ddd, J=11.5, 8.3, 3.1 Hz, 2H), 3.21-3.13 (m, 1H), 3.05 (ddd, J=12.9, 7.7, 4.6 Hz, 1H), 2.80 (dd, J=4.8, 2.8 Hz, 6H), 2.12-1.94 (m, 3H), 1.62 (dddd, J=30.9, 12.7, 8.9, 4.9 Hz, 3H), 1.18 (dt, J=8.8, 4.4 Hz, 1H), 1.01 (ddd, J=8.3, 6.0, 4.1 Hz, 1H). ES/MS 421.2 (M+H$^+$).

Example 42: (1,2-trans)-N-(4-(3-cyano-4-((tetra-hydro-2H-pyran-4-yl)oxy)phenyl)pyridin-2-yl)-2-(hydroxymethyl)cyclopropane-1-carboxamide

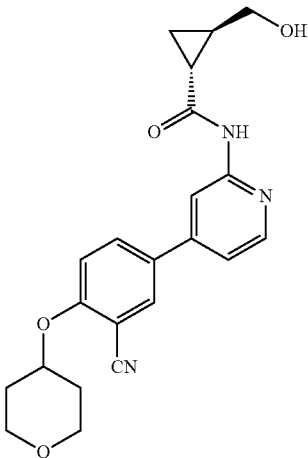 [SMILES: N#Cc1cc(-c2ccnc(NC(=O)[C@@H]3C[C@H]3CO)c2)ccc1OC1CCOCC1]

A solution of (trans-1,2)-N-(4-(3-cyano-4-((tetrahydro-2H-pyran-4-yl)oxy)phenyl)pyridin-2-yl)-2-formylcyclopropane-1-carboxamide (68 mg, 0.17 mmol) in 2 mL of THF was treated with sodium triacetoxyborohydride (184 mg, 0.87 mmol) and stirred at 60° C. for 2 h. The reaction was diluted with EtOAc and 2M Na$_2$CO$_3$ and the organic layer was dried with sodium sulfate and concentrated. Purification by RP-HPLC provided (trans-1,2)-N-(4-(3-cyano-4-((tetrahydro-2H-pyran-4-yl)oxy)phenyl)pyridin-2-yl)-2-((dimethylamino)methyl)cyclopropane-1-carboxamide as a white solid. 1H NMR (400 MHz, DMSO-d6) δ 10.87 (s, 1H), 8.34-8.21 (m, 2H), 8.07 (d, J=2.4 Hz, 1H), 7.92 (dd, J=9.0, 2.4 Hz, 1H), 7.48-7.38 (m, 2H), 4.85 (tt, J=7.9, 3.8 Hz, 1H), 3.80 (ddd, J=11.5, 5.9, 4.0 Hz, 2H), 3.48 (ddd, J=11.5, 8.3, 3.1 Hz, 2H), 3.40 (dd, J=11.3, 5.5 Hz, 1H), 3.23 (dd, J=11.3, 6.5 Hz, 1H), 2.02-1.91 (m, 2H), 1.88 (dt, J=8.4, 4.4 Hz, 1H), 1.61 (dtd, J=12.4, 8.2, 3.8 Hz, 2H), 1.51-1.38 (m, 1H), 0.95 (dt, J=8.5, 4.0 Hz, 1H), 0.77 (ddd, J=8.0, 6.2, 3.6 Hz, 1H). ES/MS 421.15 (M+H$^+$).

Example 43: (1,2-trans)-N-(4-(3-cyano-4-((tetra-hydro-2H-pyran-4-yl)oxy)phenyl)pyridin-2-yl)-2-(oxazol-5-yl)cyclopropane-1-carboxamide

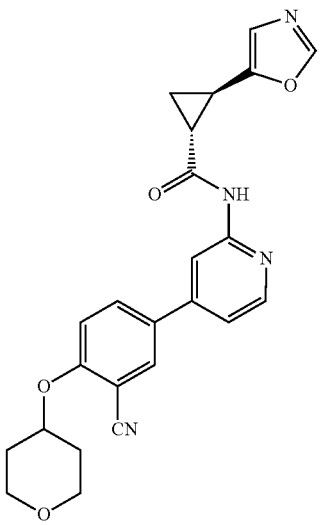 [SMILES: N#Cc1cc(-c2ccnc(NC(=O)[C@@H]3C[C@H]3c3cnco3)c2)ccc1OC1CCOCC1]

A solution of (trans-1,2)-N-(4-(3-cyano-4-((tetrahydro-2H-pyran-4-yl)oxy)phenyl)pyridin-2-yl)-2-formylcyclopropane-1-carboxamide (68 mg, 0.17 mmol) and Toluenesulfonylmethyl isocyanide (37 mg, 0.19 mmol) in 1 mL MeOH was treated with K$_2$CO$_3$ (66 mg, 0.48 mmol) and stirred at rt for 4 h. After partitioning the reaction mixture between EtOAc and saturated NaHCO$_3$, the organic layer separated and dried with sodium sulfate. Purification by RP HPLC provided as a white solid (trans-1,2)-N-(4-(3-cyano-4-((tetrahydro-2H-pyran-4-yl)oxy)phenyl)pyridin-2-yl)-1-hydroxycyclopropanecarboxamide as a white solid. 1H NMR (400 MHz, DMSO-d6) δ 12.56 (s, 1H), 8.92-8.81 (m, 2H), 8.69 (d, J=2.5 Hz, 1H), 8.59 (dd, J=9.0, 2.5 Hz, 1H), 8.44 (s, 1H), 8.21 (dd, J=6.4, 1.9 Hz, 1H), 7.92 (d, J=9.1 Hz, 1H), 7.51 (s, 1H), 5.41 (tt, J=8.0, 3.9 Hz, 1H), 4.54-4.44 (m, 2H), 4.15 (ddd, J=11.6, 8.4, 3.1 Hz, 2H), 3.28-3.18 (m, 1H), 2.99-2.88 (m, 1H), 2.62 (dt, J=5.5, 2.7 Hz, 1H), 2.41-2.19 (m, 3H), 2.11 (ddd, J=8.4, 6.6, 4.5 Hz, 1H). ES/MS 431.20 (M+H$^+$).

Example 44: (1,2-trans)-N-(4-(3-cyano-4-((tetra-hydro-2H-pyran-4-yl)oxy)phenyl)pyridin-2-yl)-2-(1,3-dioxolan-2-yl)cyclopropane-1-carboxamide

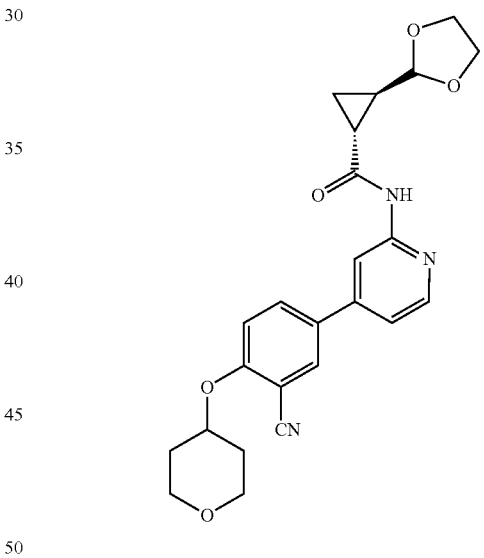

A solution of (trans-1,2)-N-(4-(3-cyano-4-((tetrahydro-2H-pyran-4-yl)oxy)phenyl)pyridin-2-yl)-2-formylcyclopropane-1-carboxamide (123 mg, 0.31 mmol) in 3 mL DCM was treated with ethylene glycol (0.35 mL, 6.3 mmol) and p-toluenesulfonic acid (3 mg, 0.016 mmol) and stirred at rt for 17 h. The reaction was diluted with EtOAc and saturated NaHCO$_3$. The organic layer was dried with sodium sulfate and concentrated. Purification by RP-HPLC provided the title compound as a white solid. 1H NMR (400 MHz, Acetonitrile-d3) δ 9.03 (s, 1H), 8.39 (s, 1H), 8.33 (d, J=5.3 Hz, 1H), 7.98 (d, J=2.4 Hz, 1H), 7.92 (dd, J=8.9, 2.4 Hz, 1H), 7.37-7.27 (m, 2H). 4.86-4.74 (m, 2H), 3.95 (ddt, J=12.2, 5.4, 3.0 Hz, 4H), 3.89-3.80 (m, 2H), 3.59 (ddd, J=11.7, 8.4, 3.2 Hz, 2H), 2.17 (s, 3H), 2.14-2.02 (m, 1H), 1.85-1.64 (m, 3H), 1.18 (ddd, J=9.0, 5.0, 4.0 Hz, 1H), 1.04 (ddd, J=8.4, 6.3, 4.0 Hz, 1H). ES/MS 436.14 (M+H$^+$).

Example 45: (1,2-trans)-N-(4-(3-cyano-4-((tetrahydro-2H-pyran-4-yl)oxy)phenyl)pyridin-2-yl)-2-(3-hydroxyazetidine-1-carbonyl)cyclopropane-1-carboxamide

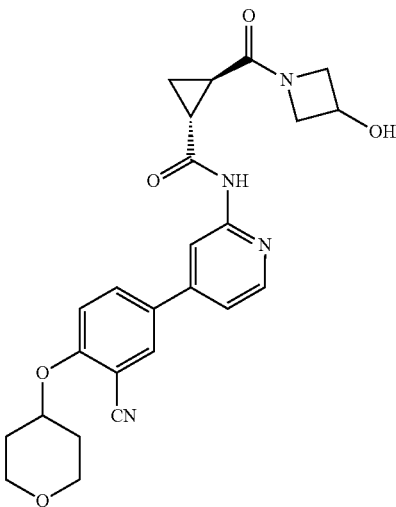 [SMILES: N#Cc1cc(-c2ccnc(NC(=O)[C@@H]3C[C@H]3C(=O)N3CC(O)C3)c2)ccc1OC1CCOCC1]

A solution of (trans-1,2)-2-((4-(3-cyano-4-((tetrahydro-2H-pyran-4-yl)oxy)phenyl)pyridin-2-yl)carbamoyl)cyclopropanecarboxylic acid (100 mg, 0.25 mmol) in 3 mL DMF and treated with HATU (112 mg, 0.29 mmol) and stirred at rt for 2 min. azetidin-3-ol hydrochloride (35 mg, 0.32 mmol) and TEA (0.103 mL, 0.74 mmol) were added and the mixture stirred at rt for 1 h. After partitioning the reaction mixture between EtOAc and saturated NaHCO$_3$, the organic layer separated and dried with sodium sulfate. Purification by RP HPLC provided (1,2-trans)-N-(4-(3-cyano-4-((tetrahydro-2H-pyran-4-yl)oxy)phenyl)pyridin-2-yl)-2-(3-hydroxyazetidine-1-carbonyl)cyclopropane-1-carboxamide as a white solid. 1H NMR (400 MHz, DMSO-d6) δ 11.02 (d, J=8.1 Hz, 1H), 8.39-8.32 (m, 1H), 8.29 (d, J=1.6 Hz, 1H), 8.10 (dd, J=2.4, 1.2 Hz, 1H), 7.96 (dt, J=8.9, 1.8 Hz, 1H), 7.55-7.42 (m, 2H), 4.89 (tt, J=7.9, 3.9 Hz, 1H), 4.48-4.35 (m, 2H), 4.06-4.01 (m, 1H), 4.01-3.80 (m, 3H), 3.62-3.48 (m, 3H), 2.41 (ddd, J=8.9, 5.4, 3.8 Hz, 1H), 2.08-1.92 (m, 3H), 1.66 (dtd, J=12.4, 8.1, 3.8 Hz, 2H), 1.22 (dddd, J=17.3, 8.6, 5.7, 3.1 Hz, 2H). ES/MS 463.2 (M+H$^+$).

Example 46: (1,2-trans)-N1-(4-(3-cyano-4-((tetrahydro-2H-pyran-4-yl)oxy)phenyl)pyridin-2-yl)-N2-(2-hydroxyethyl)cyclopropane-1,2-dicarboxamide

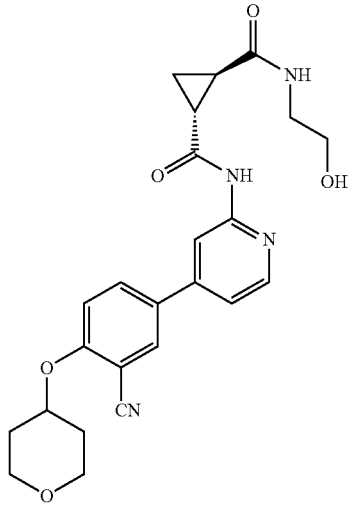 [SMILES: N#Cc1cc(-c2ccnc(NC(=O)[C@@H]3C[C@H]3C(=O)NCCO)c2)ccc1OC1CCOCC1]

A solution of (trans-1,2)-2-((4-(3-cyano-4-((tetrahydro-2H-pyran-4-yl)oxy)phenyl)pyridin-2-yl)carbamoyl)cyclopropanecarboxylic acid (100 mg, 0.25 mmol) in 3 mL DMF and treated with HATU (112 mg, 0.29 mmol) and stirred at rt for 2 min. 2-Hydroxylethylamine (19 mg, 0.32 mmol) and TEA (0.103 mL, 0.74 mmol) were added and the mixture stirred at rt for 1 h. After partitioning the reaction mixture between EtOAc and saturated NaHCO$_3$, the organic layer separated and dried with sodium sulfate. Purification by RP HPLC provided (1,2-trans)-N1-(4-(3-cyano-4-((tetrahydro-2H-pyran-4-yl)oxy)phenyl)pyridin-2-yl)-N2-(2-hydroxyethyl)cyclopropane-1,2-dicarboxamide as a white solid. 1H NMR (400 MHz, DMSO-d6) δ 10.98 (s, 1H), 8.38-8.21 (m, 3H), 8.09 (d, J=2.4 Hz, 1H), 8.05-7.91 (m, 1H), 7.52-7.41 (m, 2H), 4.89 (tt, J=8.0, 3.9 Hz, 1H), 3.85 (ddd, J=10.5, 5.8, 4.0 Hz, 2H), 3.53 (ddd, J=11.5, 8.3, 3.1 Hz, 2H), 3.39 (t, J=6.0 Hz, 2H), 3.13 (qd, J=6.0, 2.5 Hz, 2H), 2.39 (ddd, J=8.7, 5.5, 3.7 Hz, 1H), 2.12 (ddd, J=8.4, 5.9, 3.7 Hz, 1H), 2.05-1.96 (m, 2H), 1.66 (dtd, J=12.4, 8.2, 3.9 Hz, 2H), 1.18 (dt, J=8.2, 5.0 Hz, 2H). ES/MS 451.2 (M+H$^+$).

Example 47: (1,2-trans)-N-(4-(3-cyano-4-((tetrahydro-2H-pyran-4-yl)oxy)phenyl)pyridin-2-yl)-2-(3-methylisoxazol-5-yl)cyclopropane-1-carboxamide

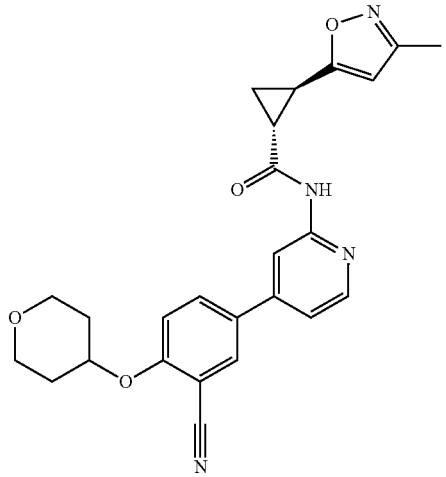 [SMILES: Cc1cc([C@@H]2C[C@H]2C(=O)Nc2cc(-c3ccc(OC4CCOCC4)c(C#N)c3)ccn2)on1]

To a chilled (0° C.) solution of propan-2-one oxime (49 mg, 0.66 mmol) in THF (1 mL) was added dropwise over 5 min 1.6 M n-butyl lithium (n-BuLi) in hexanes. The initially formed white suspension gave a colorless solution after all of the n-BuLi had been added. After an additional 30 min, (trans-1,2)-N1-(6-(3-cyano-4-((tetrahydro-2H-pyran-4-yl)oxy)phenyl)pyrimidin-4-yl)-N2-methoxy-N2-methylcyclopropane-1,2-dicarboxamide (100 mg, 0.22 mmol) in THF (2 mL) was added dropwise over 20 min. After stirring for an additional 30 min, the pale yellow solution was poured into a solution of concentrated H$_2$SO$_4$ (0.08 mL) in THF/water 4:1 (1.2 mL) and refluxed for 1 h. The chilled (ice bath) reaction mixture was carefully neutralized with NaHCO$_3$, sufficient water was added to dissolve the salts, and the mixture was extracted with ether (2×25 mL). The combined ethereal extracts were washed with brine, dried, and concentrated in vacuo. Purification by RP HPLC gave (1,2-trans)-N-(4-(3-cyano-4-((tetrahydro-2H-pyran-4-yl)oxy) phenyl)pyridin-2-yl)-2-(3-methylisoxazol-5-yl) cyclopropane-1-carboxamide as a white solid. 1H NMR (400 MHz, DMSO-d6) δ 11.04 (s, 1H), 8.39-8.30 (m, 2H), 8.11 (d, J=2.4 Hz, 1H), 7.96 (dd, J=8.9, 2.4 Hz, 1H), 7.53-7.43 (m, 2H), 6.21 (s, 1H), 4.89 (tt, J=7.8, 3.8 Hz, 1H), 3.85 (dt, J=10.5, 4.4 Hz, 2H), 3.53 (ddd, J=11.5, 8.3, 3.1 Hz, 2H), 2.55 (t, J=7.3 Hz, 2H), 2.17 (s, 3H), 2.06-1.97 (m, 2H), 1.66 (dtd, J=12.4, 8.2, 3.8 Hz, 2H), 1.50 (dtd, J=25.4, 7.4, 4.1 Hz, 2H). ES/MS 445.1 (M+H⁺).

Example 48: N-(4-(3-cyano-4-((tetrahydro-2H-pyran-4-yl)oxy)phenyl)pyridin-2-yl)spiro[2.2]pentane-1-carboxamide

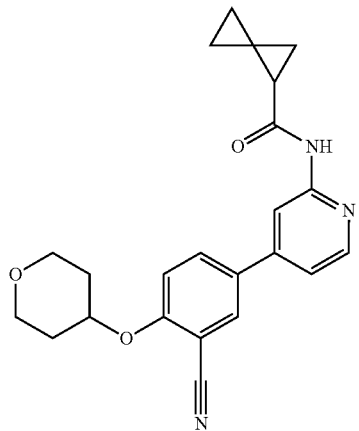 [SMILES: N#Cc1cc(-c2ccnc(NC(=O)C3CC34CC4)c2)ccc1OC1CCOCC1]

5-(2-aminopyridin-4-yl)-2-((tetrahydro-2H-pyran-4-yl)oxy) benzonitrile (50 mg, 0.169 mmol) dissolved in DMF (2 mL) was treated with HATU (128 mg. 0.337 mmol), spiro [2.2]pentane-1-carboxylic acid (26 mg, 0.187 mmol), and N,N-diisopropylethylamine (60 µL, 0.344 mmol). The reaction mixture was heated in the microwave at 110° C. for 2 h. After cooling to room temperature, the reaction mixture was diluted with ethyl acetate and washed with water. The organic layer was dried over sodium sulfate, filtered, and concentrated. The residue was purified by HPLC to give the title compound. 1H NMR (400 MHz, dmso) δ 10.70 (s, 1H), 8.33 (d, J=5.4 Hz, 2H), 8.09 (d, J=2.3 Hz, 1H), 7.96 (dd, J=9.0, 2.4 Hz, 1H), 7.48 (d, J=9.0 Hz, 1H), 7.42 (dt, J=5.2, 2.3 Hz, 1H), 4.90 (dt, J=8.0, 4.1 Hz, 1H), 3.89-3.81 (m, 2H), 3.53 (ddd, J=11.4, 8.3, 3.1 Hz, 2H), 2.36 (dd, J=7.4, 4.3 Hz, 1H), 2.07-1.96 (m, 2H), 1.66 (dtd, J=12.2, 8.1, 3.8 Hz, 2H), 1.42-1.30 (m, 2H), 0.92-0.82 (m, 3H), 0.77 (q, J=6.3, 5.6 Hz, 1H). LCMS-ESI⁺ (m/z): [M+H]⁺ calcd for C23H23N3O3: 390.2; found: 390.1.

Example 49: N-(4-(3-cyano-4-((tetrahydro-2H-pyran-4-yl)oxy)phenyl)pyridin-2-yl)-1-(fluoromethyl)cyclopropane-1-carboxamide

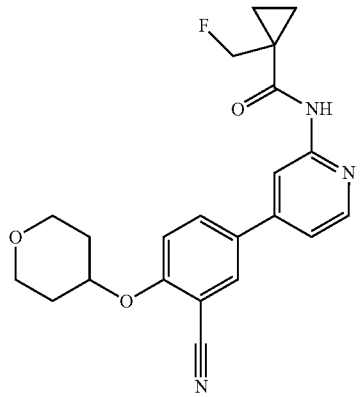 [SMILES: N#Cc1cc(-c2ccnc(NC(=O)C3(CF)CC3)c2)ccc1OC1CCOCC1]

The title compound was synthesized in the same manner as Example 48 using 1-(fluoromethyl)cyclopropane-1-carboxylic acid. 1H NMR (400 MHz, DMSO-d6) δ 9.86 (s, 1H), 8.38 (d, J=5.3 Hz, 1H), 8.27-8.24 (m, 1H), 8.13 (d, J=2.4 Hz, 1H), 7.98 (dd, J=8.9, 2.4 Hz, 1H), 7.50 (dd, J=7.7, 4.9 Hz, 2H), 4.90 (tt, J=7.8, 3.8 Hz, 1H), 4.74 (d, J=48.4 Hz, 2H), 3.85 (ddd, J=10.6, 5.8, 3.9 Hz, 2H), 3.53 (ddd, J=11.5, 8.3, 3.1 Hz, 2H), 2.01 (dt, J=12.4, 3.9 Hz, 2H), 1.67 (dtd, J=12.3, 8.2, 3.8 Hz, 2H), 1.31 (dt, J=6.8, 4.4 Hz, 2H), 1.02-0.95 (m, 2H). LCMS-ESI⁺ (m/z): [M+H]⁺ calcd for C22H22FN3O3: 396.2; found: 396.2.

Example 50: Ethyl trans-2-((4-(3-cyano-4-((tetrahydro-2H-pyran-4-yl)oxy)phenyl)pyridin-2-yl)carbamoyl)cyclopropane-1-carboxylate

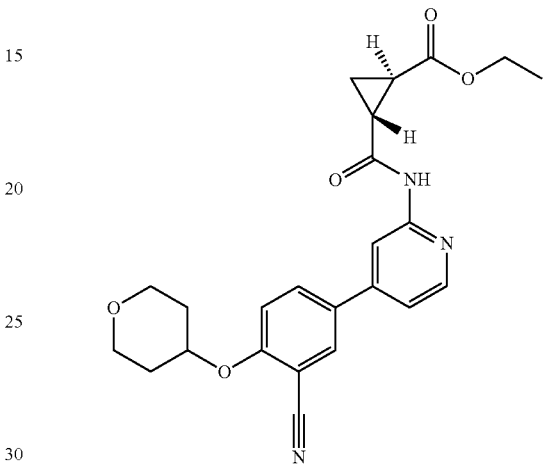

The title compound was synthesized in the same manner as Example 48 using trans-2-(ethoxycarbonyl) cyclopropane-1-carboxylic acid. 1H NMR (400 MHz, dmso) δ 11.05 (s, 1H), 8.36 (d, J=5.3 Hz, 1H), 8.28 (d, J=1.6 Hz, 1H), 8.09 (d, J=2.4 Hz, 1H), 7.95 (dd, J=8.9, 2.4 Hz, 1H), 7.50-7.44 (m, 2H), 4.89 (tt, J=7.9, 3.8 Hz, 1H), 4.09 (q, J=7.1 Hz, 2H), 3.85 (ddd, J=10.5, 6.0, 4.0 Hz, 3H), 2.58 (ddd, J=9.2, 5.8, 3.8 Hz, 1H), 2.00 (ddd, J=13.3, 6.8, 3.9 Hz, 3H), 1.66 (dtd, J=12.3, 8.1, 3.8 Hz, 2H), 1.35 (dddd, J=14.8, 9.1, 5.8, 3.7 Hz, 2H), 1.19 (t, J=7.1 Hz, 3H). LCMS-ESI⁺ (m/z): [M+H]⁺ calcd for C24H25N3O5: 436.2; found: 436.2.

Example 51: N-(4-(3-cyano-4-((tetrahydro-2H-pyran-4-yl)oxy)phenyl)pyridin-2-yl)-2-(furan-2-yl)cyclopropane-1-carboxamide

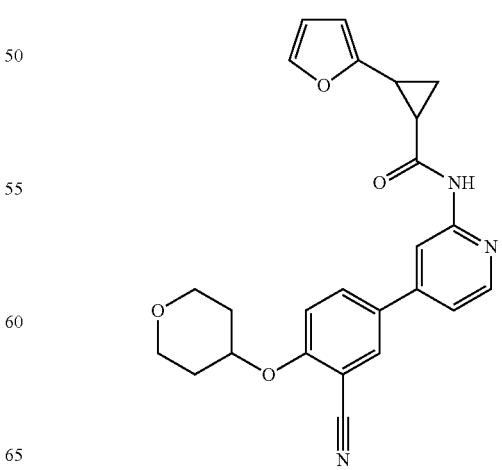

The title compound was synthesized in the same manner as Example 48 using 2-(furan-2-yl)cyclopropane-1-carboxylic acid. 1H NMR (400 MHz, dmso) δ 11.01 (s, 1H), 8.35 (d, J=5.3 Hz, 1H), 8.31 (d, J=1.6 Hz, 1H), 8.11 (d, J=2.4 Hz, 1H), 7.97 (dd, J=8.9, 2.4 Hz, 1H), 7.50 (d, J=2.3 Hz, 1H), 7.49-7.44 (m, 2H), 6.39-6.34 (m, 1H), 6.23 (d, J=3.2 Hz, 1H), 4.90 (tt, J=7.9, 3.9 Hz, 1H), 3.53 (ddd, J=11.5, 8.3, 3.2 Hz, 3H), 2.41 (dtd, J=17.0, 9.1, 7.7, 4.2 Hz, 2H), 2.02 (ddd, J=13.7, 5.6, 3.2 Hz, 2H), 1.66 (dtd, J=12.4, 8.2, 3.9 Hz, 2H), 1.43 (dt, J=9.1, 4.4 Hz, 1H), 1.37 (ddd, J=8.2, 6.4, 4.0 Hz, 1H). LCMS-ESI+ (m/z): [M+H]+ calcd for C25H23N3O4: 430.2; found: 430.2.

Example 52: Trans-N-(4-(3-cyano-4-((tetrahydro-2H-pyran-4-yl)oxy)phenyl)pyridin-2-yl)-2-(thiophen-2-yl)cyclopropane-1-carboxamide

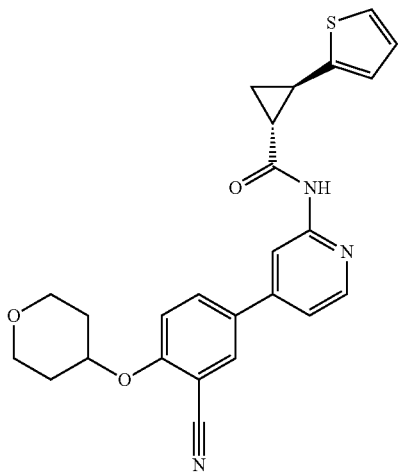

Step 1: Preparation of (E)-N-methoxy-N-methyl-3-(thiophen-2-yl)acrylamide: (E)-3-(thiophen-2-yl)acrylic acid (500 mg, 3.243 mmol) dissolved in dichloromethane (15 mL) was treated with 1-Ethyl-3-(3-dimethylaminopropyl)carbodiimide (630 mg, 3.286 mmol), N,O-Dimethylhydroxylamine hydrochloride (411 mg, 4.214 mmol), and 4-(Dimethylamino)pyridine (383 mg, 3.242 mmol). The reaction mixture was stirred at room temperature for 3 h, diluted with DCM and washed with water. The organic layer was concentrated and purified by column chromatography to give (E)-N-methoxy-N-methyl-3-(thiophen-2-yl)acrylamide.

Step 2: Preparation of Trans-N-methoxy-N-methyl-2-(thiophen-2-yl)cyclopropane-1-carboxamide: Trimethylsulfoxonium iodide (377 mg, 1.714 mmol) suspended in DMSO (4 mL) was treated with sodium hydride (103 mg, 2.575 mmol, 60% dispersion in mineral oil) at room temperature. After stirring for 20 min, (E)-N-methoxy-N-methyl-3-(thiophen-2-yl)acrylamide (170 mg, 0.862 mmol) dissolved in 2 mL of DMSO was added dropwise. The reaction mixture was stirred at room temperature for 1 h and then at 50° C. for 1 h. After cooling to room temperature, the reaction mixture was quenched with saturated ammonium chloride solution and then extracted with ethyl acetate. The organic layer was concentrated and purified by column chromatography to give trans-N-methoxy-N-methyl-2-(thiophen-2-yl)cyclopropane-1-carboxamide.

Step 3: Preparation of Trans-2-(thiophen-2-yl)cyclopropane-1-carboxylic acid: Trans-N-methoxy-N-methyl-2-(thiophen-2-yl)cyclopropane-1-carboxamide (100 mg, 0.473 mmol) dissolved in ethanol (2 mL) was treated with potassium hydroxide solution (60 μL, 30% solution in water). The reaction mixture was heated at 50° C. for 2 d. After cooling to rt, the reaction mixture was concentrated. The residue was dissolved in ethyl acetate and washed with 1N HCl solution. The organic layer was concentrated to give the crude Trans-2-(thiophen-2-yl)cyclopropane-1-carboxylic acid.

Step 4: Preparation of Trans-N-(4-(3-cyano-4-((tetrahydro-2H-pyran-4-yl)oxy)phenyl)pyridin-2-yl)-2-(thiophen-2-yl)cyclopropane-1-carboxamide: 5-(2-aminopyridin-4-yl)-2-((tetrahydro-2H-pyran-4-yl)oxy) benzonitrile (60 mg, 0.203 mmol) dissolved in DMF (2 mL) was treated with HATU (154 mg. 0.405 mmol), trans-2-(thiophen-2-yl) cyclopropane-1-carboxylic acid (60 mg, 0.357 mmol), and N,N-diisopropylethylamine (120 μL, 0.689 mmol). The reaction mixture was heated in the microwave at 110° C. for 20 min. After cooling to room temperature, the reaction mixture was diluted with ethyl acetate and washed with water. The organic layer was dried over sodium sulfate, filtered, and concentrated. The residue was purified by HPLC to give the title compound. 1H NMR (400 MHz, Chloroform-d) δ 8.83 (s, 1H), 8.21 (d, J=6.3 Hz, 1H), 7.97 (d, J=8.5 Hz, 2H), 7.49 (d, J=6.3 Hz, 1H), 7.21-7.12 (m, 2H), 6.98-6.87 (m, 2H), 4.79 (dt, J=7.1, 3.6 Hz, 1H), 4.05 (ddd, J=11.2, 7.2, 3.5 Hz, 2H), 3.69 (ddd, J=11.3, 7.1, 3.6 Hz, 2H), 2.85 (s, 1H), 2.40 (dt, J=8.7, 4.6 Hz, 1H), 2.17-2.07 (m, 2H), 1.94 (dtd, J=13.8, 7.1, 3.5 Hz, 2H), 1.78 (dt, J=9.3, 4.6 Hz, 1H), 1.57-1.48 (m, 1H). LCMS-ESI+ (m/z): [M+H]+ calcd for C23H23N3O3: 446.2; found: 446.1.

Example 53: 2-cyano-4-(6-(cyclopropanecarboxamido)pyrimidin-4-yl)-N-(2,2-difluoroethyl)benzamide

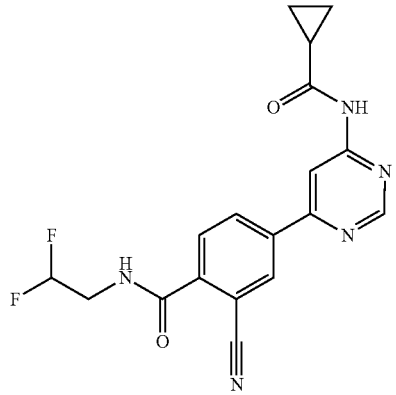 [SMILES: N#Cc1cc(-c2cc(NC(=O)C3CC3)ncn2)ccc1C(=O)NCC(F)F]

Step 1: Preparation of N-(6-chloropyrimidin-4-yl)cyclopropanecarboxamide: A mixture of 4-amino-6-chloropyrimidine (TCI, 1.2 g, 9.3 mmol) in tetrahydrofuran (25 mL) was treated with pyridine (1.1 mL, 14 mmol) in a single portion and then dropwise with cyclopropanecarbonyl chloride (1.0 mL, 11 mmol). The mixture was heated at 80° C. overnight. After cooling to room temperature, the mixture was partitioned between ethyl acetate and 10% aqueous citric acid solution. The aqueous phase was extracted three times with ethyl acetate. The combined extracts were washed once with saturated aqueous sodium chloride solution, dried over anhydrous magnesium sulfate, filtered, concentrated to dryness under reduced pressure to provide the desired material. LCMS-ESI⁺ (m/z): [M+H]⁺ calcd for C₈H₉ClN₃O, 198.0; found: 197.9.

Step 2: Preparation of (3-cyano-4-(methoxycarbonyl)phenyl)boronic acid: A mixture in dioxanes (52 mL) of bis(dibenzylideneacetone)palladium(0) (0.27 g, 0.46 mmol) and tricyclohexylphosphine (0.30 g, 1.1 mmol) was stirred for 30 minutes at room temperature. Bis(pinacolato)diboron (7.8 g, 31 mmol), potassium acetate (4.5 g, 45 mmol), and methyl 4-chloro-2-cyanobenzoate (3.0 g, 15 mmol) were then added successively. The mixture was stirred overnight at 85° C. block. Upon cooling to room temperature, the mixture was filtered through a pad of Celite diatomaceous earth and concentrated under reduced pressure. The residue was carried forward without further purification. LCMS-ESI⁺ (m/z): [2M+H]⁺ calcd for C₁₈H₁₇B₂N₂O₈ 411.1; found: 411.0.

Step 3: Preparation of methyl 2-cyano-4-(6-(cyclopropanecarboxamido)pyrimidin-4-yl)benzoate, 2-cyano-4-(6-(cyclopropanecarboxamido)pyrimidin-4-yl)benzoic acid, and 2-carbamoyl-4-(6-(cyclopropanecarboxamido)pyrimidin-4-yl)benzoic acid: A solution of crude of (3-cyano-4-(methoxycarbonyl)phenyl)boronic acid (approximately 0.62 g, 3.0 mmol) in dioxanes (6 mL) was added to a mixture of N-(6-chloropyrimidin-4-yl)cyclopropanecarboxamide (0.60 g, 3.0 mmol) and [1,1'-bis(diphenylphosphino)ferrocene] dichloropalladium(II) (0.22 g, 0.30 mmol). Saturated aqueous sodium hydrogen carbonate solution (5 mL) was added. The mixture was heated at 95° C. for 1 hour. Upon cooling, the mixture was adjusted to pH~1-2 with 10% aqueous citric acid solution. The aqueous phase was extracted three times with ethyl acetate. The combined extracts were washed once with saturated aqueous sodium chloride solution, dried over anhydrous magnesium sulfate, filtered, and concentrated under reduced pressure. The product was purified by preparative HPLC (5-75% acetonitrile in water, 0.1% trifluoroacetic acid buffer) to furnish the indicated materials. Methyl 2-cyano-4-(6-(cyclopropanecarboxamido)pyrimidin-4-yl)benzoate: LCMS-ESI⁺ (m/z): [M+H]⁺ calcd for C₁₇H₁₅N₄O₃ 323.1; found: 323.1.

2-cyano-4-(6-(cyclopropanecarboxamido)pyrimidin-4-yl)benzoic acid: LCMS-ESI⁺ (m/z): [M+H]⁺ calcd for C₁₆H₁₃N₄O₃ 309.1; found: 309.0.

2-carbamoyl-4-(6-(cyclopropanecarboxamido)pyrimidin-4-yl)benzoic acid: LCMS-ESI⁺ (m/z): [M+H]⁺ calcd for C₁₆H₁₅N₄O₄ 327.1; found: 327.0.

Step 4: Preparation of 2-cyano-4-(6-(cyclopropanecarboxamido)pyrimidin-4-yl)benzoic acid: A mixture of methyl 2-cyano-4-(6-(cyclopropanecarboxamido)pyrimidin-4-yl)benzoate (0.13 g, 0.40 mmol) in tetrahydrofuran/methanol/water (1:1:0.5, 2 mL) was treated with lithium hydroxide monohydrate (34 mg, 0.81 mmol). The mixture was heated to homogeneity with a heat gun and then allowed to cool. The mixture was concentrated under reduced pressure and carried forward without further purification as the putative lithium salt of the desired carboxylic acid. LCMS-ESI⁺ (m/z): [M+H]⁺ calcd for C₁₆H₁₃N₄O₃ 309.1; found: 309.0.

Step 5: Preparation of 2-cyano-4-(6-(cyclopropanecarboxamido)pyrimidin-4-yl)-N-(2,2-difluoroethyl)benzamide: A suspension of the lithium salt of 2-cyano-4-(6-(cyclopropanecarboxamido)pyrimidin-4-yl)benzoic acid (0.40 mmol assumed) in pyridine (2 mL) was treated successively with 2,2-difluoroethylamine (56 µL, 0.80 mmol) and propylphosphonic anhydride solution (T3P, tech., ~50% in DMF, 500 µL). The mixture was irradiated in a microwave reactor for 5 minutes at 100° C. then concentrated under reduced pressure. The residue was purified by preparative HPLC (5-80% acetonitrile in water, 0.1% trifluoroacetic acid buffer) to furnish 2-cyano-4-(6-(cyclopropanecarboxamido)pyrimidin-4-yl)-N-(2,2-difluoroethyl)benzamide. LCMS-ESI⁺ (m/z): [M+H]⁺ calcd for C₁₈H₁₆F₂N₅O₂ 372.1; found: 372.1.

Example 54: 2-cyano-4-(6-(cyclopropanecarboxamido)pyrimidin-4-yl)-N-(2,2,2-trifluoroethyl)benzamide

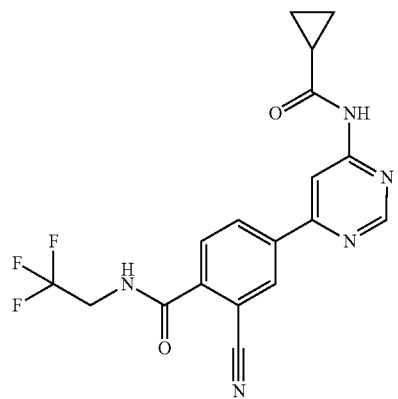 [SMILES: N#Cc1cc(-c2cc(NC(=O)C3CC3)ncn2)ccc1C(=O)NCC(F)(F)F]

2,2,2-trifluoroethylamine hydrochloride (58 mg, 0.43 mmol), followed by T3P solution (50% in DMF, 410 µL) was added to a mixture of 2-cyano-4-(6-(cyclopropanecarboxamido)pyrimidin-4-yl)benzoic acid (0.21 mmol assumed) and 2-carbamoyl-4-(6-(cyclopropanecarboxamido)pyrimidin-4-yl)benzoic acid (0.21 mmol assumed) in pyridine (2 mL). The mixture was irradiated in a microwave reactor for 5 minutes at 100° C. then quenched with water 92 mL) and concentrated under reduced pressure. The residue was purified by preparative HPLC (5-80% acetonitrile in water, 0.1% trifluoroacetic acid buffer) to furnish 2-cyano-4-(6-(cyclopropanecarboxamido)pyrimidin-4-yl)-N-(2,2,2-trifluoroethyl)benzamide. LCMS-ESI⁺ (m/z): [M+H]⁺ calcd for C₁₈H₁₅F₃N₅O₂: 390.1; found: 390.1.

Example 55: 4-acetamido-N-(4-(3-cyano-4-((tetrahydro-2H-pyran-4-yl)oxy)phenyl)pyridin-2-yl)bicyclo[1.1.1]pentane-2-carboxamide

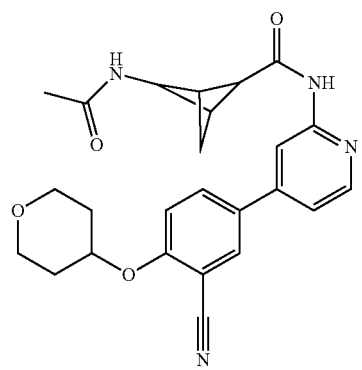 [SMILES: CC(=O)NC1C2CC1C2C(=O)Nc1cc(-c2ccc(OC3CCOCC3)c(C#N)c2)ccn1]

Step 1: Preparation of tert-butyl (4-((4-(3-cyano-4-((tetrahydro-2H-pyran-4-yl)oxy)phenyl)pyridin-2-yl)carbamoyl)bicyclo[1.1.1]pentan-2-yl)carbamate: A mixture of 3-Boc-amino-bicyclo[1.1.1]pentane-1-carboxylic acid (PharmaBlock, 0.14 g, 0.63 mmol) and 5-(2-aminopyridin-4-yl)-2-((tetrahydro-2H-pyran-4-yl)oxy)benzonitrile (0.17 g, 0.58 mmol) in DMF (5 mL) was treated sequentially with N-[(dimethylamino)-1H-1,2,3-triazolo-[4,5-b]pyridin-1-yl-methylene]-N-methylmethanaminiumhexafluorophosphate N-oxide (HATU, 0.44 g, 1.2 mmol) and N,N-diisopropylethylamine (DIEA, 0.20 mL, 1.2 mmol). The mixture was irradiated in a microwave reactor for one hour at 110° C. After cooing, the mixture was partitioned between water and ethyl acetate. The aqueous phase was extracted three times with ethyl acetate. The combined extracts were washed successively with saturated aqueous solutions of sodium hydrogen carbonate and sodium chloride, dried over anhydrous magnesium sulfate, filtered, concentrated to dryness under reduced pressure to provide the titled material. LCMS-ESI$^+$ (m/z): [M+H]$^+$ calcd for $C_{28}H_{33}N_4O_5$ 505.2; found: 505.2.

Step 2: Preparation of 4-amino-N-(4-(3-cyano-4-((tetrahydro-2H-pyran-4-yl)oxy)phenyl)pyridin-2-yl)bicyclo[1.1.1]pentane-2-carboxamide: A solution of tert-butyl (4-((4-(3-cyano-4-((tetrahydro-2H-pyran-4-yl)oxy)phenyl)pyridin-2-yl)carbamoyl)bicyclo[1.1.1]pentan-2-yl)carbamate (0.29 g, 0.58 mmol) in dichloromethane (5 mL) was treated with hydrogen chloride solution in dioxanes (4 N, 3 mL, 12 mmol). The mixture was stirred overnight at 50° C. After concentrating the mixture under reduced pressure, the residue was purified by flash chromatography (silica gel) to provide the desired material. LCMS-ESI$^+$ (m/z): [M+H]$^+$ calcd for $C_{23}H_{25}N_4O_3$ 405.2; found: 405.2.

Step 3: Preparation of 4-acetamido-N-(4-(3-cyano-4-((tetrahydro-2H-pyran-4-yl)oxy)phenyl)pyridin-2-yl)bicyclo[1.1.1]pentane-2-carboxamide: A solution of 4-amino-N-(4-(3-cyano-4-((tetrahydro-2H-pyran-4-yl)oxy)phenyl)pyridin-2-yl)bicyclo[1.1.1]pentane-2-carboxamide (82 mg, 0.20 mmol), cooled in an ice-water bath, was treated successively with N,N-diisopropylethylamine (DIEA, 70 µL, 0.41 mmol) and acetyl chloride (15 µL, 0.21 mmol). After 10 minutes, the bath was removed and the mixture was allowed to regain room temperature. The reaction was deemed complete by LC/MS analysis and concentrated under reduced pressure. The residue was purified by preparative HPLC (5-70% acetonitrile in water, 0.1% trifluoroacetic acid buffer) to furnish 4-acetamido-N-(4-(3-cyano-4-((tetrahydro-2H-pyran-4-yl)oxy)phenyl)pyridin-2-yl)bicyclo[1.1.1]pentane-2-carboxamide as its trifluoroacetic acid salt. LCMS-ESI$^+$ (m/z): [M+H]$^+$ calcd for $C_{25}H_{27}N_4O_4$: 447.2; found: 447.2.

Example 56: N-(4-(3-cyano-4-((tetrahydro-2H-pyran-4-yl)oxy)phenyl)pyridin-2-yl)bicyclo[1.1.1]pentane-2,4-dicarboxamide

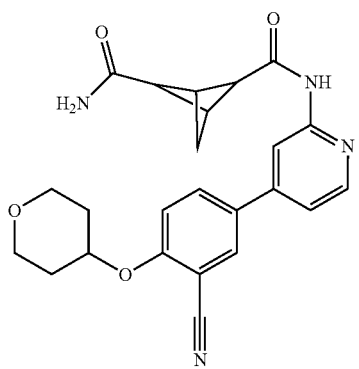 [SMILES: N#Cc1cc(-c2ccnc(NC(=O)C3C4CC3C4C(N)=O)c2)ccc1OC1CCOCC1]

Step 1: Preparation of methyl 3-((2,4-dimethoxybenzyl)carbamoyl)bicyclo[1.1.1]pentane-1-carboxylate Propylphosphonic anhydride solution (T3P, tech., ~50% in DMF, 6 mL) was added to a mixture of 3-(methoxycarbonyl)bicyclo[1.1.1]pentane-1-carboxylic acid (WuXi Apptec, 0.30 g, 1.8 mmol) and 2,4-dimethoxybenzylamine (0.40 mL, 2.6 mmol) in pyridine (1.5 mL). The mixture was heated in a microwave reactor for 20 minutes at 100° C. The mixture was then diluted with toluene and ethyl acetate and washed successively with 10% aqueous hydrochloric acid, water, saturated aqueous sodium hydrogen carbonate solution, and saturated aqueous sodium chloride solution. The organic phase was dried over anhydrous magnesium sulfate, filtered, concentrated to dryness under reduced pressure to provide the desired material, which was carried forward without further purification. LCMS-ESI$^+$ (m/z): [M+H]$^+$ calcd for $C_{17}H_{22}NO_5$ 320.1; found: 319.9.

Step 2: Preparation of 3-((2,4-dimethoxybenzyl)carbamoyl)bicyclo[1.1.1]pentane-1-carboxylic acid: A mixture of methyl 3-((2,4-dimethoxybenzyl)carbamoyl)bicyclo[1.1.1]pentane-1-carboxylate (0.56 g, 1.8 mmol) in 2-methyltetrahydrofuran/methanol/water (2:2:1, 10 mL) was treated with lithium hydroxide monohydrate. The mixture was stirred at 55° C. for 45 minutes and then, after cooling, was acidified to pH 3 with 10% aqueous citric acid solution. The aqueous mixture was extracted three times with ethyl acetate. The combined organic extracts were washed once with saturated aqueous sodium chloride solution, dried over anhydrous magnesium sulfate, filtered, concentrated to dryness under reduced pressure to give the desired material, which was carried forward without further purification. LCMS-ESI$^+$ (m/z): [M+H]$^+$ calcd for $C_{16}H_{20}NO_5$ 306.1; found: 305.9.

Step 3: Preparation of N$^2$-(4-(3-cyano-4-((tetrahydro-2H-pyran-4-yl)oxy)phenyl)pyridin-2-yl)-N$^4$-(2,4-dimethoxybenzyl)bicyclo[1.1.1]pentane-2,4-dicarboxamide: A mixture 3-((2,4-dimethoxybenzyl)carbamoyl)bicyclo[1.1.1]pentane-1-carboxylic acid (0.33 g, 1.1 mmol) and 5-(2-aminopyridin-4-yl)-2-((tetrahydro-2H-pyran-4-yl)oxy)benzonitrile (0.29 g, 0.97 mmol) in DMF (5 mL) was treated sequentially with N-[(dimethylamino)-1H-1,2,3-triazolo-[4,5-b]pyridin-1-ylmethylene]-N-methylmethanaminiumhexafluorophosphate N-oxide (HATU, 0.74 g, 1.9 mmol) and N,N-diisopropylethylamine (DIEA, 0.34 mL, 1.9 mmol). The mixture was irradiated in a microwave reactor for one hour at 110° C. After cooing, the mixture was partitioned between water and ethyl acetate. The aqueous phase was extracted three times with ethyl acetate. The combined extracts were washed successively with saturated aqueous solutions of sodium hydrogen carbonate and sodium chloride, dried over anhydrous magnesium sulfate, filtered, concentrated to dryness under reduced pressure. The residue was purified by flash chromatography (silica gel) to provide the titled material. LCMS-ESI$^+$ (m/z): [M+H]$^+$ calcd for $C_{33}H_{35}N_4O_6$ 583.3; found: 583.3.

Step 4: Preparation of N-(4-(3-cyano-4-((tetrahydro-2H-pyran-4-yl)oxy)phenyl)pyridin-2-yl)bicyclo[1.1.1]pentane-2,4-dicarboxamide: A solution of N$^2$-(4-(3-cyano-4-((tetrahydro-2H-pyran-4-yl)oxy)phenyl)pyridin-2-yl)-N$^4$-(2,4-dimethoxybenzyl)bicyclo[1.1.1]pentane-2,4-dicarboxamide (0.29 g, 0.50 mmol) in dichloromethane (2 mL) was treated with trifluoroacetic acid (4 mL). The mixture was heated at 55° C. for 30 hours and then allowed to cool to room temperature. The reaction mixture was concentrated under reduced pressure. The residue was triturated with methanol and filtered through a pad of Celite diatomaceous earth. The filtrate was concentrated under reduced pressure and then purified by preparative HPLC (5-50% acetonitrile in water, 0.1% trifluoroacetic acid buffer) to provide N-(4-(3-cyano-4-((tetrahydro-2H-pyran-4-yl)oxy)phenyl)pyridin-2-yl)bicyclo[1.1.1]pentane-2,4-dicarboxamide as its trifluoroacetic acid salt. LCMS-ESI+ (m/z): [M+H]+ calcd for $C_{24}H_{25}N_4O_4$: 433.2; found: 433.2.

Example 57: (1,2-trans)-N-(4-(3-cyano-4-(((3R,4S)-3-fluoro-1-(2-hydroxyacetyl)piperidin-4-yl)oxy)phenyl)pyridin-2-yl)-2-fluorocyclopropane-1-carboxamide

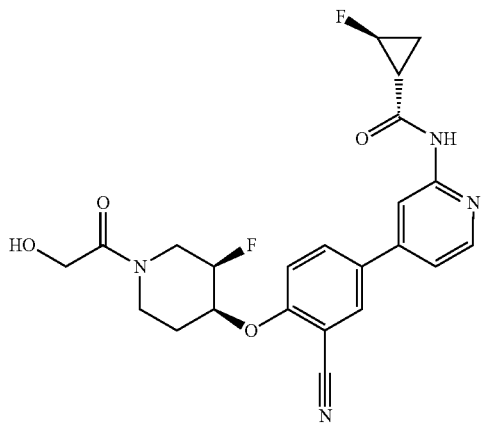

Step 1: 2-Aminopyridin-4-yl)-2-fluorobenzonitrile: In a microwave reaction vial was placed 2-amino-4-bromopyridine (924 mg, 5.34 mmol), 2-fluoro-5-(4,4,5,5-tetramethyl-1,3,2-dioxaborolan-2-yl)benzonitrile (1.2 g, 4.86 mmol), Pd(PPh$_3$)$_4$ (168 mg, 0.15 mmol) in DME (10 mL) and 2M Na$_2$CO$_3$ (7.3 mL) was added. The reaction mixture was reacted under MW condition at 140° C. for 60 minutes. The reaction mixture was filtered, concentrated, and diluted with water and extracted with CH$_2$Cl$_2$. The organic layer was separated, washed with water and brine, dried over Na$_2$SO$_4$ and concentrated. The residue was purified by silica gel column chromatography with 0-10% MeOH in CH$_2$Cl$_2$ to give the product.

Step 2: (1,2-trans)-N-(4-(3-cyano-4-fluorophenyl)pyridin-2-yl)-2-fluorocyclopropane-1-carboxamide: To a solution of 2-aminopyridin-4-yl)-2-fluorobenzonitrile (150 mg, 0.704 mmol), trans-2-fluorocyclopropanecarboxylic acid (74 mg, 0.704 mmol) and HATU (334 mg, 0.88 mmol) in anhydrous DMF (6 mL) was added DIPEA (182 mg, 1.41 mmol). The mixture was stirred at 110° C. in a microwave reactor for 1 h. After being cooled to room temperature, the mixture was diluted with water (40 mL) and extracted with EtOAc (40 mL). The organic layer was separated, washed with water (10 mL) and brine (10 mL), dried over Na$_2$SO$_4$ and concentrated. The residue was purified by silica gel column chromatography with 0-5% MeOH in CH$_2$Cl$_2$ to give the product.

Step 3: tert-butyl-trans-4-(2-cyano-4-(2-((1,2-trans)-2-fluorocyclopropane-1-carboxamido)pyridin-4-yl)phenoxy)-3-fluoropiperidine-1-carboxylate: To (3R,4S)-tert-butyl 3-fluoro-4-hydroxypiperidine-1-carboxylate (76 mg, 0.35 mmol) in Me-THF (4 mL) at 0° C. was added potassium tert-butoxide solution (1M solution in 2-methyl-2-propanol, 0.4 mL, 0.4 mmol) and stirred for 45 minutes at 0° C. Then trans N-(4-(3-cyano-4-fluorophenyl)pyridin-2-yl)-2-fluorocyclopropane-1-carboxamide (80 mg, 0.27 mmol) was added and heated at 60 C for 2 hr. Water was slowly added and the reaction mixture was evaporated under reduced pressure to give a solid which was used further without purification.

Step 4: (1,2-trans)-N-(4-(3-cyano-4-(((3R,4S)-3-fluoropiperidin-4-yl)oxy)phenyl)pyridin-2-yl)-2-fluorocyclopropane-1-carboxamide: tert-Butyl-4-(2-cyano-4-(2-((1,2-trans)-2-fluorocyclopropane-1-carboxamido)pyridin-4-yl)phenoxy)-3-fluoropiperidine-1-carboxylate (120 mg) was diluted with a mixture of DCM (2 mL) and TFA (0.5 mL). The mixture was stirred at room temperature for 1 h and then evaporated under reduced pressure. The product was used for next step.

Step 5: (1,2-trans)-N-(4-(3-cyano-4-(((3R,4S)-3-fluoro-1-(2-hydroxyacetyl)piperidin-4-yl)oxy)phenyl)pyridin-2-yl)-2-fluorocyclopropane-1-carboxamide: (1,2-trans)-N-(4-(3-cyano-4-(((3R,4S)-3-fluoropiperidin-4-yl)oxy)phenyl)pyridin-2-yl)-2-fluorocyclopropanecarboxamide] (42 mg, 0.11 mmol), HATU (80 mg, 0.21 mmol), DIPEA (41 mg, 0.32 mmol) and glycolic acid (16 mg, 0.21 mmol) were dissolved in DMF (3 mL) and stirred at room temperature for 2 hr. The mixture was diluted with water and extracted with CH$_2$Cl$_2$. The organic layer was separated, washed with water and brine, dried over Na$_2$SO$_4$ and concentrated. The residue was purified by silica gel column chromatography with 0-5% MeOH in CH$_2$Cl$_2$ to give the product. $^1$H NMR (400 MHz, DMSO-d6) δ 11.04 (s, 1H), 8.37 (dd, 1H), 8.28 (t, 1H), 8.11 (d, 1H), 7.97 (dd, 1H), 7.55 (d, 1H), 7.46 (dd, 1H), 5.15-4.65 (m, 4H), 4.31-3.99 (m, 3H), 3.70-3.15 (m, 3H), 2.65-2.52 (m, 1H), 1.94-1.80 (m, 2H), 1.53 (m, 1H), 1.33-1.16 (m, 2H). LCMS-ESI+ (m/z): [M+H]+ calcd for $C_{23}H_{22}F_2N_4O_4$: 457.2; found: 457.2.

Example 58: N-(4-(3-cyano-4-(((3R,4S)-3-fluoro-1-(2-hydroxyacetyl)piperidin-4-yl)oxy)phenyl)pyridin-2-yl)-2,2-difluorocyclopropane-1-carboxamide

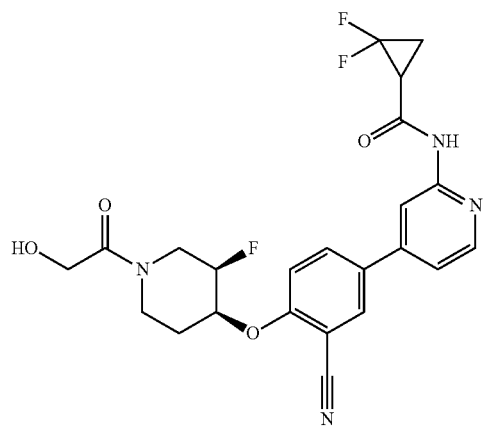 [SMILES: N#Cc1cc(-c2ccnc(NC(=O)C3CC3(F)F)c2)ccc1O[C@H]1CCN(C(=O)CO)C[C@H]1F]

Step 1: tert-Butyl (3R,4S)-4-(4-bromo-2-cyanophenoxy)-3-fluoropiperidine-1-carboxylate: (3R,4S)-tert-butyl 3-fluoro-4-hydroxypiperidine-1-carboxylate (3.62 g, 12.5 mmol) was taken up in DMA (40 mL) and cooled at 0° C. To well stirred solution was added potassium tert-butoxide (3.37 g, 30 mmol) at one portion and stirred for 40 minutes at 0° C. This solution was added substrate (5-bromo-2-fluorobenzonitrile, 3 g, 15 mmol) at 0° C. Warmed to RT and the reaction was heated at 60° C. for 2 hr. The reaction mixture was concentrated to dryness. The residue was purified by silica gel column chromatography eluted with 0-5% MeOH in CH$_2$Cl$_2$ to give the product.

Step 2: tert-Butyl (3R,4S)-4-(2-cyano-4-(4,4,5,5-tetramethyl-1,3,2-dioxaborolan-2-yl)phenoxy)-3-fluoropiperidine-1-carboxylate: To tert-butyl (3R,4S)-4-(4-bromo-2-cyanophenoxy)-3-fluoropiperidine-1-carboxylate (1.5 g, 3.76 mmol) in 1,4-Dioxane (27 mL) was added bis(pinacolato)diboron (1.91 g, 7.5 mmol), potassium acetate (1.12 g, 11.3 mmol), and Pd(dppf)Cl$_2$ (0.28 g, 0.38 mmol). The reaction was heated to 110° C. for 1 h. The reaction mixture was filtered through a pad of Celite diatomaceous earth. The filtrate was concentrated to dryness under reduced pressure. The residue was purified by silica gel column chromatography with 10-50% EtOAc in hexanes to give the desired material.

Step 3, tert-Butyl (3R,4S)-4-(4-(2-aminopyridin-4-yl)-2-cyanophenoxy)-3-fluoropiperidine-1-carboxylate: In a microwave reaction vial was placed 4-bromopyridin-2-amine (1.21 g, 6.98 mmol), tert-butyl (3R,4S)-4-(2-cyano-4-(4,4,5,5-tetramethyl-1,3,2-dioxaborolan-2-yl)phenoxy)-3-fluoropiperidine-1-carboxylate (2.83 g, 6.34 mmol), Pd(PPh$_3$)$_4$ (220 mg, 0.19 mmol) in DME (12 mL) and 2M Na$_2$CO$_3$ (9.5 mL) was added. The reaction mixture was reacted under MW condition at 140° C. for 60 minutes. The reaction mixture was filtered and concentrated. The residue was purified by silica gel column chromatography eluted with 0-10% MeOH in CH$_2$Cl$_2$ to give the product.

Step 4: tert-Butyl (3R,4S)-4-(2-cyano-4-(2-(2,2-difluorocyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (200 mg, 0.485 mmol), 2,2-difluorocyclopropane carboxylic acid (65.1 mg, 0.533 mmol) and HATU (230 mg, 0.61 mmol) in anhydrous DMF (4 mL) was added DIPEA (126 mg, 0.97 mmol). The mixture was stirred at 110° C. in a microwave reactor for 1 h. After being cooled to room temperature, the mixture was diluted with water (60 mL) and extracted with EtOAc (60 mL). The organic layer was separated, washed with water (20 mL) and brine (20 mL), dried over Na$_2$SO$_4$ and concentrated. The residue was purified by silica gel column chromatography eluted with 0-5% MeOH in CH$_2$Cl$_2$ to give the product.

Step 5: N-(4-(3-Cyano-4-(((3R,4S)-3-fluoropiperidin-4-yl)oxy)phenyl)pyridin-2-yl)-2,2-difluorocyclopropane-1-carboxamide: tert-Butyl (3R,4S)-4-(2-cyano-4-(2-(2,2-difluorocyclopropane-1-carboxamido)pyridin-4-yl)phenoxy)-3-fluoropiperidine-1-carboxylate (157 mg, 0.3 mmol) was diluted with a mixture of DCM (2 mL) and TFA (0.5 mL). The mixture was stirred at room temperature for 1 h. The reaction mixture was evaporated under reduced pressure. The residue was purified by silica gel column chromatography eluted with 0-15% MeOH in CH$_2$Cl$_2$ to give the product.

Step 6: N-(4-(3-cyano-4-(((3R,4S)-3-fluoro-1-(2-hydroxyacetyl)piperidin-4-yl)oxy)phenyl)pyridin-2-yl)-2,2-difluorocyclopropane-1-carboxamide: N-(4-(3-Cyano-4-(((3R,4S)-3-fluoropiperidin-4-yl)oxy)phenyl)pyridin-2-yl)-2,2-difluorocyclopropane-1-carboxamide (30 mg, 0.072 mmol), HATU (55 mg, 0.14 mmol), DIPEA (28 mg, 0.22 mmol) and glycolic acid (11 mg, 0.14 mmol) were dissolved in DMF (2 mL) and stirred at room temperature for 2 hr. The mixture was diluted with water and extracted with EtOAc. The organic layer was separated, washed with water and brine, dried over Na$_2$SO$_4$ and concentrated. The residue was purified by prep-HPLC to give the product. 1H NMR (400 MHz, DMSO-d6) δ 11.10 (s, 1H), 8.35 (d, 1H), 8.25 (s, 1H), 8.10 (d, 1H), 7.96 (dd, 1H), 7.52 (d, J=9.0 Hz, 1H), 7.46 (dd, 1H), 5.16-4.98 (m, 2H), 4.91 (t, 1H), 4.37-4.22 (m, 1H), 4.20-3.98 (m, 2H), 3.37-3.06 (m, 2H), 3.04-2.91 (m, 2H), 2.10-1.82 (m, 4H), 1.77 (m, 1H). LCMS-ESI$^+$ (m/z): [M+H]$^+$ calcd for C$_{23}$H$_{21}$F$_3$N$_4$O$_4$: 475.2; found: 475.2.

Example 59: (1R,2R)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide

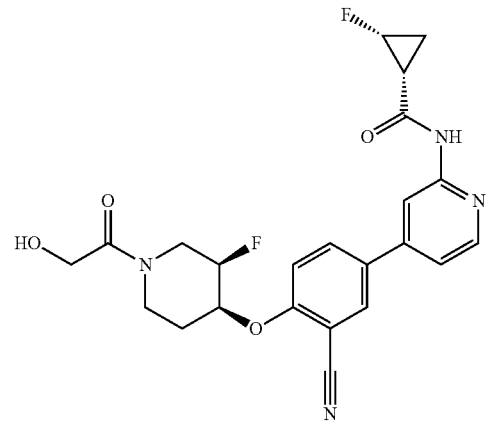 [SMILES: N#Cc1cc(-c2ccnc(NC(=O)[C@H]3C[C@H]3F)c2)ccc1O[C@H]1CCN(C(=O)CO)C[C@H]1F]

Step 1: (3R,4S)-tert-butyl 4-(2-cyano-4-(2-((1R,2R)-2-fluorocyclopropanecarboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (30 mg, 0.073 mmol), (1R,2R)-2-fluorocyclopropanecarboxylic acid (7.6 mg, 0.073 mmol) and HATU (35 mg, 0.09 mmol) in anhydrous DMF (0.6 mL) was added DIPEA (35 mg, 0.145 mmol). The mixture was stirred at 110° C. in a microwave reactor for 1 h. After being cooled to room temperature, the mixture was diluted with water and extracted with EtOAc. The organic layer was separated, washed with water, dried over Na$_2$SO$_4$ and concentrated. The residue was purified by silica gel column chromatography eluted with 0-5% MeOH in CH$_2$Cl$_2$ to give the product.

Step 2: (1R,2R)—N-(4-(3-cyano-4-(((3R,4S)-3-fluoropiperidin-4-yl)oxy)phenyl)pyridin-2-yl)-2-fluorocyclopropanecarboxamide: (3R,4S)-tert-Butyl 4-(2-cyano-4-(2-((1R,2R)-2-fluorocyclopropanecarboxamido)pyridin-4-yl)phenoxy)-3-fluoropiperidine-1-carboxylate (13 mg, 0.03 mmol) was diluted with a mixture of DCM (1 mL) and TFA (0.25 mL). The mixture was stirred at room temperature for 1 h and evaporated under reduced pressure. The product was used for next step.

Step 3: (1R,2R)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide: (1R,2R)—N-(4-(3-cyano-4-(((3R,4S)-3-fluoropiperidin-4-yl)oxy)phenyl)pyridin-2-yl)-2-fluorocyclopropanecarboxamide (10 mg, 0.025 mmol), HATU (19 mg, 0.05 mmol), DIPEA (10 mg, 0.075 mmol) and glycolic acid (4 mg, 0.05 mmol) were dissolved in DMF (1 mL) and stirred at room temperature for 2 hr. The mixture was diluted with water and extracted with EtOAc. The organic layer was separated, washed with water and brine, dried over Na$_2$SO$_4$ and concentrated. The residue was purified by prep-HPLC to give the product. $^1$H NMR (400 MHz, DMSO-d6) δ 10.99 (s, 1H), 8.33 (d, 1H), 8.26 (s, 1H), 8.10 (d, 1H), 7.97 (dd, 1H), 7.53 (d, 1H), 7.45 (dd, 1H), 5.15-4.96 (m, 2H), 4.95-4.77 (m, 1H), 4.38-4.20 (m, 0H), 4.19-3.97 (m, 2H), 3.68-3.05 (m, 4H), 2.18 (m, 1H), 1.91 (m, 2H), 1.80-1.52 (m, 2H), 1.15 (m, 1H). LCMS-ESI+ (m/z): [M+H]+ calcd for $C_{23}H_{22}F_2N_4O_4$: 457.2; found: 457.3.

Example 60: (1R,2S)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide

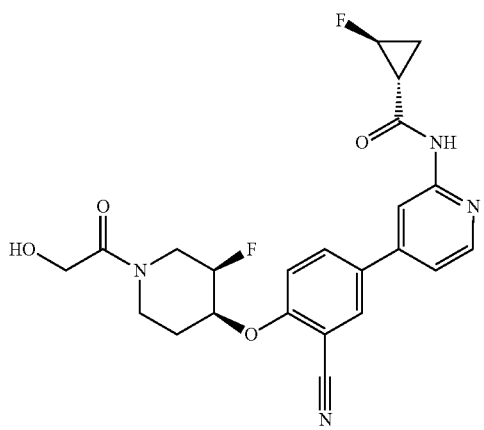 [SMILES: N#Cc1cc(-c2ccnc(NC(=O)[C@H]3C[C@@H]3F)c2)ccc1O[C@H]1CCN(C(=O)CO)C[C@H]1F]

Step 1: (1S,2S)—N-(4-(3-cyano-4-fluorophenyl)pyridin-2-yl)-2-fluorocyclopropanecarboxamide: To a solution of 5-(2-aminopyridin-4-yl)-2-fluorobenzonitrile (216 mg, 1.01 mmol), (1S,2S)-2-fluorocyclopropanecarboxylic acid (106 mg, 1.01 mmol) and HATU (481 mg, 1.27 mmol) in anhydrous DMF (8.5 mL) was added DIPEA (262 mg, 2.03 mmol). The mixture was stirred at 110° C. in a microwave reactor for 1 h. After being cooled to room temperature, the mixture was diluted with water and extracted with EtOAc. The organic layer was separated, washed with water and brine, dried over $Na_2SO_4$ and concentrated. The residue was purified by silica gel column chromatography eluted with 0-10% MeOH in $CH_2Cl_2$ to give the product.

Step 2: tert-Butyl (3R,4S)-4-(2-cyano-4-(2-((1S,2S)-2-fluorocyclopropane-1-carboxamido)pyridin-4-yl)phenoxy)-3-fluoropiperidine-1-carboxylate and tert-Butyl (3R,4S)-4-(2-cyano-4-(2-((1R,2S)-2-fluorocyclopropane-1-carboxamido)pyridin-4-yl)phenoxy)-3-fluoropiperidine-1-carboxylate: To (3R,4S)-tert-butyl 3-fluoro-4-hydroxypiperidine-1-carboxylate (191 mg, 0.83 mmol) in Me-THF (9.5 mL) at 0° C. was added potassium tert-butoxide solution (1M solution in 2-methyl-2-propanol, 0.95 mL, 0.95 mmol) and stirred for 45 minutes at 0° C. Then (1S,2S)—N-(4-(3-cyano-4-fluorophenyl)pyridin-2-yl)-2-fluorocyclopropanecarboxamide (190 mg, 0.64 mmol) was added and heated at 60° C. for 2 hr. Water was added to the mixture was diluted with water and extracted with CH2Cl2. The organic layer was separated, washed with water, dried over $Na_2SO_4$ and concentrated. The residue was purified by prep-HPLC to give two products which were assigned as the (1S,2S) cyclopropane analog and (1R,2S) cyclopropane analog.

Step 3: (1R,2S)—N-(4-(3-cyano-4-(((3R,4S)-3-fluoropiperidin-4-yl)oxy)phenyl)pyridin-2-yl)-2-fluorocyclopropanecarboxamide: ((3R,4S)-tert-butyl 4-(2-cyano-4-(2-((1R,2S)-2-fluorocyclopropanecarboxamido)pyridin-4-yl)phenoxy)-3-fluoropiperidine-1-carboxylate (28 mg, 0.06 mmol) was diluted with a mixture of DCM (1 mL) and TFA (0.25 mL). The mixture was stirred at room temperature for 1 h. The reaction mixture was evaporated under reduced pressure. The product was used for next step.

Step 4: (1R,2S)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide: (1R,2S)—N-(4-(3-cyano-4-(((3R,4S)-3-fluoropiperidin-4-yl)oxy)phenyl)pyridin-2-yl)-2-fluorocyclopropanecarboxamide (22 mg, 0.055 mmol), HATU (42 mg, 0.11 mmol), DIPEA (21 mg, 0.37 mmol) and glycolic acid (9 mg, 0.11 mmol) were dissolved in DMF (1.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. ¹H NMR (400 MHz, DMSO-d6) δ 11.04 (s, 1H), 8.33 (d, 1H), 8.21 (s, 1H), 8.07 (d, 1H), 7.93 (dd, 1H), 7.51 (d, 1H), 7.43 (dd, 1H), 5.14-4.95 (m, 2H), 4.91 (m, 1H), 4.76 (t, 1H), 4.26 (m, 1H), 4.17-3.97 (m, 2H), 3.47-3.03 (m, 3H), 2.51 (m, 1H), 1.90 (m, 2H), 1.49 (m, 1H), 1.21 (m, 1H). LCMS-ESI+ (m/z): [M+H]+ calcd for $C_{23}H_{22}F_2N_4O_4$: 457.2; found: 457.3.

Example 61: (1S,2S)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide

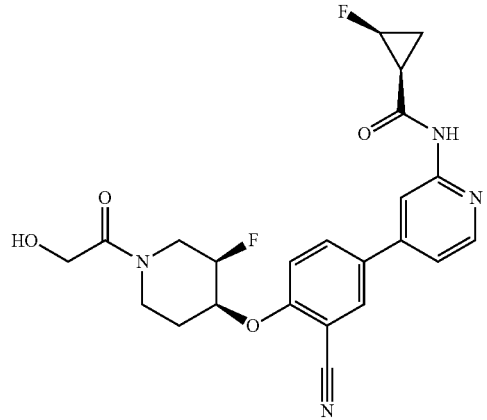 [SMILES: N#Cc1cc(-c2ccnc(NC(=O)[C@@H]3C[C@@H]3F)c2)ccc1O[C@H]1CCN(C(=O)CO)C[C@H]1F]

Step 1: (1S,2S)—N-(4-(3-cyano-4-(((3R,4S)-3-fluoropiperidin-4-yl)oxy)phenyl)pyridin-2-yl)-2-fluorocyclopropanecarboxamide: (3R,4S)-tert-Butyl 4-(2-cyano-4-(2-((1S,2S)-2-fluorocyclopropanecarboxamido)pyridin-4-yl)phenoxy)-3-fluoropiperidine-1-carboxylate (27 mg, 0.054 mmol) was diluted with a mixture of DCM (1 mL) and TFA (0.25 mL). The mixture was stirred at room temperature for 1 h. The reaction mixture was evaporated under reduced pressure. The product was used for next step.

Step 2: (1S,2S)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide: (1S,2S)—N-(4-(3-cyano-4-(((3R,4S)-3-fluoropiperidin-4-yl)oxy)phenyl)pyridin-2-yl)-2-fluorocyclopropanecarboxamide (22 mg, 0.055 mmol), HATU (42 mg, 0.11 mmol), DIPEA (21 mg, 0.17 mmol) and glycolic acid (9 mg, 0.11 mmol) were dissolved in DMF (1.5 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. 1H NMR (400 MHz, DMSO-d6) δ 11.07 (s, 1H), 8.38 (d, 1H), 8.30 (d, 1H), 8.16 (d, 1H), 8.02 (dd, 1H), 7.58 (d, 1H), 7.50 (dd, 1H), 5.21-5.00 (m, 2H), 5.01-4.79 (m, 1H), 4.33 (d, 1H), 4.15 (d, 1H), 4.07 (d, 1H), 3.61-3.10 (m, 3H), 2.80 (m, 1H), 2.23 (m, 1H), 1.96 (m, 2H), 1.86-1.57 (m, 1H), 1.21 (m, 1H). LCMS-ESI$^+$ (m/z): [M+H]$^+$ calcd for C$_{23}$H$_{22}$F$_2$N$_4$O$_4$: 457.2; found: 457.2.

Example 62: (1S,2R)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide

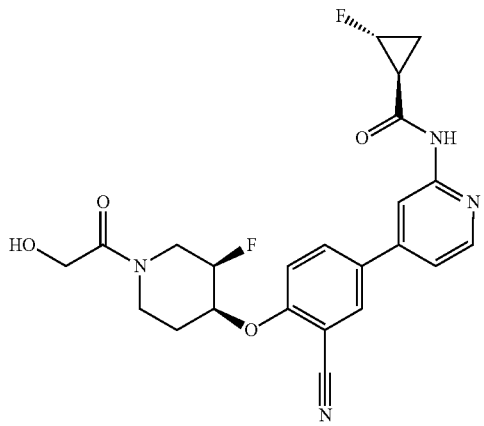 [SMILES: N#Cc1cc(-c2ccnc(NC(=O)[C@@H]3C[C@H]3F)c2)ccc1O[C@H]1CCN(C(=O)CO)C[C@H]1F]

Step 1: (1R,2R)—N-(4-(3-cyano-4-fluorophenyl)pyridin-2-yl)-2-fluorocyclopropanecarboxamide: To a solution of 5-(2-aminopyridin-4-yl)-2-fluorobenzonitrile (216 mg, 1.01 mmol), (1R,2R)-2-fluorocyclopropanecarboxylic acid (106 mg, 1.01 mmol) and HATU (481 mg, 1.27 mmol) in anhydrous DMF (8 mL) was added DIPEA (262 mg, 2.03 mmol). The mixture was stirred at 110° C. in a microwave reactor for 1 h. After being cooled to room temperature, the mixture was diluted with water and extracted with EtOAc. The organic layer was separated, washed with water and brine, dried over Na$_2$SO$_4$ and concentrated. The residue was purified by silica gel column chromatography eluted with 0-5% MeOH in CH$_2$Cl$_2$ to give the product.

Step 2: (tert-butyl (3R,4S)-4-(2-cyano-4-(2-((1R,2R)-2-fluorocyclopropane-1-carboxamido)pyridin-4-yl)phenoxy)-3-fluoropiperidine-1-carboxylate) and (tert-butyl (3R,4S)-4-(2-cyano-4-(2-((1S,2R)-2-fluorocyclopropane-1-carboxamido)pyridin-4-yl)phenoxy)-3-fluoropiperidine-1-carboxylate): To (3R,4S)-tert-butyl 3-fluoro-4-hydroxypiperidine-1-carboxylate (119 mg, 0.54 mmol) in Me-THF (6.5 mL) at 0° C. was added potassium tert-butoxide solution (1M solution in 2-methyl-2-propanol, 0.63 mL, 0.63 mmol) and stirred for 45 minutes at 0° C. Then (1R,2R)—N-(4-(3-cyano-4-fluorophenyl)pyridin-2-yl)-2-fluorocyclopropanecarboxamide (125 mg, 0.42 mmol) was added and heated at 60° C. for 2 hr. The mixture was diluted with water and extracted with CH$_2$Cl$_2$. The organic layer was separated, washed with water, dried over Na2SO4 and concentrated. The residue was purified by prep-HPLC to give two products which were assigned as the (1R,2R)-2-fluorocyclopropane carboxamide analog, and (1S,2R)-2-fluorocyclopropane carboxamide analog respectively.

Step 3, (1 S,2R)—N-(4-(3-cyano-4-(((3R,4S)-3-fluoropiperidin-4-yl)oxy)phenyl)pyridin-2-yl)-2-fluorocyclopropanecarboxamide: (3R,4S)-tert-butyl 4-(2-cyano-4-(2-((1S,2R)-2-fluorocyclopropanecarboxamido)pyridin-4-yl)phenoxy)-3-fluoropiperidine-1-carboxylate (50 mg, 0.1 mmol) was diluted with a mixture of DCM (1 mL) and TFA (0.5 mL). The mixture was stirred at room temperature for 1 h. The reaction mixture was evaporated under reduced pressure. The product was used for next step.

Step 4: (1S,2R)—N-(4-(3-cyano-4-(((3R,4S)-3-fluoro-1-(2-hydroxyacetyl)piperidin-4-yl)oxy)phenyl)pyridin-2-yl)-2-fluorocyclopropanecarboxamide: (1S,2R)—N-(4-(3-Cyano-4-(((3R,4S)-3-fluoropiperidin-4-yl)oxy)phenyl)pyridin-2-yl)-2-fluorocyclopropanecarboxamide (20 mg, 0.05 mmol), HATU (38 mg, 0.1 mmol), DIPEA (19 mg, 0.15 mmol) and glycolic acid (8 mg, 0.1 mmol) were dissolved in DMF (2 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. $^1$H NMR (400 MHz, DMSO-d6) δ 11.11 (s, 1H), 8.39 (d, 1H), 8.27 (d, 1H), 8.13 (d, 1H), 7.99 (dd, 1H), 7.57 (d, 1H), 7.49 (dd, 1H), 5.20-5.01 (m, 2H), 5.03-4.89 (m, 1H), 4.82 (m, 1H), 4.42-4.25 (m, 1H), 4.15 (m, 1H), 4.13-4.02 (m, 1H), 3.57-3.10 (m, 3H), 2.67-2.53 (m, 1H), 1.96 (m, 2H), 1.55 (m, 1H), 1.27 (m, 1H). LCMS-ESI$^+$ (m/z): [M+H]$^+$ calcd for C$_{23}$H$_{22}$F$_2$N$_4$O$_4$: 457.2; found: 457.3.

Example 63: 1-Cyano-N-(4-(3-cyano-4-(((3R,4S)-3-fluoro-1-(2-hydroxyacetyl)piperidin-4-yl)oxy)phenyl)pyridin-2-yl)cyclopropane-1-carboxamide

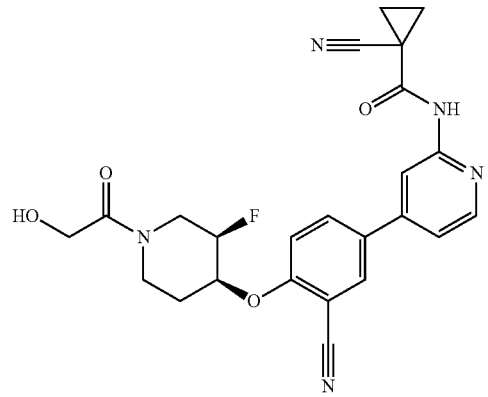 [SMILES: N#Cc1cc(-c2ccnc(NC(=O)C3(C#N)CC3)c2)ccc1O[C@H]1CCN(C(=O)CO)C[C@H]1F]

Step 1: tert-Butyl (3R,4S)-4-(2-cyano-4-(2-(1-cyanocyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (300 mg, 0.727 mmol), 1-cyanocyclopropane carboxylic acid (89 mg, 0.80 mmol) and HATU (345 mg, 0.91 mmol) in anhydrous DMF (6 mL) was added DIPEA (188 mg, 1.46 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by silica gel column chromatography eluted with 0-5% MeOH in CH$_2$Cl$_2$ to give the product.

Step 2: 1-Cyano-N-(4-(3-cyano-4-(((3R,4S)-3-fluoropiperidin-4-yl)oxy)phenyl)pyridin-2-yl)cyclopropane-1-carboxamide: tert-Butyl (3R,4S)-4-(2-cyano-4-(2-(1-cyanocyclopropane-1-carboxamido)pyridin-4-yl)phenoxy)-3-fluoropiperidine-1-carboxylate (340 mg, 0.67 mmol) was diluted with a mixture of DCM (2 mL) and TFA (0.5 mL). The mixture was stirred at room temperature for 1 h. The reaction mixture was treated with CH$_2$Cl$_2$ and aqueous NaHCO$_3$ solution. The organic layer was separated and dried. After filtration, the organic phase was concentrated and the residue was used for next step.

Step 3: 1-Cyano-N-(4-(3-cyano-4-(((3R,4S)-3-fluoro-1-(2-hydroxyacetyl)piperidin-4-yl)oxy)phenyl)pyridin-2-yl)cyclopropane-1-carboxamide: 1-Cyano-N-(4-(3-cyano-4-(((3R,4S)-3-fluoropiperidin-4-yl)oxy)phenyl)pyridin-2-yl)cyclopropane-1-carboxamide (42 mg, 0.104 mmol), HATU (79 mg, 0.207 mmol), DIPEA (40 mg, 0.31 mmol) and glycolic acid (16 mg, 0.207 mmol) were dissolved in DMF (2 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. LCMS-ESI$^+$ (m/z): [M+H]$^+$ calcd for C$_{24}$H$_{22}$FN$_5$O$_4$: 464.2; found: 464.3.

Example 64: (1R,2R)—N-(4-(3-cyano-4-(pyrrolidin-1-yl)phenyl)pyridin-2-yl)-2-fluorocyclopropane-1-carboxamide

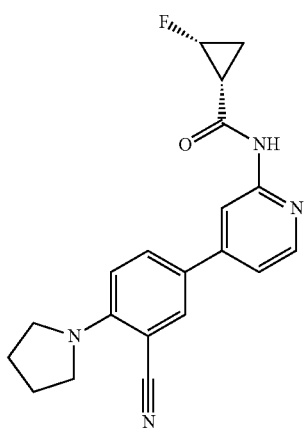 [SMILES: N#Cc1cc(-c2ccnc(NC(=O)[C@H]3C[C@H]3F)c2)ccc1N1CCCC1]

To a suspension of (1R,2R)—N-(4-(3-cyano-4-fluorophenyl)pyridin-2-yl)-2-fluorocyclopropanecarboxamide (46 mg, 0.15 mmol) in 2-PrOH (2.5 mL) was added pyrrolidine (33 mg, 0.46 mmol) and DIPEA (64 mg, 0.5 mmol) heat for 3 h at 150° C. The reaction mixture was concentrated to dryness. The residue was purified by silica gel column chromatography eluted with 0-10% MeOH in CH$_2$Cl$_2$ to give the product. LCMS-ESI$^+$ (m/z): [M+H]$^+$ calcd for C$_{20}$H$_{19}$FN$_4$O: 351.2; found: 351.2.

Example 65: (1R,2R)—N-(4-(3-cyano-4-(4-hydroxypiperidin-1-yl)phenyl)pyridin-2-yl)-2-fluorocyclopropane-1-carboxamide

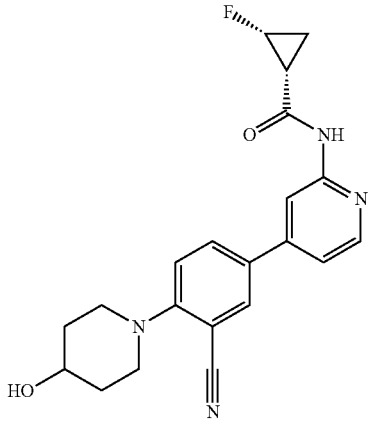 [SMILES: N#Cc1cc(-c2ccnc(NC(=O)[C@H]3C[C@H]3F)c2)ccc1N1CCC(O)CC1]

To a suspension of (1R,2R)—N-(4-(3-cyano-4-fluorophenyl)pyridin-2-yl)-2-fluorocyclopropanecarboxamide (56 mg, 0.19 mmol) in 2-PrOH (2.5 mL) was added piperidin-4-ol (57 mg, 0.56 mmol) and DIPEA (78 mg, 0.6 mmol) heat for 3 h at 150° C. The reaction mixture was concentrated to dryness and the residue was purified by silica gel column chromatography eluted with 0-10% MeOH in CH$_2$Cl$_2$ to give the product. LCMS-ESI$^+$ (m/z): [M+H]$^+$ calcd for C$_{21}$H$_{21}$FN$_4$O$_2$: 381.2; found: 381.2.

Example 66: N-(4-(3-Cyano-4-(((3R,4S)-3-fluoro-1-(2-hydroxyacetyl)piperidin-4-yl)oxy)phenyl)pyridin-2-yl)-2-(trifluoromethyl)cyclopropane-1-carboxamide

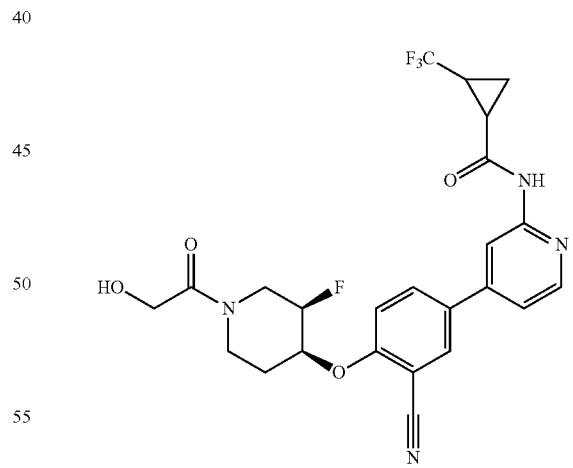

Step 1: tert-Butyl (3R,4S)-4-(2-cyano-4-(2-(2-(trifluoromethyl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (200 mg, 0.49 mmol), 2-(trifluoromethyl)cyclopropanecarboxylic acid (8 mg, 0.53 mmol) and HATU (230 mg, 0.61 mmol) in anhydrous DMF (4 mL) was added DIPEA (126 mg, 0.97 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by silica gel column chromatography eluted with 0-5% MeOH in CH$_2$Cl$_2$ to give the product.

Step 2: N-(4-(3-cyano-4-(((3R,4S)-3-fluoropiperidin-4-yl)oxy)phenyl)pyridin-2-yl)-2-(trifluoromethyl)cyclopropane-1-carboxamide: tert-Butyl (3R,4S)-4-(2-cyano-4-(2-(2-(trifluoromethyl)cyclopropane-1-carboxamido)pyridin-4-yl)phenoxy)-3-fluoropiperidine-1-carboxylate (210 mg, 0.38 mmol) was diluted with a mixture of DCM (2 mL) and TFA (0.5 mL). The mixture was stirred at room temperature for 1 h. The reaction mixture was evaporated under reduced pressure. The residue was purified by silica gel column chromatography eluted with 0-15% MeOH in CH$_2$Cl$_2$ to give the product.

Step 3: N-(4-(3-cyano-4-(((3R,4S)-3-fluoro-1-(2-hydroxyacetyl)piperidin-4-yl)oxy)phenyl)pyridin-2-yl)-2-(trifluoromethyl)cyclopropane-1-carboxamide: N-(4-(3-cyano-4-(((3R,4S)-3-fluoropiperidin-4-yl)oxy)phenyl)pyridin-2-yl)-2-(trifluoromethyl)cyclopropane-1-carboxamide (42 mg, 0.094 mmol), HATU (71 mg, 0.19 mmol), DIPEA (36 mg, 0.28 mmol) and glycolic acid (15 mg, 0.19 mmol) were dissolved in DMF (2 mL) and stirred at room temperature for 2 hr. The mixture was diluted with water and extracted with CH$_2$Cl$_2$. The organic layer was separated, washed with water, dried over Na2SO4 and concentrated. The residue was purified by prep-HPLC to give the product. $^1$H NMR (400 MHz, DMSO-d6) δ 11.09 (s, 1H), 8.34 (d, 1H), 8.26 (d, 1H), 8.07 (d, 1H), 7.94 (dd, 1H), 7.51 (d, 1H), 7.44 (dd, 1H), 5.14-4.96 (m, 2H), 4.94-4.73 (m, 1H), 4.34-4.18 (m, 1H), 4.09 (d, 1H), 4.03 (d, 1H), 3.94-3.81 (m, 1H), 3.27-3.16 (m, 1H), 3.16-3.05 (m, 1H), 2.60-2.48 (m, 1H), 2.32-2.15 (m, 1H), 2.01-1.72 (m, 2H), 1.26 (m, 2H). LCMS-ESI$^+$ (m/z): [M+H]$^+$ calcd for C$_{24}$H$_{22}$F$_4$N$_4$O$_4$: 507.2; found: 507.2.

Example 67: 2-Cyano-N-(4-(3-cyano-4-(((3R,4S)-3-fluoro-1-(2-hydroxyacetyl)piperidin-4-yl)oxy)phenyl)pyridin-2-yl)cyclopropane-1-carboxamide

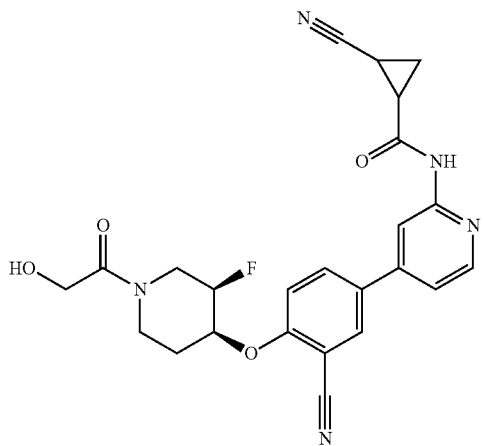 [SMILES: N#Cc1cc(-c2ccnc(NC(=O)C3CC3C#N)c2)ccc1O[C@H]1CCN(C(=O)CO)C[C@H]1F]

Step 1: tert-butyl (3R,4S)-4-(2-cyano-4-(2-(2-cyanocyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (200 mg, 0.49 mmol), 2-cyanocyclopropanecarboxylic acid (59 mg, 0.53 mmol) and HATU (230 mg, 0.61 mmol) in anhydrous DMF (4 mL) was added DIPEA (126 mg, 0.97 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by silica gel column chromatography eluted with 0-5% MeOH in CH$_2$Cl$_2$ to give the product.

Step 2: 2-Cyano-N-(4-(3-cyano-4-(((3R,4S)-3-fluoropiperidin-4-yl)oxy)phenyl)pyridin-2-yl)cyclopropane-1-carboxamide: tert-Butyl (3R,4S)-4-(2-cyano-4-(2-(2-cyanocyclopropane-1-carboxamido)pyridin-4-yl)phenoxy)-3-fluoropiperidine-1-carboxylate 98 mg, 0.19 mmol) was diluted with a mixture of DCM (1 mL) and TFA (0.25 mL). The mixture was stirred at room temperature for 1 h. The reaction mixture was evaporated under reduced pressure. The residue was purified by silica gel column chromatography eluted with 0-15% MeOH in CH$_2$Cl$_2$ to give the product.

Step 3: 2-Cyano-N-(4-(3-cyano-4-(((3R,4S)-3-fluoro-1-(2-hydroxyacetyl)piperidin-4-yl)oxy)phenyl)pyridin-2-yl)cyclopropane-1-carboxamide:
2-Cyano-N-(4-(3-cyano-4-(((3R,4S)-3-fluoropiperidin-4-yl)oxy)phenyl)pyridin-2-yl)cyclopropane-1-carboxamide (38 mg, 0.09 mmol), HATU (71 mg, 0.19 mmol), DIPEA (36 mg, 0.28 mmol) and glycolic acid (15 mg, 0.19 mmol) were dissolved in DMF (2 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. $^1$H NMR (400 MHz, DMSO-d6) δ 11.15 (s, 1H), 8.35 (d, 1H), 8.24 (d, 1H), 8.06 (d, 1H), 7.93 (dd, 1H), 7.51 (d, 1H), 7.44 (dd, 1H), 5.02 (m, 2H), 4.94-4.71 (m, 1H), 4.26 (m, 1H), 4.16-3.95 (m, 2H), 3.91-3.79 (m, 1H), 3.29-3.02 (m, 2H), 2.66 (m, 1H), 2.08 (m, 1H), 1.90-1.75 (m, 2H), 1.55 (m, 1H), 1.36 (m, 1H). LCMS-ESI$^+$ (m/z): [M+H]$^+$ calcd for C$_{24}$H$_{22}$FN$_5$O$_4$: 464.2; found: 464.2.

Example 68: (1,2-trans)-N-(4-(3-Cyano-4-(((3R,4S)-3-fluoro-1-(2-methoxyacetyl)piperidin-4-yl)oxy)phenyl)pyridin-2-yl)-2-fluorocyclopropane-1-carboxamide

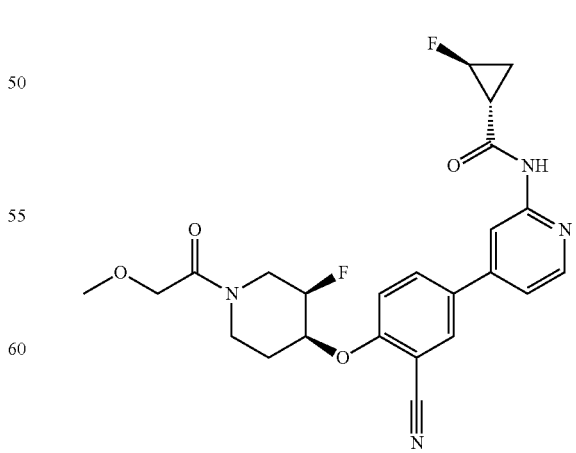

(1,2-trans)-N-(4-(3-Cyano-4-(((3R,4S)-3-fluoropiperidin-4-yl)oxy)phenyl)pyridin-2-yl)-2-fluorocyclopropane-1- carboxamide (30 mg, 0.075 mmol), HATU (57 mg, 0.15 mmol), DIPEA (29 mg, 0.23 mmol) and methoxyacetic acid (14 mg, 0.15 mmol) were dissolved in DMF (1.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. $^1$H NMR (400 MHz, DMSO-d6) δ 11.14 (s, 1H), 8.38 (d, 1H), 8.25 (d, 1H), 8.13 (d, 1H), 7.99 (dd, 1H), 7.56 (d, 1H), 7.49 (dd, 1H), 5.17-4.81 (m, 3H), 4.81 (m, 1H), 4.30 (dd, 1H), 4.18 (dd, 1H), 4.14-4.04 (m, 1H), 3.82-3.64 (m, 1H), 3.61-3.33 (m, 1H), 3.28 (s, 3H), 3.12 (m, 1H), 2.66-2.50 (m, 1H), 1.94 (m, 2H), 1.55 (m, 1H), 1.25 (m, 1H). LCMS-ESI$^+$ (m/z): [M+H]$^+$ calcd for $C_{24}H_{24}F_2N_4O_4$: 471.2; found: 471.3.

Example 69: (S)—N-(4-(3-Cyano-4-(((3R,4S)-3-fluoro-1-(2-hydroxyacetyl) piperidin-4-yl)oxy)phenyl)pyridin-2-yl)-2,2-dimethylcyclopropane-1-carboxamide

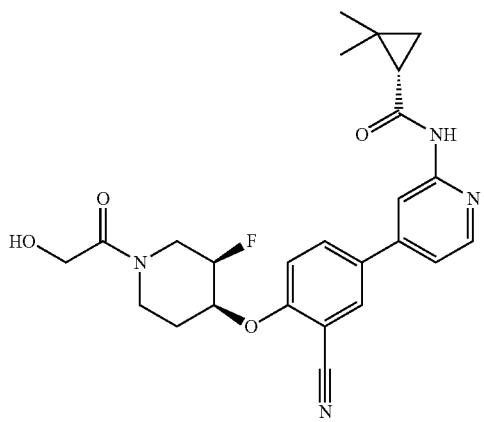 [SMILES: CC1(C)C[C@@H]1C(=O)Nc1cc(-c2ccc(O[C@H]3CCN(C(=O)CO)C[C@H]3F)c(C#N)c2)ccn1]

Step 1: tert-Butyl (3R,4S)-4-(2-cyano-4-(2-((S)-2,2-dimethylcyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (90 mg, 0.22 mmol), (S)-2,2-dimethylcyclopropanecarboxylic acid (38 mg, 0.33 mmol) and HATU (104 mg, 0.24 mmol) in anhydrous DMF (3 mL) was added DIPEA (85 mg, 0.66 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: (S)—N-(4-(3-Cyano-4-(((3R,4S)-3-fluoropiperidin-4-yl)oxy)phenyl)pyridin-2-yl)-2,2-dimethylcyclopropanecarboxamide: tert-Butyl (3R,4S)-4-(2-cyano-4-(2-((S)-2,2-dimethylcyclopropane-1-carboxamido)pyridin-4-yl)phenoxy)-3-fluoropiperidine-1-carboxylate (98 mg, 0.19 mmol) was diluted with a mixture of DCM (2 mL) and TFA (0.5 mL). The mixture stirred at room temperature for 1 h. The reaction mixture was evaporated under reduced pressure. The product was used for next step.

Step 3: (S)—N-(4-(3-Cyano-4-(((3R,4S)-3-fluoro-1-(2-hydroxyacetyl)piperidin-4-yl)oxy)phenyl)pyridin-2-yl)-2,2-dimethylcyclopropane-1-carboxamide: (S)—N-(4-(3-Cyano-4-(((3R,4S)-3-fluoropiperidin-4-yl)oxy)phenyl)pyridin-2-yl)-2,2-dimethylcyclopropanecarboxamide (38 mg, 0.09 mmol), HATU (71 mg, 0.19 mmol), DIPEA (36 mg, 0.28 mmol) and glycolic acid (15 mg, 0.19 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. $^1$H NMR (400 MHz, DMSO-d6) δ 11.22 (s, 1H), 8.36 (d, 1H), 8.19 (d, 1H), 8.12 (d, 1H), 8.04 (dd, 1H), 7.64-7.52 (m, 2H), 5.08-4.87 (m, 3H), 4.32-4.15 (m, 2H), 3.73-3.03 (m, 4H), 2.02-1.88 (m, 3H), 1.16 (d, 6H), 1.05 (m, 1H), 0.91 (m, 1H). LCMS-ESI$^+$ (m/z): [M+H]$^+$ calcd for $C_{25}H_{27}FN_4O_4$: 467.2; found: 467.3.

Example 70: N-(4-(3-Cyano-4-(((3R,4S)-3-fluoro-1-(2-hydroxyacetyl)piperidin-4-yl)oxy)phenyl)pyridin-2-yl)-2-methylcyclopropanecarboxamide

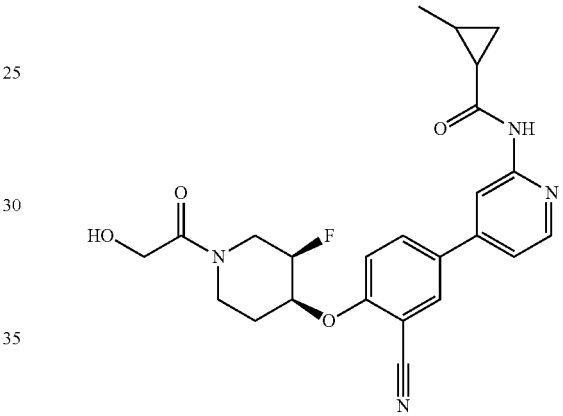

Step 1: tert-Butyl (3R,4S)-4-(2-cyano-4-(2-(2-methylcyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (90 mg, 0.22 mmol), 2-methylcyclopropanecarboxylic acid (40 mg, 0.39 mmol) and HATU (104 mg, 0.27 mmol) in anhydrous DMF (3 mL) was added DIPEA (85 mg, 0.66 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: N-(4-(3-cyano-4-(((3R,4S)-3-fluoropiperidin-4-yl)oxy)phenyl)pyridin-2-yl)-2-methylcyclopropane-1-carboxamide: tert-Butyl (3R,4S)-4-(2-cyano-4-(2-(2-methylcyclopropane-1-carboxamido)pyridin-4-yl)phenoxy)-3-fluoropiperidine-1-carboxylate (120 mg, 0.24 mmol) was diluted with a mixture of DCM (2 mL) and TFA (0.5 mL). The mixture was stirred at room temperature for 1 h. The reaction mixture was evaporated under reduced pressure. The product was used for next step.

Step 3: N-(4-(3-Cyano-4-(((3R,4S)-3-fluoro-1-(2-hydroxyacetyl)piperidin-4-yl)oxy)phenyl)pyridin-2-yl)-2-methylcyclopropanecarboxamide: N-(4-(3-Cyano-4-(((3R,4S)-3-fluoropiperidin-4-yl)oxy)phenyl)pyridin-2-yl)-2- methylcyclopropane-1-carboxamide (32 mg, 0.08 mmol), HATU (62 mg, 0.16 mmol), DIPEA (32 mg, 0.24 mmol) and glycolic acid (12 mg, 0.16 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. $^1H$ NMR (400 MHz, DMSO-d6) δ 11.06 (s, 1H), 8.35 (d, 1H), 8.21 (d, 1H), 8.16 (dd, 1H), 8.01 (dd, 1H), 7.57 (d, 1H), 7.51 (dd, 1H), 5.17-4.80 (m, 3H), 4.40-4.24 (m, 1H), 4.19-4.06 (m, 2H), 3.58-3.05 (m, 3H), 1.95 (m, 2H), 1.87-1.67 (m, 1H), 1.28 (m, 1H), 1.16-1.01 (m, 4H), 0.72 (m, 1H). LCMS-ESI$^+$ (m/z): [M+H]$^+$ calcd for $C_{24}H_{25}FN_4O_4$: 453.2; found: 453.3.

Example 71: (1,2-cis)-N-(4-(3-Cyano-4-(((3R,4S)-3-fluoro-1-(2-hydroxyacetyl)piperidin-4-yl)oxy)phenyl)pyridin-2-yl)-2-phenylcyclopropane-1-carboxamide

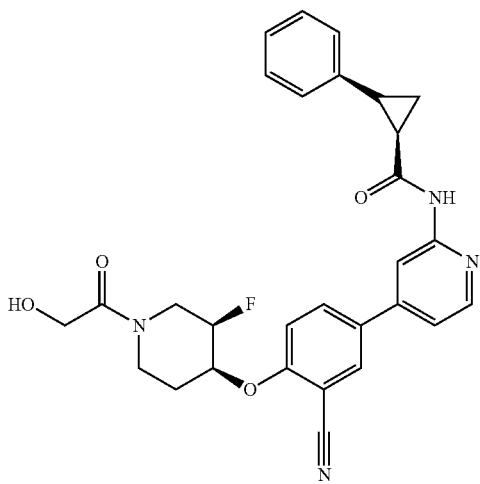

Step 1: tert-Butyl (3R,4S)-4-(2-cyano-4-(2-((1R,2S)-2-phenylcyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (90 mg, 0.22 mmol), cis-2-phenyl-cyclopropanecarboxylic acid (64 mg, 0.39 mmol) and HATU (104 mg, 0.27 mmol) in anhydrous DMF (3 mL) was added DIPEA (85 mg, 0.66 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: (1,2-cis)-N-(4-(3-cyano-4-(((3R,4S)-3-fluoropiperidin-4-yl)oxy)phenyl)pyridin-2-yl)-2-phenylcyclopropane-1-carboxamide: tert-Butyl (3R,4S)-4-(2-cyano-4-(2-((1R,2S)-2-phenylcyclopropane-1-carboxamido)pyridin-4-yl)phenoxy)-3-fluoropiperidine-1-carboxylate (0.125 g, 0.23 mmol) was diluted with a mixture of DCM (2 mL) and TFA (0.5 mL). The mixture was stirred at room temperature for 1 h. The reaction mixture was evaporated under reduced pressure. The product was used for next step.

Step 3: (1,2-Cis)-N-(4-(3-cyano-4-(((3R,4S)-3-fluoro-1-(2-hydroxyacetyl)piperidin-4-yl)oxy)phenyl)pyridin-2-yl)-2-phenylcyclopropane-1-carboxamide: (1,2-cis)-N-(4-(3-cyano-4-(((3R,4S)-3-fluoropiperidin-4-yl)oxy)phenyl)pyridin-2-yl)-2-phenylcyclopropane-1-carboxamide (50 mg, 0.11 mmol), HATU (83 mg, 0.22 mmol), DIPEA (42 mg, 0.33 mmol) and glycolic acid (17 mg, 0.22 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. LCMS-ESI$^+$ (m/z): [M+H]$^+$ calcd for $C_{29}H_{27}FN_4O_4$: 515.2; found: 515.3.

Example 72: (1R,2R)—N-(4-(3-cyano-4-(((3R,4S)-3-fluoro-1-(2-hydroxyacetyl)piperidin-4-yl)oxy)phenyl)pyridin-2-yl)-2-methylcyclopropane-1-carboxamide

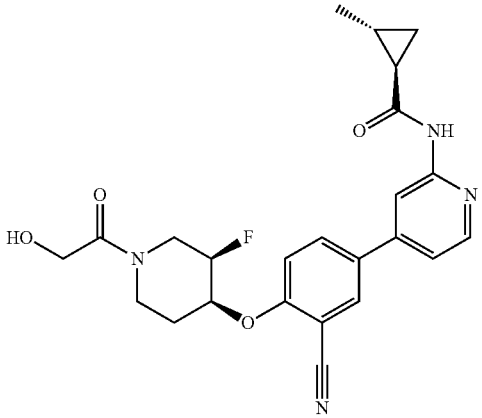 [SMILES: C[C@@H]1C[C@H]1C(=O)Nc1cc(-c2ccc(O[C@H]3CCN(C(=O)CO)C[C@H]3F)c(C#N)c2)ccn1]

Step 1: tert-Butyl (3R,4S)-4-(2-cyano-4-(2-((1R,2R)-2-methylcyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (150 mg, 0.36 mmol), (1R,2R)-2-methylcyclopropanecarboxylic acid (55 mg, 0.55 mmol) and HATU (173 mg, 0.46 mmol) in anhydrous DMF (3 mL) was added DIPEA (141 mg, 1.1 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: (1R,2R)—N-(4-(3-cyano-4-(((3R,4S)-3-fluoropiperidin-4-yl)oxy)phenyl)pyridin-2-yl)-2-methylcyclopropane-1-carboxamide: tert-Butyl (3R,4S)-4-(2-cyano-4-(2-((1R,2R)-2-methylcyclopropane-1-carboxamido)pyridin-4-yl)phenoxy)-3-fluoropiperidine-1-carboxylate (170 mg, 0.34 mmol) was diluted with a mixture of DCM (2 mL) and TFA (0.5 mL). The mixture was stirred at room temperature for 1 h. The reaction mixture was evaporated under reduced pressure. The product was used for next step.

Step 3: (1R,2R)—N-(4-(3-Cyano-4-(((3R,4S)-3-fluoro-1-(2-hydroxyacetyl)piperidin-4-yl)oxy)phenyl)pyridin-2-yl)-2-methylcyclopropane-1-carboxamide: (1R,2R)—N-(4-(3-cyano-4-(((3R,4S)-3-fluoropiperidin-4-yl)oxy)phenyl)pyridin-2-yl)-2-methylcyclopropane-1-carboxamide (42 mg, 0.11 mmol), HATU (81 mg, 0.21 mmol), DIPEA (41 mg, 0.32 mmol) and glycolic acid (16 mg, 0.21 mmol) were dissolved in DMF (2 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. $^1$H NMR (400 MHz, DMSO-d6) δ 11.16 (s, 1H), 8.36 (d, 1H), 8.17 (d, 2H), 8.02 (dd, 1H), 7.67-7.47 (m, 2H), 5.20-4.87 (m, 3H), 4.44-4.25 (m, 1H), 4.14 (d, 1H), 3.72-3.08 (m, 3H), 2.87 (s, 1H), 1.95 (m, 2H), 1.76 (m, 1H), 1.42-1.24 (m, 1H), 1.17-1.01 (m, 4H), 0.74 (m, 1H). LCMS-ESI$^+$ (m/z): [M+H]$^+$ calcd for C$_{24}$H$_{25}$FN$_4$O$_4$: 453.2; found: 453.3.

Example 73: (1,2-cis)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylic acid

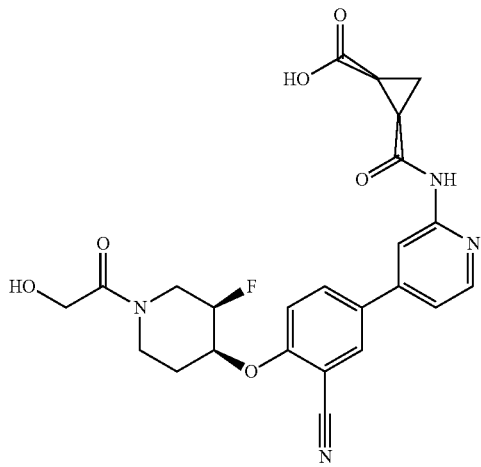 [SMILES: N#Cc1cc(-c2ccnc(NC(=O)[C@@H]3C[C@@H]3C(=O)O)c2)ccc1O[C@H]1CCN(C(=O)CO)C[C@H]1F]

To a suspension of 5-(2-(2,4-dioxo-3-azabicyclo[3.1.0] hexan-3-yl)pyridin-4-yl)-2-(((3R,4S)-3-fluoro-1-(2-hydroxyacetyl)piperidin-4-yl)oxy)benzonitrile (25 mg, 0.054 mmol) in dry THF (0.6 mL) was added a solution of LiOH (1 M, 0.3 mL, 0.3 mmol). The reaction mixture was stirred at room temperature for 2 hours. The mixture was purified by pre-HPLC to give the product. LCMS-ESI$^+$ (m/z): [M+H]$^+$ calcd for C$_{24}$H$_{23}$FN$_4$O$_6$: 483.2; found: 483.3.

Example 74: (1,2-cis)-N-(4-(3-Cyano-4-(((3R,4S)-3-fluoro-1-(2-hydroxyacetyl)piperidin-4-yl)oxy)phenyl)pyridin-2-yl)-2-(hydroxymethyl)cyclopropane-1-carboxamide

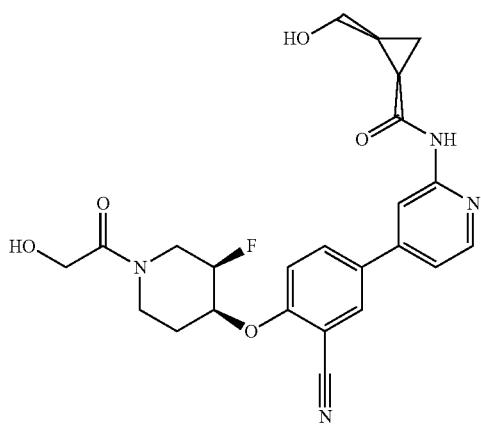 [SMILES: N#Cc1cc(-c2ccnc(NC(=O)[C@@H]3C[C@@H]3CO)c2)ccc1O[C@H]1CCN(C(=O)CO)C[C@H]1F]

To a suspension of 5-(2-(2,4-dioxo-3-azabicyclo[3.1.0] hexan-3-yl)pyridin-4-yl)-2-(((3R,4S)-3-fluoro-1-(2-hydroxyacetyl)piperidin-4-yl)oxy)benzonitrile (25 mg, 0.054 mmol) in isopropanol (0.46 mL) and water (0.08 mL) was added NaBH$_4$ (17 mg, 0.45 mmol). The reaction mixture was stirred at room temperature for 1 hour and then concentrated under reduced pressure. The mixture was purified by pre-HPLC to give the product. LCMS-ESI$^+$ (m/z): [M+H]$^+$ calcd for C$_{24}$H$_{25}$FN$_4$O$_5$: 469.2; found: 469.2.

Example 75: N-(4-(3-Cyano-4-(((3R,4S)-3-fluoro-1-(3-methyl-1H-1,2,4-triazole-5-carbonyl)piperidin-4-yl)oxy)phenyl)pyridin-2-yl)-2-methylcyclopropane-1-carboxamide

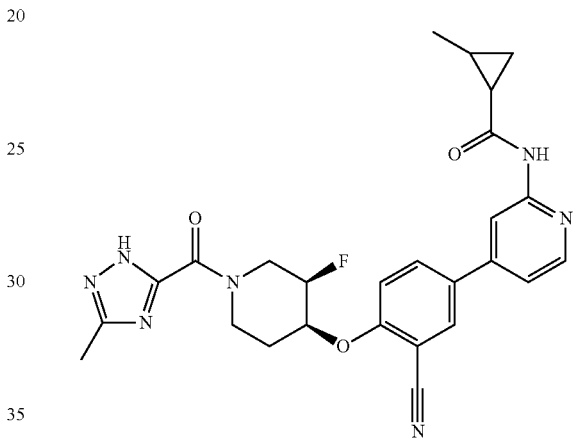

N-(4-(3-cyano-4-(((3R,4S)-3-fluoropiperidin-4-yl)oxy) phenyl)pyridin-2-yl)-2-methylcyclopropane-1-carboxamide (32 mg, 0.08 mmol), HATU (62 mg, 0.16 mmol), DIPEA (31 mg, 0.24 mmol) and 3-methyl-1H-1,2,4-triazole-5-carboxylic acid (21 mg, 0.16 mmol) were dissolved in DMF (2 mL) and stirred at room temperature for 2 hr. The mixture was diluted with water and extracted with CH$_2$Cl$_2$. The organic layer was separated, washed with water, dried over Na$_2$SO$_4$ and concentrated. The residue was purified by prep-HPLC to give the product. $^1$H NMR (400 MHz, DMSO-d6) δ 11.24 (s, 1H), 8.36 (d, 1H), 8.19 (m, 1H), 8.14 (s, 1H), 8.04 (dd, 1H), 7.68-7.50 (m, 2H), 5.26-4.91 (m, 2H), 4.74 (s, 1H), 4.60-4.48 (m, 1H), 3.89-3.72 (m, 1H), 3.61-3.18 (m, 2H), 2.38 (s, 3H), 2.12-1.84 (m, 2H), 1.83-1.70 (m, 1H), 1.44-1.25 (m, 1H), 1.18-1.00 (m, 4H), 0.75 (m, 1H). LCMS-ESI$^+$ (m/z): [M+H]$^+$ calcd for C$_{26}$H$_{26}$FN$_7$O$_3$: 504.2; found: 504.3.

Example 76: N-(4-(3-Cyano-4-(((3R,4S)-3-fluoro-1-(2-hydroxyacetyl)piperidin-4-yl)oxy)phenyl)pyridin-2-yl)-2-(1H-1,2,4-triazol-3-yl)cyclopropane-1-carboxamide

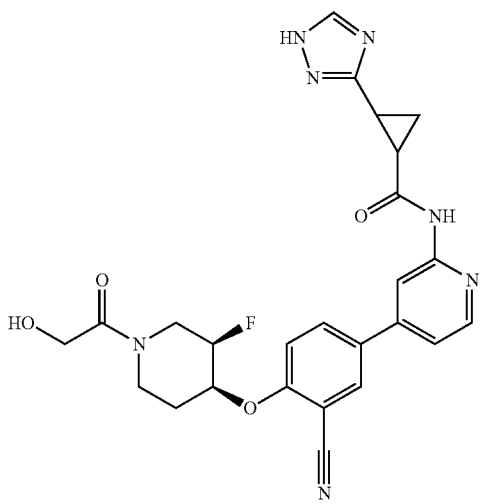 [SMILES: N#Cc1cc(-c2ccnc(NC(=O)C3CC3c3nc[nH]n3)c2)ccc1O[C@H]1CCN(C(=O)CO)C[C@H]1F]

Step 1: tert-Butyl (3R,4S)-4-(4-(2-(2-(1H-1,2,4-triazol-3-yl)cyclopropane-1-carboxamido)pyridin-4-yl)-2-cyanophenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (70 mg, 0.17 mmol), 2-(1H-1,2,4-triazol-3-yl)cyclopropanecarboxylic acid (39 mg, 0.26 mmol) and HATU (81 mg, 0.21 mmol) in anhydrous DMF (2 mL) was added DIPEA (66 mg, 0.51 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: N-(4-(3-Cyano-4-(((3R,4S)-3-fluoropiperidin-4-yl)oxy)phenyl)pyridin-2-yl)-2-(1H-1,2,4-triazol-3-yl)cyclopropane-1-carboxamide: tert-Butyl (3R,4S)-4-(4-(2-(2-(1H-1,2,4-triazol-3-yl)cyclopropane-1-carboxamido)pyridin-4-yl)-2-cyanophenoxy)-3-fluoropiperidine-1-carboxylate (35 mg, 0.06 mmol) was diluted with a mixture of DCM (1 mL) and TFA (0.25 mL). The mixture was stirred at room temperature for 1 h. The reaction mixture was evaporated under reduced pressure. The product was used for next step.

Step 3: N-(4-(3-Cyano-4-(((3R,4S)-3-fluoro-1-(2-hydroxyacetyl)piperidin-4-yl)oxy)phenyl)pyridin-2-yl)-2-(1H-1,2,4-triazol-3-yl)cyclopropane-1-carboxamide: N-(4-(3-Cyano-4-(((3R,4S)-3-fluoropiperidin-4-yl)oxy)phenyl)pyridin-2-yl)-2-(1H-1,2,4-triazol-3-yl)cyclopropane-1-carboxamide (29 mg, 0.065 mmol), HATU (49 mg, 0.13 mmol), DIPEA (26 mg, 0.19 mmol) and glycolic acid (10 mg, 0.13 mmol) were dissolved in DMF (1.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. LCMS-ESI$^+$ (m/z): [M+H]$^+$ calcd for $C_{25}H_{24}FN_7O_4$: 506.2; found: 506.2.

Example 77: N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide

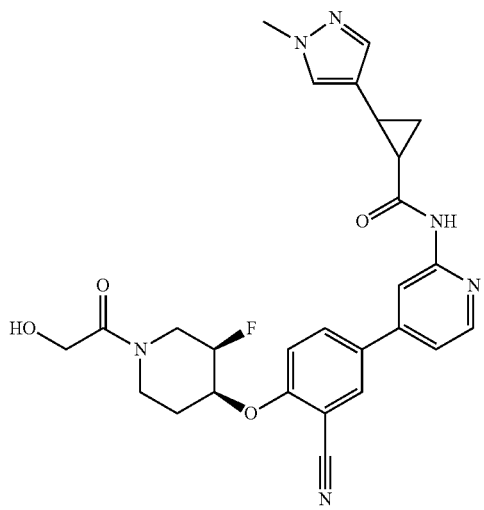 [SMILES: Cn1cc(C2CC2C(=O)Nc2cc(-c3ccc(O[C@H]4CCN(C(=O)CO)C[C@H]4F)c(C#N)c3)ccn2)cn1]

Step 1: tert-Butyl (3R,4S)-4-(2-cyano-4-(2-(2-(1-methyl-1H-pyrazol-4-yl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (70 mg, 0.17 mmol), 2-(1-methyl-1H-pyrazol-4-yl)cyclopropanecarboxylic acid (42 mg, 0.26 mmol) and HATU (81 mg, 0.21 mmol) in anhydrous DMF (2 mL) was added DIPEA (66 mg, 0.51 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: N-(4-(3-cyano-4-(((3R,4S)-3-fluoropiperidin-4-yl)oxy)phenyl)pyridin-2-yl)-2-(1-methyl-1H-pyrazol-4-yl)cyclopropane-1-carboxamide: tert-Butyl (3R,4S)-4-(2-cyano-4-(2-(2-(1-methyl-1H-pyrazol-4-yl)cyclopropane-1-carboxamido)pyridin-4-yl)phenoxy)-3-fluoropiperidine-1-carboxylate (46 mg, 0.08 mmol) was diluted with a mixture of DCM (1 mL) and TFA (0.25 mL). The mixture was stirred at room temperature for 1 h. The reaction mixture was evaporated under reduced pressure. The product was used for next step.

Step 3: N-(4-(3-Cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide: N-(4-(3-cyano-4-(((3R,4S)-3-fluoropiperidin-4-yl)oxy)phenyl)pyridin-2-yl)-2-(1-methyl-1H-pyrazol-4-yl)cyclopropane-1-carboxamide (38 mg, 0.08 mmol), HATU (63 mg, 0.16 mmol), DIPEA (32 mg, 0.25 mmol) and glycolic acid (13 mg, 0.16 mmol) were dissolved in DMF (1.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. $^1$H NMR (400 MHz, DMSO-d6) δ 10.90

(s, 1H), 8.35-8.24 (m, 2H), 8.09 (d, 1H), 7.95 (dd, 1H), 7.57-7.46 (m, 2H), 7.41 (dd, 1H), 7.22 (d, 1H), 5.17-4.95 (m, 2H), 4.96-4.78 (m, 1H), 4.27 (m, 1H), 4.18-3.98 (m, 2H), 3.70 (s, 3H), 3.59-2.97 (m, 2H), 2.23-2.02 (m, 2H), 1.90 (m, 2H), 1.76 (m, 1H), 1.32 (m, 1H), 1.14 (m, 1H). LCMS-ESI+ (m/z): [M+H]+ calcd for $C_{27}H_{27}FN_6O_4$: 519.2; found: 519.2.

Example 78: N-(4-(3-Cyano-4-(((3R,4S)-3-fluoro-1-(2-hydroxyacetyl)piperidin-4-yl)oxy)phenyl)pyridin-2-yl)-1-fluorocyclopropane-1-carboxamide

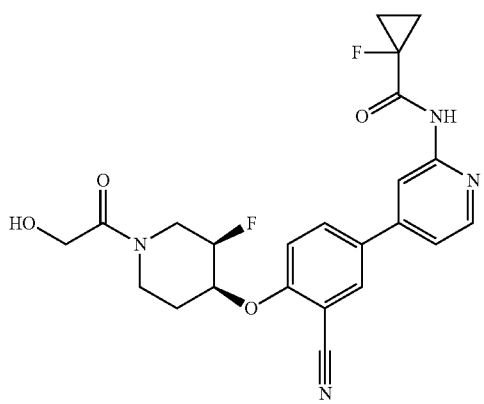 [SMILES: N#Cc1cc(-c2ccnc(NC(=O)C3(F)CC3)c2)ccc1O[C@H]1CCN(C(=O)CO)C[C@H]1F]

Step 1: N-(4-(3-cyano-4-fluorophenyl)pyridin-2-yl)-1-fluorocyclopropane-1-carboxamide: To a solution of 5-(2-aminopyridin-4-yl)-2-fluorobenzonitrile (216 mg, 1.01 mmol), 1-fluorocyclopropanecarboxylic acid (106 mg, 1.01 mmol) and HATU (481 mg, 1.27 mmol) in anhydrous DMF (8 mL) was added DIPEA (262 mg, 2.03 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: tert-Butyl (3R,4S)-4-(2-cyano-4-(2-(1-fluorocyclopropane-1-carboxamido)pyridin-4-yl)phenoxy)-3-fluoropiperidine-1-carboxylate: To tert-butyl (3R,4S)-3-fluoro-4-hydroxypiperidine-1-carboxylate (95 mg, 0.43 mmol) in Me-THF (6 mL) at 0 C was added potassium tert-butoxide solution (1M solution in 2-methyl-2-propanol, 0.5 mL, 0.5 mmol) and stirred for 45 minutes at 0 C. Then N-(4-(3-cyano-4-fluorophenyl)pyridin-2-yl)-1-fluorocyclopropane-1-carboxamide (100 mg, 0.33 mmol) was added and heated at 60° C. for 2 hr. Water was slowly added and the reaction mixture was evaporated under reduced pressure. The residue was purified by silica gel column chromatography eluted with 0-10% MeOH in $CH_2Cl_2$ to give the product.

Step 3: N-(4-(3-Cyano-4-(((3R,4S)-3-fluoropiperidin-4-yl)oxy)phenyl)pyridin-2-yl)-1-fluorocyclopropane-1-carboxamide: tert-Butyl (3R,4S)-4-(2-cyano-4-(2-(1-fluorocyclopropane-1-carboxamido)pyridin-4-yl)phenoxy)-3-fluoropiperidine-1-carboxylate (120 mg, 0.24 mmol) was diluted with a mixture of DCM (1 mL) and TFA (0.25 mL). The mixture was stirred at room temperature for 1 h. The reaction mixture was evaporated under reduced pressure. The product was used for next step.

Step 4: N-(4-(3-cyano-4-(((3R,4S)-3-fluoro-1-(2-hydroxyacetyl)piperidin-4-yl)oxy)phenyl)pyridin-2-yl)-1-fluorocyclopropane-1-carboxamide: N-(4-(3-Cyano-4-(((3R,4S)-3-fluoropiperidin-4-yl)oxy)phenyl)pyridin-2-yl)-1-fluorocyclopropane-1-carboxamide (90 mg, 0.23 mmol), HATU (172 mg, 0.45 mmol), DIPEA (88 mg, 0.68 mmol) and glycolic acid (34 mg, 0.45 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. LCMS-ESI+ (m/z): [M+H]+ calcd for $C_{23}H_{22}F_2N_4O_4$: 457.2; found: 457.3.

Example 79: (1,2-cis)-$N^1$-(4-(3-cyano-4-(((3R,4S)-3-fluoro-1-(2-hydroxyacetyl)piperidin-4-yl)oxy)phenyl)pyridin-2-yl)-$N^2$,$N^2$-dimethylcyclopropane-1,2-dicarboxamide

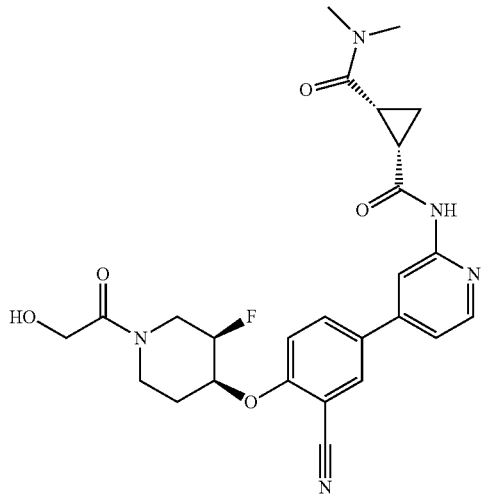 [SMILES: CN(C)C(=O)[C@@H]1C[C@@H]1C(=O)Nc1cc(-c2ccc(O[C@H]3CCN(C(=O)CO)C[C@H]3F)c(C#N)c2)ccn1]

Step 1: tert-butyl (3R,4S)-4-(2-cyano-4-(2-((1S,2R)-2-(dimethylcarbamoyl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (70 mg, 0.17 mmol), (1,2-cis)-2-(dimethylcarbamoyl)cyclopropanecarboxylic acid (40 mg, 0.26 mmol) and HATU (81 mg, 0.21 mmol) in anhydrous DMF (2 mL) was added DIPEA (66 mg, 0.51 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: (1,2-cis)-$N^1$-(4-(3-cyano-4-(((3R,4S)-3-fluoropiperidin-4-yl)oxy)phenyl)pyridin-2-yl)-$N^2$,$N^2$-dimethylcyclopropane-1,2-dicarboxamide: tert-Butyl (3R,4S)-4-(2-cyano-4-(2-((1S,2R)-2-(dimethylcarbamoyl)cyclopropane-1-carboxamido)pyridin-4-yl)phenoxy)-3-fluoropiperidine-1-carboxylate (27 mg, 0.05 mmol) was diluted with a mixture of DCM (1 mL) and TFA (0.25 mL). The mixture stirred at room temperature for 1 h. The reaction mixture was evaporated under reduced pressure. The product was used for next step.

Step 3: (1,2-cis)-N¹-(4-(3-cyano-4-(((3R,4S)-3-fluoro-1-(2-hydroxyacetyl)piperidin-4-yl)oxy)phenyl)pyridin-2-yl)-N²,N²-dimethylcyclopropane-1,2-dicarboxamide: (1,2-cis)-N¹-(4-(3-cyano-4-(((3R,4S)-3-fluoropiperidin-4-yl)oxy)phenyl)pyridin-2-yl)-N²,N²-dimethylcyclopropane-1,2-dicarboxamide (22 mg, 0.05 mmol), HATU (37 mg, 0.1 mmol), Henig base (19 mg, 0.15 mmol) and glycolic acid (7 mg, 0.09 mmol) were dissolved in DMF (1.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. LCMS-ESI⁺ (m/z): [M+H]⁺ calcd for $C_{26}H_{28}FN_5O_5$: 510.2; found: 510.2.

Example 80: (1,3-trans)-N-(4-(3-Cyano-4-(((3R,4S)-3-fluoro-1-(2-hydroxyacetyl)piperidin-4-yl)oxy)phenyl)pyridin-2-yl)-3-hydroxycyclobutane-1-carboxamide

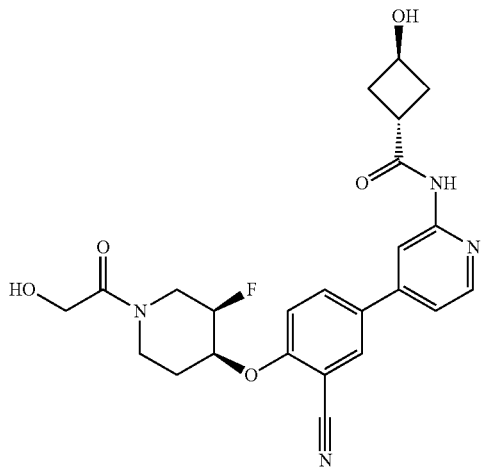 [SMILES: N#Cc1cc(-c2ccnc(NC(=O)[C@H]3C[C@H](O)C3)c2)ccc1O[C@H]1CCN(C(=O)CO)C[C@H]1F]

Step 1: (1,3-trans)-tert-Butyl (3R,4S)-4-(2-cyano-4-(2-((3-hydroxycyclobutane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (100 mg, 0.24 mmol), trans-3-hydroxycyclobutanecarboxylic acid (42 mg, 0.36 mmol) and HATU (115 mg, 0.30 mmol) in anhydrous DMF (2 mL) was added DIPEA (94 mg, 0.73 mmol). The mixture was stirred at 110° C. in a microwave reactor for 1 h. After being cooled to room temperature, the mixture was diluted with water and extracted with EtOAc. The organic layer was separated, washed with water and brine, dried over $Na_2SO_4$ and concentrated. The residue was purified by pre-HPLC to give the product.

Step 2: (1,3-trans)-N-(4-(3-Cyano-4-(((3R,4S)-3-fluoropiperidin-4-yl)oxy)phenyl)pyridin-2-yl)-3-hydroxycyclobutane-1-carboxamide: (1,3-trans)-tert-butyl (3R,4S)-4-(2-cyano-4-(2-((3-hydroxycyclobutane-1-carboxamido)pyridin-4-yl)phenoxy)-3-fluoropiperidine-1-carboxylate (94 mg, 0.18 mmol) was diluted with a mixture of DCM (1 mL) and TFA (0.25 mL). The mixture was stirred at room temperature for 1 h. The reaction mixture was evaporated under reduced pressure. The product was used for next step.

Step 3: (1,3-trans)-N-(4-(3-cyano-4-(((3R,4S)-3-fluoro-1-(2-hydroxyacetyl)piperidin-4-yl)oxy)phenyl)pyridin-2-yl)-3-hydroxycyclobutane-1-carboxamide: (1,3-trans)-N-(4-(3-Cyano-4-(((3R,4S)-3-fluoropiperidin-4-yl)oxy)phenyl)pyridin-2-yl)-3-hydroxycyclobutane-1-carboxamide (70 mg, 0.17 mmol), HATU (130 mg, 0.34 mmol), DIPEA (66 mg, 0.51 mmol) and glycolic acid (26 mg, 0.34 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. LCMS-ESI⁺ (m/z): [M+H]⁺ calcd for $C_{24}H_{25}FN_4O_5$: 469.2; found: 469.2.

Example 81: N-(4-(3-Cyano-4-(((3R,4S)-3-fluoro-1-(2-hydroxyacetyl)piperidin-4-yl)oxy)phenyl)pyridin-2-yl)-2-(1H-imidazol-4-yl)cyclopropane-1-carboxamide

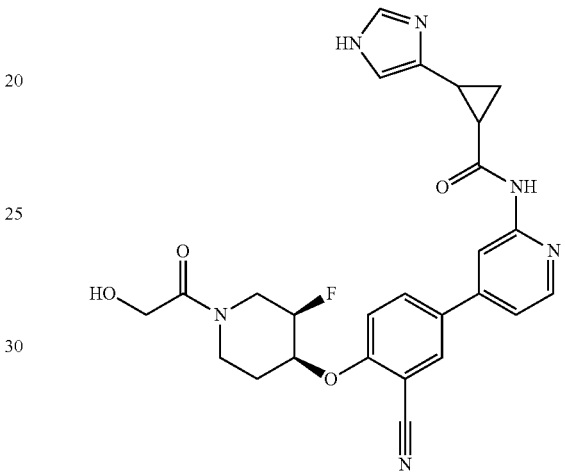

Step 1: tert-Butyl (3R,4S)-4-(4-(2-(2-(1H-imidazol-4-yl)cyclopropane-1-carboxamido)pyridin-4-yl)-2-cyanophenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (70 mg, 0.17 mmol), 2-(1H-imidazol-4-yl)cyclopropanecarboxylic acid (39 mg, 0.26 mmol) and HATU (81 mg, 0.21 mmol) in anhydrous DMF (2 mL) was added DIPEA (66 mg, 0.51 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by silica gel column chromatography eluted with 0-5% MeOH in $CH_2Cl_2$ to give the product.

Step 2: N-(4-(3-Cyano-4-(((3R,4S)-3-fluoropiperidin-4-yl)oxy)phenyl)pyridin-2-yl)-2-(1H-imidazol-4-yl)cyclopropane-1-carboxamide: tert-Butyl (3R,4S)-4-(4-(2-(2-(1H-imidazol-4-yl)cyclopropane-1-carboxamido)pyridin-4-yl)-2-cyanophenoxy)-3-fluoropiperidine-1-carboxylate (15 mg, 0.03 mmol) was diluted with a mixture of DCM (1 mL) and TFA (0.25 mL). The mixture was stirred at room temperature for 1 h. The reaction mixture was evaporated under reduced pressure. The product was used for next step.

Step 3: N-(4-(3-cyano-4-(((3R,4S)-3-fluoro-1-(2-hydroxyacetyl)piperidin-4-yl)oxy)phenyl)pyridin-2-yl)-2-(1H-imidazol-4-yl)cyclopropane-1-carboxamide: N-(4-(3-cyano-4-(((3R,4S)-3-fluoropiperidin-4-yl)oxy)phenyl)pyridin-2-yl)-2-(1H-imidazol-4-yl)cyclopropane-1-carboxamide (12 mg, 0.03 mmol), HATU (21 mg, 0.06 mmol), DIPEA (10 mg, 0.08 mmol) and glycolic acid (4 mg, 0.05 mmol) were dissolved in DMF (1.0 mL) and stirred at room temperature for 2 hr. The mixture was diluted with water and extracted with CH₂Cl₂. The organic layer was separated, washed with water and brine, dried over Na₂SO₄ and concentrated. The residue was purified by prep-HPLC to give the product. ¹H NMR (400 MHz, DMSO-d6) δ 10.98 (s, 1H), 8.94 (d, 1H), 8.39-8.23 (m, 2H), 8.07 (d, 1H), 7.94 (dd, 1H), 7.52 (d, 1H), 7.49-7.38 (m, 2H), 5.04-4.68 (m, 3H), 4.37-3.96 (m, 4H), 3.22-3.00 (m, 1H), 2.34-2.23 (m, 1H), 1.99-1.65 (m, 2H), 1.45 (m, 2H). LCMS-ESI⁺ (m/z): [M+H]⁺ calcd for $C_{26}H_{25}FN_6O_4$: 505.2; found: 505.1.

Example 82: (1,2-cis)-N1-(4-(3-cyano-4-(((3R,4S)-3-fluoro-1-(2-hydroxyacetyl)piperidin-4-yl)oxy)phenyl)pyridin-2-yl)cyclopropane-1,2-dicarboxamide

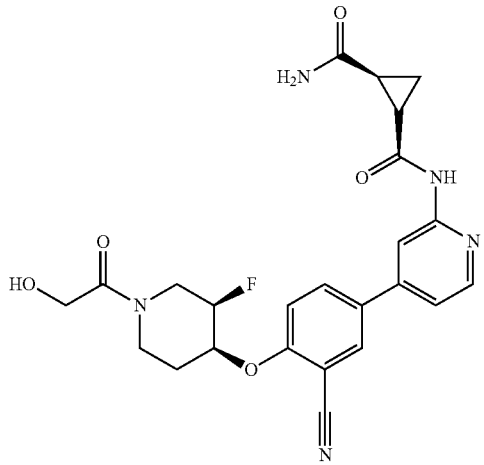

A solution of (1S,2R)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylic acid (22 mg, 0.05 mmol), NH₄Cl (15 mg, 0.27 mmol), DIPEA (48 mg, 0.37 mmol) and HATU (20 mg, 0.05 mmol) in anhydrous DMF (0.5 mL) was heated at 40° C. under nitrogen for 16 h. The mixture was purified by pre-HPLC to give the product. LCMS-ESI⁺ (m/z): [M+H]⁺ calcd for $C_{24}H_{24}FN_5O_5$: 482.2; found: 482.2.

Example 83: Methyl (1,2-trans)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylate

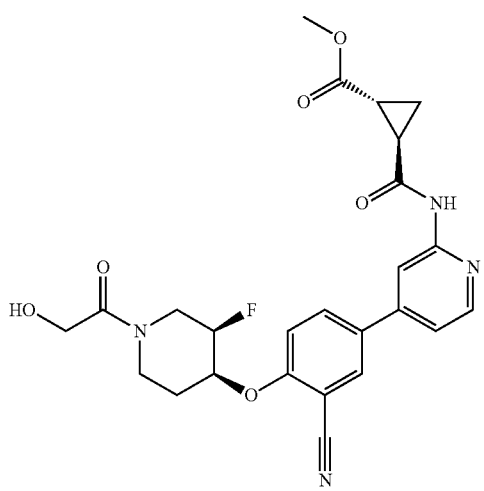 [SMILES: COC(=O)[C@@H]1C[C@H]1C(=O)Nc1cc(-c2ccc(O[C@H]3CCN(C(=O)CO)C[C@H]3F)c(C#N)c2)ccn1]

Step 1: tert-Butyl (3R,4S)-4-(2-cyano-4-(2-((1,2-trans)-2-(methoxycarbonyl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (120 mg, 0.29 mmol), (1R,2R)-rel-2-(methoxycarbonyl)cyclopropanecarboxylic acid (76 mg, 0.52 mmol) and HATU (138 mg, 0.36 mmol) in anhydrous DMF (4 mL) was added DIPEA (113 mg, 0.87 mmol). The mixture was stirred at 110° C. in a microwave reactor for 1 h. After being cooled to room temperature, the mixture was diluted with water and extracted with CH₂Cl₂. The organic layer was separated, washed with water and brine, dried over Na₂SO₄ and concentrated. The residue was purified by prep-HPLC to give the product.

Step 2: Methyl (1,2-trans)-2-((4-(3-cyano-4-(((3R,4S)-3-fluoropiperidin-4-yl)oxy)phenyl)pyridin-2-yl)carbamoyl)cyclopropane-1-carboxylate: tert-Butyl (3R,4S)-4-(2-cyano-4-(2-((1,2-trans)-2-(methoxycarbonyl)cyclopropane-1-carboxamido)pyridin-4-yl)phenoxy)-3-fluoropiperidine-1-carboxylate (25 mg, 0.05 mmol) was diluted with a mixture of DCM (1 mL) and TFA (0.25 mL). The mixture was stirred at room temperature for 1 h. The reaction mixture was evaporated under reduced pressure. The product was used for next step.

Step 3: Methyl (1,2-trans)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylate: Methyl-(1,2-trans)-2-((4-(3-cyano-4-(((3R,4S)-3-fluoropiperidin-4-yl)oxy)phenyl)pyridin-2-yl)carbamoyl)cyclopropane-1-carboxylate (20 mg, 0.05 mmol), HATU (35 mg, 0.09 mmol), DIPEA (18 mg, 0.14 mmol) and glycolic acid (7 mg, 0.09 mmol) were dissolved in DMF (1.5 mL) and stirred at room temperature for 2 hr. The mixture was diluted with water and extracted with CH₂Cl₂. The organic layer was separated, washed with water, dried over Na₂SO₄ and concentrated. The residue was purified by prep-HPLC to give the product. ¹H NMR (400 MHz, DMSO-d6) δ 11.02 (s, 1H), 8.32 (dd, 1H), 8.29-8.20 (m, 1H), 8.07 (d, 1H), 7.94 (dd, 1H), 7.51 (d, 1H), 7.42 (dd, 1H), 5.12-4.81 (m, 3H), 4.16-3.93 (m, 4H), 3.59 (s, 3H), 3.56-2.99 (m, 2H), 2.54 (m, 1H), 2.04-1.77 (m, 3H), 1.31 (m, 2H). LCMS-ESI⁺ (m/z): [M+H]⁺ calcd for $C_{25}H_{25}FN_4O_6$: 497.2; found: 497.3.

Example 84: (1,2-trans)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylic acid

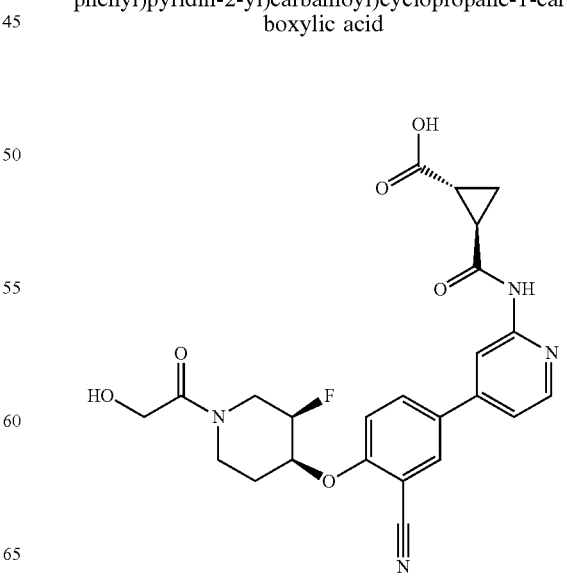

Add 1 N lithium hydroxide (0.2 mL, 25.6 mmol) to a solution of methyl trans-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylate (13 mg, 0.03 mmol) in tetrahydrofuran (0.3 mL). Stir vigorously for 3 hours at room temperature. The mixture was acidified with 1N hydrochloric acid to pH 3. Purify it with Gilson HPLC to give the product. The mixture was purified by prep-HPLC to give the product. LCMS-ESI$^+$ (m/z): [M+H]$^+$ calcd for $C_{24}H_{23}FN_4O_6$: 483.2; found: 483.3.

Example 85: (1,2-trans)-N-(4-(3-cyano-4-(((3R,4S)-3-fluoro-1-(2-hydroxyacetyl)piperidin-4-yl)oxy)phenyl)pyridin-2-yl)cyclopropane-1,2-dicarboxamide

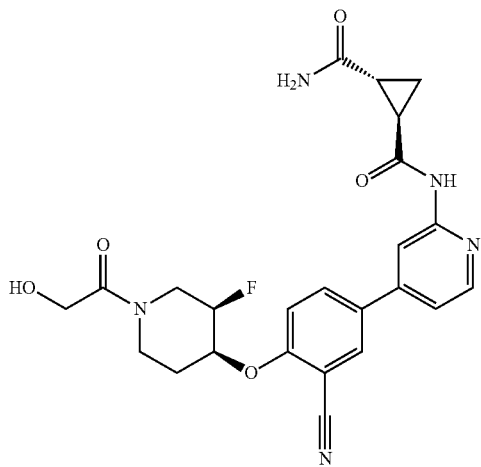 [SMILES: N#Cc1cc(-c2ccnc(NC(=O)[C@@H]3C[C@H]3C(N)=O)c2)ccc1O[C@H]1CCN(C(=O)CO)C[C@H]1F]

A solution of (1,2-trans)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylic acid (10 mg, 0.046 mmol), NH$_4$Cl (15 mg, 0.27 mmol), DIPEA (48 mg, 0.37 mmol) and HATU (24 mg, 0.052 mmol) in anhydrous DMF (0.5 mL) was heated at 40° C. under nitrogen for 16 h. The mixture was diluted with water and extracted with CH$_2$Cl$_2$. The organic layer was separated, washed with water, dried over Na$_2$SO$_4$ and concentrated. The residue was purified by prep-HPLC to give the product. LCMS-ESI$^+$ (m/z): [M+H]$^+$ calcd for $C_{24}H_{24}FN_5O_5$: 482.2; found: 482.3.

Example 86: (1,2 trans)-N-(4-(3-cyano-4-((tetrahydro-2H-pyran-4-yl)oxy)phenyl)pyridin-2-yl)-2-nitrocyclopropane-1-carboxamide

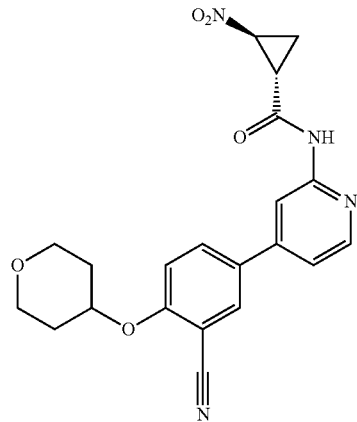 [SMILES: N#Cc1cc(-c2ccnc(NC(=O)[C@H]3C[C@@H]3[N+](=O)[O-])c2)ccc1OC1CCOCC1]

To a solution of 5-(2-aminopyridin-4-yl)-2-((tetrahydro-2H-pyran-4-yl)oxy)benzonitrile (25 mg, 0.085 mmol), trans-2-nitrocyclopropanecarboxylic acid (17 mg, 0.127 mmol) and HATU (64 mg, 0.17 mmol) in anhydrous DMF (1 mL) was added DIPEA (33 mg, 0.25 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by prep-HPLC to give the product. LCMS-ESI$^+$ (m/z): [M+H]$^+$ calcd for $C_{21}H_{20}N_4O_5$: 409.1; found: 409.1.

Example 87: (1R,2R)—N-(4-(3-cyano-4-((tetrahydro-2H-pyran-4-yl)oxy)phenyl)pyridin-2-yl)-2-phenylcyclopropane-1-carboxamide

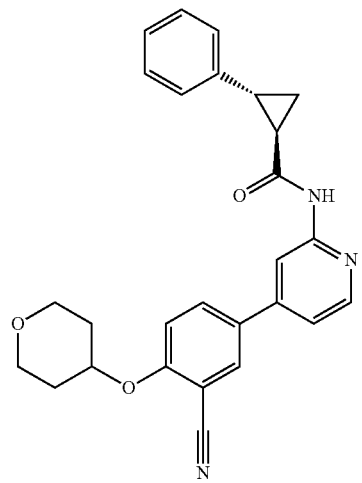 [SMILES: N#Cc1cc(-c2ccnc(NC(=O)[C@@H]3C[C@H]3c3ccccc3)c2)ccc1OC1CCOCC1]

To a solution of 5-(2-aminopyridin-4-yl)-2-((tetrahydro-2H-pyran-4-yl)oxy)benzonitrile (25 mg, 0.085 mmol), (1R,2R)-2-phenylcyclopropane-1-carboxylic acid (21 mg, 0.13 mmol) and HATU (64 mg, 0.17 mmol) in anhydrous DMF (1 mL) was added DIPEA (33 mg, 0.25 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by prep-HPLC to give the product. LCMS-ESI$^+$ (m/z): [M+H]$^+$ calcd for $C_{27}H_{25}N_3O_3$: 440.2; found: 440.2.

215

Example 88: (1,2-trans)-N-(4-(3-cyano-4-((tetrahydro-2H-pyran-4-yl)oxy)phenyl)pyridin-2-yl)-[1,1'-bi(cyclopropane)]-2-carboxamide

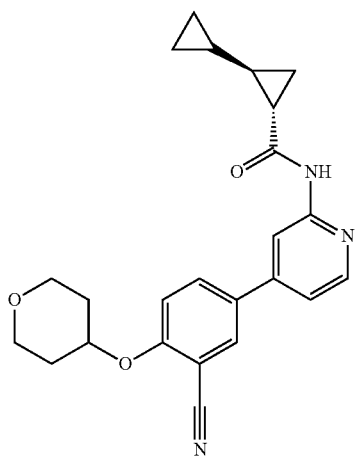 [SMILES: N#Cc1cc(-c2ccnc(NC(=O)[C@H]3C[C@@H]3C3CC3)c2)ccc1OC1CCOCC1]

To a solution of 5-(2-aminopyridin-4-yl)-2-((tetrahydro-2H-pyran-4-yl)oxy)benzonitrile (25 mg, 0.085 mmol), trans-[1,1'-bi(cyclopropane)]-2-carboxylic acid (16 mg, 0.13 mmol) and HATU (64 mg, 0.17 mmol) in anhydrous DMF (1 mL) was added DIPEA (33 mg, 0.25 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the product. LCMS-ESI$^+$ (m/z): [M+H]$^+$ calcd for $C_{24}H_{25}N_3O_3$: 404.2; found: 404.2.

Example 89: (1,2-trans)-N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide

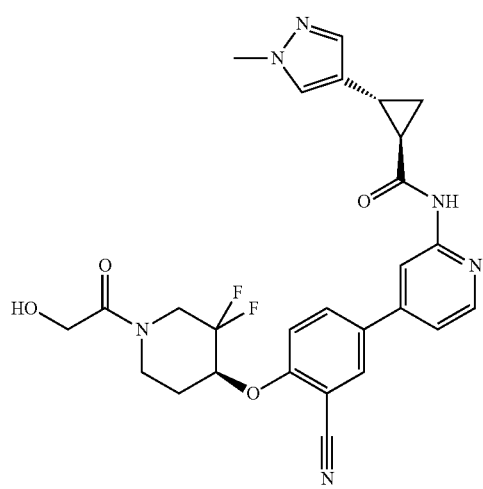 [SMILES: Cn1cc([C@@H]2C[C@H]2C(=O)Nc2cc(-c3ccc(O[C@H]4CCN(C(=O)CO)CC4(F)F)c(C#N)c3)ccn2)cn1]

216

Step 1: (1,2-trans)-N-(4-(3-cyano-4-fluorophenyl)pyridin-2-yl)-2-(1-methyl-1H-pyrazol-4-yl)cyclopropane-1-carboxamide:

To a solution of 5-(2-aminopyridin-4-yl)-2-fluorobenzonitrile (216 mg, 1.01 mmol), trans-2-(1-methyl-1H-pyrazol-4-yl)cyclopropane carboxylic acid (252 mg, 1.52 mmol) and HATU (481 mg, 2.03 mmol) in anhydrous DMF (8.5 mL) was added DIPEA (392 mg, 3.1 mmol). The mixture was stirred at 110° C. in a microwave reactor for 1 h. After being cooled to room temperature, the mixture was diluted with water (60 mL) and extracted with $CH_2Cl_2$ (60 mL). The organic layer was separated, washed with water (20 mL) and brine (20 mL), dried over $Na_2SO_4$ and concentrated. The residue was purified by silica gel column chromatography with 0-5% MeOH in $CH_2Cl_2$ to give the product.

Step 2: (tert-butyl (S)-4-(2-cyano-4-(2-(((1,2-trans)-2-(1-methyl-1H-pyrazol-4-yl)cyclopropane-1-carboxamido)pyridin-4-yl)phenoxy)-3,3-difluoropiperidine-1-carboxylate: To tert-butyl (S)-3,3-difluoro-4-hydroxypiperidine-1-carboxylate (88 mg, 0.37 mmol) in Me-THF (6 mL) at 0° C. was added potassium tert-butoxide solution (1M solution in 2-methyl-2-propanol, 0.43 mL) and stirred for 45 minutes at 0° C. Then (1,2-trans)-N-(4-(3-cyano-4-fluorophenyl)pyridin-2-yl)-2-(1-methyl-1H-pyrazol-4-yl)cyclopropane-1-carboxamide was added and heated at 60° C. for 2 hr. Water was slowly added and the reaction mixture was evaporated under reduced pressure. The residue was purified by silica gel column with 0-10% MeOH in $CH_2Cl_2$ to give the product.

Step 3: (1,2 trans)-N-(4-(3-cyano-4-(((S)-3,3-difluoropiperidin-4-yl)oxy)phenyl)pyridin-2-yl)-2-(1-methyl-1H-pyrazol-4-yl)cyclopropane-1-carboxamide: tert-Butyl (S)-4-(2-cyano-4-(2-((1,2-trans)-2-(1-methyl-1H-pyrazol-4-yl)cyclopropane-1-carboxamido)pyridin-4-yl)phenoxy)-3,3-difluoropiperidine-1-carboxylate (135 mg, 0.23 mmol) was diluted with a mixture of DCM (3 mL) and TFA (0.74 mL). The mixture was stirred at room temperature for 1 h. The reaction mixture was evaporated under reduced pressure. The product was used for next step.

Step 4: (1,2-trans)-N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide: (1,2-trans)-N-(4-(3-cyano-4-(((S)-3,3-difluoropiperidin-4-yl)oxy)phenyl)pyridin-2-yl)-2-(1-methyl-1H-pyrazol-4-yl)cyclopropane-1-carboxamide (38 mg, 0.08 mmol), HATU (60 mg, 0.16 mmol), DIPEA (31 mg, 0.24 mmol) and glycolic acid (12 mg, 0.16 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by Gilson prep-HPLC to give the product. 1H NMR (400 MHz, DMSO-d6) δ 11.05 (s, 1H), 8.36 (d, 1H), 8.33-8.21 (m, 1H), 8.17 (d, 1H), 8.04 (dt, 1H), 7.61 (d, 1H), 7.54 (s, 1H), 7.53-7.43 (m, 1H), 7.28 (d, 1H), 5.32 (m, 1H), 4.23-3.98 (m, 3H), 3.74 (s, 3H), 2.20 (m, 1H), 2.12 (m, 1H), 2.03-1.72 (m, 2H), 1.38 (m, 1H), 1.20 (m, 1H). LCMS-ESI$^+$ (m/z): [M+H]$^+$ calcd for $C_{27}H_{26}F_2N_6O_4$: 537.2; found: 537.2.

Example 90: (1,2-trans)-N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide

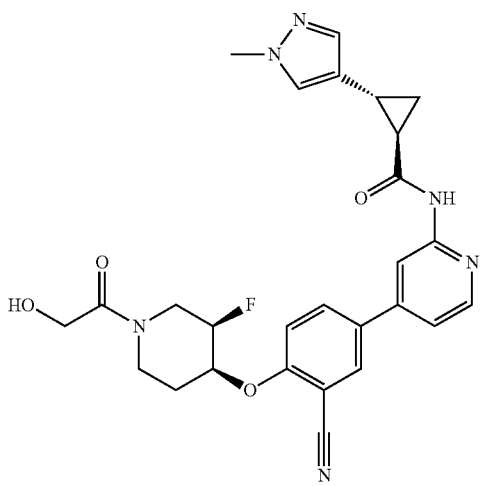

Step 1: tert-Butyl (3R,4S)-4-(2-cyano-4-(2-((1,2-trans)-2-(1-methyl-1H-pyrazol-4-yl)cyclopropane-1-carboxamido)pyridin-4-yl)phenoxy)-3-fluoropiperidine-1-carboxylate: To tert-butyl (3R,4S)-3-fluoro-4-hydroxypiperidine-1-carboxylate (88 mg, 0.4 mmol) in Me-THF (6 mL) at 0° C. was added potassium tert-butoxide solution (1M solution in 2-methyl-2-propanol, 0.46 mL) and stirred for 45 minutes at 0° C. Then (1,2-trans)-N-(4-(3-cyano-4-fluorophenyl)pyridin-2-yl)-2-(1-methyl-1H-pyrazol-4-yl)cyclopropane-1-carboxamide (103 mg, 0.29 mmol) was added and heated at 60° C. for 2 hr. Water was slowly added and the reaction mixture was evaporated under reduced pressure. The residue was purified by silica gel column with 0-10% MeOH in CH$_2$Cl$_2$ to give the product.

Step 2: (1,2-trans)-N-(4-(3-cyano-4-(((3R,4S)-3-fluoropiperidin-4-yl)oxy)phenyl)pyridin-2-yl)-2-(1-methyl-1H-pyrazol-4-yl)cyclopropane-1-carboxamide: (tert-Butyl (3R,4S)-4-(2-cyano-4-(2-((1,2-trans)-2-(1-methyl-1H-pyrazol-4-yl)cyclopropane-1-carboxamido)pyridin-4-yl)phenoxy)-3-fluoropiperidine-1-carboxylate (150 mg, 0.27 mmol) was diluted with a mixture of DCM (3 mL) and TFA (0.75 mL). The mixture was stirred at room temperature for 1 h. The reaction mixture was evaporated under reduced pressure. The product was used for next step.

Step 3: (1,2 trans)-N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide: (1,2-trans)-N-(4-(3-cyano-4-(((3R,4S)-3-fluoropiperidin-4-yl)oxy)phenyl)pyridin-2-yl)-2-(1-methyl-1H-pyrazol-4-yl)cyclopropane-1-carboxamide (40 mg, 0.087 mmol), HATU (66 mg, 0.17 mmol), DIPEA (34 mg, 0.26 mmol) and glycolic acid (13 mg, 0.17 mmol) were dissolved in DMF (2.5 mL) and stirred at room temperature for 2 hr. The mixture was diluted with water and extracted with DCM. The organic layer was separated, washed with water, dried over Na$_2$SO$_4$ and concentrated. The residue was purified by prep-HPLC to give the product. 1H NMR (400 MHz, DMSO-d6) δ 11.03 (s, 1H), 8.35 (d, 1H), 8.33-8.24 (m, 1H), 8.14 (t, 1H), 8.00 (m, 1H), 7.61-7.51 (m, 2H), 7.49 (d, 1H), 7.27 (s, 1H), 5.19-4.87 (m, 3H), 4.21-4.01 (m, 3H), 3.74 (s, 3H), 3.46-3.07 (m, 2H), 2.27-2.06 (m, 2H), 2.01-1.71 (m, 2H), 1.38 (m, 1H), 1.27-1.12 (m, 1H). LCMS-ESI$^+$ (m/z): [M+H]$^+$ calcd for C$_{27}$H$_{27}$FN$_6$O$_4$: 519.2; found: 519.2.

Example 91: (1,2-trans)-N-(4-(3-cyano-4-((tetrahydro-2H-pyran-4-yl)oxy)phenyl)pyridin-2-yl)-2-propylcyclopropane-1-carboxamide

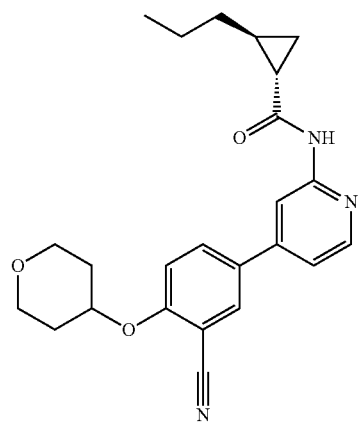 [SMILES: CCC[C@H]1C[C@@H]1C(=O)Nc1cc(-c2ccc(OC3CCOCC3)c(C#N)c2)ccn1]

To a solution of 5-(2-aminopyridin-4-yl)-2-((tetrahydro-2H-pyran-4-yl)oxy)benzonitrile (25 mg, 0.085 mmol), trans-2-propylcyclopropane-1-carboxylic acid (16 mg, 0.13 mmol) and HATU (64 mg, 0.17 mmol) in anhydrous DMF (1 mL) was added DIPEA (33 mg, 0.25 mmol). The mixture was stirred at 110° C. in a microwave reactor for 1 h. After being cooled to room temperature, the mixture was diluted with water and extracted with CH$_2$Cl$_2$. The organic layer was separated, washed with water, dried over Na$_2$SO$_4$ and concentrated. The residue was purified by pre-HPLC to give the product. 1H NMR (400 MHz, DMSO-d6) δ 10.94 (s, 1H), 8.33 (dd, 1H), 8.29-8.19 (m, 1H), 8.11 (d, 1H), 7.96 (dd, 1H), 7.54-7.40 (m, 2H), 4.89 (m, 1H), 3.84 (m, 2H), 3.52 (m, 2H), 2.08-1.93 (m, 2H), 1.85-1.74 (m, 1H), 1.65 (m, 2H), 1.47-1.15 (m, 4H), 1.03 (m, 1H), 0.88 (t, 3H), 0.77-0.64 (m, 1H). LCMS-ESI$^+$ (m/z): [M+H]$^+$ calcd for C$_{24}$H$_{27}$N$_3$O$_3$: 406.2; found: 406.2.

Example 92: (S)—N-(4-(3-cyano-4-(2-methylpyrrolidin-1-yl)phenyl)pyridin-2-yl)cyclopropanecarboxamide

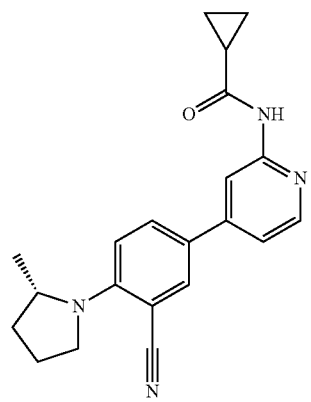 [SMILES: C[C@H]1CCCN1c1ccc(-c2ccnc(NC(=O)C3CC3)c2)cc1C#N]

To a solution of N-(4-(3-cyano-4-fluorophenyl)pyridin-2-yl)cyclopropanecarboxamide (150 mg, 0.533 mmol) in 5 mL iPrOH was added (S)-2-methylpyrrolidine (137 mg, 1.60 mmol) and DIEA (0.279 mL, 1.60 mmol) and stirred 140° C. in a microwave for 60 min. Purification by flash column chromatography gave (S)—N-(4-(3-cyano-4-(2-methylpyrrolidin-1-yl)phenyl)pyridin-2-yl)cyclopropanecarboxamide as a white solid. 1H NMR (400 MHz, DMSO-d6) δ 11.18 (s, 1H), 8.28 (d, J=5.6 Hz, 1H), 8.16 (d, J=1.8 Hz, 1H), 7.91 (d, J=2.4 Hz, 1H), 7.79 (dd, J=9.2, 2.5 Hz, 1H), 7.50 (dd, J=5.7, 1.8 Hz, 1H), 6.95 (d, J=9.2 Hz, 1H), 4.33 (td, J=6.6, 4.7 Hz, 1H), 3.81 (ddd, J=9.9, 7.4, 5.9 Hz, 1H), 3.50 (ddd, J=10.0, 7.5, 6.0 Hz, 1H), 2.18-1.94 (m, 3H), 1.96-1.81 (m, 1H), 1.73-1.61 (m, 1H), 1.16 (d, J=6.1 Hz, 3H), 0.90-0.82 (m, 4H). ES/MS 347.25 (M+H+).

Example 93: (S)—N-(4-(3-cyano-4-(2-(hydroxymethyl)pyrrolidin-1-yl)phenyl)pyridin-2-yl)cyclopropanecarboxamide

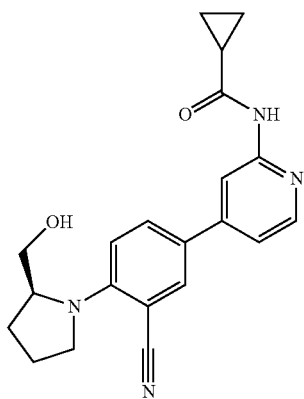 [SMILES: N#Cc1cc(-c2ccnc(NC(=O)C3CC3)c2)ccc1N1CCC[C@H]1CO]

To a solution of N-(4-(3-cyano-4-fluorophenyl)pyridin-2-yl)cyclopropanecarboxamide (150 mg, 0.533 mmol) in 5 mL iPrOH was added (S)-pyrrolidin-2-ylmethanol (162 mg, 1.60 mmol) and DIEA (0.279 mL, 1.60 mmol) and stirred 140° C. in a microwave for 60 min. Purification by flash column chromatography gave (S)—N-(4-(3-cyano-4-(2-(hydroxymethyl)pyrrolidin-1-yl)phenyl)pyridin-2-yl)cyclopropanecarboxamide as a white solid. 1H NMR (400 MHz, DMSO-d6) δ 11.13 (s, 1H), 8.28 (d, J=5.6 Hz, 1H), 8.17 (d, J=1.7 Hz, 1H), 7.89 (d, J=2.4 Hz, 1H), 7.78 (dd, J=9.2, 2.5 Hz, 1H), 7.49 (dd, J=5.6, 1.8 Hz, 1H), 7.02 (d, J=9.2 Hz, 1H), 4.29-4.18 (m, 1H), 3.84 (ddd, J=9.9, 7.3, 5.4 Hz, 1H), 3.55-3.44 (m, 2H), 3.40 (dd, J=11.1, 6.7 Hz, 1H), 2.10-1.94 (m, 4H), 1.98-1.82 (m, 1H), 0.91-0.79 (m, 4H). ES/MS 363.22 (M+H+).

Example 94: (S)—N-(4-(3-cyano-4-(3-methoxypyrrolidin-1-yl)phenyl)pyridin-2-yl)cyclopropanecarboxamide

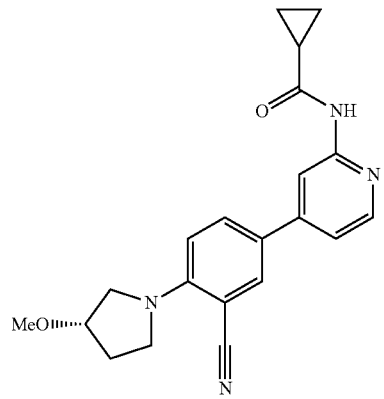 [SMILES: CO[C@H]1CCN(c2ccc(-c3ccnc(NC(=O)C4CC4)c3)cc2C#N)C1]

To a solution of N-(4-(3-cyano-4-fluorophenyl)pyridin-2-yl)cyclopropanecarboxamide (150 mg, 0.533 mmol) in 5 mL iPrOH was added (S)-3-methoxypyrrolidine (162 mg, 1.60 mmol) and DIEA (0.279 mL, 1.60 mmol) and stirred 140° C. in a microwave for 60 min. Purification by flash column chromatography gave (S)—N-(4-(3-cyano-4-(3-methoxypyrrolidin-1-yl)phenyl)pyridin-2-yl)cyclopropanecarboxamide as a white solid. ¹H NMR (400 MHz, DMSO-d6) δ 11.05 (s, 1H), 8.28 (d, J=5.5 Hz, 1H), 8.23-8.17 (m, 1H), 7.90 (d, J=2.4 Hz, 1H), 7.78 (dd, J=9.1, 2.4 Hz, 1H), 7.47 (dd, J=5.6, 1.8 Hz, 1H), 6.90 (d, J=9.1 Hz, 1H), 4.10 (tt, J=4.6, 2.2 Hz, 1H), 3.77 (dd, J=11.1, 4.5 Hz, 1H), 3.67-3.54 (m, 3H), 3.26 (s, 3H), 2.10 (s, 1H), 2.10-1.94 (m, 2H), 0.88-0.79 (m, 4H). ES/MS 363.14 (M+H+).

Example 95: (R)-1-(2-cyano-4-(2-(cyclopropanecarboxamido)pyridin-4-yl)phenyl)pyrrolidine-2-carboxamide

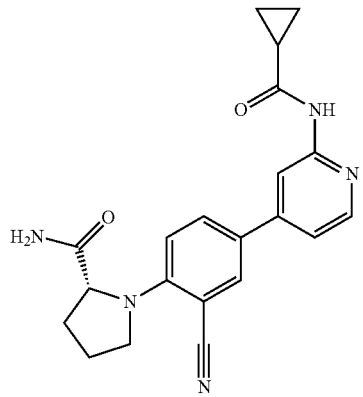 [SMILES: N#Cc1cc(-c2ccnc(NC(=O)C3CC3)c2)ccc1N1CCC[C@@H]1C(N)=O]

To a solution of N-(4-(3-cyano-4-fluorophenyl)pyridin-2-yl)cyclopropanecarboxamide (150 mg, 0.533 mmol) in 5 mL iPrOH was added (R)-pyrrolidine-2-carboxamide (187 mg, 1.60 mmol) and DIEA (0.279 mL, 1.60 mmol) and stirred 140° C. in a microwave for 60 min. Purification by flash column chromatography gave (R)-1-(2-cyano-4-(2-(cyclopropanecarboxamido)pyridin-4-yl)phenyl)pyrrolidine-2- carboxamide as a white solid. 1H NMR (400 MHz, DMSO-d6) δ 11.20 (s, 1H), 8.28 (d, J=5.7 Hz, 1H), 8.15 (d, J=1.7 Hz, 1H), 7.90 (d, J=2.4 Hz, 1H), 7.80 (dd, J=9.2, 2.4 Hz, 1H), 7.58 (d, J=1.9 Hz, 1H), 7.50 (dd, J=5.7, 1.8 Hz, 1H), 7.16 (d, J=1.8 Hz, 1H), 6.70 (d, J=9.2 Hz, 1H), 4.40 (dd, J=8.1, 3.6 Hz, 1H), 3.99 (dt, J=9.3, 6.1 Hz, 1H), 3.72 (dt, J=9.4, 6.7 Hz, 1H), 2.31-2.17 (m, 1H), 2.05-1.89 (m, 4H), 0.90-0.82 (m, 4H). ES/MS 376.20 (M+H$^+$).

Example 96: (R)—N-(4-(3-cyano-4-(2-methylpyrrolidin-1-yl)phenyl)pyridin-2-yl)cyclopropanecarboxamide

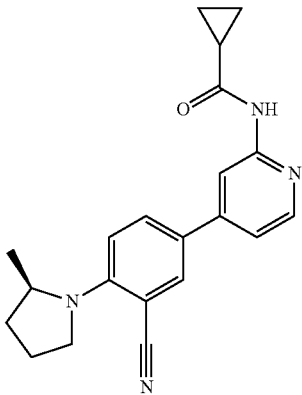

To a solution of N-(4-(3-cyano-4-fluorophenyl)pyridin-2-yl)cyclopropanecarboxamide (150 mg, 0.533 mmol) in 5 mL iPrOH was added (R)-2-methylpyrrolidine (137 mg, 1.60 mmol) and DIEA (0.279 mL, 1.60 mmol) and stirred 140° C. in a microwave for 60 min. Purification by flash column chromatography gave (R)—N-(4-(3-cyano-4-(2-methylpyrrolidin-1-yl)phenyl)pyridin-2-yl)cyclopropanecarboxamide as a white solid. $^1$H NMR (400 MHz, DMSO-d6) δ 11.17 (s, 1H), 8.27 (d, J=5.6 Hz, 1H), 8.17 (d, J=1.7 Hz, 1H), 7.91 (d, J=2.4 Hz, 1H), 7.78 (dd, J=9.2, 2.5 Hz, 1H), 7.49 (dd, J=5.6, 1.8 Hz, 1H), 6.95 (d, J=9.2 Hz, 1H), 4.32 (td, J=6.5, 4.7 Hz, 1H), 3.81 (ddd, J=9.9, 7.4, 5.9 Hz, 1H), 3.50 (ddd, J=9.9, 7.5, 6.0 Hz, 1H), 2.18-1.81 (m, 4H), 1.68 (ddd, J=11.1, 6.3, 4.6 Hz, 1H), 1.16 (d, J=6.1 Hz, 3H), 0.86 (d, J=5.5 Hz, 4H). ES/MS 347.23 (M+H$^+$).

Example 97: (R)—N-(4-(3-cyano-4-(3-methoxypyrrolidin-1-yl)phenyl)pyridin-2-yl)cyclopropanecarboxamide

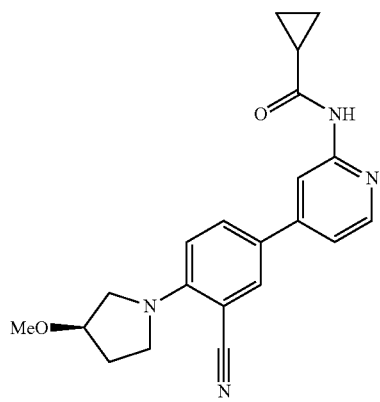 [SMILES: CO[C@@H]1CCN(c2ccc(-c3ccnc(NC(=O)C4CC4)c3)cc2C#N)C1]

To a solution of N-(4-(3-cyano-4-fluorophenyl)pyridin-2-yl)cyclopropanecarboxamide (150 mg, 0.533 mmol) in 5 mL iPrOH was added RS)-3-methoxypyrrolidine (162 mg, 1.60 mmol) and DIEA (0.279 mL, 1.60 mmol) and stirred 140° C. in a microwave for 60 min. Purification by flash column chromatography gave (R)—N-(4-(3-cyano-4-(3-methoxypyrrolidin-1-yl)phenyl)pyridin-2-yl)cyclopropanecarboxamide (80 mg, 41% yield) as a white solid. 1H NMR (400 MHz, DMSO-d6) δ 11.16 (s, 1H), 8.31-8.24 (m, 1H), 8.17 (d, J=1.7 Hz, 1H), 7.91 (d, J=2.4 Hz, 1H), 7.79 (dd, J=9.1, 2.4 Hz, 1H), 7.50 (dd, J=5.7, 1.8 Hz, 1H), 6.90 (d, J=9.2 Hz, 1H), 4.09 (td, J=4.4, 2.1 Hz, 1H), 3.77 (dd, J=11.2, 4.5 Hz, 1H), 3.67-3.57 (m, 3H), 3.26 (s, 3H), 2.16-2.01 (m, 1H), 2.05-1.94 (m, 2H), 0.89-0.79 (m, 4H). ES/MS 363.24 (M+H$^+$).

Example 98: N-(4-(3-cyano-4-((tetrahydro-2H-pyran-4-yl)methyl)phenyl)pyridin-2-yl)cyclopropanecarboxamide

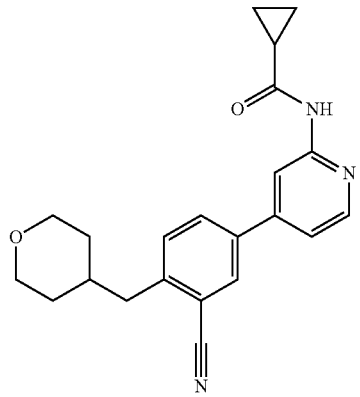 [SMILES: N#Cc1cc(-c2ccnc(NC(=O)C3CC3)c2)ccc1CC1CCOCC1]

Step 1: Preparation of (5-(2-aminopyridin-4-yl)-2-bromobenzonitrile: A suspension of 2-bromo-5-iodobenzonitrile (308 mg, 1 mmol) and 4-(4,4,5,5-tetramethyl-1,3,2-dioxaborolan-2-yl)pyridin-2-amine (220 mg, 1 mmol) in 1,2-Dimethoxyethane (5 mL) was treated with 2M sodium carbonate solution (2 mL, 4 mmol) and Tetrakis(triphenylphosphine)palladium (116 mg, 0.1 mmol). The mixture was heated in a microwave reactor for 30 minutes at 135° C. The cooled reaction mixture was quenched with water and extracted with dichloromethane for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{12}H_9BrN_3$: 275.1; found: 275.9.

Step 2: Preparation 5-(2-aminopyridin-4-yl)-2-((tetrahydro-2H-pyran-4-yl)methyl)benzonitrile: To a MeI vial, add 4-Methylenetetrahydro-2H-pyran (2.2 eq), 9-BBN (0.5M solution in tetrahydrofuran, 3.3 eq) and the clear reaction mixture was heated at 50° C. for 1 h. Then cool to room temperature, transferred to a sealed tube containing (5-(2-aminopyridin-4-yl)-2-bromobenzonitrile (1 eq) in THF (1 mL). Sodium hydroxide solution (1N, 3 eq), Tetrakis (triphenylphosphine)palladium were added and the vial was sealed. The reaction mixture was heated at 80° C. for 2 hr. The reaction was separate between water and dichloromethane, and was extracted with for three times. The combined extracts were washed once with saturated aqueous sodium chloride solution, dried over anhydrous sodium sulfate, filtered, and concentrated under reduced pressure. The crude residue was purified by flash chromatography (silica gel) to give the desired product as yellow solid. LCMS-ESI+ (m/z): [M+H]+ calcd for $C_{18}H_{20}N_3O$: 294.4; found: 294.2.

Step 3: Preparation of N-(4-(3-cyano-4-((tetrahydro-2H-pyran-4-yl)methyl)phenyl)pyridin-2-yl)cyclopropanecarboxamide: In a 10 mL vial, 5-(2-aminopyridin-4-yl)-2-((tetrahydro-2H-pyran-4-yl)methyl)benzonitrile (170 mg, 0.58 mmol) was dissolved in in N-Methyl-2-pyrrolidone (2.5 mL). N,N-diisopropylethylamine (0.51 ML, 2.89 mmol) and cyclopropanecarbonyl chloride (0.21 ML, 2.32 mmol) were added and the mixture was heated at 75° C. for 45 minutes. Then cool to room temperature and 7N ammonia in MeOH (1.5 mL) was added and stirred at room temperature for 45 min. The reaction mixture was dissolved in DMSO (5 mL) and purified with Prep HPLC. Collect fractions and neutralize with saturated sodium carbonate. Extract with dichloromethane for three times. Combine organic layers, dried with sodium sulfate, filter and evaporate to give product as light yellow. LCMS-ESI+ (m/z): [M+H]+ calcd for $C_{22}H_{24}N_3O_2$: 363.4; found: 363.1. 1H NMR (400 MHz, DMSO-d6) δ 10.93 (s, 1H), 8.43-8.33 (m, 2H), 8.13 (d, J=2.0 Hz, 1H), 7.94 (dd, J=8.1, 2.1 Hz, 1H), 7.59 (d, J=8.2 Hz, 1H), 7.49-7.36 (m, 1H), 3.81 (dd, J=11.4, 4.1 Hz, 2H), 3.22 (td, J=11.7, 2.0 Hz, 2H), 2.78 (d, J=7.2 Hz, 2H), 2.07-1.63 (m, 2H), 1.47 (d, J=12.3 Hz, 2H), 1.30 (td, J=12.3, 4.3 Hz, 2H), 0.89-0.75 (m, 4H).

Example 99: (1,2-trans)-N-(4-(3-cyano-4-((tetrahydro-2H-pyran-4-yl)oxy)phenyl)pyridin-2-yl)-2-(4-(trifluoromethoxy)phenyl)cyclopropane-1-carboxamide

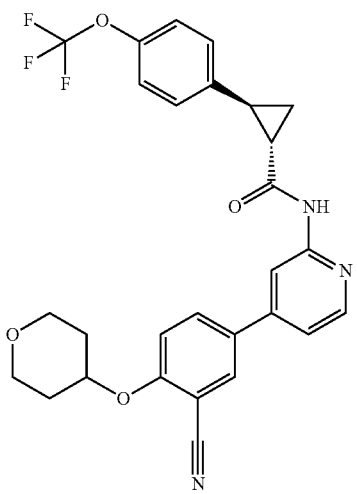

To a solution of 5-(2-aminopyridin-4-yl)-2-((tetrahydro-2H-pyran-4-yl)oxy)benzonitrile (75 mg, 0.25 mmol), trans-2-(4-(trifluoromethoxy)phenyl)cyclopropane-1-carboxylic acid (94 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by pre-HPLC to give the product. 1H NMR (400 MHz, DMSO-d6) δ 10.93 (s, 1H), 8.40-8.26 (m, 2H), 8.09 (d, 1H), 7.95 (dd, 1H), 7.48 (d, 1H), 7.43 (dd, 1H), 7.33-7.18 (m, 5H), 4.88 (m, 1H), 3.83 (m, 2H), 3.51 (m, 2H), 2.44-2.29 (m, 2H), 2.07-1.91 (m, 2H), 1.65 (m, 2H), 1.56-1.33 (m, 2H). LCMS-ESI+ (m/z): [M+H]+ calcd for $C_{28}H_{24}F_3N_3O_4$: 524.2; found: 524.2.

Example 100: (1, 2-trans)-N-(4-(3-cyano-4-((tetrahydro-2H-pyran-4-yl)oxy)phenyl)pyridin-2-yl)-2-(pyridin-3-yl)cyclopropane-1-carboxamide

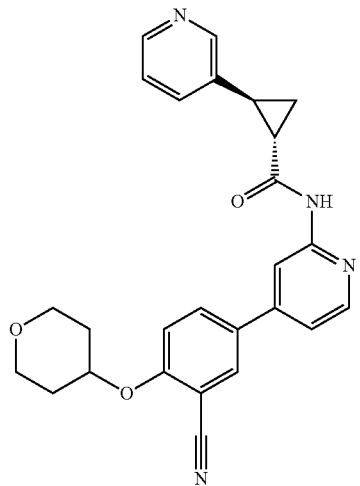 [SMILES: N#Cc1cc(-c2ccnc(NC(=O)[C@H]3C[C@@H]3c3cccnc3)c2)ccc1OC1CCOCC1]

To a solution of 5-(2-aminopyridin-4-yl)-2-((tetrahydro-2H-pyran-4-yl)oxy)benzonitrile (75 mg, 0.25 mmol), (1,2 trans)-2-(pyridin-3-yl)cyclopropane-1-carboxylic acid (62 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by pre-HPLC to give the product. 1H NMR (400 MHz, DMSO-d6) δ 10.97 (s, 1H), 8.75 (d, 1H), 8.65 (dd, 1H), 8.41-8.28 (m, 2H), 8.08 (m, 2H), 7.95 (dd, 1H), 7.77 (dd, 1H), 7.53-7.39 (m, 2H), 4.88 (m, 1H), 3.83 (m, 2H), 3.51 (m, 2H), 2.61 (m, 1H), 2.09-1.91 (m, 2H), 1.77-1.48 (m, 4H). LCMS-ESI+ (m/z): [M+H]+ calcd for $C_{26}H_{24}N_4O_3$: 441.2; found: 441.2.

Example 101: (1,2-trans)-N-(4-(3-cyano-4-((tetrahydro-2H-pyran-4-yl)oxy)phenyl)pyridin-2-yl)-2-(difluoromethyl)cyclopropane-1-carboxamide

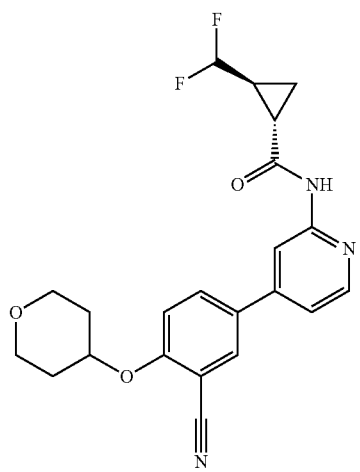 [SMILES: N#Cc1cc(-c2ccnc(NC(=O)[C@H]3C[C@@H]3C(F)F)c2)ccc1OC1CCOCC1]

To a solution of 5-(2-aminopyridin-4-yl)-2-((tetrahydro-2H-pyran-4-yl)oxy)benzonitrile (75 mg, 0.25 mmol), (1,2-trans)-2-(difluoromethyl)cyclopropane-1-carboxylic acid (52 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with CH2Cl2. The organic layer was separated, washed with water, dried over $Na_2SO_4$ and concentrated. The residue was purified by pre-HPLC to give the product. 1H NMR (400 MHz, DMSO-d6) δ 11.09 (s, 1H), 8.35 (d, 1H), 8.27 (s, 1H), 8.09 (d, 1H), 7.94 (dd, 1H), 7.53-7.39 (m, 2H), 5.97 (td, 1H), 4.87 (m, 1H), 3.93-3.74 (m, 2H), 3.51 (m, 2H), 2.31 (m, 1H), 2.07-1.92 (m, 2H), 1.90-1.75 (m, 1H), 1.63 (m, 2H), 1.22-1.03 (m, 2H). LCMS-ESI+ (m/z): [M+H]+ calcd for $C_{22}H_{21}F_2N_3O_3$: 414.2; found: 414.2.

Example 102: trans-1,2-N-(4-(3-cyano-4-((tetrahydro-2H-pyran-4-yl)oxy)phenyl)pyridin-2-yl)-2-(isoxazol-5-yl)cyclopropane-1-carboxamide

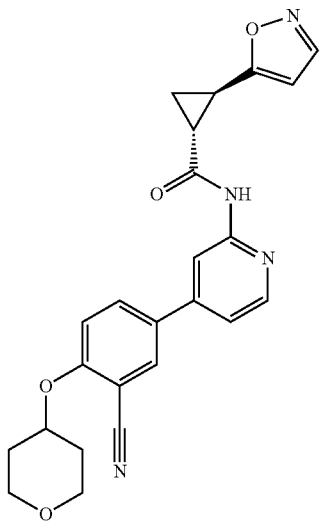 [SMILES: N#Cc1cc(-c2ccnc(NC(=O)[C@@H]3C[C@H]3c3ccno3)c2)ccc1OC1CCOCC1]

Step 1: A stirred solution of trans-1-2-(2-((4-(3-cyano-4-((tetrahydro-2H-pyran-4-yl)oxy)phenyl)pyridin-2-yl)carbamoyl)cyclopropane-1-carboxylic acid (prepared via the procedure of: (1,2-trans)-2-((4-(3-cyano-4-(((3R,4S)-3-fluoro-1-(2-hydroxyacetyl)piperidin-4-yl)oxy)phenyl)pyridin-2-yl)carbamoyl)cyclopropane-1-carboxylic acid—Example 84) in 25 mL DMF was treated with HATU (1.88 g, 4.96 mmol) and stirred for 2 min. N,O-dimethylhydroxylamine (0.75 g, 7.44 mmol) and DIEA (3.39 mL, 19.8 mmol) were added and the mixture stirred for 1 h. The reaction was partitioned between EtOAc and saturated aqueous solution of $NaHCO_3$, and the organic layer separated was dried ($MgSO_4$), filtered and concentrated. Purification by silica gel chromatography (EtOAc-hexanes) provided trans-1,2-N1-(4-(3-cyano-4-((tetrahydro-2H-pyran-4-yl)oxy)phenyl)pyridin-2-yl)-N2-methoxy-N2-methylcyclopropane-1,2-dicarboxamide as an off-white solid.

Step 2: To a chilled (0° C.) solution of acetylaldehyde oxime (101 mg, 1.71 mmol) in THF (12 mL) was added dropwise over 5 min 2.5 M n-butyllithium in hexanes (1.37 mL, 3.46 mmol). The initially formed white suspension gave a colorless solution after all of the base had been added.

After an additional 30 min, trans-1,2-$N^1$-(4-(3-cyano-4-((tetrahydro-2H-pyran-4-yl)oxy)phenyl)pyridin-2-yl)-$N^2$-methoxy-$N^2$-methylcyclopropane-1,2-dicarboxamide (Example 38) (896 mg, 5.00 mmol) in THF (20 mL) was added dropwise over 20 min. After stirring for an additional 30 min, the pale yellow solution was poured into a solution of concentrated $H_2SO_4$ (1.0 mL) in THF/water 4:1 (14 mL) and refluxed for 1 h. The chilled (ice bath) reaction mixture was carefully neutralized with $NaHCO_3$, sufficient water was added to dissolve the salts, and the mixture was extracted with ether (2×25 mL). The combined ethereal extracts were washed with brine, dried, and concentrated in vacuo to a yellow oil which was purified RP HPLC to provide trans-1,2-N-(4-(3-cyano-4-((tetrahydro-2H-pyran-4-yl)oxy)phenyl)pyridin-2-yl)-2-(isoxazol-5-yl)cyclopropane-1-carboxamide as a yellow solid. LCMS-ESI+ (m/z): calculated for $C_{24}H_{22}N_4O_4$ 431.16. found: 431.06 (M+H+). 1H NMR (400 MHz, DMSO-d6) δ 11.07 (s, 1H), 8.47 (d, J=1.8 Hz, 1H), 8.40-8.30 (m, 2H), 8.12 (d, J=2.4 Hz, 1H), 7.97 (dd, J=8.9, 2.4 Hz, 1H), 7.53-7.41 (m, 2H), 6.37 (s, 1H), 4.90 (tt, J=7.9, 3.8 Hz, 1H), 3.85 (ddd, J=11.5, 5.9, 3.9 Hz, 2H), 3.53 (ddd, J=11.5, 8.4, 3.1 Hz, 2H), 2.60 (dddd, J=18.8, 8.3, 5.9, 4.0 Hz, 2H), 2.01 (dd, J=13.5, 4.5 Hz, 2H), 1.73-1.47 (m, 4H).

Example 103: (1S,2S)—N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-3-yl)cyclopropane-1-carboxamide

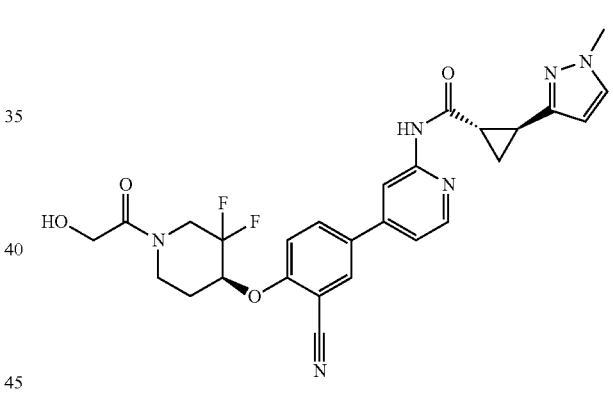

Step 1: A solution of tert-butyl (S)-3,3-difluoro-4-hydroxypiperidine-1-carboxylate (1.775 g, 7.48 mmol) in 6 mL was added in one portion to a well stirred solution of KOtBu (0.916 mg, 8.162 mmol, 1M) in THF at 0° C. After stirring for 40 min, 5-(6-aminopyrimidin-4-yl)-2-fluorobenzonitrile (1.43 g, 6.73 mmol) was added and the reaction heated to 60° C. for 2 h. The reaction mixture was cooled to rt and 10 mL of water was added. The reaction was then concentrated under reduced pressure and partitioned between EtOAc and water. The organic phase was dried (MgSO4), filtered and concentrated to give tert-butyl (S)-4-(4-(2-aminopyridin-4-yl)-2-cyanophenoxy)-3,3-difluoropiperidine-1-carboxylate which was used without purification. LCMS-ESI+ (m/z): calculated for $C_{22}H_{25}F_2N_4O_3$: 431.2. found: 431.2 (M+H+).

Step 2: To a solution of tert-butyl (S)-4-(4-(2-aminopyridin-4-yl)-2-cyanophenoxy)-3,3-difluoropiperidine-1-carboxylate (240 mg, 0.558 mmol) and (1S,2S)-2-(1-methyl-1H-pyrazol-3-yl)cyclopropane-1-carboxylic acid (0.11 g, 0.67 mmol) (prepared by the method of Hisao Nishiyama, Norikazu Soeda, Tomonari Naito, Yukihiro Motoyama, *Tet-* rahedron: Asymmetry, 1998, 2865-2869) in DMF (5.0 mL) was added HATU (254 mg, 0.67 mmol) and TEA (0.155 mL, 1.2 mmol) were added. After 30 min at rt, the reaction was diluted with water (30 mL) and EtOAc (30 mL) and the organic phase was dried (MgSO₄), filtered and concentrated to give tert-butyl (S)-4-(2-cyano-4-(2-((1S,2S)-2-(1-methyl-1H-pyrazol-3-yl)cyclopropane-1-carboxamido)pyridin-4-yl)phenoxy)-3,3-difluoropiperidine-1-carboxylate which was used without purification. LCMS-ESI+ (m/z): calculated for $C_{30}H_{33}F_2N_6O_4$: 579.3. found: 579.1 (M+H+).

Step 3: A solution of tert-butyl (S)-4-(2-cyano-4-(2-((1S,2S)-2-(1-methyl-1H-pyrazol-3-yl)cyclopropane-1-carboxamido)pyridin-4-yl)phenoxy)-3,3-difluoropiperidine-1-carboxylate (0.140 mg, 0.242 mmol) in 3 mL DCM was treated with 3 mL of TFA and stirred for 30 min. The reaction was concentrated to dryness under reduced pressure and the residue partitioned between EtOAc and pH 10 carbonate buffer. The organic layer was separated and concentrated to give (1S,2S)—N-(4-(3-cyano-4-(((S)-3,3-difluoropiperidin-4-yl)oxy)phenyl)pyridin-2-yl)-2-(1-methyl-1H-pyrazol-3-yl)cyclopropane-1-carboxamide which was used without purification. LCMS-ESI+ (m/z): calculated for $C_{25}H_{25}F_2N_6O_2$: 479.2. found: 479.2 (M+H+).

Step 4: To a solution of (1S,2S)—N-(4-(3-cyano-4-(((S)-3,3-difluoropiperidin-4-yl)oxy)phenyl)pyridin-2-yl)-2-(1-methyl-1H-pyrazol-3-yl)cyclopropane-1-carboxamide (71 mg, 0.148 mmol) in 2 mL DMF was added glycolic acid (14 mg, 0.178 mmol), HATU (68 mg, 0.178 mmol) and TEA (62 mL, 0.445 mmol) and stirred at rt for 2 h. The reaction was concentrated and purified by prep HPLC (5-95% acetonitrile in water, 0.1% trifluoroacetic acid buffer) to give the title compound. LCMS-ESI+ (m/z): calculated for $C_{27}H_{26}F_2N_6O_4$: 537.2. found: 537.3 (M+H+). 1H NMR (400 MHz, DMSO-d6) δ 10.96 (s, 1H), 8.39-8.30 (m, 2H), 8.16 (d, J=2.4 Hz, 1H), 8.04 (dd, J=9.0, 2.4 Hz, 1H), 7.61 (d, J=9.0 Hz, 1H), 7.54 (d, J=2.1 Hz, 1H), 7.47 (dd, J=5.3, 1.7 Hz, 1H), 6.05 (d, J=2.2 Hz, 1H), 5.33 (td, J=8.2, 3.8 Hz, 1H), 4.16 (d, J=15.5 Hz, 2H), 4.09-3.95 (m, 1H), 3.86 (t, J=16.9 Hz, 1H), 3.74 (s, 3H), 3.66-3.35 (m, 2H), 2.38-2.26 (m, 2H), 2.12 (s, 2H), 1.98 (s, 1H), 1.39 (ddd, J=8.9, 5.4, 3.6 Hz, 1H), 1.31 (ddd, J=8.1, 6.5, 3.6 Hz, 1H).

Example 104: Tert-butyl (S)-4-(2-cyano-4-(6-(cyclopropanecarboxamido)pyrimidin-4-yl)phenoxy)-3,3-difluoropiperidine-1-carboxylate

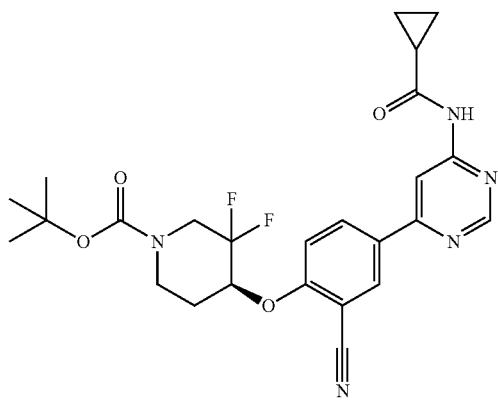 [SMILES: CC(C)(C)OC(=O)N1CC[C@H](Oc2ccc(-c3cc(NC(=O)C4CC4)ncn3)cc2C#N)C(F)(F)C1]

To a solution of tert-butyl (S)-3,3-difluoro-4-hydroxypiperidine-1-carboxylate (219 mg, 0.92 mmol) in Me-THF (10 mL) at 0° C. was added potassium tert-butoxide solution (1.0 M, 1.06 mL, 1.06 mmol) in one portion and stirred at that temperature. After 45 min, N-(6-(3-cyano-4-fluorophenyl)pyrimidin-4-yl)cyclopropanecarboxamide (200 mgs, 0.71 mmol) was added in one portion and warmed to room temperature. The reaction was heated at 60° C. for 3 h. The reaction was quenched with minimum amount of water, concentrated to dryness to give tert-butyl (S)-4-(2-cyano-4-(6-(cyclopropanecarboxamido)pyrimidin-4-yl)phenoxy)-3,3-difluoropiperidine-1-carboxylate. LCMS-ESI+ (m/z): [M+H]+ calcd for C25H27F2N5O4 500.5. found: 500.1.

Example 105: N-(6-(3-cyano-4-fluorophenyl)pyrimidin-4-yl)cyclopropanecarboxamide

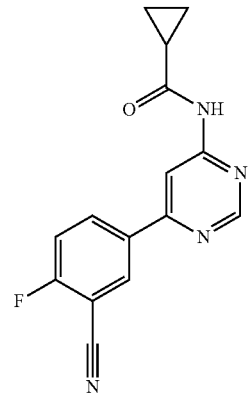 [SMILES: N#Cc1cc(-c2cc(NC(=O)C3CC3)ncn2)ccc1F]

Step 1: To a mixture 6-chloropyrimidin-4-amine (500 mgs, 3.86 mmol) and 2-fluoro-5-(4,4,5,5-tetramethyl-1,3,2-dioxaborolan-2-yl)benzonitrile (954 mgs, 3.86 mmol) in DME (10 mL) was added 2.0 M aq Na2CO3 (4.2 mL, 8.34 mmol) and Pd(PPh3)4 catalyst (122 mgs, 0.11 mmol). The reaction mixture was heated at 130° C. for 2 hr. The mixture was then diluted with water and the stirred at rt. The resulting solids were filtered and washed with water and dried to give 5-(6-aminopyrimidin-4-yl)-2-fluorobenzonitrile which was used further without purification. LCMS-ESI+ (m/z): [M+H]+ calcd for C11H17FN4 215.2. found: 215.1.

Step 2: To above solution of 5-(6-aminopyrimidin-4-yl)-2-fluorobenzonitrile (621 mgs, 2.9 mmol) in NMP (4.0 mL) and DIPEA (1.55 mL, 9.0 mmol) cyclopropanecarbonyl chloride (0.8 mL, 9.0 mmol) was slowly added. After 30 min at rt, the reaction mixture was heated at 85° C. for 2 h. The reaction mixture was then cooled to rt and Ammonia in Methanol (7N, 8.0 mL) was added and stirred at rt. After 1 h, the reaction mixture was concentrated, diluted with water (30 mL) and the resulting solids were filtered and washed with water and diethylether and dried to give N-(6-(3-cyano-4-fluorophenyl)pyrimidin-4-yl)cyclopropanecarboxamide. LCMS-ESI+ (m/z): [M+H]+ calcd for C15H11FN4O, 283.3. found: 283.1.

Example 106: N-(6-(3-cyano-4-((1,1,1-trifluoropropan-2-yl)oxy)phenyl)pyrimidin-4-yl)cyclopropanecarboxamide

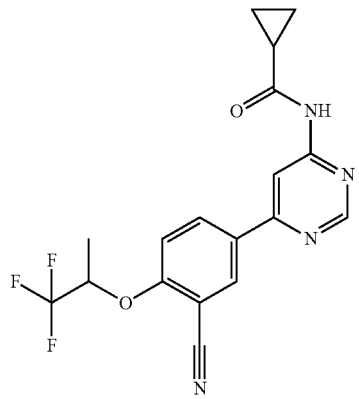 [SMILES: CC(Oc1ccc(-c2cc(NC(=O)C3CC3)ncn2)cc1C#N)C(F)(F)F]

To a solution of 1,1,1-trifluoropropan-2-ol 0.1 mL, 1.1 mmol) in Me-THF (5 mL) at 0° C. was added potassium tert-butoxide solution (1.0 M, 1.06 mL, 1.1 mmol) in one portion and stirred at that temperature. After 45 min, N-(6-(3-cyano-4-fluorophenyl)pyrimidin-4-yl)cyclopropanecarboxamide (100 mgs, 0.35 mmol) was added in one portion and warmed to room temperature. The reaction was heated at 60° C. for 1 h. The reaction was quenched with minimum amount of water, and the residue was purified by reverse phase HPLC to give the title compound. LCMS-ESI+ (m/z): [M+H]+ calcd for $C_{18}H_{15}F_3N_4O_2$ 376.3. found: 376.1.

Example 107: N-(6-(3-cyano-4-(((3R,4S)-3-fluoro-1-(2-methyloxazole-5-carbonyl)piperidin-4-yl)oxy)phenyl)pyrimidin-4-yl)cyclopropanecarboxamide

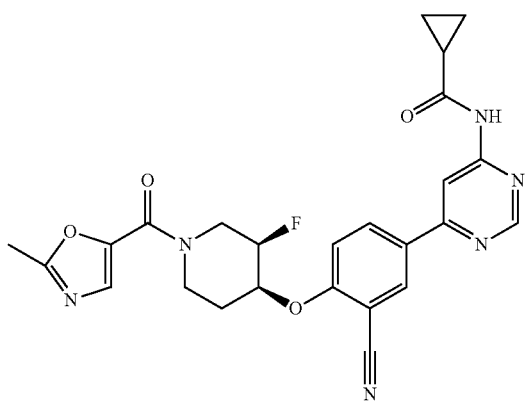 [SMILES: Cc1ncc(C(=O)N2CC[C@H](Oc3ccc(-c4cc(NC(=O)C5CC5)ncn4)cc3C#N)[C@H](F)C2)o1]

The title compound was prepared following a similar procedure to Example 27 using 2-methyloxazole-5-carboxylic acid. 1H NMR (400 MHz, DMSO-d6) δ 11.30 (s, 1H), 8.88 (d, J=1.2 Hz, 1H), 8.47 (d, J=1.2 Hz, 1H), 8.34 (d, J=2.3 Hz, 1H), 8.28 (dd, J=9.0, 2.4 Hz, 1H), 7.56 (d, J=8.9 Hz, 2H), 5.23-5.08 (m, 3H), 4.29 (d, J=76.2 Hz, 2H), 3.8-3.10 (m, 4H), 2.01 (ddt, J=10.1, 6.7, 3.3 Hz, 3H), 0.91-0.76 (m, 4H). LCMS-ESI+ (m/z): [M+H]+ calcd for $C_{25}H_{23}FN_6O_4$: 491.2; found: 491.2.

Example 108: (1R,2R)—N-(4-(3-cyano-4-((tetrahydro-2H-pyran-4-yl)oxy)phenyl)pyridin-2-yl)-2-(3-methyl-1,2,4-oxadiazol-5-yl)cyclopropane-1-carboxamide

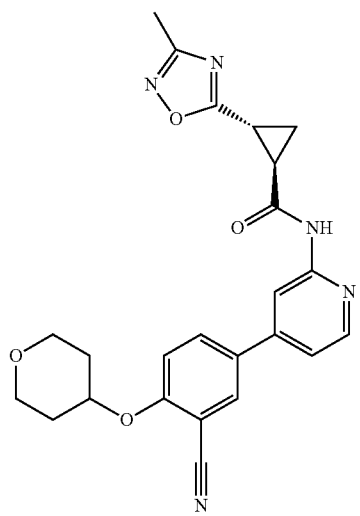 [SMILES: Cc1noc([C@@H]2C[C@H]2C(=O)Nc2cc(-c3ccc(OC4CCOCC4)c(C#N)c3)ccn2)n1]

Step 1: Preparation of methyl (1R,2R)-2-(3-methyl-1,2,4-oxadiazol-5-yl)cyclopropane-1-carboxylate: (1R,2R)-2-(methoxycarbonyl)cyclopropane-1-carboxylic acid (500 mg, 3.46 mmol), (E)-N'-hydroxyacetimidamide (514 mg, 6.9 mmol), DIPEA (0.35 ml, 3.46 mmol) and HATU (1450 mg, 3.81 mmol), were dissolved in DMF (5 ml). Reaction mixture was stirred at 90° C. for 2 h and then cooled down to room temperature. Reaction mixture was diluted with DCM and washed with water and saturated aqueous solution of LiCl. The organic layer was dried over MgSO4 and concentrated to give the title compound.

Step 2: Preparation of (1R,2R)-2-(3-methyl-1,2,4-oxadiazol-5-yl)cyclopropane-1-carboxylic acid: methyl (1R,2R)-2-(3-methyl-1,2,4-oxadiazol-5-yl)cyclopropane-1-carboxylate (500 mg, 2.74 mmol) was dissolved in methanol (5 mL) and then treated with Lithium hydroxide (2M solution in water). Reaction mixture was stirred at room temperature for 2 h and then concentrated. Solids were suspended in ethyl acetate and then acidified to reach a pH~2.5 with 1N HCl aqueous solution. The organic layer was extracted, dried over MgSO4 and concentrated under reduced pressure to give the title compound.

Step 3: Preparation of (1R,2R)-2-(3-methyl-1,2,4-oxadiazol-5-yl)cyclopropane-1-carbonyl chloride: To a solution of (1R,2R)-2-(3-methyl-1,2,4-oxadiazol-5-yl)cyclopropane-1-carboxylic acid (50 mg, 0.297 mmol) in dichloromethane (5 ml) was cooled down to 0° C. in an ice-bath. Oxalyl chloride (0.27 ml, 2.97 mmol) was added dropwise and then DMF (0.1 ml) under nitrogen. The reaction mixture was stirred for 30 minutes at 0° C. and then at room temperature for 30 min. The excessive solvent was removed on ratovapor and dried under high vacuum for 2 hrs to yield (1R,2R)-2-(3-methyl-1,2,4-oxadiazol-5-yl)cyclopropane-1-carbonyl chloride.

Step 4: Preparation of (1R,2R)—N-(4-(3-cyano-4-((tetrahydro-2H-pyran-4-yl)oxy)phenyl)pyridin-2-yl)-2-(3-methyl-1,2,4-oxadiazol-5-yl)cyclopropane-1-carboxamide. To a solution of the 5-(2-aminopyridin-4-yl)-2-((tetrahydro-2H-pyran-4-yl)oxy)benzonitrile (0.35 mmol, 1.2 equiv) in NMP (5 mL) was added DIPEA (0.29 mmol, 1.0 equiv), followed by (1R,2R)-2-(3-methyl-1,2,4-oxadiazol-5-yl)cyclopropane-1-carbonyl chloride. Mixture was stirred at 80° C. until no starting material was visible by TLC. Upon completion, the reaction mixture was separated between ethyl acetate and water. The combined organics were washed with water and brine. After drying over MgSO₄ and evaporation under reduced pressure, the crude product was purified via preparative HPLC (5-65% acetonitrile in water, 0.1% trifluoroacteic acid buffer) to yield (1R,2R)—N-(4-(3-cyano-4-((tetrahydro-2H-pyran-4-yl)oxy)phenyl)pyridin-2-yl)-2-(3-methyl-1,2,4-oxadiazol-5-yl)cyclopropane-1-carboxamide. LCMS-ESI+ (m/z): [M+H]+ calcd for $C_{24}H_{23}N_5O_4$: 446.2; found: 446.2.

Example 109: N-(6-(3-cyano-4-hydroxyphenyl)pyrimidin-4-yl)cyclopropanecarboxamide

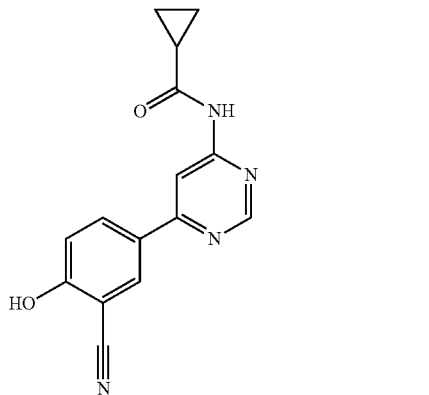 [SMILES: N#Cc1cc(-c2cc(NC(=O)C3CC3)ncn2)ccc1O]

2-Fluoro-5-(4,4,5,5-tetramethyl-1,3,2-dioxaborolan-2-yl)benzonitrile (30 mg, 0.1 mmol) and 2-(methylsulfonyl)ethan-1-ol (13 mg, 0.1 mmol) were dissolved in DMF at room temperature. NaH 60% dispersion in mineral oil (9 mg, 0.21 mmol) was slowly added and then stirred for 24 h. Reaction mixture was diluted with EtOAc and washed with water. Organic layer was dried over MgSO₄ and evaporated under reduced pressure. The crude product was purified via preparative HPLC (5-65% acetonitrile in water, 0.1% trifluoroacteic acid buffer) to yield N-(6-(3-cyano-4-hydroxyphenyl)pyrimidin-4-yl)cyclopropanecarboxamide. LCMS-ESI+ (m/z): [M+H]+ calcd for $C_{15}H_{12}N_4O_2$: 281.1; found: 281.1.

Example 110: (R)—N-(6-(3-cyano-4-((3,3-difluoro-1-(2-hydroxyacetyl)piperidin-4-yl)oxy)phenyl)pyrimidin-4-yl)cyclopropanecarboxamide

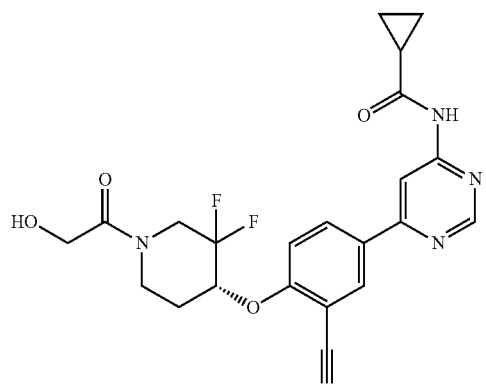

The title compound was prepared following a similar procedure to Example 27 using (R)-1-(3,3-difluoro-4-hydroxypiperidin-1-yl)-2-hydroxyethan-1-one and 2-hydroxyacetic acid. 1H NMR (400 MHz, DMSO-d6) δ 11.12 (s, 1H), 8.71 (d, J=1.2 Hz, 1H), 8.31 (d, J=1.2 Hz, 1H), 8.18 (d, J=2.3 Hz, 1H), 8.13 (dd, J=8.9, 2.3 Hz, 1H), 7.41 (d, J=9.1 Hz, 1H), 5.52 (d, J=1.0 Hz, 1H), 5.14 (td, J=8.3, 4.0 Hz, 1H), 4.65 (s, 1H), 4.01-3.18 (m, 3H), 3.10 (d, J=1.0 Hz, 2H), 1.99-1.57 (m, 3H), 0.75-0.58 (m, 4H). LCMS-ESI+ (m/z): [M+H]+ calcd for $C_{22}H_{21}F_2N_5O_4$: 458.2; found: 458.1.

Example 111: N-(6-(3-cyano-4-(((3R,4R)-3-fluoro-1-(2-hydroxyacetyl)piperidin-4-yl)oxy)phenyl)pyrimidin-4-yl)cyclopropanecarboxamide

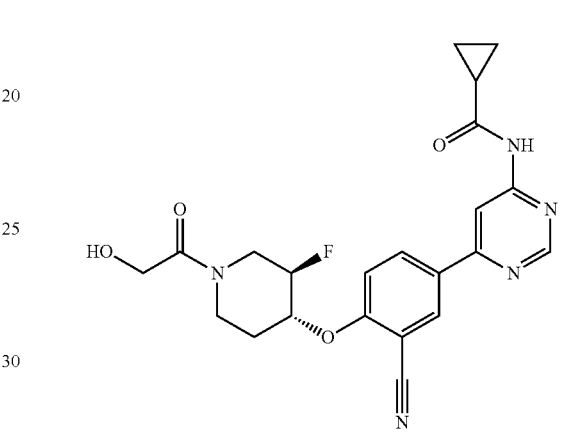

The title compound was prepared following a similar procedure to Example 27 using tert-butyl (3R,4R)-3-fluoro-4-hydroxypiperidine-1-carboxylate and 2-hydroxyacetic acid. LCMS-ESI+ (m/z): [M+H]+ calcd for $C_{22}H_{22}FN_5O_4$: 440.2; found: 440.2.

Example 112: N-(6-(3-cyano-4-(((2S,4S)-1-(2-hydroxyacetyl)-2-methylpiperidin-4-yl)oxy)phenyl)pyrimidin-4-yl)cyclopropanecarboxamide

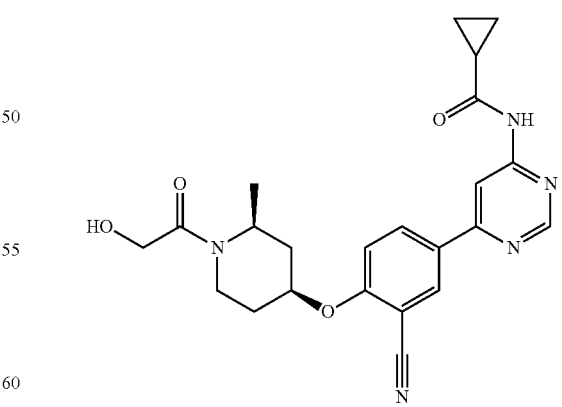

The title compound was prepared following a similar procedure to Example 27 using tert-butyl (2S,4S)-4-hydroxy-2-methylpiperidine-1-carboxylate and 2-hydroxyacetic acid. LCMS-ESI+ (m/z): [M+H]+ calcd for $C_{23}H_{25}N_5O_4$: 436.2; found: 436.1.

Example 113: (1R,2R)—N-(6-(3-cyano-4-(((S)-3,3-difluoro-1-(2-hydroxyacetyl)piperidin-4-yl)oxy)phenyl)pyrimidin-4-yl)-2-(6-methoxypyridin-3-yl)cyclopropane-1-carboxamide

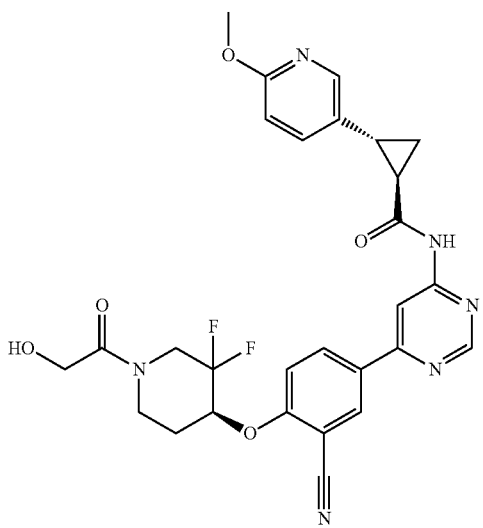 [SMILES: COc1ccc([C@@H]2C[C@H]2C(=O)Nc2cc(-c3ccc(O[C@H]4CCN(C(=O)CO)CC4(F)F)c(C#N)c3)ncn2)cn1]

Step 1: Preparation of ethyl (E)-3-(6-methoxypyridin-3-yl)acrylate: To a stirred solution of ethyl 2-(diethoxyphosphoryl)acetate (1634 mgs, 7.29 mmol) at 0° C. was added sodium hydride 60% suspension in mineral oil (291 mg, 7.29 mmol) in portions over a period of 30 min, followed by the addition of 6-methoxynicotinaldehyde (1000 mg, 7.29 mmol). The resulting mixture was stirred at 0° C. for 1 h and then at ambient temperature for 18 h. The solution was diluted with EtOAc and water. Organic phase was separated, washed with water, dried over MgSO4, filtered, and concentrated in vacuo. The residue was purified by normal phase chromatography eluting with 1:1 hexane:ethyl acetate to give the title compound.

Step 2: Preparation of ethyl (1R,2R)-2-(6-methoxypyridin-3-yl)cyclopropane-1-carboxylate: A Suspension of sodium hydride 60% suspension in mineral oil (218 mgs, 5.45 mmol) on DMSO was added Trimethylsulfoxonium iodide (1200 mgs, 5.45 mmol). The mixture was stirred at room temperature for 40 minutes and then ethyl (E)-3-(6-methoxypyridin-3-yl) acrylate (1130 mgs, 5.43 mmol) was added in portions. Reaction mixture was stirred at room temperature for 10 min. The solution was diluted with EtOAc and water. Organic phase was separated, washed with water, dried over MgSO4, filtered, and concentrated in vacuo. The residue was purified by normal phase chromatography eluting with 1:1 hexane:ethyl acetate to give the title compound.

Step 3: (1R,2R)-2-(6-methoxypyridin-3-yl)cyclopropane-1-carboxylic acid: ethyl (1R,2R)-2-(6-methoxypyridin-3-yl)cyclopropane-1-carboxylate (1130 mg, 5.10 mmol) was dissolved in ethanol (6 mL) and then treated with lithium hydroxide (2M solution in water). Reaction mixture was stirred at room temperature for 2 h and then concentrated. Solids were suspended on ethyl acetate and then acidified to reach a pH~2.5 with 1N HCl aqueous solution. The organic layer was extracted, dried over MgSO4 and concentrated to give the title compound.

Step 4: Preparation of (1R,2R)-2-(6-methoxypyridin-3-yl)cyclopropane-1-carbonyl chloride: To a solution of (1R,2R)-2-(6-methoxypyridin-3-yl)cyclopropane-1-carboxylic acid (150 mg, 0.75 mmol) in dichloromethane (6 ml) was cooled down to 0° C. in an ice-bath. Oxalyl chloride (0.22 ml, 2.58 mmol) was added and then DMF (0.1 ml) under nitrogen atmosphere. The reaction mixture was stirred for 30 minutes at 0° C. and then at room temperature for 30 min. The excessive solvent was removed on ratovapor and dried under high vacuum for 2 hrs to yield the title compound.

Step 5: Preparation of tert-butyl (S)-4-(2-cyano-4-(6-((1R,2R)-2-(6-methoxypyridin-3-yl)cyclopropane-1-carboxamido)pyrimidin-4-yl)phenoxy)-3,3-difluoropiperidine-1-carboxylate. To a solution of the tert-butyl (S)-4-(4-(6-aminopyrimidin-4-yl)-2-cyanophenoxy)-3,3-difluoropiperidine-1-carboxylate (150 mgs, 0.34 mmol) in 1,4-dioxane (5 mL) was added TEA (0.69 mmol, 1.0 equiv), followed by (1R,2R)-2-(6-methoxypyridin-3-yl)cyclopropane-1-carbonyl chloride (147 mgs, 0.69 mmol). Mixture was stirred at 80° C. until no starting material was visible by TLC. Upon completion, reaction mixture was cooled down to room temperature and a 7N solution of ammonia in methanol was added under stirring conditions. Mixture was separated between ethyl acetate and water and the combined organics were washed with water and brine. Organic phase was dried over MgSO4 and evaporated under reduced pressure to yield the title compound.

Step 6: Preparation of (1R,2R)—N-(6-(3-cyano-4-(((S)-3,3-difluoro-1-(2-hydroxyacetyl)piperidin-4-yl)oxy)phenyl)pyrimidin-4-yl)-2-(6-methoxypyridin-3-yl)cyclopropane-1-carboxamide: The title compound was prepared following a similar procedure to Example 27 using tert-butyl (S)-3,3-difluoro-4-hydroxypiperidine-1-carboxylate and 2-hydroxyacetic acid. 1H NMR (400 MHz, DMSO-d6) δ 11.3 (s, 1H), 8.93 (d, J=1.2 Hz, 1H), 8.56 (d, J=1.2 Hz, 1H), 8.41 (d, J=2.3 Hz, 1H), 8.35 (dd, J=9.0, 2.3 Hz, 1H), 8.07 (d, J=2.5 Hz, 1H), 7.63 (d, J=9.1 Hz, 1H), 7.48 (dd, J=8.6, 2.5 Hz, 1H), 6.76 (d, J=8.5 Hz, 1H), 5.35 (s, 1H), 4.85 (s, 1H), 4.23-3.93 (m, 3H), 3.80 (s, 4H), 3.48 (s, 1H), 2.37-2.30 (m, 1H), 2.05 (d, J=63.7 Hz, 3H), 1.59-1.37 (m, 2H), 1.22-1.16 (m, 1H). LCMS-ESI+ (m/z): [M+H]+ calcd for $C_{28}H_{26}F_2N_6O_5$: 565.2; found: 565.2.

Example 114: (1R,2R)—N-(6-(3-cyano-4-(((S)-3,3-difluoro-1-(2-hydroxyacetyl)piperidin-4-yl)oxy)phenyl)pyrimidin-4-yl)-2-(1-methyl-1H-imidazol-2-yl)cyclopropane-1-carboxamide

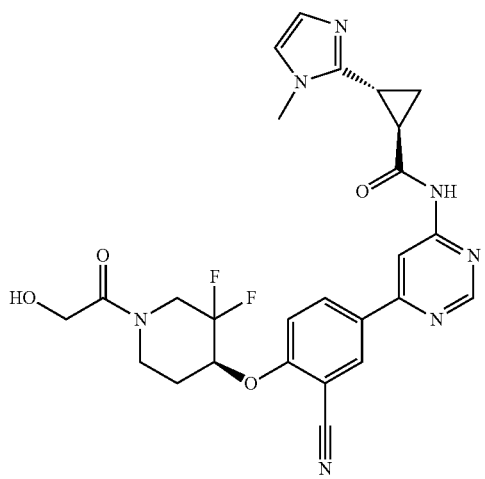 [SMILES: Cn1ccnc1[C@@H]1C[C@H]1C(=O)Nc1cc(-c2ccc(O[C@H]3CCN(C(=O)CO)CC3(F)F)c(C#N)c2)ncn1]

The title compound was prepared following a similar procedure to Example 113 using 1-methyl-1H-imidazole-2-carbaldehyde instead of 6-methoxynicotinaldehyde. LCMS-ESI+ (m/z): [M+H]+ calcd for $C_{26}H_{25}F_2N_7O_4$: 538.2; found: 538.2.

Example 115: (1R,2R)—N-(4-(3-cyano-4-(((S)-3,3-difluoro-1-(2-hydroxyacetyl)piperidin-4-yl)oxy)phenyl)pyridin-2-yl)-2-(6-cyclopropylpyridin-3-yl)cyclopropane-1-carboxamide

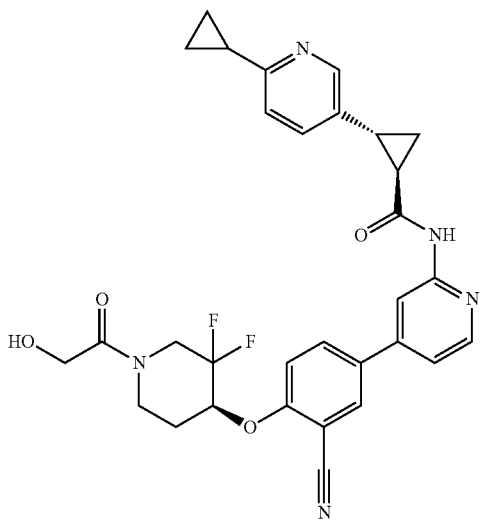 [SMILES: N#Cc1cc(-c2ccnc(NC(=O)[C@@H]3C[C@H]3c3ccc(C4CC4)nc3)c2)ccc1O[C@H]1CCN(C(=O)CO)CC1(F)F]

Step 1: Preparation of tert-butyl (S)-4-(4-(2-((1R,2R)-2-(6-bromopyridin-3-yl)cyclopropane-1-carboxamido)pyridin-4-yl)-2-cyanophenoxy)-3,3-difluoropiperidine-1-carboxylate: The title compound was prepared following a similar procedure to Example 27 using 6-bromonicotinaldehyde.

Step 2: Preparation of tert-butyl(S)-4-(2-cyano-4-(2-((1R,2R)-2-(6-cyclopropylpyridin-3-yl)cyclopropane-1-carboxamido)pyridin-4-yl)phenoxy)-3,3-difluoropiperidine-1-carboxylate: Tert-butyl (S)-4-(4-(2-((1R,2R)-2-(6-bromopyridin-3-yl)cyclopropane-1-carboxamido)pyridin-4-yl)-2-cyanophenoxy)-3,3-difluoropiperidine-1-carboxylate (50 mgs, 0.076 mmol), cyclopropyl-boronic acid (10 mgs, 0.115 mmol), and tricyclohexylphosphine (21 mgs, 0.076 mmol), were dissolved in toluene (5 ml) under stirring conditions. A solution of potassium phosphate (56 mg, 0.26 mmol) in water (1 ml) was added, followed by palladium(II) acetate (1 mg, 0.004 mmol). The reaction mixture was refluxed gently under nitrogen atmosphere for 24 h. Reaction mixture was evaporated under reduced pressure and solids used for next step.

Step 3: Preparation of (1R,2R)—N-(4-(3-cyano-4-(((S)-3,3-difluoro-1-(2-hydroxyacetyl)piperidin-4-yl)oxy)phenyl)pyridin-2-yl)-2-(6-cyclopropylpyridin-3-yl)cyclopropane-1-carboxamide: The title compound was prepared following a similar procedure to Example 27 using tert-butyl (S)-3,3-difluoro-4-hydroxypiperidine-1-carboxylate and 2-hydroxyacetic acid. $^1$H NMR (400 MHz, Methanol-$d_4$) δ 8.37-8.31 (m, 1H), 8.25 (d, J=2.2 Hz, 1H), 8.09 (d, J=2.3 Hz, 1H), 8.03 (dd, J=8.9, 2.4 Hz, 1H), 7.75 (s, 1H), 7.55-7.42 (m, 2H), 7.39 (dd, J=5.3, 1.8 Hz, 1H), 7.15 (d, J=8.2 Hz, 1H), 5.15 (dd, J=9.7, 4.8 Hz, 1H), 4.31 (d, J=3.7 Hz, 2H), 4.09-3.77 (m, 2H), 3.68-3.60 (m, 2H), 2.74-2.43 (m, 2H), 2.33-1.99 (m, 4H), 1.67 (dt, J=9.4, 4.9 Hz, 1H), 1.47-1.21 (m, 2H), 1.11-0.96 (m, 2H). LCMS-ESI+ (m/z): [M+H]+ calcd for $C_{31}H_{29}F_2N_5O_4$: 574.2; found: 574.2.

Example 116: (1,2-Trans)-2-cyano-N-(4-(3-cyano-4-((tetrahydro-2H-pyran-4-yl)oxy)phenyl)pyridin-2-yl)cyclopropane-1-carboxamide

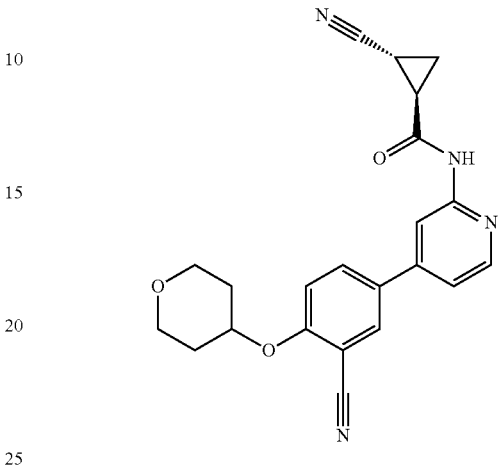

To a solution of 5-(2-aminopyridin-4-yl)-2-((tetrahydro-2H-pyran-4-yl)oxy)benzonitrile (75 mg, 0.25 mmol), trans-2-cyanocyclopropane-1-carboxylic acid (42 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the title compound. LCMS-ESI+ (m/z): [M+H]+ calcd for $C_{22}H_{20}N_4O_3$: 389.2; found: 389.1.

Example 117: N-(4-(3-Cyano-4-((tetrahydro-2H-pyran-4-yl)oxy)phenyl)pyridin-2-yl)-5-oxaspiro[2.4]heptane-1-carboxamide

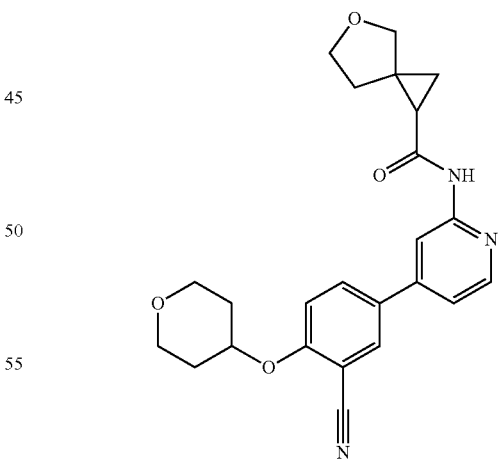

To a solution of 5-(2-aminopyridin-4-yl)-2-((tetrahydro-2H-pyran-4-yl)oxy)benzonitrile (75 mg, 0.25 mmol), 5-oxaspiro[2.4]heptane-1-carboxylic acid (42 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the title compound. LCMS-ESI$^+$ (m/z): [M+H]$^+$ calcd for $C_{24}H_{25}N_3O_4$: 420.2; found: 420.1.

Example 118: (1R,5S,6R)—N-(4-(3-cyano-4-((tetrahydro-2H-pyran-4-yl)oxy)phenyl)pyridin-2-yl)-3-oxabicyclo[3.1.0]hexane-6-carboxamide

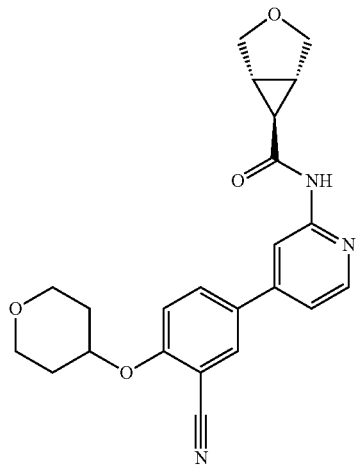 [SMILES: N#Cc1cc(-c2ccnc(NC(=O)[C@H]3[C@@H]4COC[C@@H]43)c2)ccc1OC1CCOCC1]

To a solution of 5-(2-aminopyridin-4-yl)-2-((tetrahydro-2H-pyran-4-yl)oxy)benzonitrile (75 mg, 0.25 mmol), (1R,5S,6R)-3-oxabicyclo[3.1.0]hexane-6-carboxylic acid-trans (49 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by preparative HPLC to give the title compound. LCMS-ESI$^+$ (m/z): [M+H]$^+$ calcd for $C_{23}H_{23}N_3O_4$: 406.2; found: 406.2.

Example 119: (1,2-Trans)-N-(4-(3-cyano-4-((tetrahydro-2H-pyran-4-yl)oxy)phenyl)pyridin-2-yl)-2-(3-fluorophenyl)cyclopropane-1-carboxamide

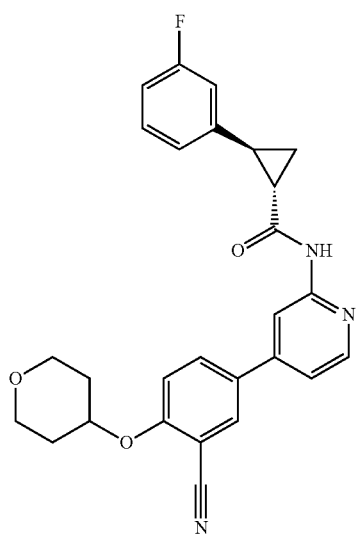 [SMILES: N#Cc1cc(-c2ccnc(NC(=O)[C@H]3C[C@@H]3c3cccc(F)c3)c2)ccc1OC1CCOCC1]

To a solution of 5-(2-aminopyridin-4-yl)-2-((tetrahydro-2H-pyran-4-yl)oxy)benzonitrile (75 mg, 0.25 mmol), trans-2-(3-fluorophenyl)cyclopropane-1-carboxylic acid (62 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the title compound. LCMS-ESI$^+$ (m/z): [M+H]$^+$ calcd for $C_{27}H_{24}FN_3O_3$: 458.2; found: 458.2.

Example 120: (1,2-Trans)-N-(4-(3-cyano-4-((tetrahydro-2H-pyran-4-yl)oxy)phenyl)pyridin-2-yl)-2-(1-methyl-1H-pyrazol-4-yl)cyclopropane-1-carboxamide

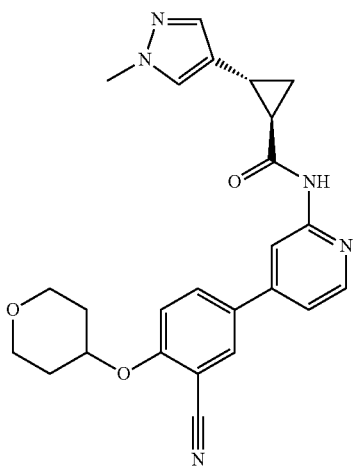 [SMILES: Cn1cc([C@@H]2C[C@H]2C(=O)Nc2cc(-c3ccc(OC4CCOCC4)c(C#N)c3)ccn2)cn1]

To a solution of 5-(2-aminopyridin-4-yl)-2-((tetrahydro-2H-pyran-4-yl)oxy)benzonitrile (75 mg, 0.25 mmol), trans-2-(1-methyl-1H-pyrazol-4-yl)cyclopropane-1-carboxylic acid (94 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the title compound. 1H NMR (400 MHz, DMSO-d$_6$) δ 11.00 (s, 1H), 8.35 (d, 1H), 8.28 (d, 1H), 8.12 (d, 1H), 7.98 (dd, 1H), 7.54 (s, 1H), 7.53-7.40 (m, 2H), 7.28 (d, 1H), 4.90 (m, 1H), 3.85 (m, 2H), 3.75 (s, 3H), 3.53 (m, 2H), 2.28-2.09 (m, 2H), 2.09-1.93 (m, 2H), 1.67 (m, 2H), 1.44-1.32 (m, 1H), 1.20 (m, 1H). LCMS-ESI$^+$ (m/z): [M+H]$^+$ calcd for $C_{25}H_{25}N_5O_3$: 444.2; found: 444.2.

Example 121: (1R,2R)—N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide

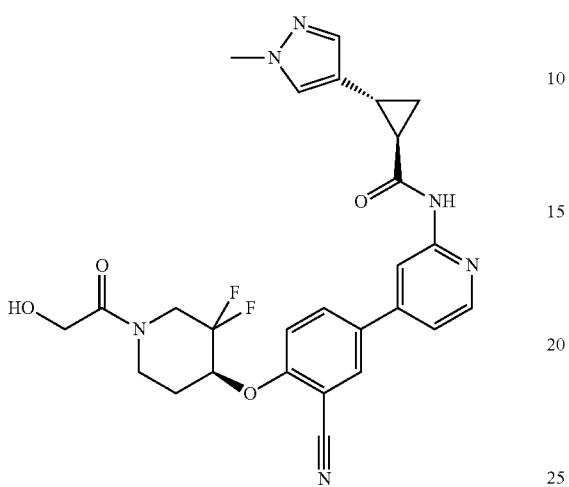

The title compound was prepared by chiral separation of (1,2-trans)-N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide and stereochemistry was tentatively assigned as 1R,2R. 1H NMR (400 MHz, Methanol-$d_4$) δ 8.35 (d, 1H), 8.15 (d, 1H), 8.11-8.00 (m, 2H), 7.56 (dd, 2H), 7.49 (s, 1H), 7.36 (s, 1H), 5.18 (dd, 1H), 4.31 (d, 2H), 3.97 (dd, 1H), 3.83 (s, 3H), 3.63 (t, 2H), 2.44 (m, 1H), 2.15 (d, 2H), 2.04 (m, 1H), 1.63 (m 1H), 1.43-1.20 (m, 2H). LCMS-ESI$^+$ (m/z): [M+H]$^+$ calcd for $C_{27}H_{26}F_2N_6O_4$: 537.2; found: 537.2.

Example 122: (1S, 2S)—N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide

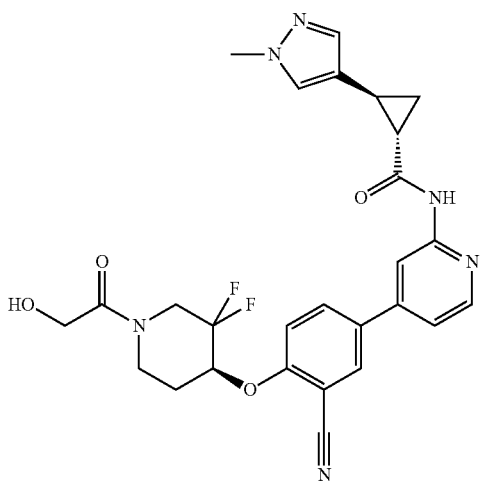 [SMILES: Cn1cc([C@H]2C[C@@H]2C(=O)Nc2cc(-c3ccc(O[C@H]4CCN(C(=O)CO)CC4(F)F)c(C#N)c3)ccn2)cn1]

The title compound was prepared by chiral separation of (1,2-trans)-N-(4-(3-cyano-4-(((S)-3,3-difluoro-1-(2-hydroxyacetyl)piperidin-4-yl)oxy)phenyl)pyridin-2-yl)-2-(1-methyl-1H-pyrazol-4-yl)cyclopropane-1-carboxamide and stereochemistry was tentatively assigned as 1S,2S. 1H NMR (400 MHz, Methanol-$d_4$) δ 8.40-8.26 (m, 2H), 8.09 (d, 1H), 8.03 (dd, 1H), 7.54-7.46 (m, 2H), 7.45-7.39 (m, 1H), 7.35 (s, 1H), 5.15 (dd, 1H), 4.31 (s, 2H), 4.11-3.90 (m, 1H), 3.83 (s, 3H), 3.63 (s, 2H), 2.37 (m, 1H), 2.25-1.98 (m, 3H), 1.56 (m, 1H), 1.27 (m, 2H). LCMS-ESI$^+$ (m/z): [M+H]$^+$ calcd for $C_{27}H_{26}F_2N_6O_4$: 537.2; found: 537.2.

Example 123: (1,2-Trans)-N-(4-(3-cyano-4-((tetrahydro-2H-pyran-4-yl)oxy)phenyl)pyridin-2-yl)-2-(thiazol-4-yl)cyclopropane-1-carboxamide

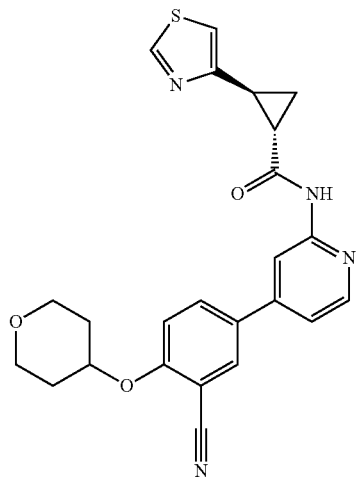 [SMILES: N#Cc1cc(-c2ccnc(NC(=O)[C@H]3C[C@@H]3c3cscn3)c2)ccc1OC1CCOCC1]

Step 1: (1,2-Trans)-2-(thiazol-4-yl)cyclopropane-1-carboxylic acid: To a solution of 4-bromothiazole (58 mg, 0.35 mmol) in toluene (8 mL) was added methyl (1R,2R-rel)-2-(4,4,5,5-tetramethyl-1,3,2-dioxaborolan-2-yl)cyclopropane-1-carboxylate (79 mg, 0.35 mmol), Pd(dba)$_2$ (17.5 mg), butyldi-1-adamantylphosphine (25 mg) and Cs$_2$CO$_3$ (342 mg, 1.1 mmol). The resulting mixture was stirred at 90° C. for 9 h, cooled to room temperature, filtered through a fritted pad of Celite diatomaceous earth, eluting with CH$_2$Cl$_2$, and concentrated in vacuo. The residue was purified by silica gel column chromatography with 0-5% MeOH in CH$_2$Cl$_2$ to give a compound. To a solution of this compound in MeOH (0.5 mL) was added 2 N NaOH (0.4 mL) slowly. The reaction solution was stirred at room temperature for 2 h then diluted with H$_2$O (2 mL). After extraction with ether, the aqueous layer was acidified with 2 N HCl. The resulting solution was concentrated to dryness and the crude product was used for next step without further purification.

Step 2: (1,2-Trans)-N-(4-(3-cyano-4-((tetrahydro-2H-pyran-4-yl)oxy)phenyl)pyridin-2-yl)-2-(thiazol-4-yl)cyclopropane-1-carboxamide: To a solution of 5-(2-aminopyridin-4-yl)-2-((tetrahydro-2H-pyran-4-yl)oxy)benzonitrile (43 mg, 0.15 mmol), trans-2-(thiazol-4-yl)cyclopropane-1-carboxylic acid (20 mg) and HATU (111 mgs, 0.29 mmol) in anhydrous DMF (1.2 mL) was added DIPEA (56 mg, 0.44 mmol). The mixture was stirred at 110° C. in a microwave reactor for 1 h. After being cooled to room temperature, the mixture was filtered. The filtrate was purified by prep-HPLC to give the title compound. LCMS-ESI$^+$ (m/z): [M+H]$^+$ calcd for $C_{24}H_{22}N_4O_3S$: 447.1; found: 447.0.

Example 124: (1R,5S,6R-rel)-N-(4-(3-cyano-4-((tetrahydro-2H-pyran-4-yl)oxy)phenyl)pyridin-2-yl)-3-azabicyclo[3.1.0]hexane-6-carboxamide

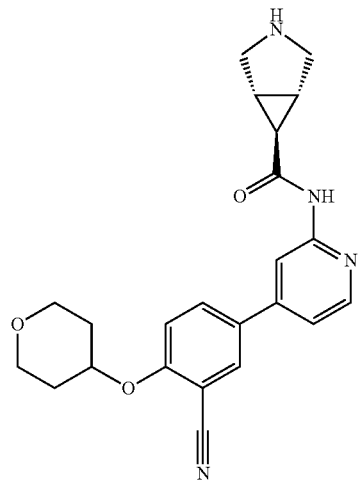 [SMILES: N#Cc1cc(-c2ccnc(NC(=O)[C@H]3[C@@H]4CNC[C@@H]43)c2)ccc1OC1CCOCC1]

Step 1: tert-Butyl (1R,5S,6R-rel)-6-((4-(3-cyano-4-((tetrahydro-2H-pyran-4-yl)oxy)phenyl)pyridin-2-yl)carbamoyl)-3-azabicyclo[3.1.0]hexane-3-carboxylate: To a solution of 5-(2-aminopyridin-4-yl)-2-((tetrahydro-2H-pyran-4-yl)oxy)benzonitrile (75 mg, 0.25 mmol), (1R,5S,6R-rel)-3-(tert-butoxycarbonyl)-3-azabicyclo[3.1.0]hexane-6-carboxylic acid (87 mg, 0.38 mmol) and HATU (194 mg, 0.51 mmol) in anhydrous DMF (2 mL) was added DIPEA (99 mg, 0.76 mmol). The mixture was stirred at 110° C. in a microwave reactor for 1 h. After being cooled to room temperature, the mixture was diluted with water and extracted with $CH_2Cl_2$. The organic layer was separated, washed with water, dried over $Na_2SO_4$ and concentrated. The residue was purified by prep-HPLC to give the product.

Step 2: (1R,5S,6R-rel)-N-(4-(3-cyano-4-((tetrahydro-2H-pyran-4-yl)oxy)phenyl)pyridin-2-yl)-3-azabicyclo[3.1.0]hexane-6-carboxamide: tert-Butyl (1R,5S,6r-rel)-6-((4-(3-cyano-4-((tetrahydro-2H-pyran-4-yl)oxy)phenyl)pyridin-2-yl)carbamoyl)-3-azabicyclo[3.1.0]hexane-3-carboxylate (70 mg, 0.14 mmol) was diluted with a mixture of DCM (2 mL) and TFA (0.5 mL), mixture stirred at room temperature for 1 h. The reaction mixture was evaporated under reduced pressure. The product was purified by pre-HPLC to give the title compound. LCMS-ESI$^+$ (m/z): [M+H]$^+$ calcd for $C_{23}H_{24}N_4O_3$: 405.2; found: 405.2.

Example 125: (1R,2R)—N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide

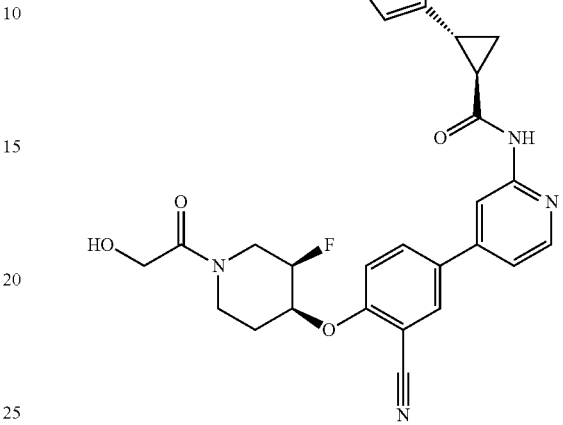

The title compound was prepared by chiral separation of (1,2-trans)-N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide and stereochemistry was tentatively assigned as 1R, 2R. 1H NMR (400 MHz, Methanol-$d_4$) δ 8.34 (d, 1H), 8.14 (d, 1H), 8.06 (dd, 1H), 7.97 (s, 1H), 7.72-7.55 (m, 1H), 7.55-7.45 (m, 2H), 7.36 (s, 1H), 5.21-4.91 (m, 2H), 4.43-3.90 (m, 3H), 3.83 (s, 3H), 3.78-3.35 (m, 2H), 2.45 (m, 1H), 2.03 (m, 3H), 1.64 (m, 1H), 1.37 (m, 1H), 1.28 (s, 1H). LCMS-ESI$^+$ (m/z): [M+H]$^+$ calcd for $C_{27}H_{27}FN_6O_4$: 519.2; found: 519.2.

Example 126: (1S,2S)—N-(4-(3-Cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide

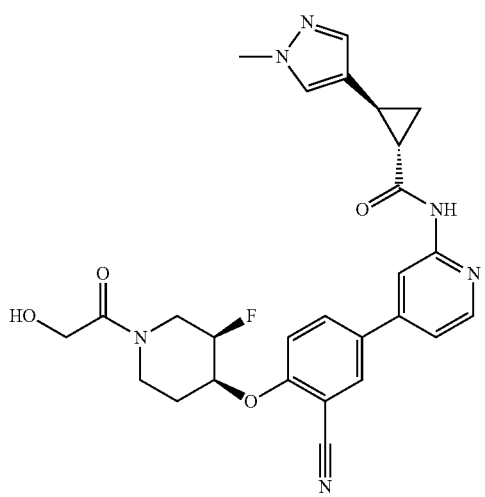 [SMILES: Cn1cc([C@H]2C[C@@H]2C(=O)Nc2cc(-c3ccc(O[C@H]4CCN(C(=O)CO)C[C@H]4F)c(C#N)c3)ccn2)cn1]

The title compound was prepared by chiral separation of (1,2-trans)-N-(4-(3-cyano-4-(((3R,4S)-3-fluoro-1-(2-hydroxyacetyl)piperidin-4-yl)oxy)phenyl)pyridin-2-yl)-2-(1-methyl-1H-pyrazol-4-yl)cyclopropane-1-carboxamide and stereochemistry was tentatively assigned as 1S,2S. 1H NMR (400 MHz, Methanol-d₄) δ 8.34 (d, 1H), 8.23 (s, 1H), 8.08 (d, 1H), 8.01 (dd, 1H), 7.46 (dd, 3H), 7.35 (s, 1H), 5.17-4.90 (m, 2H), 4.45-4.08 (m, 3H), 3.99 (m, 1H), 3.83 (s, 3H), 3.80-3.33 (m, 2H), 2.39 (m, 1H), 2.05 (m, 3H), 1.58 (m, 1H), 1.28 (m, 2H). LCMS-ESI⁺ (m/z): [M+H]⁺ calcd for $C_{27}H_{27}FN_6O_4$: 519.2; found: 519.2.

Example 127: (1, 2-Trans)-2-cyano-N-(4-(3-cyano-4-((tetrahydro-2H-pyran-4-yl)oxy)phenyl)pyridin-2-yl)cyclopropane-1-carboxamide

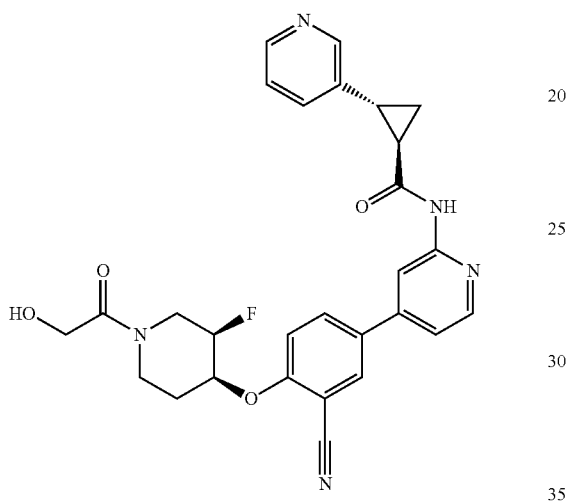

Step 1: (tert-Butyl (3R,4S)-4-(2-cyano-4-(2-((1,2-trans)-2-(1-methyl-1H-pyrazol-4-yl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (120 mg, 0.29 mmol), (1,2-trans)-2-(pyridin-3-yl)cyclopropane-1-carboxylic acid (95 mg, 0.58 mmol) and HATU (243 mg, 0.64 mmol) in anhydrous DMF (4 mL) was added DIPEA (113 mg, 0.87 mmol). The mixture was stirred at 110° C. in a microwave reactor for 1 h. After being cooled to room temperature, the mixture was diluted with water and extracted with CH₂Cl₂. The organic layer was separated, washed with water, dried over Na₂SO₄ and concentrated. The residue was purified by prep-HPLC to give the product.

Step 2: (1,2-Trans)-N-(4-(3-cyano-4-(((3R,4S)-3-fluoropiperidin-4-yl)oxy)phenyl)pyridin-2-yl)-2-(pyridin-3-yl)cyclopropane-1-carboxamide: (tert-Butyl (3R,4S)-4-(2-cyano-4-(2-((1,2-trans)-2-(1-methyl-1H-pyrazol-4-yl)cyclopropane-1-carboxamido)pyridin-4-yl)phenoxy)-3-fluoropiperidine-1-carboxylate (108 mg, 0.19 mmol) was diluted with a mixture of DCM (2 mL) and TFA (0.5 mL), mixture stirred at room temperature for 1 h. The reaction mixture was evaporated under reduced pressure. The product was used for next step.

Step 3: (1,2-Trans)-N-(4-(3-cyano-4-(((3R,4S)-3-fluoropiperidin-4-yl)oxy)phenyl)pyridin-2-yl)-2-(pyridin-3-yl)cyclopropane-1-carboxamide (45 mg, 0.1 mmol), HATU (75 mg, 0.2 mmol), Hünig's base (i.e., N,N-diisopropylethylamine) (38 mg, 0.3 mmol) and glycolic acid (15 mg, 0.2 mmol) were dissolved in DMF (2.5 mL) and stirred at room temperature for 2 hr. The mixture was diluted with water and extracted with CH₂Cl₂. The organic layer was separated, washed with water, dried over Na₂SO₄ and concentrated. The residue was purified by prep-HPLC to give the title compound. 1H NMR (400 MHz, DMSO-d6) δ 10.98 (s, 1H), 8.77 (d, 1H), 8.67 (dd, 1H), 8.37 (d, 2H), 8.17-8.05 (m, 2H), 8.00 (dd, 1H), 7.80 (dd, 1H), 7.57 (d, 1H), 7.47 (dd, 1H), 5.24-4.84 (m, 2H), 4.22-3.82 (m, 3H), 3.74-3.07 (m, 3H), 2.64 (m, 1H), 2.52 (m, 1H), 1.96-1.81 (m, 2H), 1.68-1.52 (m, 2H). LCMS-ESI⁺ (m/z): [M+H]⁺ calcd for $C_{28}H_{26}FN_5O_4$: 516.2; found: 516.2.

Example 128: (1,2-Trans)-N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide

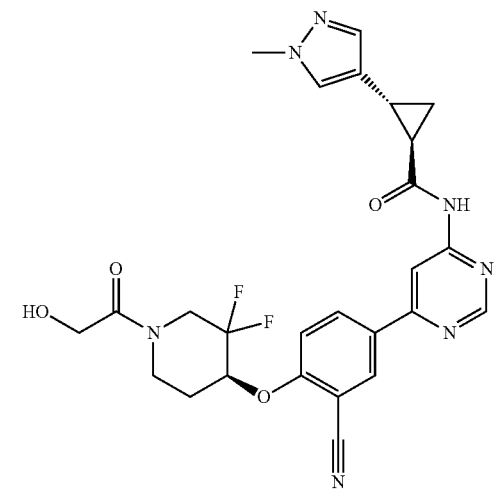 [SMILES: Cn1cc([C@@H]2C[C@H]2C(=O)Nc2cc(-c3ccc(O[C@H]4CCN(C(=O)CO)CC4(F)F)c(C#N)c3)ncn2)cn1]

Step 1: (Tert-Butyl (S)-4-(2-cyano-4-(6-((1,2-trans)-2-(1-methyl-1H-pyrazol-4-yl)cyclopropane-1-carboxamido)pyrimidin-4-yl)phenoxy)-3,3-difluoropiperidine-1-carboxylate: To tert-Butyl (S)-3,3-difluoro-4-hydroxypiperidine-1-carboxylate (97 mg, 0.41 mmol) in 2-methyltetrahydrofuran (3 mL) at 0° C. was added potassium tert-butoxide solution (0.47 mL, 1.0 M solution in 2-methyl-2-propanol) and stirred for 45 minutes at 0° C. Then (1,2-trans)-N-(6-(3-cyano-4-fluorophenyl)pyrimidin-4-yl)-2-(1-methyl-1H-pyrazol-4-yl)cyclopropane-1-carboxamide (114 mg, 0.31 mmol) was added and heated at 60° C. for 2 hr. Water was slowly added and the reaction mixture was evaporated under reduced pressure. The residue was purified by prep-HPLC to give the product.

Step 2: (1,2-Trans)-N-(6-(3-cyano-4-(((S)-3,3-difluoropiperidin-4-yl)oxy)phenyl)pyrimidin-4-yl)-2-(1-methyl-1H-pyrazol-4-yl)cyclopropane-1-carboxamide: (tert-Butyl (S)-4-(2-cyano-4-(6-((1,2-trans)-2-(1-methyl-1H-pyrazol-4-yl)cyclopropane-1-carboxamido)pyrimidin-4-yl)phenoxy)-3,3-difluoropiperidine-1-carboxylate (64 mg, 0.11 mmol) was diluted with a mixture of DCM (1.5 mL) and TFA (0.4 mL), mixture stirred at room temperature for 1 h. The reaction mixture was evaporated under reduced pressure. The product was used for next step.

Step 3: (1,2-Trans)-N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide: (1,2-Trans)-N-(6-(3-Cyano-4-(((S)-3,3-difluoropiperidin-4-yl)oxy)phenyl)pyrimidin-4-yl)-2-(1- methyl-1H-pyrazol-4-yl)cyclopropane-1-carboxamide (53 mg, 0.11 mmol), HATU (84 mg, 0.22 mmol), Hünig's base (i.e., N,N-diisopropylethylamine) (43 mg, 0.33 mmol) and glycolic acid (17 mg, 0.22 mmol) were dissolved in DMF (2.5 mL) and stirred at room temperature for 2 hr. The mixture was diluted with water and extracted with $CH_2Cl_2$. The organic layer was separated, washed with water, dried over $Na_2SO_4$ and concentrated. The residue was purified by prep-HPLC to give the product. 1H NMR (400 MHz, DMSO-d6) δ 11.30 (s, 1H), 8.92 (d, 1H), 8.54 (d, 1H), 8.41 (d, 1H), 8.35 (dd, 1H), 7.63 (d, 1H), 7.55 (s, 1H), 7.28 (s, 1H), 5.35 (m, 1H), 4.16-3.80 (m, 4H), 3.75 (s, 3H), 3.53 (m, 2H), 2.32-1.98 (m, 4H), 1.42 (m, 1H), 1.33-1.16 (m, 1H). LCMS-ESI$^+$ (m/z): [M+H]$^+$ calcd for $C_{26}H_{25}F_2N_7O_4$: 538.2; found: 538.1.

Example 129: (1,2-Trans)-N-(6-(3-cyano-4-(((S)-3,3-difluoro-1-(2-hydroxyacetyl)piperidin-4-yl)oxy)phenyl)pyrimidin-4-yl)-2-(pyridin-3-yl)cyclopropane-1-carboxamide

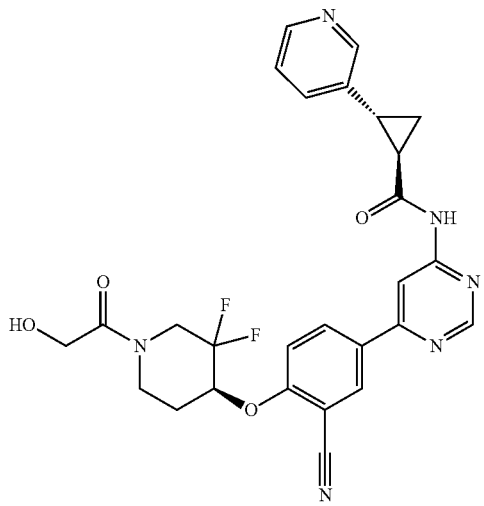 [SMILES: N#Cc1cc(-c2cc(NC(=O)[C@@H]3C[C@H]3c3cccnc3)ncn2)ccc1O[C@H]1CCN(C(=O)CO)CC1(F)F]

Step 1: (tert-Butyl (S)-4-(2-cyano-4-(6-((1,2-trans)-2-(pyridin-3-yl)cyclopropane-1-carboxamido)pyrimidin-4-yl)phenoxy)-3,3-difluoropiperidine-1-carboxylate: To a solution of tert-butyl (S)-4-(4-(6-aminopyrimidin-4-yl)-2-cyanophenoxy)-3,3-difluoropiperidine-1-carboxylate (85 mg, 0.2 mmol) in 1,4-dioxane (5 mL) was added triethylamine (0.1 mL, 0.65 mmol), followed by (1,2-trans)-2-(pyridin-3-yl)cyclopropane-1-carbonyl chloride (100 mg, 0.6 mmol) and the mixture was stirred at reflux overnight. The reaction mixture was separated between $CH_2Cl_2$ and water. The aqueous layer was further extracted with $CH_2Cl_2$, and the combined organics were washed with water and brine. After drying over $Na_2SO_4$ and evaporation under reduced pressure, the residue was purified by prep-HPLC to give the product. Step 2: (1,2-Trans)-N-(6-(3-cyano-4-(((S)-3,3-difluoropiperidin-4-yl)oxy)phenyl)pyrimidin-4-yl)-2-(pyridin-3-yl)cyclopropane-1-carboxamide: (tert-Butyl (S)-4-(2-cyano-4-(6-((1,2-trans)-2-(pyridin-3-yl)cyclopropane-1-carboxamido)pyrimidin-4-yl)phenoxy)-3,3-difluoropiperidine-1-carboxylate (45 mg, 0.08 mmol) was treated with a mixture of DCM (1.5 mL) and TFA (0.4 mL), mixture stirred at room temperature for 1 h. The reaction mixture was evaporated under reduced pressure. The product was used for next step.

Step 3: (1,2-Trans)-N-(6-(3-cyano-4-(((S)-3,3-difluoro-1-(2-hydroxyacetyl)piperidin-4-yl)oxy)phenyl)pyrimidin-4-yl)-2-(pyridin-3-yl)cyclopropane-1-carboxamide: (1,2-Trans)-N-(6-(3-cyano-4-(((S)-3,3-difluoropiperidin-4-yl)oxy)phenyl)pyrimidin-4-yl)-2-(pyridin-3-yl)cyclopropane-1-carboxamide (20 mg, 0.04 mmol), HATU (32 mg, 0.08 mmol), DIPEA (17 mg, 0.33 mmol) and glycolic acid (7 mg, 0.08 mmol) were dissolved in DMF (1.2 mL) and stirred at room temperature for 2 hr. The mixture was filtered and the filtrate was purified by prep-HPLC to give the title compound. 1H NMR (400 MHz, Methanol-d4) δ 8.78 (d, 1H), 8.62 (s, 1H), 8.53 (d, 1H), 8.38-8.32 (m, 1H), 8.29 (m, 1H), 8.16-7.95 (m, 1H), 7.71 (dd, 1H), 7.44 (d, 1H), 5.10 (dd, 1H), 4.34-4.07 (m, 2H), 4.02-3.68 (m, 2H), 3.67-3.43 (m, 2H), 2.69 (m, 1H), 2.32 (m, 1H), 2.06 (m, 2H), 1.75 (m, 1H), 1.54 (m, 1H), 1.36-1.06 (m, 1H). LCMS-ESI$^+$ (m/z): [M+H]$^+$ calcd for $C_{27}H_{24}F_2N_6O_4$: 535.2; found: 535.2.

Example 130: (1,2-Trans)-N-(4-(3-cyano-4-(((3R,4S)-1-((S)-2,3-dihydroxypropanoyl)-3-fluoropiperidin-4-yl)oxy)phenyl)pyridin-2-yl)-2-(1-methyl-1H-pyrazol-4-yl)cyclopropane-1-carboxamide

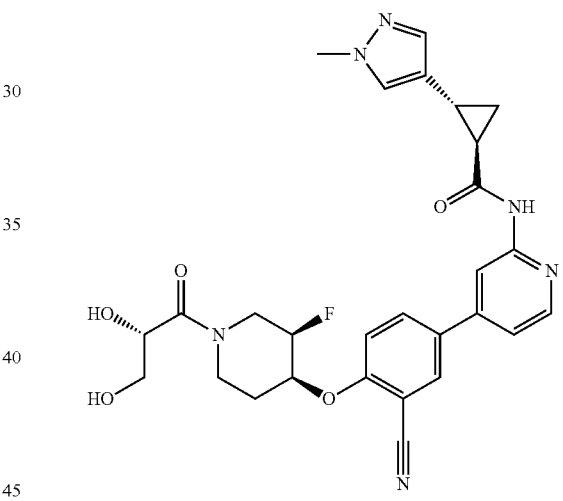

(1,2-Trans)-N-(4-(3-cyano-4-(((3R,4S)-3-fluoropiperidin-4-yl)oxy)phenyl)pyridin-2-yl)-2-(1-methyl-1H-pyrazol-4-yl)cyclopropane-1-carboxamide (50 mg, 0.1 mmol), HATU (83 mg, 0.21 mmol), DIPEA (43 mg, 0.3 mmol) and (S)-2,3-dihydroxypropanoic acid (23 mg, 0.15 mmol) were dissolved in DMF (3 mL) and stirred at room temperature for 16 hr. The mixture was diluted with water and extracted with $CH_2Cl_2$. The organic layer was separated, washed with water, dried over $Na_2SO_4$ and concentrated. The residue was purified by prep-HPLC to give the product. 1H NMR (400 MHz, Methanol-d4) δ 8.36 (dd, 1H), 8.26 (d, 1H), 8.15 (dd, 1H), 7.89 (dd, 1H), 7.63 (s, 1H), 7.61-7.54 (m, 2H), 7.51 (d, 1H), 5.27-4.96 (m, 1H), 4.73-4.39 (m, 2H), 4.36-3.90 (m, 3H), 3.88 (s, 3H), 3.83-3.55 (m, 3H), 2.51 (m, 1H), 2.19-2.01 (m, 3H), 1.85-1.69 (m, 1H), 1.60-1.44 (m, 1H). LCMS-ESI$^+$ (m/z): [M+H]$^+$ calcd for $C_{28}H_{29}FN_6O_5$: 549.2; found: 549.2.

Example 131: (1,2-Trans)-N-(4-(3-cyano-4-(((S)-1-((S)-2,3-dihydroxypropanoyl)-3,3-difluoropiperidin-4-yl)oxy)phenyl)pyridin-2-yl)-2-(1-methyl-1H-pyrazol-4-yl)cyclopropane-1-carboxamide

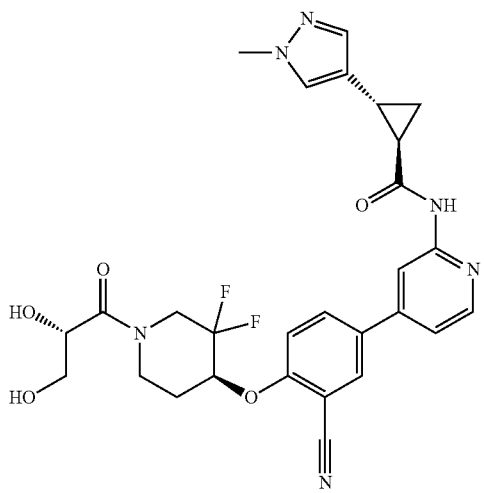 [SMILES: Cn1cc([C@@H]2C[C@H]2C(=O)Nc2cc(-c3ccc(O[C@H]4CCN(C(=O)[C@@H](O)CO)CC4(F)F)c(C#N)c3)ccn2)cn1]

(1,2-Trans)-N-(4-(3-cyano-4-(((S)-3,3-difluoropiperidin-4-yl)oxy)phenyl)pyridin-2-yl)-2-(1-methyl-1H-pyrazol-4-yl)cyclopropane-1-carboxamide (45 mg, 0.09 mmol), HATU (72 mg, 0.19 mmol), DIPEA (36 mg, 0.28 mmol) and (S)-2,3-dihydroxypropanoic acid (20 mg, 0.19 mmol) were dissolved in DMF (3 mL) and stirred at room temperature for 16 hr. The mixture was filtered and the residue was purified by prep-HPLC to give the product. 1H NMR (400 MHz, Methanol-d4) δ 8.37 (d, 1H), 8.28 (m, 1H), 8.17 (dd, 1H), 7.89 (dd, 1H), 7.74-7.55 (m, 4H), 5.24 (m, 1H), 4.56 (m, 2H), 4.44-3.97 (m, 4H), 3.93 (s, 3H), 3.86-3.57 (m, 2H), 2.57 (m, 1H), 2.36-1.98 (m, 3H), 1.76 (m, 1H), 1.54 (s, 1H). LCMS-ESI+ (m/z): [M+H]+ calcd for $C_{28}H_{28}F_2N_6O_5$: 567.2; found: 567.2.

Example 132: (1,2-Trans)-N-(6-(3-cyano-4-(((S)-1-((S)-2,3-dihydroxypropanoyl)-3,3-difluoropiperidin-4-yl)oxy)phenyl)pyrimidin-4-yl)-2-(1-methyl-1H-pyrazol-4-yl)cyclopropane-1-carboxamide

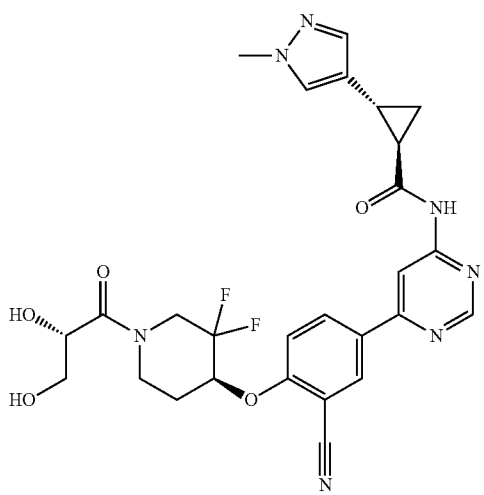 [SMILES: Cn1cc([C@@H]2C[C@H]2C(=O)Nc2cc(-c3ccc(O[C@H]4CCN(C(=O)[C@@H](O)CO)CC4(F)F)c(C#N)c3)ncn2)cn1]

(1,2-Trans)-N-(6-(3-cyano-4-(((S)-3,3-difluoropiperidin-4-yl)oxy)phenyl)pyrimidin-4-yl)-2-(1-methyl-1H-pyrazol-4-yl)cyclopropane-1-carboxamide (36 mg, 0.075 mmol), HATU (57 mg, 0.15 mmol), DIPEA (29 mg, 0.23 mmol) and (S)-2,3-dihydroxypropanoic acid (16 mg, 0.15 mmol) were dissolved in DMF (2.5 mL) and stirred at room temperature for 16 hr. The mixture was filtered and the residue was purified by prep-HPLC to give the product. 1H NMR (400 MHz, Methanol-d4) δ 8.89 (d, 1H), 8.60 (m, 1H), 8.42 (m, 1H), 8.35 (m, 1H), 7.58-7.49 (m, 2H), 7.41 (d, 1H), 5.28-5.08 (m, 1H), 4.56 (m, 1H), 4.32-3.91 (m, 4H), 3.85 (s, 3H), 3.82-3.54 (m, 2H), 2.42 (m, 1H), 2.32-2.01 (m, 3H), 1.61 (m, 1H), 1.32 (m, 1H). LCMS-ESI+ (m/z): [M+H]+ calcd for $C_{27}H_{27}F_2N_7O_5$: 568.2; found: 568.1.

Example 133: (1,2-Trans)-N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide

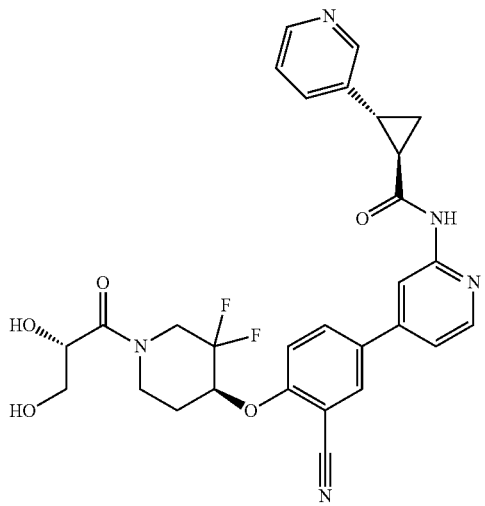 [SMILES: N#Cc1cc(-c2ccnc(NC(=O)[C@@H]3C[C@H]3c3cccnc3)c2)ccc1O[C@H]1CCN(C(=O)[C@@H](O)CO)CC1(F)F]

(1,2-Trans)-N-(4-(3-cyano-4-(((S)-3,3-difluoropiperidin-4-yl)oxy)phenyl)pyridin-2-yl)-2-(pyridin-3-yl)cyclopropane-1-carboxamide (43 mg, 0.09 mmol), HATU (69 mg, 0.18 mmol), DIPEA (35 mg, 0.27 mmol) and (S)-2,3-dihydroxypropanoic acid (19 mg, 0.18 mmol) were dissolved in DMF (2.5 mL) and stirred at room temperature for 16 hr. The mixture was filtered and the residue was purified by prep-HPLC to give the title compound. 1H NMR (400 MHz, Methanol-d4) δ 8.82 (d, 1H), 8.71 (m, 1H), 8.44-8.33 (m, 2H), 8.18 (s, 1H), 8.15 (d, 1H), 8.08 (dd, 1H), 7.98 (dd, 1H), 7.62-7.50 (m, 2H), 5.18 (m, 1H), 4.66-3.45 (m, 7H), 2.94-2.79 (m, 1H), 2.53-2.39 (m, 1H), 2.18 (d, 2H), 1.89 (m, 1H), 1.79-1.63 (m, 1H). LCMS-ESI+ (m/z): [M+H]+ calcd for $C_{29}H_{27}F_2N_5O_5$: 564.2; found: 564.2.

Example 134: (1,2-Trans)-N-(4-(3-cyano-4-(((S)-3,3-difluoro-1-(2-hydroxyacetyl)piperidin-4-yl)oxy)phenyl)pyridin-2-yl)-2-(pyridin-3-yl)cyclopropane-1-carboxamide

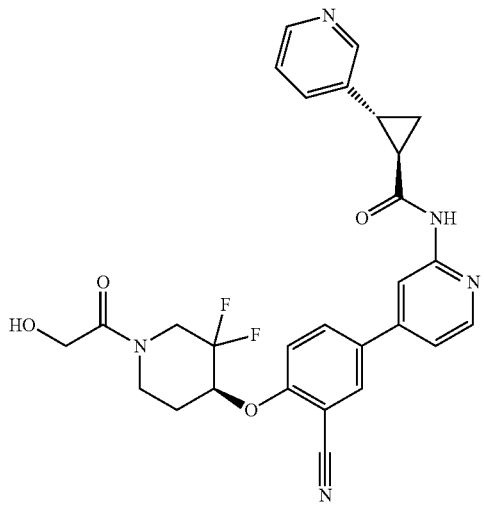

(1,2-Trans)-N-(4-(3-cyano-4-(((S)-3,3-difluoropiperidin-4-yl)oxy)phenyl)pyridin-2-yl)-2-(pyridin-3-yl)cyclopropane-1-carboxamide (43 mg, 0.09 mmol), HATU (69 mg, 0.18 mmol), DIPEA (35 mg, 0.27 mmol) and glycolic acid (19 mg, 0.18 mmol) were dissolved in DMF (2.5 mL) and stirred at room temperature for 16 hr. The mixture was filtered and the residue was purified by prep-HPLC to give the product. 1H NMR (400 MHz, Methanol-d4) δ 8.73 (d, 1H), 8.61 (m, 1H), 8.34-8.23 (m, 2H), 8.06 (m, 2H), 7.98 (dd, 1H), 7.89 (m, 1H), 7.53-7.41 (m, 2H), 5.09 (m, 1H), 4.22 (m, 2H), 4.00-3.70 (m, 2H), 3.61-3.46 (m, 2H), 2.82-2.69 (m, 1H), 2.43-2.29 (m, 1H), 2.06 (m, 2H), 1.80 (m, 1H), 1.62 (m, 1H). LCMS-ESI$^+$ (m/z): [M+H]$^+$ calcd for $C_{28}H_{25}F_2N_5O_4$: 534.2; found: 534.2.

Example 135: (1R,2R)—N-(4-(3-cyano-4-(((3R,4S)-3-fluoro-1-(2-hydroxyacetyl)piperidin-4-yl)oxy)phenyl)pyridin-2-yl)-2-(pyridin-3-yl)cyclopropane-1-carboxamide

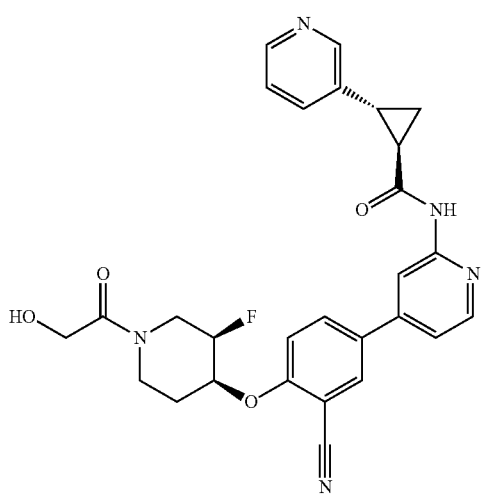 [SMILES: N#Cc1cc(-c2ccnc(NC(=O)[C@@H]3C[C@H]3c3cccnc3)c2)ccc1O[C@H]1CCN(C(=O)CO)C[C@H]1F]

The title compound was prepared by chiral separation of (1,2-trans)-N-(4-(3-cyano-4-(((3R,4S)-3-fluoro-1-(2-hydroxyacetyl)piperidin-4-yl)oxy)phenyl)pyridin-2-yl)-2-(pyridin-3-yl)cyclopropane-1-carboxamide and stereochemistry was tentatively assigned as 1R,2R. 1H NMR (400 MHz, Methanol-d4) δ 8.47 (d, 1H), 8.38 (dd, 2H), 8.35-8.28 (m, 1H), 8.04 (d, 1H), 7.98 (dd, 1H), 7.66 (m, 1H), 7.47-7.33 (m, 3H), 5.15-4.90 (m, 2H), 4.29 (m, 2H), 4.27-3.32 (m, 4H), 2.60 (m, 1H), 2.40-2.25 (m, 1H), 2.24-1.91 (m, 2H), 1.72 (m, 1H), 1.48 (m, 1H). LCMS-ESI$^+$ (m/z): [M+H]$^+$ calcd for $C_{28}H_{26}FN_5O_4$: 516.2; found: 516.2.

Example 136: (1S,2S)—N-(4-(3-cyano-4-(((3R,4S)-3-fluoro-1-(2-hydroxyacetyl)piperidin-4-yl)oxy)phenyl)pyridin-2-yl)-2-(pyridin-3-yl)cyclopropane-1-carboxamide

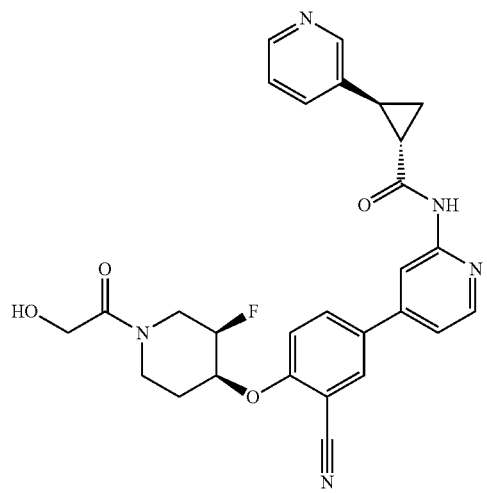 [SMILES: N#Cc1cc(-c2ccnc(NC(=O)[C@H]3C[C@@H]3c3cccnc3)c2)ccc1O[C@H]1CCN(C(=O)CO)C[C@H]1F]

The title compound was prepared by chiral separation of (1,2-trans)-N-(4-(3-cyano-4-(((3R,4S)-3-fluoro-1-(2-hydroxyacetyl)piperidin-4-yl)oxy)phenyl)pyridin-2-yl)-2-(pyridin-3-yl)cyclopropane-1-carboxamide and stereochemistry was tentatively assigned as 1S,2S. 1H NMR (400 MHz, Methanol-d4) δ 8.52-8.43 (m, 1H), 8.43-8.35 (m, 2H), 8.33 (d, 1H), 8.04 (d, 1H), 7.98 (dd, 1H), 7.68 (m, 1H), 7.49-7.32 (m, 3H), 5.16-4.89 (m, 2H), 4.29 (s, 2H), 4.27-3.33 (m, 4H), 2.60 (m, 1H), 2.31 (m, 1H), 2.23-1.93 (m, 2H), 1.72 (m, 1H), 1.48 (m, 1H). LCMS-ESI$^+$ (m/z): [M+H]$^+$ calcd for $C_{28}H_{26}FN_5O_4$: 516.2; found: 516.2.

Example 137: (1R,2R)—N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide

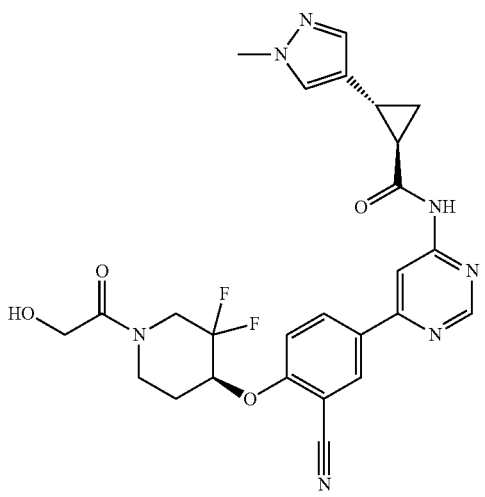 [SMILES: Cn1cc([C@@H]2C[C@H]2C(=O)Nc2cc(-c3ccc(O[C@H]4CCN(C(=O)CO)CC4(F)F)c(C#N)c3)ncn2)cn1]

The title compound was prepared by chiral separation of (1,2-trans)-N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide and stereochemistry was tentatively assigned as 1R,2R. 1H NMR (400 MHz, Methanol-d4) δ 8.84 (d, 1H), 8.56 (d, 1H), 8.39 (d, 1H), 8.33 (dd, 1H), 7.49 (d, 2H), 7.35 (s, 1H), 5.25-5.08 (m, 1H), 4.31 (m, 2H), 4.09-3.85 (m, 2H), 3.83 (s, 3H), 3.63 (m, 2H), 2.39 (m, 1H), 2.25-2.01 (m, 3H), 1.68-1.52 (m, 1H), 1.28 (m, 1H). LCMS-ESI+ (m/z): [M+H]+ calcd for $C_{26}H_{25}F_2N_7O_4$: 538.2.2; found: 538.2.

Example 138: (1S,2S)—N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide

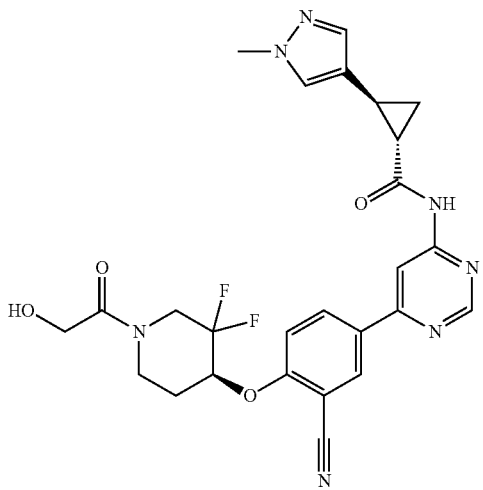 [SMILES: Cn1cc([C@H]2C[C@@H]2C(=O)Nc2cc(-c3ccc(O[C@H]4CCN(C(=O)CO)CC4(F)F)c(C#N)c3)ncn2)cn1]

The title compound was prepared by chiral separation of (1,2-trans)-N-(6-(3-cyano-4-(((S)-3,3-difluoro-1-(2-hydroxyacetyl)piperidin-4-yl)oxy)phenyl)pyrimidin-4-yl)-2-(1-methyl-1H-pyrazol-4-yl)cyclopropane-1-carboxamide and stereochemistry was tentatively assigned as 1S,2S. 1H NMR (400 MHz, Methanol-d4) δ 8.84 (d, 1H), 8.56 (d, 1H), 8.38 (d, 1H), 8.33 (dd, 1H), 7.50 (d, 2H), 7.36 (s, 1H), 5.18 (m, 1H), 4.33 (m, 2H), 4.08-3.86 (m, 2H), 3.83 (s, 3H), 3.63 (m, 2H), 2.40 (m, 1H), 2.25-1.99 (m, 3H), 1.58 (m, 1H), 1.29 (m, 1H). LCMS-ESI+ (m/z): [M+H]+ calcd for $C_{26}H_{25}F_2N_7O_4$: 538.2; found: 538.2.

Example 139: (1R,2R)—N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide

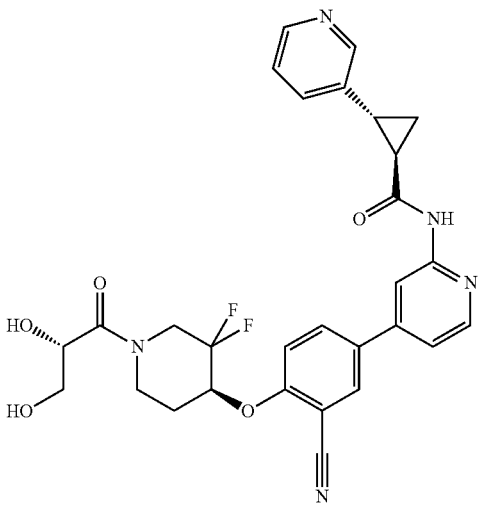 [SMILES: N#Cc1cc(-c2ccnc(NC(=O)[C@@H]3C[C@H]3c3cccnc3)c2)ccc1O[C@H]1CCN(C(=O)[C@@H](O)CO)CC1(F)F]

The title compound was prepared by chiral separation of (1,2-trans)-N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide and stereochemistry was tentatively assigned as 1R,2R. 1H NMR (400 MHz, Methanol-d4) δ 8.37 (s, 1H), 8.29 (d, 2H), 8.25 (d, 1H), 7.98 (d, 1H), 7.93 (dd, 1H), 7.55 (m, 1H), 7.41 (d, 1H), 7.29 (m, 2H), 5.06 (m, 1H), 4.73-3.39 (m, 7H), 2.50 (m, 1H), 2.22 (m, 1H), 2.18-1.95 (m, 2H), 1.63 (m, 1H), 1.38 (m, 1H). LCMS-ESI+ (m/z): [M+H]+ calcd for $C_{29}H_{27}F_2N_5O_5$: 564.2; found: 564.2.

Example 140: (1S, 2S)—N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide

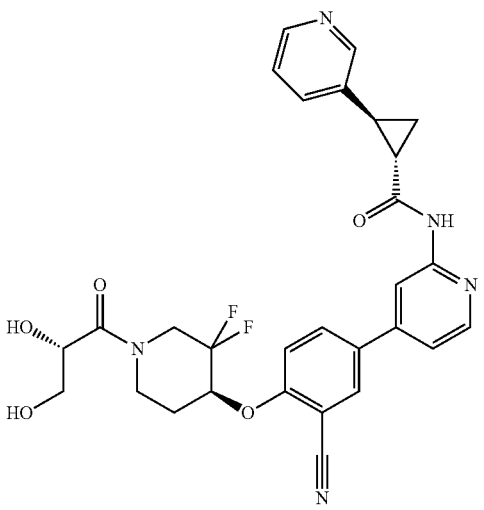 [SMILES: N#Cc1cc(-c2ccnc(NC(=O)[C@H]3C[C@@H]3c3cccnc3)c2)ccc1O[C@H]1CCN(C(=O)[C@@H](O)CO)CC1(F)F]

The title compound was prepared by chiral separation of (1,2-trans)-N-(4-(3-cyano-4-(((S)-1-((S)-2,3-dihydroxypropanoyl)-3,3-difluoropiperidin-4-yl)oxy)phenyl)pyridin-2-yl)-2-(pyridin-3-yl)cyclopropane-1-carboxamide and stereochemistry was tentatively assigned as 1S,2S. 1H NMR (400 MHz, Methanol-d4) δ 8.41 (s, 1H), 8.33 (s, 1H), 8.28 (s, 1H), 8.24 (d, 1H), 7.98 (d, 1H), 7.92 (dd, 1H), 7.63 (m, 1H), 7.41 (d, 1H), 7.36 (dd, 1H), 7.29 (dd, 1H), 5.05 (m, 1H), 4.74-3.38 (m, 7H), 2.53 (m, 1H), 2.23 (m, 1H), 2.07 (m, 2H), 1.64 (m, 1H), 1.40 (m, 1H). LCMS-ESI+ (m/z): [M+H]+ calcd for $C_{29}H_{27}F_2N_5O_5$: 564.2.2; found: 564.2.

Example 141: (1R,2R)—N-(4-(3-cyano-4-(((S)-3,3-difluoro-1-(2-hydroxyacetyl)piperidin-4-yl)oxy)phenyl)pyridin-2-yl)-2-(pyridin-3-yl)cyclopropane-1-carboxamide

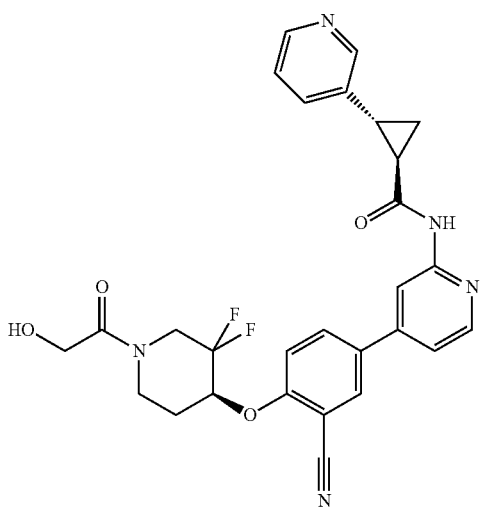 [SMILES: N#Cc1cc(-c2ccnc(NC(=O)[C@@H]3C[C@H]3c3cccnc3)c2)ccc1O[C@H]1CCN(C(=O)CO)CC1(F)F]

The title compound was prepared by chiral separation of (1,2-trans)-N-(4-(3-cyano-4-(((S)-3,3-difluoro-1-(2-hydroxyacetyl)piperidin-4-yl)oxy)phenyl)pyridin-2-yl)-2-(pyridin-3-yl)cyclopropane-1-carboxamide and stereochemistry was tentatively assigned as 1R,2R. 1H NMR (400 MHz, Methanol-d4) δ 8.56 (s, 1H), 8.47 (s, 1H), 8.26 (d, 2H), 7.99 (d, 1H), 7.94 (m, 2H), 7.61 (m, 1H), 7.42 (m, 1H), 7.33 (dd, 1H), 5.05 (m, 1H), 4.22 (m, 2H), 4.03-3.66 (m, 2H), 3.63-3.42 (m, 2H), 2.62 (m, 1H), 2.29 (m, 1H), 2.20-1.93 (m, 2H), 1.71 (m, 1H), 1.49 (m, 1H). LCMS-ESI+ (m/z): [M+H]+ calcd for $C_{28}H_{25}F_2N_5O_4$: 534.2; found: 534.2.

Example 142: (1S,2S)—N-(4-(3-cyano-4-(((S)-3,3-difluoro-1-(2-hydroxyacetyl)piperidin-4-yl)oxy)phenyl)pyridin-2-yl)-2-(pyridin-3-yl)cyclopropane-1-carboxamide

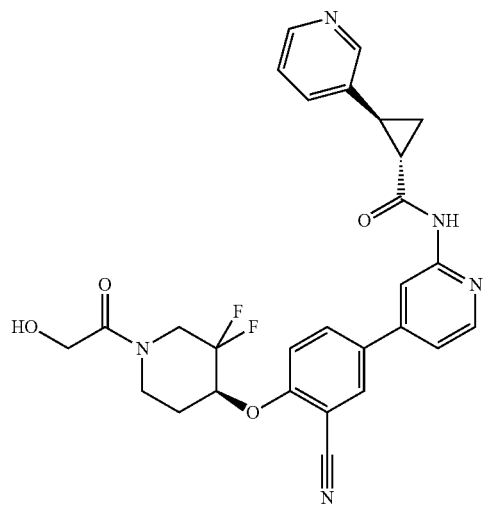 [SMILES: N#Cc1cc(-c2ccnc(NC(=O)[C@H]3C[C@@H]3c3cccnc3)c2)ccc1O[C@H]1CCN(C(=O)CO)CC1(F)F]

The title compound was prepared by chiral separation of (1,2-trans)-N-(4-(3-cyano-4-(((S)-3,3-difluoro-1-(2-hydroxyacetyl)piperidin-4-yl)oxy)phenyl)pyridin-2-yl)-2-(pyridin-3-yl)cyclopropane-1-carboxamide and stereochemistry was tentatively assigned as 1S,2S. 1H NMR (400 MHz, Methanol-d4) δ 8.53 (s, 1H), 8.44 (d, 1H), 8.26 (d, 2H), 7.99 (d, 1H), 7.93 (dd, 1H), 7.88 (d, 1H), 7.56 (dd, 1H), 7.42 (d, 1H), 7.32 (dd, 1H), 5.06 (m, 1H), 4.22 (m, 2H), 4.00-3.68 (m, 2H), 3.51 (m, 2H), 2.61 (m, 1H), 2.28 (m, 1H), 2.18-1.97 (m, 2H), 1.78-1.61 (m, 1H), 1.47 (m, 1H). LCMS-ESI+ (m/z): [M+H]+ calcd for $C_{28}H_{25}F_2N_5O_4$: 534.2; found: 534.2.

Example 143: (1,2-Trans)-N-(6-(3-cyano-4-(((3R,4S)-3-fluoro-1-(2-hydroxyacetyl)piperidin-4-yl)oxy)phenyl)pyrimidin-4-yl)-2-(1-methyl-1H-pyrazol-4-yl)cyclopropane-1-carboxamide

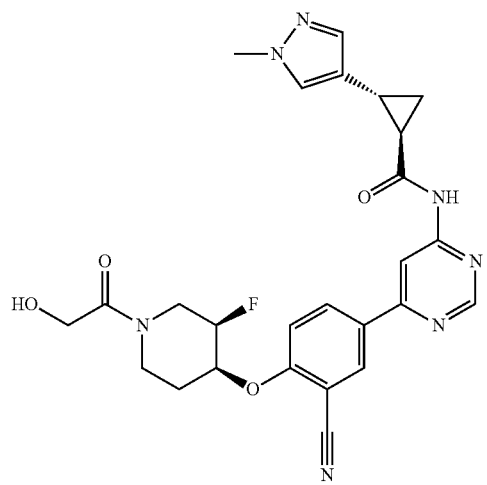

(1,2-Trans)-N-(6-(3-cyano-4-(((3R,4S)-3-fluoropiperidin-4-yl)oxy)phenyl)pyrimidin-4-yl)-2-(1-methyl-1H-pyrazol-4-yl)cyclopropane-1-carboxamide (23 mg, 0.05 mmol), HATU (38 mg, 0.1 mmol), DIPEA (20 mg, 0.15 mmol) and glycolic acid (8 mg, 0.1 mmol) were dissolved in DMF (1.5 mL) and stirred at room temperature for 2 hr. The mixture was filtered and the filtrate was purified by prep-HPLC to give the product. 1H NMR (400 MHz, Methanol-d4) δ 8.88 (t, 1H), 8.59 (m, 1H), 8.39 (d, 1H), 8.33 (dd, 1H), 7.53 (d, 1H), 7.49 (d, 1H), 7.42 (m, 1H), 5.23-4.92 (m, 2H), 4.30 (d, 2H), 4.26-3.92 (m, 1H), 3.85 (s, 3H), 3.81-3.38 (m, 2H), 2.42 (m, 1H), 2.23-2.00 (m, 3H), 1.61 (m, 1H), 1.32 (m, 1H). LCMS-ESI$^+$ (m/z): [M+H]$^+$ calcd for $C_{26}H_{26}FN_7O_4$: 520.2; found: 520.1.

Example 144: (1,2-Trans)-N-(6-(3-cyano-4-(((S)-1-((S)-2,3-dihydroxypropanoyl)-3,3-difluoropiperidin-4-yl)oxy)phenyl)pyrimidin-4-yl)-2-(pyridin-3-yl)cyclopropane-1-carboxamide

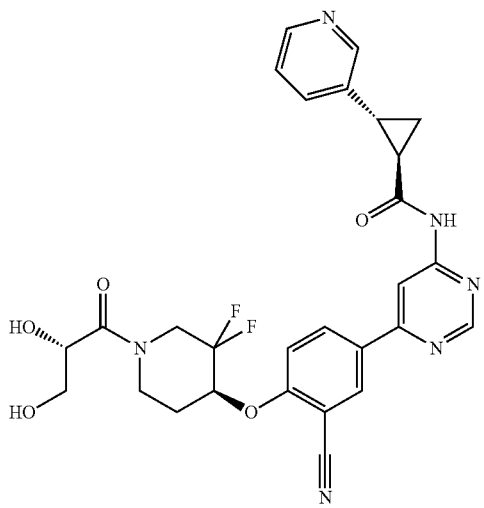 [SMILES: N#Cc1cc(-c2cc(NC(=O)[C@@H]3C[C@H]3c3cccnc3)ncn2)ccc1O[C@H]1CCN(C(=O)[C@@H](O)CO)CC1(F)F]

(1,2-Trans)-N-(6-(3-cyano-4-(((S)-3,3-difluoropiperidin-4-yl)oxy)phenyl)pyrimidin-4-yl)-2-(29 mg, 0.06 mmol), HATU (47 mg, 0.18 mmol), DIPEA (25 mg, 0.18 mmol) and (S)-2,3-dihydroxypropanoic acid (13 mg, 0.12 mmol) were dissolved in DMF (2 mL) and stirred at room temperature for 16 hr. The mixture was filtered and the filtrate was purified by prep-HPLC to give the title compound. 1H NMR (400 MHz, Methanol-d4) δ 8.79 (d, 1H), 8.71 (d, 1H), 8.60 (d, 1H), 8.53 (d, 1H), 8.34 (d, 1H), 8.27 (m, 2H), 7.86 (m 1H), 7.44 (d, 1H), 5.20-5.03 (m, 1H), 4.47 (m, 1H), 4.39-3.36 (m, 6H), 2.82-2.68 (m, 1H), 2.36 (m, 1H), 2.08 (m, 2H), 1.87-1.72 (m, 1H), 1.58 (m, 1H). LCMS-ESI$^+$ (m/z): [M+H]$^+$ calcd for $C_{28}H_{26}F_2N_6O_5$: 565.2; found: 565.2.

Example 145: N-(4-(3-Cyano-4-(((3R,4S)-3-fluoro-1-(2-hydroxyacetyl)piperidin-4-yl)oxy)phenyl)pyridin-2-yl)-2-(1-methyl-1H-1,2,4-triazol-3-yl)cyclopropane-1-carboxamide

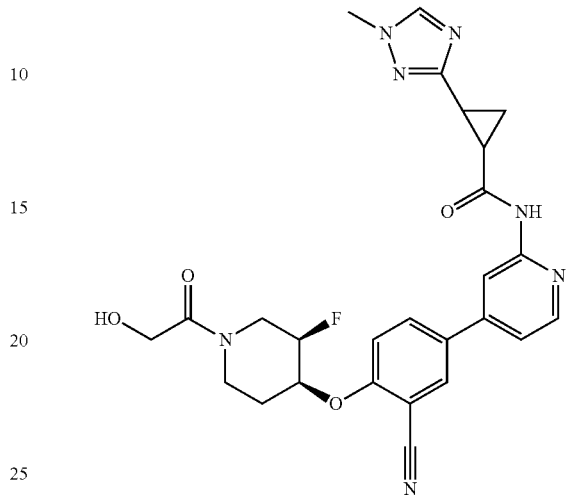

Step 1: tert-Butyl (3R,4S)-4-(4-(2-(2-(1H-1,2,4-triazol-3-yl)cyclopropane-1-carboxamido)pyridin-4-yl)-2-cyanophenoxy)-3-fluoropiperidine-1-carboxylate: To a solution of tert-butyl-(3R,4S)-4-(4-(2-aminopyridin-4-yl)-2-cyanophenoxy)-3-fluoropiperidine-1-carboxylate (70 mg, 0.17 mmol), 2-(1H-1,2,4-triazol-3-yl)cyclopropanecarboxylic acid (39 mg, 0.26 mmol) and HATU (81 mg, 0.34 mmol) in anhydrous DMF (2 mL) was added DIPEA (66 mg, 0.51 mmol). The mixture was stirred at 110° C. in a microwave reactor for 1 h. After being cooled to room temperature, the mixture was filtered and the residue was purified by prep-HPLC to give the product.

Step 2: tert-Butyl (3R,4S)-4-(2-cyano-4-(2-(2-(1-methyl-1H-1,2,4-triazol-3-yl)cyclopropane-1-carboxamido)pyridin-4-yl)phenoxy)-3-fluoropiperidine-1-carboxylate: To a solution of tert-butyl (3R,4S)-4-(4-(2-(2-(1H-1,2,4-triazol-3-yl)cyclopropane-1-carboxamido)pyridin-4-yl)-2-cyanophenoxy)-3-fluoropiperidine-1-carboxylate (20 mg, 0.04 mmol) in DMF (0.2 mL) was added potassium carbonate (13 mg, 0.09 mmol) and iodomethane (12 mg, 0.08 mmol). After 2 h the reaction mixture was partitioned between H$_2$O and ethyl acetate. The organic phase was collected, dried with sodium sulfate, filtered and concentrated under reduced pressure. The residue was purified by prep-HPLC to give a product.

Step 3: N-(4-(3-Cyano-4-(((3R,4S)-3-fluoro-1-(2-hydroxyacetyl)piperidin-4-yl)oxy)phenyl)pyridin-2-yl)-2-(1-methyl-1H-1,2,4-triazol-3-yl)cyclopropane-1-carboxamide: tert-Butyl (3R,4S)-4-(2-cyano-4-(2-(2-(1-methyl-1H-1,2,4-triazol-3-yl)cyclopropane-1-carboxamido)pyridin-4-yl)phenoxy)-3-fluoropiperidine-1-carboxylate (2 mg) was diluted with DCM (0.5 mL) and TFA (0.1 mL), mixture stirred at room temperature for 1 h. The reaction mixture was evaporated under reduced pressure to a residue, which was dissolved in DMF (0.25 mL). HATU (4 mg), DIPEA (2 mg) and glycolic acid (1 mg) were added to the solution and the mixture was stirred at room temperature for 16 hr. The mixture was filtered and the residue was purified by prep-HPLC to give the tile compound. LCMS-ESI$^+$ (m/z): [M+H]$^+$ calcd for $C_{26}H_{26}FN_7O_4$: 520.2; found: 520.1.

Example 146: (1, 2-Trans)-N-(6-(3-cyano-4-(((3R,4S)-1-((S)-2,3-dihydroxypropanoyl)-3-fluoropiperidin-4-yl)oxy)phenyl)pyrimidin-4-yl)-2-(1-methyl-1H-pyrazol-4-yl)cyclopropane-1-carboxamide

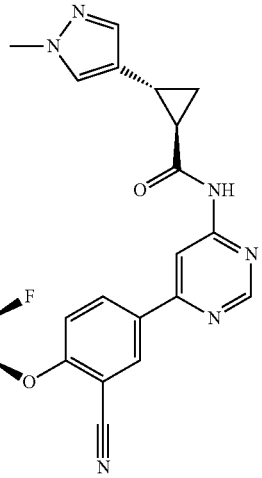

(1,2-Trans)-N-(6-(3-cyano-4-(((3R,4S)-3-fluoropiperidin-4-yl)oxy)phenyl)pyrimidin-4-yl)-2-(1-methyl-1H-pyrazol-4-yl)cyclopropane-1-carboxamide (12 mg, 0.026 mmol), HATU (20 mg, 0.052 mmol), DIPEA (10 mg, 0.08 mmol) and glycolic acid (6 mg, 0.052 mmol) were dissolved in DMF (1 mL) and stirred at room temperature for 16 hr. The mixture was filtered and the residue was purified by prep-HPLC to give the product. 1H NMR (400 MHz, Methanol-d4) δ 8.93 (d, 1H), 8.61 (d, 1H), 8.38 (d, 1H), 8.31 (dd, 1H), 7.61 (s, 1H), 7.56-7.47 (m, 2H), 5.27-4.90 (m, 2H), 4.77-3.91 (m, 4H), 3.88 (s, 3H), 3.83-3.43 (m, 2H), 2.45 (m, 1H), 2.26-1.98 (m, 3H), 1.63 (m, 1H), 1.35 (m, 1H). LCMS-ESI⁺ (m/z): [M+H]⁺ calcd for $C_{27}H_{28}FN_7O_5$: 550.2; found: 550.1.

Example 147: (1,2-Trans)-N-(6-(3-cyano-4-(((3R,4S)-3-fluoro-1-(2-hydroxyacetyl)piperidin-4-yl)oxy)phenyl)pyrimidin-4-yl)-2-(pyridin-3-yl)cyclopropane-1-carboxamide

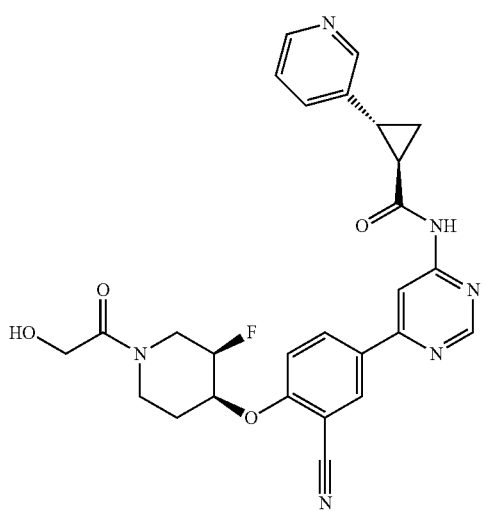 [SMILES: N#Cc1cc(-c2cc(NC(=O)[C@@H]3C[C@H]3c3cccnc3)ncn2)ccc1O[C@H]1CCN(C(=O)CO)C[C@H]1F]

(1,2-Trans)-N-(6-(3-cyano-4-(((3R,4S)-3-fluoropiperidin-4-yl)oxy)phenyl)pyrimidin-4-yl)-2-(pyridin-3-yl)cyclopropane-1-carboxamide (26 mg, 0.06 mmol), HATU (43 mg, 0.11 mmol), DIPEA (22 mg, 0.17 mmol) and glycolic acid (9 mg, 0.11 mmol) were dissolved in DMF (2 mL) and stirred at room temperature for 2 hrs. The mixture was filtered and the filtrate was purified by prep-HPLC to give the product. 1H NMR (400 MHz, Methanol-d4) δ 8.86 (d, 1H), 8.80 (s, 1H), 8.69 (d, 1H), 8.59 (d, 1H), 8.40 (d, 1H), 8.35 (m, 2H), 7.96 (dd, 1H), 7.47 (d, 1H), 5.13-4.88 (m, 2H), 4.29 (s, 2H), 4.26-3.33 (m, 4H), 2.84 (m, 1H), 2.51-2.38 (m, 1H), 2.10 (m, 2H), 1.87 (m, 1H), 1.67 (m, 1H). LCMS-ESI⁺ (m/z): [M+H]⁺ calcd for $C_{27}H_{25}FN_6O_4$: 517.2; found: 517.2.

Example 148: (1,2-Trans)-N-(4-(3-cyano-4-(((3R,4S)-3-fluoro-1-(2-hydroxyacetyl)piperidin-4-yl)oxy)phenyl)pyridin-2-yl)-2-(5-methylthiophen-2-yl)cyclopropane-1-carboxamide

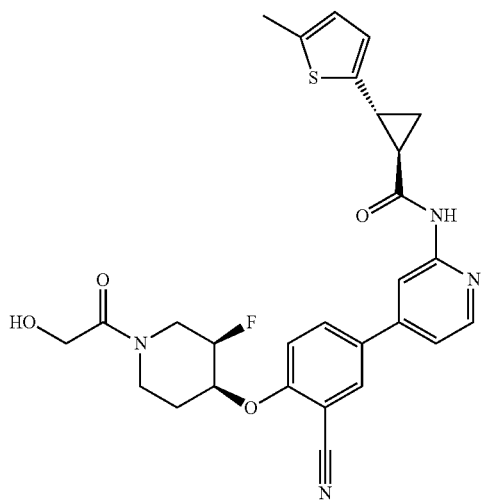 [SMILES: Cc1ccc([C@@H]2C[C@H]2C(=O)Nc2cc(-c3ccc(O[C@H]4CCN(C(=O)CO)C[C@H]4F)c(C#N)c3)ccn2)s1]

Step 1: Tert-Butyl (3R,4S)-4-(2-cyano-4-(2-((1,2-trans)-2-(5-methylthiophen-2-yl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (100 mg, 0.24 mmol), (1,2-trans)-2-(5-methylthiophen-2-yl)cyclopropane-1-carboxylic acid (66 mg, 0.36 mmol) and HATU (115 mg, 0.49 mmol) in anhydrous DMF (2.5 mL) was added DIPEA (94 mg, 0.73 mmol). The mixture was stirred at 110° C. in a microwave reactor for 1 h. After being cooled to room temperature, the mixture was diluted with water and extracted with EtOAc. The organic layer was separated, washed with water and brine, dried over $Na_2SO_4$ and concentrated. The residue was purified by prep-HPLC to give the product.

Step 2: (1,2-Trans)-N-(4-(3-cyano-4-(((3R,4S)-3-fluoropiperidin-4-yl)oxy)phenyl)pyridin-2-yl)-2-(5-methylthiophen-2-yl)cyclopropane-1-carboxamide: tert-Butyl (3R,4S)-4-(2-cyano-4-(2-((1,2-trans)-2-(5-methylthiophen-2-yl)cyclopropane-1-carboxamido)pyridin-4-yl)phenoxy)-3-fluoropiperidine-1-carboxylate (78 mg, 0.13 mmol) was diluted with DCM (2.5 mL) and TFA (0.6 mL), mixture stirred at room temperature for 1 h. The reaction mixture was evaporated under reduced pressure. The product was used for next step.

Step 3: (1,2-Trans)-N-(4-(3-cyano-4-(((3R,4S)-3-fluoro-1-(2-hydroxyacetyl)piperidin-4-yl)oxy)phenyl)pyridin-2- yl)-2-(5-methylthiophen-2-yl)cyclopropane-1-carboxamide: (1,2-Trans)-N-(4-(3-cyano-4-(((3R,4S)-3-fluoropiperidin-4-yl)oxy)phenyl)pyridin-2-yl)-2-(5-methylthiophen-2-yl)cyclopropane-1-carboxamide (32 mg, 0.07 mmol), HATU (51 mg, 0.13 mmol), DIPEA (26 mg, 0.2 mmol) and glycolic acid (10 mg, 0.13 mmol) were dissolved in DMF (2 mL) and stirred at room temperature for 2 hrs. The mixture was filtered and the filtrate was purified by prep-HPLC to give the product. LCMS-ESI$^+$ (m/z): [M+H]$^+$ calcd for $C_{28}H_{27}FN_4O_4S$: 535.2; found: 535.2.

Example 149: (1,2-Trans)-N-(4-(3-cyano-4-(((3R,4S)-3-fluoro-1-(2-hydroxyacetyl)piperidin-4-yl)oxy)phenyl)pyridin-2-yl)-2-(pyrimidin-5-yl)cyclopropane-1-carboxamide

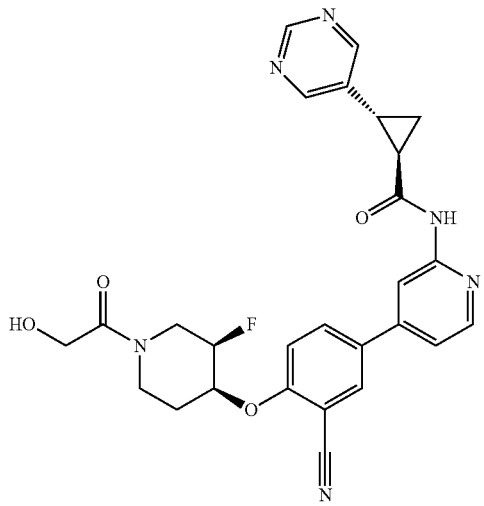 [SMILES: N#Cc1cc(-c2ccnc(NC(=O)[C@@H]3C[C@H]3c3cncnc3)c2)ccc1O[C@H]1CCN(C(=O)CO)C[C@H]1F]

Step 1: tert-Butyl (3R,4S)-4-(2-cyano-4-(2-((1,2-trans)-2-(pyrimidin-5-yl)cyclopropane-1-carboxamido)pyridin-4-yl)phenoxy)-3-fluoropiperidine-1-carboxylate: To a solution of tert-butyl (3R,4S)-4-(4-(2-aminopyridin-4-yl)-2-cyanophenoxy)-3-fluoropiperidine-1-carboxylate (70 mg, 0.17 mmol), (1,2-trans)-2-(pyrimidin-5-yl)cyclopropane-1-carboxylic acid (30 mg, 0.26 mmol) and HATU (81 mg, 0.18 mmol) in anhydrous DMF (2 mL) was added DIPEA (66 mg, 0.51 mmol). The mixture was stirred at 110° C. in a microwave reactor for 1 h. The mixture was filtered and the filtrate was purified by prep-HPLC to give the product.

Step 2: (1,2-Trans)-N-(4-(3-cyano-4-(((3R,4S)-3-fluoropiperidin-4-yl)oxy)phenyl)pyridin-2-yl)-2-(pyrimidin-5-yl)cyclopropane-1-carboxamide: tert-Butyl (3R,4S)-4-(2-cyano-4-(2-((1,2-trans)-2-(pyrimidin-5-yl)cyclopropane-1-carboxamido)pyridin-4-yl)phenoxy)-3-fluoropiperidine-1-carboxylate (19 mg, 0.03 mmol) was diluted with DCM (0.6 mL) and TFA (0.2 mL), mixture stirred at room temperature for 1 h. The reaction mixture was evaporated under reduced pressure. The product was used for next step.

Step 3: (1,2-Trans)-N-(4-(3-cyano-4-(((3R,4S)-3-fluoro-1-(2-hydroxyacetyl)piperidin-4-yl)oxy)phenyl)pyridin-2-yl)-2-(pyrimidin-5-yl)cyclopropane-1-carboxamide: (1,2-Trans)-N-(4-(3-cyano-4-(((3R,4S)-3-fluoropiperidin-4-yl)oxy)phenyl)pyridin-2-yl)-2-(pyrimidin-5-yl)cyclopropane-1-carboxamide (16 mg, 0.035 mmol), HATU (27 mg, 0.07 mmol), DIPEA (14 mg, 0.11 mmol) and glycolic acid (6 mg, 0.07 mmol) were dissolved in DMF (1 mL) and stirred at room temperature for 2 hrs. The mixture was filtered and the filtrate was purified by Gilson prep-HPLC to give the product. 1H NMR (400 MHz, DMSO-d6) δ 10.99 (s, 1H), 9.03 (s, 1H), 8.69 (s, 2H), 8.44-8.28 (m, 2H), 8.13 (d, 1H), 8.00 (dd, 1H), 7.57 (d, 1H), 7.47 (dd, 1H), 5.18-4.88 (m, 3H), 4.40-4.00 (m, 2H), 3.72-3.07 (m, 3H), 2.46 (m, 1H), 2.08-1.72 (m, 3H), 1.58 (m, 2H). LCMS-ESI$^+$ (m/z): [M+H]$^+$ calcd for $C_{27}H_{25}FN_6O_4$: 517.2; found: 517.2.

Example 150: Trans-N-(4-(3-cyano-4-((tetrahydro-2H-pyran-4-yl)oxy)phenyl)pyridin-2-yl)-2-(furan-2-yl)cyclopropane-1-carboxamide

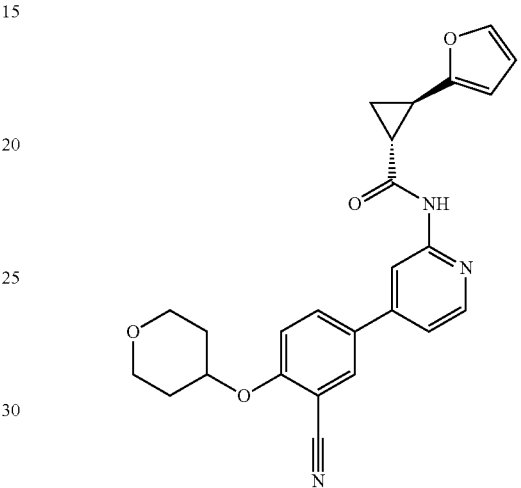

Step 1: Preparation of (E)-3-(furan-2-yl)-N-methoxy-N-methylacrylamide: (E)-3-(furan-2-yl)acrylic acid (500 mg, 3.620 mmol) dissolved in dichloromethane (15 mL) was treated with 1-Ethyl-3-(3-dimethylaminopropyl)carbodiimide (702 mg, 3.662 mmol), N,O-dimethylhydroxylamine hydrochloride (459 mg, 4.706 mmol), and 4-(dimethylamino)pyridine (427 mg, 3.614 mmol). The reaction mixture was stirred at room temperature for 3 h, diluted with dichloromethane and washed with water. The organic layer was concentrated and purified by column chromatography to give (E)-3-(furan-2-yl)-N-methoxy-N-methylacrylamide.

Step 2: Preparation of Trans-2-(furan-2-yl)-N-methoxy-N-methylcyclopropane-1-carboxamide: Trimethylsulfoxonium iodide (678 mg, 3.082 mmol) suspended in dimethyl sulfoxide (9 mL) was treated with sodium hydride (174 mg, 4.350 mmol, 60% dispersion in mineral oil) at room temperature. After stirring for 20 min, (E)-3-(furan-2-yl)-N-methoxy-N-methylacrylamide (285 mg, 1.573 mmol) dissolved in 2 mL of dimethyl sulfoxide was added dropwise. The reaction mixture was stirred at room temperature for 1 h and then at 50° C. for 1 h. After cooling to room temperature, the reaction mixture was quenched with saturated ammonium chloride solution and then extracted with ethyl acetate. The organic layer was concentrated and purified by column chromatography to give trans-2-(furan-2-yl)-N-methoxy-N-methylcyclopropane-1-carboxamide.

Step 3: Preparation of Trans-2-(furan-2-yl)cyclopropane-1-carboxylic acid: Trans-2-(furan-2-yl)-N-methoxy-N-methylcyclopropane-1-carboxamide (238 mg, 1.219 mmol) dissolved in ethanol (5 mL) was treated with potassium hydroxide solution (160 μL, 30% solution in water). The reaction mixture was heated at 50° C. for 2 d. After cooling to rt, the reaction mixture was concentrated. The residue was dissolved in ethyl acetate and washed with 1N HCl solution. The organic layer was concentrated to give the crude trans-2-(furan-2-yl)cyclopropane-1-carboxylic acid.

Step 4: Preparation of Trans-N-(4-(3-cyano-4-((tetrahydro-2H-pyran-4-yl)oxy)phenyl)pyridin-2-yl)-2-(furan-2-yl)cyclopropane-1-carboxamide: 5-(2-aminopyridin-4-yl)-2-((tetrahydro-2H-pyran-4-yl)oxy) benzonitrile (60 mg, 0.203 mmol) dissolved in dimethyl formamide (2 mL) was treated with HATU (154 mg. 0.405 mmol), trans-2-(furan-2-yl)cyclopropane-1-carboxylic acid (60 mg, 0.357 mmol), and N,N-diisopropylethylamine (120 µL, 0.689 mmol). The reaction mixture was heated in the microwave at 110° C. for 25 min. After cooling to room temperature, the reaction mixture was diluted with ethyl acetate and washed with water. The organic layer was dried over sodium sulfate, filtered, and concentrated. The residue was purified by HPLC to give the title compound. 1H NMR (400 MHz, Chloroform-d) δ 8.41 (s, 1H), 8.12 (dd, J=20.0, 7.6 Hz, 2H), 7.98 (s, 1H), 7.59 (d, J=6.5 Hz, 1H), 6.30 (d, J=3.0 Hz, 1H), 6.16 (d, J=3.3 Hz, 1H), 4.04 (ddd, J=11.2, 6.8, 3.7 Hz, 2H), 3.68 (ddd, J=11.5, 7.5, 3.6 Hz, 2H), 2.74 (s, 1H), 2.40 (s, 2H), 2.11 (s, 3H), 1.94 (s, 2H), 1.69 (d, J=9.3 Hz, 2H). LCMS-ESI+ (m/z): [M+H]+ calcd for C25H23N3O4: 430.2; found: 430.1.

Example 151: Trans-N-(4-(3-cyano-4-((tetrahydro-2H-pyran-4-yl)oxy)phenyl)pyridin-2-yl)-2-(pyridin-4-yl)cyclopropane-1-carboxamide

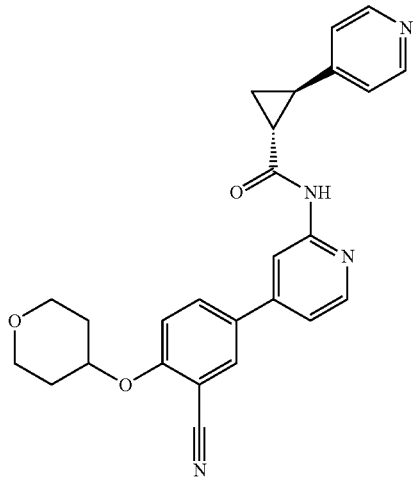 [SMILES: N#Cc1cc(-c2ccnc(NC(=O)[C@@H]3C[C@H]3c3ccncc3)c2)ccc1OC1CCOCC1]

Step 1: Preparation of (E)-N-(4-(3-cyano-4-((tetrahydro-2H-pyran-4-yl)oxy)phenyl)pyridin-2-yl)-3-(pyridin-4-yl)acrylamide: 5-(2-aminopyridin-4-yl)-2-((tetrahydro-2H-pyran-4-yl)oxy) benzonitrile (200 mg, 0.677 mmol) dissolved in dimethyl formamide (5 mL) was treated with HATU (514 mg. 1.353 mmol), (E)-3-(pyridin-4-yl)acrylic acid (155 mg, 1.039 mmol), and N,N-diisopropylethylamine (440 µL, 2.526 mmol). The reaction mixture was heated in the microwave at 110° C. for 1 h. After cooling to room temperature, the reaction mixture was diluted with dichloromethane and washed with water. The organic layer was dried over sodium sulfate, filtered, and concentrated. The residue was purified by column chromatography to give (E)-N-(4-(3-cyano-4-((tetrahydro-2H-pyran-4-yl)oxy)phenyl)pyridin-2-yl)-3-(pyridin-4-yl)acrylamide.

Step 2: Preparation of Trans-N-(4-(3-cyano-4-((tetrahydro-2H-pyran-4-yl)oxy)phenyl)pyridin-2-yl)-2-(pyridin-4-yl)cyclopropane-1-carboxamide: Trimethylsulfoxonium iodide (30 mg, 0.322 mmol) suspended in dimethyl sulfoxide (2 mL) was treated with sodium hydride (15 mg, 0.375 mmol, 60% dispersion in mineral oil) at room temperature. After stirring for 30 min, (E)-N-(4-(3-cyano-4-((tetrahydro-2H-pyran-4-yl)oxy)phenyl)pyridin-2-yl)-3-(pyridin-4-yl)acrylamide (77 mg, 0.181 mmol) dissolved in 2 mL of dimethyl sulfoxide was added dropwise. The reaction mixture was stirred at room temperature for 1 h and then at 50° C. for 1 h. An additional 5 mg of sodium hydride and 10 mg of trimethylsulfoxonium iodide were added. Reaction mixture was heated at 50° C. for another day. After cooling to room temperature, the reaction mixture was quenched with saturated ammonium chloride solution and then extracted with ethyl acetate. The organic layer was concentrated and purified by HPLC to give the title compound. 1H NMR (400 MHz, Chloroform-d) δ 8.94-8.89 (m, 1H), 8.77-8.71 (m, 2H), 8.21 (d, J=6.3 Hz, 1H), 7.98 (d, J=2.4 Hz, 1H), 7.91 (dd, J=8.9, 2.5 Hz, 1H), 7.57 (d, J=6.1 Hz, 2H), 7.49 (dd, J=6.3, 1.8 Hz, 1H), 7.16 (d, J=9.0 Hz, 1H), 4.79 (dt, J=7.2, 3.6 Hz, 1H), 4.04 (m, 3H), 3.67 (m, 2H), 2.78 (dt, J=9.6, 5.6 Hz, 1H), 2.68 (td, J=8.0, 7.0, 3.6 Hz, 1H), 2.15-2.00 (m, 3H), 1.94 (ddt, J=10.1, 6.7, 3.6 Hz, 2H), 1.62 (dt, J=8.5, 5.7 Hz, 1H). LCMS-ESI+ (m/z): [M+H]+ calcd for C26H24N4O3: 441.2; found: 441.1.

Example 152: N-(6-(3-cyano-4-(((S)-3,3-difluoro-1-((S)-5-oxopyrrolidine-2-carbonyl)piperidin-4-yl)oxy)phenyl)pyrimidin-4-yl)cyclopropanecarboxamide

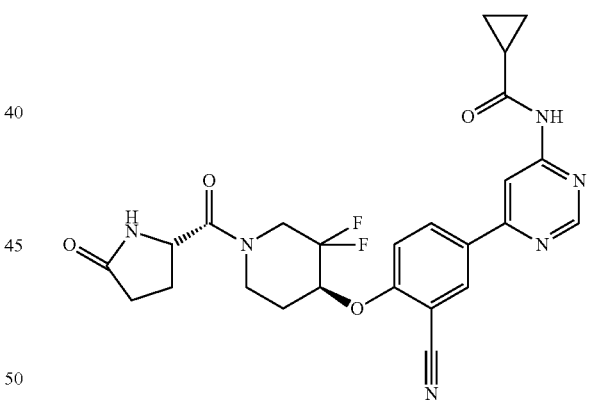

(S)—N-(6-(3-cyano-4-((3,3-difluoropiperidin-4-yl)oxy)phenyl)pyrimidin-4-yl)cyclopropanecarboxamide (50 mg, 0.125 mmol) dissolved in dimethyl formamide (2 mL) was treated with HATU (95 mg. 0.250 mmol), (S)-5-oxopyrrolidine-2-carboxylic acid (24 mg, 0.186 mmol), and N,N-diisopropylethylamine (80 µL, 0.459 mmol). The reaction mixture was stirred at room temperature for 30 min. The reaction mixture was diluted with dichloromethane and washed with water. The organic layer was dried over sodium sulfate, filtered, and concentrated. The residue was purified by HPLC to give the title compound. 1H NMR (400 MHz, DMSO-d6) δ 11.33 (s, 1H), 8.93 (d, J=1.2 Hz, 1H), 8.53 (d, J=1.2 Hz, 1H), 8.40 (d, J=2.3 Hz, 1H), 8.35 (dd, J=9.0, 2.3 Hz, 1H), 7.78 (s, 1H), 7.62 (t, J=7.3 Hz, 1H), 5.36 (s, 1H), 4.63 (s, 1H), 4.24-4.07 (m, 1H), 3.82 (d, J=49.7 Hz, 2H), 3.51 (dd, J=25.9, 12.3 Hz, 1H), 2.34 (s, 1H), 2.17-2.03 (m, 4H), 2.01 (m, 1H), 1.86 (s, 1H), 0.94-0.85 (m, 4H). LCMS-ESI+ (m/z): [M+H]+ calcd for C25H24F2N6O4: 511.2; found: 511.2.

Example 153: (S)—N-(6-(3-cyano-4-((1-(2-cyano-acetyl)-3,3-difluoropiperidin-4-yl)oxy)phenyl)pyrimidin-4-yl)cyclopropanecarboxamide

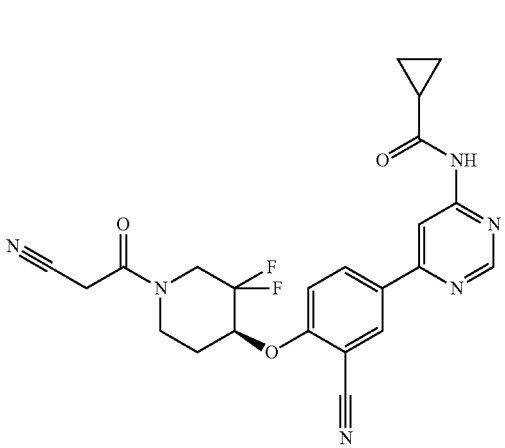 [SMILES: N#CCC(=O)N1CC[C@H](Oc2ccc(-c3cc(NC(=O)C4CC4)ncn3)cc2C#N)C(F)(F)C1]

The title compound was synthesized in the same manner as Example 152 using 2-cyanoacetic acid. 1H NMR (400 MHz, DMSO-d6) δ 11.36 (s, 1H), 8.93 (d, J=1.2 Hz, 1H), 8.53 (d, J=1.3 Hz, 1H), 8.40 (d, J=2.3 Hz, 1H), 8.35 (dd, J=9.0, 2.3 Hz, 1H), 7.62 (d, J=9.1 Hz, 1H), 5.36 (dt, J=8.3, 5.0 Hz, 1H), 4.21 (s, 2H), 4.08-3.83 (m, 2H), 3.62-3.41 (m, 2H), 2.12-1.98 (m, 2H), 0.92-0.85 (m, 4H). LCMS-ESI+ (m/z): [M+H]+ calcd for C23H20F2N6O3: 467.2; found: 467.2.

Example 154: (S)—N-(6-(3-cyano-4-((3,3-difluoro-1-(3-hydroxypropanoyl)piperidin-4-yl)oxy)phenyl)pyrimidin-4-yl)cyclopropanecarboxamide

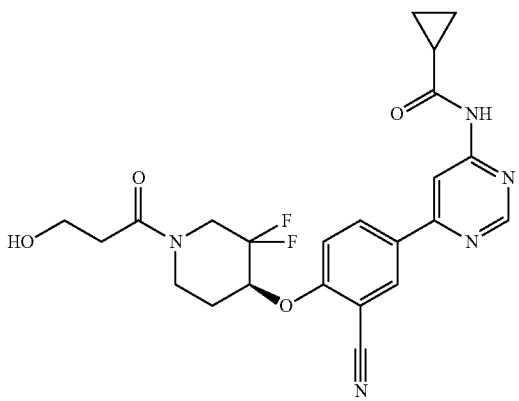 [SMILES: N#Cc1cc(-c2cc(NC(=O)C3CC3)ncn2)ccc1O[C@H]1CCN(C(=O)CCO)CC1(F)F]

The title compound was synthesized in the same manner as Example 152 using 3-hydroxypropanoic acid. 1H NMR (400 MHz, DMSO-d6) δ 11.35 (s, 1H), 8.93 (d, J=1.2 Hz, 1H), 8.53 (d, J=1.3 Hz, 1H), 8.40 (d, J=2.3 Hz, 1H), 8.34 (dd, J=9.0, 2.4 Hz, 1H), 7.62 (dd, J=9.1, 2.3 Hz, 1H), 5.35 (s, 2H), 4.08 (s, 1H), 3.77 (m, 2H), 3.60-3.42 (m, 2H), 2.55 (dt, J=11.4, 6.4 Hz, 2H), 2.11-2.03 (m, 2H), 1.89 (d, J=59.4 Hz, 2H), 0.89 (m, 4H). LCMS-ESI+ (m/z): [M+H]+ calcd for C23H23F2N5O4: 472.2; found: 472.1.

Example 155: N-(6-(3-cyano-4-(((S)-3,3-difluoro-1-((S)-2-oxooxazolidine-4-carbonyl)piperidin-4-yl)oxy)phenyl)pyrimidin-4-yl)cyclopropanecarboxamide

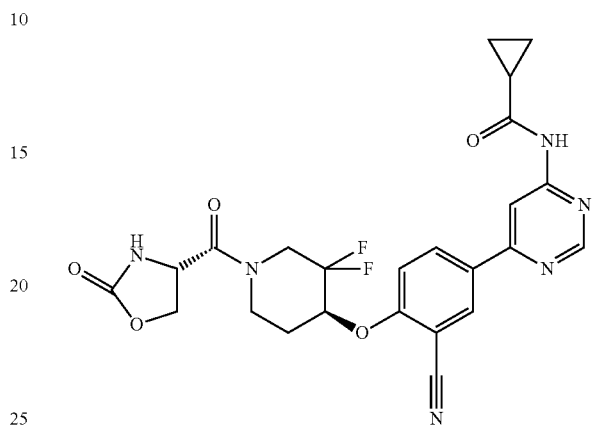

The title compound was synthesized in the same manner as Example 152 using (S)-2-oxooxazolidine-4-carboxylic acid. 1H NMR (400 MHz, DMSO-d6) δ 11.36 (s, 1H), 8.93 (d, J=1.2 Hz, 1H), 8.53 (d, J=1.3 Hz, 1H), 8.40 (d, J=2.3 Hz, 1H), 8.35 (dd, J=9.0, 2.3 Hz, 1H), 8.04 (s, 1H), 7.62 (t, J=9.5 Hz, 1H), 5.37 (d, J=4.7 Hz, 1H), 4.89 (td, J=8.7, 4.1 Hz, 1H), 4.51 (dt, J=14.2, 8.8 Hz, 1H), 4.24 (ddd, J=29.5, 8.5, 4.1 Hz, 2H), 3.92-3.82 (m, 1H), 3.69 (d, J=15.8 Hz, 1H), 3.52-3.40 (m, 1H), 2.14 (s, 1H), 2.12-1.97 (m, 2H), 0.89 (m, 4H). LCMS-ESI+ (m/z): [M+H]+ calcd for C24H22F2N6O5: 513.2; found: 513.2.

Example 156: Trans-N-(4-(3-cyano-4-(((3R,4S)-3-fluoro-1-(2-hydroxyacetyl)piperidin-4-yl)oxy)phenyl)pyridin-2-yl)-2-(5-methyl-1,3,4-oxadiazol-2-yl)cyclopropane-1-carboxamide

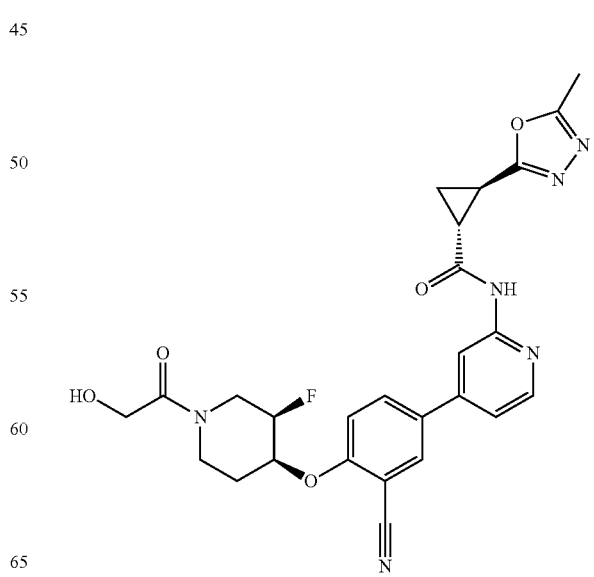

Step 1: Preparation of tert-butyl (3R,4S)-4-(2-cyano-4-(trans-2-(2-(ethoxycarbonyl)cyclopropane-1-carboxamido)pyridin-4-yl)phenoxy)-3-fluoropiperidine-1-carboxylate: Tert-butyl (3R,4S)-4-(4-(2-aminopyridin-4-yl)-2-cyanophenoxy)-3-fluoropiperidine-1-carboxylate (800 mg, 1.940 mmol) dissolved in dimethyl formamide (9 mL) was treated with HATU (1400 mg. 3.684 mmol), trans-2-(ethoxycarbonyl)cyclopropane-1-carboxylic acid (460 mg, 2.909 mmol), and N,N-diisopropylethylamine (1100 µL, 6.315 mmol). The reaction mixture was stirred at room temperature for 30 min. The reaction mixture was diluted with dichloromethane and washed with water. The organic layer was dried over sodium sulfate, filtered, and concentrated. The residue was purified by column chromatography to give tert-butyl (3R,4S)-4-(2-cyano-4-(trans-2-(2-(ethoxycarbonyl)cyclopropane-1-carboxamido)pyridin-4-yl)phenoxy)-3-fluoropiperidine-1-carboxylate.

Step 2: Preparation of trans-2-((4-(4-(((3R,4S)-1-(tert-butoxycarbonyl)-3-fluoropiperidin-4-yl)oxy)-3-cyanophenyl)pyridin-2-yl)carbamoyl)cyclopropane-1-carboxylic acid: Tert-butyl (3R,4S)-4-(2-cyano-4-(trans-2-(2-(ethoxycarbonyl)cyclopropane-1-carboxamido)pyridin-4-yl)phenoxy)-3-fluoropiperidine-1-carboxylate (348 mg, 0.630 mmol) dissolved in 2-methyltetrahydrofuran (5 mL) and methanol (1 mL) was treated with sodium hydroxide (100 mg. 2.500 mmol) dissolved in water (500 µL). The reaction mixture was stirred at room temperature for 2 h. An additional 10 mg of sodium hydroxide was added and the reaction mixture was stirred at room temperature overnight. The reaction mixture was concentrated. The residue was dissolved in ethyl acetate and washed with 1N HCl solution. The organic layer was dried over sodium sulfate, filtered, and concentrated to give trans-2-((4-(4-(((3R,4S)-1-(tert-butoxycarbonyl)-3-fluoropiperidin-4-yl)oxy)-3-cyanophenyl)pyridin-2-yl)carbamoyl)cyclopropane-1-carboxylic acid.

Step 3: Preparation of tert-butyl (3R,4S)-4-(4-(trans-2(2-(2-acetylhydrazine-1-carbonyl)cyclopropane-1-carboxamido)pyridin-4-yl)-2-cyanophenoxy)-3-fluoropiperidine-1-carboxylate: Trans-2-((4-(4-(((3R,4S)-1-(tert-butoxycarbonyl)-3-fluoropiperidin-4-yl)oxy)-3-cyanop9henyl)pyridin-2-yl)carbamoyl)cyclopropane-1-carboxylic acid (135 mg, 0.257 mmol) dissolved in dimethyl formamide (3 mL) was treated with HATU (195 mg. 0.513 mmol), acetic hydrazide (28 mg, 0.378 mmol), and N,N-diisopropylethylamine (160 µL, 0.919 mmol). The reaction mixture was stirred at room temperature for 30 min. The reaction mixture was diluted with dichloromethane and washed with water. The organic layer was dried over sodium sulfate, filtered, and concentrated. The residue was purified by column chromatography to give tert-butyl (3R,4S)-4-(4-(trans-2(2-(2-acetylhydrazine-1-carbonyl)cyclopropane-1-carboxamido)pyridin-4-yl)-2-cyanophenoxy)-3-fluoropiperidine-1-carboxylate.

Step 4: Preparation of tert-butyl (3R,4S)-4-(2-cyano-4-(2-(trans-2-(5-methyl-1,3,4-oxadiazol-2-yl)cyclopropane-1-carboxamido)pyridin-4-yl)phenoxy)-3-fluoropiperidine-1-carboxylate: (3R,4S)-4-(4-(trans-2(2-(2-acetylhydrazine-1-carbonyl)cyclopropane-1-carboxamido)pyridin-4-yl)-2-cyanophenoxy)-3-fluoropiperidine-1-carboxylate (140 mg, 0.241 mmol) dissolved in dichloromethane (3 mL) was treated with 2-chloro-1,3-dimethylimidazolinium chloride (40 mg, 0.237 mmol) followed by triethylamine (50 µL, 0.692 mmol). The reaction mixture was stirred at room temperature overnight. The reaction mixture was diluted with dichloromethane and washed with water. The organic layer was dried over sodium sulfate, filtered, and concentrated. The residue was purified by column chromatography to give tert-butyl (3R,4S)-4-(2-cyano-4-(2-(trans-2-(5-methyl-1,3,4-oxadiazol-2-yl)cyclopropane-1-carboxamido)pyridin-4-yl)phenoxy)-3-fluoropiperidine-1-carboxylate.

Step 5: Preparation of trans-N-(4-(3-cyano-4-(((3R,4S)-3-fluoropiperidin-4-yl)oxy)phenyl)pyridin-2-yl)-2-(5-methyl-1,3,4-oxadiazol-2-yl)cyclopropane-1-carboxamide: Tert-butyl (3R,4S)-4-(2-cyano-4-(2-((trans-2-(5-methyl-1,3,4-oxadiazol-2-yl)cyclopropane-1-carboxamido)pyridin-4-yl)phenoxy)-3-fluoropiperidine-1-carboxylate (35 mg, 0.062 mmol) dissolved in dichloromethane (1 mL) was treated with trifluoroacetic acid (100 µL, 1.307 mmol). The reaction mixture was stirred at room temperature for 30 min and then concentrated to give trans-N-(4-(3-cyano-4-(((3R,4S)-3-fluoropiperidin-4-yl)oxy)phenyl)pyridin-2-yl)-2-(5-methyl-1,3,4-oxadiazol-2-yl)cyclopropane-1-carboxamide.

Step 6: Preparation of trans-N-(4-(3-cyano-4-(((3R,4S)-3-fluoro-1-(2-hydroxyacetyl)piperidin-4-yl)oxy)phenyl)pyridin-2-yl)-2-(5-methyl-1,3,4-oxadiazol-2-yl)cyclopropane-1-carboxamide: Trans-N-(4-(3-cyano-4-(((3R,4S)-3-fluoropiperidin-4-yl)oxy)phenyl)pyridin-2-yl)-2-(5-methyl-1,3,4-oxadiazol-2-yl)cyclopropane-1-carboxamide (25 mg, 0.054 mmol) dissolved in dichloromethane (1 mL) was treated with HATU (40 mg, 0.105 mmol), glycolic acid (6 mg, 0.079 mmol), and N,N-diisopropylethylamine (40 µL, 0.230 mmol). The reaction mixture was stirred at room temperature for 30 min. It was then diluted with dichloromethane and washed with water. The organic layer was dried over sodium sulfate, filtered, and concentrated. The residue was purified by HPLC to give the title compound. 1H NMR (400 MHz, DMSO-d6) δ 11.07 (s, 1H), 8.37 (d, J=5.2 Hz, 1H), 8.33 (s, 1H), 8.12 (d, J=2.4 Hz, 1H), 7.99 (dd, J=8.9, 2.5 Hz, 1H), 7.56 (d, J=9.0 Hz, 1H), 7.47 (dd, J=5.3, 1.7 Hz, 1H), 5.14-5.00 (m, 2H), 4.95 (s, 1H), 4.31 (s, 2H), 4.14 (d, J=5.9 Hz, 2H), 4.06 (d, J=14.9 Hz, 2H), 2.70 (dd, J=8.5, 4.3 Hz, 1H), 2.58 (ddd, J=9.9, 6.1, 4.1 Hz, 2H), 2.44 (s, 2H), 1.95 (d, J=6.2 Hz, 2H), 1.63-1.48 (m, 2H). LCMS-ESI+ (m/z): [M+H]+ calcd for C26H25FN6O5: 521.2; found: 521.2.

Example 157: N-(4-(3-cyano-4-(((S)-1-((S)-2,3-dihydroxypropanoyl)-3,3-difluoropiperidin-4-yl)oxy)phenyl)pyridin-2-yl)cyclopropanecarboxamide

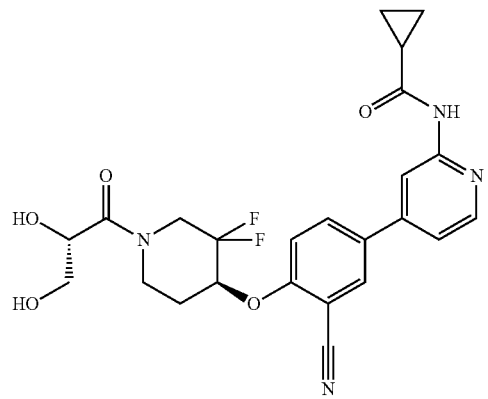 [SMILES: N#Cc1cc(-c2ccnc(NC(=O)C3CC3)c2)ccc1O[C@H]1CCN(C(=O)[C@@H](O)CO)CC1(F)F]

Step 1: Preparation of 5-(2-aminopyridin-4-yl)-2-fluorobenzonitrile: (3-cyano-4-fluorophenyl)boronic acid (500 mg, 3.032 mmol) and 4-bromopyridin-2-amine (575 mg, 3.323 mmol) suspended in dioxane (8 mL) was treated with

[1,1'-Bis(diphenylphosphino)ferrocene]palladium(II) dichloride (222 mg. 0.323 mmol) and sodium carbonate (4400 µL, 8.800 mmol, 2M solution in water). The reaction mixture heated at 90° C. for 1 h. After cooling to room temperature, the reaction mixture was concentrated. The residue was suspended in ethyl acetate and washed with water. The organic layer was dried over sodium sulfate, filtered, and concentrated. The residue was purified by column chromatography to give 5-(2-aminopyridin-4-yl)-2-fluorobenzonitrile.

Step 2: Preparation of tert-butyl (S)-4-(4-(2-aminopyridin-4-yl)-2-cyanophenoxy)-3,3-difluoropiperidine-1-carboxylate: Tert-butyl (S)-3,3-difluoro-4-hydroxypiperidine-1-carboxylate (336 mg, 1.416 mmol) dissolved in 2-methyltetrahydrofuran (10 mL) was cooled to 0° C. and then treated with potassium tert-butoxide (143 mg. 1.275 mmol). The reaction mixture was stirred at 0° C. for 20 min before 5-(2-aminopyridin-4-yl)-2-fluorobenzonitrile (272 mg, 1.276 mmol) was added. The reaction mixture was stirred at room temperature for 5 min and then heated at 60° C. for 30 min. After cooling to room temperature, the reaction mixture was concentrated. The residue was suspended in ethyl acetate and washed with water. The organic layer was concentrated to give tert-butyl (S)-4-(4-(2-aminopyridin-4-yl)-2-cyanophenoxy)-3,3-difluoropiperidine-1-carboxylate.

Step 3: Preparation of tert-butyl (S)-4-(2-cyano-4-(2-(cyclopropanecarboxamido)pyridin-4-yl)phenoxy)-3,3-difluoropiperidine-1-carboxylate: Tert-butyl (S)-4-(4-(2-aminopyridin-4-yl)-2-cyanophenoxy)-3,3-difluoropiperidine-1-carboxylate (270 mg, 0.627 mmol) dissolved in N-methyl-2-pyrrolidone (3 mL) was treated with N,N-diisopropylethylamine (330 µL, 1.895 mmol) and cyclopropanecarbonyl chloride (170 µL, 1.873 mmol). The reaction mixture heated at 60° C. for 20 min. After cooling to room temperature, 7M ammonia in methanol solution (1 mL) was then added dropwise and reaction mixture was stirred at room temperature for 30 min. The reaction mixture was diluted with diethyl ether and washed with water. The organic layer was dried over sodium sulfate, filtered, and concentrated. The residue was purified by column chromatography to give tert-butyl (S)-4-(2-cyano-4-(2-(cyclopropanecarboxamido)pyridin-4-yl)phenoxy)-3,3-difluoropiperidine-1-carboxylate.

Step 4: Preparation of (S)—N-(4-(3-cyano-4-((3,3-difluoropiperidin-4-yl)oxy)phenyl)pyridin-2-yl)cyclopropanecarboxamide: Tert-butyl (S)-4-(2-cyano-4-(2-(cyclopropanecarboxamido)pyridin-4-yl)phenoxy)-3,3-difluoropiperidine-1-carboxylate (330 mg, 0.662 mmol) dissolved in dichloromethane (5 mL) was treated with trifluoroacetic acid (1000 µL, 13.07 mmol). The reaction mixture was stirred at room temperature for 3 h and then concentrated to give (S)—N-(4-(3-cyano-4-((3,3-difluoropiperidin-4-yl)oxy)phenyl)pyridin-2-yl)cyclopropanecarboxamide.

Step 5: Preparation of N-(4-(3-cyano-4-(((S)-1-((S)-2,3-dihydroxypropanoyl)-3,3-difluoropiperidin-4-yl)oxy)phenyl)pyridin-2-yl)cyclopropanecarboxamide: (S)—N-(4-(3-cyano-4-((3,3-difluoropiperidin-4-yl)oxy)phenyl)pyridin-2-yl)cyclopropanecarboxamide (138 mg, 0.346 mmol) dissolved in dimethyl formamide (3 mL) was treated with glyceric acid hemicalcium salt (106 mg, 0.370 mmol) and hydroxybenzotriazole (57 mg, 0.372 mmol). The reaction mixture was stirred at room temperature for 5 min before 1-Ethyl-3-(3-dimethylaminopropyl)carbodiimide (72 mg, 0.376 mmol) was added. The reaction mixture was stirred at room temperature overnight. The reaction mixture was diluted with dichloromethane and washed with water. The organic layer was dried over sodium sulfate, filtered, and concentrated. The residue was purified by HPLC to give the title compound. 1H NMR (400 MHz, DMSO-d6) δ 10.92 (s, 1H), 8.36 (d, J=5.3 Hz, 1H), 8.32 (d, J=1.6 Hz, 1H), 8.13 (d, J=2.4 Hz, 1H), 8.01 (dd, J=8.9, 2.4 Hz, 1H), 7.60 (d, J=9.0 Hz, 1H), 7.44 (dd, J=5.3, 1.7 Hz, 1H), 5.31 (ddt, J=12.7, 8.1, 4.0 Hz, 1H), 4.38 (s, 2H), 4.13 (s, 3H), 3.46 (m, 2H), 2.13 (s, 1H), 2.02 (m, 3H), 0.89 (m, 4H). LCMS-ESI+ (m/z): [M+H]+ calcd for C24H24F2N4O5: 487.2; found: 487.2.

Example 158: (S)-2-(4-(2-cyano-4-(6-(cyclopropanecarboxamido)pyrimidin-4-yl)phenoxy)-3,3-difluoropiperidin-1-yl)-2-oxoethyl dihydrogen phosphate

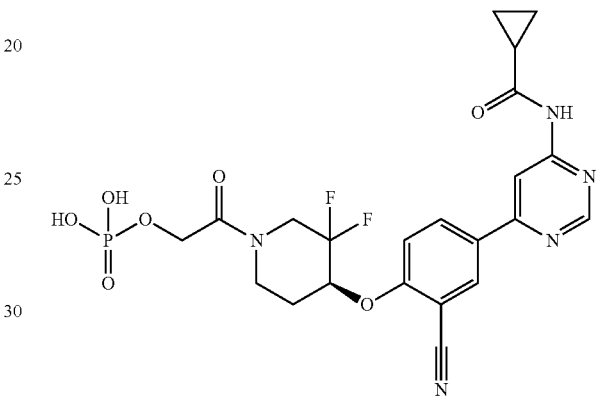

To solution (S)—N-(6-(3-cyano-4-((3,3-difluoro-1-(2-hydroxyacetyl)piperidin-4-yl)oxy)phenyl)pyrimidin-4-yl)cyclopropanecarboxamide (208 mg, 0.45 mmol) in DCM/2-methyltetrahydrofuran/DMF, 1-tetrazole (350 mgs, 5 mmol) and di-tert-butyl diethylphosphoramidite (340 mg, 1.36 mmol) was added and stirred at rt for 1 h. The mixture was then cooled to −45° C., and mCPBA (235 mg) was added and stirred at that temperature for 5 min and then at rt for 2 h. The reaction mixture was then diluted with DCM and washed with sat'd NaHCO₃ and dried (MgSO₄). The mixture was then filtered, concentrated and purified silica gel column chromatography with ethyl acetate to give (S)-di-tert-butyl-(2-(4-(2-cyano-4-(6-(cyclopropanecarboxamido)pyrimidin-4-yl)phenoxy)-3,3-difluoropiperidin-1-yl)-2-oxoethyl) phosphate.

To a solution of (S)-di-tert-butyl-(2-(4-(2-cyano-4-(6-(cyclopropanecarboxamido)pyrimidin-4-yl)phenoxy)-3,3-difluoropiperidin-1-yl)-2-oxoethyl) phosphate in DCM (2 mL) was added 4.0M HCl in dioxane (0.7 mL) and stirred at rt for 30 min and reaction mixture was diluted with diethyl ether and stirred at rt for 16 h. The resulting solids were filtered, washed with ether and dried to give the title compound. LCMS-ESI+ (m/z): [M+H]+ calcd for $C_{22}H_{22}F_2N_5O_7P$ 537.4. found: 538.1. 1H NMR (400 MHz, DMSO-d6) δ 11.36 (s, 1H), 8.93 (d, J=1.2 Hz, 1H), 8.53 (d, J=1.2 Hz, 1H), 8.45-8.28 (m, 2H), 7.63 (d, J=9.1 Hz, 1H), 5.36 (dd, J=13.4, 7.7 Hz, 1H), 4.57 (dd, J=16.1, 7.9 Hz, 2H), 4.06-3.60 (br m, 6H), 2.23-1.81 (m, 3H), 0.93-0.78 (m, 4H).

Example 159: 2-((S)-4-(2-cyano-4-(6-(cyclopropanecarboxamido)pyrimidin-4-yl)phenoxy)-3,3-difluoropiperidin-1-yl)-2-oxoethyl L-Alaninate

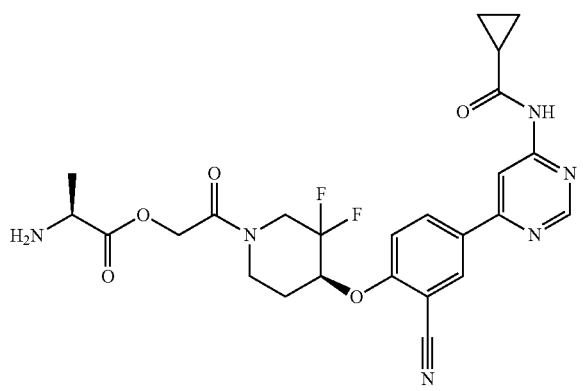 [SMILES: C[C@H](N)C(=O)OCC(=O)N1CC[C@H](Oc2ccc(-c3cc(NC(=O)C4CC4)ncn3)cc2C#N)C(F)(F)C1]

To solution (S)—N-(6-(3-cyano-4-((3,3-difluoro-1-(2-hydroxyacetyl)piperidin-4-yl)oxy)phenyl)pyrimidin-4-yl)cyclopropanecarboxamide (50 mgs, 0.11 mmol), Boc-Ala-OH (104 mgs, 0.27 mmol) and HATU (104 mgs, 0.27 mmol) in DMF (1 mL) was added DMAP (13 mgs, 0.55 mmol) and DIPEA (0.1 mL) and stirred at rt for 16 h. The mixture was then concentrated and purified silica gel column chromatography (0-3% Methanol/ethyl acetate) to give 2-((S)-4-(2-cyano-4-(6-(cyclopropanecarboxamido)pyrimidin-4-yl)phenoxy)-3,3-difluoropiperidin-1-yl)-2-oxoethyl (tert-butoxycarbonyl)-L-alaninate which was then treated with 4.0M HCl in dioxane (0.5 mL) in DCM (2 mL) was added and stirred at rt for 1 h The resulting reaction mixture was then stirred at rt for 1 h and concentrated and dried to give the title compound. LCMS-ESI+ (m/z): [M+H]+ calcd for $C_{25}H_{26}F_2N_6O_5$ 528. Found: 529.1.

Example 160: 2-((S)-4-(2-cyano-4-(6-(cyclopropanecarboxamido)pyrimidin-4-yl)phenoxy)-3,3-difluoropiperidin-1-yl)-2-oxoethyl D-Alaninate

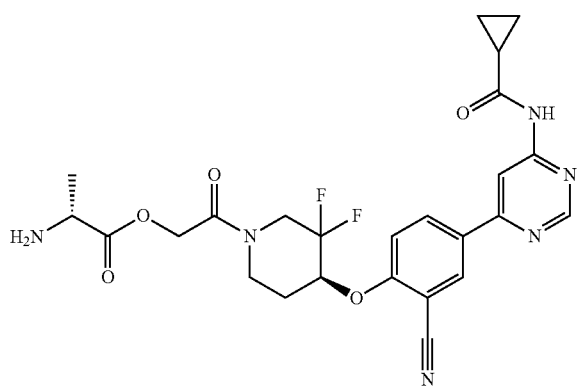 [SMILES: C[C@@H](N)C(=O)OCC(=O)N1CC[C@H](Oc2ccc(-c3cc(NC(=O)C4CC4)ncn3)cc2C#N)C(F)(F)C1]

To solution (S)—N-(6-(3-cyano-4-((3,3-difluoro-1-(2-hydroxyacetyl)piperidin-4-yl)oxy)phenyl)pyrimidin-4-yl)cyclopropanecarboxamide (50 mg, 0.11 mmol), (tert-butoxycarbonyl)-D-alanine (52 mg, 0.27 mmol) and HATU (104 mg, 0.27 mmol) in DMF (1 mL) was added DMAP (14 mg, 0.55 mmol) and DIPEA (0.1 mL) and stirred at rt for 16 h. The mixture was then concentrated and purified silica gel column chromatography (0-3% Methanol/ethyl acetate) to give 2-((S)-4-(2-cyano-4-(6-(cyclopropanecarboxamido)pyrimidin-4-yl)phenoxy)-3,3-difluoropiperidin-1-yl)-2-oxoethyl (tert-butoxycarbonyl)-D-alaninate which was then treated with 4.0M HCl in dioxane (0.5 mL) in DCM (2 mL). The resulting reaction mixture was then stirred at rt for 1 h and concentrated and dried to give the title compound. LCMS-ESI+ (m/z): [M+H]+ calcd for $C_{25}H_{26}F_2N_6O_5$ 528. Found: 529.1.

Biological Assay for TBK1 and IKKε:

Enzymatic activity of IKKε and TBK1 was measured using a homogeneous time resolved fluorescence resonance energy transfer (TR-FRET) assay that monitors enzyme dependent phosphorylation of a biotinylated serine/threonine peptide substrate. An increase in the amount of phosphorylated peptide results in an increase in TR-FRET signal. TBK1 and IKKε were expressed and purified as full length recombinant proteins. Detection reagents for the assay were purchased from Cisbio. TBK1 and IKKε enzymes were assayed under initial rate conditions in the presence of 2×Km ATP (40-80 μM) and 1 μM peptide, hepes (pH 7), 0.1 mM orthovanadate, 0.02% $NaN_3$, 0.01% BSA, 10 mM $MgCl2$, 0.01% (v/v) tritonX, 1 mM dithiothreitol, 0.5% (v/v) DMSO at the following concentrations for each enzyme: TBK1 at 2.5 nM and IKKε at 0.3 nM. After an assay reaction time of 240 minutes at 25° C., reactions were terminated with EDTA.

Amount of phosphorylated peptide was determined by the addition of 125 nM streptavidin XL665 and europium cryptate labeled anti-phospho monoclonal antibody and the resulting TR-FRET signal was recorded on an Envision plate reader (Ex: 340 nm; Em: 615/665 nm; 100 μs delay and 200 μs read window). Data was normalized based on a positive (1 μM Staurosporine) and negative (DMSO) controls and $IC_{50}$ values calculated from the fit of the dose-response curves to a four-parameter equation. All IC50 values represent geometric mean values of a minimum of four determinations. These assays generally produced results within 3-fold of the reported mean.

Results

Table 1 below depicts IKKε-IC50 (nM) and TBK1-$IC_{50}$ (nM) values for the compounds described herein.

| Example | Structure | TBK1-IC$_{50}$ (nM) | IKKε IC$_{50}$ (nM) |
|---|---|---|---|
| 1 | 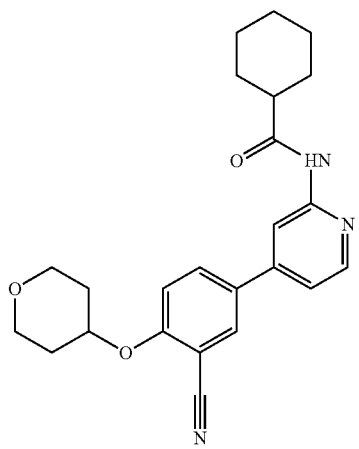 [SMILES: N#Cc1cc(-c2ccnc(NC(=O)C3CCCCC3)c2)ccc1OC1CCOCC1] | 755.1 | 330.9 |
| 2 | 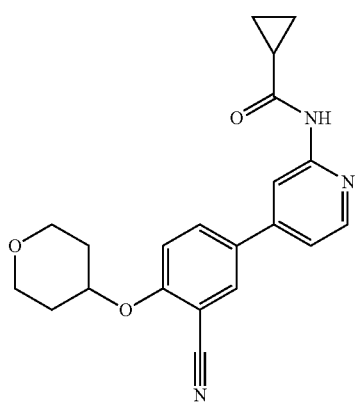 [SMILES: N#Cc1cc(-c2ccnc(NC(=O)C3CC3)c2)ccc1OC1CCOCC1] | 28.1 | 115.0 |
| 3 | 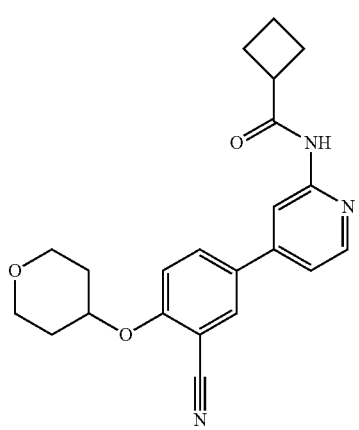 [SMILES: N#Cc1cc(-c2ccnc(NC(=O)C3CCC3)c2)ccc1OC1CCOCC1] | 334.5 | 284.1 |

-continued

| Example | Structure | TBK1-IC$_{50}$ (nM) | IKKε IC$_{50}$ (nM) |
|---------|-----------|---------------------|---------------------|
| 4 | 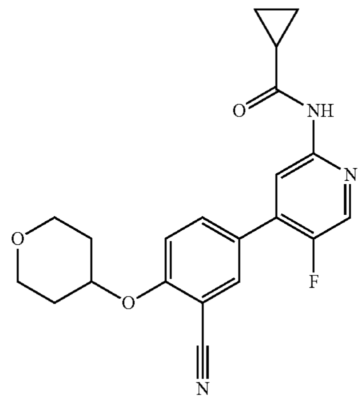 [SMILES: N#Cc1cc(-c2cc(NC(=O)C3CC3)ncc2F)ccc1OC1CCOCC1] | 43.6 | 327.4 |
| 5 | 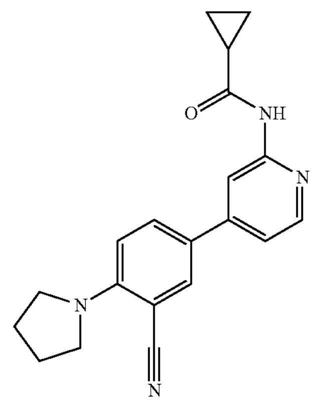 [SMILES: N#Cc1cc(-c2ccnc(NC(=O)C3CC3)c2)ccc1N1CCCC1] | 13.9 | 68.2 |
| 6 | 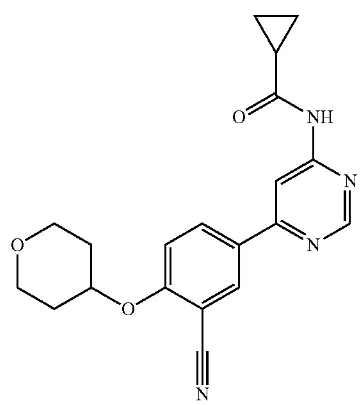 [SMILES: N#Cc1cc(-c2cc(NC(=O)C3CC3)ncn2)ccc1OC1CCOCC1] | 48.5 | 297.6 |
| 7 | 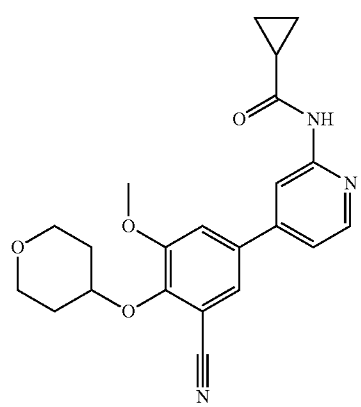 [SMILES: COc1cc(-c2ccnc(NC(=O)C3CC3)c2)cc(C#N)c1OC1CCOCC1] | 491.6 | >1000 |

-continued
| Example | Structure | TBK1-IC$_{50}$ (nM) | IKKε IC$_{50}$ (nM) |
|---|---|---|---|
| 8 | 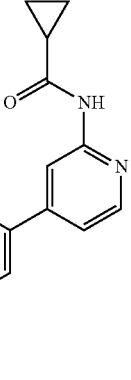 | 10.4 | 25.1 |
| 9 | 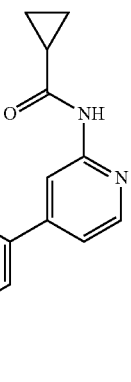 | 15.2 | 46.4 |
| 10 | 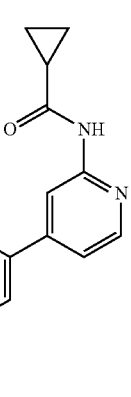 | 4.2 | 7.4 |
| 11 | 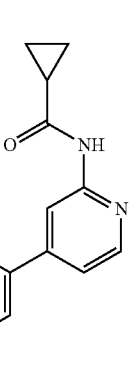 | 10.2 | 26.3 |

-continued

| Example | Structure | TBK1-IC$_{50}$ (nM) | IKKε IC$_{50}$ (nM) |
|---|---|---|---|
| 12 | 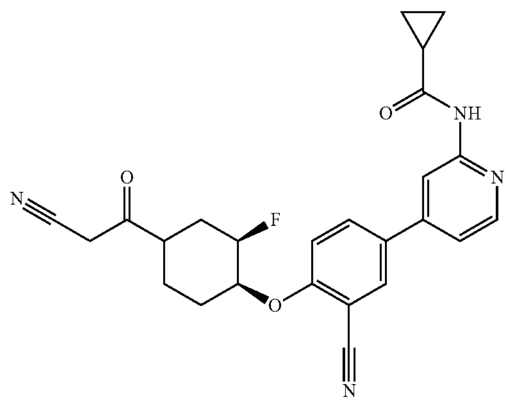 | 37.3 | 121.5 |
| 13 | 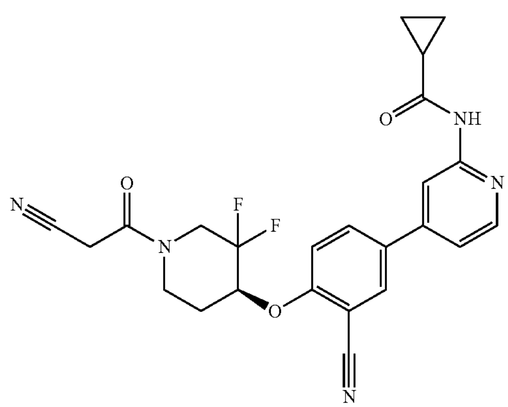 [SMILES: N#CCC(=O)N1CC[C@H](Oc2ccc(-c3ccnc(NC(=O)C4CC4)c3)cc2C#N)C(F)(F)C1] | 12.4 | 44.0 |
| 14 | 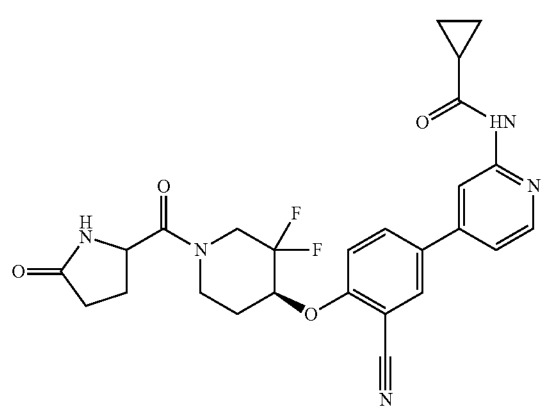 [SMILES: N#Cc1cc(-c2ccnc(NC(=O)C3CC3)c2)ccc1O[C@H]1CCN(C(=O)C2CCC(=O)N2)CC1(F)F] | 5.5 | 18.5 |

-continued

| Example | Structure | TBK1-IC$_{50}$ (nM) | IKKε IC$_{50}$ (nM) |
|---|---|---|---|
| 15 | 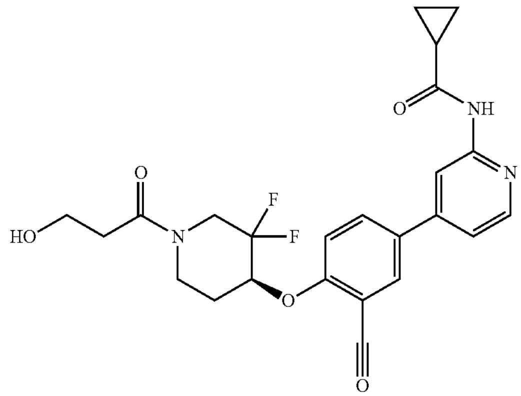 | 23.2 | 84.2 |
| 16 | 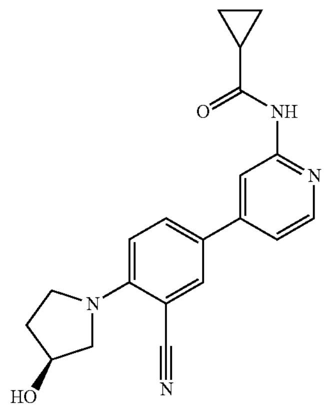 [SMILES: N#Cc1cc(-c2ccnc(NC(=O)C3CC3)c2)ccc1N1CC[C@H](O)C1] | 52.3 | 353.2 |
| 17 | 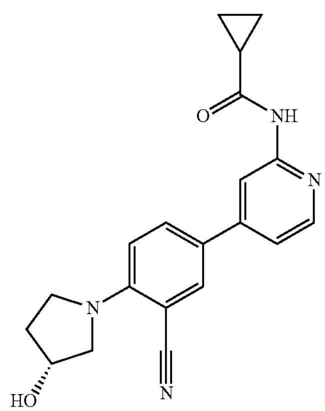 [SMILES: N#Cc1cc(-c2ccnc(NC(=O)C3CC3)c2)ccc1N1CC[C@@H](O)C1] | 41.6 | 231.8 |
| 18 | 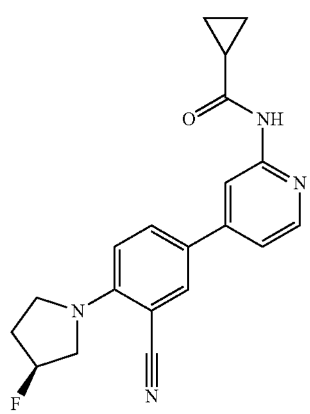 [SMILES: N#Cc1cc(-c2ccnc(NC(=O)C3CC3)c2)ccc1N1CC[C@H](F)C1] | 20.3 | 61.3 |

-continued

| Example | Structure | TBK1-IC$_{50}$ (nM) | IKKε IC$_{50}$ (nM) |
|---|---|---|---|
| 19 | 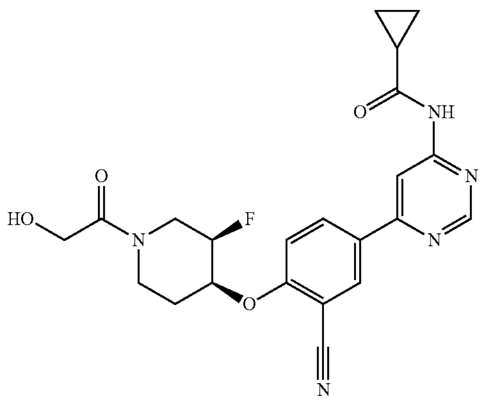 | 15.6 | 53.1 |
| 20 | 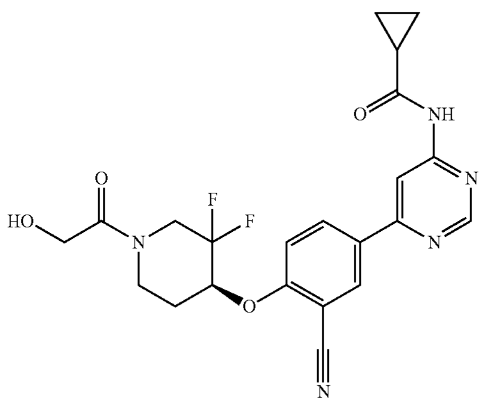 | 4.8 | 9.5 |
| 21 | 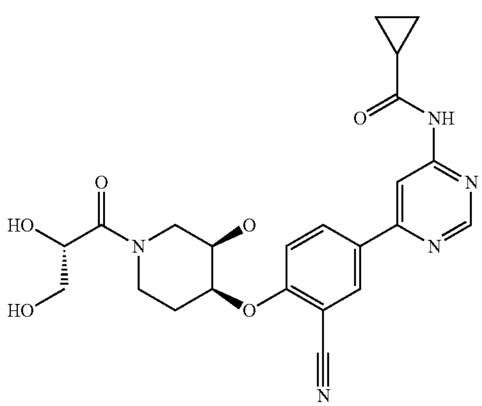 | 6.1 | 31.3 |
| 22 | 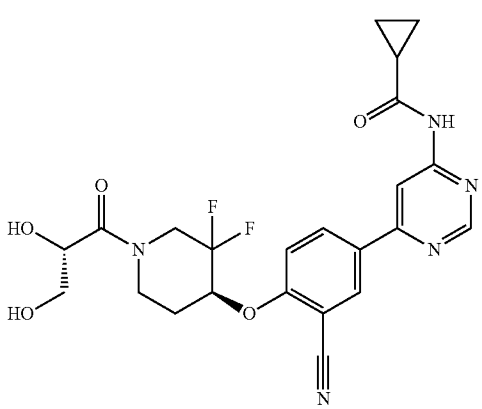 [SMILES: N#Cc1cc(-c2cc(NC(=O)C3CC3)ncn2)ccc1O[C@H]1CCN(C(=O)[C@@H](O)CO)CC1(F)F] | 2.8 | 9.0 |

-continued

| Example | Structure | TBK1-IC$_{50}$ (nM) | IKKε IC$_{50}$ (nM) |
|---|---|---|---|
| 23 | 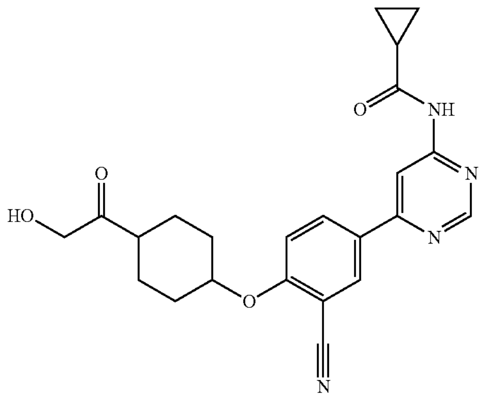 | 66.1 | 160.1 |
| 24 | 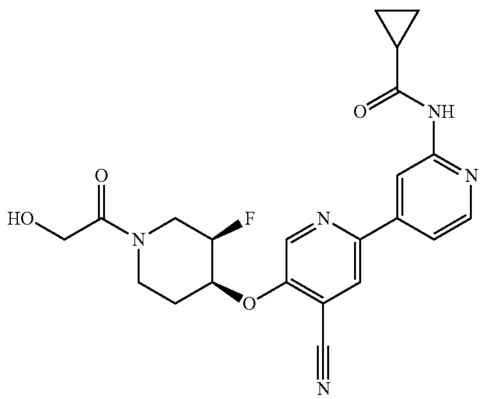 | 86.1 | 191.9 |
| 25 | 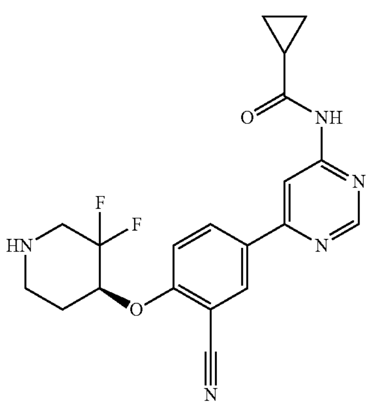 [SMILES: N#Cc1cc(-c2cc(NC(=O)C3CC3)ncn2)ccc1O[C@H]1CCNCC1(F)F] | 93.3 | 297.4 |
| 26 | 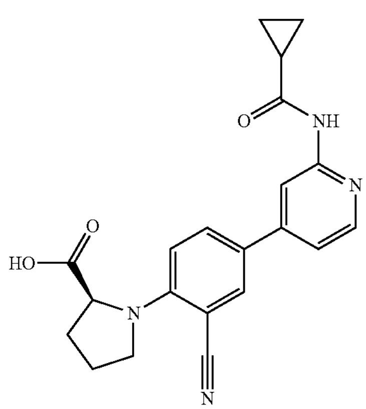 [SMILES: N#Cc1cc(-c2ccnc(NC(=O)C3CC3)c2)ccc1N1CCC[C@H]1C(=O)O] | 755.0 | >1000 |

-continued

| Example | Structure | TBK1-IC$_{50}$ (nM) | IKKε IC$_{50}$ (nM) |
|---|---|---|---|
| 27 | 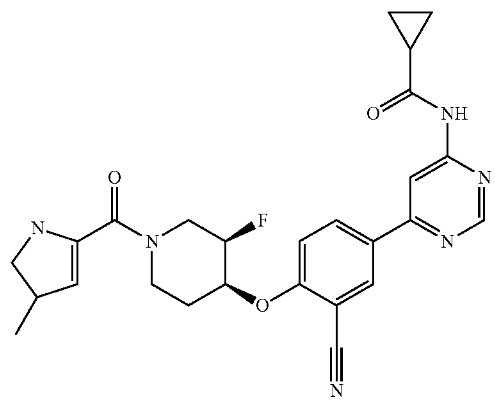 [SMILES: CC1C=C(C(=O)N2CC[C@H](Oc3ccc(-c4cc(NC(=O)C5CC5)ncn4)cc3C#N)[C@H](F)C2)NC1] | 18.1 | 29.6 |
| 28 | 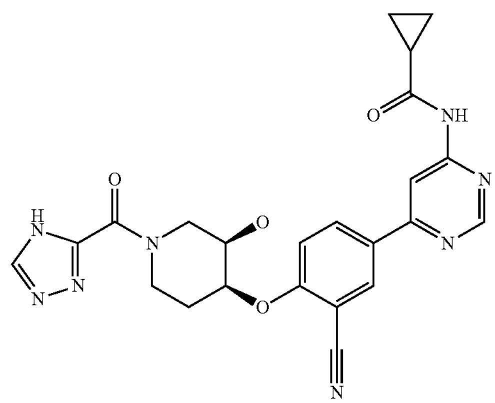 [SMILES: N#Cc1cc(-c2cc(NC(=O)C3CC3)ncn2)ccc1O[C@H]1CCN(C(=O)c2nnc[nH]2)C[C@H]1O] | 8.0 | 12.4 |
| 29 | 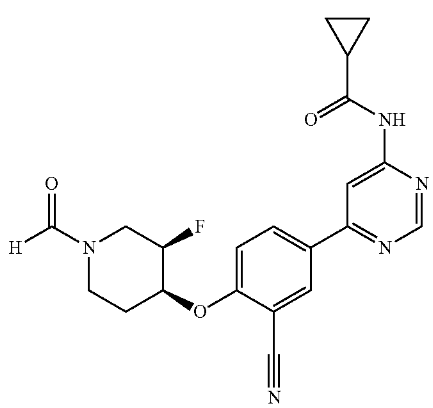 [SMILES: N#Cc1cc(-c2cc(NC(=O)C3CC3)ncn2)ccc1O[C@H]1CCN(C=O)C[C@H]1F] | 46.6 | 127.7 |
| 30 | 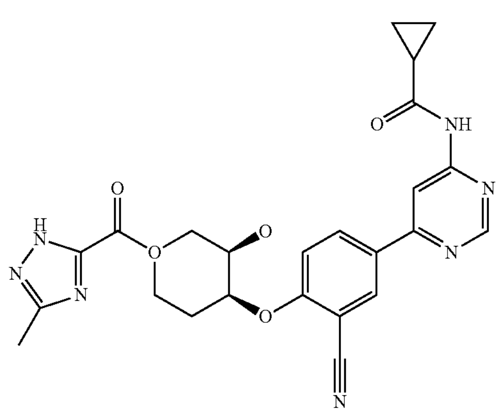 | 7.2 | 7.4 |

-continued

| Example | Structure | TBK1-IC$_{50}$ (nM) | IKKε IC$_{50}$ (nM) |
|---|---|---|---|
| 31 | 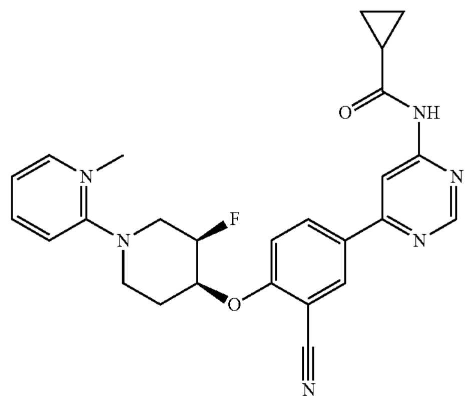 | >1000 | >1000 |
| 32 | 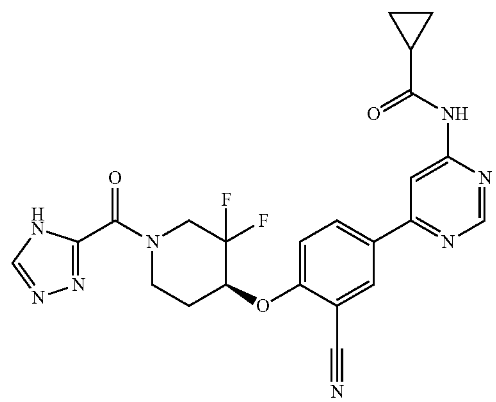 [SMILES: N#Cc1cc(-c2cc(NC(=O)C3CC3)ncn2)ccc1O[C@H]1CCN(C(=O)c2nnc[nH]2)CC1(F)F] | 5.6 | 7.1 |
| 33 | 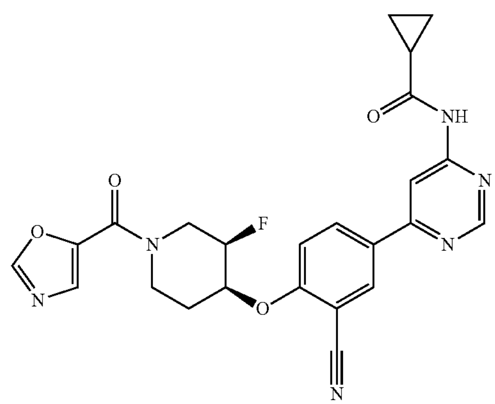 [SMILES: N#Cc1cc(-c2cc(NC(=O)C3CC3)ncn2)ccc1O[C@H]1CCN(C(=O)c2cnco2)C[C@H]1F] | 47.6 | 167.3 |
| 34 | 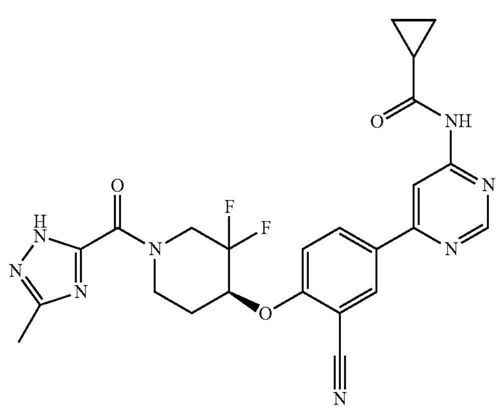 [SMILES: Cc1n[nH]c(C(=O)N2CC[C@H](Oc3ccc(-c4cc(NC(=O)C5CC5)ncn4)cc3C#N)C(F)(F)C2)n1] | 4.2 | 4.6 |

| Example | Structure | TBK1-IC$_{50}$ (nM) | IKKε IC$_{50}$ (nM) |
|---|---|---|---|
| 35 | 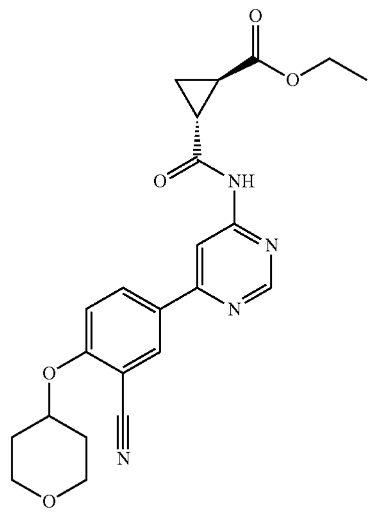 [SMILES: CCOC(=O)[C@@H]1C[C@H]1C(=O)Nc1cc(-c2ccc(OC3CCOCC3)c(C#N)c2)ncn1] | 484.7 | >1000 |
| 36 | 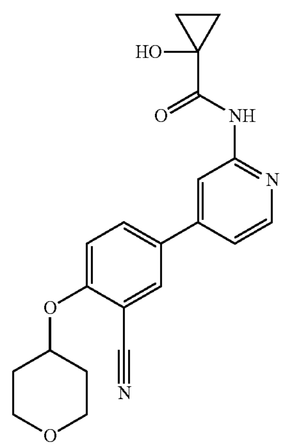 [SMILES: N#Cc1cc(-c2ccnc(NC(=O)C3(O)CC3)c2)ccc1OC1CCOCC1] | >1000 | >1000 |
| 37 | 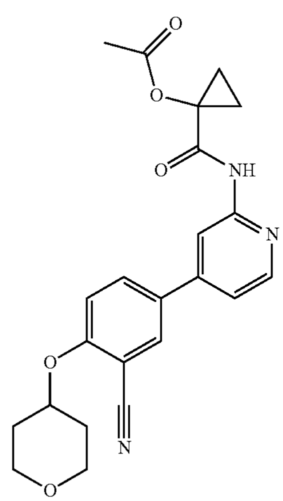 [SMILES: CC(=O)OC1(C(=O)Nc2cc(-c3ccc(OC4CCOCC4)c(C#N)c3)ccn2)CC1] | >1000 | >1000 |

-continued
| Example | Structure | TBK1-IC$_{50}$ (nM) | IKKε IC$_{50}$ (nM) |
|---|---|---|---|
| 38 | 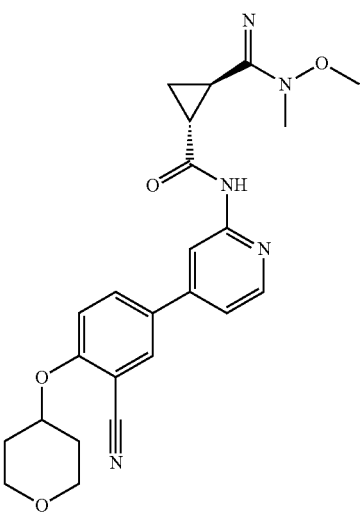 [SMILES: CON(C)C(=N)[C@@H]1C[C@H]1C(=O)Nc1cc(-c2ccc(OC3CCOCC3)c(C#N)c2)ccn1] | 305.4 | 253.0 |
| 39 | 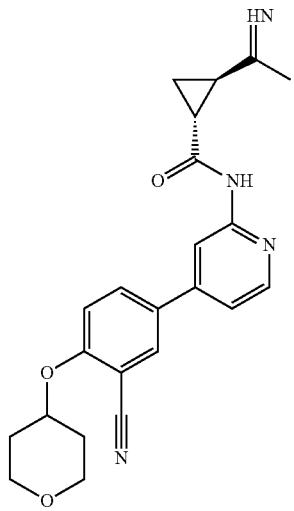 [SMILES: CC(=N)[C@@H]1C[C@H]1C(=O)Nc1cc(-c2ccc(OC3CCOCC3)c(C#N)c2)ccn1] | 96.3 | 73.2 |
| 40 | 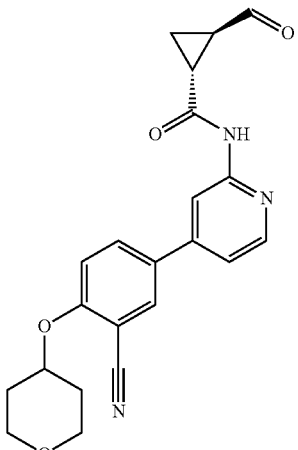 | 61.5 | 65.0 |

| Example | Structure | TBK1-IC$_{50}$ (nM) | IKKε IC$_{50}$ (nM) |
|---|---|---|---|
| 41 | 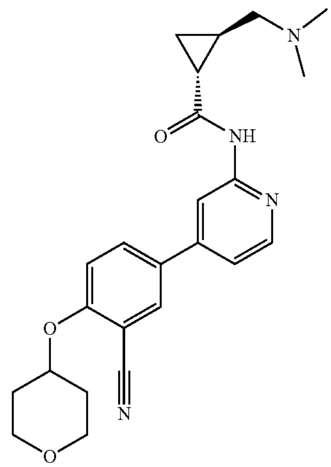 [SMILES: CN(C)C[C@@H]1C[C@H]1C(=O)Nc1cc(-c2ccc(OC3CCOCC3)c(C#N)c2)ccn1] | 267.4 | 80.3 |
| 42 | 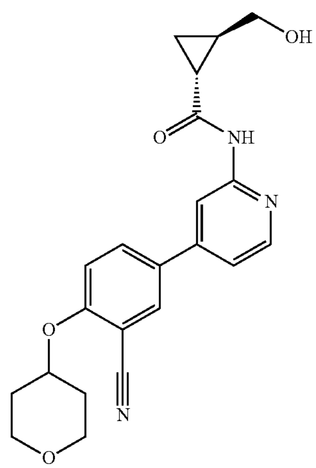 [SMILES: N#Cc1cc(-c2ccnc(NC(=O)[C@@H]3C[C@H]3CO)c2)ccc1OC1CCOCC1] | 62.1 | 48.2 |
| 43 | 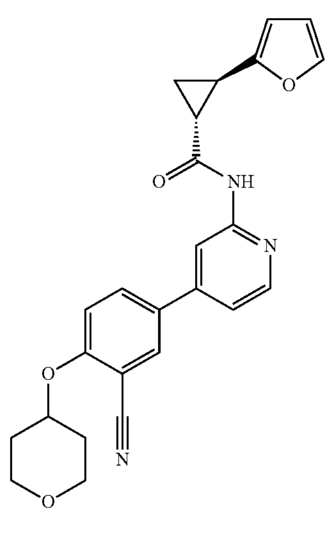 [SMILES: N#Cc1cc(-c2ccnc(NC(=O)[C@@H]3C[C@H]3c3ccco3)c2)ccc1OC1CCOCC1] | 61.3 | 146.1 |

-continued

| Example | Structure | TBK1-IC$_{50}$ (nM) | IKKε IC$_{50}$ (nM) |
|---|---|---|---|
| 44 | 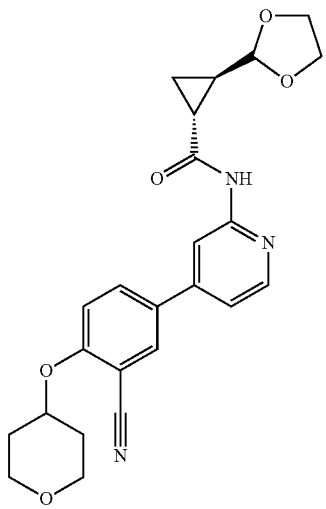 [SMILES: N#Cc1cc(-c2ccnc(NC(=O)[C@@H]3C[C@H]3C3OCCO3)c2)ccc1OC1CCOCC1] | 33.3 | 192.5 |
| 45 | 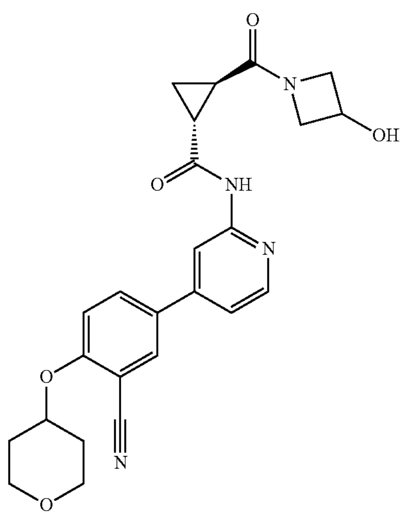 [SMILES: N#Cc1cc(-c2ccnc(NC(=O)[C@@H]3C[C@H]3C(=O)N3CC(O)C3)c2)ccc1OC1CCOCC1] | 444.4 | 426.8 |
| 46 | 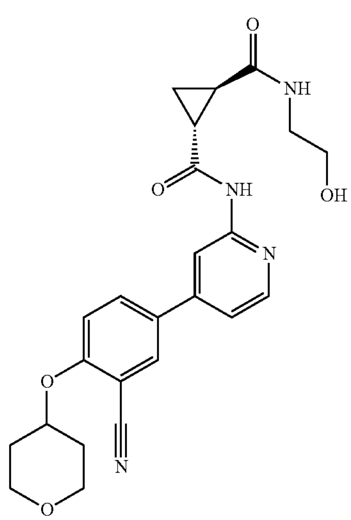 [SMILES: N#Cc1cc(-c2ccnc(NC(=O)[C@@H]3C[C@H]3C(=O)NCCO)c2)ccc1OC1CCOCC1] | 301.7 | 428.8 |

| Example | Structure | TBK1-IC$_{50}$ (nM) | IKKε IC$_{50}$ (nM) |
|---|---|---|---|
| 47 | 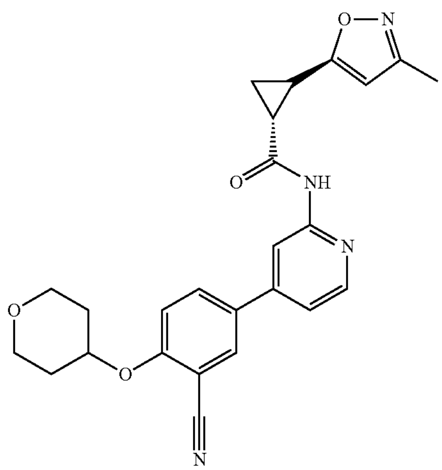 | 29.4 | 269.4 |
| 48 | 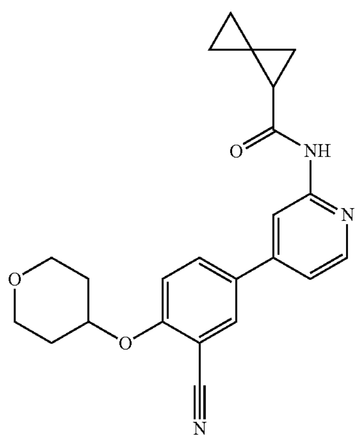 [SMILES: N#Cc1cc(-c2ccnc(NC(=O)C3CC34CC4)c2)ccc1OC1CCOCC1] | 268.2 | 512.1 |
| 49 | 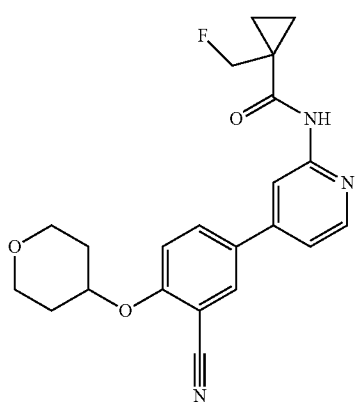 [SMILES: N#Cc1cc(-c2ccnc(NC(=O)C3(CF)CC3)c2)ccc1OC1CCOCC1] | >1000 | >1000 |

-continued

| Example | Structure | TBK1-IC$_{50}$ (nM) | IKKε IC$_{50}$ (nM) |
|---|---|---|---|
| 50 | 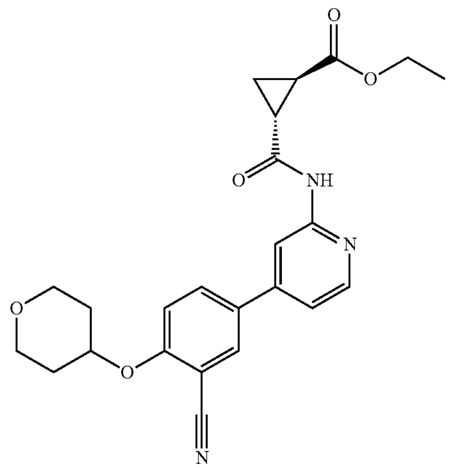 [SMILES: CCOC(=O)[C@@H]1C[C@H]1C(=O)Nc1cc(-c2ccc(OC3CCOCC3)c(C#N)c2)ccn1] | 230.4 | 535.4 |
| 51 | 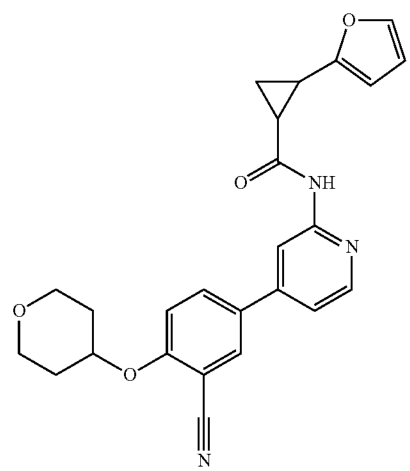 [SMILES: N#Cc1cc(-c2ccnc(NC(=O)C3CC3c3ccco3)c2)ccc1OC1CCOCC1] | 57.8 | 425.9 |
| 52 | 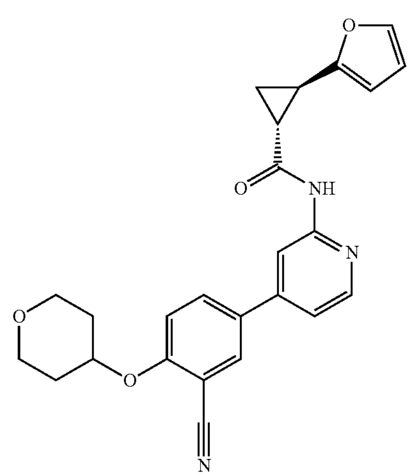 [SMILES: N#Cc1cc(-c2ccnc(NC(=O)[C@@H]3C[C@H]3c3ccco3)c2)ccc1OC1CCOCC1] | 60.1 | 837.6 |

-continued

| Example | Structure | TBK1-IC$_{50}$ (nM) | IKKε IC$_{50}$ (nM) |
|---------|-----------|---------------------|----------------------|
| 53 | 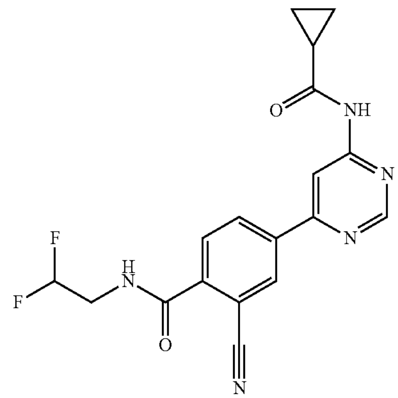 [SMILES: N#Cc1cc(-c2cc(NC(=O)C3CC3)ncn2)ccc1C(=O)NCC(F)F] | 761.7 | >1000 |
| 54 | 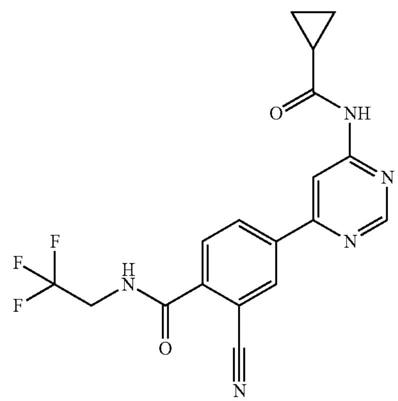 [SMILES: N#Cc1cc(-c2cc(NC(=O)C3CC3)ncn2)ccc1C(=O)NCC(F)(F)F] | 883.3 | >1000 |
| 55 | 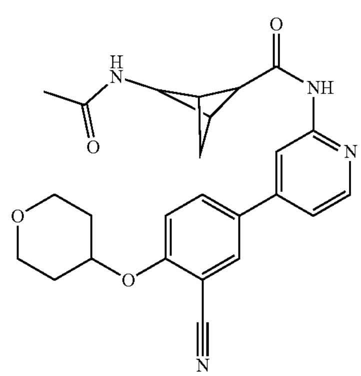 [SMILES: CC(=O)NC1C2CC1C2C(=O)Nc1cc(-c2ccc(OC3CCOCC3)c(C#N)c2)ccn1] | >1000 | >1000 |

-continued
| Example | Structure | TBK1-IC$_{50}$ (nM) | IKKε IC$_{50}$ (nM) |
|---------|-----------|---------------------|---------------------|
| 56 | 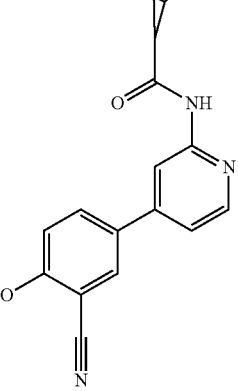 | >1000 | 443.7 |
| 57 | 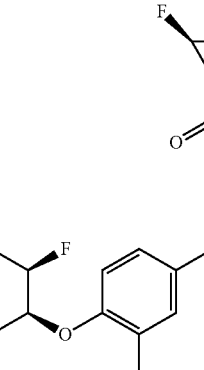 | 17.0 | 26.2 |
| 58 | 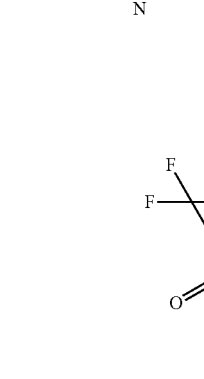 | 48.6 | 30.1 |

-continued
| Example | Structure | TBK1-IC50 (nM) | IKKε IC50 (nM) |
|---|---|---|---|
| 59 | 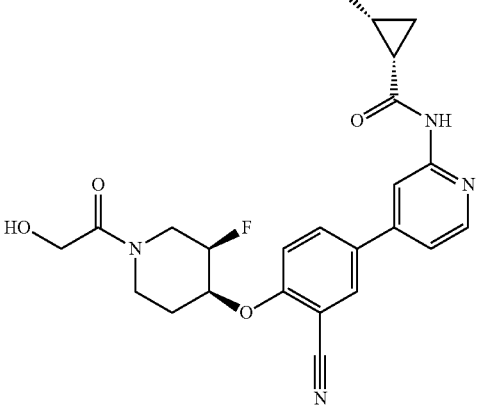 | 33.8 | 39.7 |
| 60 | 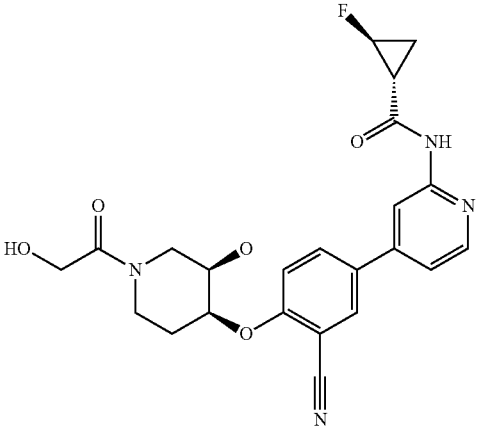 [SMILES: N#Cc1cc(-c2ccnc(NC(=O)[C@H]3C[C@@H]3F)c2)ccc1O[C@H]1CCN(C(=O)CO)C[C@H]1O] | 15.7 | 46.3 |
| 61 | 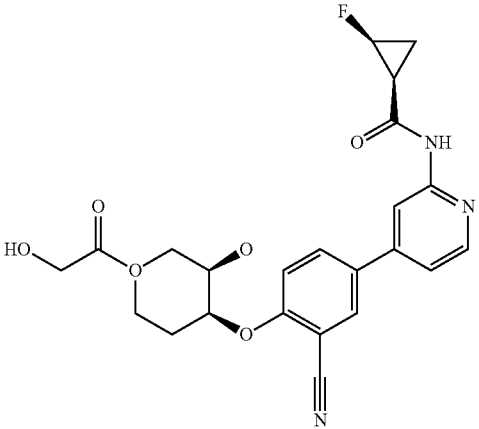 | 16.4 | 32.2 |

-continued
| Example | Structure | TBK1-IC$_{50}$ (nM) | IKKϵ IC$_{50}$ (nM) |
|---|---|---|---|
| 62 | 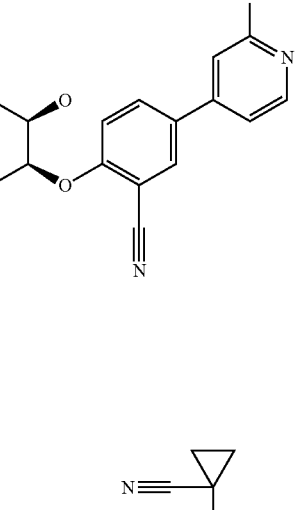 | 16.7 | 16.2 |
| 63 | 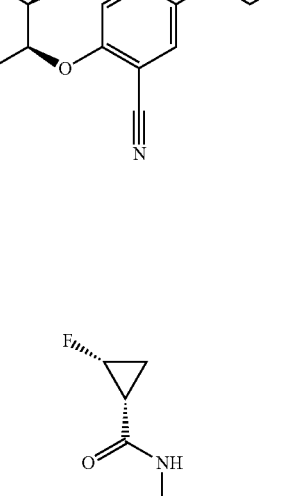 | >1000 | >1000 |
| 64 | 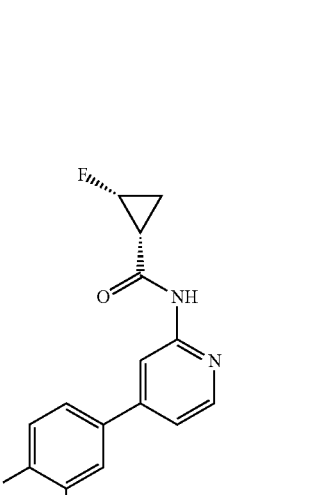 | 85.3 | 578.2 |

| Example | Structure | TBK1-IC$_{50}$ (nM) | IKKε IC$_{50}$ (nM) |
|---|---|---|---|
| 65 | 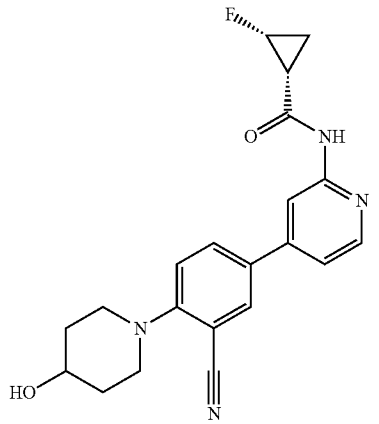 [SMILES: N#Cc1cc(-c2ccnc(NC(=O)[C@H]3C[C@H]3F)c2)ccc1N1CCC(O)CC1] | 469.8 | >1000 |
| 66 | 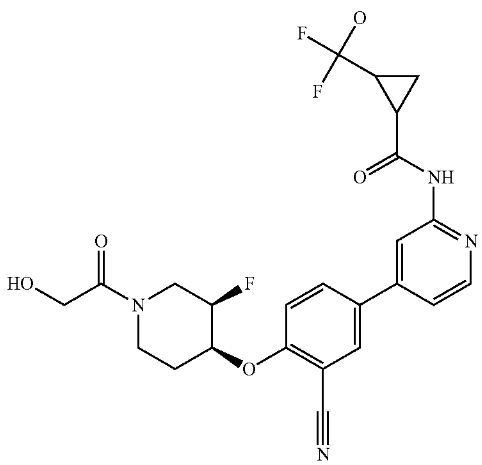 [SMILES: N#Cc1cc(-c2ccnc(NC(=O)C3CC3C(O)(F)F)c2)ccc1O[C@H]1CCN(C(=O)CO)C[C@H]1F] | 28.3 | 107.5 |
| 67 | 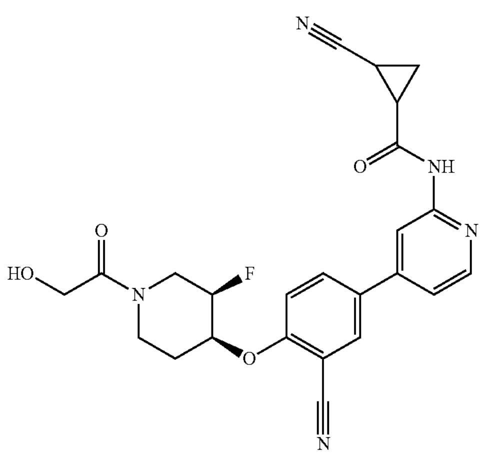 [SMILES: N#Cc1cc(-c2ccnc(NC(=O)C3CC3C#N)c2)ccc1O[C@H]1CCN(C(=O)CO)C[C@H]1F] | 26.1 | 68.4 |

-continued
| Example | Structure | TBK1-IC$_{50}$ (nM) | IKKε IC$_{50}$ (nM) |
|---|---|---|---|
| 68 | 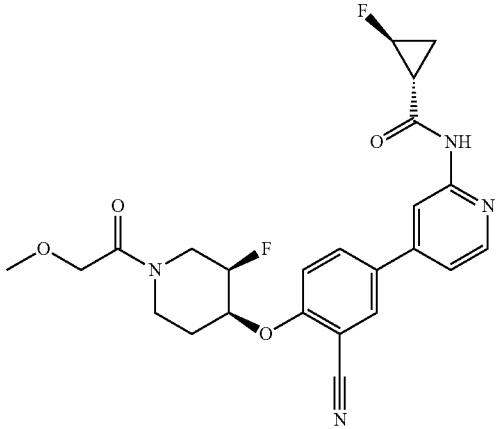 [SMILES: COCC(=O)N1CC[C@H](Oc2ccc(-c3ccnc(NC(=O)[C@H]4C[C@@H]4F)c3)cc2C#N)[C@H](F)C1] | 34.2 | 87.8 |
| 69 | 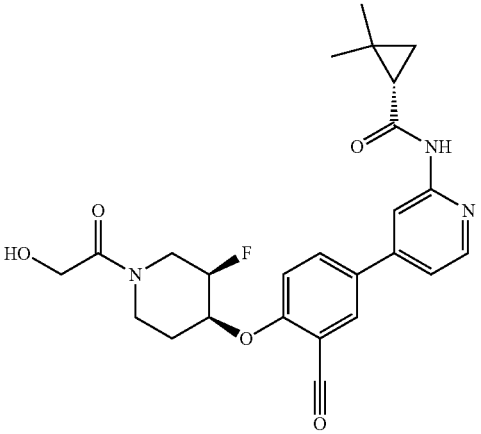 | 43.9 | 133.2 |
| 70 | 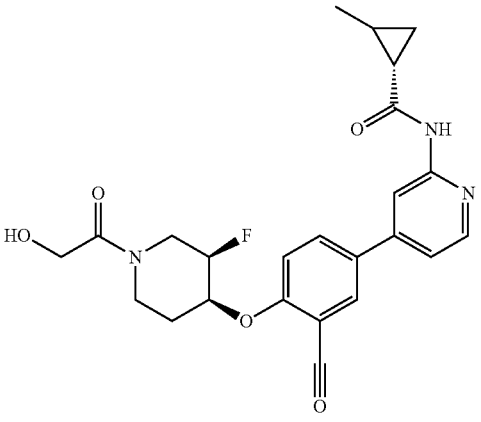 | 8.9 | 26.1 |

| Example | Structure | TBK1-IC$_{50}$ (nM) | IKKε IC$_{50}$ (nM) |
|---|---|---|---|
| 71 | 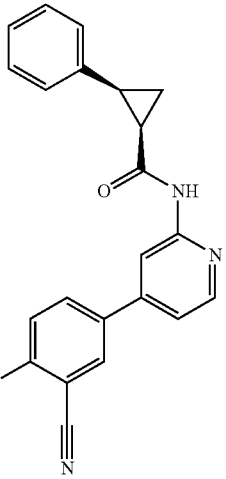 | 51.4 | 116.6 |
| 72 | 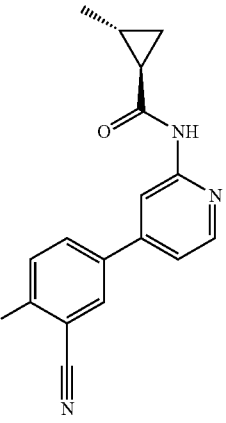 | 16.5 | 43.7 |
| 73 | 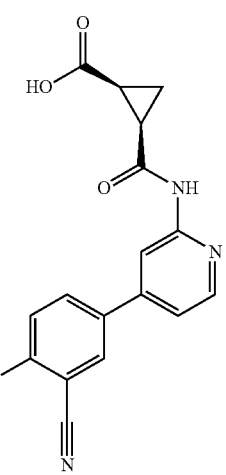 | 739.6 | >1000 |

| Example | Structure | TBK1-IC$_{50}$ (nM) | IKKε IC$_{50}$ (nM) |
|---------|-----------|---------------------|---------------------|
| 74 | 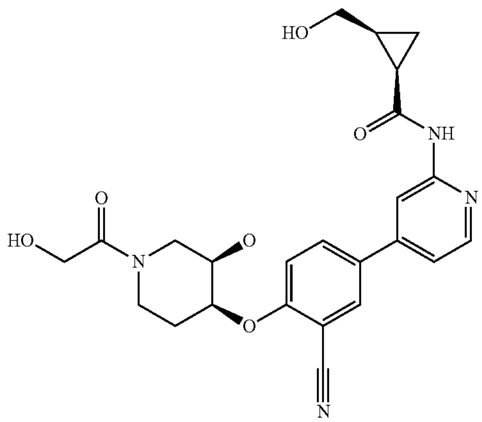 [SMILES: N#Cc1cc(-c2ccnc(NC(=O)[C@@H]3C[C@@H]3CO)c2)ccc1O[C@H]1CCN(C(=O)CO)C[C@H]1O] | 99.3 | 145.2 |
| 75 | 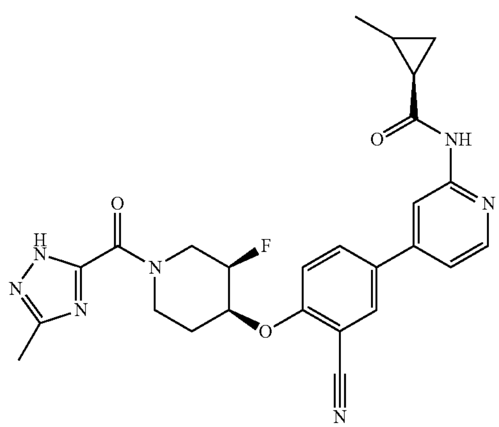 [SMILES: Cc1n[nH]c(C(=O)N2CC[C@H](Oc3ccc(-c4ccnc(NC(=O)[C@@H]5CC5C)c4)cc3C#N)[C@H](F)C2)n1] | 6.1 | 7.1 |
| 76 | 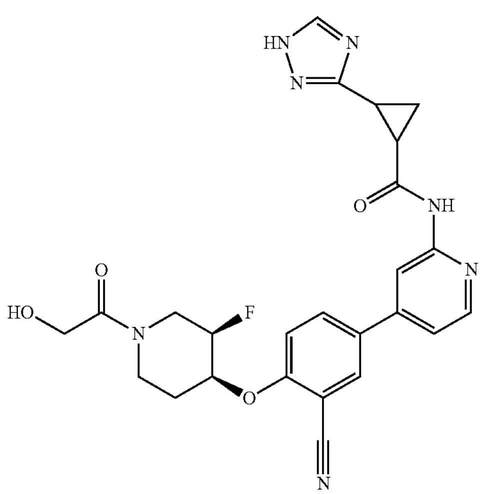 [SMILES: N#Cc1cc(-c2ccnc(NC(=O)C3CC3c3nc[nH]n3)c2)ccc1O[C@H]1CCN(C(=O)CO)C[C@H]1F] | 256.3 | 356.8 |

-continued

| Example | Structure | TBK1-IC$_{50}$ (nM) | IKKε IC$_{50}$ (nM) |
|---|---|---|---|
| 77 | 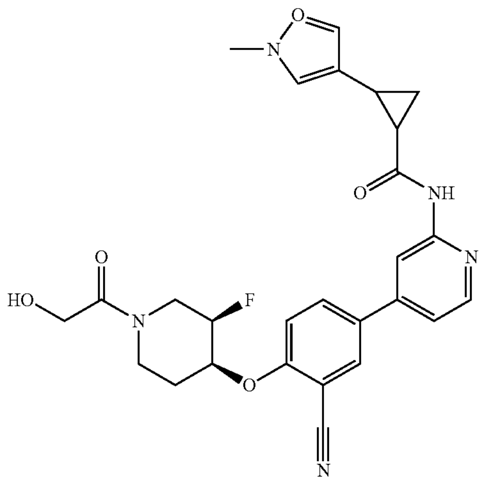 | 10.3 | 24.7 |
| 78 | 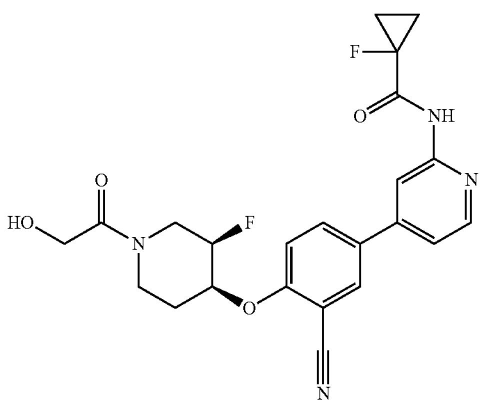 [SMILES: N#Cc1cc(-c2ccnc(NC(=O)C3(F)CC3)c2)ccc1O[C@H]1CCN(C(=O)CO)C[C@H]1F] | 399.7 | 294.1 |
| 79 | 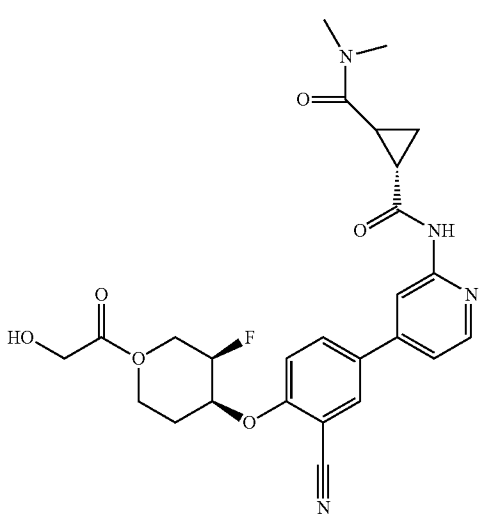 | >1000 | >1000 |

-continued

| Example | Structure | TBK1-IC$_{50}$ (nM) | IKKε IC$_{50}$ (nM) |
|---------|-----------|---------------------|---------------------|
| 80 | 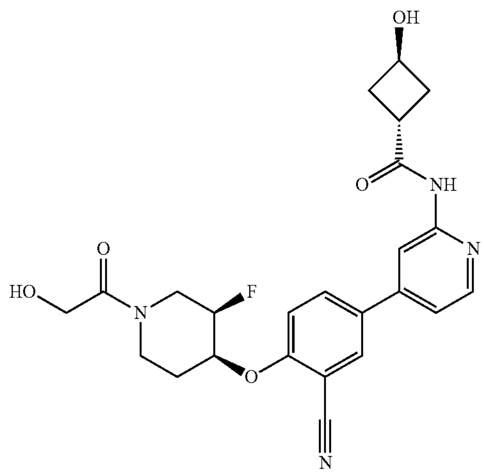 [SMILES: N#Cc1cc(-c2ccnc(NC(=O)[C@H]3C[C@H](O)C3)c2)ccc1O[C@H]1CCN(C(=O)CO)C[C@H]1F] | 111.1 | 75.2 |
| 81 | 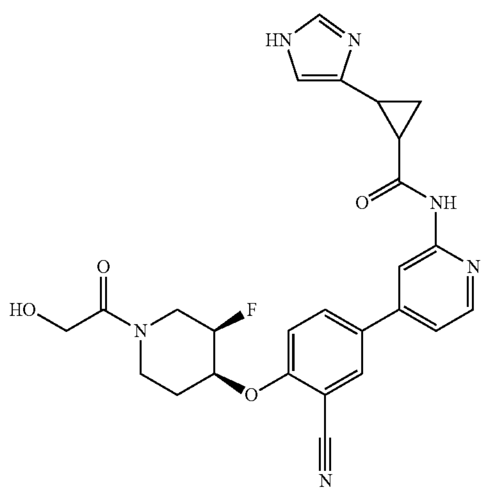 [SMILES: N#Cc1cc(-c2ccnc(NC(=O)C3CC3c3c[nH]cn3)c2)ccc1O[C@H]1CCN(C(=O)CO)C[C@H]1F] | 18.8 | 47.0 |
| 82 | 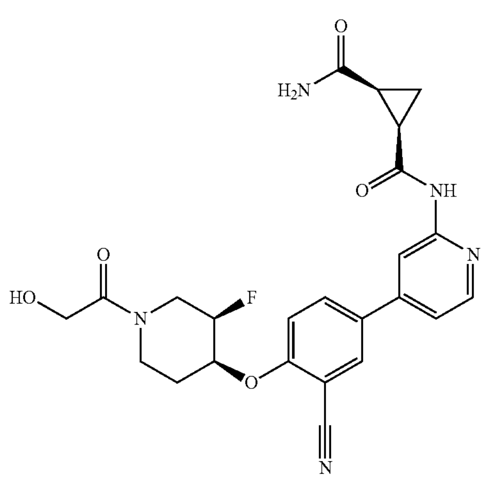 | 607.3 | 856.6 |

| Example | Structure | TBK1-IC$_{50}$ (nM) | IKKε IC$_{50}$ (nM) |
|---|---|---|---|
| 83 | 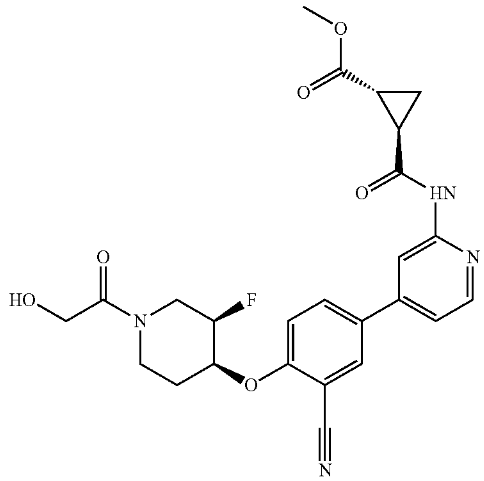 [SMILES: COC(=O)[C@@H]1C[C@H]1C(=O)Nc1cc(-c2ccc(O[C@H]3CCN(C(=O)CO)C[C@H]3F)c(C#N)c2)ccn1] | 47.9 | 53.3 |
| 84 | 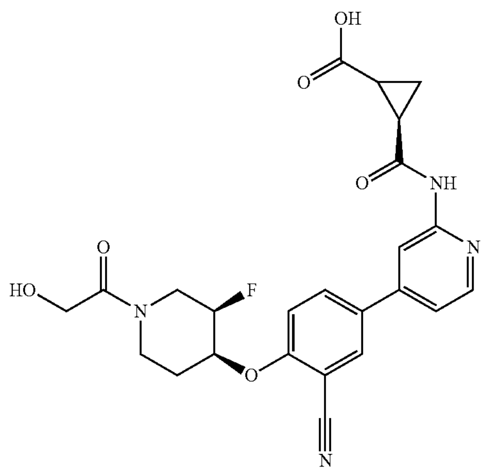 | 333.2 | 134.9 |
| 85 | 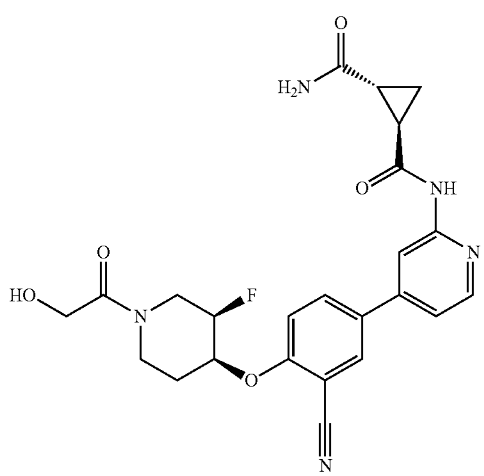 | 108.5 | 114.8 |

-continued

| Example | Structure | TBK1-IC$_{50}$ (nM) | IKKε IC$_{50}$ (nM) |
|---------|-----------|---------------------|---------------------|
| 86 | 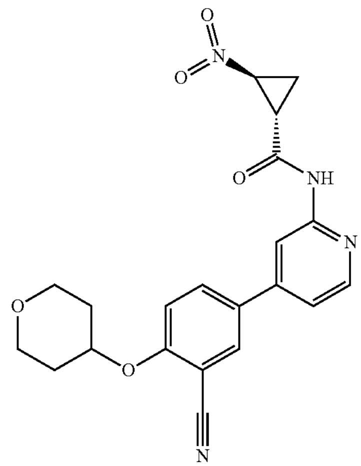 [SMILES: N#Cc1cc(-c2ccnc(NC(=O)[C@H]3C[C@@H]3[N+](=O)[O-])c2)ccc1OC1CCOCC1] | 529.2 | 314.2 |
| 87 | 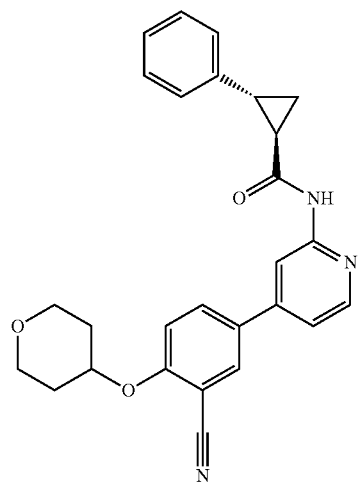 [SMILES: N#Cc1cc(-c2ccnc(NC(=O)[C@@H]3C[C@H]3c3ccccc3)c2)ccc1OC1CCOCC1] | 425.8 | 777.4 |
| 88 | 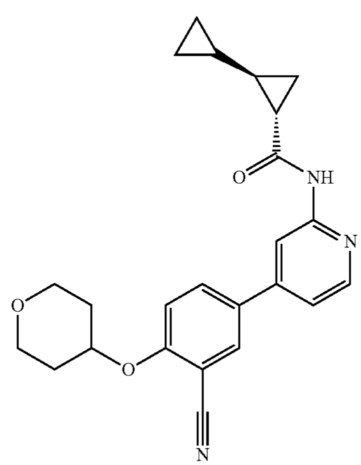 [SMILES: N#Cc1cc(-c2ccnc(NC(=O)[C@H]3C[C@@H]3C3CC3)c2)ccc1OC1CCOCC1] | 58.8 | 313.8 |

-continued
| Example | Structure | TBK1-IC$_{50}$ (nM) | IKKε IC$_{50}$ (nM) |
|---|---|---|---|
| 89 | 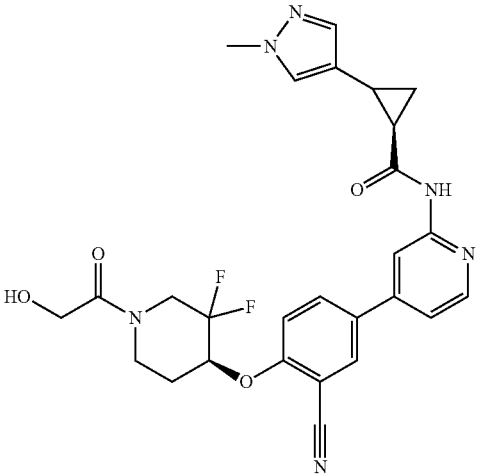 | 4.5 | 2.4 |
| 90 | 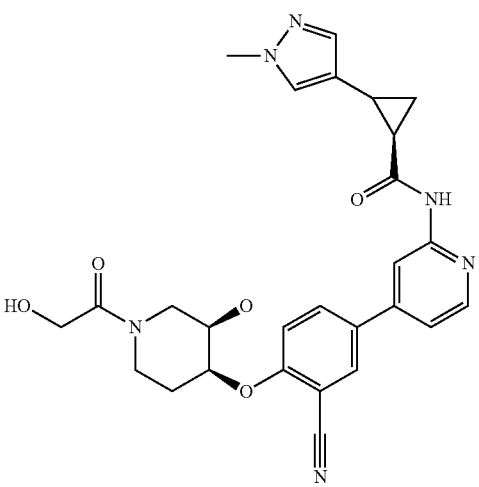 [SMILES: Cn1cc(C2C[C@H]2C(=O)Nc2cc(-c3ccc(O[C@H]4CCN(C(=O)CO)C[C@H]4O)c(C#N)c3)ccn2)cn1] | 5.6 | 9.5 |
| 91 | 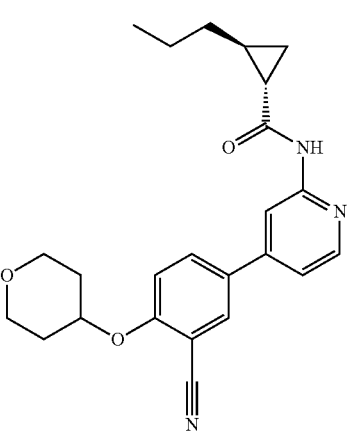 [SMILES: CCC[C@H]1C[C@@H]1C(=O)Nc1cc(-c2ccc(OC3CCOCC3)c(C#N)c2)ccn1] | 44.1 | 266.2 |

-continued

| Example | Structure | TBK1-IC$_{50}$ (nM) | IKKε IC$_{50}$ (nM) |
|---|---|---|---|
| 92 | 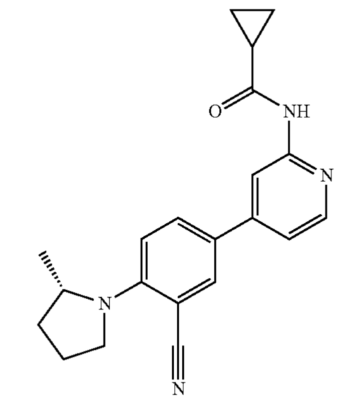 [SMILES: C[C@H]1CCCN1c1ccc(-c2ccnc(NC(=O)C3CC3)c2)cc1C#N] | 20.3 | 127.8 |
| 93 | 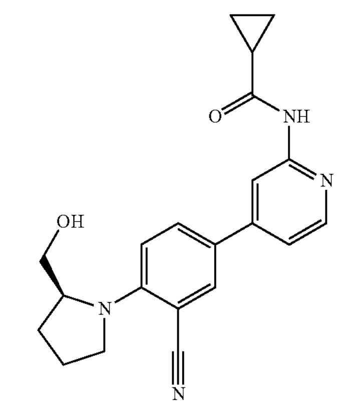 [SMILES: N#Cc1cc(-c2ccnc(NC(=O)C3CC3)c2)ccc1N1CCC[C@H]1CO] | 70.3 | 508.1 |
| 94 | 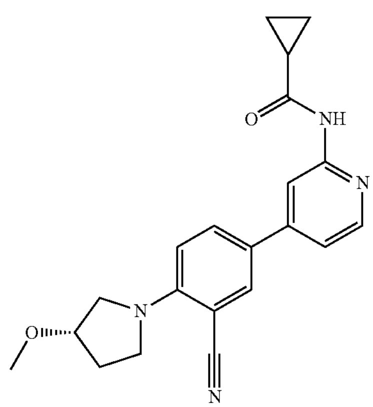 [SMILES: CO[C@H]1CCN(c2ccc(-c3ccnc(NC(=O)C4CC4)c3)cc2C#N)C1] | 120.5 | 195.3 |
| 95 | 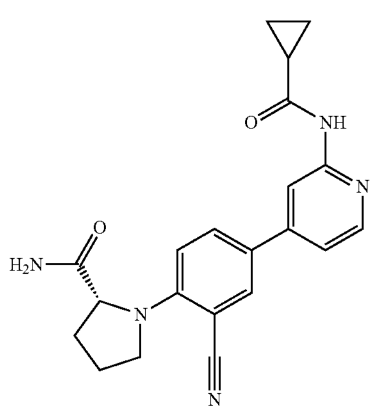 [SMILES: N#Cc1cc(-c2ccnc(NC(=O)C3CC3)c2)ccc1N1CCC[C@@H]1C(N)=O] | 258.4 | >1000 |

-continued

| Example | Structure | TBK1-IC$_{50}$ (nM) | IKKε IC$_{50}$ (nM) |
|---|---|---|---|
| 96 | 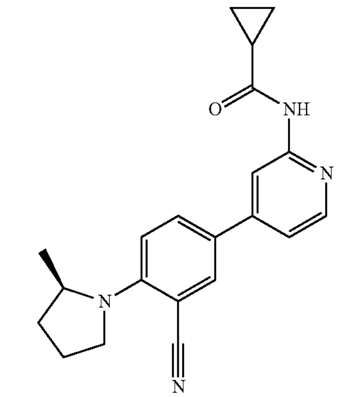 [SMILES: C[C@@H]1CCCN1c1ccc(-c2ccnc(NC(=O)C3CC3)c2)cc1C#N] | 33.0 | 231.1 |
| 97 | 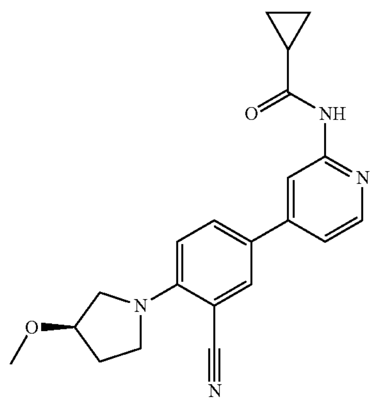 [SMILES: CO[C@@H]1CCN(c2ccc(-c3ccnc(NC(=O)C4CC4)c3)cc2C#N)C1] | 270.1 | 477.4 |
| 98 | 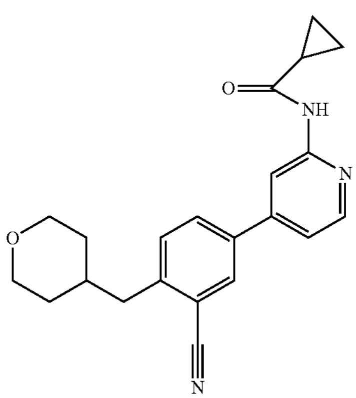 [SMILES: N#Cc1cc(-c2ccnc(NC(=O)C3CC3)c2)ccc1CC1CCOCC1] | >1000 | >1000 |

-continued

| Example | Structure | TBK1-IC$_{50}$ (nM) | IKKε IC$_{50}$ (nM) |
|---|---|---|---|
| 99 | 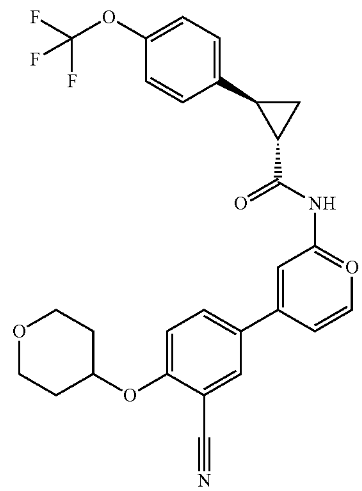 | >1000 | >1000 |
| 100 | 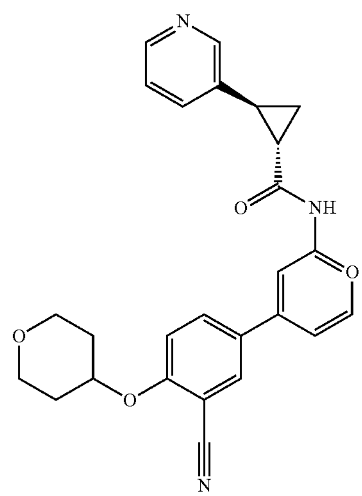 | 20.3 | 129.7 |
| 101 | 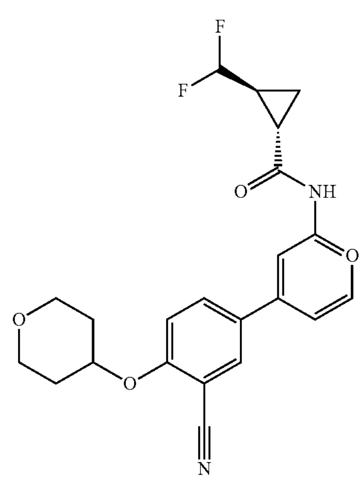 | 96.8 | >1000 |

-continued
| Example | Structure | TBK1-IC$_{50}$ (nM) | IKKε IC$_{50}$ (nM) |
|---|---|---|---|
| 102 | 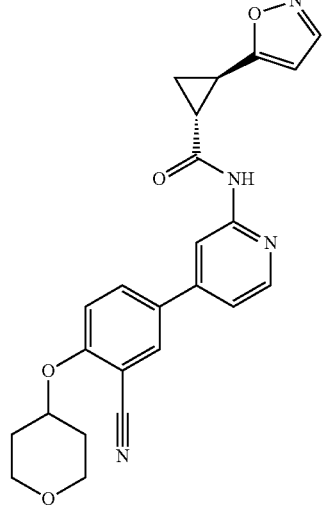 | 33.4 | 195.9 |
| 103 | 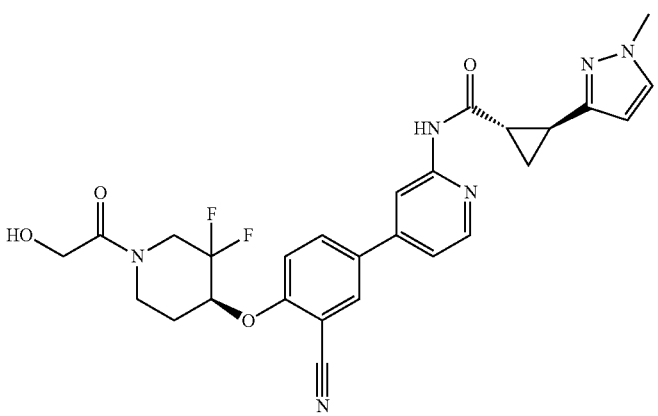 [SMILES: Cn1ccc([C@H]2C[C@@H]2C(=O)Nc2cc(-c3ccc(O[C@H]4CCN(C(=O)CO)CC4(F)F)c(C#N)c3)ccn2)n1] | 5.7 | 14.3 |
| 104 | 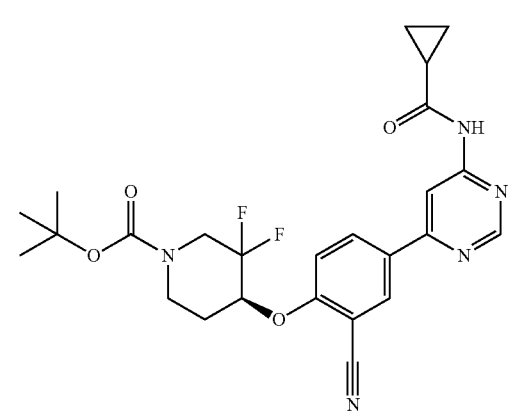 [SMILES: CC(C)(C)OC(=O)N1CC[C@H](Oc2ccc(-c3cc(NC(=O)C4CC4)ncn3)cc2C#N)C(F)(F)C1] | >1000 | >1000 |

-continued

| Example | Structure | TBK1-IC$_{50}$ (nM) | IKKε IC$_{50}$ (nM) |
|---|---|---|---|
| 105 | 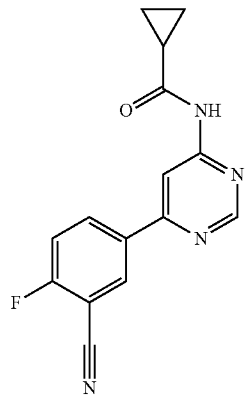 [SMILES: N#Cc1cc(-c2cc(NC(=O)C3CC3)ncn2)ccc1F] | >1000 | >1000 |
| 106 | 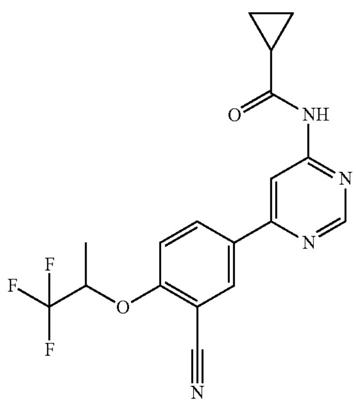 [SMILES: CC(Oc1ccc(-c2cc(NC(=O)C3CC3)ncn2)cc1C#N)C(F)(F)F] | 301.0 | >1000 |
| 107 | 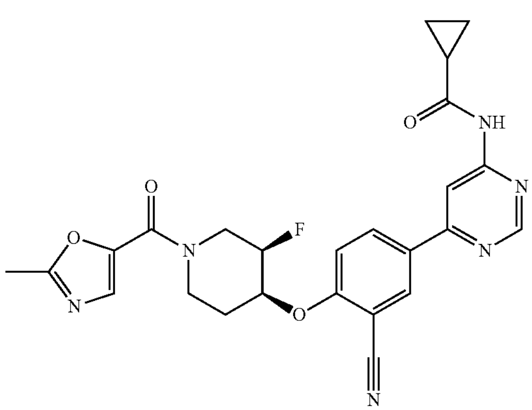 [SMILES: Cc1ncc(C(=O)N2CC[C@H](Oc3ccc(-c4cc(NC(=O)C5CC5)ncn4)cc3C#N)[C@H](F)C2)o1] | 48.9 | 160.3 |

-continued

| Example | Structure | TBK1-IC$_{50}$ (nM) | IKKε IC$_{50}$ (nM) |
|---|---|---|---|
| 108 | 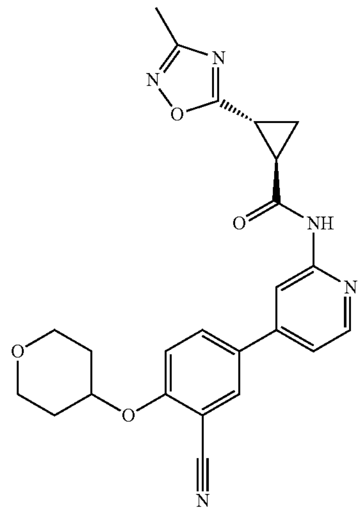 [SMILES: Cc1noc([C@@H]2C[C@H]2C(=O)Nc2cc(-c3ccc(OC4CCOCC4)c(C#N)c3)ccn2)n1] | 185.7 | 322.3 |
| 109 | 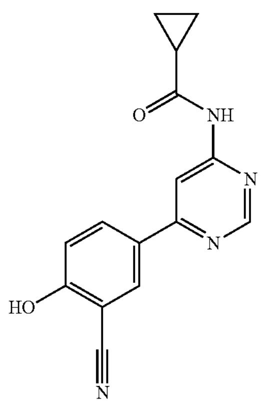 [SMILES: N#Cc1cc(-c2cc(NC(=O)C3CC3)ncn2)ccc1O] | 825.6 | >1000 |
| 110 | 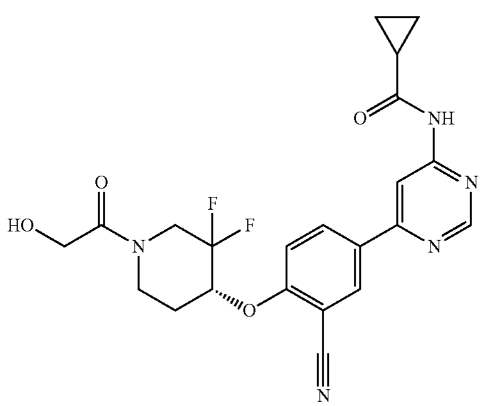 [SMILES: N#Cc1cc(-c2cc(NC(=O)C3CC3)ncn2)ccc1O[C@@H]1CCN(C(=O)CO)CC1(F)F] | 317.5 | 736.8 |

-continued
| Example | Structure | TBK1-IC$_{50}$ (nM) | IKKε IC$_{50}$ (nM) |
|---|---|---|---|
| 111 | 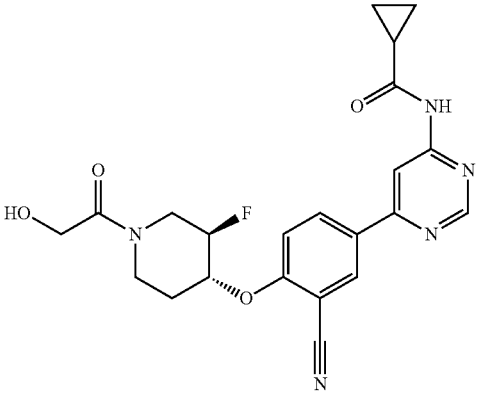 [SMILES: N#Cc1cc(-c2cc(NC(=O)C3CC3)ncn2)ccc1O[C@@H]1CCN(C(=O)CO)C[C@H]1F] | 105.5 | 253.6 |
| 112 | 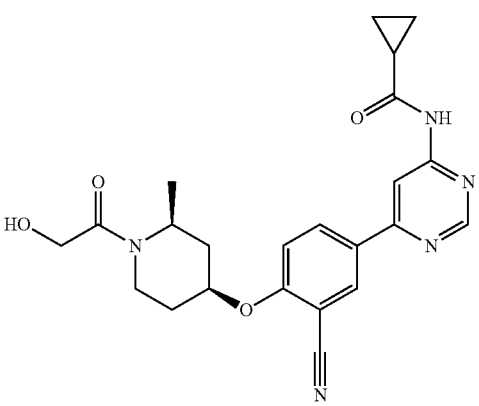 [SMILES: C[C@H]1C[C@@H](Oc2ccc(-c3cc(NC(=O)C4CC4)ncn3)cc2C#N)CCN1C(=O)CO] | 107.4 | 209.3 |
| 113 | 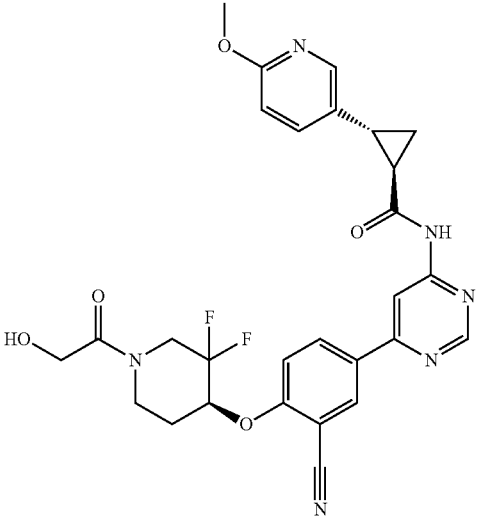 [SMILES: COc1ccc([C@@H]2C[C@H]2C(=O)Nc2cc(-c3ccc(O[C@H]4CCN(C(=O)CO)CC4(F)F)c(C#N)c3)ncn2)cn1] | 8.1 | >1000 |

-continued

| Example | Structure | TBK1-IC$_{50}$ (nM) | IKKε IC$_{50}$ (nM) |
|---|---|---|---|
| 114 | 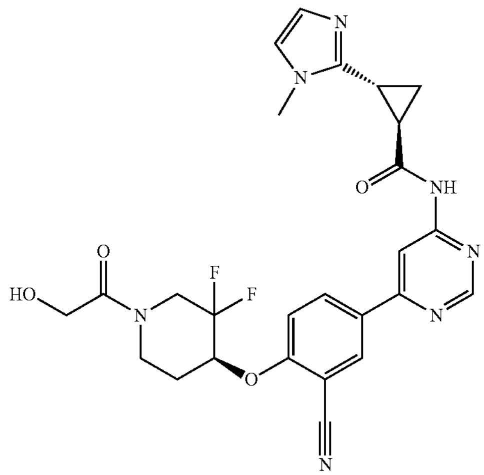 [SMILES: Cn1ccnc1[C@@H]1C[C@H]1C(=O)Nc1cc(-c2ccc(O[C@H]3CCN(C(=O)CO)CC3(F)F)c(C#N)c2)ncn1] | 180.8 | 36.0 |
| 115 | 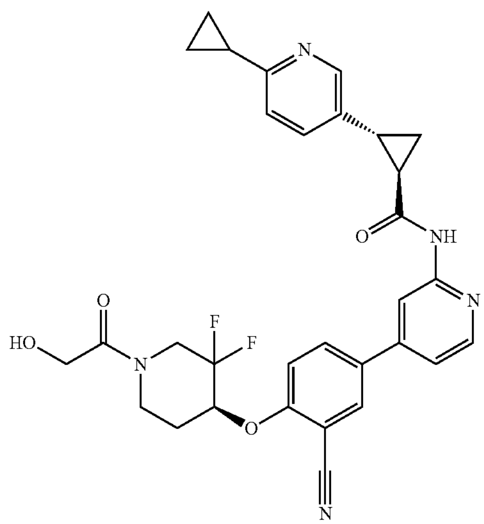 [SMILES: N#Cc1cc(-c2ccnc(NC(=O)[C@@H]3C[C@H]3c3ccc(C4CC4)nc3)c2)ccc1O[C@H]1CCN(C(=O)CO)CC1(F)F] | 8.1 | 7.1 |
| 116 | 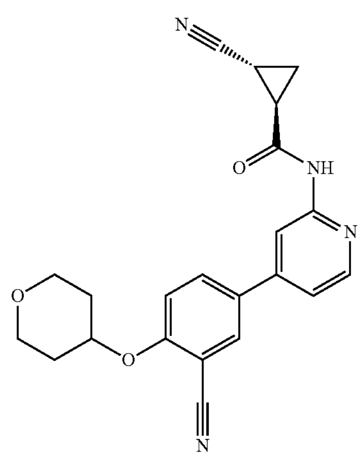 [SMILES: N#Cc1cc(-c2ccnc(NC(=O)[C@@H]3C[C@H]3C#N)c2)ccc1OC1CCOCC1] | 180.6 | 470.8 |

| Example | Structure | TBK1-IC$_{50}$ (nM) | IKKε IC$_{50}$ (nM) |
|---|---|---|---|
| 117 | 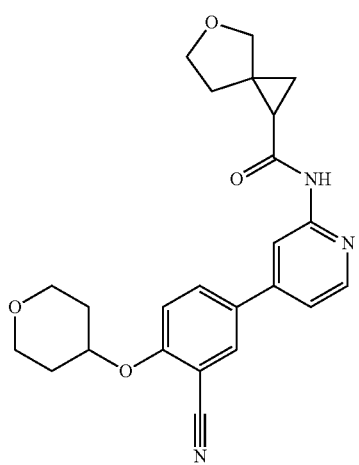 [SMILES: N#Cc1cc(-c2ccnc(NC(=O)C3CC34CCOC4)c2)ccc1OC1CCOCC1] | 851.0 | >1000 |
| 118 | 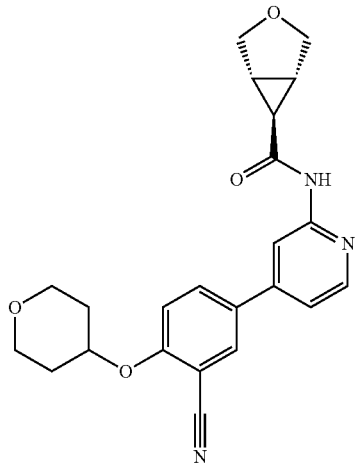 [SMILES: N#Cc1cc(-c2ccnc(NC(=O)[C@H]3[C@@H]4COC[C@@H]43)c2)ccc1OC1CCOCC1] | 870.9 | 631.9 |
| 119 | 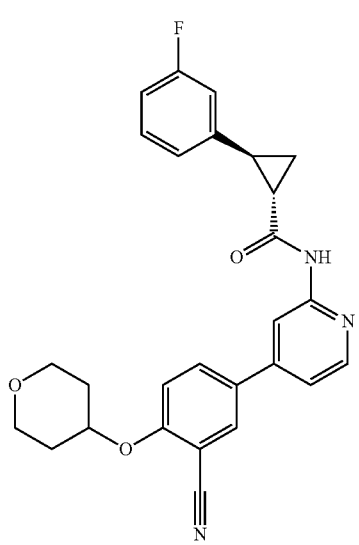 [SMILES: N#Cc1cc(-c2ccnc(NC(=O)[C@H]3C[C@@H]3c3cccc(F)c3)c2)ccc1OC1CCOCC1] | 99.3 | >1000 |

| Example | Structure | TBK1-IC$_{50}$ (nM) | IKKε IC$_{50}$ (nM) |
|---|---|---|---|
| 120 | 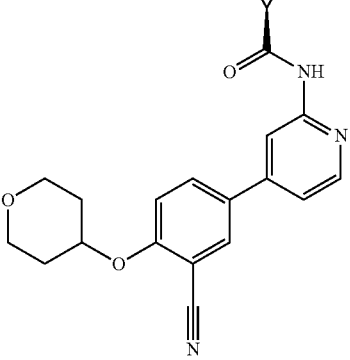 | 29.1 | 180.5 |
| 121 | 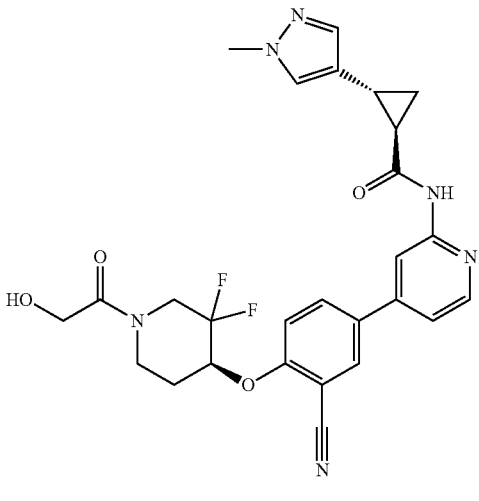 [SMILES: Cn1cc([C@@H]2C[C@H]2C(=O)Nc2cc(-c3ccc(O[C@H]4CCN(C(=O)CO)CC4(F)F)c(C#N)c3)ccn2)cn1] | 7.2 | 6.2 |
| 122 | 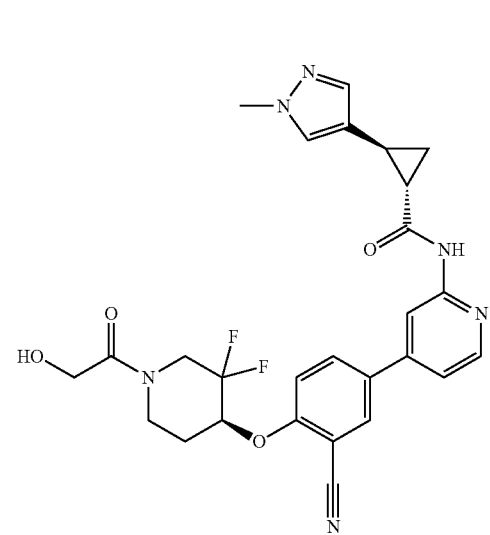 [SMILES: Cn1cc([C@H]2C[C@@H]2C(=O)Nc2cc(-c3ccc(O[C@H]4CCN(C(=O)CO)CC4(F)F)c(C#N)c3)ccn2)cn1] | 6.0 | 4.9 |

-continued

| Example | Structure | TBK1-IC$_{50}$ (nM) | IKKε IC$_{50}$ (nM) |
|---|---|---|---|
| 123 | 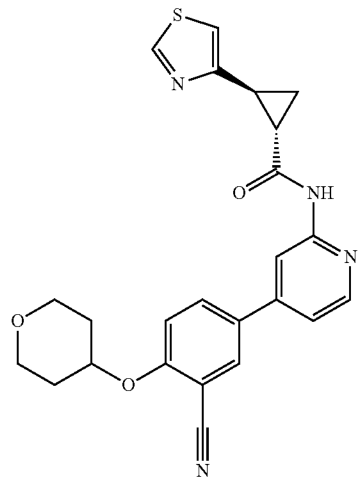 [SMILES: N#Cc1cc(-c2ccnc(NC(=O)[C@H]3C[C@@H]3c3cscn3)c2)ccc1OC1CCOCC1] | 938.3 | >1000 |
| 124 | 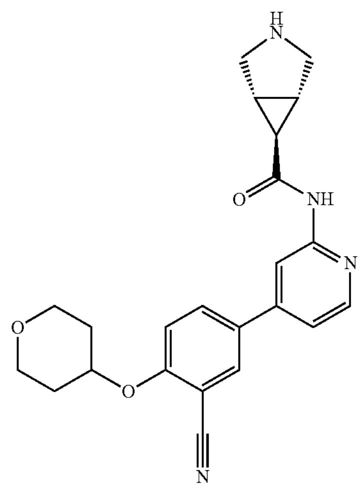 [SMILES: N#Cc1cc(-c2ccnc(NC(=O)[C@H]3[C@@H]4CNC[C@@H]43)c2)ccc1OC1CCOCC1] | 627.6 | 316.4 |
| 125 | 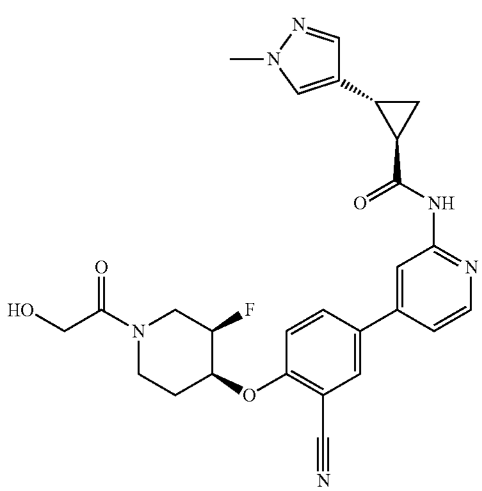 | 18.9 | 31.4 |

| Example | Structure | TBK1-IC$_{50}$ (nM) | IKKε IC$_{50}$ (nM) |
| --- | --- | --- | --- |
| 126 | 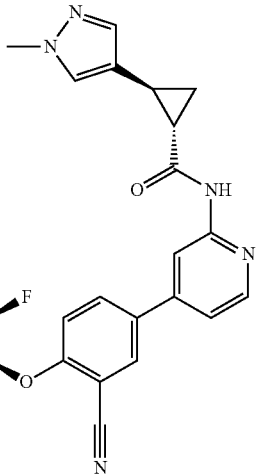 | 5.7 | 14.0 |
| 127 | 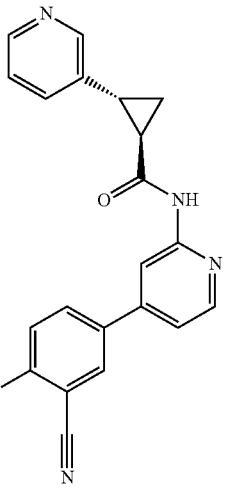 | 12.2 | 33.2 |
| 128 | 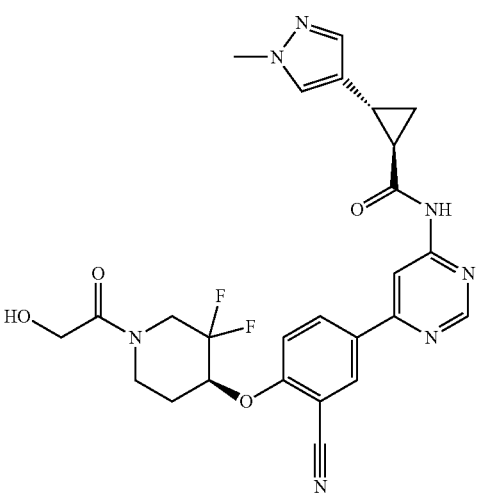 [SMILES: Cn1cc([C@@H]2C[C@H]2C(=O)Nc2cc(-c3ccc(O[C@H]4CCN(C(=O)CO)CC4(F)F)c(C#N)c3)ncn2)cn1] | 7.2 | 15.8 |

-continued

| Example | Structure | TBK1-IC$_{50}$ (nM) | IKKε IC$_{50}$ (nM) |
|---|---|---|---|
| 129 | 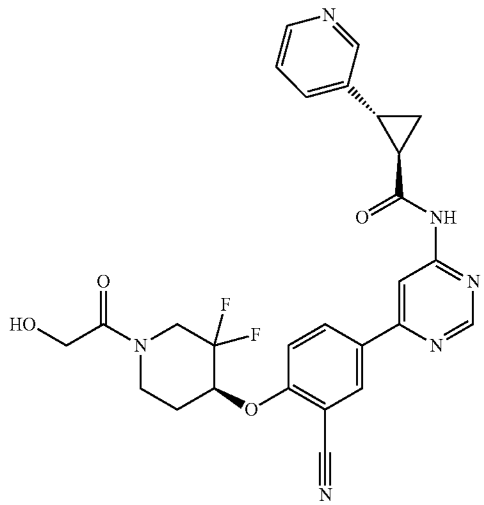 [SMILES: N#Cc1cc(-c2cc(NC(=O)[C@@H]3C[C@H]3c3cccnc3)ncn2)ccc1O[C@H]1CCN(C(=O)CO)CC1(F)F] | 9.3 | 32.2 |
| 130 | 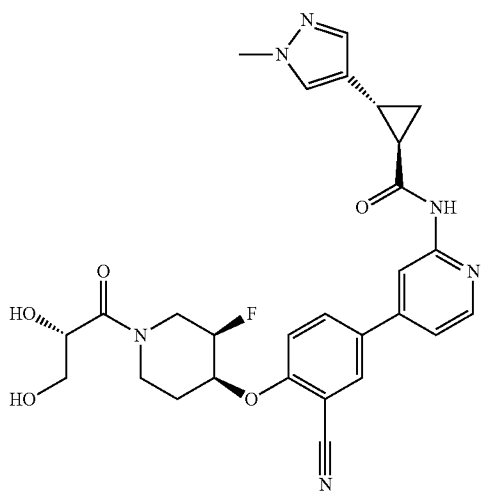 [SMILES: Cn1cc([C@@H]2C[C@H]2C(=O)Nc2cc(-c3ccc(O[C@H]4CCN(C(=O)[C@@H](O)CO)C[C@H]4F)c(C#N)c3)ccn2)cn1] | 6.1 | 15.6 |
| 131 | 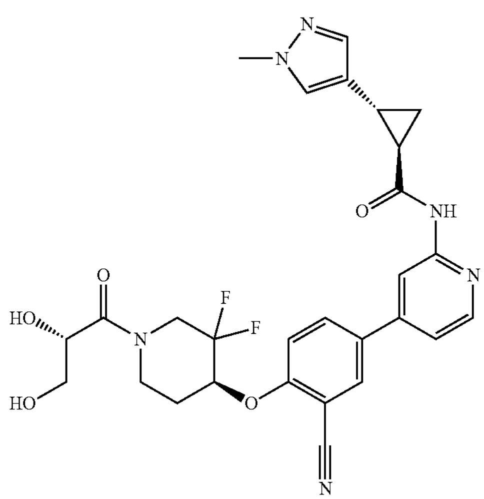 | 6.6 | 11.6 |

-continued

| Example | Structure | TBK1-IC$_{50}$ (nM) | IKKε IC$_{50}$ (nM) |
| --- | --- | --- | --- |
| 132 | 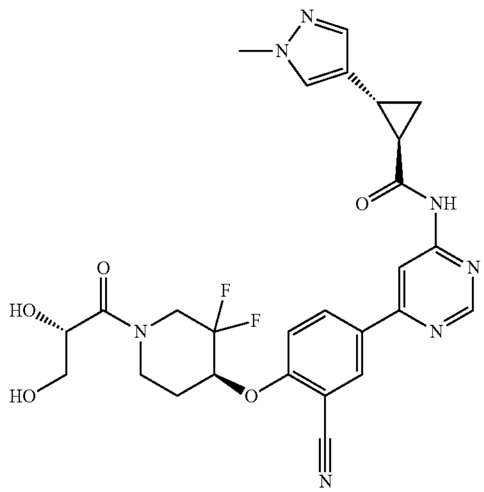 | 4.7 | 12.3 |
| 133 | 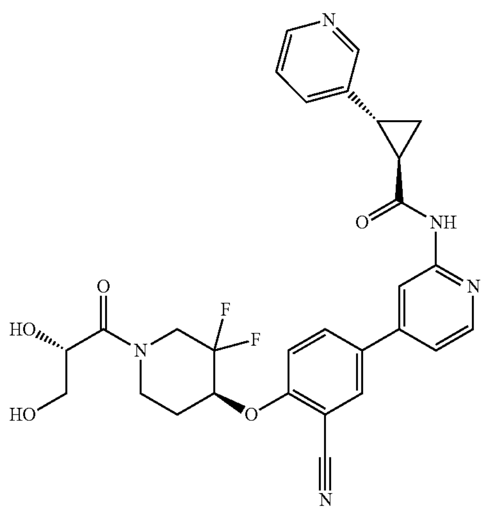 [SMILES: N#Cc1cc(-c2ccnc(NC(=O)[C@@H]3C[C@H]3c3cccnc3)c2)ccc1O[C@H]1CCN(C(=O)[C@@H](O)CO)CC1(F)F] | 6.4 | 9.9 |
| 134 | 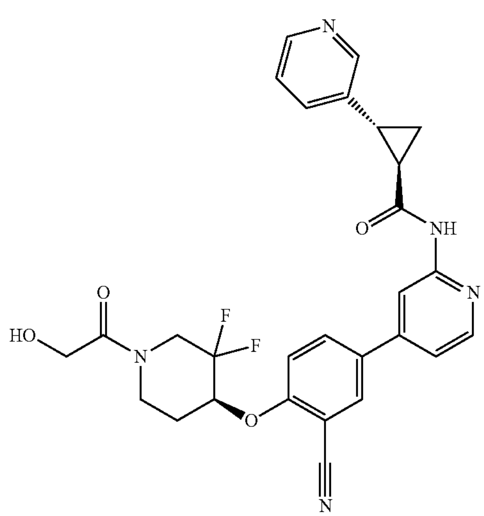 [SMILES: N#Cc1cc(-c2ccnc(NC(=O)[C@@H]3C[C@H]3c3cccnc3)c2)ccc1O[C@H]1CCN(C(=O)CO)CC1(F)F] | 7.4 | 10.9 |

| Example | Structure | TBK1-IC$_{50}$ (nM) | IKKε IC$_{50}$ (nM) |
|---|---|---|---|
| 135 | 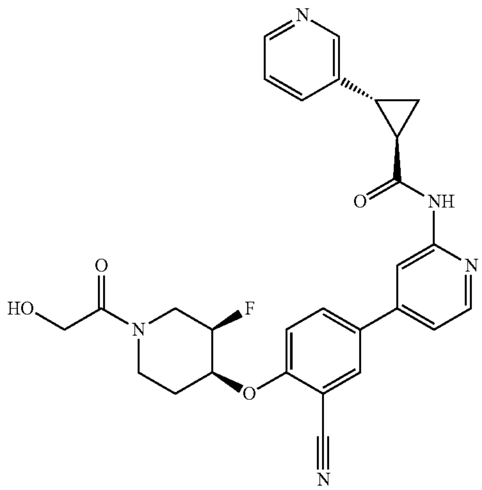 [SMILES: N#Cc1cc(-c2ccnc(NC(=O)[C@@H]3C[C@H]3c3cccnc3)c2)ccc1O[C@H]1CCN(C(=O)CO)C[C@H]1F] | 21.4 | 27.4 |
| 136 | 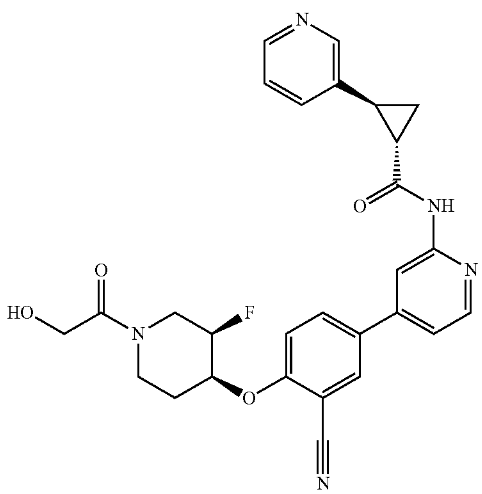 [SMILES: N#Cc1cc(-c2ccnc(NC(=O)[C@H]3C[C@@H]3c3cccnc3)c2)ccc1O[C@H]1CCN(C(=O)CO)C[C@H]1F] | 3.5 | 10.4 |
| 137 | 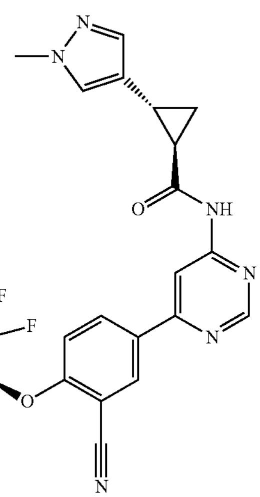 | 21.4 | 17.6 |

-continued

| Example | Structure | TBK1-IC$_{50}$ (nM) | IKKε IC$_{50}$ (nM) |
|---------|-----------|---------------------|---------------------|
| 138 | 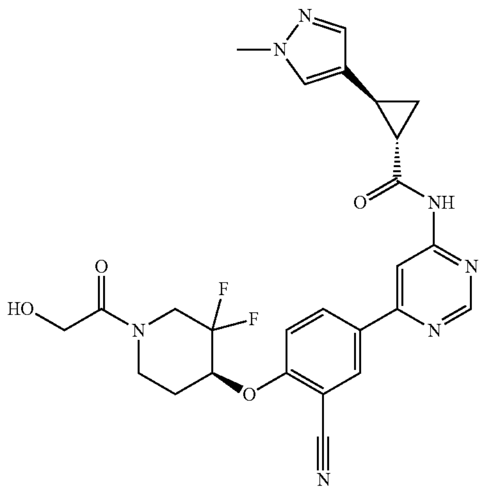 [SMILES: Cn1cc([C@H]2C[C@@H]2C(=O)Nc2cc(-c3ccc(O[C@H]4CCN(C(=O)CO)CC4(F)F)c(C#N)c3)ncn2)cn1] | 5.9 | 9.2 |
| 139 | 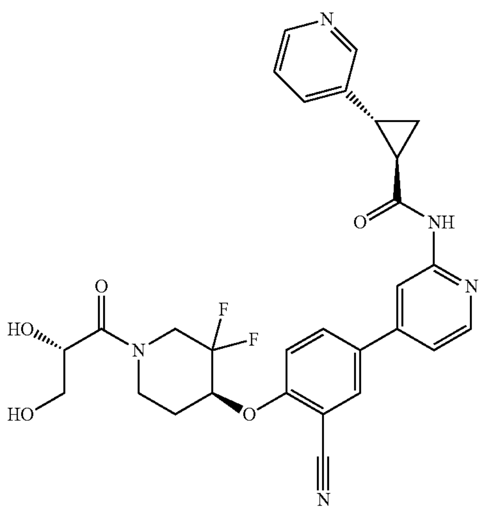 [SMILES: N#Cc1cc(-c2ccnc(NC(=O)[C@@H]3C[C@H]3c3cccnc3)c2)ccc1O[C@H]1CCN(C(=O)[C@@H](O)CO)CC1(F)F] | 15.8 | 16.1 |
| 140 | 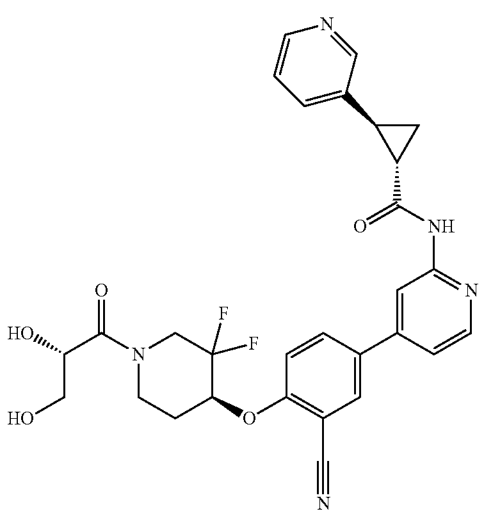 [SMILES: N#Cc1cc(-c2ccnc(NC(=O)[C@H]3C[C@@H]3c3cccnc3)c2)ccc1O[C@H]1CCN(C(=O)[C@@H](O)CO)CC1(F)F] | 4.6 | 5.9 |

| Example | Structure | TBK1-IC$_{50}$ (nM) | IKKε IC$_{50}$ (nM) |
|---|---|---|---|
| 141 | 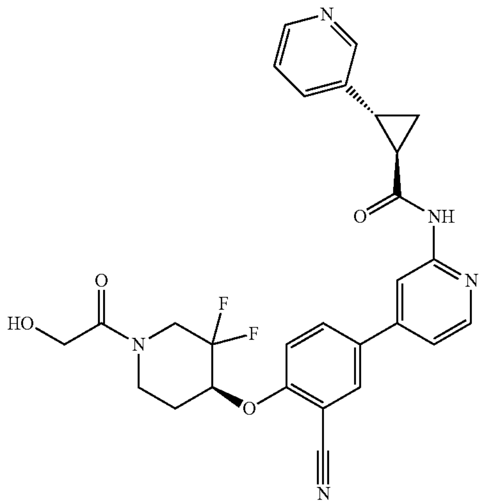 [SMILES: N#Cc1cc(-c2ccnc(NC(=O)[C@@H]3C[C@H]3c3cccnc3)c2)ccc1O[C@H]1CCN(C(=O)CO)CC1(F)F] | 17.3 | 11.2 |
| 142 | 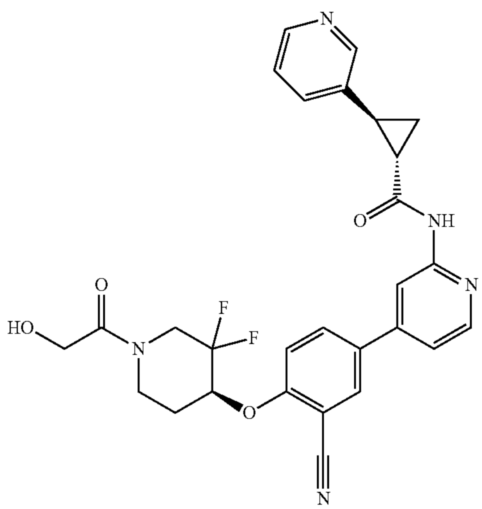 [SMILES: N#Cc1cc(-c2ccnc(NC(=O)[C@H]3C[C@@H]3c3cccnc3)c2)ccc1O[C@H]1CCN(C(=O)CO)CC1(F)F] | 5.7 | 6.0 |
| 143 | 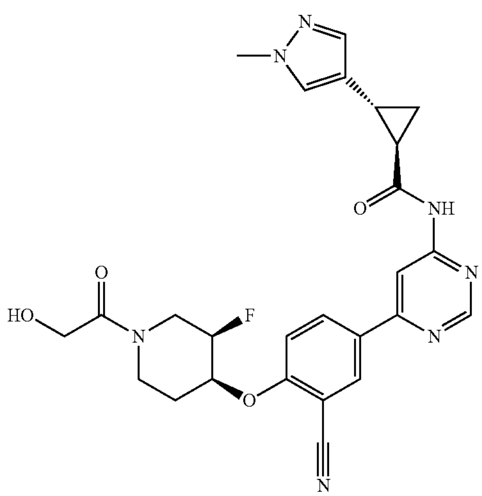 | 19.9 | 44.3 |

| Example | Structure | TBK1-IC$_{50}$ (nM) | IKKε IC$_{50}$ (nM) |
|---|---|---|---|
| 144 | 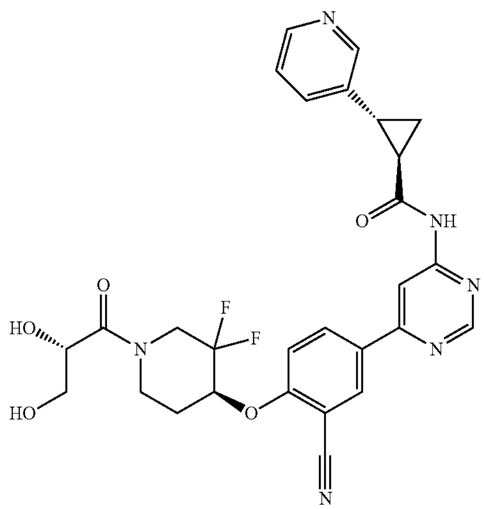 | 7.1 | 9.0 |
| 145 | 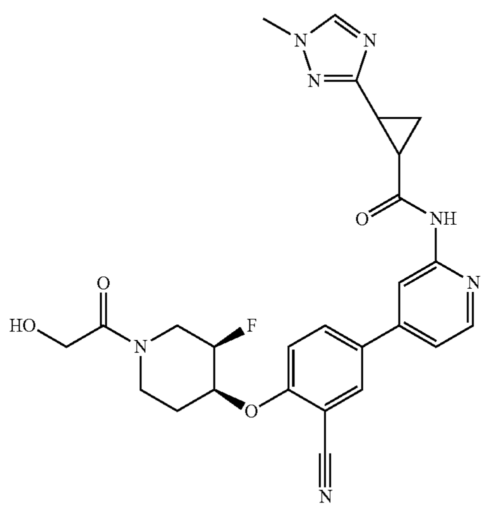 [SMILES: Cn1cnc(C2CC2C(=O)Nc2cc(-c3ccc(O[C@H]4CCN(C(=O)CO)C[C@H]4F)c(C#N)c3)ccn2)n1] | >1000 | >1000 |
| 146 | 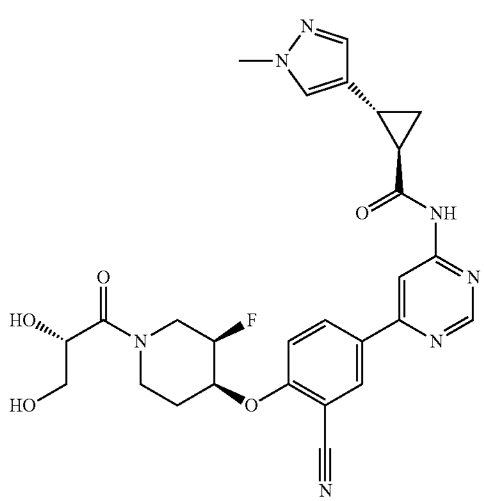 | 16.1 | 30.8 |

-continued

| Example | Structure | TBK1-IC$_{50}$ (nM) | IKKε IC$_{50}$ (nM) |
|---|---|---|---|
| 147 | 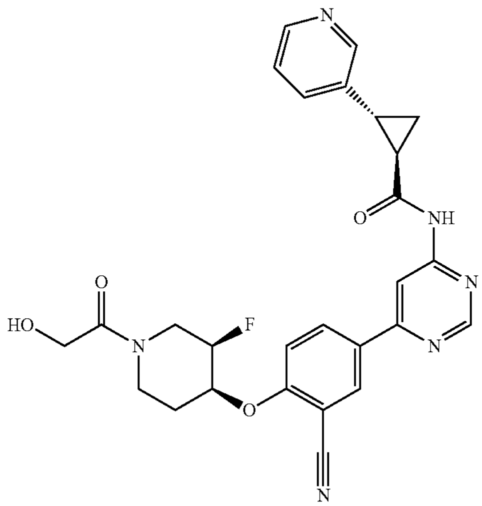 [SMILES: N#Cc1cc(-c2cc(NC(=O)[C@@H]3C[C@H]3c3cccnc3)ncn2)ccc1O[C@H]1CCN(C(=O)CO)C[C@H]1F] | 15.7 | 36.5 |
| 148 | 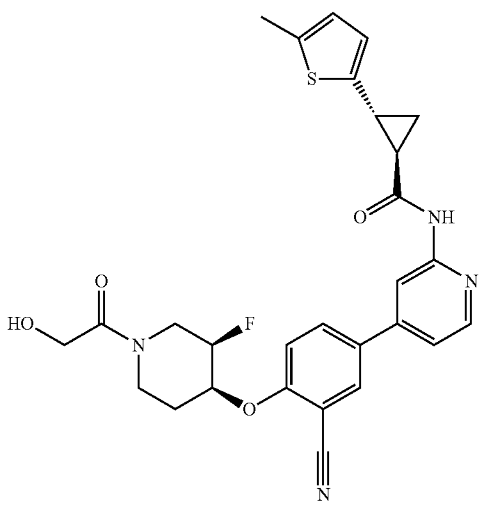 [SMILES: Cc1ccc([C@@H]2C[C@H]2C(=O)Nc2cc(-c3ccc(O[C@H]4CCN(C(=O)CO)C[C@H]4F)c(C#N)c3)ccn2)s1] | — | — |
| 149 | 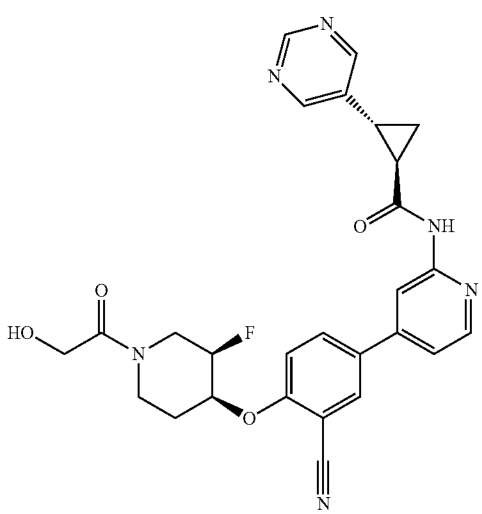 [SMILES: N#Cc1cc(-c2ccnc(NC(=O)[C@@H]3C[C@H]3c3cncnc3)c2)ccc1O[C@H]1CCN(C(=O)CO)C[C@H]1F] | 15.9 | 99.2 |

-continued
| Example | Structure | TBK1-IC$_{50}$ (nM) | IKKε IC$_{50}$ (nM) |
|---|---|---|---|
| 150 | 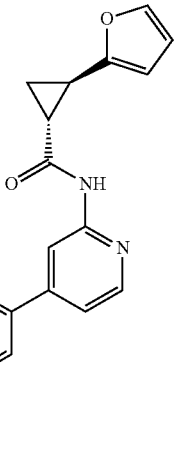 | 70.5 | 635.7 |
| 151 | 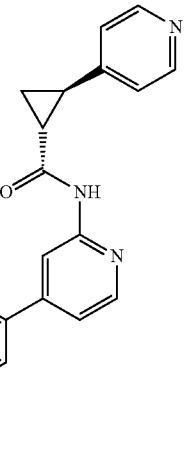 | 75.6 | 200.2 |
| 152 | 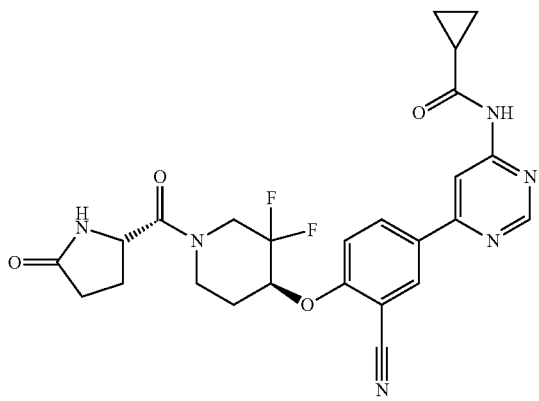 | 9.4 | 53.3 |

-continued

| Example | Structure | TBK1-IC$_{50}$ (nM) | IKKε IC$_{50}$ (nM) |
|---|---|---|---|
| 153 | 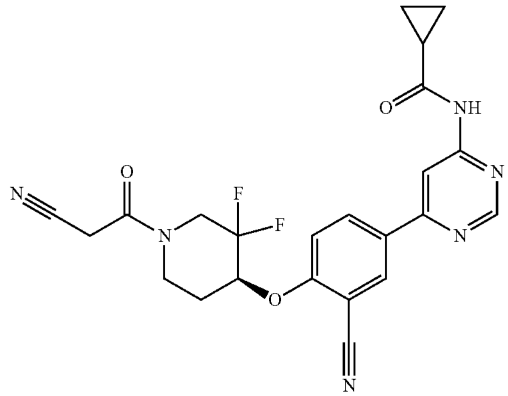 [SMILES: N#CCC(=O)N1CC[C@H](Oc2ccc(-c3cc(NC(=O)C4CC4)ncn3)cc2C#N)C(F)(F)C1] | 23.6 | 139.9 |
| 154 | 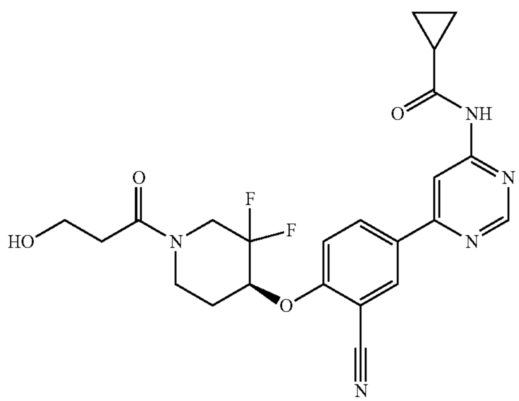 [SMILES: N#Cc1cc(-c2cc(NC(=O)C3CC3)ncn2)ccc1O[C@H]1CCN(C(=O)CCO)CC1(F)F] | 41.5 | 387.5 |
| 155 | 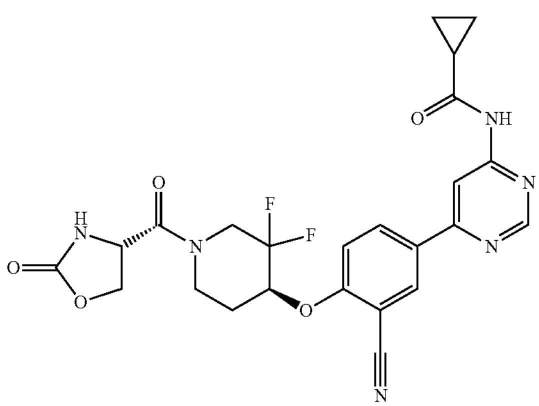 | 7.0 | 52.6 |

| Example | Structure | TBK1-IC$_{50}$ (nM) | IKKε IC$_{50}$ (nM) |
|---|---|---|---|
| 156 | 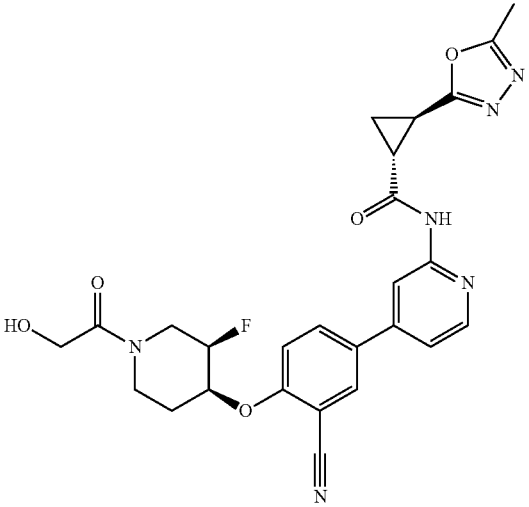 [SMILES: Cc1nnc([C@@H]2C[C@H]2C(=O)Nc2cc(-c3ccc(O[C@H]4CCN(C(=O)CO)C[C@H]4F)c(C#N)c3)ccn2)o1] | 36.6 | 41.0 |
| 157 | 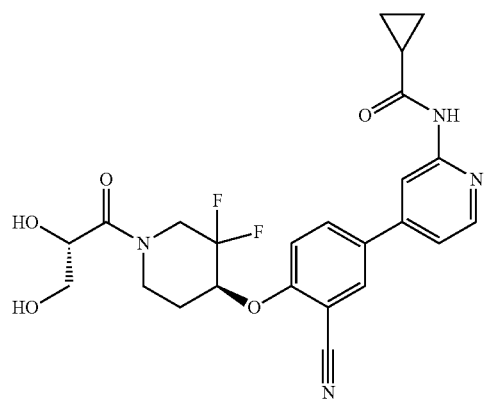 [SMILES: N#Cc1cc(-c2ccnc(NC(=O)C3CC3)c2)ccc1O[C@H]1CCN(C(=O)[C@@H](O)CO)CC1(F)F] | 4.4 | 4.7 |
| 158 | 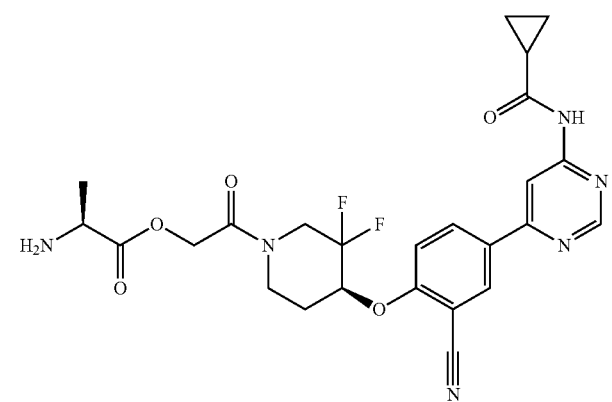 [SMILES: C[C@H](N)C(=O)OCC(=O)N1CC[C@H](Oc2ccc(-c3cc(NC(=O)C4CC4)ncn3)cc2C#N)C(F)(F)C1] | 14.8 | 46.8 |

| Example | Structure | TBK1-IC$_{50}$ (nM) | IKKε IC$_{50}$ (nM) |
|---|---|---|---|
| 159 | 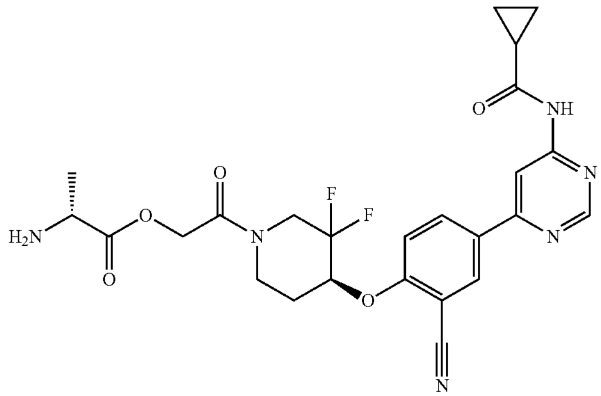 [SMILES: C[C@@H](N)C(=O)OCC(=O)N1CC[C@H](Oc2ccc(-c3cc(NC(=O)C4CC4)ncn3)cc2C#N)C(F)(F)C1] | 12.8 | 39.3 |
| 160 | 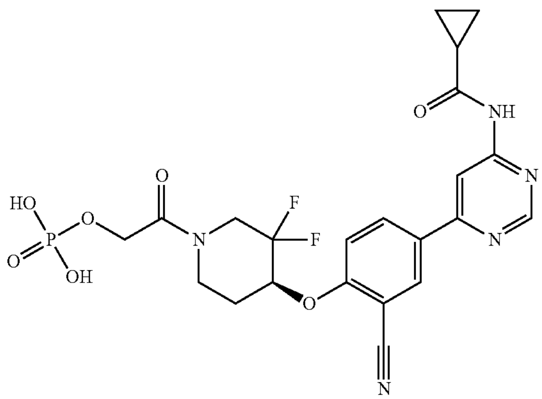 [SMILES: N#Cc1cc(-c2cc(NC(=O)C3CC3)ncn2)ccc1O[C@H]1CCN(C(=O)COP(=O)(O)O)CC1(F)F] | 11.5 | 22.0 |

Structure-Activity Relationship (SAR) Studies:

It was surprisingly found that the alpha carbon atom of the heteroaryl group shown below (designated with an arrow) is important to biological activity. For example, as shown in Scheme 15, replacing this carbon atom with a nitrogen atom resulted in a decrease of biological activity.

Scheme 15

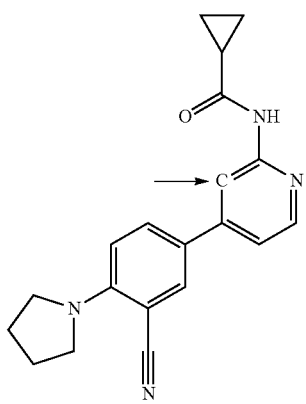

TBK1-IC50 = 13.9 nM
IKKE-IC50 = 68.2 nM

-continued

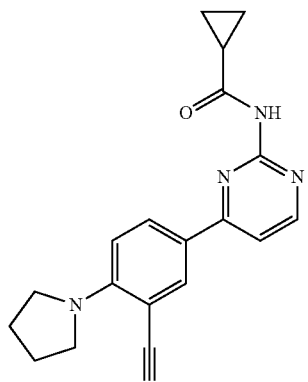

TBK1-IC50 = 700.1 nM
IKKE-IC50 = >1000 nM

Additionally, it was observed that biological activity generally increases when Ring A is a cycloalkyl group (e.g., a cyclopropyl ring). For example, replacing the cyclopropyl ring in the compound on the far left in Scheme 16 with an aromatic ring or alkyl group resulted in a decrease in the inhibition of TANK binding kinase 1 (TBK1). Replacing the cyclopropyl ring with an alkyl group resulted in a decrease in the inhibition of I-Kappa-B kinase (IKKε).

Scheme 16

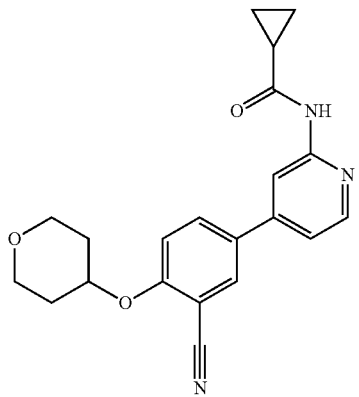

TBK1-IC50 = 28.1 nM
IKKE-IC50 = 115.0 nM

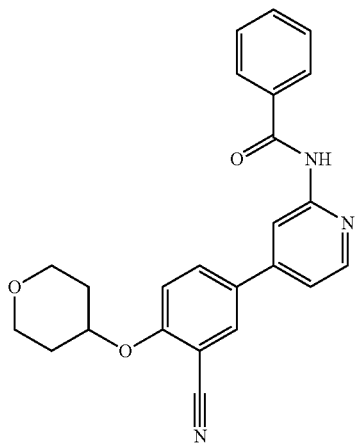

TBK1-IC50 = 393.6 nM
IKKE-IC50 = 95.9 nM

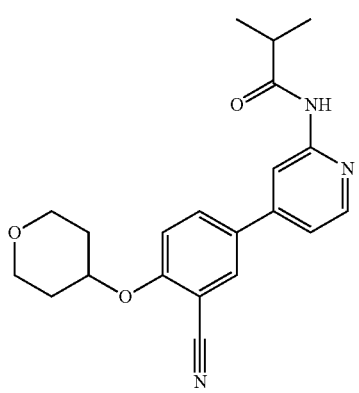

TBK1-IC50 = >1000 nM
IKKE-IC50 = 809.2 nM

The invention claimed is:
1. A compound of formula (I):

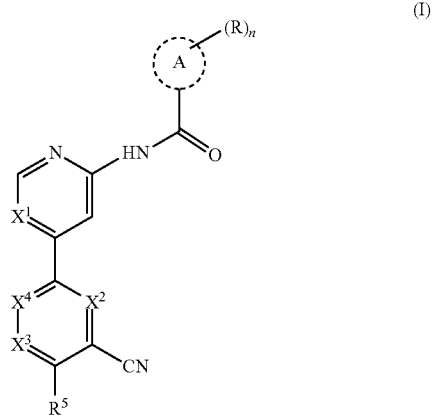

wherein:
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_{1-6}$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclyl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —S(O)(R$^a$)=NR$^b$, —N$_3$, —CN, and —NO$_2$;
Ring A is C$_{3-8}$ cycloalkyl or C$_{5-8}$ cycloalkenyl;
X$^1$ is CR$^1$ or N;
X$^2$ is CR$^2$ or N;
X$^3$ is CR$^3$ or N;
X$^4$ is CR$^4$ or N; provided that no more than two of X$^2$, X$^3$ and X$^4$ are N; and provided that when X$^2$ is N, X$^4$ is CR$^4$;
R$^1$ is H, halo, —CN, C$_{1-3}$ haloalkyl, or C$_{1-3}$ alkyl;
R$^2$ is H or halo;
R$^3$ is selected from the group consisting of H, halo, —OR$^a$, C$_{1-6}$ alkyl, C$_{0-3}$alkylC$_{6-10}$ aryl, and C$_{0-3}$alkylC$_{3-6}$ cycloalkyl;
R$^4$ is H or halo;
R$^5$ is selected from the group consisting of H, hydroxyl, C$_{1-6}$ alkyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_2$NR$^a$R$^b$, —NR$^a$S(O)$_2$R$^b$, C$_{6-10}$ aryl, C$_{3-10}$ cycloalkyl, 5-10 membered heteroaryl, 3-12 membered heterocyclyl and —O—R$^6$, wherein each C$_{1-6}$ alkyl, C$_{6-10}$ aryl, C$_{3-10}$ cycloalkyl, 5-10 membered heteroaryl and 3-12 membered heterocyclyl is optionally substituted with one to five R$^7$ groups; provided that when X$^1$ is CR$^1$, R$^5$ is not H, hydroxyl, C$_{1-6}$ alkyl, halogen, or C$_{3-10}$ cycloalkyl;

R⁶ is $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with one to five R⁷ groups; provided that when X¹ is CR¹, R⁶ is not $C_{1-6}$ alkyl or $C_{1-6}$ haloalkyl;

each R⁷ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₀₋₂Rᵃ, —S(O)(Rᵃ)=NRᵇ, —S(O)₂NRᵃRᵇ, —NRᵃS(O)₂Rᵇ, —N₃, —CN, or —NO₂; or two R⁷ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with one to five groups independently selected from the group consisting of halogen, $C_{1-6}$ alkyl, $C_{1-6}$ heteroalkyl, $C_{1-6}$ haloalkyl, oxo, imino, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₀₋₂Rᵃ, —S(O)₂NRᵃRᵇ, —S(O)(Rᵃ)=NRᵇ, —NRᵃS(O)₂Rᵇ, —N₃, —CN, and —NO₂; and each Rᵃ and each Rᵇ is independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)NH₂, —C(O)NH($C_{1-6}$ alkyl), —C(O)N($C_{1-6}$ alkyl)₂ or absent, each of which is optionally substituted with one to three groups independently selected from the group consisting of $C_{1-6}$ alkyl, $C_{2-6}$ alkenyl, —CN, —OH, —OC$_{1-3}$ alkyl, and —NH₂; or Rᵃ and Rᵇ together with the atoms to which they are attached form a 3-12 membered heterocyclyl optionally substituted with one to three groups independently selected from the group consisting of $C_{1-6}$ alkyl, $C_{1-6}$ alkyl-OH, $C_{2-6}$ alkenyl, —CN, —OH, —OC$_{1-3}$ alkyl, and —NH₂, or a pharmaceutically acceptable salt thereof.

2. A compound of formula (Ia):

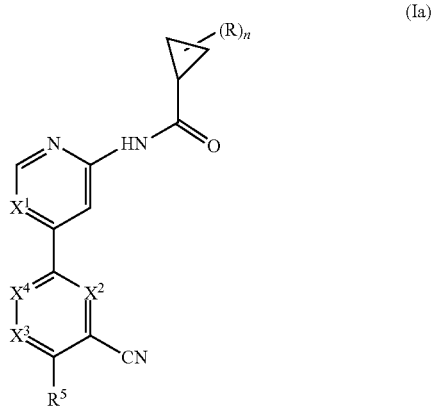

(Ia)

wherein:
n is 0, 1, 2 or 3;

each R is independently halogen, oxo, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₁₋₂Rᵃ, —S(O)(Rᵃ)=NRᵇ, —S(O)₂NRᵃRᵇ, —NRᵃS(O)₂Rᵇ, —N₃, —CN, —NO₂, $C_{1-6}$ alkyl, $C_{1-6}$ haloalkyl, $C_{1-6}$ alkyl-OH, $C_{3-10}$ cycloalkyl, $C_{1-6}$ heteroalkyl, 3-12 membered heterocyclyl, $C_{6-10}$ aryl, or 5-10 membered heteroaryl; or two R groups together with the atom(s) to which they are attached form a fused, spiro or bridged $C_{3-10}$ cycloalkyl or 3-12 membered heterocyclyl; and wherein each $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, fused, spiro or bridged cycloalkyl or heterocyclyl is optionally substituted with one to five groups independently selected from the group consisting of halogen, $C_{1-6}$ alkyl, $C_{1-6}$ heteroalkyl, $C_{1-6}$ haloalkyl, oxo, imino, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₀₋₂Rᵃ, —S(O)₂NRᵃRᵇ, —NRᵃS(O)₂Rᵇ, —S(O)(Rᵃ)=NRᵇ, —N₃, —CN, and —NO₂;

X¹ is CR¹ or N;
X² is CR² or N;
X³ is CR³ or N;
X⁴ is CR⁴ or N; provided that no more than two of X², X³ and X⁴ are N; and provided that when X² is N, X⁴ is CR⁴;

R¹ is H, halo, —CN, $C_{1-3}$ haloalkyl, or $C_{1-3}$ alkyl;
R² is H or halo;
R³ is selected from the group consisting of H, halo, —ORᵃ, $C_{1-6}$ alkyl, $C_{0-3}$alkyl$C_{6-10}$ aryl, and $C_{1-3}$alkyl$C_{3-6}$ cycloalkyl;
R⁴ is H or halo;
R⁵ is selected from the group consisting of H, hydroxyl, $C_{1-6}$ alkyl, —NRᵃRᵇ, halogen, —C(O)Rᵃ, —C(O)ORᵃ, —C(O)NRᵃRᵇ, —OC(O)NRᵃRᵇ, —NRᵃC(O)Rᵇ, —NRᵃC(O)ORᵇ, —S(O)₂NRᵃRᵇ, —NRᵃS(O)₂Rᵇ, $C_{6-10}$ aryl, $C_{3-10}$ cycloalkyl, 5-10 membered heteroaryl, 3-12 membered heterocyclyl and —O—R⁶, wherein each $C_{1-6}$ alkyl, $C_{6-10}$ aryl, $C_{3-10}$ cycloalkyl, 5-10 membered heteroaryl and 3-12 membered heterocyclyl is optionally substituted with one to five R⁷ groups; provided that when X¹ is CR¹, R⁵ is not H, hydroxyl, $C_{1-6}$ alkyl, halogen, or $C_{3-10}$ cycloalkyl;

R⁶ is $C_{1-6}$ alkyl, $C_{1-6}$ haloalkyl, $C_{6-10}$ aryl, 5-10 membered heteroaryl, $C_{3-10}$ cycloalkyl, or 3-12 membered heterocyclyl, each of which is optionally substituted with one to five R⁷ groups; provided that when X¹ is CR¹, R⁶ is not $C_{1-6}$ alkyl or $C_{1-6}$ haloalkyl;

each R⁷ is independently $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, halogen, oxo, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₀₋₂Rᵃ, —S(O)(Rᵃ)=NRᵇ, —S(O)₂NRᵃRᵇ, —NRᵃS(O)₂Rᵇ, —N₃, —CN, or —NO₂; or two R⁷ groups together with the atom(s) to which they are attached form a fused, spiro or bridged $C_{3-10}$ cycloalkyl or 3-12 membered heterocyclyl; wherein each $C_{1-6}$ alkyl, $C_{3-10}$ cycloalkyl, $C_{1-6}$ heteroalkyl, 3-12 membered heterocyclyl, $C_{6-10}$ aryl, and 5-10 membered heteroaryl is optionally substituted with one to five groups independently selected from the group consisting of halogen, $C_{1-6}$ alkyl, $C_{1-6}$ heteroalkyl, $C_{1-6}$ haloalkyl, oxo, imino, —ORᵃ, —C(O)Rᵃ, —C(O)ORᵃ, —C(O)NRᵃRᵇ, —OC(O)NRᵃRᵇ, —NRᵃRᵇ, —NRᵃC(O)Rᵇ, —NRᵃC(O)ORᵇ, —S(O)₀₋₂Rᵃ, —S(O)₂NRᵃRᵇ, —S(O)(Rᵃ)=NRᵇ, —NRᵃS(O)₂Rᵇ, —N₃, —CN, and —NO₂; and each Rᵃ and each Rᵇ is independently H, $C_{1-6}$ alkyl, $C_{2-6}$ alkenyl, $C_{3-10}$ cycloalkyl, $C_{1-6}$ heteroalkyl, 3-12 membered heterocyclyl, $C_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with one to three groups independently selected from the group consisting of C$_{1-6}$ alkyl, C$_{2-6}$ alkenyl, —CN, —OH, —OC$_{1-3}$ alkyl, and —NH$_2$; or R$^a$ and R$^b$ together with the atoms to which they are attached form a 3-12 membered heterocyclyl optionally substituted with one to three groups independently selected from the group consisting of C$_{1-6}$ alkyl, C$_{1-6}$ alkyl-OH, C$_{2-6}$ alkenyl, —CN, —OH, —OC$_{1-3}$ alkyl, and —NH$_2$, or a pharmaceutically acceptable salt thereof.

3. A compound of formula (Ie):

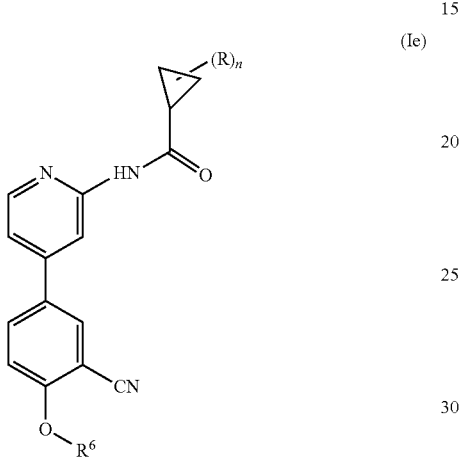

(Ie)

wherein:

n is 0, 1, 2 or 3;

each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_{1-6}$ haloalkyl, C$_{1-6}$ alkyl-OH, C$_{3-8}$ cycloalkyl, C$_{1-6}$ heteroalkyl, 3-8 membered heterocyclyl, C$_{6-10}$ aryl, or 5-10 membered heteroaryl; or two R groups together with the atom(s) to which they are attached form a fused, spiro or bridged C$_{3-6}$ cycloalkyl or 3-8 membered heterocyclyl; and wherein each C$_{1-6}$ alkyl, C$_{3-8}$ cycloalkyl, C$_{1-6}$ heteroalkyl, 3-8 membered heterocyclyl, C$_{6-10}$ aryl, 5-10 membered heteroaryl, fused, spiro or bridged cycloalkyl or heterocyclyl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —S(O)(R$^a$)=NR$^b$, —N$_3$, —CN, and —NO$_2$;

R$^6$ is C$_{6-10}$ aryl, 5-10 membered heteroaryl, C$_{3-10}$ cycloalkyl, or 3-8 membered heterocyclyl, each of which is optionally substituted with one to five R$^7$ groups;

each R$^7$ is independently C$_{1-6}$ alkyl, C$_{3-10}$ cycloalkyl, C$_{1-6}$ heteroalkyl, 3-8 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-8}$ cycloalkyl, C$_{1-6}$ heteroalkyl, 3-8 membered heterocyclyl, C$_{6-10}$ aryl, and 5-10 membered heteroaryl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —S(O)(R$^a$)=NR$^b$, —NR$^a$S(O)$_2$R$^b$, —N$_3$, —CN, and —NO$_2$; and each R$^a$ and each R$^b$ is independently H, C$_{1-6}$ alkyl, C$_{2-6}$ alkenyl, C$_{3-8}$ cycloalkyl, C$_{1-6}$ heteroalkyl, 3-8 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with one to three groups independently selected from the group consisting of C$_{1-6}$ alkyl, C$_{2-6}$ alkenyl, —CN, —OH, —OC$_{1-3}$ alkyl, and —NH$_2$; or R$^a$ and R$^b$ together with the atoms to which they are attached form a 3-8 membered heterocyclyl optionally substituted with one to three groups independently selected from the group consisting of C$_{1-6}$ alkyl, C$_{1-6}$ alkyl-OH, C$_{2-6}$ alkenyl, —CN, —OH, —OC$_{1-3}$ alkyl, and —NH$_2$, or a pharmaceutically acceptable salt thereof.

4. A compound of formula (If)

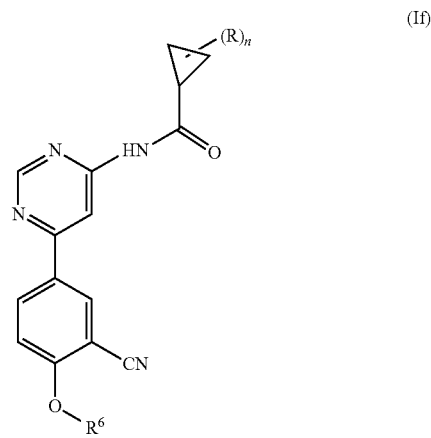

(If)

wherein:

n is 0, 1, 2 or 3;

each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_{1-6}$ haloalkyl, C$_{1-6}$ alkyl-OH, C$_{3-8}$ cycloalkyl, C$_{1-6}$ heteroalkyl, 3-8 membered heterocyclyl, C$_{6-10}$ aryl, or 5-10 membered heteroaryl; or two R groups together with the atom(s) to which they are attached form a fused, spiro or bridged C$_{3-6}$ cycloalkyl or 3-8 membered heterocyclyl; and wherein each C$_{1-6}$ alkyl, C$_{3-8}$ cycloalkyl, C$_{1-6}$ heteroalkyl, 3-8 membered heterocyclyl, C$_{6-10}$ aryl, 5-10 membered heteroaryl, fused, spiro or bridged cycloalkyl or heterocyclyl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —S(O)(R$^a$)=NR$^b$, —N$_3$, —CN, and —NO$_2$;

R$^6$ is C$_{6-10}$ aryl, 5-10 membered heteroaryl, C$_{3-10}$ cycloalkyl, or 3-8 membered heterocyclyl, each of which is optionally substituted with one to five R$^7$ groups;

each R$^7$ is independently C$_{1-6}$ alkyl, C$_{3-10}$ cycloalkyl, C$_{1-6}$ heteroalkyl, 3-8 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-8}$ cycloalkyl, C$_{1-6}$ heteroalkyl, 3-8 membered heterocyclyl, C$_{6-10}$ aryl, and 5-10 membered heteroaryl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —S(O)(R$^a$)=NR$^b$, —NR$^a$S(O)$_2$R$^b$, —N$_3$, —CN, and —NO$_2$; and each R$^a$ and each R$^b$ is independently H, C$_{1-6}$ alkyl, C$_{2-6}$ alkenyl, C$_{3-8}$ cycloalkyl, C$_{1-6}$ heteroalkyl, 3-8 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with one to three groups independently selected from the group consisting of C$_{1-6}$ alkyl, C$_{2-6}$ alkenyl, —CN, —OH, —OC$_{1-3}$ alkyl, and —NH$_2$; or R$^a$ and R$^b$ together with the atoms to which they are attached form a 3-8 membered heterocyclyl optionally substituted with one to three groups independently selected from the group consisting of C$_{1-6}$ alkyl, C$_{1-6}$ alkyl-OH, C$_{2-6}$ alkenyl, —CN, —OH, —OC$_{1-3}$ alkyl, and —NH$_2$, or a pharmaceutically acceptable salt thereof.

5. The compound of claim 1, or a pharmaceutically acceptable salt thereof, wherein X$^1$ is CR$^1$.

6. The compound of claim 1, or a pharmaceutically acceptable salt thereof, wherein X$^1$ is N.

7. The compound of claim 1, or a pharmaceutically acceptable salt thereof, wherein X$^2$ is CR$^2$.

8. The compound of claim 1, or a pharmaceutically acceptable salt thereof, wherein X$^2$ is N, X$^3$ is CR$^3$ and X$^4$ is CR$^4$.

9. The compound of claim 1, or a pharmaceutically acceptable salt thereof, wherein R is halo, —CN, C$_{1-3}$ alkyl, C$_{1-3}$ alkylhalide, C$_{1-6}$ alkyl-OH, —C(O)H, —C(O)—NH$_2$, —COOH, —C(O)OC$_{1-3}$alkyl, —C(O)NHC$_{1-3}$alkyl, —CH$_2$N(CH$_3$)$_2$, —C(O)-azetidinyl-OH, phenyl, or 5-6 membered heterocyclyl optionally substituted with C$_{1-3}$ alkyl, —NH$_2$, or —OH.

10. The compound of claim 1, or a pharmaceutically acceptable salt thereof, wherein R$^5$ is selected from the group consisting of tetrahydropyranyl, tetrahydrofuranyl, pyrrolidinyl, oxetanylmethyl, 1-(oxetan-3-yl)pyrrolidinyl, oxo-propanylnitrile-pyrrolinyl and piperidinyl.

11. The compound of claim 1, or a pharmaceutically acceptable salt thereof, wherein R$^5$ is N-pyrrolidinyloxy or N-piperidinyloxy substituted with C$_{1-6}$ alkoxycarbonyl, hydroxyl C$_{1-6}$ alkylcarbonyl, hydroxyl 3-6 membered heterocyclyl, halo 3-6 membered heterocyclyl, C$_{1-6}$ alkylcarbonyl or C$_{3-6}$ cycloalkyl-C$_{1-6}$ alkoxy.

12. The compound of claim 11, or a pharmaceutically acceptable salt thereof, wherein the R$^5$ group is further substituted with one or two fluoro groups.

13. The compound of claim 1, or a pharmaceutically acceptable salt thereof, wherein R$^5$ is:

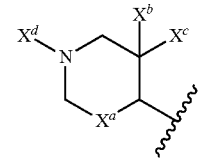

X$^a$ is a bond or C(R$^x$)(R$^y$), wherein R$^x$ and R$^y$ are independently selected from the group consisting of H, halo and methyl;

X$^b$ and X$^c$ are independently selected from the group consisting of H, halo and methyl; and X$^d$ is H; or C$_{1-6}$ alkyl, C$_{3-10}$ cycloalkyl, C$_{1-6}$ heteroalkyl, 3-12 membered heterocyclyl, C$_{6-10}$ aryl, or 5-10 membered heteroaryl, each of which is optionally substituted with one to five groups selected from the group consisting of C$_{1-6}$ alkyl, C$_{1-6}$ heteroalkyl, hydroxyl, C$_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, and halogen.

14. The compound of claim 13, or a pharmaceutically acceptable salt thereof, wherein X$^d$ is C$_{1-6}$ alkyl substituted with hydroxyl.

15. The compound of claim 13, or a pharmaceutically acceptable salt thereof, wherein X$^a$ is CH$_2$.

16. The compound of claim 13, or a pharmaceutically acceptable salt thereof, wherein X$^b$ and X$^c$ are each fluoro.

17. The compound of claim 13, or a pharmaceutically acceptable salt thereof, where X$^b$ is fluoro.

18. The compound of claim 1, or a pharmaceutically acceptable salt thereof, wherein R$^5$ is substituted with one R$^7$ group selected from the group consisting of C$_{1-6}$ alkoxycarbonyl, hydroxyl C$_{1-6}$ alkylcarbonyl, C$_{1-6}$ alkylcarbonyl and C$_{3-6}$ cycloalkyl-C$_{1-6}$ alkoxy.

19. The compound of claim 1, or a pharmaceutically acceptable salt thereof, wherein the Ring A-(R)$_n$ group of formula (I)

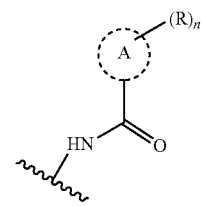

is selected from the group consisting of:

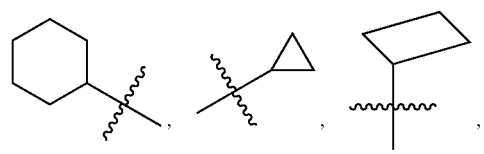

381
-continued
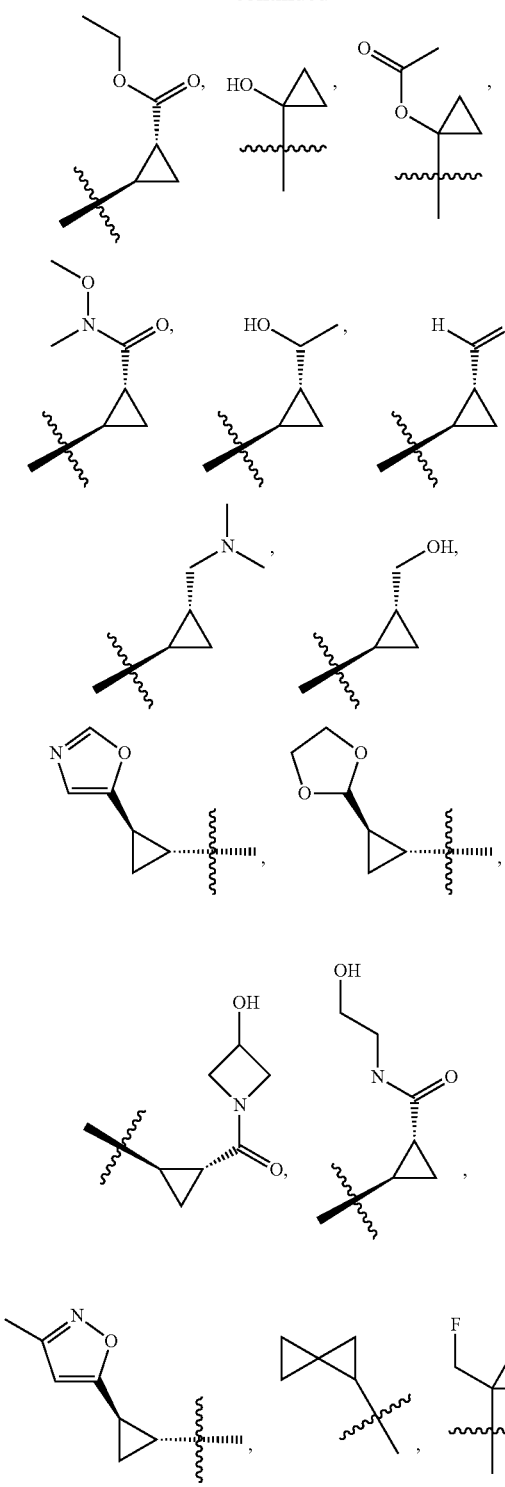
382
-continued
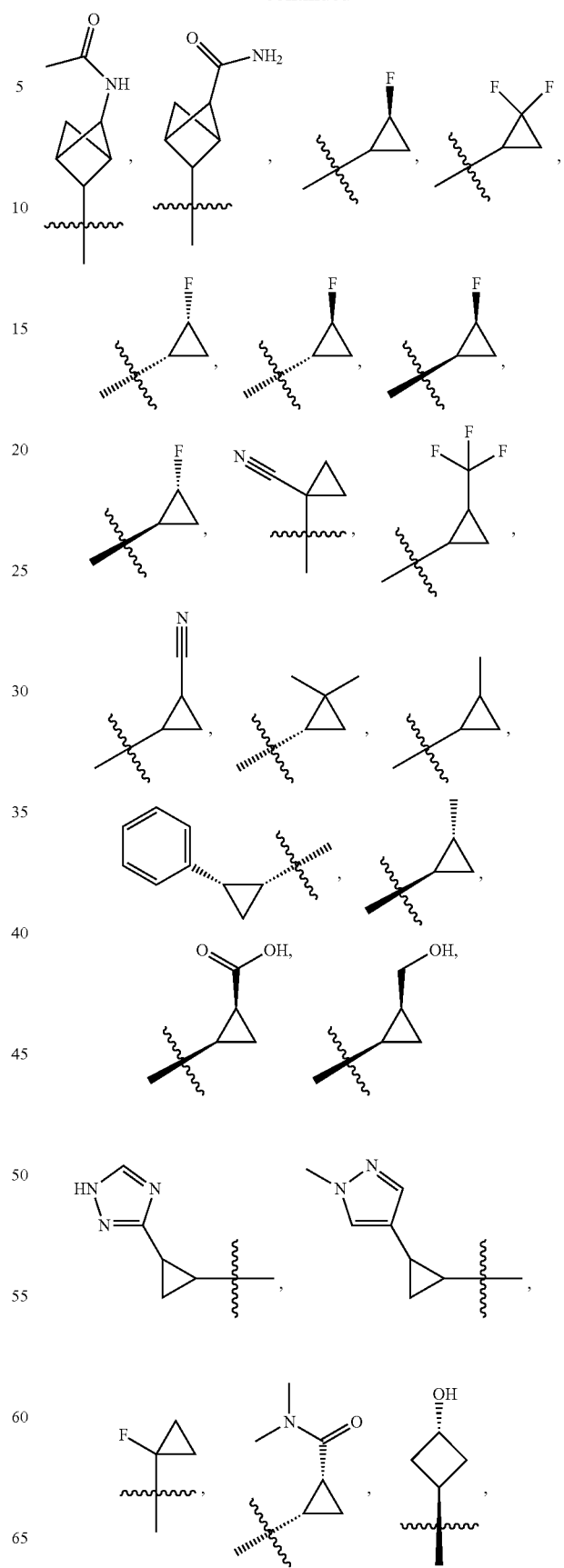

383
-continued
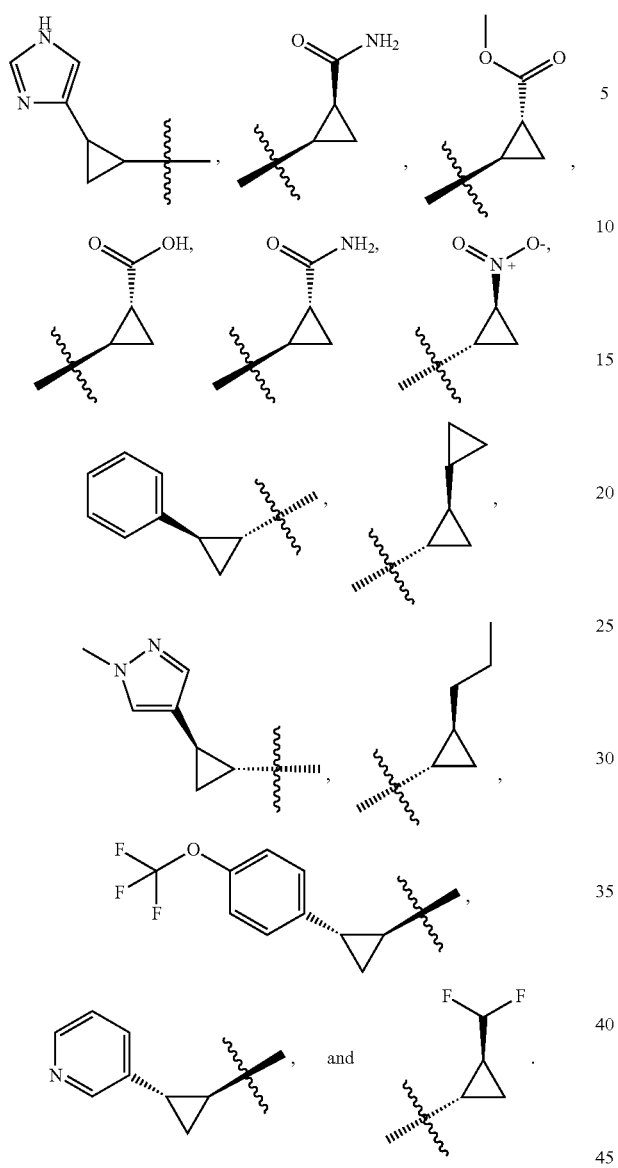
20. The compound of claim 1, or a pharmaceutically acceptable salt thereof, wherein $R^5$ is selected from the group consisting of:
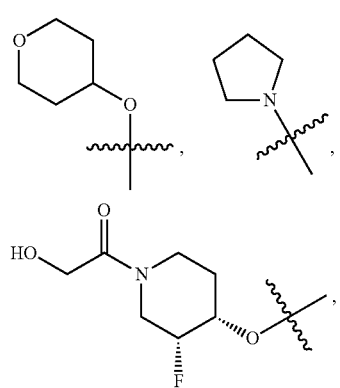
384
-continued
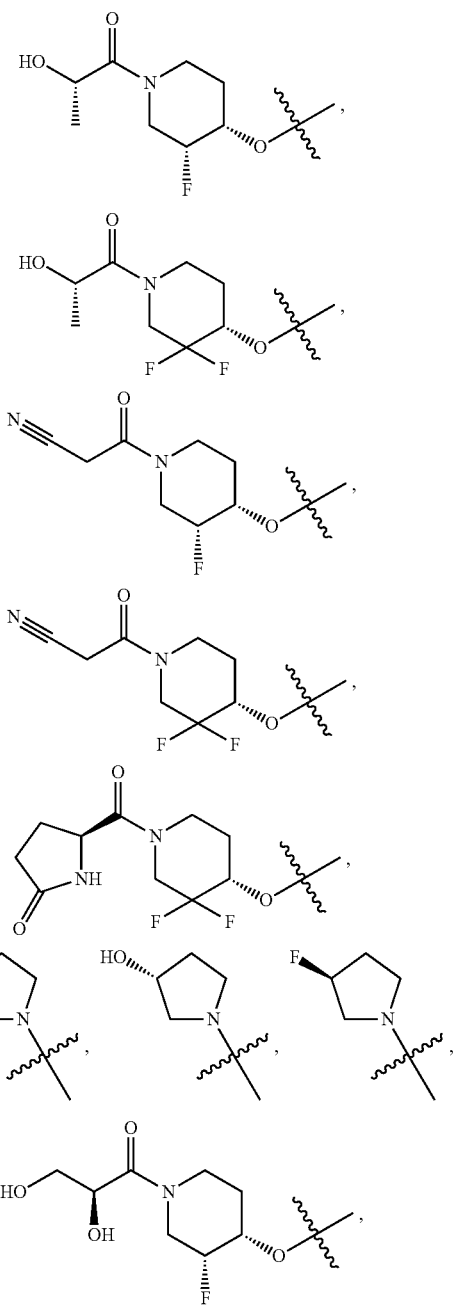

-continued
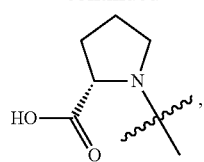
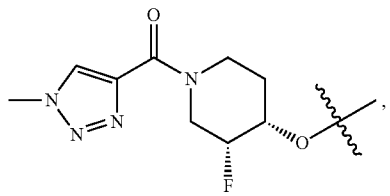
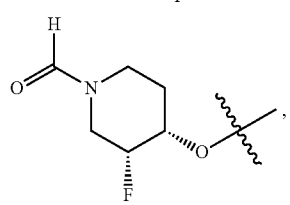
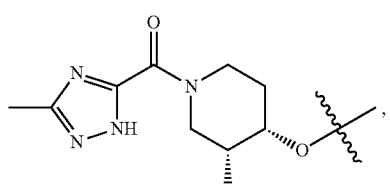
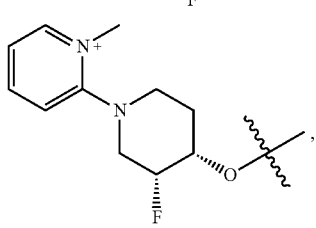
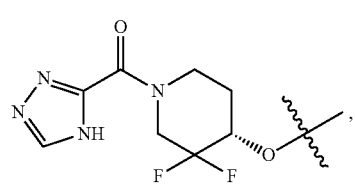
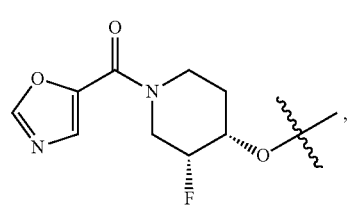
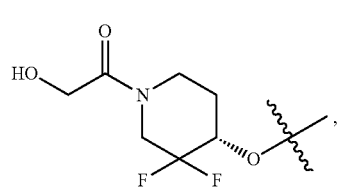
-continued
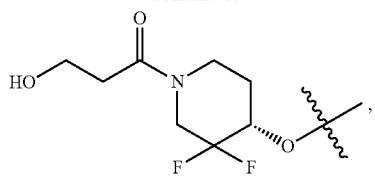
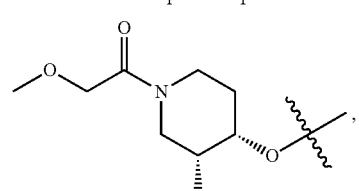
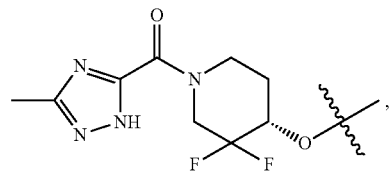
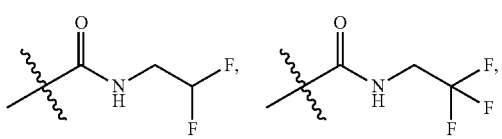
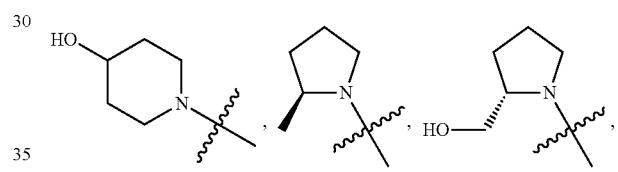
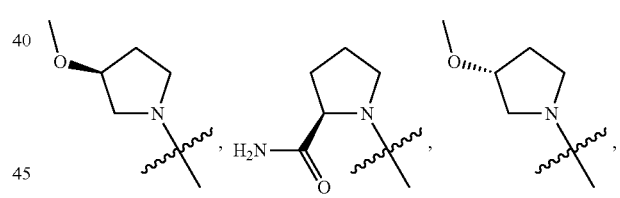
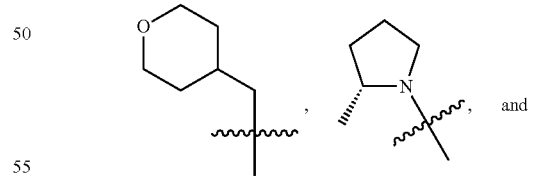, and
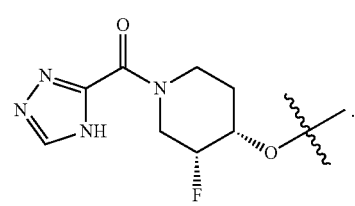

21. A compound selected from the group consisting of:
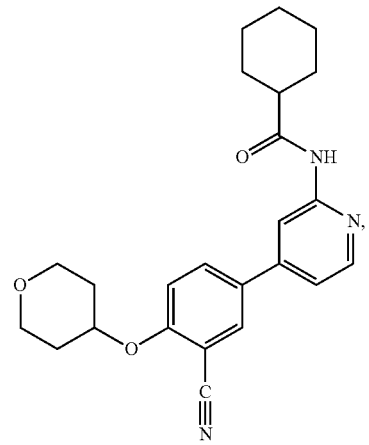
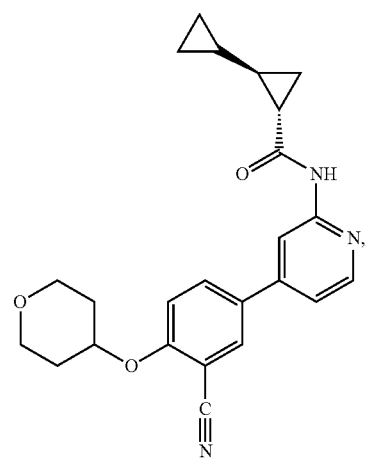
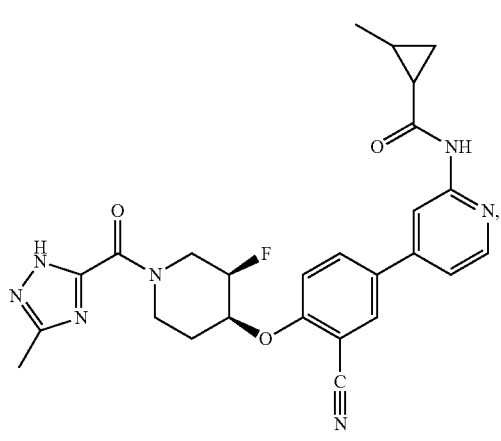
-continued
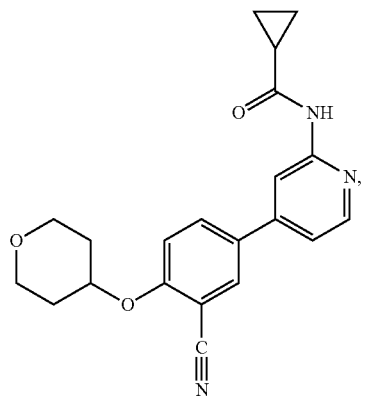
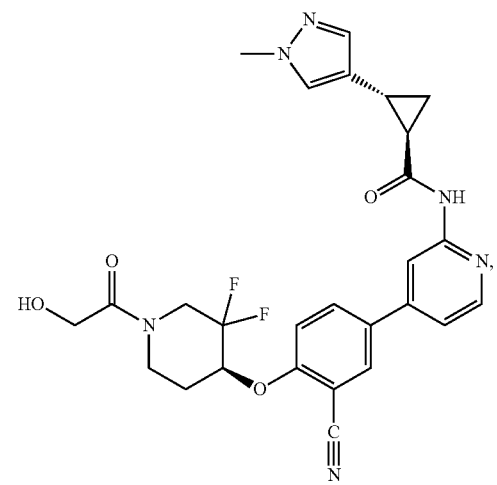
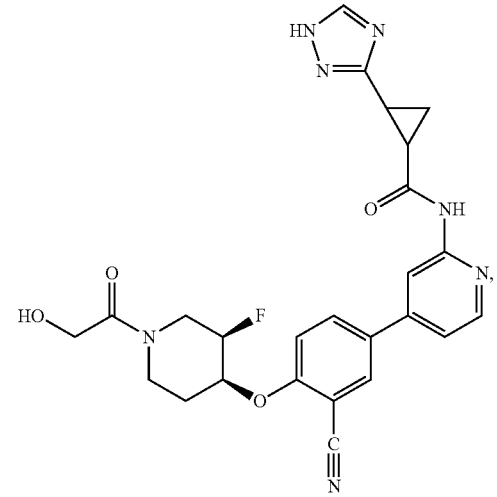

389
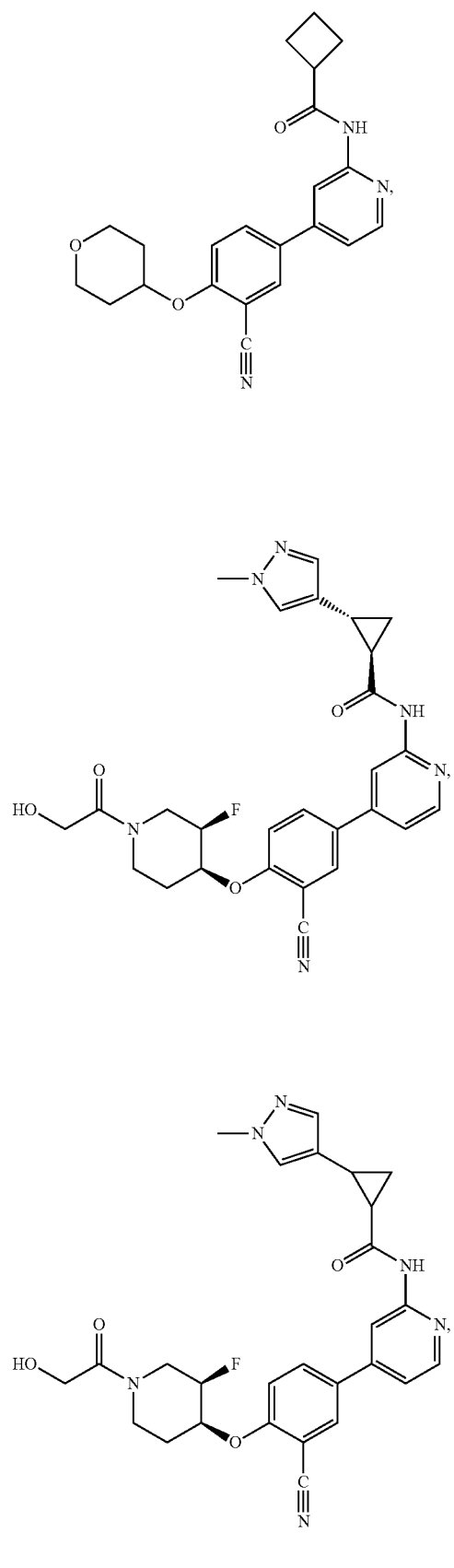
390
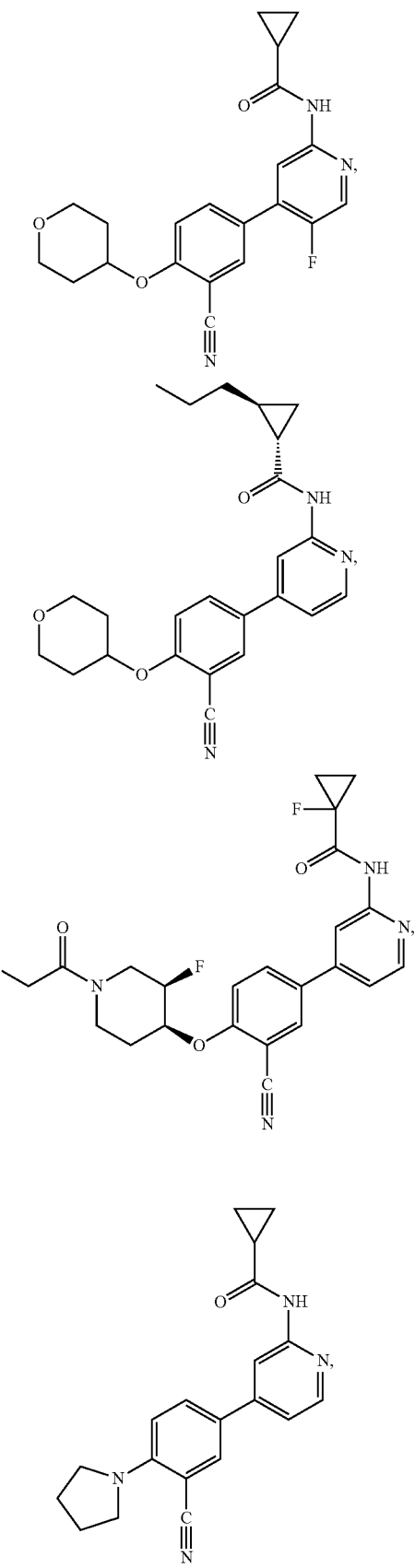

391
-continued
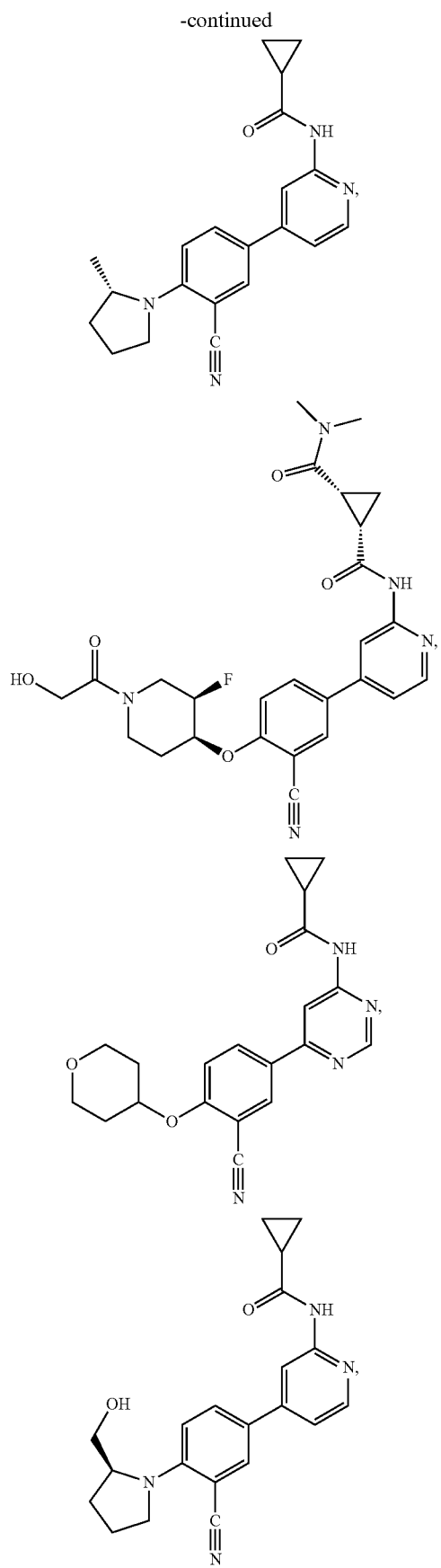
392
-continued
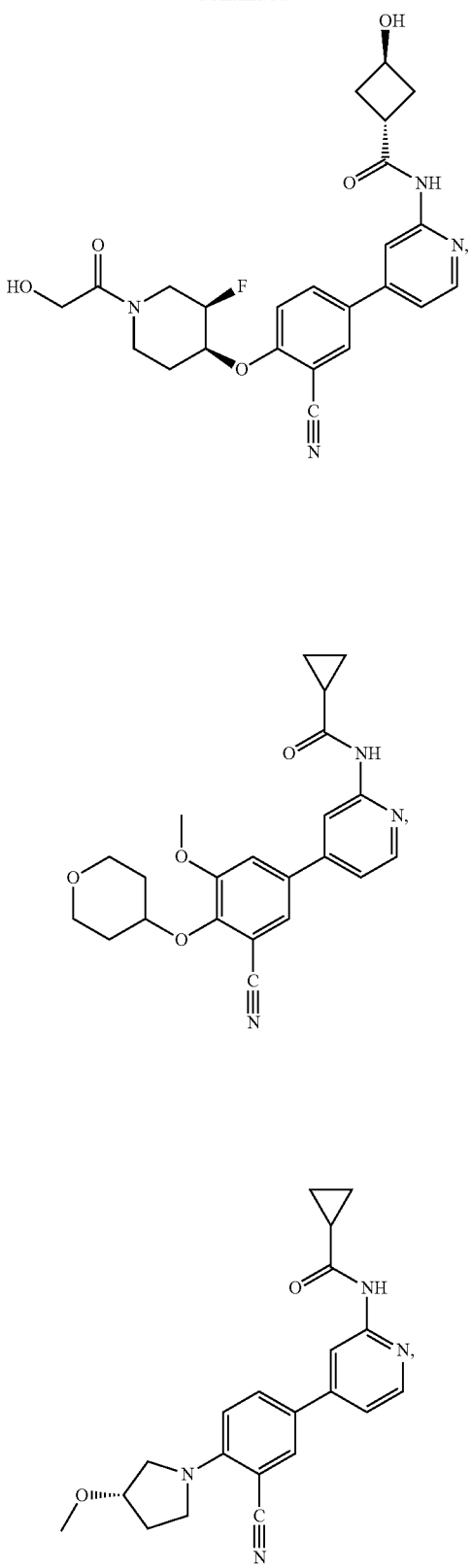

393
-continued
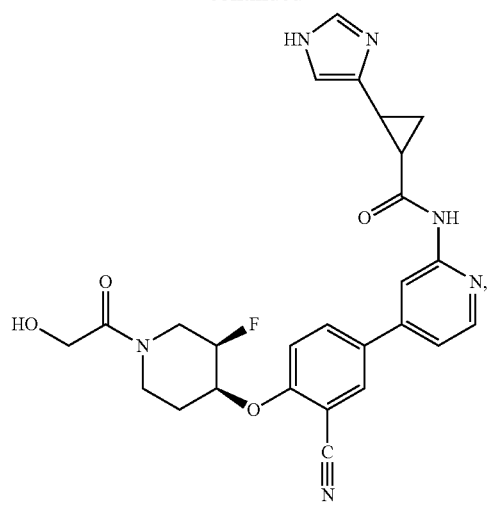
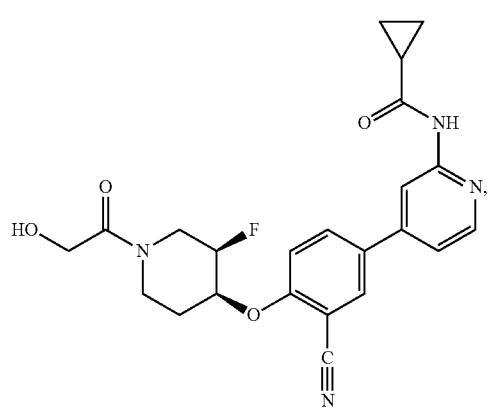
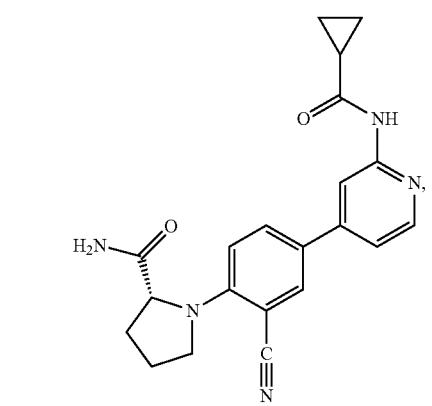
394
-continued
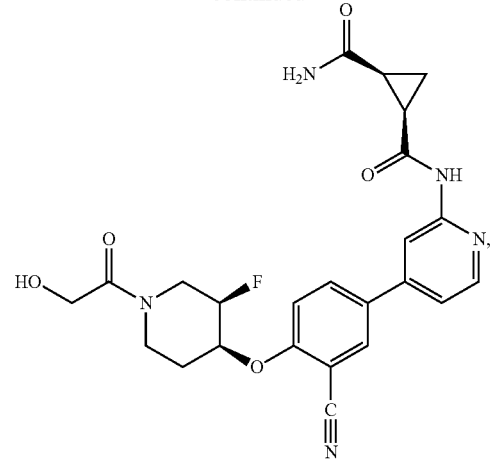
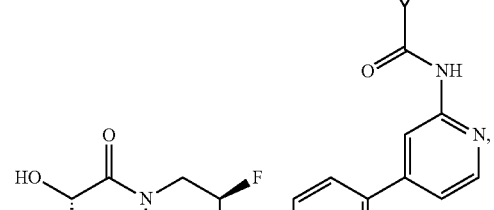
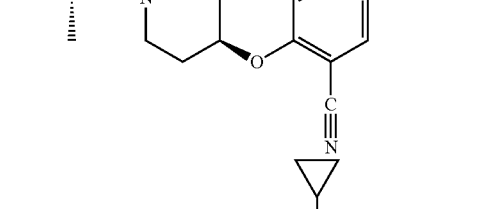
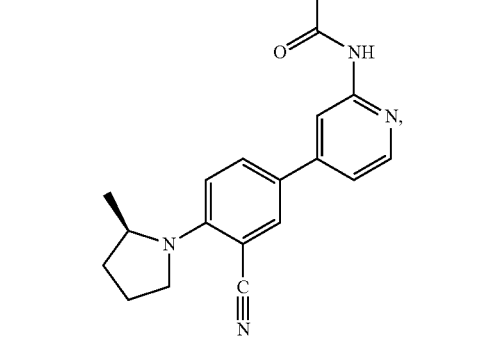
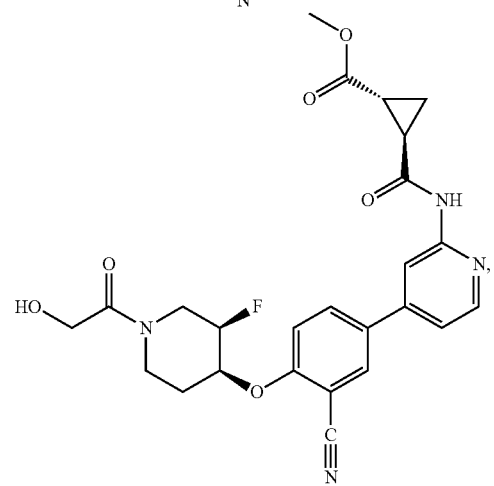

395
-continued
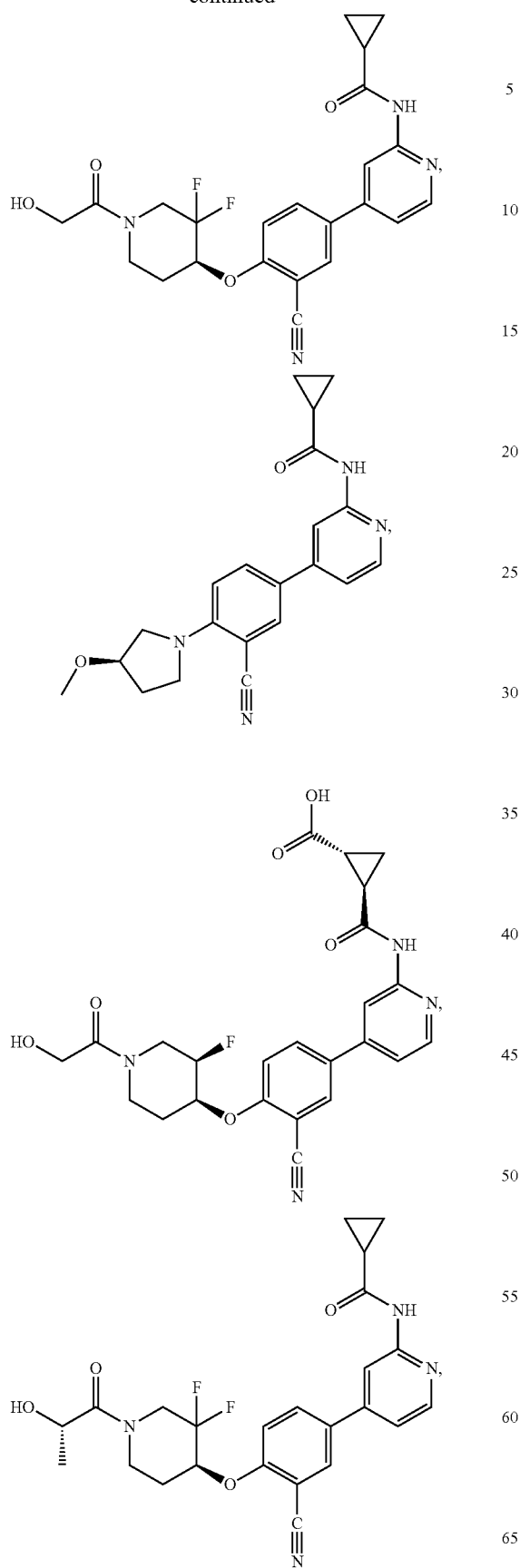
396
-continued
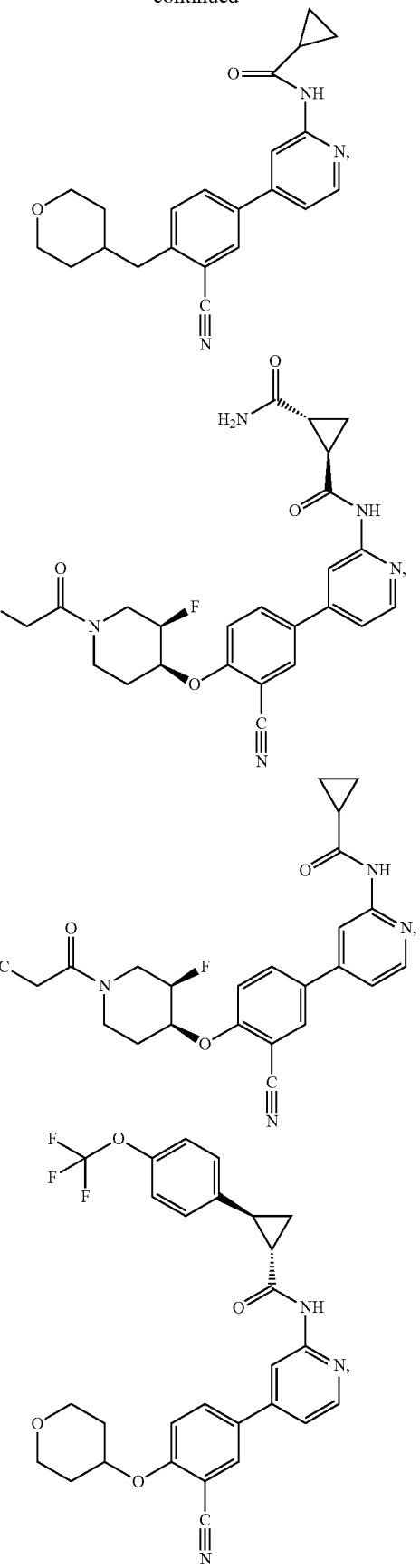

397
-continued
398
-continued
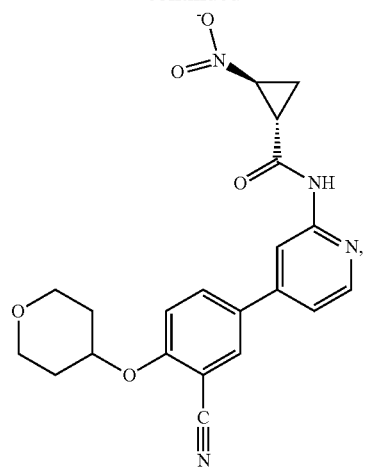
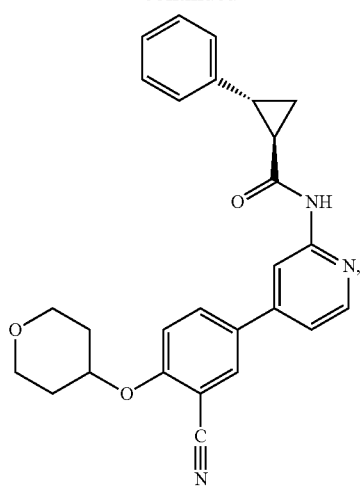

399
-continued
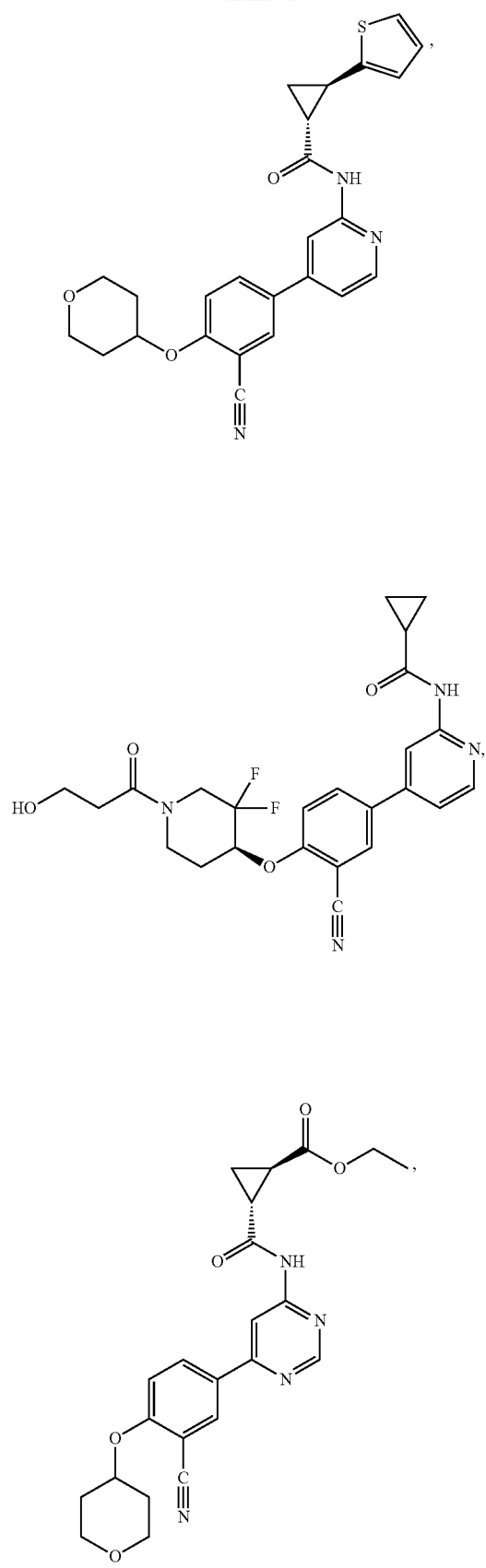
400
-continued
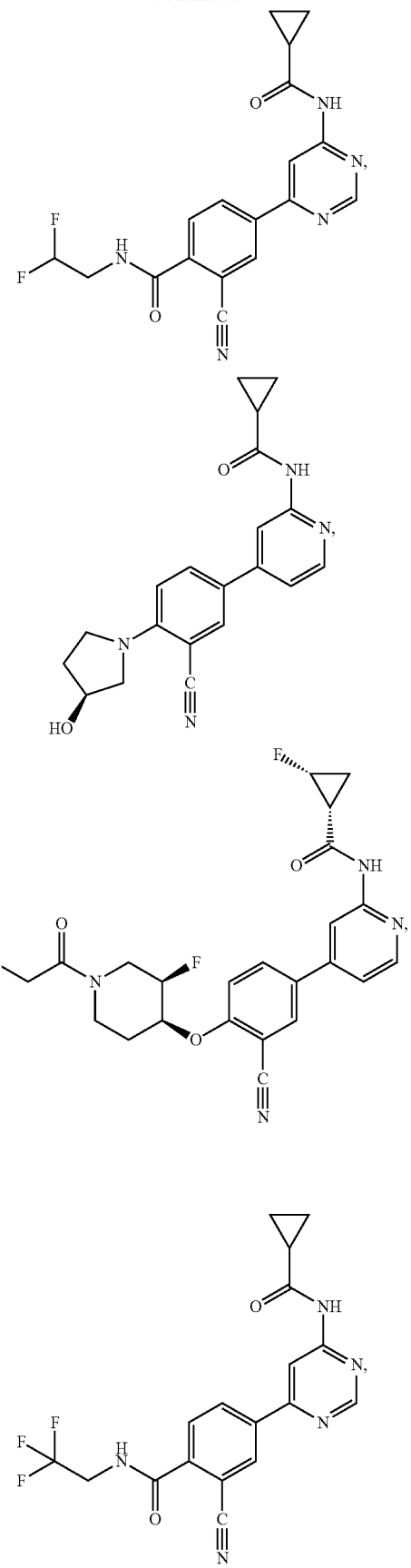

401
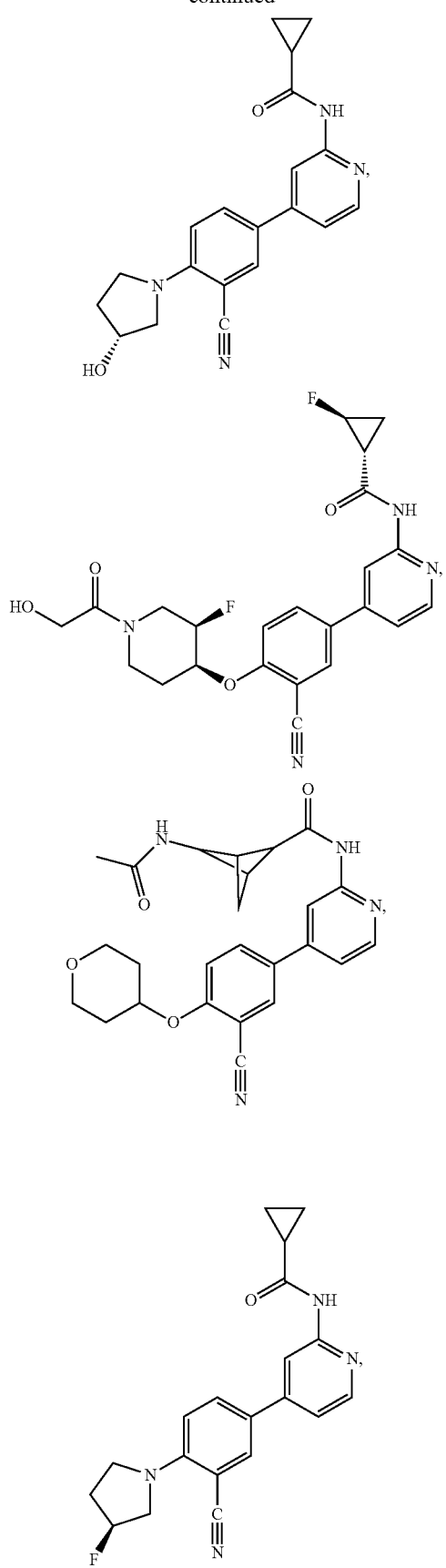
402
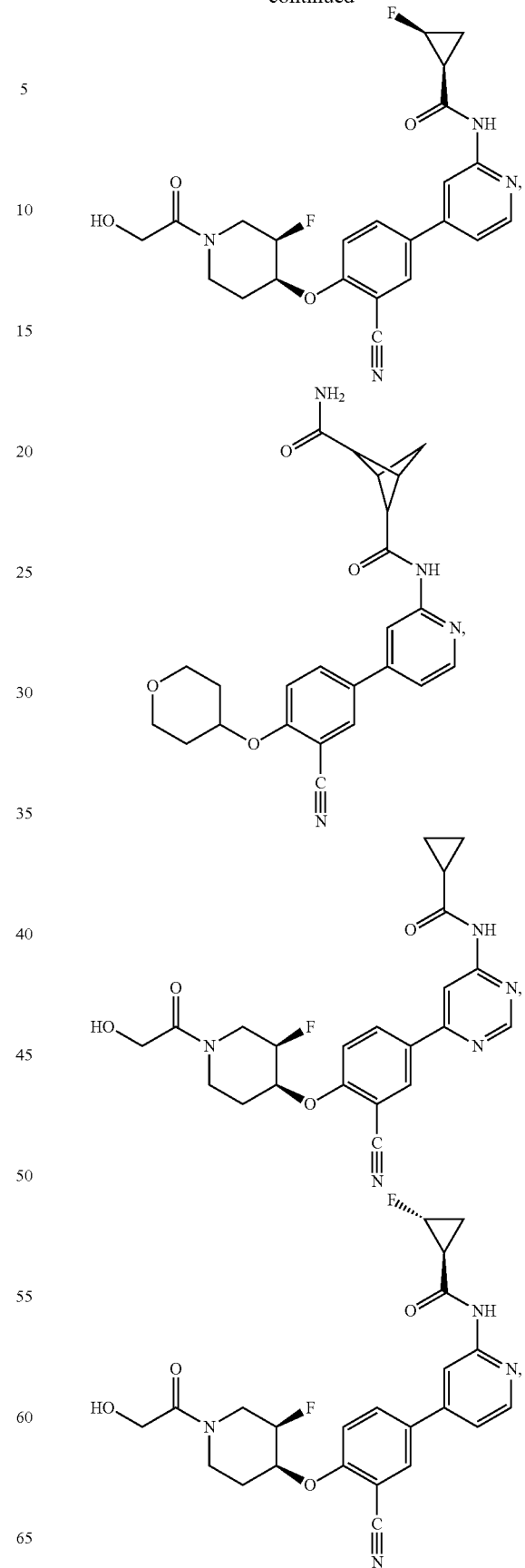

403
-continued
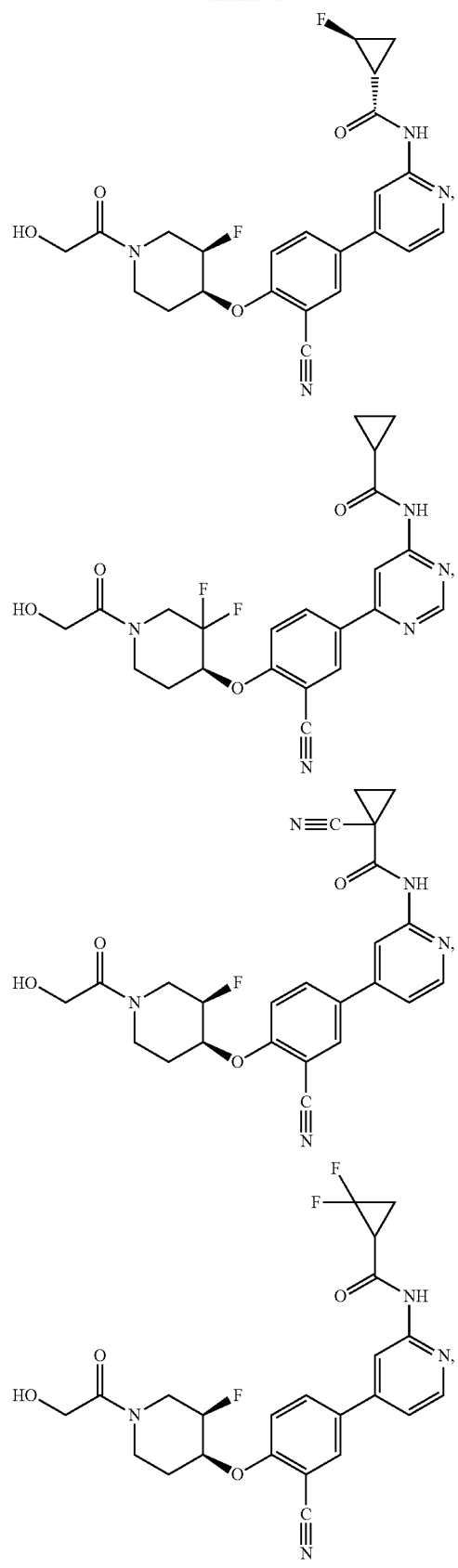
404
-continued
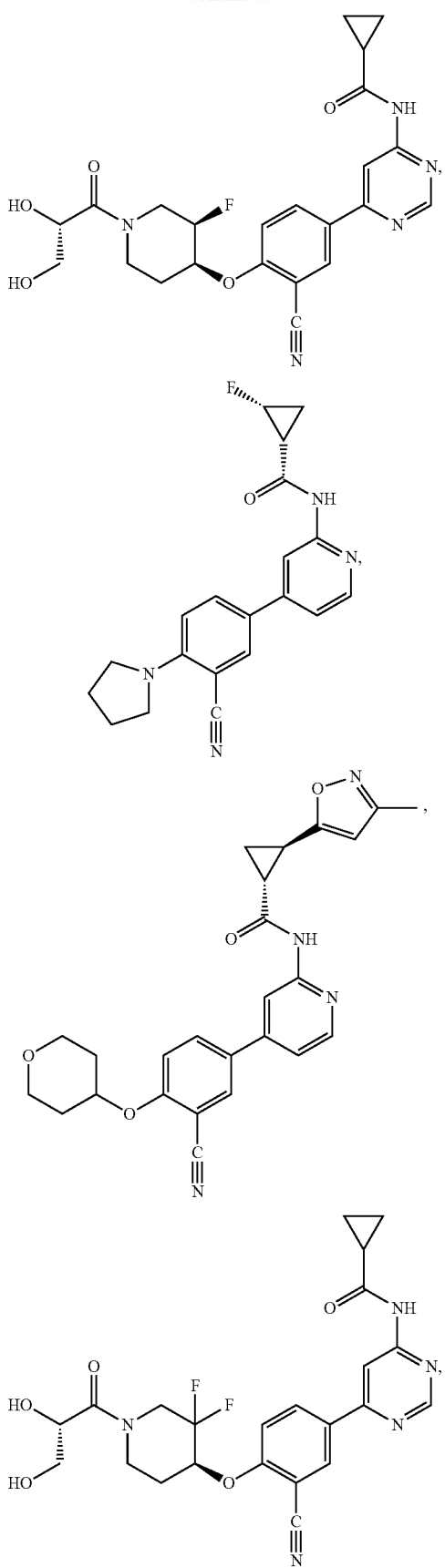

405
-continued
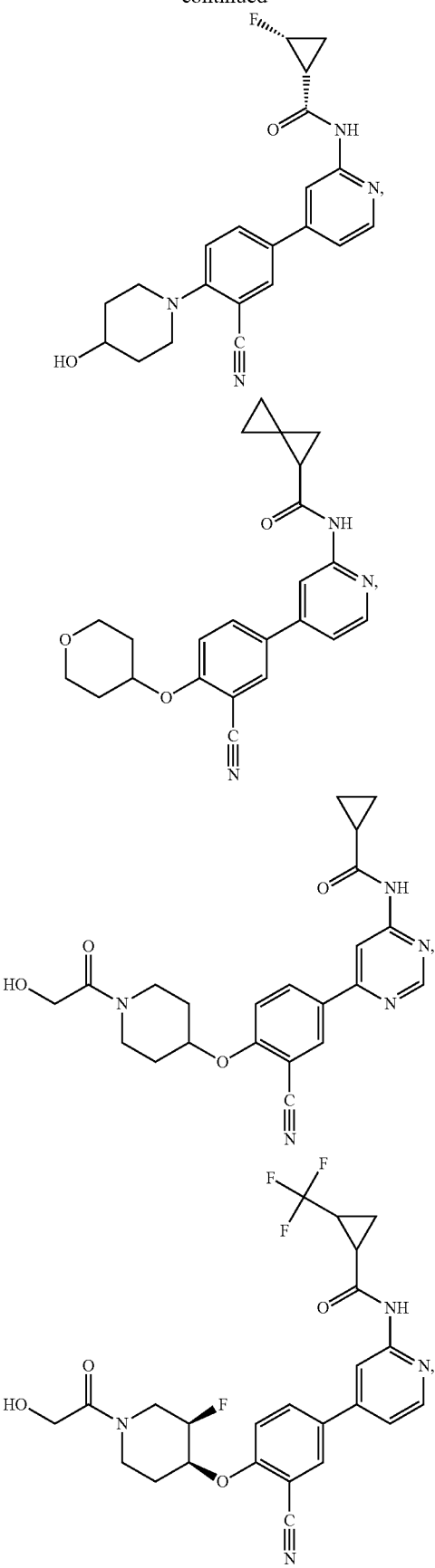
406
-continued
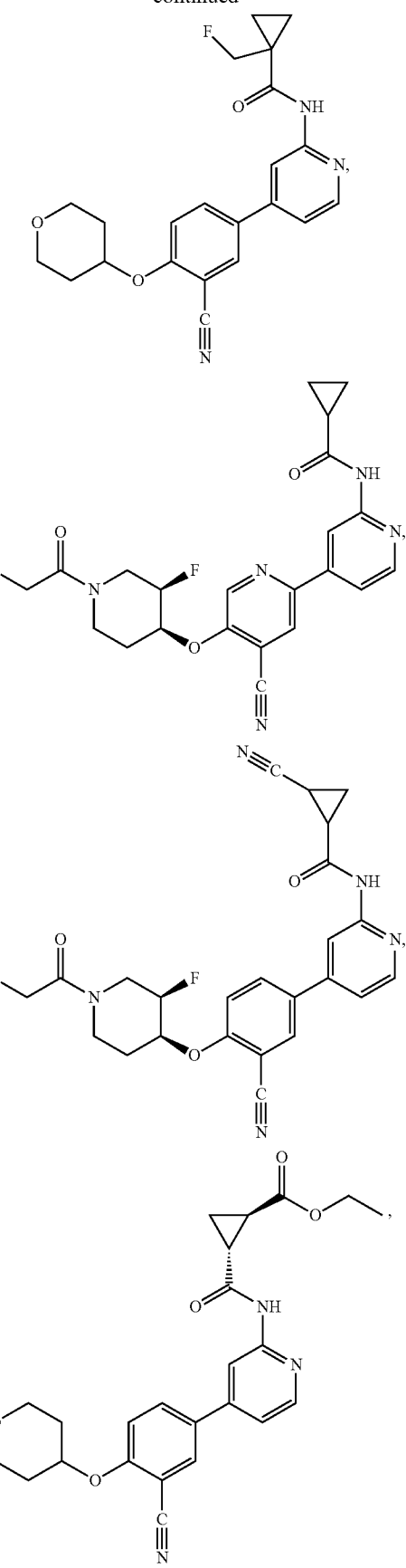

407
-continued
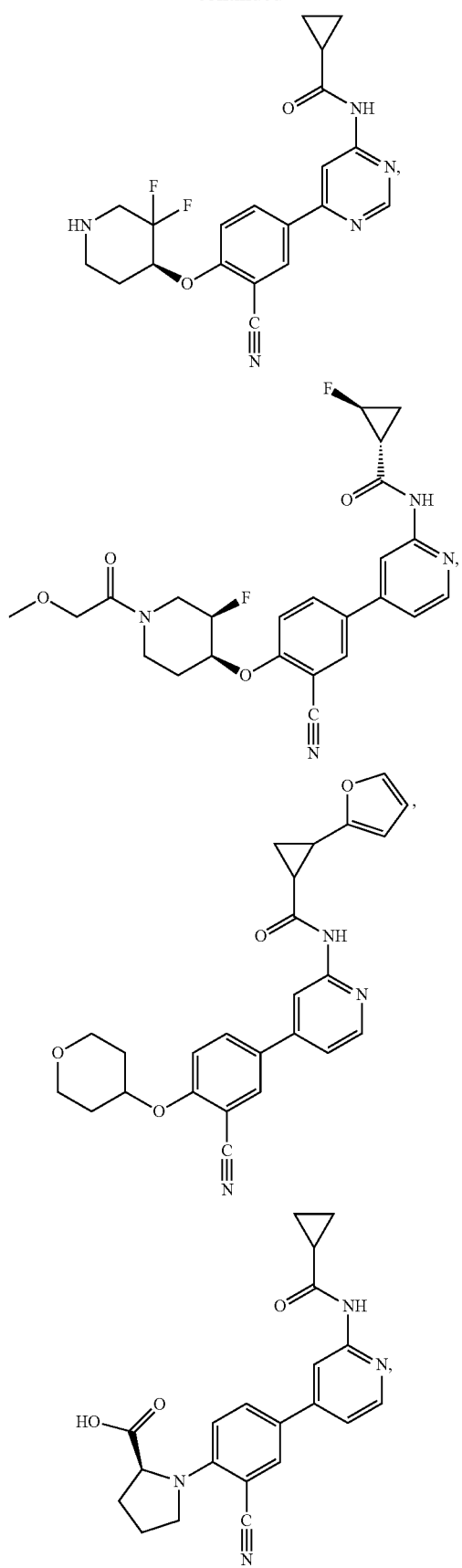
408
-continued
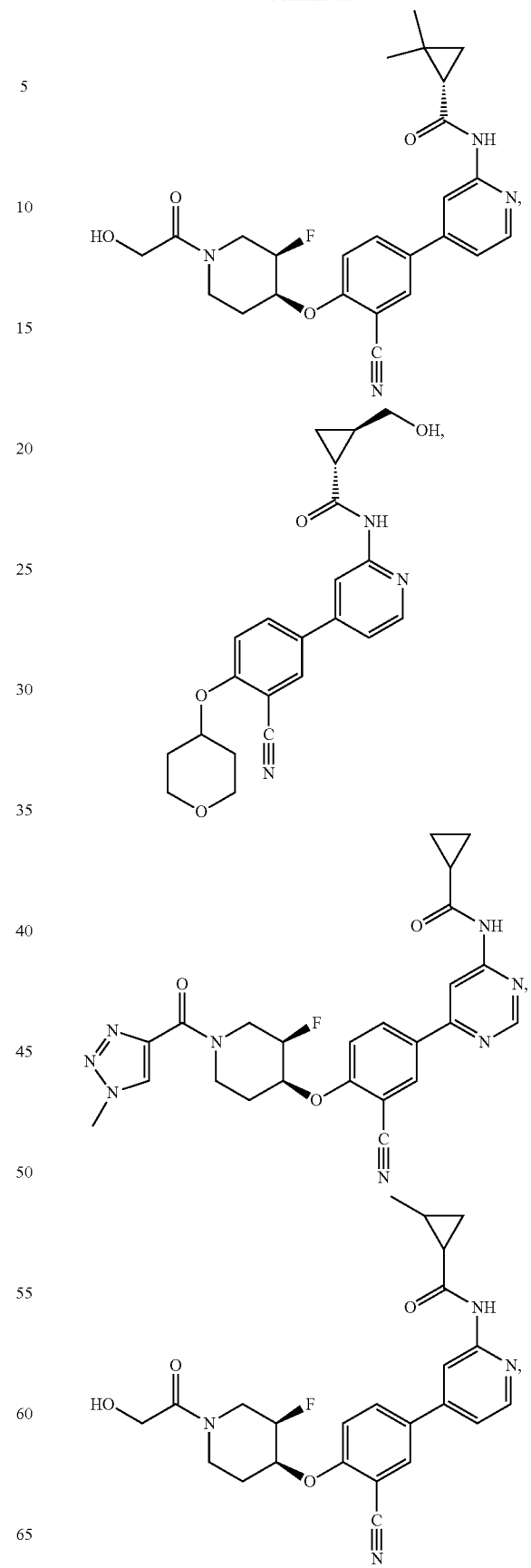

409
-continued
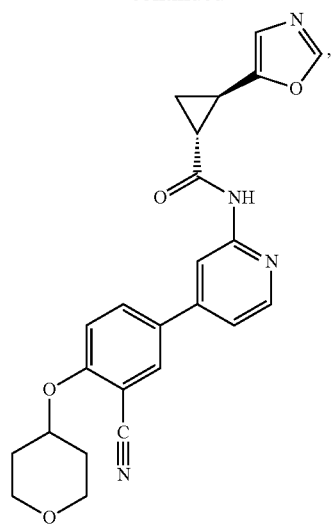
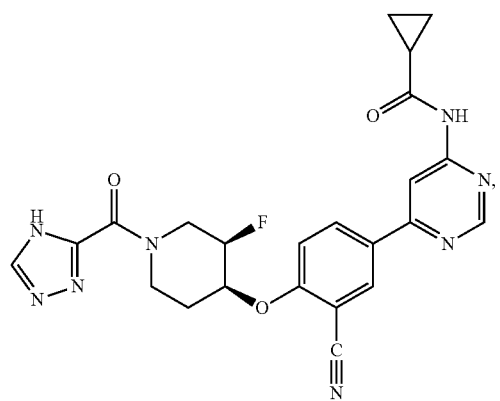
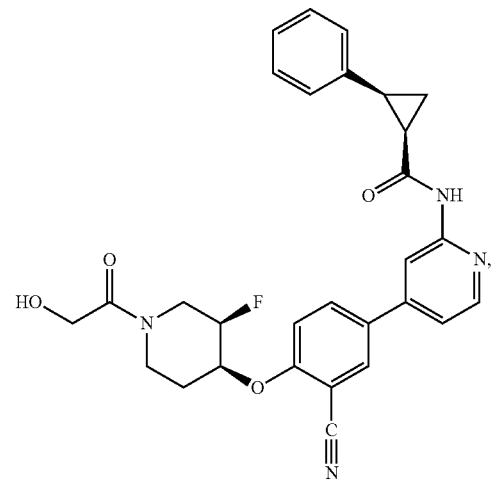
410
-continued
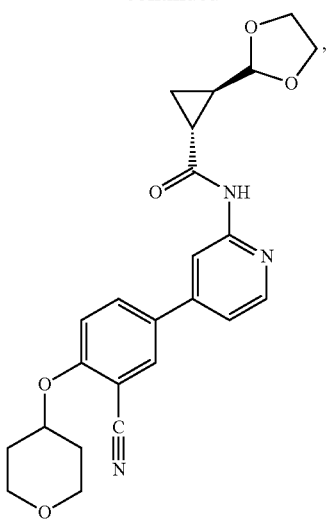
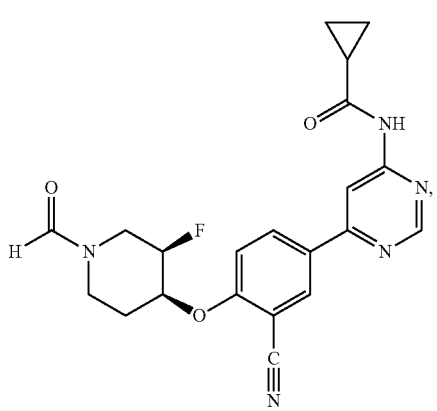
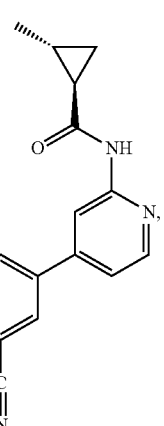

411
-continued
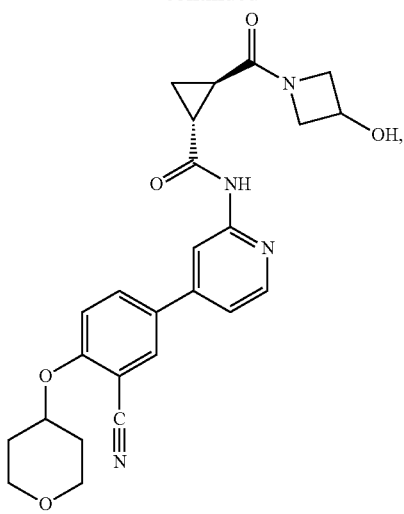
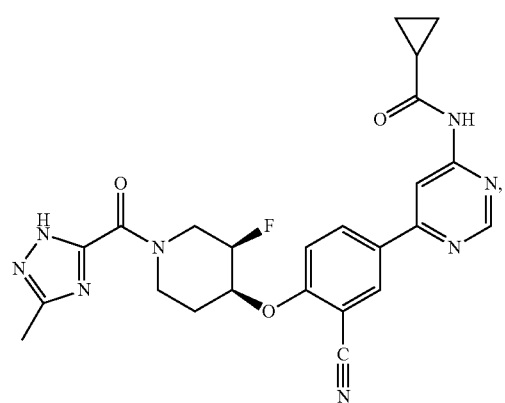
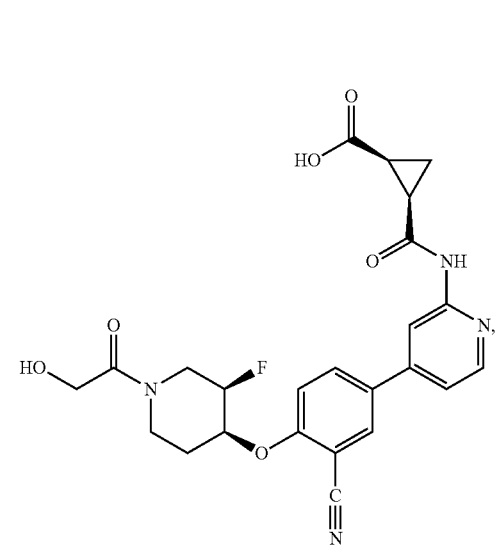
412
-continued
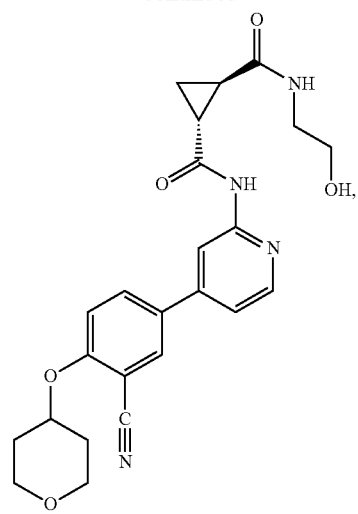
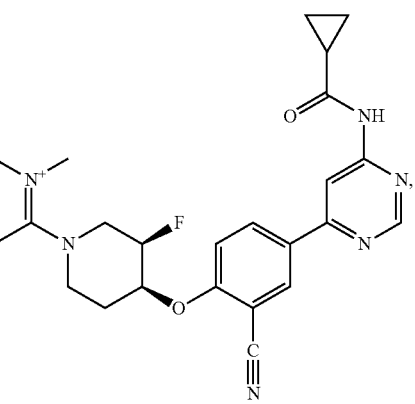
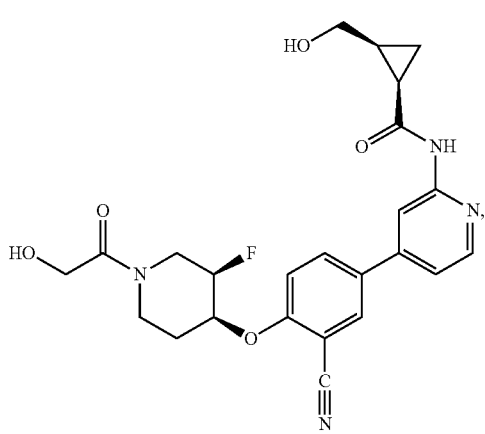

413
-continued
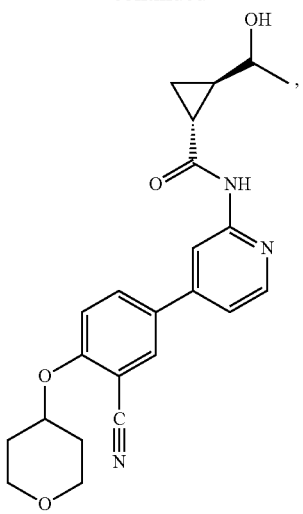
414
-continued
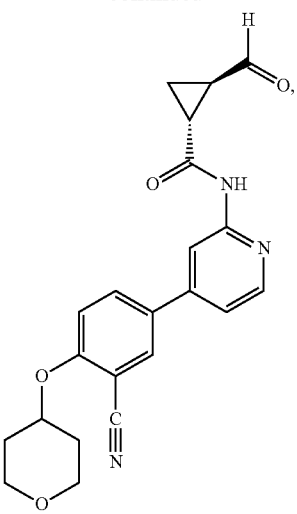
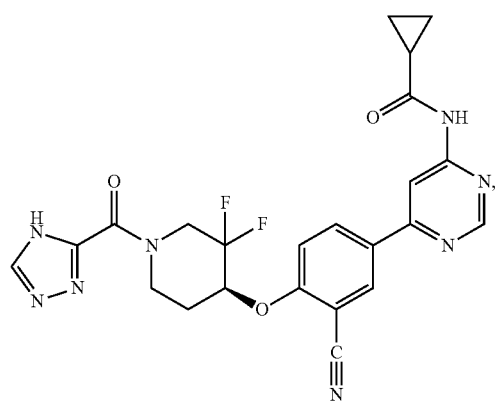
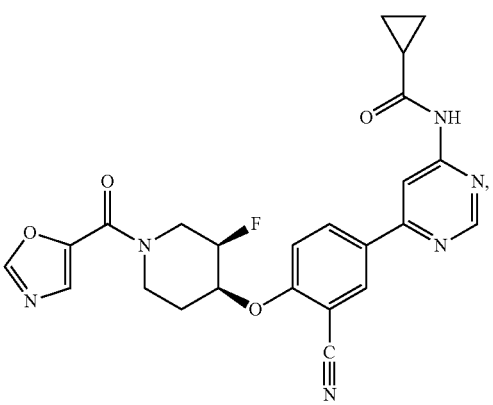
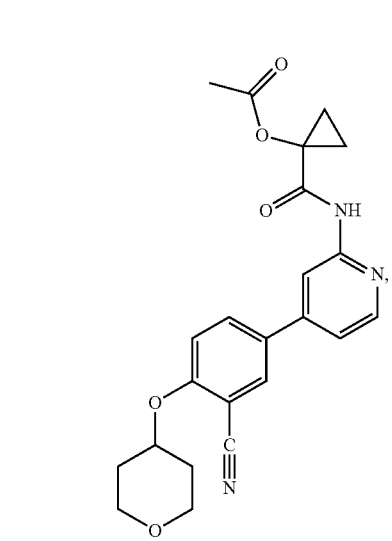
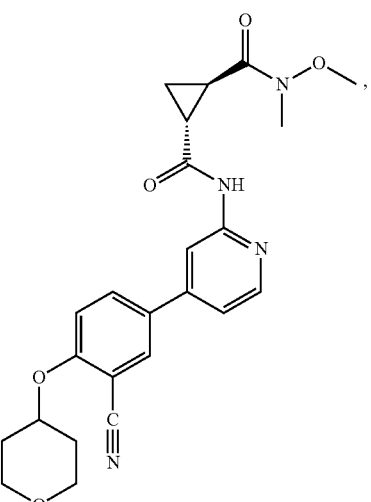

415
-continued

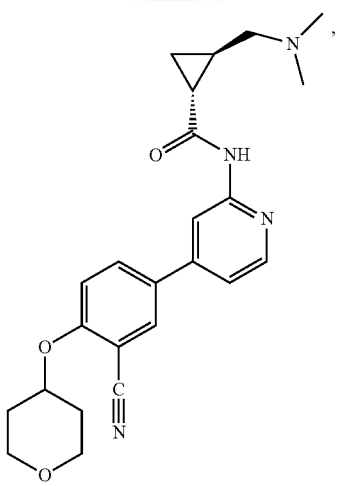

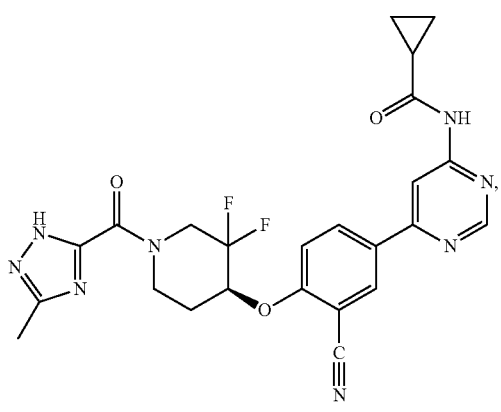

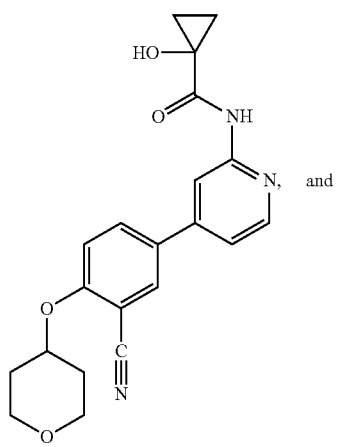

416
-continued

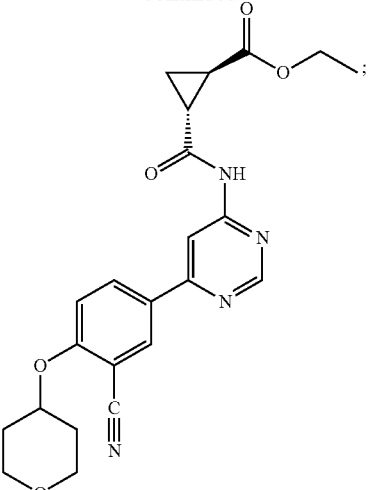

or a pharmaceutically acceptable salt thereof.

22. A pharmaceutical composition comprising the compound of claim 1, or a pharmaceutically acceptable salt thereof, and a pharmaceutically acceptable carrier.

23. A compound of formula (Ig):

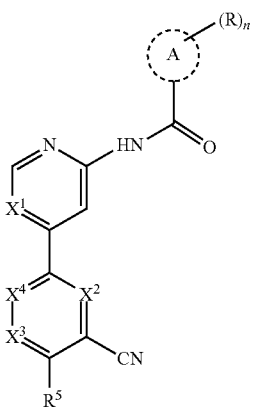

(Ig)

wherein:
n is 0, 1, 2 or 3;
each R is independently halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, —NO$_2$, C$_{1-6}$ alkyl, C$_{1-6}$ haloalkyl, C$_{1-6}$ alkyl-OH, C$_{3-10}$ cycloalkyl, C$_{1-6}$ heteroalkyl, 3-12 membered heterocyclyl, C$_{6-10}$ aryl, or 5-10 membered heteroaryl; or two R groups together with the atom(s) to which they are attached form a fused, spiro or bridged C$_{3-10}$ cycloalkyl or 3-12 membered heterocyclyl; and wherein each C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, fused, spiro or bridged cycloalkyl or heterocyclyl is optionally substituted with one to five groups independently selected from the group consisting of halogen, C$_{1-6}$ alkyl, C$_{1-6}$ alkoxyhaloalkyl, C$_{3-8}$ cycloalkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —S(O)(R$^a$)=NR$^b$, —N$_3$, —CN, and —NO$_2$;

Ring A is C$_{3-8}$ cycloalkyl or C$_{5-8}$ cycloalkenyl;

X$^1$ is CR$^1$ or N;

X$^2$ is CR$^2$ or N;

X$^3$ is CR$^3$ or N;

X$^4$ is CR$^4$ or N; provided that no more than two of X$^2$, X$^3$ and X$^4$ are N; and provided that when X$^2$ is N, X$^4$ is CR$^4$;

R$^1$ is H, halo, —CN, C$_{1-3}$ haloalkyl, or C$_{1-3}$ alkyl;

R$^2$ is H or halo;

R$^3$ is selected from the group consisting of hydrogen, halo, —OR$^a$, C$_{1-6}$ alkyl, C$_{0-3}$alkylC$_{6-10}$ aryl, and C$_{0-3}$alkylC$_{3-6}$ cycloalkyl;

R$^4$ is H or halo;

R$^5$ is selected from the group consisting of H, hydroxyl, C$_{1-6}$ alkyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_2$NR$^a$R$^b$, —NR$^a$S(O)$_2$R$^b$, C$_{6-10}$ aryl, C$_{3-10}$ cycloalkyl, 5-10 membered heteroaryl, 3-12 membered heterocyclyl and —O—R$^6$, wherein each C$_{1-6}$ alkyl, C$_{6-10}$ aryl, C$_{3-10}$ cycloalkyl, 5-10 membered heteroaryl and 3-12 membered heterocyclyl is optionally substituted with one to five R$^7$ groups; provided that when X$^1$ is CR$^1$, R$^5$ is not H, hydroxyl, C$_{1-6}$ alkyl, halogen, or C$_{3-10}$ cycloalkyl;

R$^6$ is C$_{1-6}$ alkyl, C$_{1-6}$ haloalkyl, C$_{6-10}$ aryl, 5-10 membered heteroaryl, C$_{3-10}$ cycloalkyl, or 3-12 membered heterocyclyl, each of which is optionally substituted with one to five R$^7$ groups; provided that when X$^1$ is CR$^1$, R$^6$ is not C$_{1-6}$ alkyl or C$_{1-6}$ haloalkyl;

each R$^7$ is independently C$_{1-6}$ alkyl, C$_{3-10}$ cycloalkyl, C$_{1-6}$ heteroalkyl, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)(R$^a$)=NR$^b$, —S(O)$_2$NR$^a$R$^b$, —NR$^a$S(O)$_2$R$^b$, —N$_3$, —CN, or —NO$_2$; or two R$^7$ groups together with the atom(s) to which they are attached form a fused, spiro or bridged C$_{3-10}$ cycloalkyl or 3-12 membered heterocyclyl; wherein each C$_{1-6}$ alkyl, C$_{3-10}$ cycloalkyl, C$_{1-6}$ heteroalkyl, 3-12 membered heterocyclyl, C$_{6-10}$ aryl, and 5-10 membered heteroaryl is optionally substituted with one to five groups independently selected from the group consisting of halogen, C$_{1-6}$ alkyl, C$_{1-6}$ heteroalkyl, C$_{1-6}$ haloalkyl, oxo, imino, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —S(O)(R$^a$)=NR$^b$, —NR$^a$S(O)$_2$R$^b$, —N$_3$, —CN, and —NO$_2$; and each R$^a$ and each R$^b$ is independently H, C$_{1-6}$ alkyl, C$_{2-6}$ alkenyl, C$_{3-10}$ cycloalkyl, C$_{1-6}$ heteroalkyl, 3-12 membered heterocyclyl, C$_{6-10}$ aryl, 5-10 membered heteroaryl, —C(O)NH$_2$, —C(O)NH(C$_{1-6}$ alkyl), —C(O)N(C$_{1-6}$ alkyl)$_2$ or absent, each of which is optionally substituted with one to three groups independently selected from the group consisting of C$_{1-6}$ alkyl, C$_{2-6}$ alkenyl, halogen, oxo, —CN, —OH, —OC$_{1-3}$ alkyl, —NH$_2$, —OC(O)CH(CH$_3$)NH$_2$, and —OP(O)(OH)$_2$; or R$^a$ and R$^b$ together with the atoms to which they are attached form a 3-12 membered heterocyclyl optionally substituted with one to three groups independently selected from the group consisting of C$_{1-6}$ alkyl, C$_{1-6}$ alkyl-OH, C$_{2-6}$ alkenyl, —CN, —OH, —OC$_{1-3}$ alkyl, and —NH$_2$, or a pharmaceutically acceptable salt thereof.

24. The compound of claim 23, or a pharmaceutically acceptable salt thereof, wherein X$^1$ is CR$^1$.

25. The compound claim 23, or a pharmaceutically acceptable salt thereof, wherein X$^1$ is N.

26. The compound of claim 23, or a pharmaceutically acceptable salt thereof, wherein X$^2$ is CR$^2$.

27. The compound of claim 23, or a pharmaceutically acceptable salt thereof, wherein X$^2$ is N, X$^3$ is CR$^3$ and X$^4$ is CR$^4$.

28. The compound of claim 23, or a pharmaceutically acceptable salt thereof, wherein X$^2$ is CR$^2$, X$^3$ is CR$^3$ and X$^4$ is CR$^4$.

29. The compound of claim 23, or a pharmaceutically acceptable salt thereof, wherein each R is independently halo, —CN, C$_{1-3}$ alkyl, C$_{1-3}$ alkylhalide, C$_{1-3}$ alkyl-OH, —C(O)H, —C(O)—NH$_2$, —COOH, —C(O)OC$_{1-3}$alkyl, —C(O)NHC$_{1-3}$alkyl, —CH$_2$N(CH$_3$)$_2$, —C(O)-azetidinyl-OH, phenyl, or 5-6 membered heterocyclyl optionally substituted with C$_{1-3}$ alkyl, —NH$_2$, or —OH.

30. The compound of claim 23, or a pharmaceutically acceptable salt thereof, wherein R$^5$ is selected from the group consisting of tetrahydropyranyl, tetrahydrofuranyl, pyrrolidinyl, oxetanylmethyl, 1-(oxetan-3-yl)pyrrolidinyl, oxo-propanylnitrile-pyrrolinyl and piperidinyl.

31. The compound of claim 23, or a pharmaceutically acceptable salt thereof, wherein R$^5$ is N-pyrrolidinyloxy or N-piperidinyloxy substituted with C$_{1-6}$ alkoxycarbonyl, hydroxyl C$_{1-6}$ alkylcarbonyl, hydroxyl 3-6 membered heterocyclyl, halo 3-6 membered heterocyclyl, or C$_{3-6}$ cycloalkyl-C$_{1-6}$ alkoxy, and wherein the R$^5$ group is optionally further substituted with one to five R$^7$ groups.

32. The compound of claim 31, or a pharmaceutically acceptable salt thereof, wherein the R$^7$ groups are one or two fluoro groups.

33. The compound of claim 28, or a pharmaceutically acceptable salt thereof, wherein R$^5$ is:

X$^a$ is a bond or C(R$^x$)(R$^y$), wherein R$^x$ and R$^y$ are independently selected from the group consisting of H, halogen and methyl;

X$^b$ and X$^c$ are independently selected from the group consisting of H, halogen and methyl; and X$^d$ is H; or C$_{1-6}$ alkyl, C$_{3-10}$ cycloalkyl, C$_{1-6}$ heteroalkyl, 3-12 membered heterocyclyl, C$_{6-10}$ aryl, or 5-10 membered heteroaryl, each of which is optionally substituted with one to five groups selected from the group consisting of C$_{1-6}$ alkyl, C$_{1-6}$ heteroalkyl, hydroxyl, C$_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, and halogen.

34. The compound of claim 33, or a pharmaceutically acceptable salt thereof, wherein X$^d$ is C$_{1-6}$ alkyl substituted with hydroxyl.

35. The compound of claim 33, or a pharmaceutically acceptable salt thereof, wherein X$^a$ is CH$_2$.

36. The compound of claim 33, or a pharmaceutically acceptable salt thereof, wherein $X^b$ and $X^c$ are each fluoro.

37. The compound of claim 33, or a pharmaceutically acceptable salt thereof, wherein $X^b$ is fluoro.

38. The compound of claim 23, or a pharmaceutically acceptable salt thereof, wherein $R^5$ is —$OR^6$ and is substituted with one $R^7$ group selected from the group consisting of $C_{1-6}$ alkoxycarbonyl, hydroxyl $C_{1-6}$ alkylcarbonyl, $C_{1-6}$ $C_{1-6}$ alkylcarbonyl and $C_{3-6}$ cycloalkyl-$C_{1-6}$ alkoxy.

39. The compound of claim 23, or a pharmaceutically acceptable salt thereof, wherein $R^5$ is:

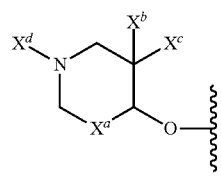

$X^a$ is a bond or $C(R^x)(R^y)$, wherein $R^x$ and $R^y$ are independently selected from the group consisting of H, halogen and methyl;

$X^b$ and $X^c$ are independently selected from the group consisting of H, halogen and methyl; and $X^d$ is H; or $C_{1-6}$ alkyl, $C_{3-10}$ cycloalkyl, $C_{1-6}$ heteroalkyl, 3-12 membered heterocyclyl, $C_{6-10}$ aryl, 5-10 membered heteroaryl, or —C(O)C1-6 alkyl, each of which is optionally substituted with one to five groups selected from the group consisting of $C_{1-6}$ alkyl, $C_{1-6}$ heteroalkyl, hydroxyl, $C_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, and halogen.

40. The compound of claim 23, or a pharmaceutically acceptable salt thereof, wherein $R^5$ is:

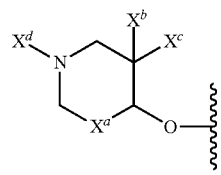

$X^a$ is CH$_2$; $X^b$ and $X^c$ are each halogen; and $X^d$ is —C(O)C$_{1-6}$ alkyl substituted with hydroxyl.

41. The compound of claim 23, or a pharmaceutically acceptable salt thereof, wherein the Ring A-(R)$_n$ group in the compound

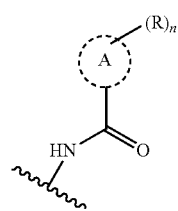

is selected from the group consisting of:

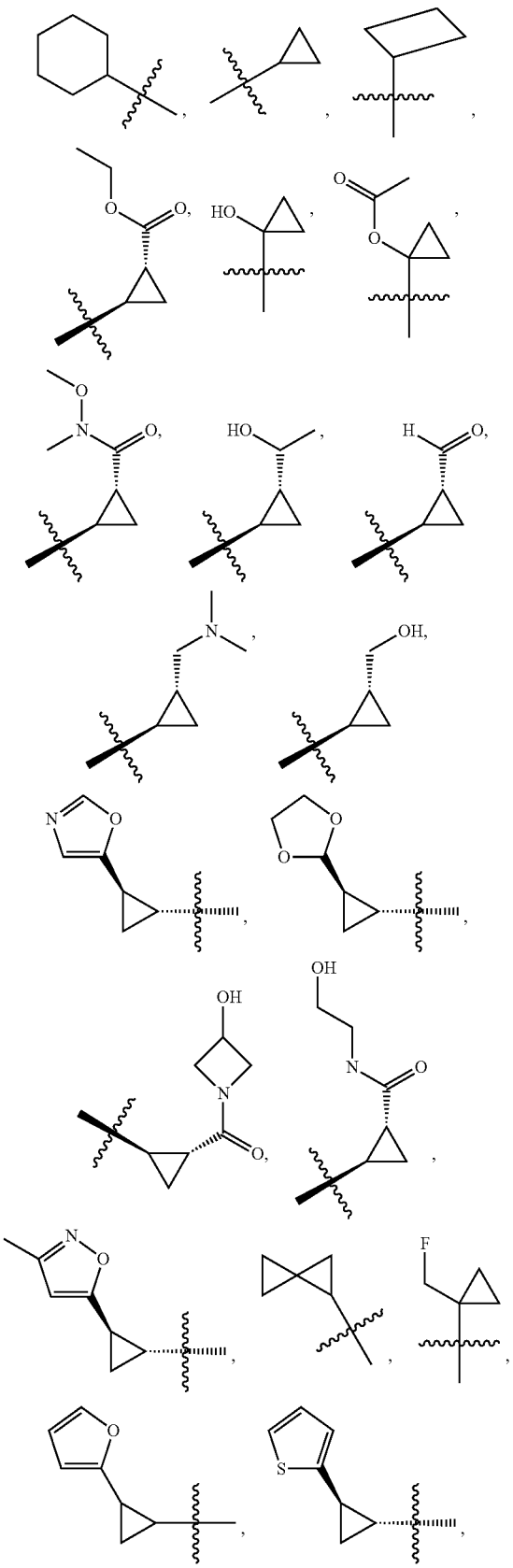

-continued
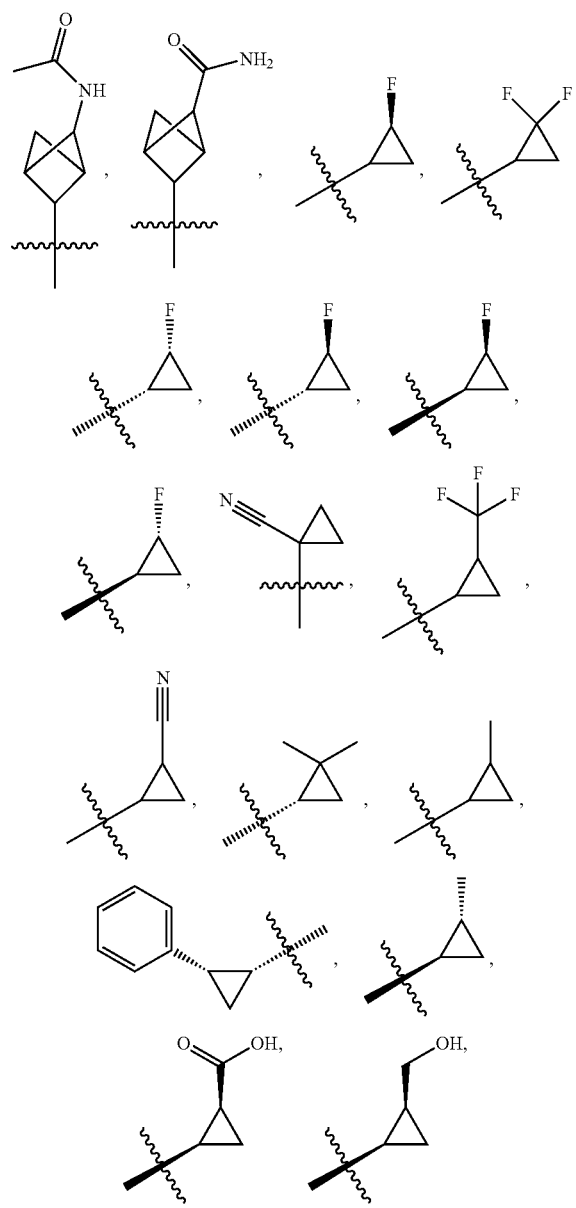
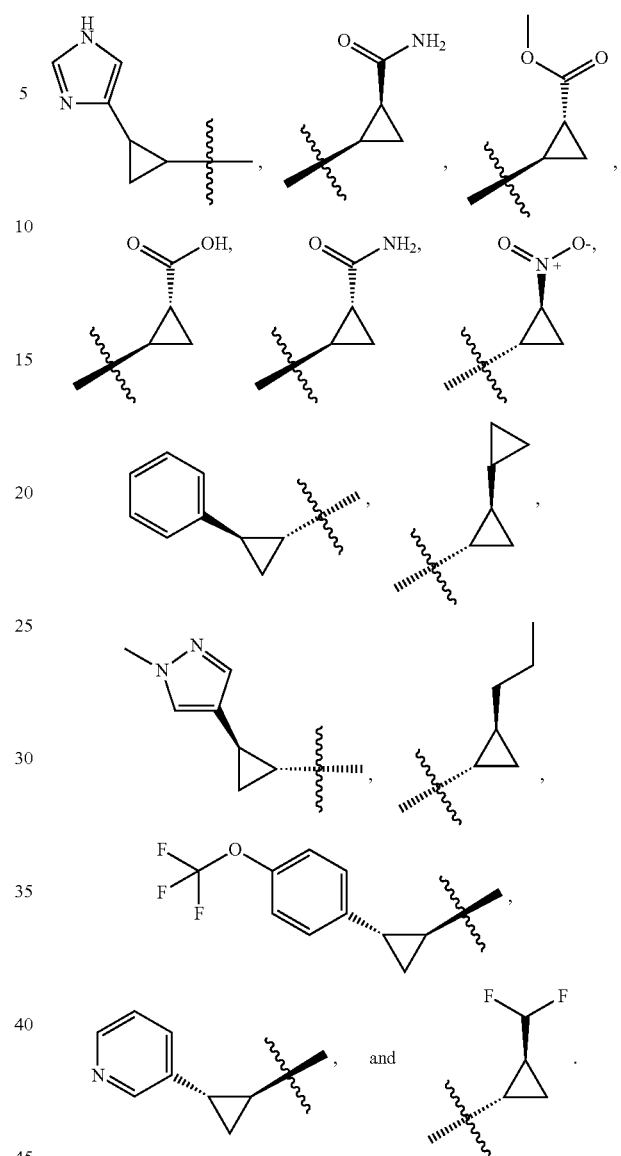
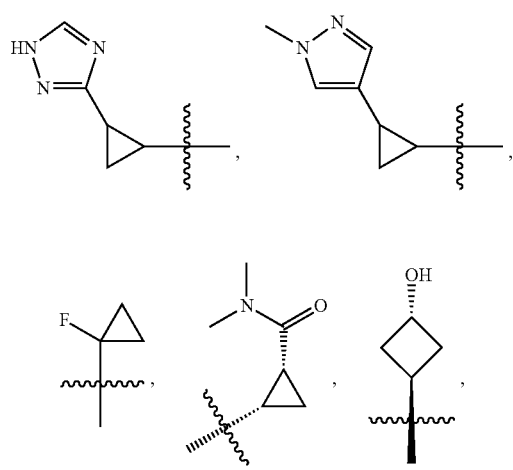
42. The compound of claim 23, or a pharmaceutically acceptable salt thereof, wherein $R^5$ is selected from the group consisting of:
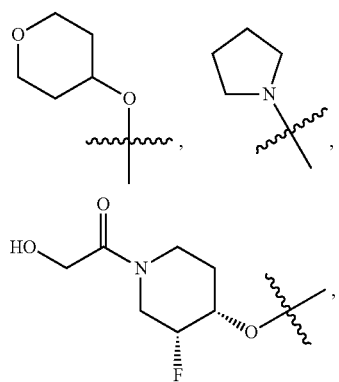

423
-continued
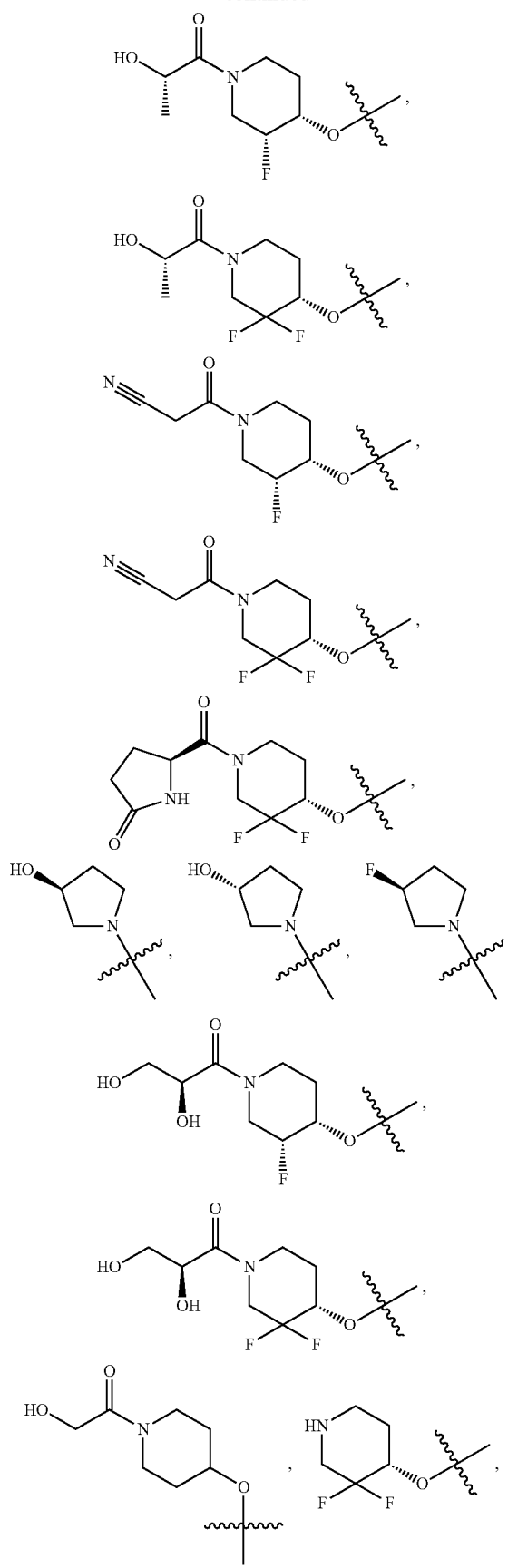
424
-continued
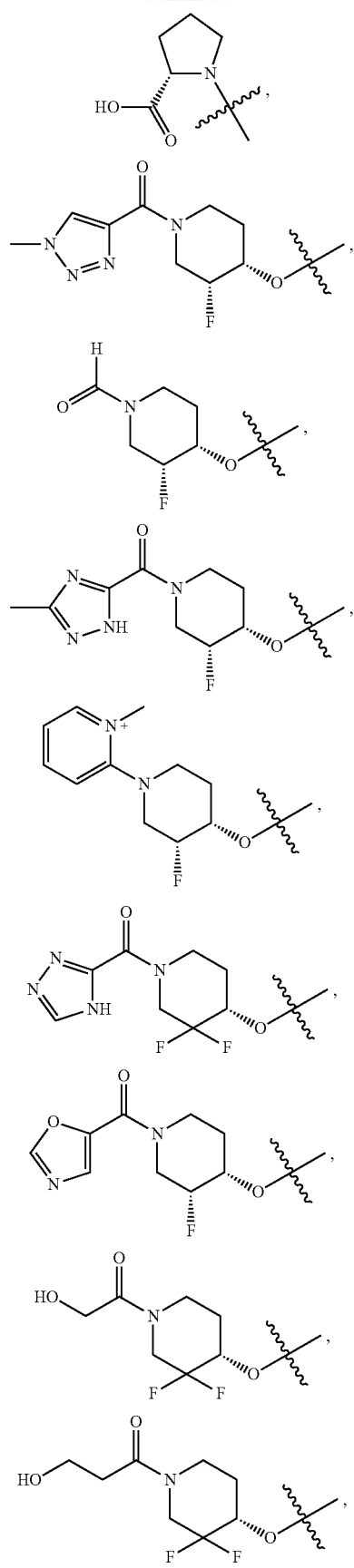

-continued
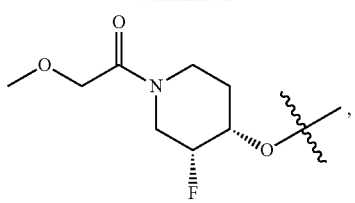
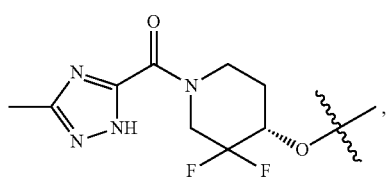
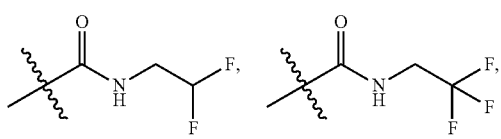
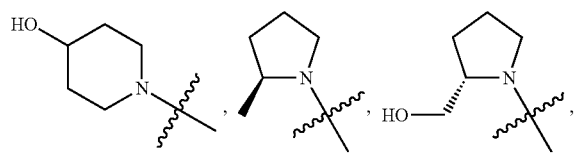
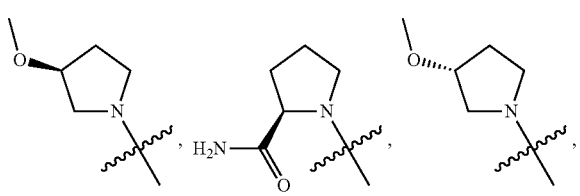
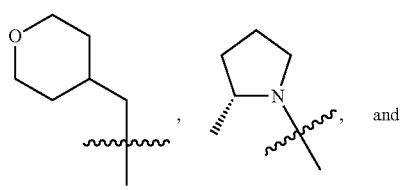
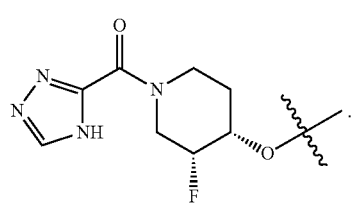
43. A compound selected from the group consisting of:
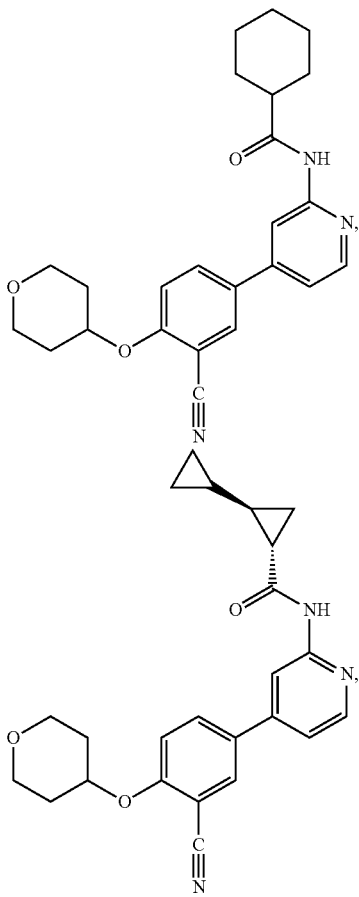
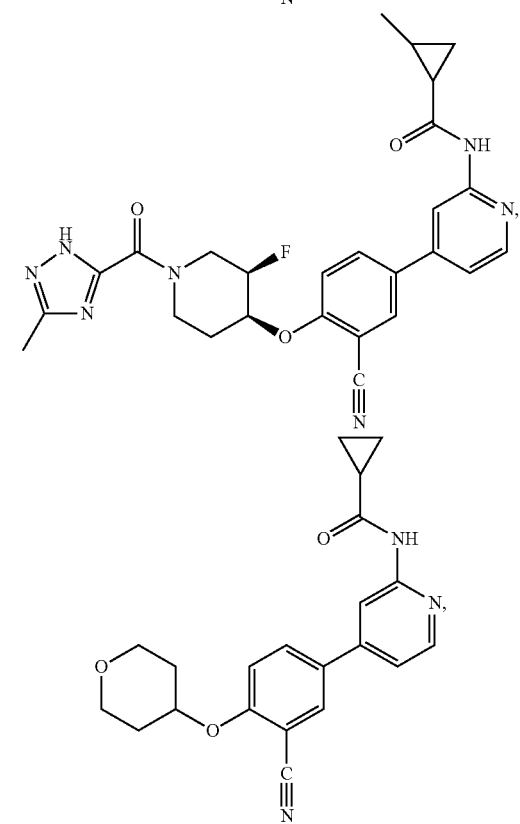

427
-continued
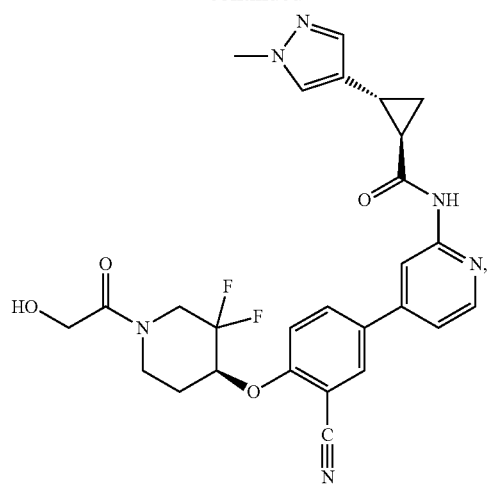
428
-continued
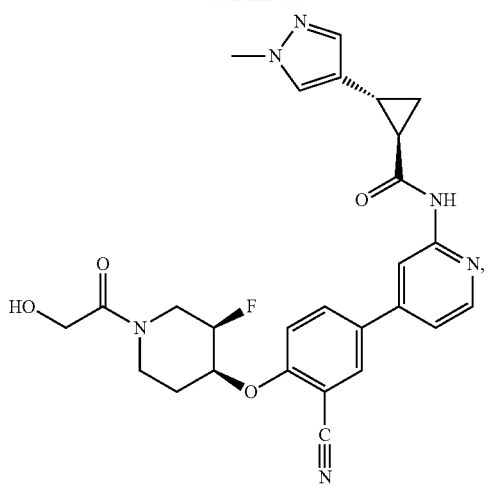
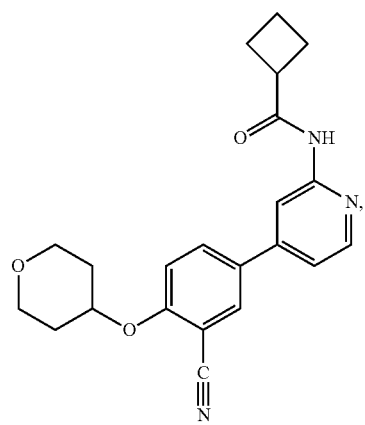
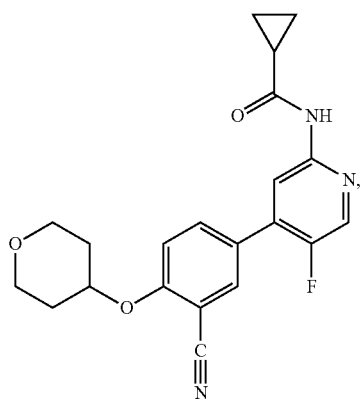

| 429 -continued | 430 -continued |
|---|---|
| 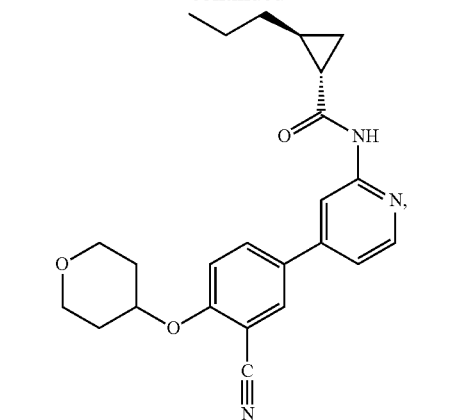 | 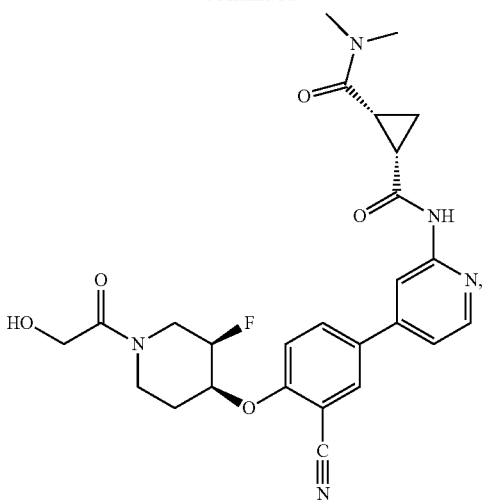 |
| | 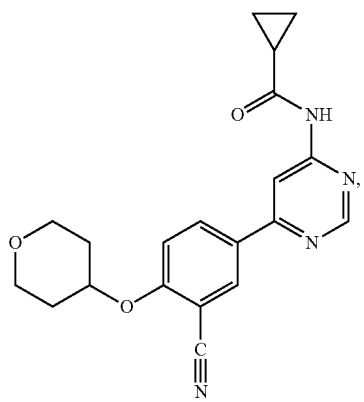 |
| | 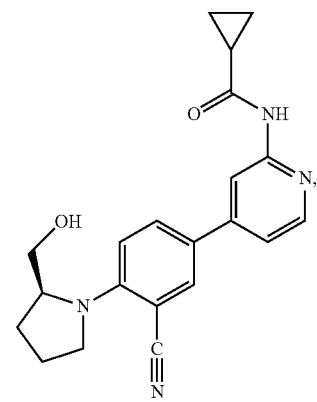 |

431
-continued
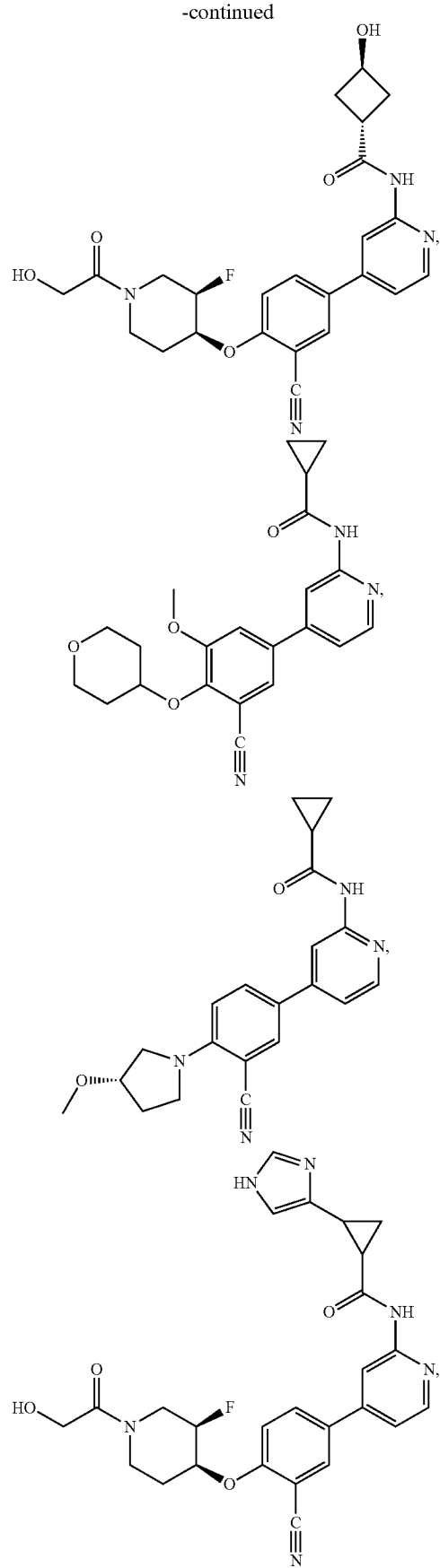
432
-continued
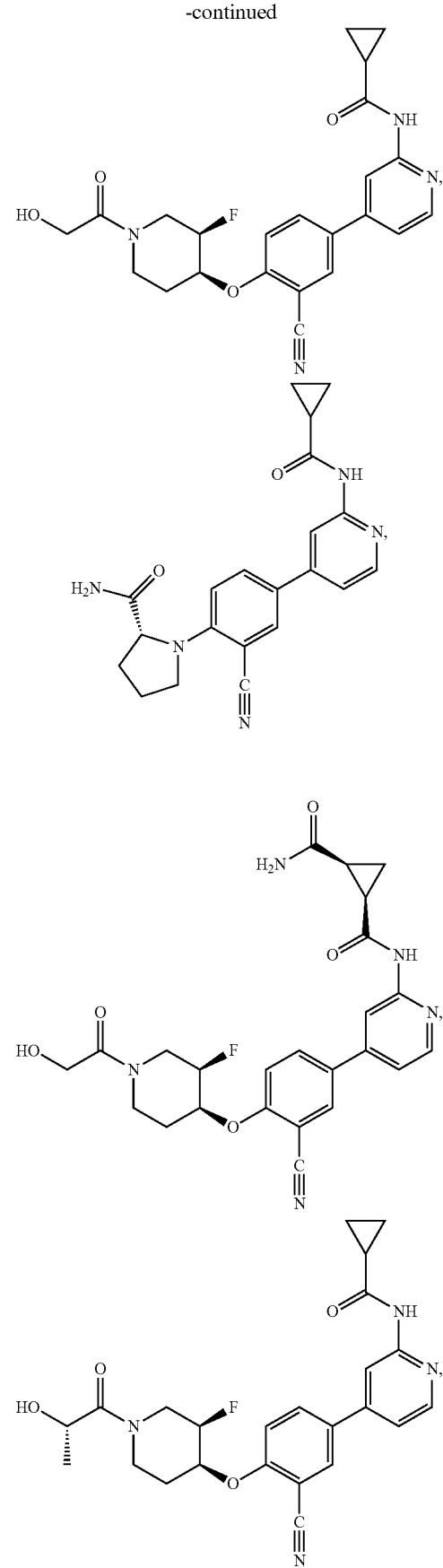

433
-continued
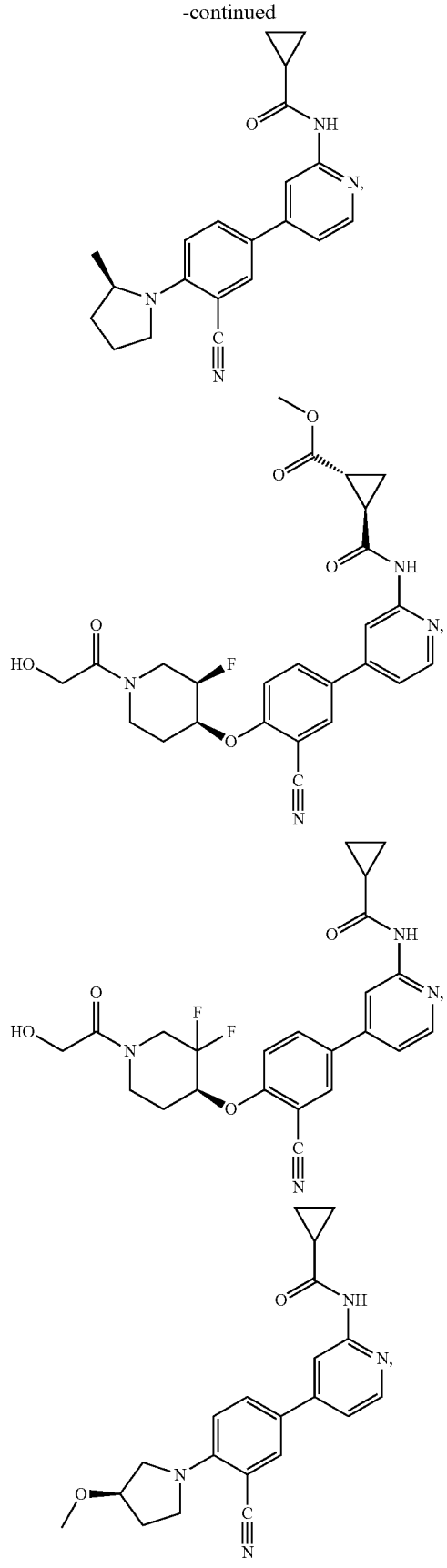
434
-continued
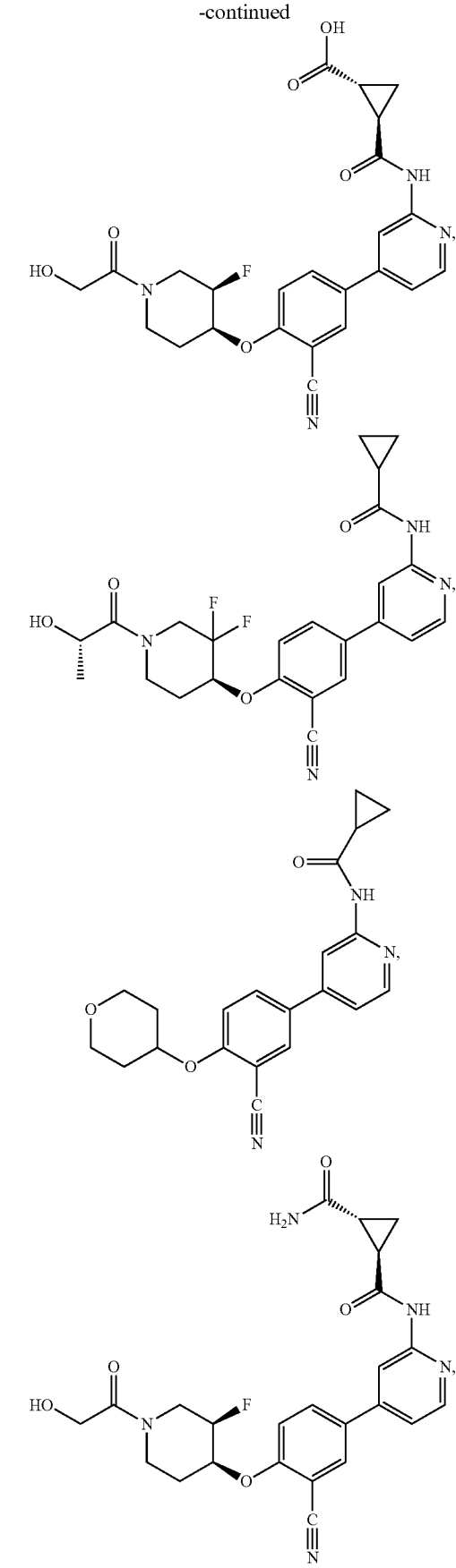

435
-continued
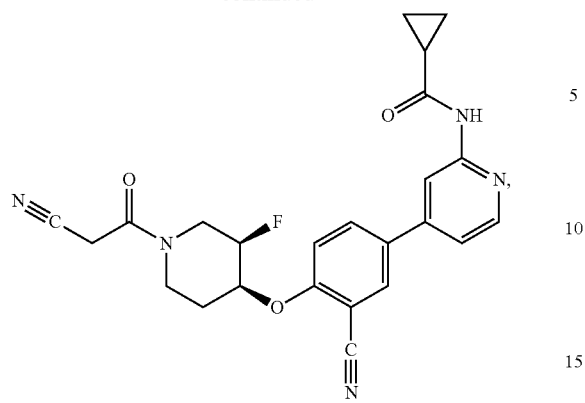
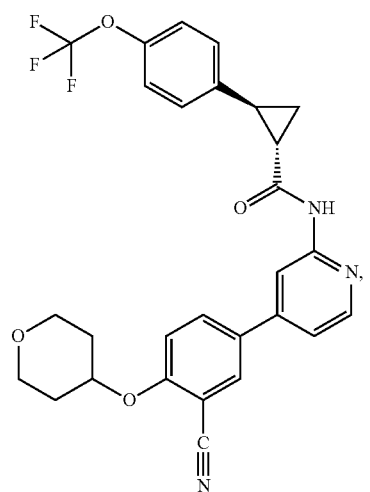
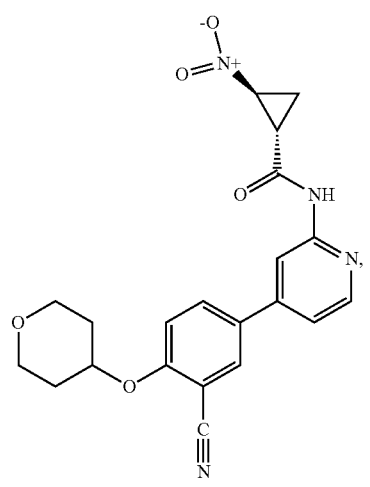
436
-continued
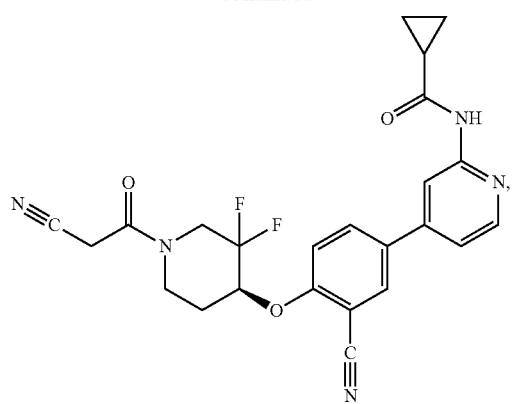
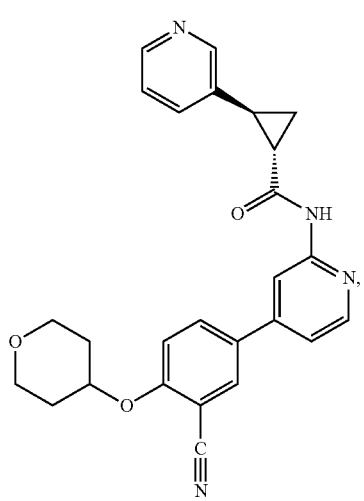
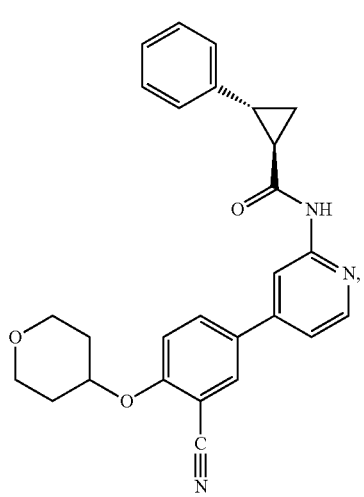

437
-continued
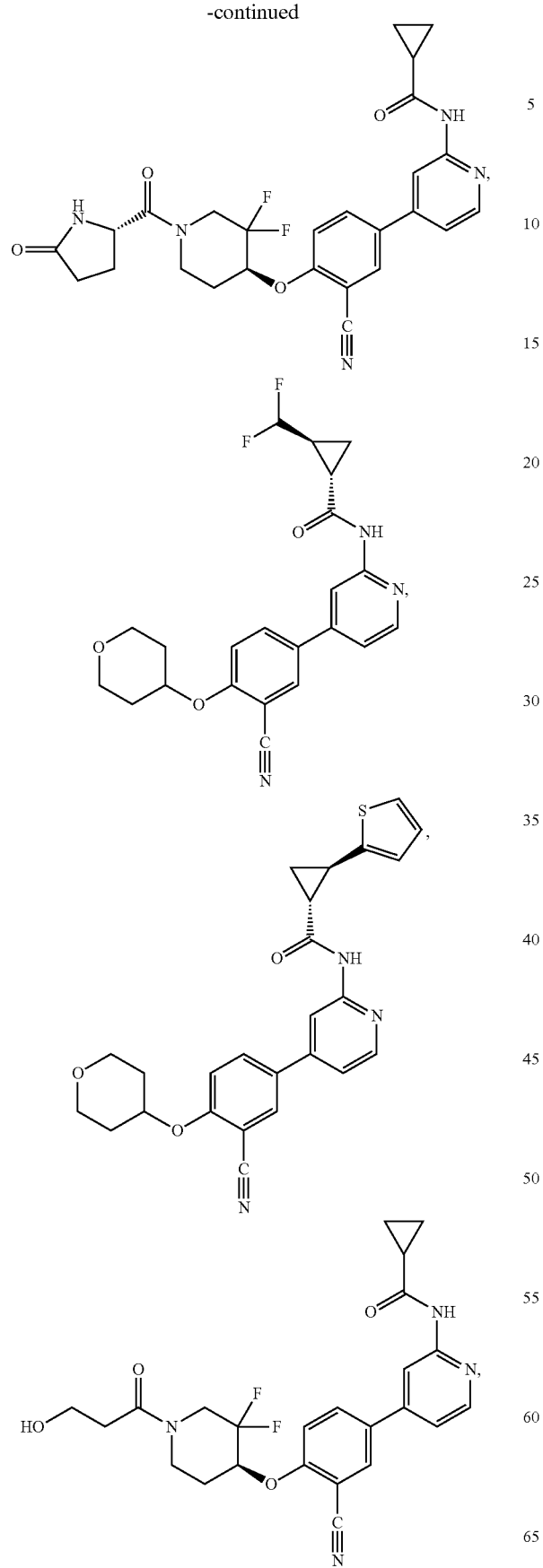
438
-continued
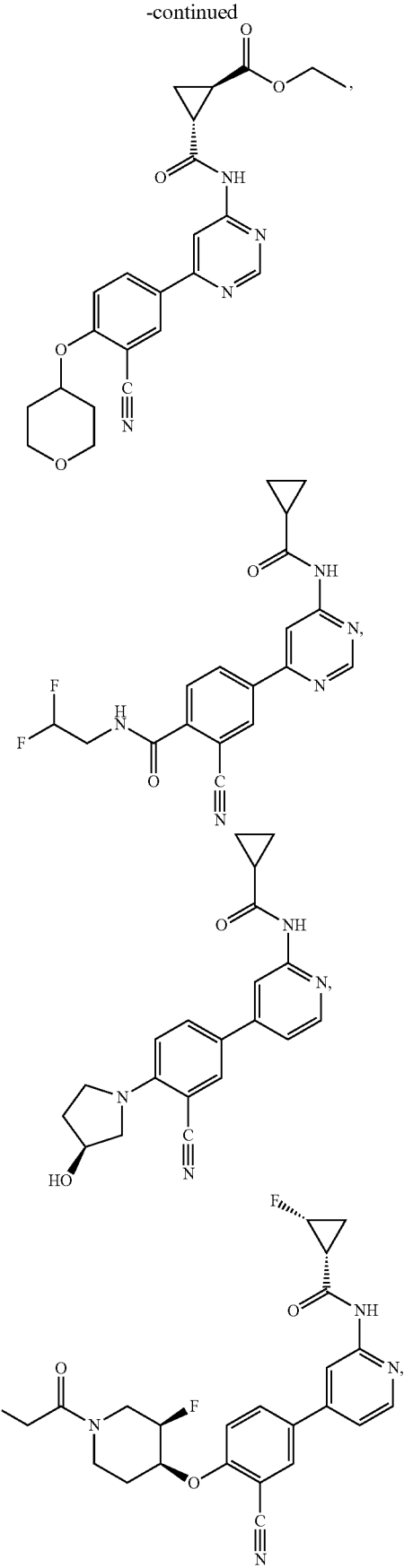

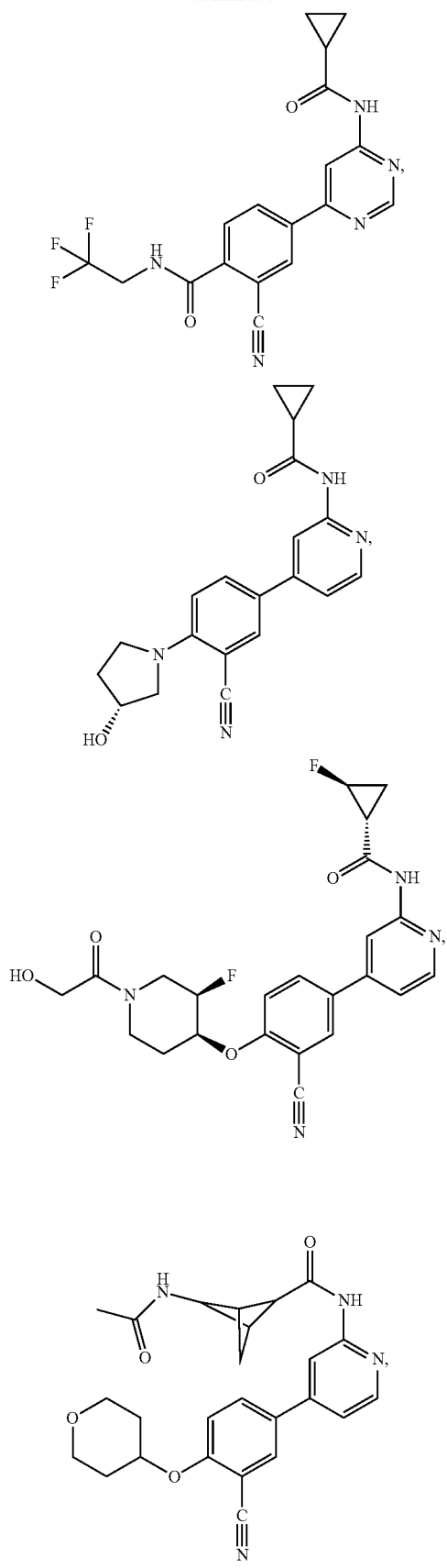
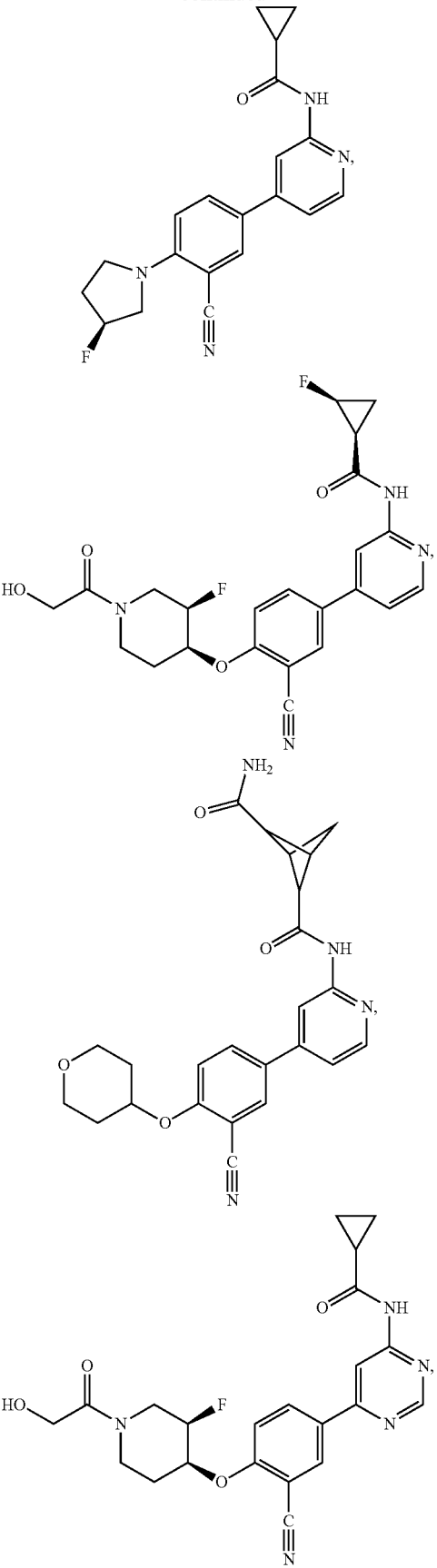

441
-continued
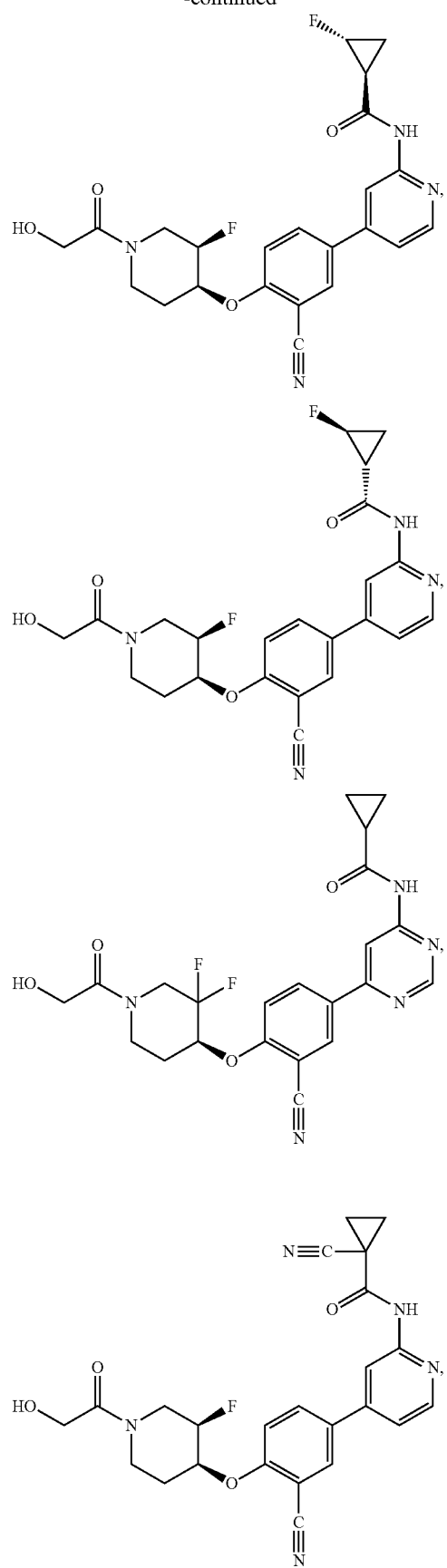
442
-continued
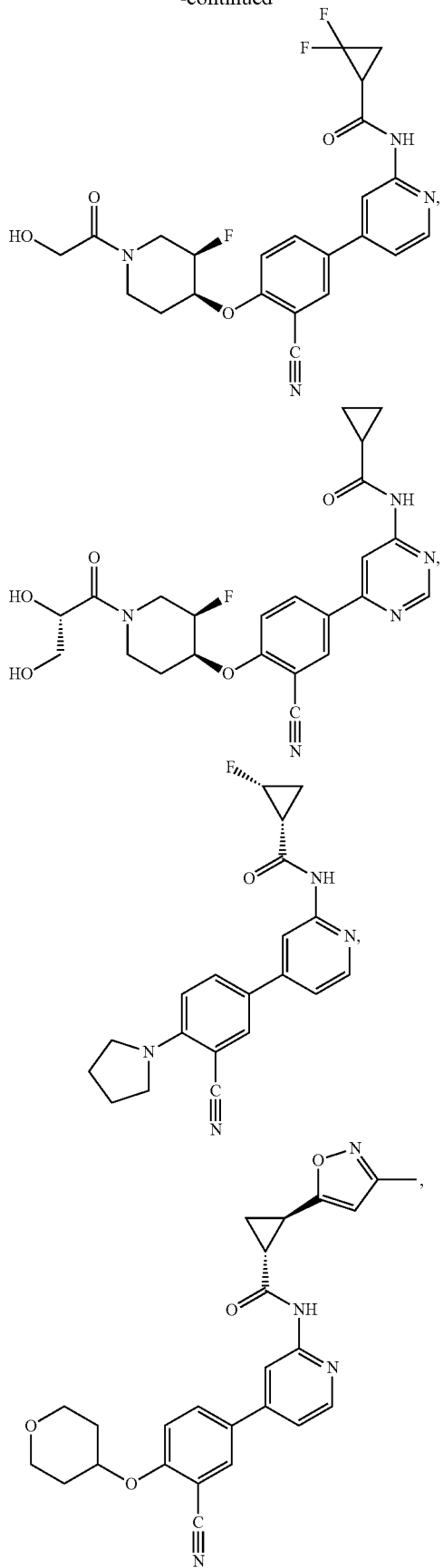

443
-continued
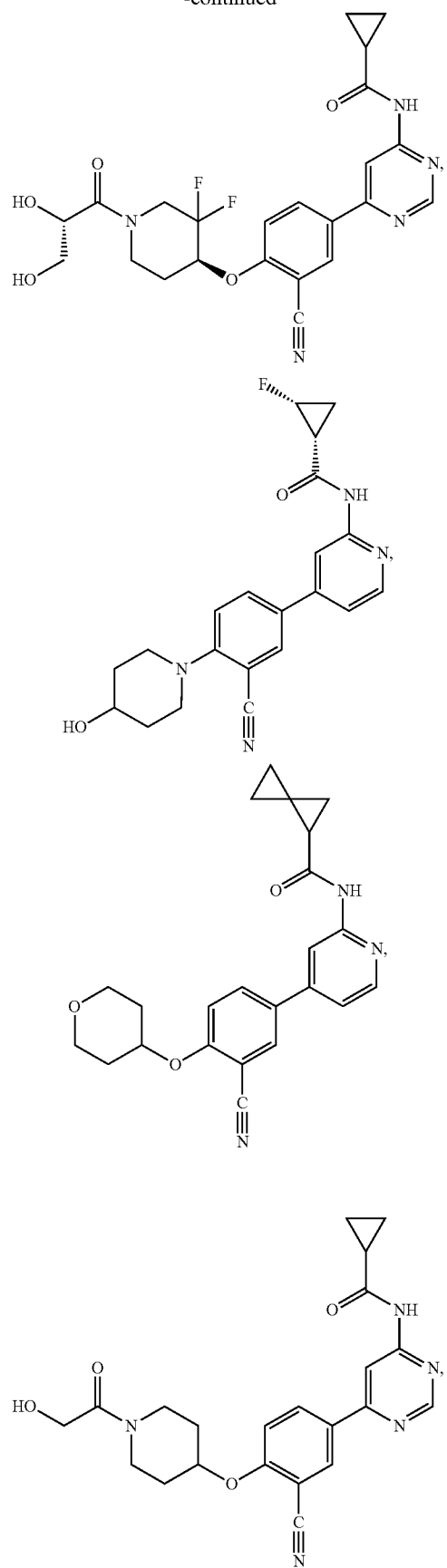
444
-continued
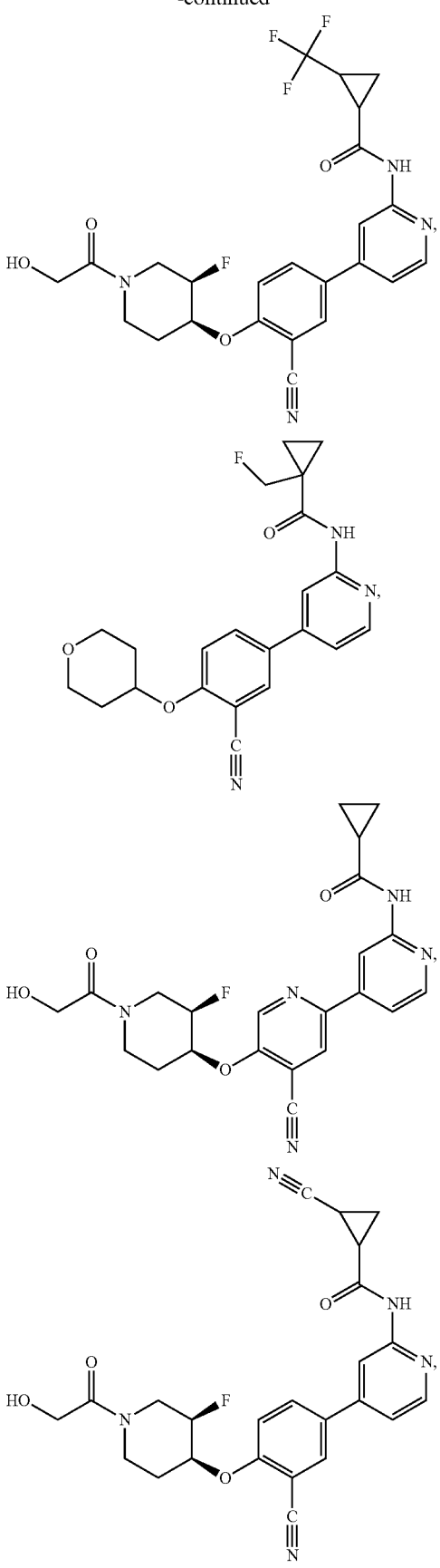

445
-continued
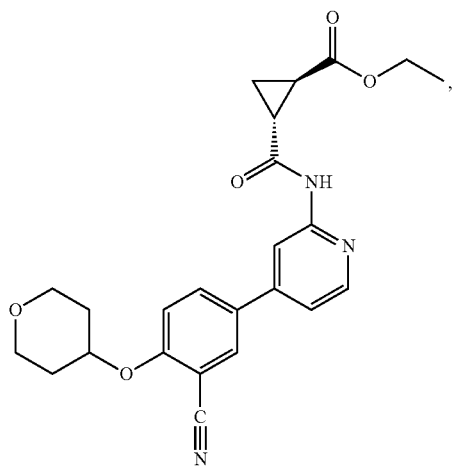
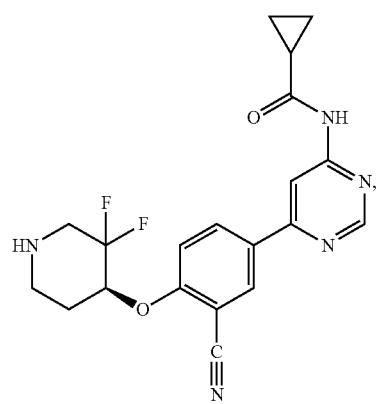
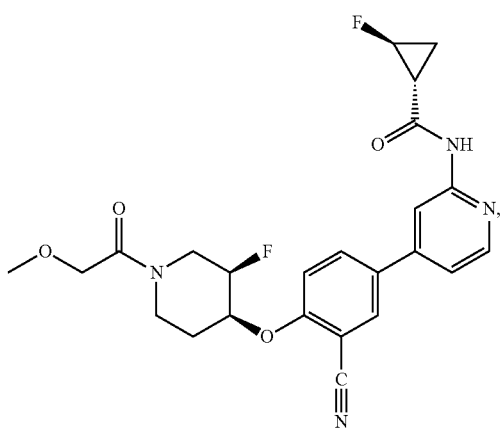
446
-continued
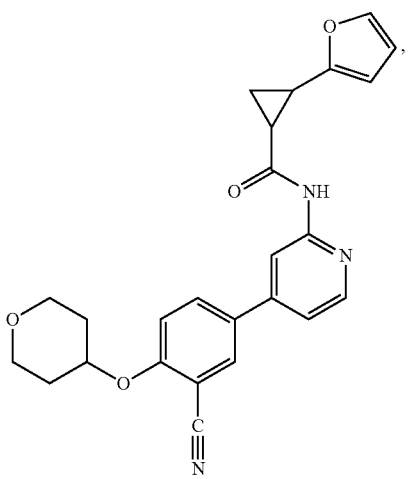
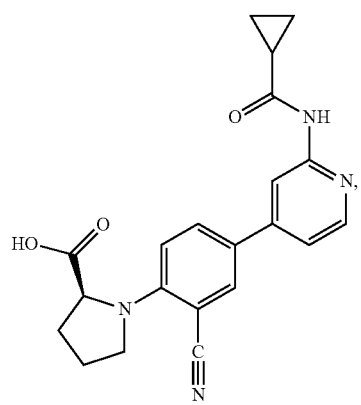
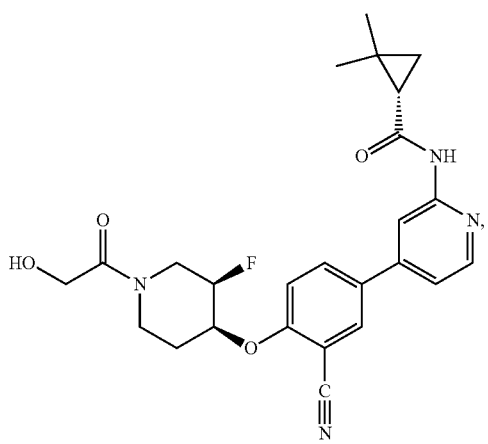

447
-continued
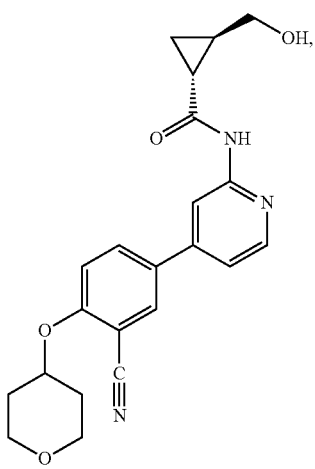
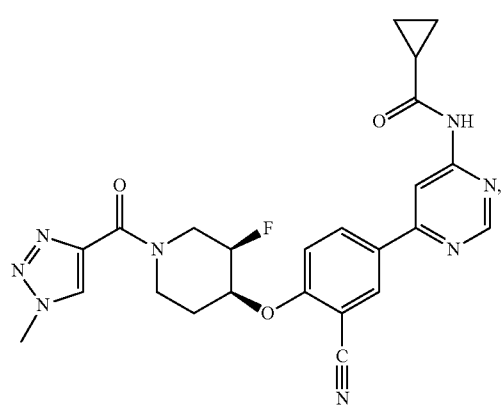
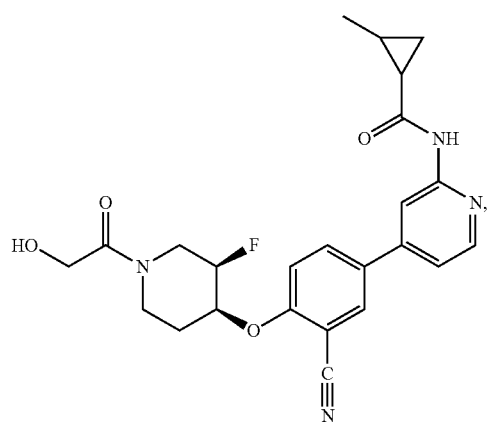
448
-continued
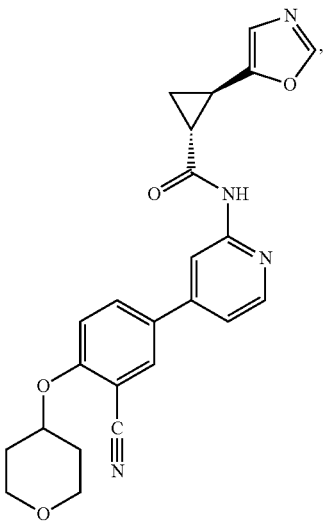
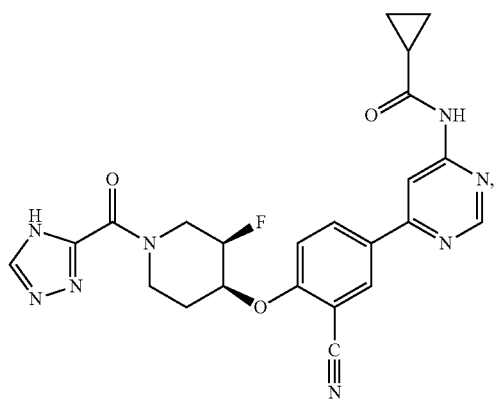
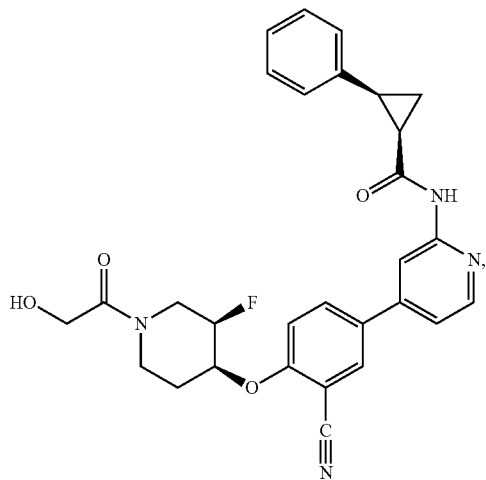

449
-continued
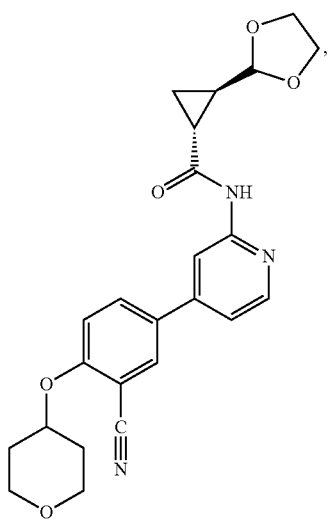
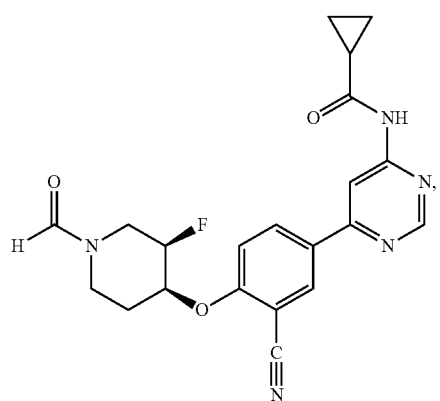
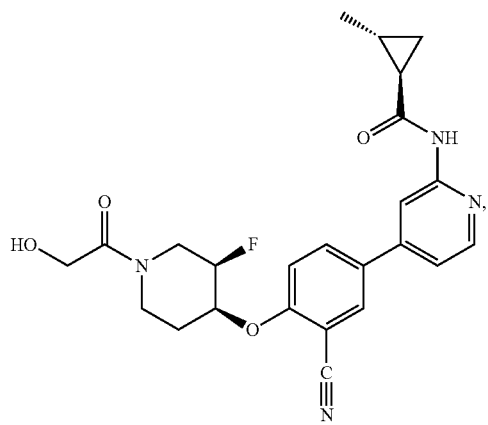
450
-continued
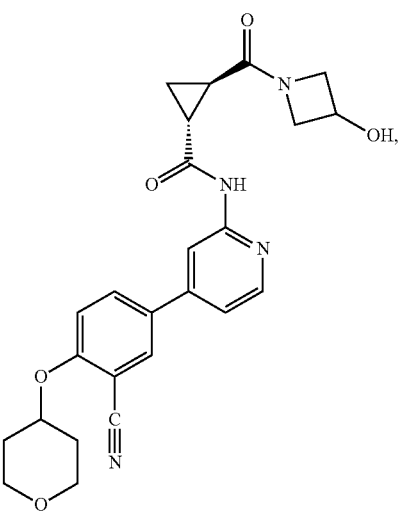
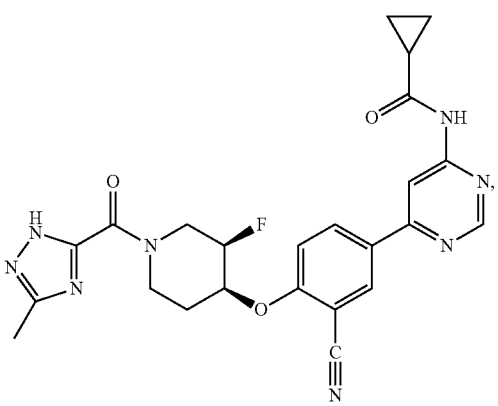
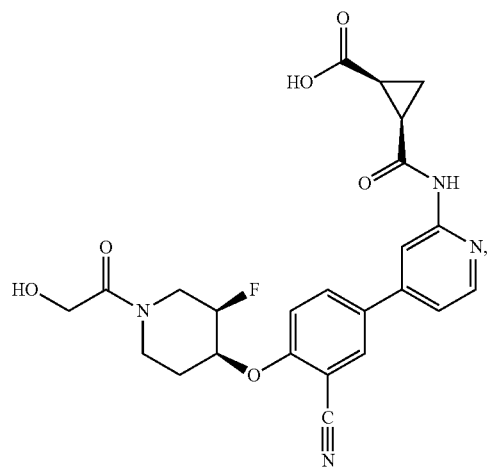

451
-continued
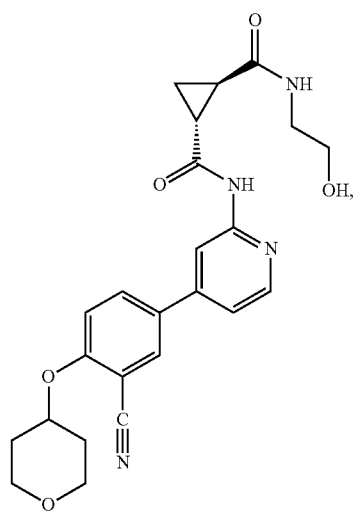
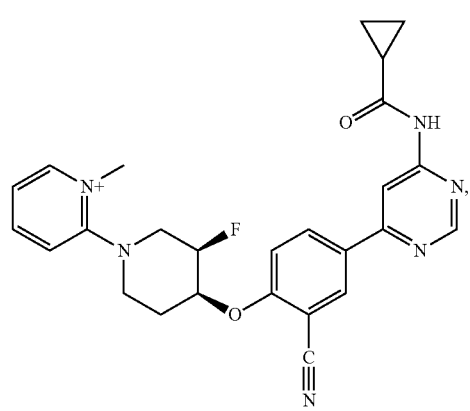
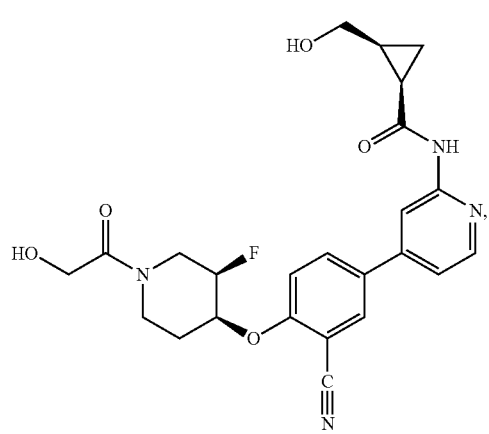
452
-continued
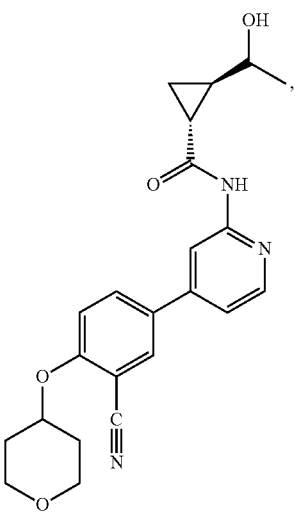
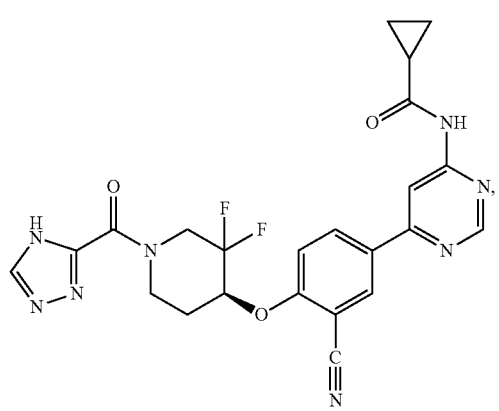
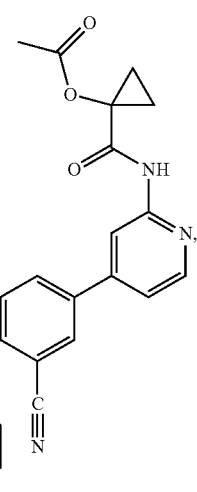

| 453 | 454 |
|---|---|
| -continued | -continued |
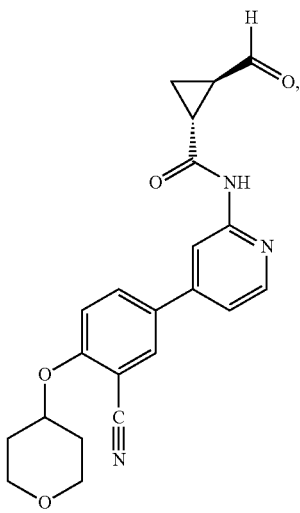 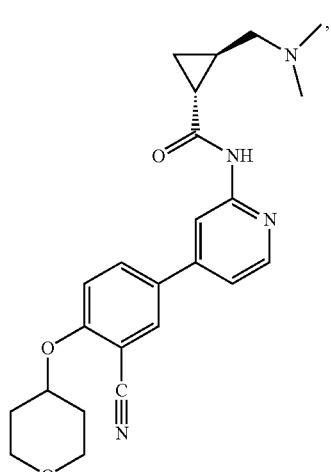
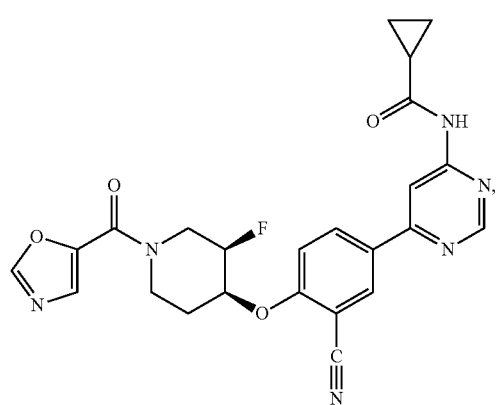 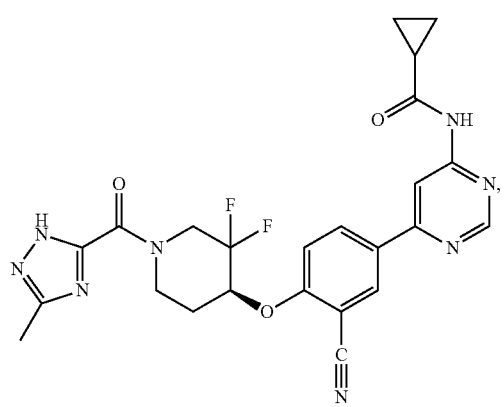
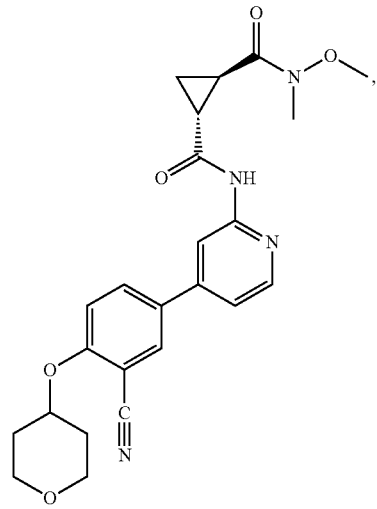 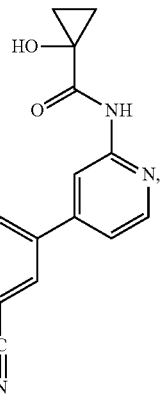

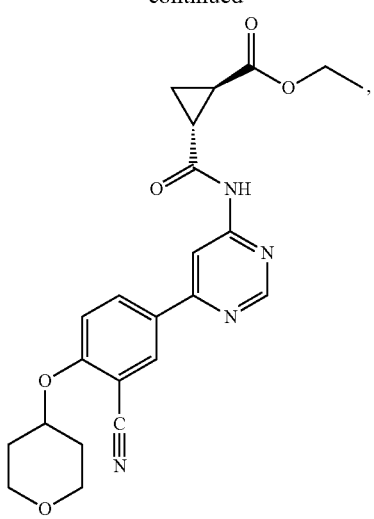
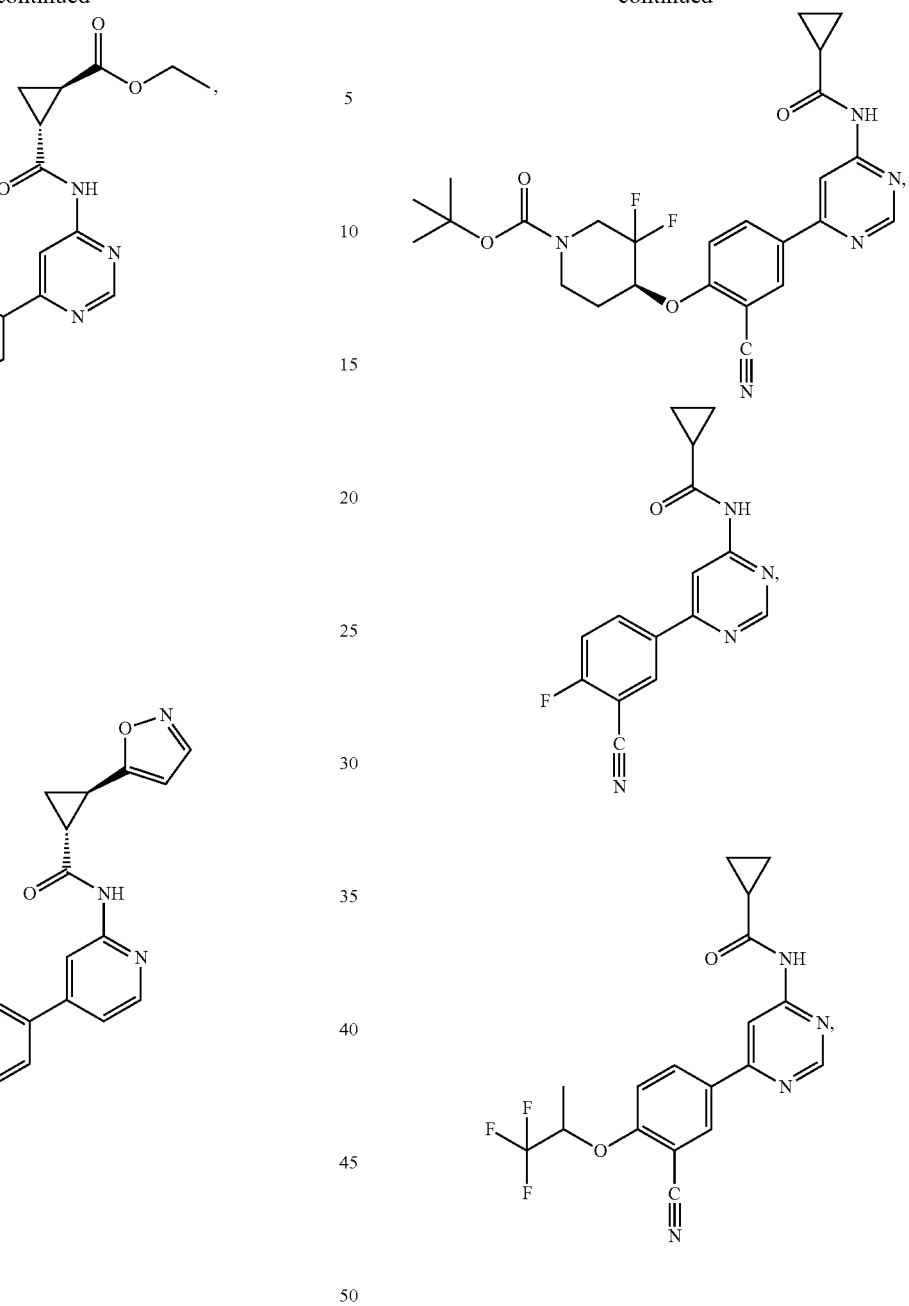
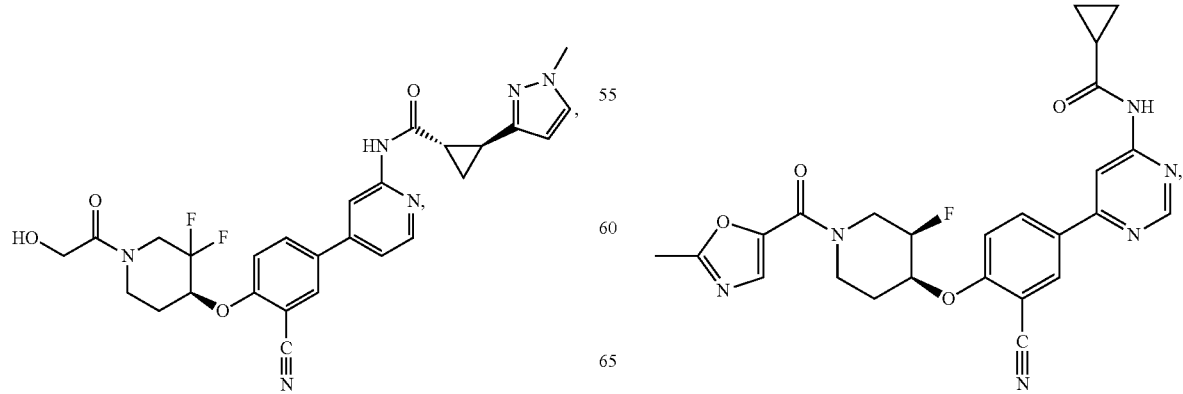

457
-continued
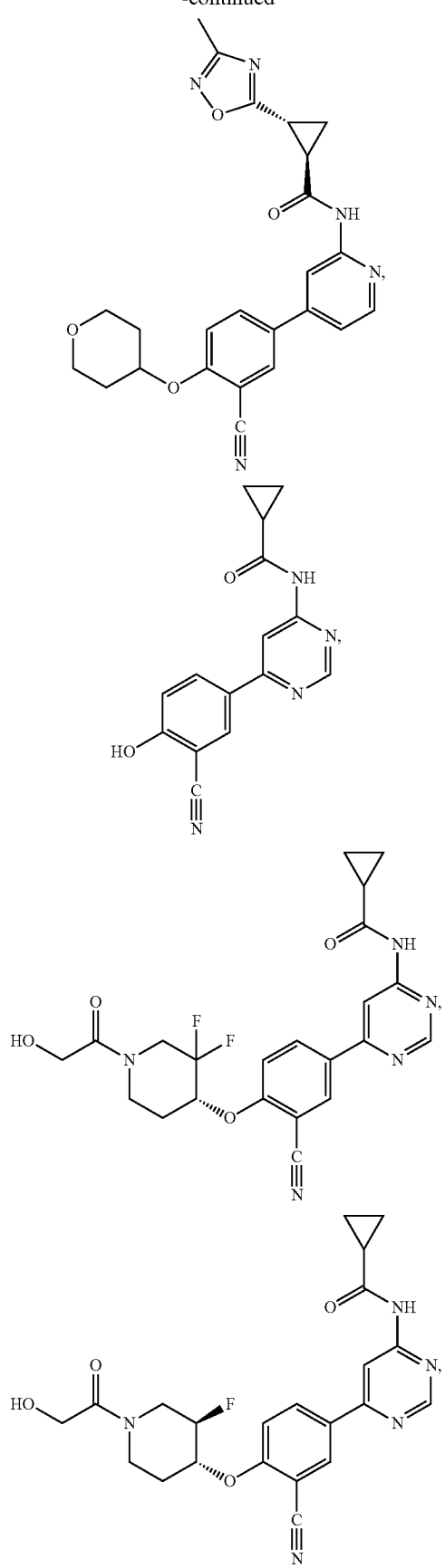
458
-continued
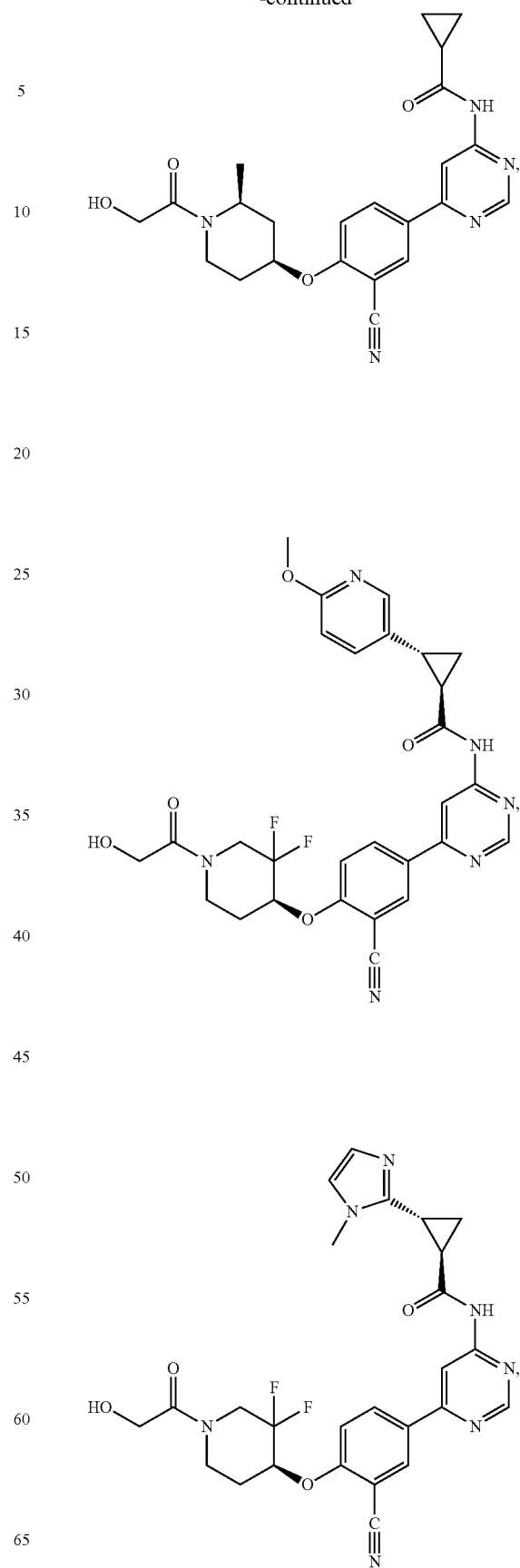

459
-continued
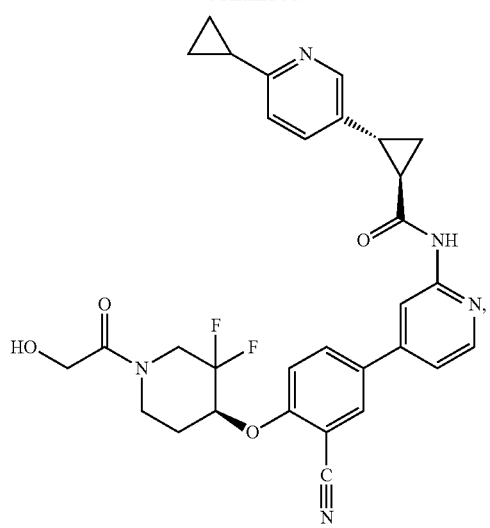
460
-continued
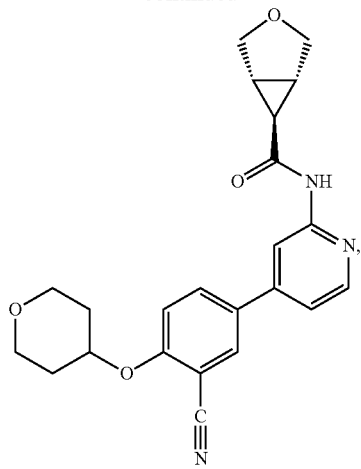
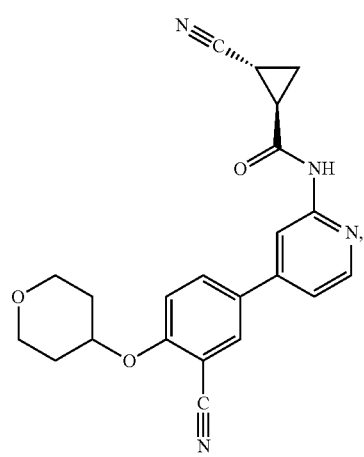
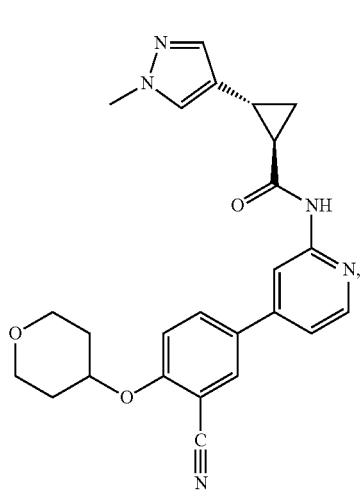
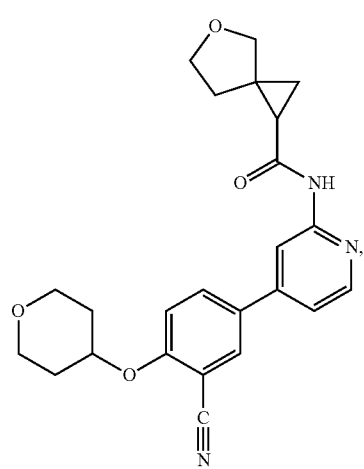

461
-continued
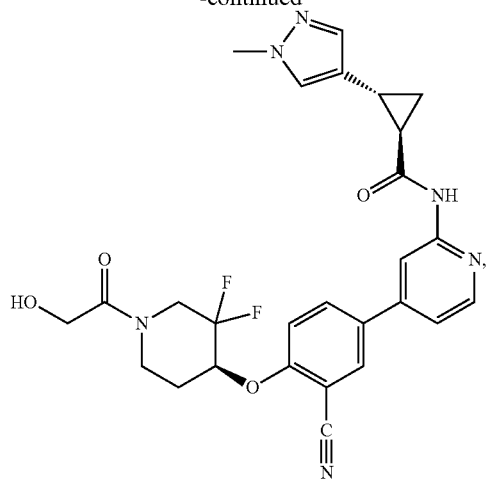
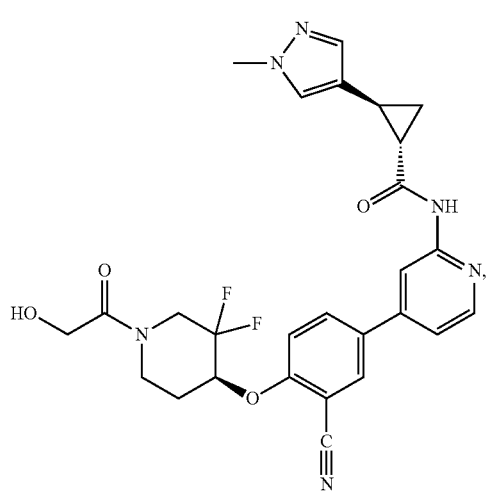
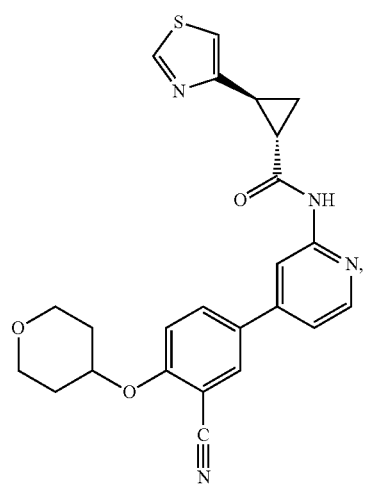
462
-continued
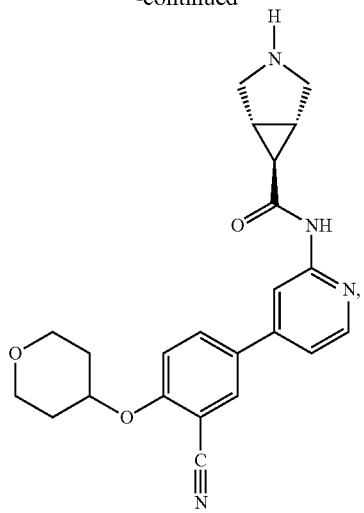
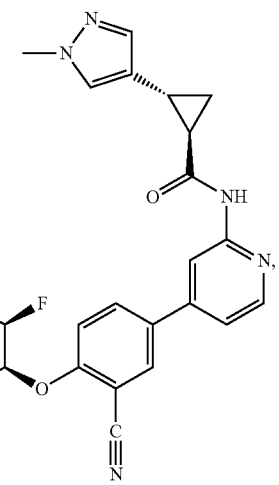
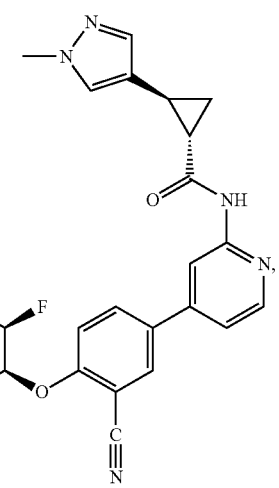

463
-continued
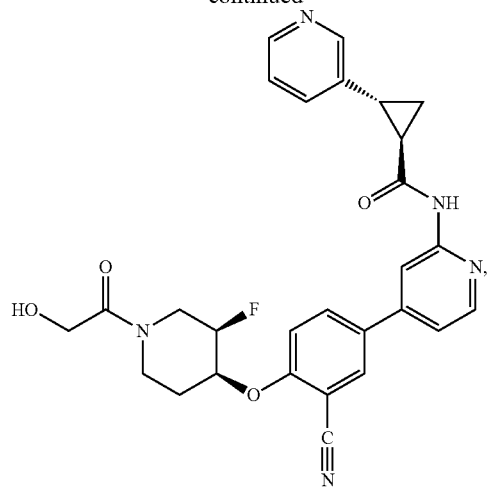
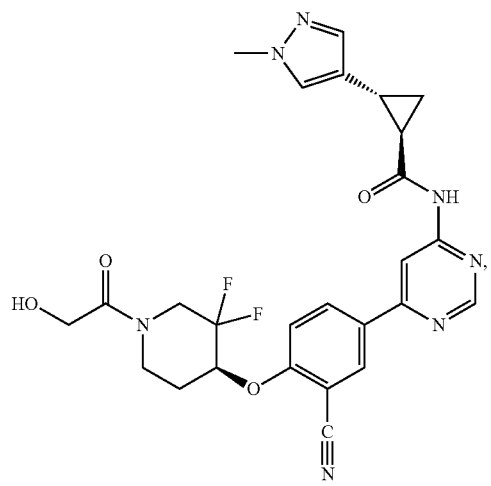
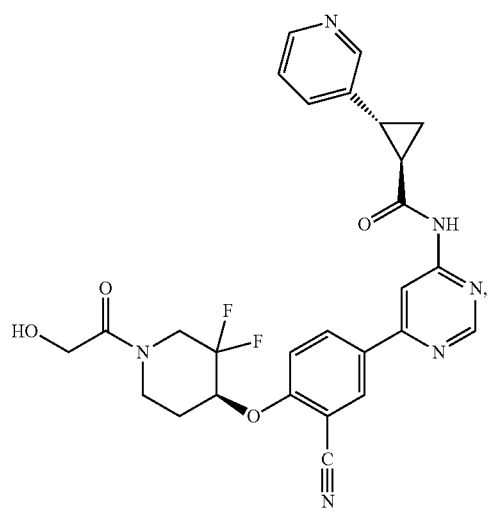
464
-continued
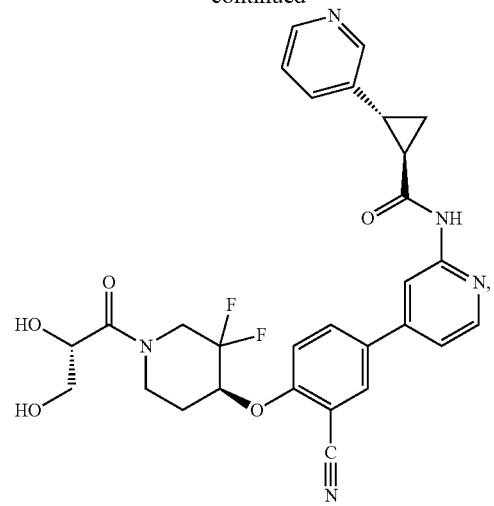
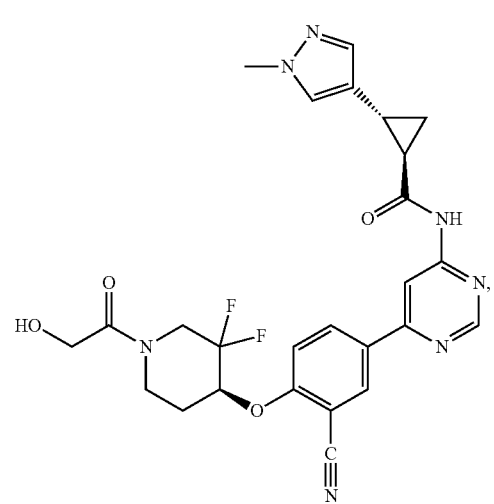
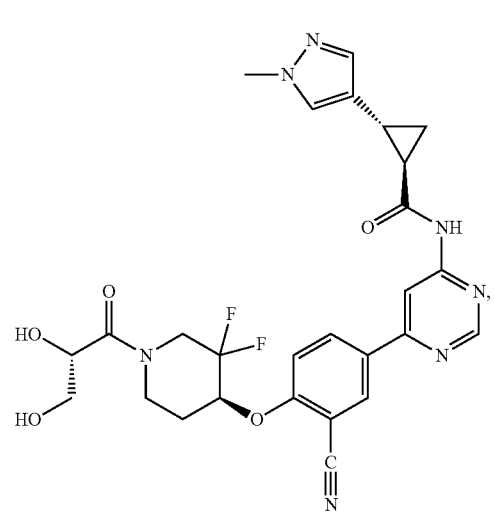

465
-continued
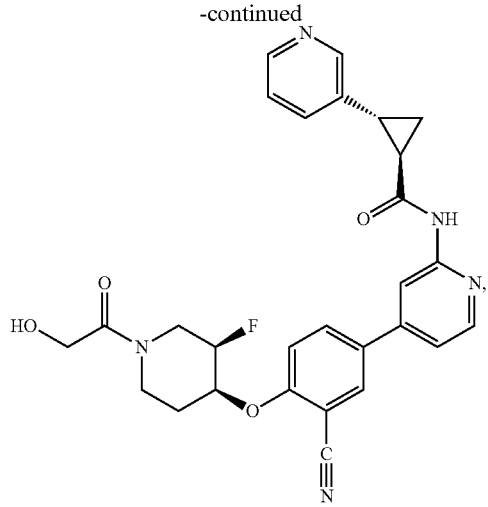
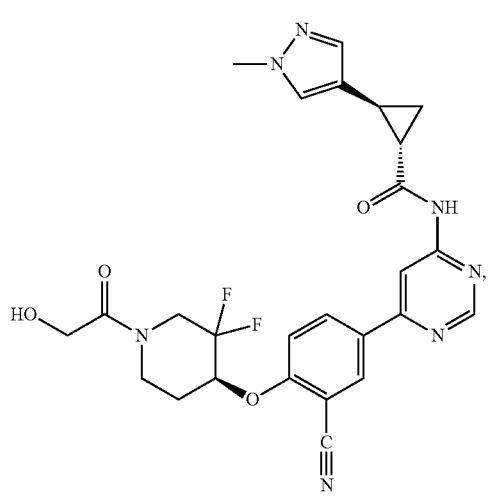
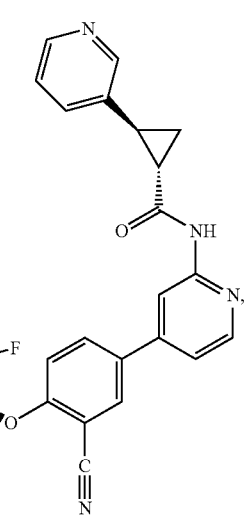
466
-continued
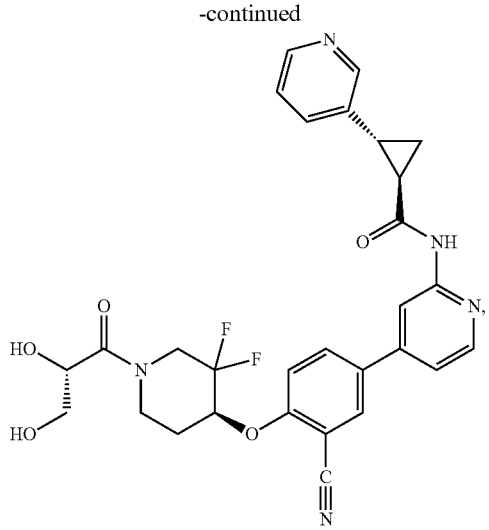
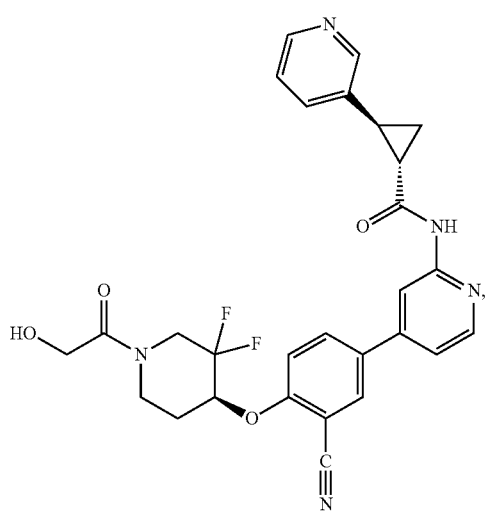

467
-continued
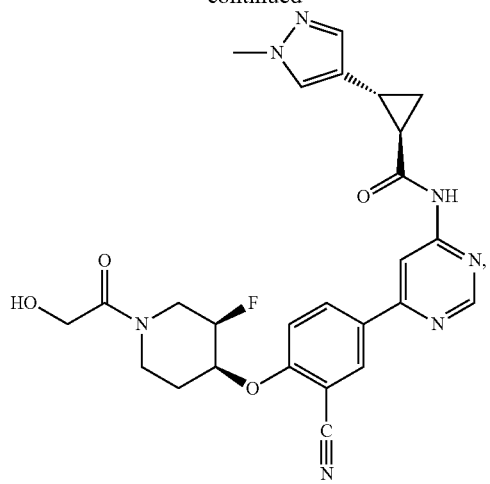
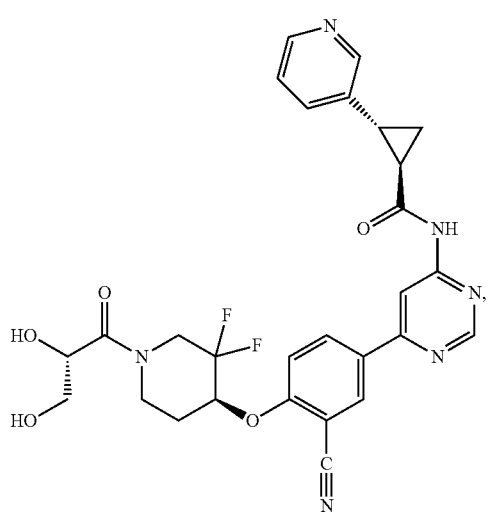
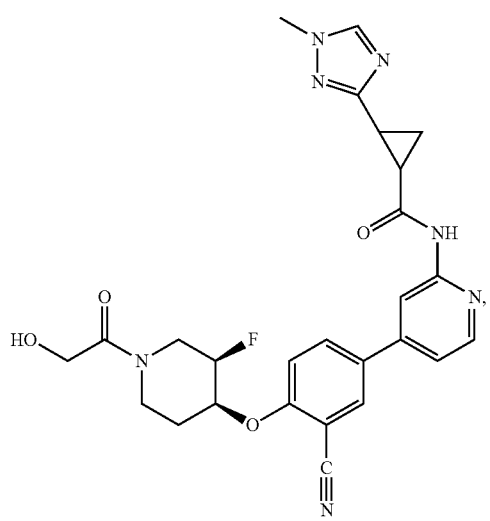
468
-continued
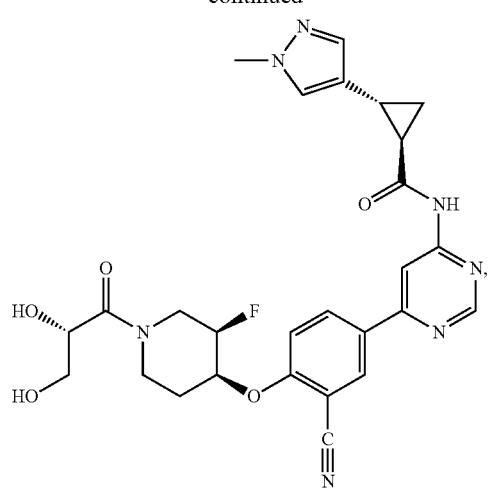
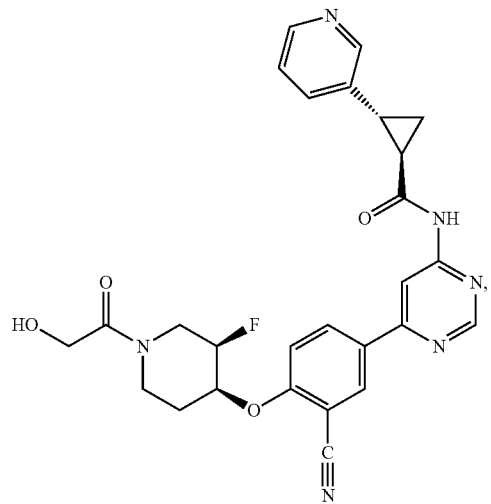
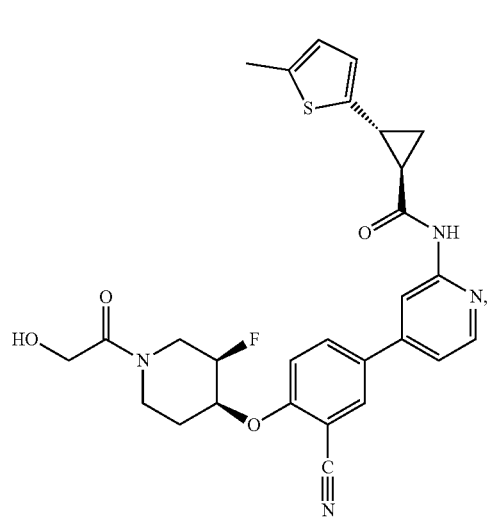

469
-continued
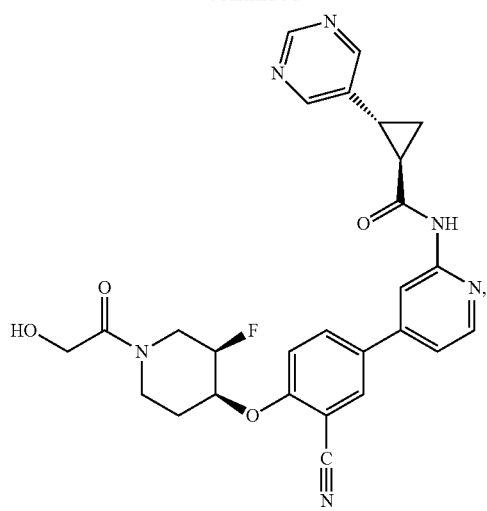
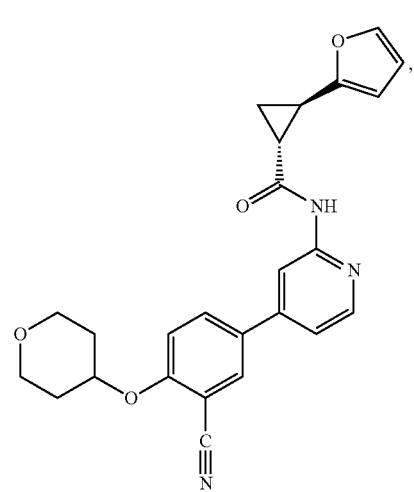
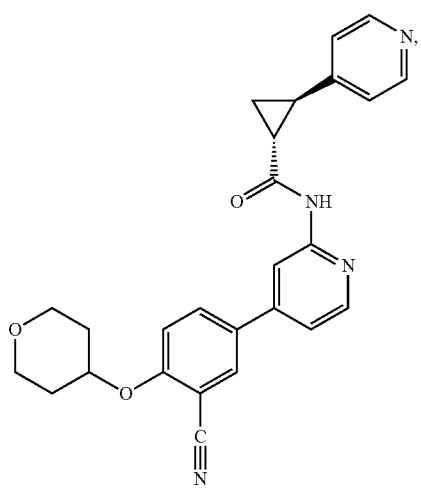
470
-continued
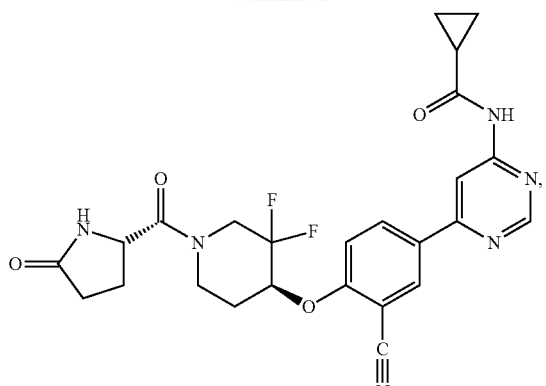
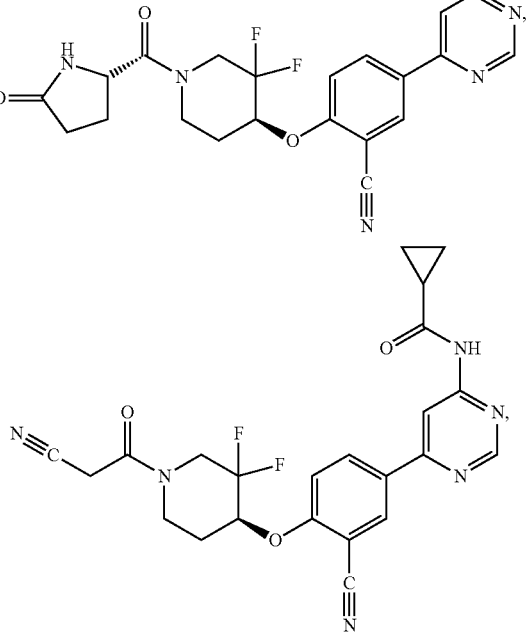
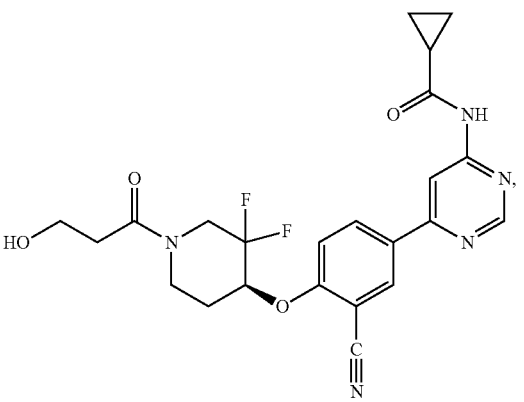
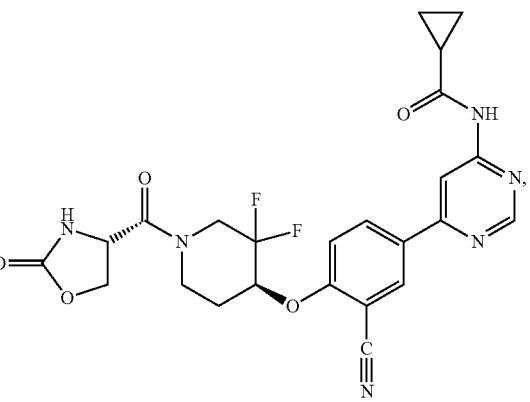

471
-continued
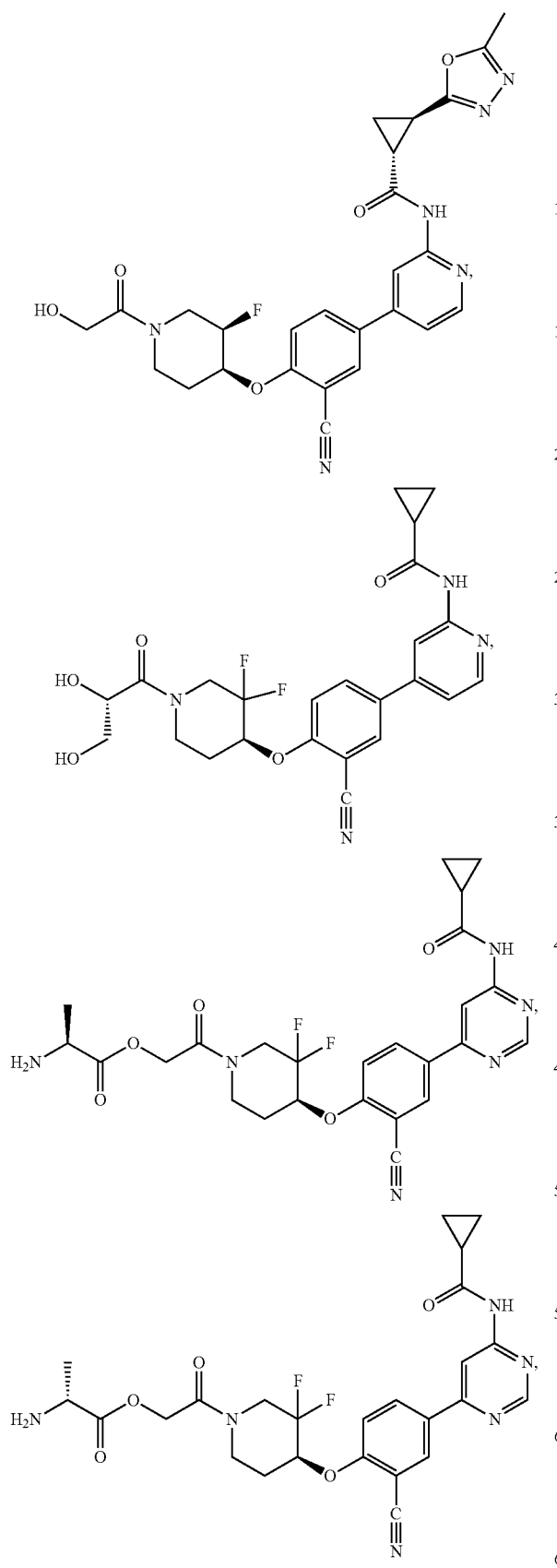
472
-continued
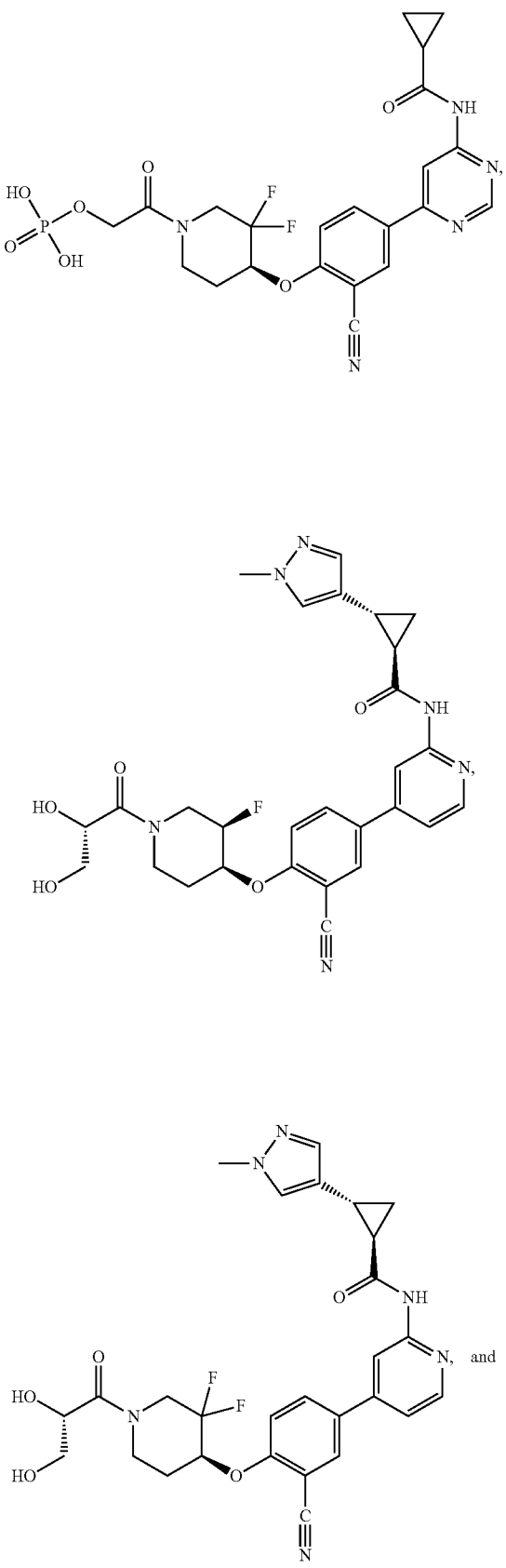

473
-continued
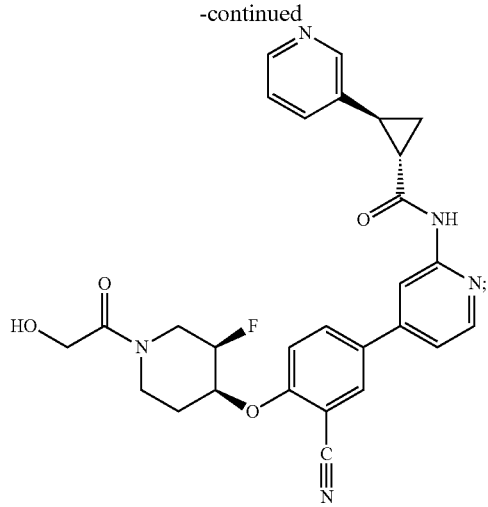
or a pharmaceutically acceptable salt thereof.
44. A compound selected from the group consisting of:
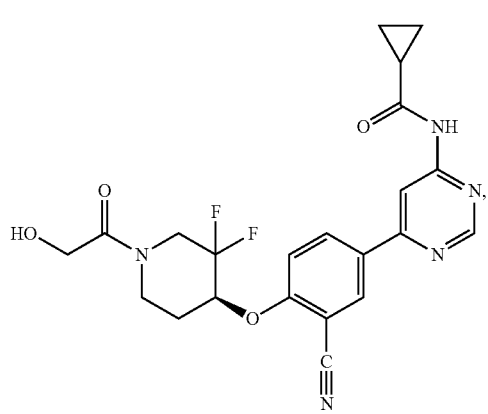 [SMILES: N#Cc1cc(-c2cc(NC(=O)C3CC3)ncn2)ccc1O[C@H]1CCN(C(=O)CO)CC1(F)F]
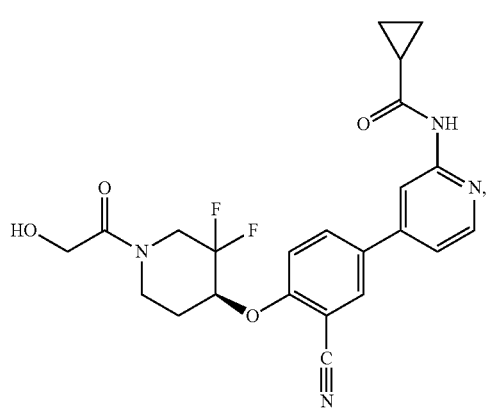 [SMILES: N#Cc1cc(-c2ccnc(NC(=O)C3CC3)c2)ccc1O[C@H]1CCN(C(=O)CO)CC1(F)F]
474
-continued
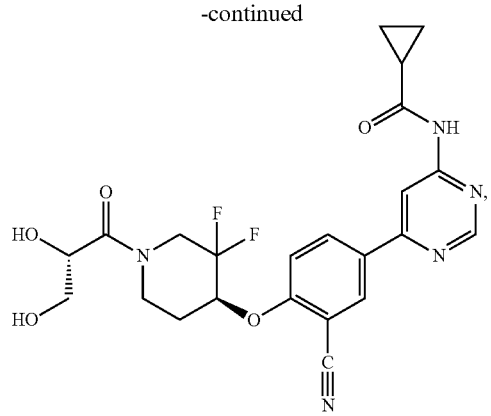
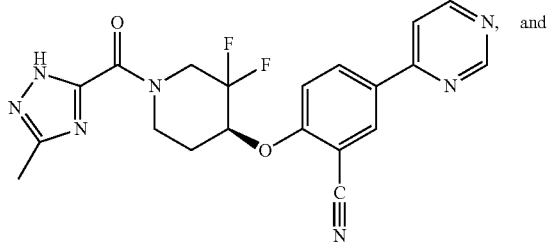
and
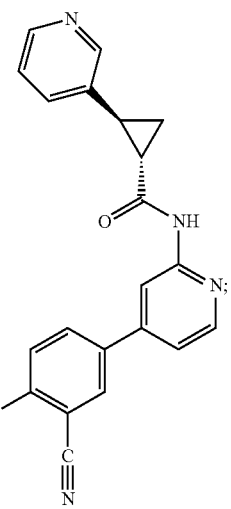
or a pharmaceutically acceptable salt thereof.

45. The compound of claim 44, wherein the compound is

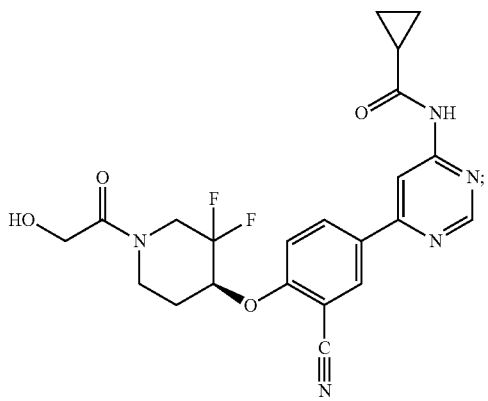

or a pharmaceutically acceptable salt thereof.

46. The compound of claim 44, wherein the compound is

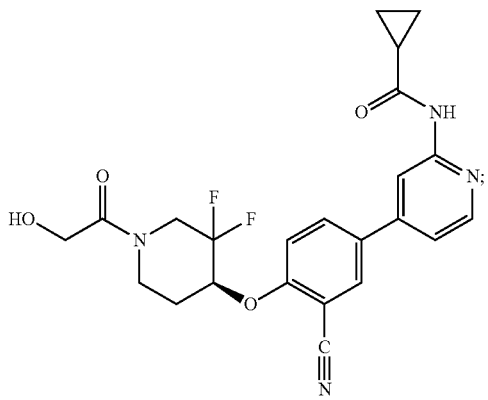

or a pharmaceutically acceptable salt thereof.

47. The compound of claim 44, wherein the compound is

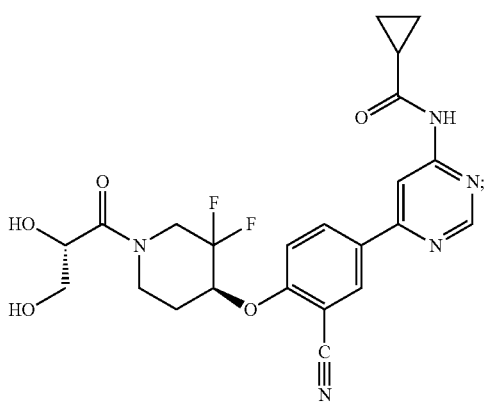 [SMILES: N#Cc1cc(-c2cc(NC(=O)C3CC3)ncn2)ccc1O[C@H]1CCN(C(=O)[C@@H](O)CO)CC1(F)F]

or a pharmaceutically acceptable salt thereof.

48. The compound of claim 44, wherein the compound is

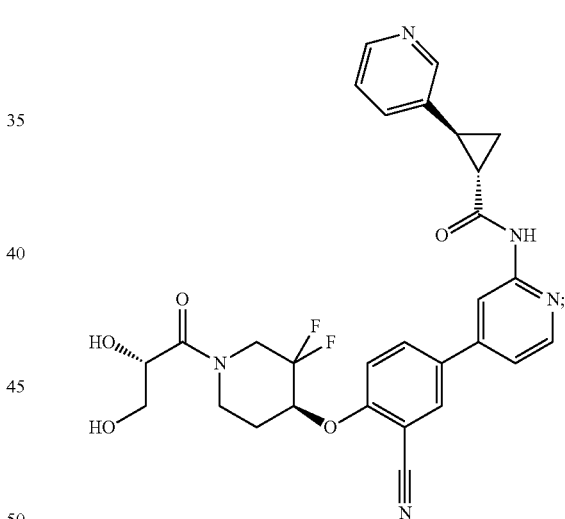

or a pharmaceutically acceptable salt thereof.

49. The compound of claim 44, wherein the compound is

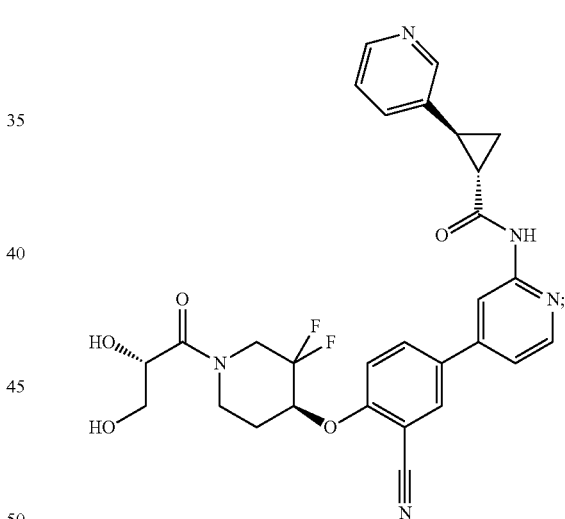

or a pharmaceutically acceptable salt thereof.

50. A pharmaceutical composition comprising the compound of claim 23, or a pharmaceutically acceptable salt thereof, and a pharmaceutically acceptable carrier.

51. The pharmaceutical composition of claim 50 in a solid oral dosage form.

52. The pharmaceutical composition of claim 51, wherein the solid oral dosage form is a tablet or capsule.

53. The compound of claim 23, wherein the pharmaceutically acceptable salt of the compound is the hydrochloride salt.

54. A compound selected from the group consisting of:
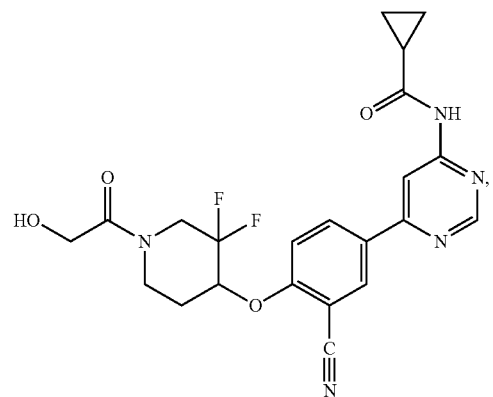
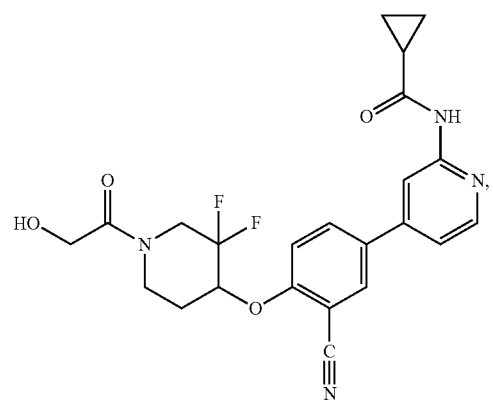
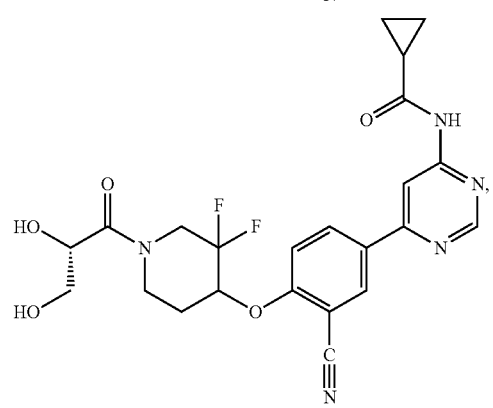
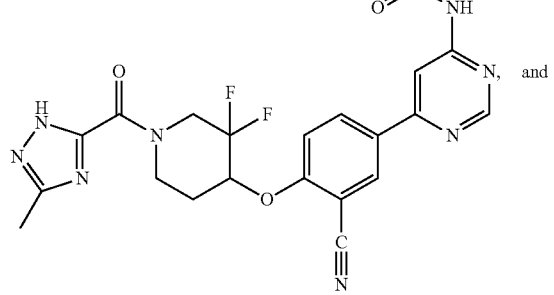
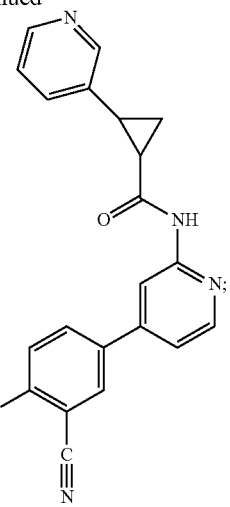
or a pharmaceutically acceptable salt thereof.
55. The compound of claim 51, wherein the compound
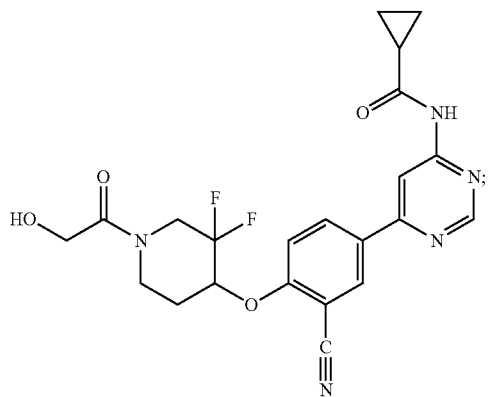 [SMILES: N#Cc1cc(-c2cc(NC(=O)C3CC3)ncn2)ccc1OC1CCN(C(=O)CO)CC1(F)F]
or a pharmaceutically acceptable salt thereof.
56. The compound of claim 54, wherein the compound is
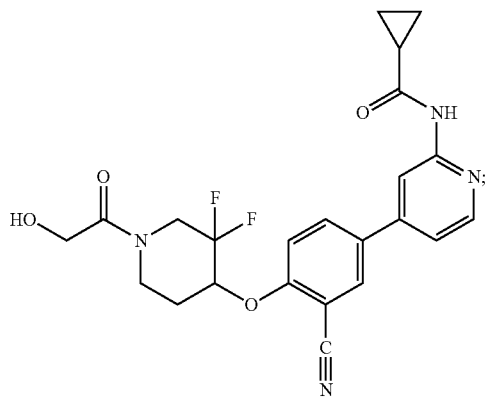 [SMILES: N#Cc1cc(-c2ccnc(NC(=O)C3CC3)c2)ccc1OC1CCN(C(=O)CO)CC1(F)F]
or a pharmaceutically acceptable salt thereof.

57. The compound of claim 54, wherein the compound is
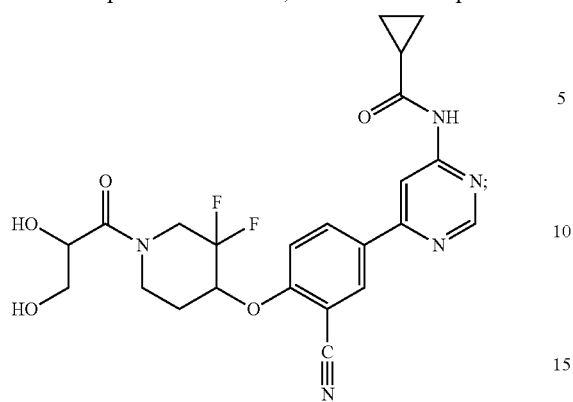
or a pharmaceutically acceptable salt thereof.
58. The compound of claim 54, wherein the compound is
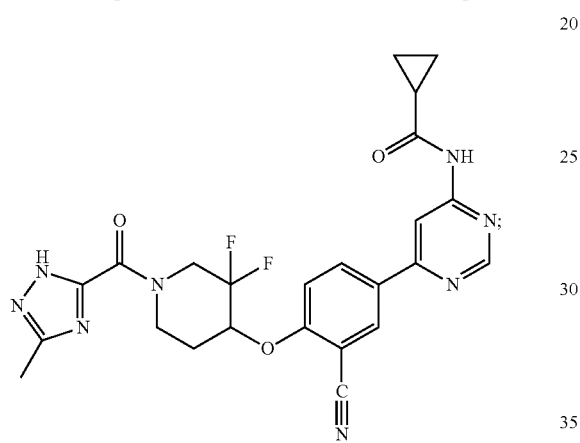
or a pharmaceutically acceptable salt thereof.
59. The compound of claim 54, wherein the compound is
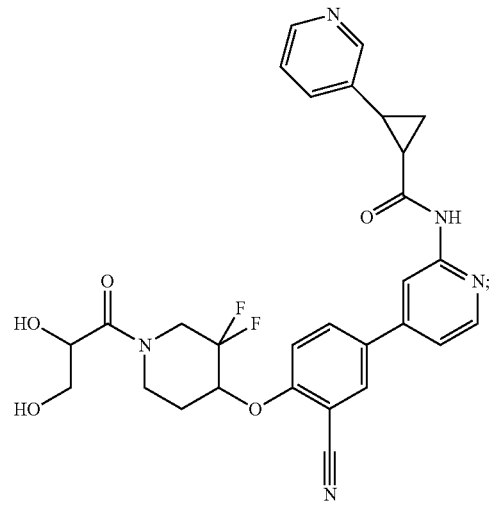 [SMILES: N#Cc1cc(-c2ccnc(NC(=O)C3CC3c3cccnc3)c2)ccc1OC1CCN(C(=O)C(O)CO)CC1(F)F]
or a pharmaceutically acceptable salt thereof.
* * * * *